United States Patent
Meyer, Jr. et al.

(10) Patent No.: US 9,144,239 B2
(45) Date of Patent: *Sep. 29, 2015

(54) MACROCYCLIC PICOLINAMIDES AS FUNGICIDES

(71) Applicant: DOW AGROSCIENCES LLC, Indianapolis, IN (US)

(72) Inventors: Kevin G. Meyer, Jr., Zionsville, IN (US); Karla Bravo-Altamirano, Carmel, IN (US); James M. Renga, Indianapolis, IN (US); Jessica Herrick, Zionsville, IN (US); Benjamin Nugent, Brownsburg, IN (US); Timothy Boebel, Indianapolis, IN (US); Fangzheng Li, Carmel, IN (US); Nick X. Wang, Westfield, IN (US); W. John Owen, Carmel, IN (US); Paul Graupner, Carmel, IN (US); Chenglin Yao, Westfield, IN (US); Ronald J. Heemstra, Fishers, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/288,933

(22) Filed: May 28, 2014

(65) Prior Publication Data

US 2014/0275171 A1 Sep. 18, 2014

Related U.S. Application Data

(62) Division of application No. 13/888,084, filed on May 6, 2013, now Pat. No. 8,785,479.

(60) Provisional application No. 61/643,753, filed on May 7, 2012.

(51) Int. Cl.
| | | |
|---|---|---|
| *C07D 321/00* | (2006.01) | |
| *C07D 405/12* | (2006.01) | |
| *A01N 43/24* | (2006.01) | |
| *A01N 43/40* | (2006.01) | |
| *A01N 47/18* | (2006.01) | |

(52) U.S. Cl.
CPC ............... *A01N 43/24* (2013.01); *A01N 43/40* (2013.01); *A01N 47/18* (2013.01); *C07D 321/00* (2013.01); *C07D 405/12* (2013.01); *A01N 2300/00* (2013.01)

(58) Field of Classification Search
None
See application file for complete search history.

(56) References Cited

U.S. PATENT DOCUMENTS

| | | |
|---|---|---|
| 6,355,660 B1 | 3/2002 | Ricks et al. |
| 6,521,622 B1 | 2/2003 | Ricks et al. |
| 6,706,740 B2 | 3/2004 | Ricks et al. |
| 6,861,390 B2 | 3/2005 | Meyer et al. |
| 7,250,389 B1 | 7/2007 | Sakanaka et al. |
| 8,785,479 B2 * | 7/2014 | Meyer et al. .................. 514/357 |
| 2004/0171838 A1 | 9/2004 | Meyer et al. |
| 2004/0186296 A1 | 9/2004 | Niyaz et al. |
| 2004/0192924 A1 | 9/2004 | Meyer et al. |
| 2007/0060579 A1 | 3/2007 | Wachendorff-Neumann et al. |
| 2007/0066629 A1 | 3/2007 | Blasco et al. |
| 2011/0082160 A1 | 4/2011 | Owen et al. |

FOREIGN PATENT DOCUMENTS

| | | |
|---|---|---|
| EP | 1 516 874 | 3/2005 |
| WO | WO 2012/070015 | 5/2012 |

OTHER PUBLICATIONS

International Searching Authority, International Search Report for PCT/US2013/039732, dated Oct. 18, 2013., 3 pages.
Anonymous, Synergistic Fungicidal Compositions of Heterocyclic Aromatic Amides and Triazoles, IP.COM, Electronic Publication, 2004, 1-10.

* cited by examiner

*Primary Examiner* — Zinna Northington Davis
(74) *Attorney, Agent, or Firm* — C. W. Arnett; Faegre Baker Daniels LLP

(57) ABSTRACT

The invention relates to macrocyclic picolinamides of Formula I and their use as fungicides.

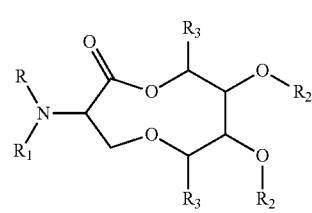

20 Claims, No Drawings

MACROCYCLIC PICOLINAMIDES AS FUNGICIDES

CROSS REFERENCE TO RELATED APPLICATIONS

This Application is a continuation application of U.S. patent application Ser. No. 13/888,084, filed May 6, 2010, now U.S. Pat No. 8,785,479, issued Jul. 22, 2014, which claims the benefit of U.S. Provisional Patent Application Ser. No. 61/643,753 filed on May 7, 2012, the disclosures of which are expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to macrocyclic picolinamides and their use as fungicides. The compounds of the present disclosure may offer protection against ascomycetes, basidiomycetes, deuteromycetes and oomycetes.

One embodiment of the present disclosure may include compounds of Formula I:

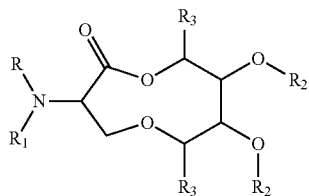

I

R is H or C(O)R$_6$;
R$_1$ is H, C(O)R$_6$, or Q;
Q is

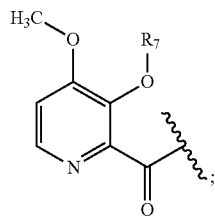

R$_2$ is independently H, alkyl, alkenyl, aryl, heterocyclyl, each substituted with 0, 1 or multiple R$_5$, or —C(O)R$_5$;
R$_3$ is independently H, alkyl, or alkenyl, each substituted with 0, 1 or multiple R$_5$;
R$_4$ is independently alkyl or alkoxy, substituted with 0, 1, or multiple R$_5$;
R$_5$ is alkyl, alkenyl, halo, haloalkyl, alkoxy, haloalkoxy, C(O)R$_8$, arylalkoxy, or aryl;
R$_6$ is alkoxy or benzyloxy;
R$_7$ is H, —C(O)R$_4$, or —CH$_2$OC(O)R$_4$; and
R$_8$ is H, alkyl, alkenyl, halo, haloalkyl, alkoxy, haloalkoxy, arylalkoxy, or aryl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by the those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl and the like.

The term "aryl" refers to any aromatic, mono- or bi-cyclic, containing 0 heteroatoms.

The term "heterocycle" refers to any aromatic or non-aromatic ring, mono- or bi-cyclic, containing one or more heteroatoms The term "alkoxy" refers to an —OR substituent.
The term "cyano" refers to a —C≡N substituent.
The term "hydroxyl" refers to an —OH substituent.
The term "amino" refers to a —NH$_2$ substituent.
The term "arylalkoxy" refers to —O(CH$_2$)$_n$Ar where n is an integer selected from the list 1, 2, 3, 4, 5, or 6.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "halogen" or "halo" refers to one or more halogen atoms, defined as F, Cl, Br, and I.

The term "nitro" refers to a —NO$_2$ substituent.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxinecopper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3, 3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithiine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis (dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlomitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vemolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; impact stage: *Septoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). It may be understood by those skilled in the art that each $R_2$ may be differentially substituted. The following descriptions and examples are provided for illustrative purposes and should not be construed as limiting in terms of substituents or substitution patterns.

In Scheme I, a mixture of compounds of Formula III, IV and V can be formed from compound of Formula II using an alkyl halide such as benzyl bromide (BnBr) and a quaternary amine salt such as tetrabutylammonium iodide (($Bu)_4N^+I^-$) and a base such as sodium hydroxide (NaOH) in an aprotic solvent such as dichloromethane (DCM, $CH_2Cl_2$). Compounds of Formula VI and VII, where $R_2$ is alkyl can be formed from compounds of Formula III and IV, respectively, using a base such as sodium hydride (NaH) and an alkyl halide such as butyl iodide (BuI), in an aprotic solvent such N,N-dimethylformamide (DMF). Compounds of Formula VIII and IX, where $R_2$ is alkyl, can be prepared from compounds of Formula VI and VII, respectively, by treatment with ozone in the presence of sodium bicarbonate ($NaHCO_3$) in a solvent mixture such as DCM/methanol (MeOH), with subsequent quenching of the reaction using a reducing agent such as sodium borohydride ($NaBH_4$) and a salt such as sodium acetate (NaOAc) in a solvent such as water ($H_2O$).

In Scheme II, compounds of Formula XI, where $R_2$ is alkenyl, can be prepared from compounds of Formula X by treatment with an allyl carbonate such as bis(2-methylallyl) carbonate, in the presence of a catalyst such as tetrakis(triphenylphosphine)-palladium(0) ($Pd(PPh_3)_4$) in an aprotic solvent such as tetrahydrofuran (THF) at an elevated temperature. Compounds of Formula XII, where $R_2$ is alk-

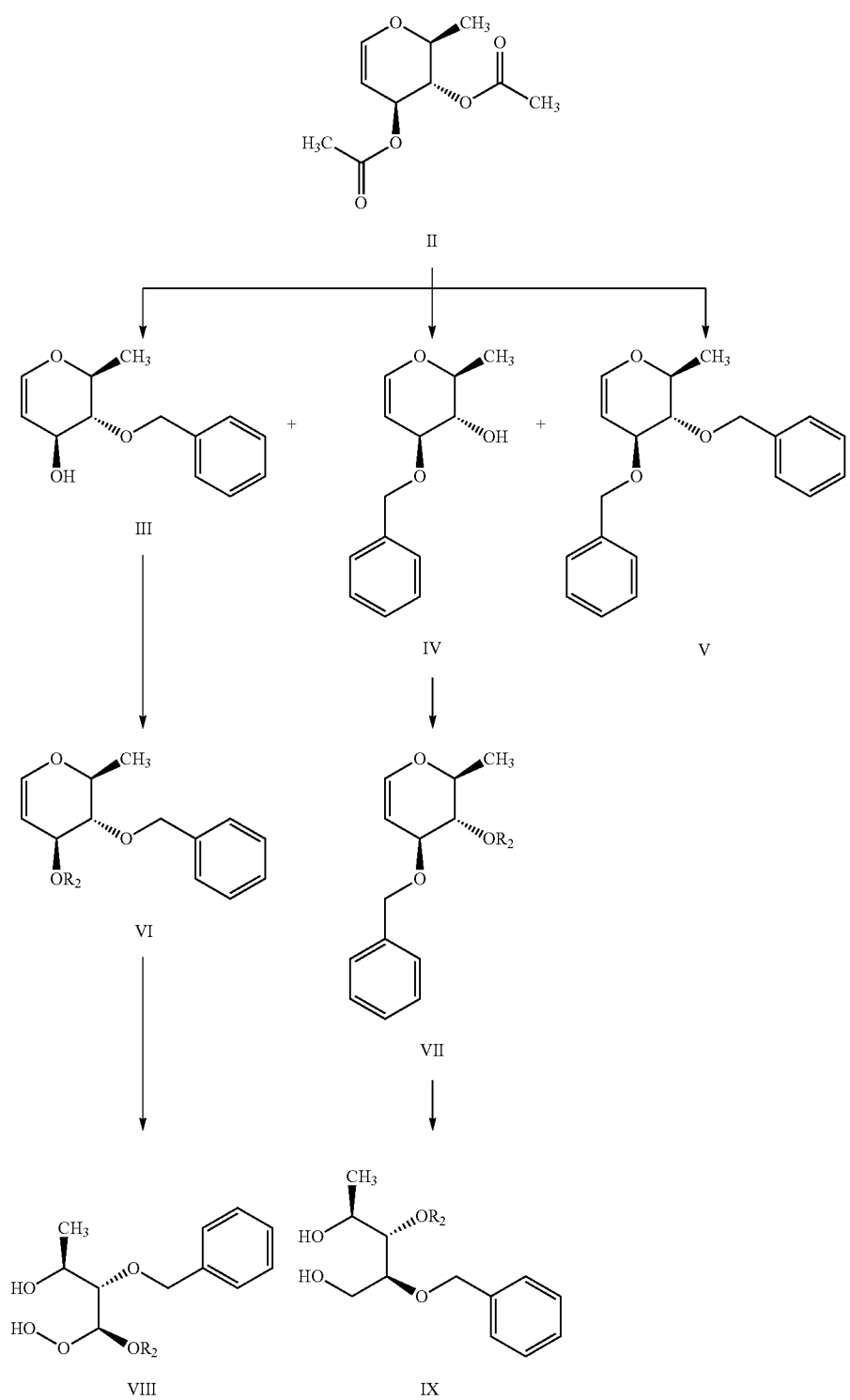

Scheme I enyl, can be prepared from compounds of Formula XI by treatment with a reducing agent, such as lithium aluminum hydride (LAH) in an aprotic solvent such as THF.

Scheme II

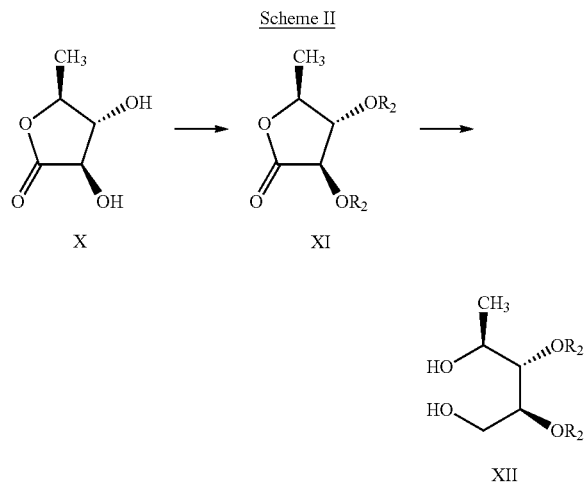

In Scheme III, compounds of Formula XIV, where $R_2$ is alkenyl can be prepared from compounds of Formula XIII by treatment with an allyl carbonate such as bis(2-methylallyl) carbonate, in the presence of a catalyst such as $Pd(PPh_3)_4$ in an aprotic solvent such as THF at an elevated temperature. Compounds of Formula XV, where $R_2$ is alkenyl, can be prepared from compounds of Formula XIV by treatment with a reducing agent, such as LAH in an aprotic solvent such as THF.

Scheme III

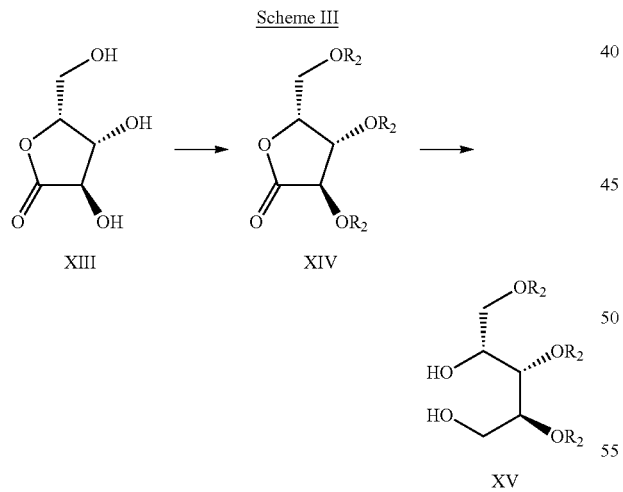

In Scheme IV, compounds of Formula XVII, where $R_2$ is a substituted alkyl or alkenyl can be prepared from compounds of Formula XVI by treatment with a base such as NaH and an alkyl halide such as benzyl halide or 3-bromo-2-methylpropene in an aprotic solvent such as DMF. Compounds of Formula XVIII, where $R_2$ is as above, can be prepared from compounds of Formula XVII by treatment with a reducing agent, such as LAH in an aprotic solvent such as THF.

Scheme IV

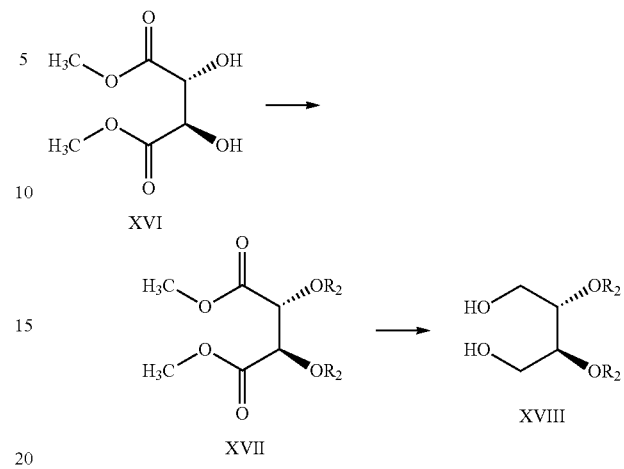

In Scheme V, compounds of Formula XX, where $R_2$ is alkyl or alkenyl, PG is Cbz or Boc, and $R_3$ is as originally defined, can be prepared from compounds of Formula XIX, where $R_2$ is substituted alkyl or alkenyl, and $R_3$ is as originally defined, by treatment with a protected aziridine, such as (S)-1-tert-butyl 2-methyl aziridine-1,2-dicarboxylate in the presence of a Lewis acid such as boron trifluoride diethyl etherate ($BF_3$-$Et_2O$), in an aprotic solvent such as DCM.

Scheme V

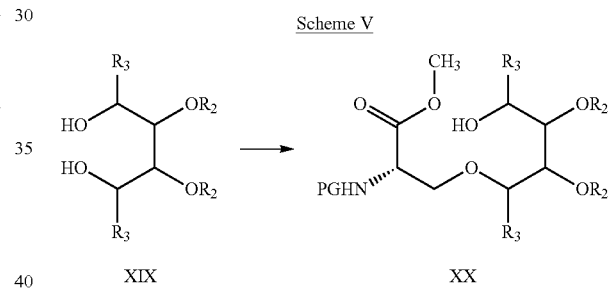

In Scheme VI, compounds of Formula XXII, where $R_2$ and PG are as defined above and $R_3$ is as originally defined, can be prepared from compounds of Formula XXI, where $R_2$ and PG are as defined above and $R_3$ is as originally defined, by treatment with an oxidizing agent, such as sulfur trioxide pyridine complex, in the presence of an organic amine base such as, for example, triethylamine (TEA) in a solvent mixture such as DCM/dimethylsulfoxide (DMSO). Compounds of Formula XXIIIa and XXIVa, where $R_2$ and PG are as defined above, $R_3$ is as originally defined and $R_9$ is alkyl can be prepared from compounds of Formula XXII by treatment with an organometallic reagent such as methylmagnesium bromide in an aprotic solvent such as THF.

Scheme VI

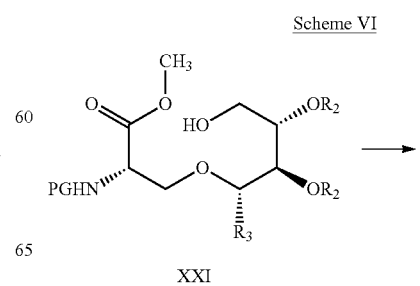

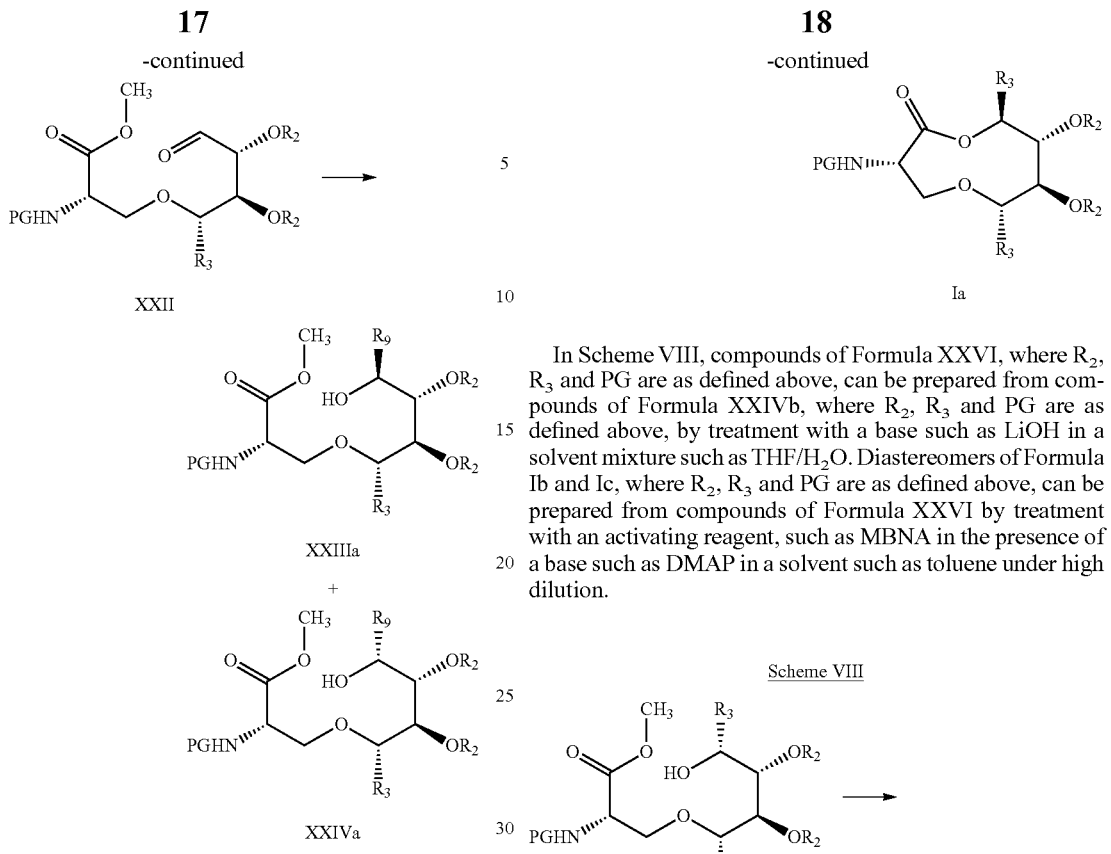

In Scheme VII, compounds of Formula XXV, where $R_2$, $R_3$ and PG are as defined above, can be prepared from compounds of Formula XXIIIb, where $R_2$, $R_3$ and PG are as defined above, by treatment with a base such as lithium hydroxide (LiOH) in a solvent mixture such as THF/$H_2O$. Compounds of Formula Ia, where $R_2$, $R_3$ and PG are as defined above, can be prepared from compounds of Formula XXV by treatment with an activating reagent, such as 2-methyl-6-nitrobenzoic anhydride (MNBA) in the presence of a base such as 4-dimethylaminopyridine (DMAP) in a solvent such as toluene.

In Scheme VIII, compounds of Formula XXVI, where $R_2$, $R_3$ and PG are as defined above, can be prepared from compounds of Formula XXIVb, where $R_2$, $R_3$ and PG are as defined above, by treatment with a base such as LiOH in a solvent mixture such as THF/$H_2O$. Diastereomers of Formula Ib and Ic, where $R_2$, $R_3$ and PG are as defined above, can be prepared from compounds of Formula XXVI by treatment with an activating reagent, such as MBNA in the presence of a base such as DMAP in a solvent such as toluene under high dilution.

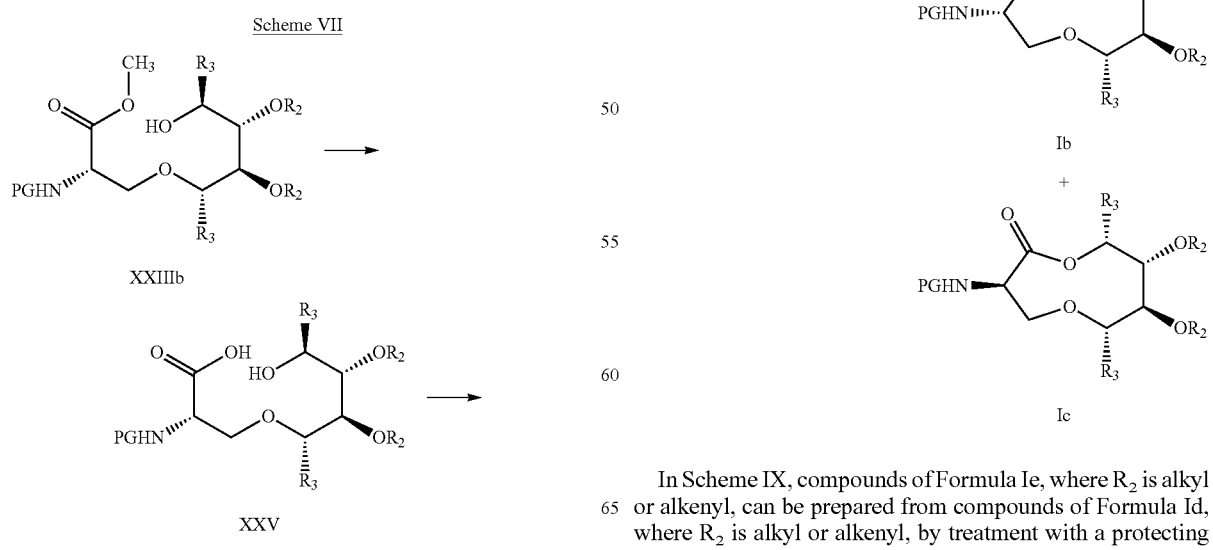

In Scheme IX, compounds of Formula Ie, where $R_2$ is alkyl or alkenyl, can be prepared from compounds of Formula Id, where $R_2$ is alkyl or alkenyl, by treatment with a protecting group such as di-tert-butyl dicarbonate in the presence of a base such as DMAP in an aprotic solvent such as acetonitrile (CH₃CN). Compounds of Formula If, where R₂ is as defined above, can be prepared from compounds of Formula Ie by treatment with hydrogen in the presence of a catalyst such as palladium on carbon (Pd/C) in a solvent such as ethyl acetate (EtOAc). Compounds of Formula Ig, where R₂ is as defined above and R₁₀ is acyl, can be prepared from compounds of Formula Id, where R₂ is as defined above, by treatment with hydrogen in the presence of a catalyst such as Pd/C in a solvent such as EtOAc, followed by treatment with an acyl halide such as isobutyryl chloride in the presence of a base such as DMAP in an aprotic solvent such as pyridine. Compounds of Formula Ih, where R₂ is as defined above and R₁₀ is alkyl or alkenyl, can be prepared from compounds of Formula If, where R₂ is as defined above, by treatment with an alkylating reagent such as trimethyloxonium tetrafluoroborate in the presence of an amine such as N,N,N',N'-tetramethyl-1,8-naphthalenediamine (Proton-Sponge™) in an aprotic solvent such as DCM. Alternatively, compounds of Formula Ih can be prepared from compounds of Formula If by treatment with an allyl carbonate such as bis(2-methylallyl) carbonate, in the presence of a catalyst such as tris(dibenzylideneacetone)dipalladium(0) (Pd₂(dba)₃) and a ligand such as 1,1'-bis(diphenylphosphino)ferrocene (dppf) in an aprotic solvent such as THF at an elevated temperature, such as 60° C.

Scheme IX

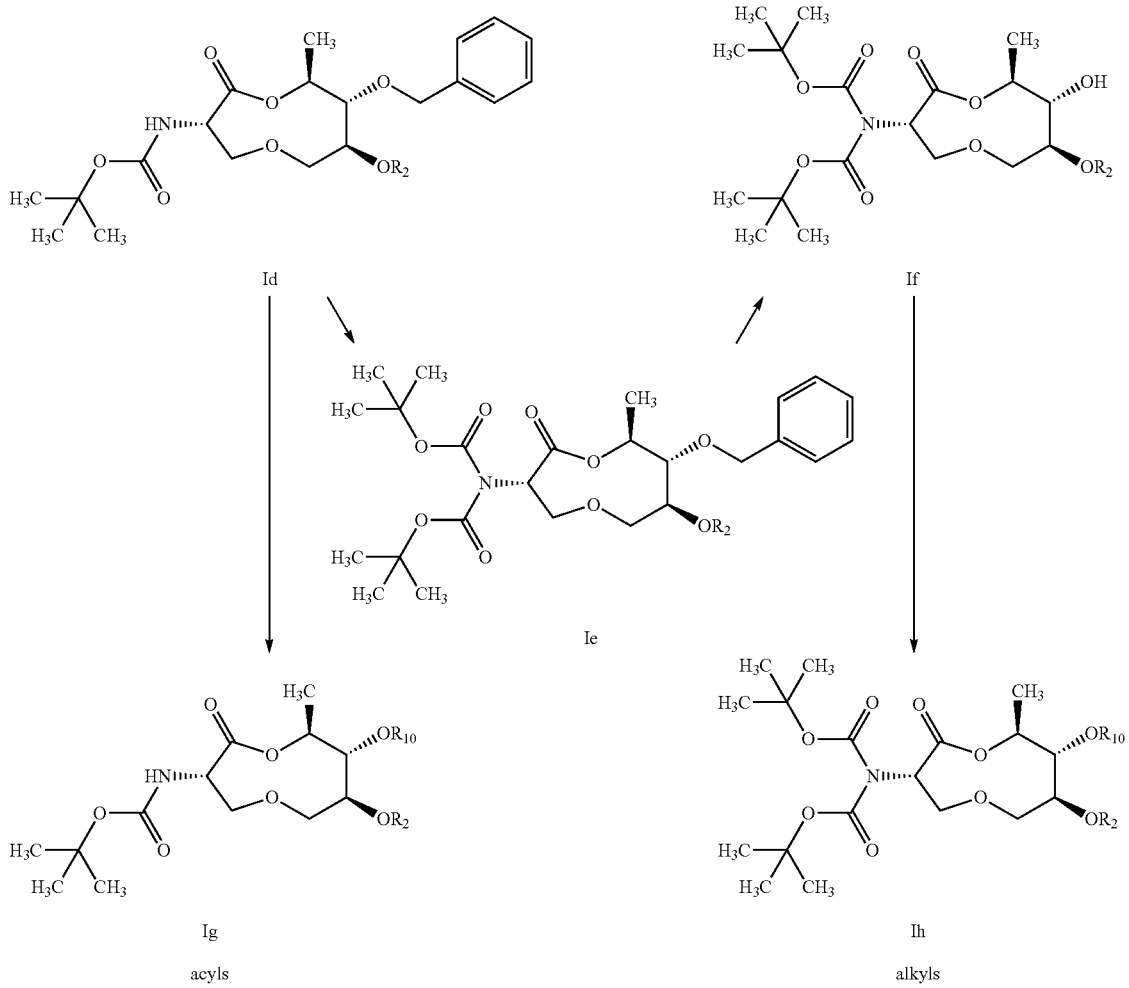

Ig
acyls

Ih
alkyls

In Scheme X, compounds of Formula Ij, where R₂ is alkyl, can be prepared from compounds of Formula II, where R₂ is alkyl, by treatment with ozone in the presence of sodium bicarbonate (NaHCO₃) in a solvent mixture such as DCM/MeOH, with subsequent quenching of the reaction using a reducing agent such as dimethyl sulfide ((CH₃)₂S, DMS). Compounds of Formula Ik, where R₂ is alkyl, can be prepared from compounds of Formula Ij by treatment with a fluorinating agent such as Deoxo-Fluor® in a solvent such as DCM. Compounds of Formula Il, where R₂ is alkyl, can be prepared from compounds of Formula II by treatment with ozone in the presence of NaHCO₃ in a solvent mixture such as DCM/MeOH, with subsequent quenching of the reaction using a reducing agent such as sodium borohydride (NaBH₄) and a salt such as sodium acetate (NaOAc) in a solvent such as H₂O. Compounds of Formula Im, where R₂ is alkyl, can be prepared from compounds of Formula II by treatment with an alkylating agent such as trimethyloxonium tetrafluoroborate in the presence of an amine base, such as Proton-Sponge™, in a solvent such as DCM.

Scheme X

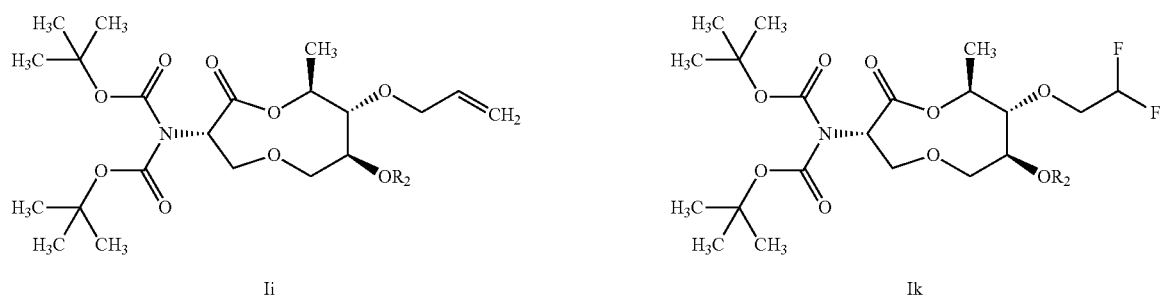

Ii            Ik

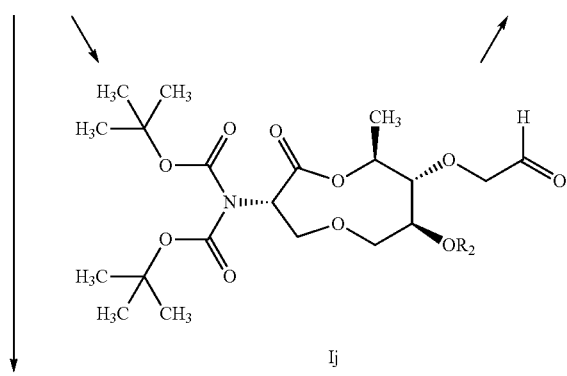

Ij

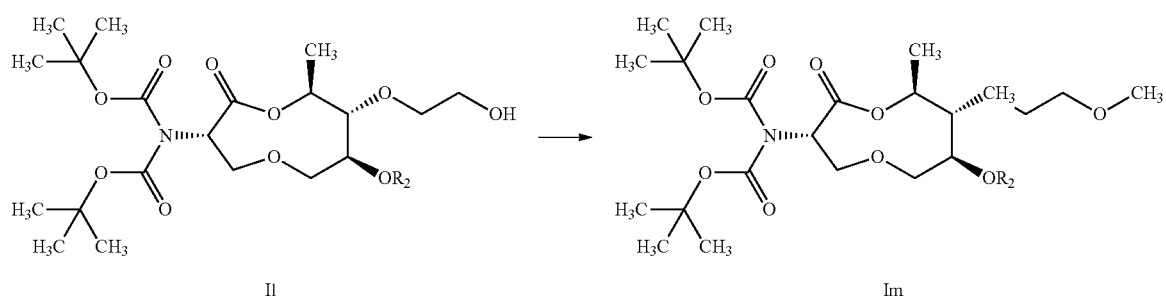

Il            Im

In Scheme XI, compounds of Formula Io can be prepared from compounds of Formula In by treatment with a protecting group such as di-tert-butyl dicarbonate in the presence of a base such as DMAP in an aprotic solvent such as $CH_3CN$. Compounds of Formula Ip can be prepared from compounds of Formula Io by treatment with hydrogen in the presence of a catalyst such as Pd/C in a solvent such as EtOAc. Compounds of Formula Iq can be prepared from compounds of Formula Ip by treatment with an alkylating reagent such as trimethyloxonium tetrafluoroborate in the presence of an amine such as Proton-Sponge™ in an aprotic solvent such as DCM. Alternatively, compounds of Formula Iq can be prepared from compounds of Formula Ip by treatment with an allyl carbonate such as bis(2-methylallyl)carbonate, in the presence of a catalyst such as $Pd_2(dba)_3$ and a ligand such as dppf in an aprotic solvent such as THF at an elevated temperature. Alternatively, compounds of Formula Iq can be prepared from compounds of Formula Ip by treatment with an organometallic species such as bis(acetato-O)triphenylbismuth(V) in the presence of a catalyst such as copper(II) acetate in a solvent such as DCM. Alternatively, compounds of Formula Iq can be prepared from compounds of Formula Ip by treatment with an acyl halide such as isobutyryl chloride in the presence of a base such as DMAP in an aprotic solvent such as pyridine.

Scheme XI

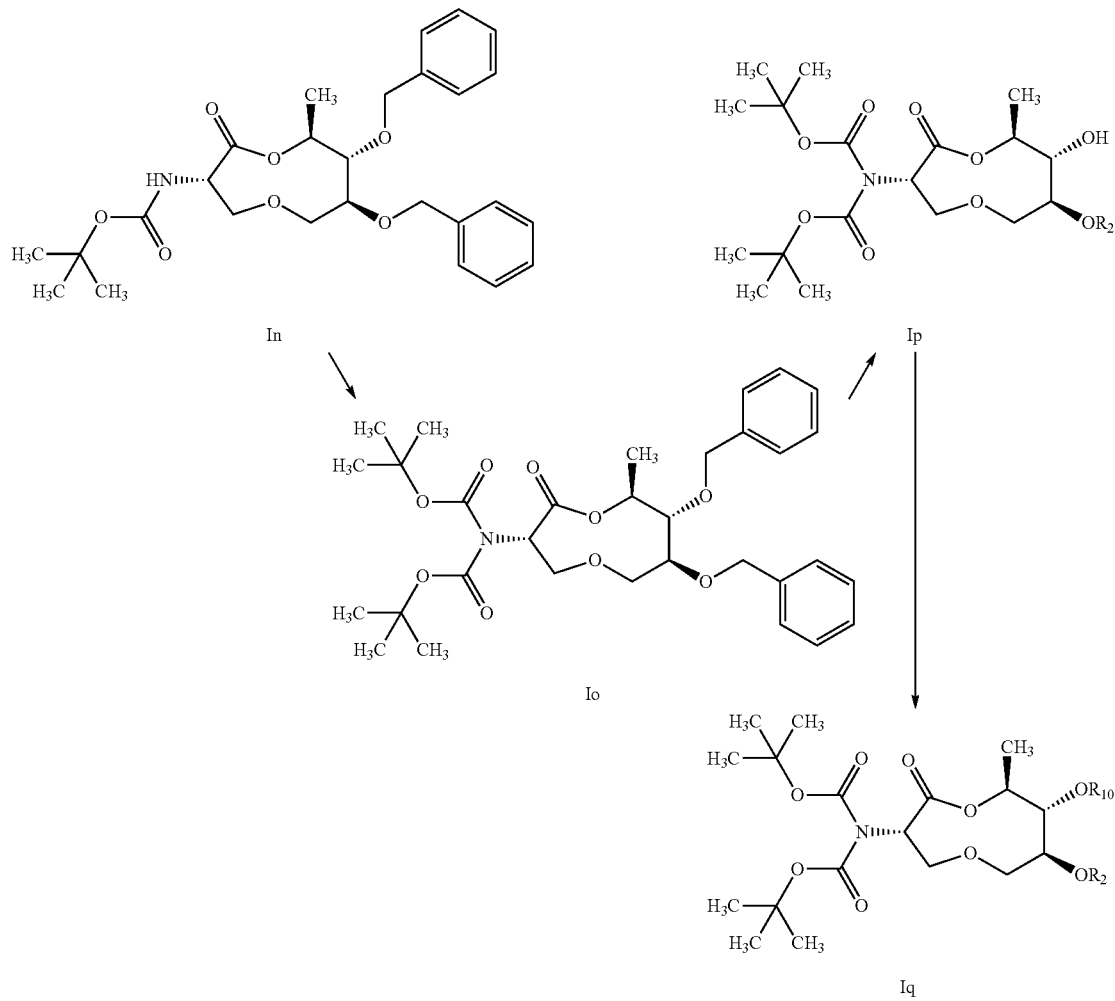

In Scheme XII, compounds of Formula Iu, where $R_2$ and $R_3$ are as originally defined, can be prepared from compounds of Formula Ir or compounds of Formula Is, where $R_2$ and $R_3$ are as originally defined, by treatment with an acid such as a 4.0 M hydrogen chloride (HCl) solution in dioxane in a solvent such as DCM. Alternatively, compounds of Formula Iu, where $R_2$ and $R_3$ are as originally defined, can be prepared from compounds of Formula Ir or compounds of Formula Is, where $R_2$ and $R_3$ are as originally defined, by treatment with trimethylsilyl trifluoromethanesulfonate in the presence of a base such 2,6-lutidine in an aprotic solvent such as DCM, followed by treatment with a protic solvent such as MeOH. Alternatively, compounds of Formula Iu, where $R_2$ and $R_3$ are as originally defined, can be prepared from compounds of Formula It, where $R_2$ and $R_3$ are as originally defined, by treatment with hydrogen in the presence of a catalyst such as Pd/C in a solvent such as EtOAc. Compounds of Formula Iv, where $R_2$ and $R_3$ are as originally defined, can be prepared from compounds of Formula Iu, where $R_2$ and $R_3$ are as originally defined, by treatment with 3-hydroxy-4-methoxypicolinic acid in the presence of a base such as 4-methylmorpholine and a peptide coupling reagent such as O-(7-azabenzotriazol-1-yl)-N,N,N',N'-tetramethyluronium hexafluorophosphate (HATU) and benzotriazol-1-yl-oxytripyrrolidinophosphonium hexafluorophosphate (PyBOP) in an aprotic solvent such as DCM.

Scheme XII

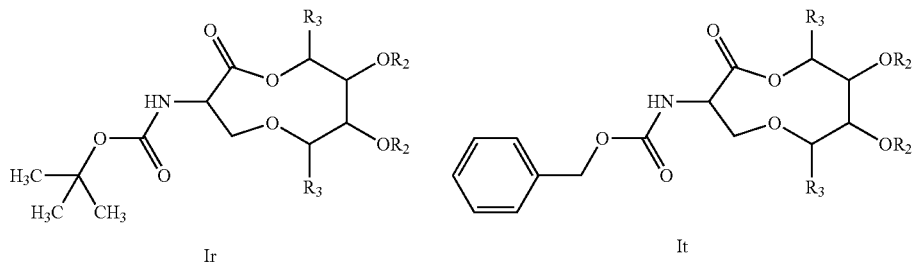

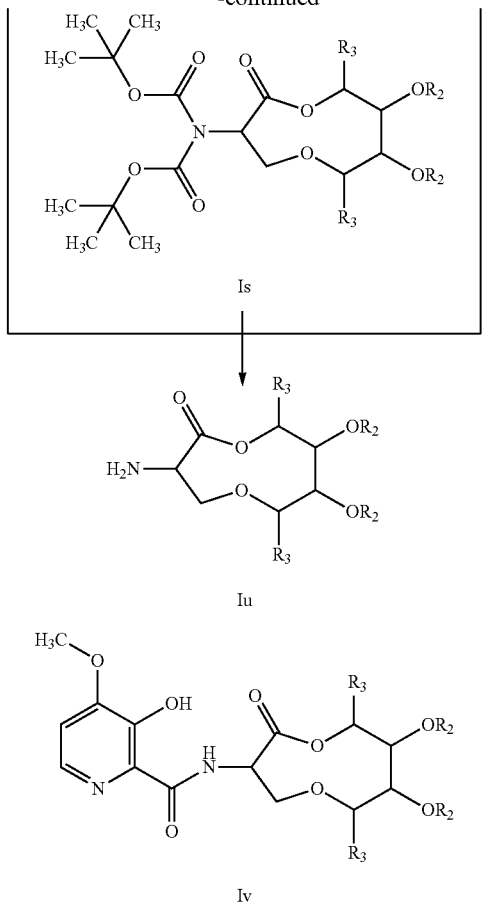

In Scheme XIII, compounds of Formula Ix, where $R_2$, $R_3$ and $R_7$ are as originally defined, can be prepared from compound of Formula Iw, where $R_2$ and $R_3$ are as originally defined, by treatment with the appropriate alkyl halide in the presence of a reagent such as sodium iodide (NaI) and a base such as sodium carbonate ($Na_2CO_3$) in a solvent such as acetone or an acyl halide in the presence of an amine base, such as pyridine or triethylamine, in an aprotic solvent such as DCM.

The following examples are presented to illustrate the various aspects of the compounds of the present disclosure and should not be construed as limitations to the claims.

EXAMPLES

Example 1

Step 1: Preparation of (3R,4S,5S)-5-methyl-3,4-bis(2-methylallyloxy)dihydrofuran-2(3H)-one

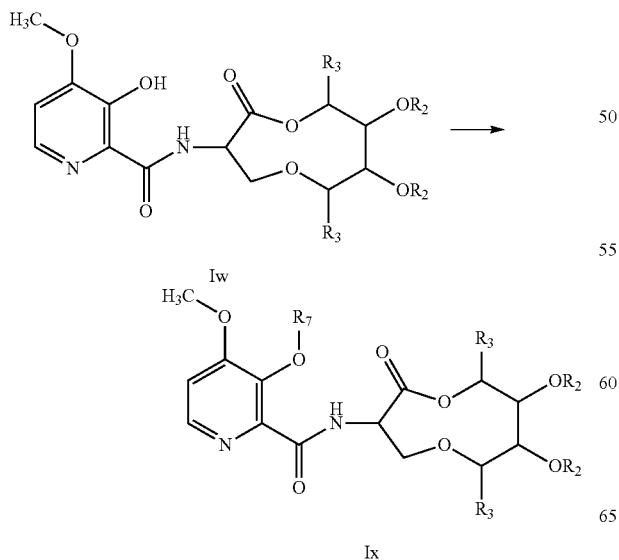

To a stirred solution of (3R,4R,5S)-3,4-dihydroxy-5-methyldihydrofuran-2(3H)-one (1.3 grams (g), 9.84 millimole (mmol)) and Pd(Ph$_3$P)$_4$ (0.569 g, 0.492 mmol) in anhydrous THF (9 milliliters (mL)) under nitrogen (N$_2$) was added bis(2-methylallyl)carbonate. After stirring the solution at 60° C. for 1 hour (h) (CO$_2$ evolution ceased), the reaction mixture was cooled and the solvent was evaporated. The crude product was purified by flash chromatography (silica gel (SiO$_2$)) to yield the title compound as a colorless oil (2.3 g, 97%): $^1$H NMR (400 MHz, CDCl$_3$) δ 5.04 (dd, J=1.9, 0.9 Hz, 1H), 5.00-4.98 (m, 1H), 4.97-4.93 (m, 2H), 4.47-4.38 (m, 1H), 4.36-4.27 (m, 1H), 4.23-4.00 (m, 4H), 3.82 (t, J=7.2 Hz, 1H), 1.78 (s, 3H), 1.75 (s, 3H), 1.48 (d, J=6.3 Hz, 3H); $^{13}$C NMR (101 MHz, CDCl$_3$) δ 172.65, 141.07, 140.92, 113.54, 113.14, 84.19, 79.31, 76.57, 74.53, 74.51, 19.48, 19.35, 19.00; EIMS m/z 240 [M$^+$].

Example 1

Step 2: Preparation of (2S,3S,4S)-2,3-bis(2-methylallyloxy)pentane-1,4-diol

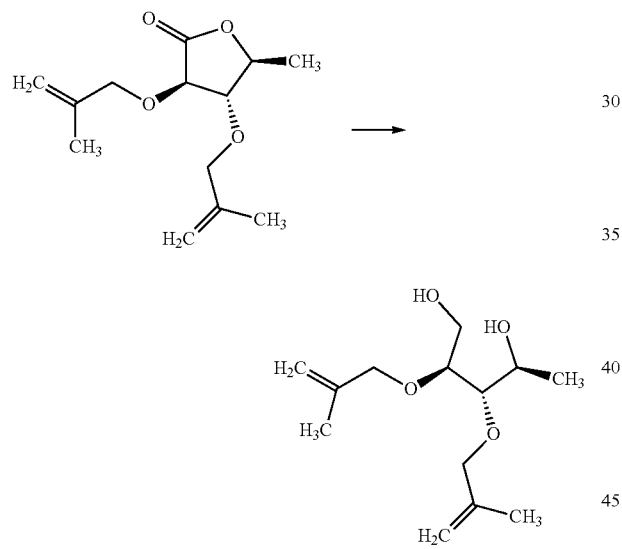

To a solution of (3R,4S,5S)-5-methyl-3,4-bis(2-methylallyloxy)dihydrofuran-2(3H)-one (1 g, 4.16 mmol) in THF (10 mL) at 0° C. was added 1.0 M LAH (9.57 mL, 9.57 mmol) in THF over 15 min. The mixture was warmed to room temperature and stirred for 2 h, then carefully added dropwise to an ice cold saturated aqueous ammonium chloride (NH$_4$Cl) solution (100 mL). The phases were separated and the aqueous layer was extracted with DCM. The combined organic layers were dried over sodium sulfate (Na$_2$SO$_4$), filtered, and the filtrate was concentrated. Purification by flash chromatography (SiO$_2$) afforded the title compound as a colorless oil (920 mg, 90%): $^1$H NMR (400 MHz, CDCl$_3$) δ 4.99 (d, J=7.8 Hz, 2H), 4.91 (d, J=8.9 Hz, 2H), 4.09-3.92 (m, 5H), 3.93-3.83 (m, 1H), 3.82-3.73 (m, 1H), 3.70 (q, J=4.7 Hz, 1H), 3.39 (dd, J=6.0, 5.0 Hz, 1H), 3.14 (s, 1H), 2.46 (s, 1H), 1.77 (s, 3H), 1.76 (s, 3H), 1.26 (d, J=6.3 Hz, 3H); $^{13}$C NMR (101 MHz, CDCl$_3$) δ 141.95, 141.75, 112.99, 112.79, 81.57, 79.41, 75.52, 74.57, 67.60, 61.33, 19.67, 19.63, 19.61.

Example 1

Step 3: Preparation of (S)-methyl 2-(benzyloxycarbonylamino)-3-((2S,3S,4S)-4-hydroxy-2,3-bis(2-methylallyloxy)pentyloxy)propanoate and (S)-methyl 2-(benzyloxycarbonylamino)-3-((2S,3S,4S)-5-hydroxy-3,4-bis(2-methylallyloxy)pentan-2-yloxy)propanoate

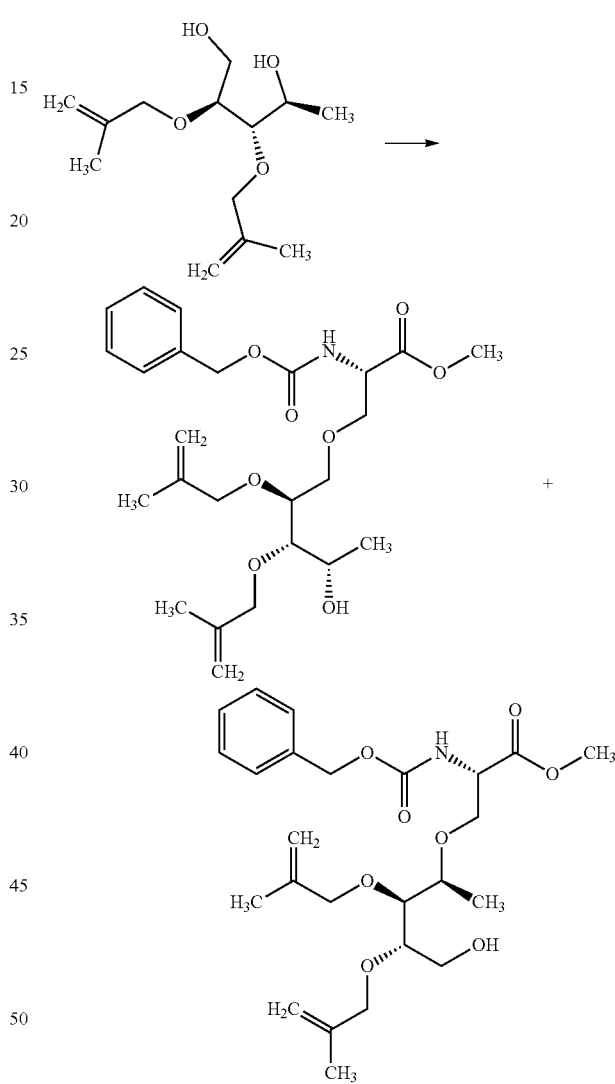

To a solution of (2S,3S,4S)-2,3-bis(2-methylallyloxy)pentane-1,4-diol (920 milligrams (mg), 3.77 mmol) and (S)-1-benzyl 2-methyl aziridine-1,2-dicarboxylate (0.739 mL, 3.74 mmol) in anhydrous chloroform (CHCl$_3$; 5 mL) was added BF$_3$-Et$_2$O (26 microliters (μL) 0.55 mmol) at 0° C. and the solution was stirred at 0° C. for 3 h. The crude reaction mixture was concentrated and purified by flash chromatography (SiO$_2$) to furnish (S)-methyl 2-(benzyloxycarbonylamino)-3-((2S,3S,4S)-4-hydroxy-2,3-bis(2-methylallyloxy)-pentyloxy)-propanoate as a colorless oil (620 mg, 35%) and (S)-methyl 2-(benzyloxycarbonylamino)-3-((2S, 3S,4S)-5-hydroxy-3,4-bis(2-methylallyloxy)pentan-2-yloxy)propanoate as a colorless oil (300 mg, 17%).

(S)-methyl 2-(benzyloxycarbonylamino)-3-((2S,3S,4S)-4-hydroxy-2,3-bis(2-methylallyloxy)-pentyloxy)propanoate: $^1$H NMR (400 MHz, CDCl$_3$) δ 7.43-7.29 (m, 5H), 5.75 (d, J=8.7 Hz, 1H), 5.17-5.07 (m, 2H), 5.01-4.91 (m, 2H), 4.87 (t, J=5.3 Hz, 2H), 4.51 (dt, J=8.7, 3.0 Hz, 1H), 4.07-3.90 (m, 5H), 3.90-3.79 (m, 1H), 3.75 (s, 2H), 3.74-3.61 (m, 5H), 3.29-3.18 (m, 1H), 3.11 (d, J=4.0 Hz, 1H), 1.78-1.68 (m, 6H), 1.21 (d, J=6.3 Hz, 3H); $^{13}$C NMR (101 MHz, CDCl$_3$) δ 170.66, 156.01, 142.04, 141.83, 136.25, 128.52, 128.17, 128.08, 112.79, 112.65, 81.18, 78.26, 75.51, 74.77, 71.42, 70.68, 67.74, 67.05, 54.43, 52.57, 19.91, 19.66, 19.55; ESIMS m/z 502.4 ([M+Na]$^+$).

(S)-methyl 2-(benzyloxycarbonylamino)-3-((2S,3S,4S)-5-hydroxy-3,4-bis(2-methylallyloxy)pentan-2-yloxy)propanoate: $^1$H NMR (400 MHz, CDCl$_3$) δ 7.41-7.28 (m, 5H), 5.69 (d, J=8.5 Hz, 1H), 5.18-5.08 (m, 2H), 5.04-4.93 (m, 2H), 4.92-4.80 (m, 2H), 4.48 (dt, J=8.7, 3.3 Hz, 1H), 4.07-3.93 (m, 5H), 3.87 (dd, J=9.3, 3.1 Hz, 1H), 3.78-3.66 (m, 5H), 3.65-3.53 (m, 2H), 3.48-3.40 (m, 2H), 1.84-1.64 (m, 6H), 1.19 (d, J=6.3 Hz, 3H); $^{13}$C NMR (101 MHz, CDCl$_3$) δ 170.82, 156.04, 142.39, 142.34, 136.24, 128.51, 128.47, 128.17, 128.09, 128.04, 112.12, 112.05, 81.47, 79.72, 76.63, 76.14, 74.82, 68.72, 67.04, 61.85, 54.45, 52.53, 19.68, 19.61, 15.33; ESIMS m/z 502.4 ([M+Na]$^+$).

Example 1

Step 4: Preparation of benzyl (3S,7S,8S,9S)-9-methyl-7,8-bis(2-methylallyloxy)-2-oxo-1,5-dioxonan-3-ylcarbamate (compound 126)

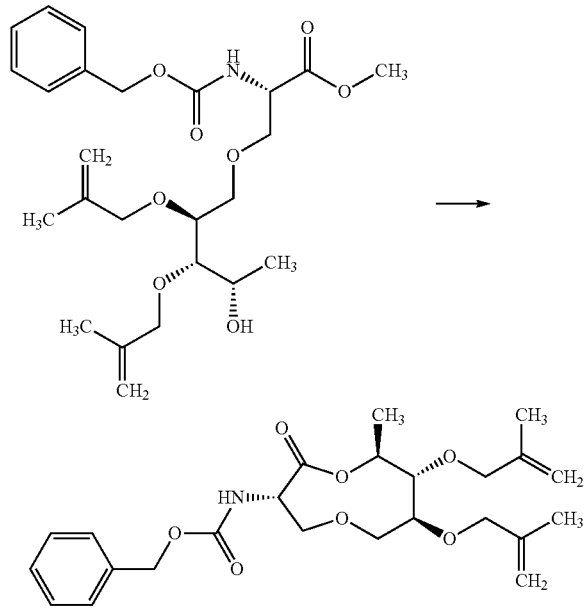

To a solution of (S)-methyl 2-(benzyloxycarbonylamino)-3-((2S,3S,4S)-4-hydroxy-2,3-bis(2-methylallyloxy)pentyloxy)propanoate (480 mg, 1.001 mmol) in THF/H$_2$O (18 mL, 2:1 ratio) was added LiOH (71.9 mg, 3.00 mmol) and the solution was allowed to stir for 40 minutes (min) at ambient temperature. The crude reaction mixture was diluted with EtOAc and washed with 1 Normal (N) aqueous HCl. The phases were separated and the aqueous phase was extracted with EtOAc (3×20 mL). The combined organic layers were dried over Na$_2$SO$_4$, filtered, and concentrated to furnish the intermediate acid as a colorless oil which was dissolved in anhydrous toluene (50 mL) and added to a solution of MNBA (521 mg, 1.512 mmol) and DMAP (693 mg, 5.67 mmol) in toluene (180 mL) over the course of 3 h via syringe pump. After the addition was completed the reaction mixture was stirred for 1 h, concentrated, and purified by flash chromatography (SiO$_2$) to afford the title compound as a white foam (281 mg, 62%): $^1$H NMR (400 MHz, CDCl$_3$) δ 7.40-7.28 (m, 5H), 5.55 (d, J=7.7 Hz, 1H), 5.10 (s, 2H), 5.01-4.91 (m, 3H), 4.85 (d, J=1.2 Hz, 2H), 4.69 (dd, J=12.1, 6.7 Hz, 1H), 4.32 (d, J=11.7 Hz, 1H), 3.99-3.89 (m, 4H), 3.85 (d, J=11.3 Hz, 1H), 3.74 (dd, J=11.9, 4.5 Hz, 1H), 3.60-3.51 (m, 1H), 3.33-3.23 (m, 2H), 1.72 (d, J=6.2 Hz, 6H), 1.44 (d, J=6.3 Hz, 3H); $^{13}$C NMR (101 MHz, CDCl$_3$) δ 170.85, 155.71, 142.26, 142.02, 136.10, 128.57, 128.25, 128.11, 112.33, 112.02, 84.95, 83.01, 77.63, 75.87, 74.89, 74.66, 72.86, 67.14, 54.26, 19.81, 19.66, 18.63; ESIMS m/z 470.3 ([M+Na]$^+$).

Compound 127 was prepared in a similar manner as described in example 1, step 4 starting from (S)-methyl 2-(benzyloxycarbonylamino)-3-((2S,3S,4S)-5-hydroxy-3,4-bis(2-methylallyloxy)pentan-2-yloxy)propanoate.

Compound 157 was prepared in a similar manner as described in example 1, steps 3 and 4 starting from 1,6-dideoxy-3,4-O-isopropylidene-D-mannitol. 1,6-Dideoxy-3,4-O-isopropylidene-D-mannitol was made using the procedures disclosed in *Heterocycles*, 2007, 74, 983-989.

Example 1

Step 5: Preparation of (3S,7S,8S,9S)-3-amino-7,8-diisobutoxy-9-methyl-1,5-dioxonan-2-one (compound 160)

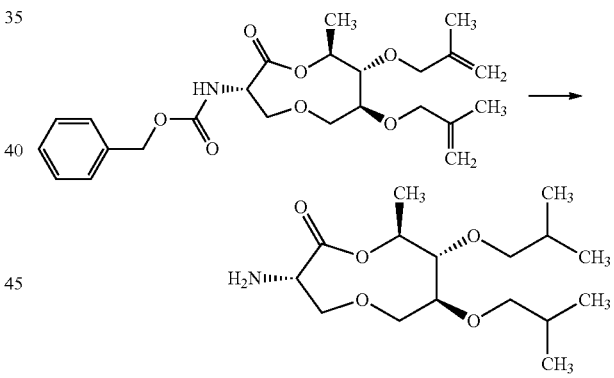

Benzyl (3S,7S,8S,9S)-9-methyl-7,8-bis(2-methylallyloxy)-2-oxo-1,5-dioxonan-3-ylcarbamate (265 mg, 0.592 mmol) was dissolved in EtOAc (8 mL) in a 50 mL high pressure reactor with a stir bar and Pd/C (5%, 30 mg) was added. The reactor was sealed and purged with H$_2$ (4×), then charged to ~600 pounds per square inch (psi) with H$_2$. The reactor was warmed to 50° C. and stirred at 50° C. for 12 h. The reaction mixture was filtered through a pad of Celite® and the filtrate was concentrated to afford the title compound as a white solid (170 mg, 91%): mp 144-146° C.; $^1$H NMR (400 MHz, CDCl$_3$) δ 4.82 (dq, J=8.5, 6.3 Hz, 1H), 3.97-3.84 (m, 1H), 3.78 (t, J=7.0 Hz, 1H), 3.72-3.53 (m, 3H), 3.44-3.29 (m, 2H), 3.29-3.12 (m, 4H), 1.82 (ttd, J=13.4, 6.5, 2.5 Hz, 2H), 1.42 (d, J=6.3 Hz, 3H), 0.99-0.78 (m, 12H); $^{13}$C NMR (101 MHz, CDCl$_3$) δ 175.66, 84.70, 83.85, 80.55, 77.57, 74.90, 72.72, 72.70, 29.11, 28.87, 19.58, 19.48, 19.45, 19.38, 18.61; ESIMS m/z 318.8 ([M+H]$^+$).

Compound 132 and 162 were prepared in a similar manner as described in example 1, step 5.

Example 1

Step 6: Preparation of N-((3S,7S,8S,9S)-7,8-diisobutoxy-9-methyl-2-oxo-1,5-dioxonan-3-yl)-3-hydroxy-4-methoxypicolinamide (compound 1)

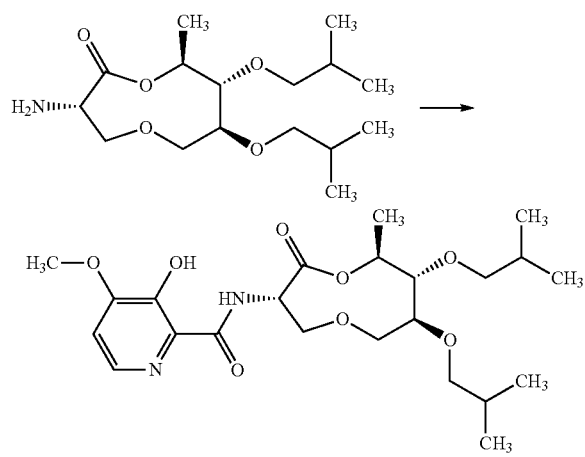

To a mixture of (3S,7S,8S,9S)-3-amino-7,8-diisobutoxy-9-methyl-1,5-dioxonan-2-one (170 mg, 0.536 mmol), 3-hydroxy-4-methoxypicolinic acid (136 mg, 0.803 mmol) and HATU (336 mg, 0.857 mmol) in a vial was added CH$_2$Cl$_2$ (3 mL), followed by 4-methylmorpholine (0.353 mL, 3.21 mmol), and the resulting suspension was stirred at room temperature for 3 h. The resulting orange solution was directly purified by flash chromatography (SiO$_2$) to afford the title compound as a white solid (176 mg, 70%): $^1$H NMR (400 MHz, CDCl$_3$) δ 11.95 (s, 1H), 8.68 (d, J=8.0 Hz, 1H), 8.00 (d, J=5.2 Hz, 1H), 6.87 (d, J=5.2 Hz, 1H), 5.10-5.00 (m, 1H), 4.97 (dt, J=12.6, 6.3 Hz, 1H), 4.10-4.01 (m, 1H), 3.94 (s, 3H), 3.87-3.78 (m, 2H), 3.71 (dd, J=8.4, 6.1 Hz, 1H), 3.66-3.57 (m, 1H), 3.38-3.28 (m, 2H), 3.28-3.17 (m, 3H), 1.90-1.76 (m, 2H), 1.45 (t, J=5.8 Hz, 3H), 0.98-0.88 (m, 12H); $^{13}$C NMR (101 MHz, CDCl$_3$) δ 170.33, 168.95, 155.38, 148.76, 140.66, 130.23, 109.58, 84.84, 83.75, 80.60, 77.74, 75.32, 73.97, 73.23, 56.11, 52.19, 29.13, 28.89, 19.60, 19.48, 19.47, 19.39, 18.66; ESIMS m/z 469.4 ([M+H]$^+$).

Compounds 4 and 27 were prepared in a similar manner as described in example 1, step 6.

Example 2

Step 1: Preparation of (S)-methyl 2-(benzyloxycarbonylamino)-3-((2S,3S)-2,3-bis(benzyloxy)-4-hydroxybutoxy)propanoate

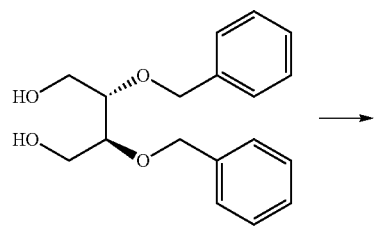

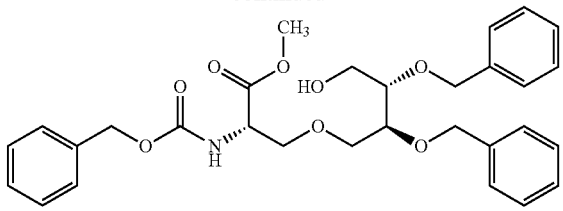

To a solution of (2S,3S)-2,3-bis(benzyloxy)butane-1,4-diol (283 mg, 0.935 mmol), prepared as disclosed in *Journal of Organic Chemistry* 1991, 56(3), 1321-1322, and (S)-1-benzyl 2-methyl aziridine-1,2-dicarboxylate (110 mg, 0.468 mmol) in CH$_2$Cl$_2$ (1.5 mL) at −78° C. was added BF$_3$-OEt$_2$ (10 μL, 0.081 mmol), and the reaction mixture was stirred at −78° C. for 1 h, slowly warmed to 0° C., and then stirred at 0° C. for 3 h. The reaction mixture was directly purified by flash chromatography (SiO$_2$) to afford the title compound as a colorless oil (208 mg, 83%): $^1$H NMR (400 MHz, CDCl$_3$) δ 7.45-7.20 (m, 16H), 5.70 (d, J=8.5 Hz, 1H), 4.70-4.54 (m, 6H), 4.53-4.46 (m, 1H), 3.93 (dd, J=9.5, 3.2 Hz, 1H), 3.80-3.53 (m, 9H), 2.09-1.96 (m, 1H); $^{13}$C NMR (101 MHz, CDCl$_3$) δ 170.72, 156.04, 138.16, 138.08, 136.24, 128.54, 128.49, 128.47, 128.20, 128.13, 127.99, 127.91, 127.89, 127.86, 79.03, 78.10, 73.09, 72.88, 71.40, 71.08, 67.08, 61.40, 54.46, 52.60; ESIMS m/z 538.4 ([M+H]$^+$).

Example 2

Step 2: Preparation of (S)-methyl 2-(benzyloxycarbonylamino)-3-((2S,3S)-2,3-bis(benzyloxy)-4-hydroxybutoxy)propanoate (compound 128)

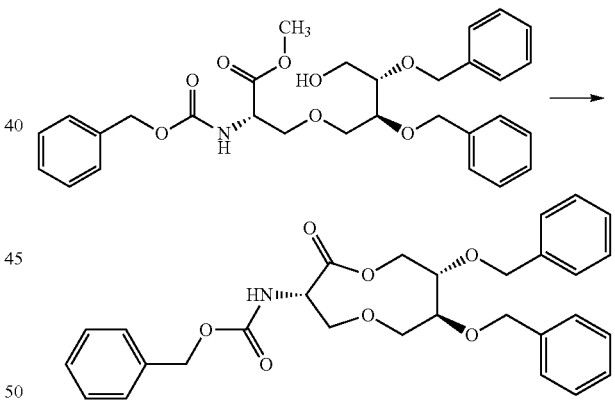

Compound 128 was prepared in a similar manner as described in Example 1, Step 4 starting from (S)-methyl 2-(benzyloxycarbonylamino)-3-((2S,3S)-2,3-bis(benzyloxy)-4-hydroxybutoxy)propanoate: $^1$H NMR (400 MHz, CDCl$_3$) δ 7.37-7.24 (m, 15H), 5.54 (d, J=8.0 Hz, 1H), 5.11 (s, 2H), 4.80-4.61 (m, 6H), 4.09 (dd, J=11.5, 3.9 Hz, 1H), 3.99 (dd, J=11.5, 6.7 Hz, 1H), 3.78 (dt, J=8.4, 3.8 Hz, 2H), 3.72-3.63 (m, 1H), 3.56 (dd, J=11.5, 6.0 Hz, 1H), 3.49-3.39 (m, 1H); $^{13}$C NMR (101 MHz, CDCl$_3$) δ 171.66, 155.61, 138.01, 137.98, 136.10, 128.59, 128.50, 128.45, 128.28, 128.15, 127.91, 127.89, 127.82, 81.63, 79.43, 73.96, 73.80, 73.26, 72.96, 67.17, 63.80, 54.10; ESIMS m/z 506.3 ([M+H]$^+$).

Compound 186 was prepared in the same manner as described in Example 2, Step 2 using (S)-methyl 2-(((benzyloxy)carbonyl)amino)-3-((2S,3S)-4-hydroxy-2,3-bis((2-methylallyl)oxy)butoxy)propanoate as starting material.

Compound 187 was prepared in two steps from (2S,3S)-2,3-bis((2-methylallyl)oxy)butane-1,4-diol: Step 1 was performed in a similar manner as described in Example 2, Step 1 but using (R)-1-tert-butyl 2-methyl aziridine-1,2-dicarboxylate instead of the corresponding (S)-enantiomer; Step 2 was performed in the same manner as described in Example 2, Step 2.

Example 2

Step 3: Preparation of (3S,7S,8S)-3-amino-7,8-bis(benzyloxy)-1,5-dioxonan-2-one (compound 129)

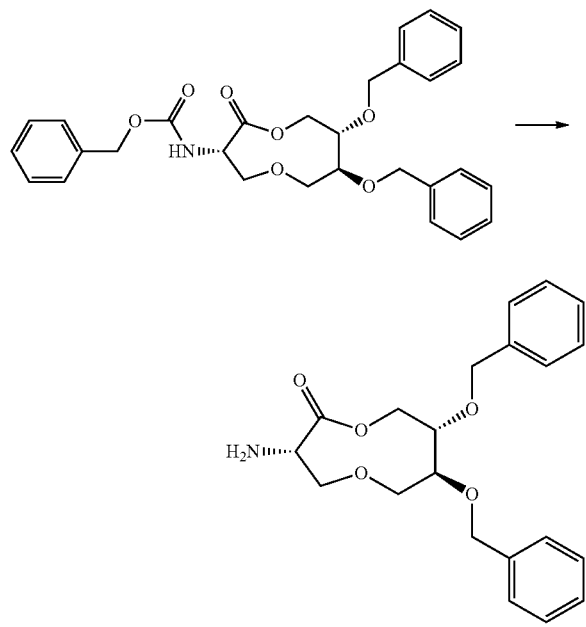

Benzyl (3S,7S,8S)-7,8-bis(benzyloxy)-2-oxo-1,5-dioxonan-3-ylcarbamate (71 mg, 0.140 mmol) was dissolved in MeOH (1 mL) and EtOAc (1 mL) and 2.0 molar (M) ammonia in ethanol (EtOH) (35 µL, 0.070 mmol) and 5% Pd/C (10 mass wt. %) were added. The air was removed by two cycles of evacuating the flask under vacuum and backfilling with $H_2$. The reaction mixture was placed under an atmosphere of $H_2$ (balloon, ~1 atmosphere) and stirred at room temperature for 2 h. The reaction mixture was filtered through Celite®, and the filtrate was concentrated to afford the title compound as an off-white solid (47 mg, 91%): $^1$H NMR (400 MHz, CDCl$_3$) δ 7.79-6.92 (m, 10H), 4.79-4.53 (m, 6H), 4.14 (dd, J=11.4, 3.6 Hz, 1H), 3.97 (dd, J=11.4, 7.2 Hz, 1H), 3.87-3.74 (m, 3H), 3.73-3.56 (m, 2H), 3.45 (ddd, J=7.8, 6.0, 1.8 Hz, 1H), 3.25 (dd, J=11.5, 7.9 Hz, 1H); $^{13}$C NMR (101 MHz, CDCl$_3$) δ 175.95, 138.09, 138.04, 128.46, 128.40, 128.00, 127.88, 127.85, 127.74, 81.49, 79.46, 75.01, 73.66, 72.75, 71.53, 63.47, 54.33; ESIMS m/z 372.9 ([M+H]$^+$).

Compound 170 was prepared from compound 186 in a similar manner as described in Example 2, Step 3 but in the absence of ammonia (see also Example 1, Step 5).

Step 4: Preparation of N-((3S,7S,8S)-7,8-bis(benzyloxy)-2-oxo-1,5-dioxonan-3-yl)-3-hydroxy-4-methoxypicolinamide (compound 5)

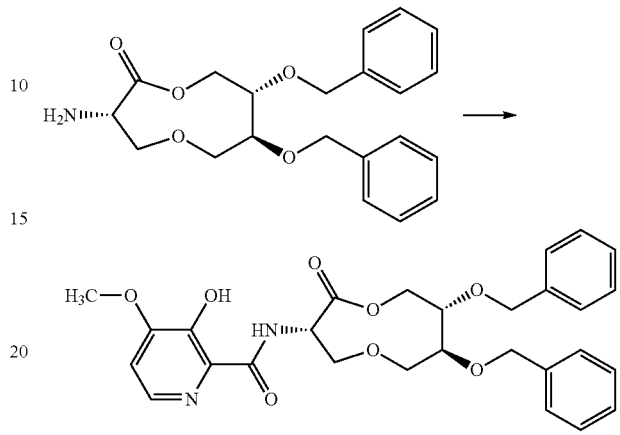

To a mixture of (3S,7S,8S)-3-amino-7,8-bis(benzyloxy)-1,5-dioxonan-2-one (47 mg, 0.127 mmol), 3-hydroxy-4-methoxypicolinic acid (32.1 mg, 0.190 mmol) and HATU (80 mg, 0.202 mmol) in a vial were added CH$_2$Cl$_2$ (1.5 mL), followed by 4-methylmorpholine (0.083 mL, 0.759 mmol), and the resulting suspension was stirred at room temperature for 12 h. The resulting orange solution was directly purified by flash chromatography (SiO$_2$) to afford the title compound as a white foam (32 mg, 48%): $^1$H NMR (400 MHz, CDCl$_3$) δ 11.90 (d, J=0.6 Hz, 1H), 8.61 (d, J=8.2 Hz, 1H), 8.49 (d, J=5.2 Hz, 1H), 7.43-7.24 (m, 11H), 6.86 (d, J=5.2 Hz, 1H), 5.03 (ddd, J=8.2, 6.8, 6.0 Hz, 1H), 4.80-4.62 (m, 5H), 4.21-4.07 (m, 2H), 3.93 (s, 3H), 3.85 (s, 1H), 3.79-3.65 (m, 2H), 3.55-3.47 (m, 1H); $^{13}$C NMR (101 MHz, CDCl$_3$) δ 170.83, 168.92, 155.37, 148.76, 140.66, 137.97, 137.94, 130.17, 128.48, 128.43, 127.91, 127.89, 127.87, 127.81, 109.61, 81.52, 79.29, 73.80, 73.44, 73.24, 72.97, 63.91, 56.10, 52.25; ESIMS m/z 524.1 ([M+H]$^+$).

Compound 8 was prepared in the same manner as described in Example 2, Step 4 using compound 170 as starting material.

Example 3

Step 1: Preparation of (2R,3R)-dimethyl 2,3-bis((2-methylallyl)oxy)succinate

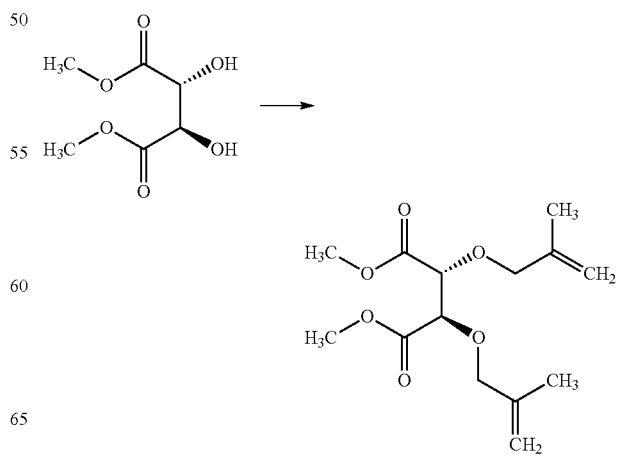

To a cooled (−10° C.) suspension of NaH (60% dispersion in mineral oil, 6.73 g, 168 mmol) in DMF (240 mL) was added dropwise a solution of (+)-dimethyl L-tartrate (15.0 g, 84.0 mmol) in DMF (40 mL) over a period of 30 min. After the addition was complete, the mixture was stirred for another 30 min at −10° C., and then 3-bromo-2-methylpropene (25.5 mL, 253 mmol) was added while maintaining the reaction temperature below 0° C. The mixture was stirred for 1.5 h at −10° C., quenched with H$_2$O and saturated aqueous sodium chloride (NaCl, brine), and extracted with EtOAc. The phases were separated and the aqueous phase was further extracted with EtOAc. The combined organic phases were washed with brine, dried over magnesium sulfate (MgSO$_4$), filtered, and concentrated to yield a yellow oil. Purification by flash chromatography (SiO$_2$, hexanes/EtOAc gradient) yielded the title compound as a colorless oil (17.05 g, 71%): IR (neat) 2953, 1758, 1435, 1270, 1203, 1106 cm$^{-1}$; $^1$H NMR (400 MHz, CDCl$_3$) δ 4.92-4.86 (m, 4H), 4.37 (s, 2H), 4.19 (d, J=12.3 Hz, 2H), 3.82 (d, J=12.3 Hz, 2H), 3.77 (s, 6H), 1.68 (s, 6H); $^{13}$C NMR (101 MHz, CDCl$_3$) δ 169.84, 141.04, 114.10, 78.60, 75.66, 52.22, 19.52; HRMS-ESI (m/z) [M]$^+$ calcd for C$_{14}$H$_{22}$O$_6$, 286.1416; found, 286.1417.

Example 3

Step 2: Preparation of (2S,3S)-2,3-bis((2-methylallyl)oxy)butane-1,4-diol

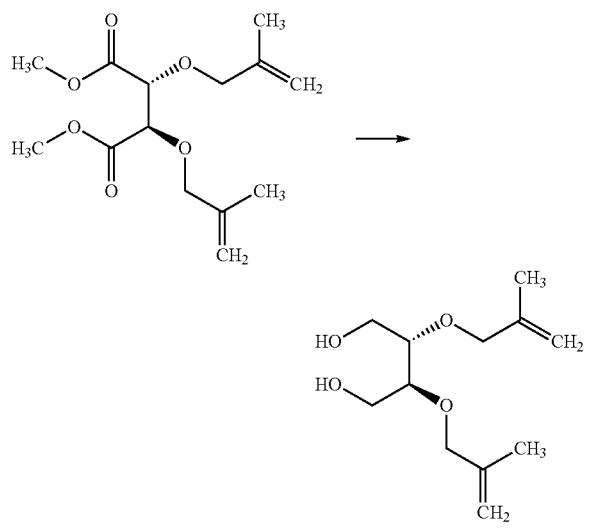

To a solution of (2R,3R)-dimethyl 2,3-bis((2-methylallyl)oxy)succinate (14.7 g, 51.3 mmol) in THF (130 mL) at 0° C. was added slowly a 1.0 M solution of LAH in THF (257 mL, 257 mmol). The mixture was warmed to room temperature and stirred for 2 h, carefully quenched by the addition of EtOAc at 0° C., and then treated with a saturated aqueous solution of potassium sodium tartrate (Rochelle's salt). The phases were separated and the aqueous layer was extracted with EtOAc. The combined organic phases were washed with brine, dried over Na$_2$SO$_4$, filtered, and concentrated. The residue was purified by flash chromatography (SiO$_2$, hexanes/EtOAc gradient) to yield the title compound as a colorless oil (10.87 g, 92%): IR (neat) 3388, 2918, 2880, 1656, 1452, 1046 cm$^{-1}$; $^1$H NMR (400 MHz, CDCl$_3$) δ 4.98 (s, 2H), 4.90 (s, 2H), 4.03 (s, 4H), 3.81 (d, J=11.7 Hz, 2H), 3.71 (d, J=11.9 Hz, 2H), 3.64-3.59 (m, 2H), 2.57-2.47 (m, 2H), 1.75 (s, 6H); $^{13}$C NMR (101 MHz, CDCl$_3$) δ 142.16, 112.85, 78.75, 74.52, 60.85, 19.68; HRMS-ESI (m/z) [M]$^+$ calcd for C$_{12}$H$_{22}$O$_4$, 230.1518; found, 230.1519.

Example 3

Step 3: Preparation of (S)-methyl 2-(((benzyloxy)carbonyl)amino)-3-((2S,3S)-4-hydroxy-2,3-bis((2-methylallyl)oxy)butoxy)propanoate

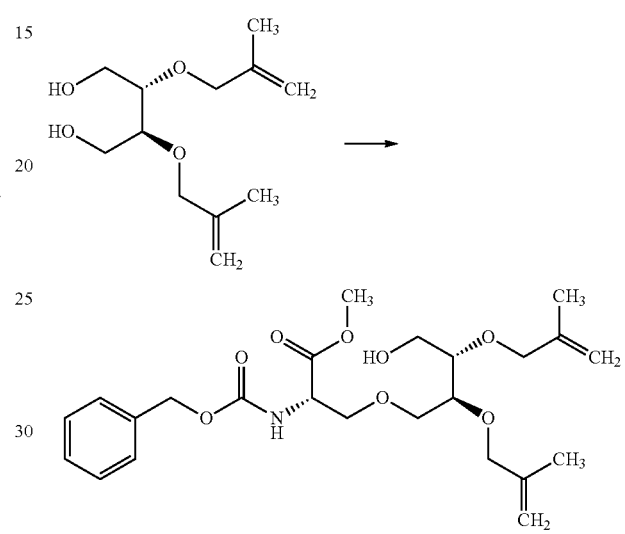

The title compound was prepared in the same manner as described in Example 2, Step 1 to give a colorless oil (6.14 g, 62%): $^1$H NMR (400 MHz, CDCl$_3$) δ 7.34 (dt, J=12.4, 4.7 Hz, 5H), 5.73 (d, J=8.5 Hz, 1H), 5.13 (s, 2H), 4.96 (dd, J=2.3, 1.0 Hz, 2H), 4.88 (d, J=8.5 Hz, 2H), 4.49 (dt, J=8.6, 3.1 Hz, 1H), 4.04-3.91 (m, 5H), 3.75 (s, 3H), 3.73-3.46 (m, 7H), 1.73 (d, J=6.3 Hz, 6H); $^{13}$C NMR (101 MHz, CDCl$_3$) δ 170.69, 156.01, 142.12, 136.23, 128.51, 128.16, 128.07, 112.58, 78.57, 78.19, 74.92, 74.65, 71.41, 70.89, 67.04, 61.38, 54.44, 52.58, 19.55; ESIMS m/z 488.3 ([M+Na]$^+$).

Example 3

Step 4: Preparation of (S)-methyl 2-(((benzyloxy)carbonyl)amino)-3-((2S,3R)-2,3-bis((2-methylallyl)oxy)-4-oxobutoxy)propanoate

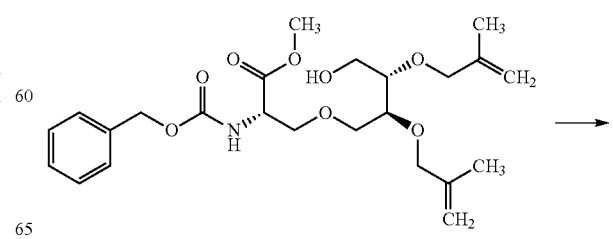

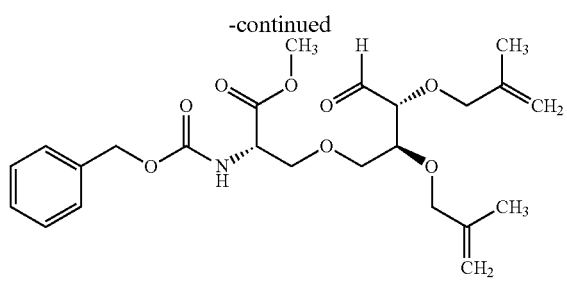

To a solution of (S)-methyl 2-(((benzyloxy)carbonyl)amino)-3-((2S,3S)-4-hydroxy-2,3-bis((2-methylallyl)oxy)butoxy)propanoate (3.96 g, 8.51 mmol) in CH$_2$Cl$_2$/DMSO (56.7 mL, ratio: 5/1) at 0° C. was added TEA (5.93 ml, 42.5 mmol) followed by sulfur trioxide pyridine complex (4.06 g, 25.5 mmol) and the reaction was slowly warmed to room temperature and stirred for 2 h. The reaction mixture was quenched with saturated aqueous NH$_4$Cl and extracted with EtOAc. The combined organic phases were washed with H$_2$O and brine, dried over MgSO$_4$, filtered, and the filtrate was concentrated. The crude residue was purified by flash chromatography (SiO$_2$, hexanes/EtOAc gradient) to provide the title compound as a colorless oil (3.26 g, 83% yield): IR (neat) 3360, 2951, 1721, 1512, 1209, 1053 cm$^{-1}$; $^1$H NMR (400 MHz, CDCl$_3$) δ 9.69 (d, J=1.0 Hz, 1H), 7.41-7.27 (m, 5H), 5.65 (d, J=8.7 Hz, 1H), 5.17-5.08 (m, 2H), 4.96-4.92 (m, 2H), 4.90 (d, J=14.8 Hz, 2H), 4.47 (dt, J=8.7, 2.9 Hz, 1H), 4.10 (d, J=12.4 Hz, 1H), 3.97-3.88 (m, 4H), 3.85-3.78 (m, 2H), 3.75 (s, 3H), 3.65 (dd, J=9.5, 3.2 Hz, 1H), 3.62 (d, J=4.5 Hz, 2H), 1.74 (s, 3H), 1.69 (s, 3H); $^{13}$C NMR (101 MHz, CDCl$_3$) δ 202.61, 170.65, 156.16, 141.73, 141.27, 136.42, 128.63, 128.26, 128.17, 113.83, 113.23, 82.49, 78.16, 75.45, 75.01, 71.55, 69.39, 67.16, 54.49, 52.70, 19.62, 19.55; ESIMS m/z 486.2 ([M+Na]$^+$).

Example 3

Step 5: Preparation of (S)-methyl 2-(((benzyloxy)carbonyl)amino)-3-(((2S,3S,4S)-4-hydroxy-2,3-bis((2-methylallyl)oxy)hexyl)oxy)propanoate and (S)-methyl 2-(((benzyloxy)carbonyl)amino)-3-(((2S,3S,4R)-4-hydroxy-2,3-bis((2-methylallyl)oxy)hexyl)oxy)propanoate

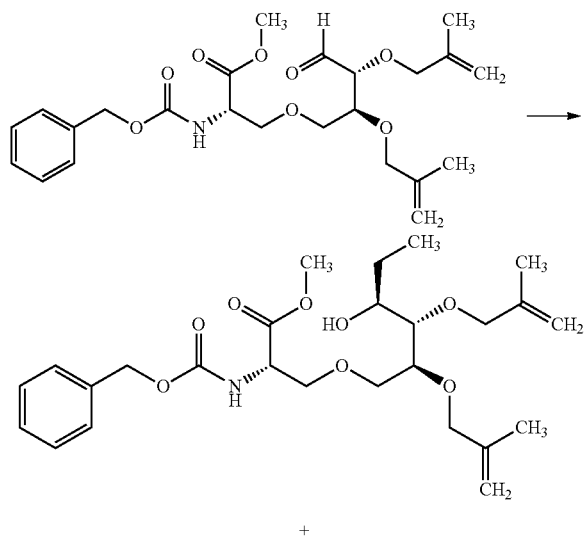

A 1.0 M solution of ethylmagnesium bromide in tert-butyl methyl ether (1.804 ml, 1.804 mmol) was added slowly to a solution of (S)-methyl 2-(((benzyloxy)carbonyl)amino)-3-(((2S,3R)-2,3-bis((2-methylallyl)oxy)-4-oxobutoxy)propanoate (0.400 g, 0.863 mmol) in THF (6.0 ml) at −78° C. and the reaction was stirred for 30 min at −78° C., then warmed to −40° C. and stirred for 2 h at −40° C., and warmed to 0° C. over a 2 h period. The reaction was quenched at 0° C. with saturated aqueous NH$_4$Cl and extracted with EtOAc. The combined organic phases were washed with brine, dried over MgSO$_4$, filtered, and concentrated. The crude residue was purified by flash chromatography on (SiO$_2$, hexanes/EtOAc gradient) to provide the title compounds as colorless oils.

(S)-methyl 2-(((benzyloxy)carbonyl)amino)-3-(((2S,3S,4S)-4-hydroxy-2,3-bis((2-methylallyl)oxy)hexyl)oxy)propanoate (35.0 mg, 8%): IR (neat) 3443, 2919, 1272, 1509, 1454, 1209, 1084 cm$^{-1}$; $^1$H NMR (400 MHz, CDCl$_3$) δ 7.39-7.23 (m, 5H), 5.76 (d, J=8.7 Hz, 1H), 5.11 (s, 2H), 4.97-4.91 (m, 2H), 4.86 (s, 2H), 4.50 (dt, J=8.3, 2.9 Hz, 1H), 4.05-3.88 (m, 4H), 3.77-3.57 (m, 5H), 3.73 (s, 3H), 3.27 (dd, J=7.1, 3.6 Hz, 1H), 3.14 (d, J=3.9 Hz, 1H), 1.77-1.60 (m, 8H), 1.49-1.36 (m, 1H), 0.97 (t, J=7.4 Hz, 3H); $^{13}$C NMR (101 MHz, CDCl$_3$) δ 170.72, 156.09, 142.05, 141.86, 136.30, 128.54, 128.19, 128.13, 112.82, 112.70, 79.63, 78.22, 75.23, 74.79, 72.79, 71.40, 70.68, 67.09, 54.50, 52.59, 26.71, 19.72, 19.61, 10.0; ESIMS m/z 494.3 ([M+H]$^+$).

(S)-methyl 2-(((benzyloxy)carbonyl)amino)-3-(((2S,3S,4R)-4-hydroxy-2,3-bis((2-methylallyl)oxy)hexyl)oxy)propanoate (150 mg, 35%): IR (neat) 3355, 2936, 1719, 1513, 1455, 1210, 1056 cm$^{-1}$; $^1$H NMR (400 MHz, CDCl$_3$) δ 7.40-7.26 (m, 5H), 5.74 (d, J=8.7 Hz, 1H), 5.12 (s, 2H), 4.97-4.92 (m, 2H), 4.87 (s, 2H), 4.51 (dt, J=8.7, 3.0 Hz, 1H), 4.05-3.89 (m, 4H), 3.77-3.57 (m, 5H), 3.74 (s, 3H), 3.28 (dd, J=7.1, 3.7 Hz, 1H), 3.14 (d, J=3.6 Hz, 1H), 1.73 (s, 3H), 1.72 (s, 3H), 1.72-1.58 (m, 2H), 1.48-1.35 (m, 1H), 0.97 (t, J=7.4 Hz, 3H); $^{13}$C NMR (101 MHz, CDCl$_3$) δ 170.80, 156.12, 142.39, 142.27, 136.36, 128.56, 128.20, 128.11, 112.51, 112.34, 80.58, 78.66, 76.51, 74.98, 72.04, 71.42, 71.39, 67.07, 54.57, 52.60, 27.65, 19.77, 19.63, 10.42; ESIMS m/z 516.3 ([M+Na]$^+$).

Example 3

Step 6: Preparation of benzyl ((3S,7S,8S,9S)-9-ethyl-7,8-bis((2-methylallyl)oxy)-2-oxo-1,5-dioxonan-3-yl)carbamate (compound 88)

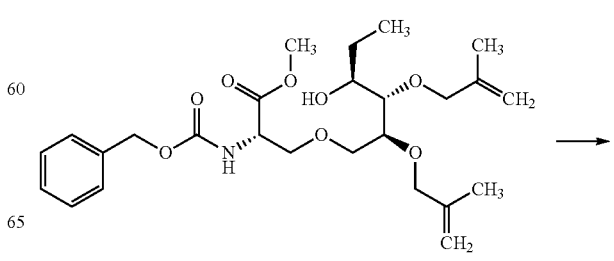

-continued

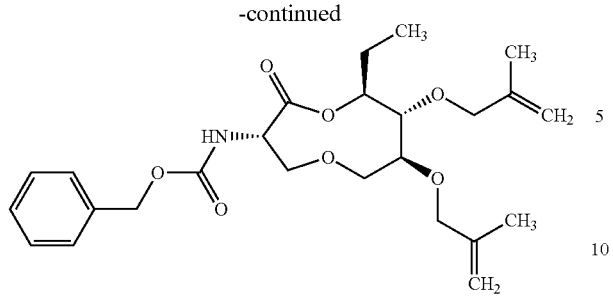

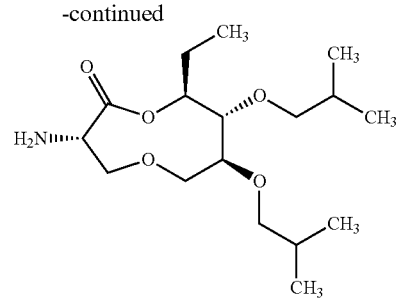

Compound 88 was prepared in a similar manner as described in Example 1, Step 4 using $CH_2Cl_2$ instead of toluene as the reaction solvent in the cyclization step, to afford the title compound as a white solid (82.1 mg, 45%): mp 108-110° C.; IR (neat) 3288, 2925, 2879, 1752, 1689, 1555, 1330, 1197 cm$^{-1}$; $^1$H NMR (400 MHz, CDCl$_3$) δ 7.41-7.27 (m, 5H), 5.60 (d, J=7.5 Hz, 1H), 5.10 (s, 2H), 4.98-4.88 (m, 3H), 4.88-4.81 (m, 2H) 4.74-4.64 (m, 1H), 4.33 (d, J=11.8 Hz, 1H), 3.96 (s, 2H), 3.95-3.80 (m, 4H), 3.53 (dd, J=11.9, 6.0 Hz, 1H), 3.38-3.25 (m, 2H), 2.07-1.95 (m, 1H), 1.72 (d, J=4.7 Hz, 6H), 1.72-1.61 (m, 1H), 0.96 (t, J=7.4 Hz, 3H); $^{13}$C NMR (101 MHz, CDCl$_3$) δ 171.00, 155.85, 142.43, 142.12, 136.25, 128.69, 128.36, 128.23, 112.41, 112.00, 83.44, 83.36, 75.92, 74.66, 67.24, 54.84, 25.32, 19.91, 19.78, 9.61; ESIMS m/z 462.3 ([M+H]$^+$).

Compound 89 was prepared in a two step sequence from (S)-methyl 2-(((benzyloxy)carbonyl)amino)-3-((2S,3R)-2,3-bis((2-methylallyl)oxy)-4-oxobutoxy)propanoate, in a similar manner as described in Example 3, Step 5 using a 2.9 M solution of isopropylmagnesium bromide in 2-methyltetrahydrofuran instead of a 1.0 M solution of ethylmagnesium bromide in tert-butyl methyl ether, followed by a saponification-cyclization as described in Example 3, Step 6.

Compound 155 was prepared in the same manner as described in Example 3, Steps 4 to 6, starting from (S)-methyl 2-(benzyloxycarbonylamino)-3-((2S,3S,4S)-5-hydroxy-3,4-bis(2-methylallyloxy)pentan-2-yloxy)propanoate (see Example 1, Step 3).

Compound 156 was prepared in the same manner as described in Example 3, Steps 4 to 6, starting from (S)-methyl 3-(((2S,3S,4S)-3,4-bis(benzyloxy)-5-hydroxypentan-2-yl)oxy)-2-((tert-butoxycarbonyl)amino)propanoate (see Example 8, Step 2).

Example 3

Step 7: Preparation of (3S,7S,8S,9S)-3-amino-9-ethyl-7,8-diisobutoxy-1,5-dioxonan-2-one (compound 121)

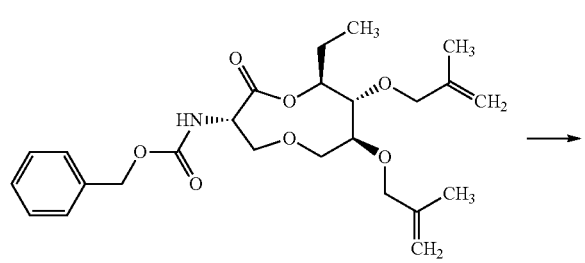

Compound 121 was prepared in the same manner as described in Example 1, Step 5 to give the title compound as a colorless oil (71.2 mg, 93%): IR (neat) 3364, 2954, 2873, 1742, 1467, 1183, 1094 cm$^{-1}$; $^1$H NMR (400 MHz, CDCl$_3$) δ 4.79 (td, J=8.8, 3.1 Hz, 1H), 3.92 (dd, J=11.7, 6.8 Hz, 1H), 3.78 (t, J=6.4 Hz, 1H), 3.68 (dd, J=8.4, 6.1 Hz, 1H), 3.62 (d, J=3.7 Hz, 2H), 3.45 (dd, J=11.7, 6.0 Hz, 1H), 3.36-3.13 (m, 5H), 2.08-1.95 (m, 1H), 1.88-1.74 (m, 2H), 1.72-1.58 (m, 3H), 0.97 (t, J=7.4 Hz, 3H), 0.92-0.86 (m, 12H); HRMS-ESI (m/z) [M]$^+$ calcd for $C_{17}H_{33}NO_5$, 331.2359; found, 331.2350.

Compound 161 was prepared in a similar manner as described in Example 3, Step 7.

Example 3

Step 8: Preparation of N-((3S,7S,8S,9S)-9-ethyl-7,8-diisobutoxy-2-oxo-1,5-dioxonan-3-yl)-3-hydroxy-4-methoxypicolinamide (compound 21)

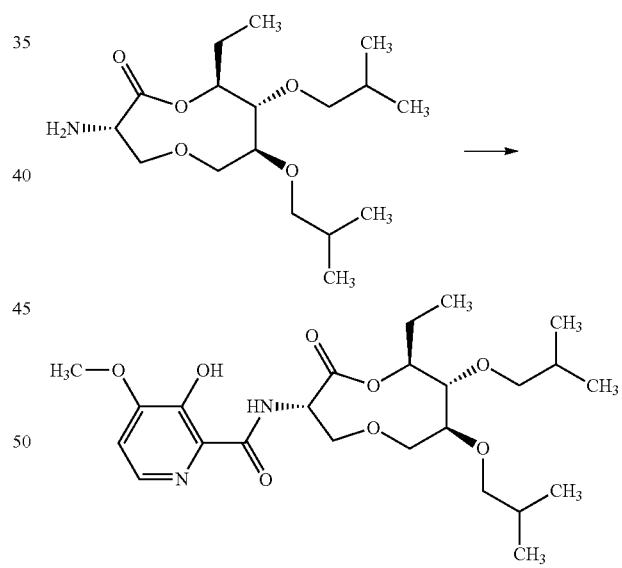

Compound 21 was prepared in the same manner as described in Example 1, Step 6 to give the title compound as a white solid (60.50 mg, 62%): mp 119-121° C.; $^1$H NMR (400 MHz, CDCl$_3$) δ 11.95 (s, 1H), 8.73 (d, J=8.0 Hz, 1H), 8.00 (d, J=5.2 Hz, 1H), 6.86 (d, J=5.2 Hz, 1H), 5.03 (ddd, J=8.0, 6.3, 4.2 Hz, 1H), 4.93 (td, J=8.8, 2.9 Hz, 1H), 4.04 (dd, J=12.0, 6.3 Hz, 1H), 3.94 (s, 3H), 3.89 (dd, J=12.0, 4.0 Hz, 1H), 3.85 (d, J=12.0 Hz, 1H), 3.71 (dd, J=8.4, 6.2 Hz, 1H), 3.58 (dd, J=11.6, 6.0 Hz, 1H), 3.37-3.14 (m, 5H), 2.03 (dqd, J=14.9, 7.5, 2.9 Hz, 1H), 1.81 (dp, J=13.2, 6.6 Hz, 2H), 1.72-1.59 (m, 1H), 0.97 (t, J=7.4 Hz, 3H), 0.93-0.86 (m, 12H); $^{13}$C NMR (151 MHz, CDCl$_3$) δ 170.53, 169.10, 155.49, 148.90, 140.81, 130.47, 109.71, 84.19, 83.34, 80.50, 77.84, 77.76, 76.80, 74.99, 56.23, 52.79, 29.26, 29.01, 25.30, 19.72, 19.62, 19.60, 19.53, 9.64; HRMS-ESI (m/z) [M]+ calcd for $C_{24}H_{38}N_2O_8$, 482.2628; found, 482.2647.

Compounds 25 and 26 were prepared in a similar manner as described in Example 3, Step 8.

Example 4

Step 1: Preparation of benzyl ((3S,7S,8S,9R)-9-ethyl-7,8-bis((2-methylallyl)oxy)-2-oxo-1,5-dioxonan-3-yl)carbamate (compound 90) and benzyl ((3R,7S,8S,9R)-9-ethyl-7,8-bis((2-methylallyl)oxy)-2-oxo-1,5-dioxonan-3-yl)carbamate (compound 91)

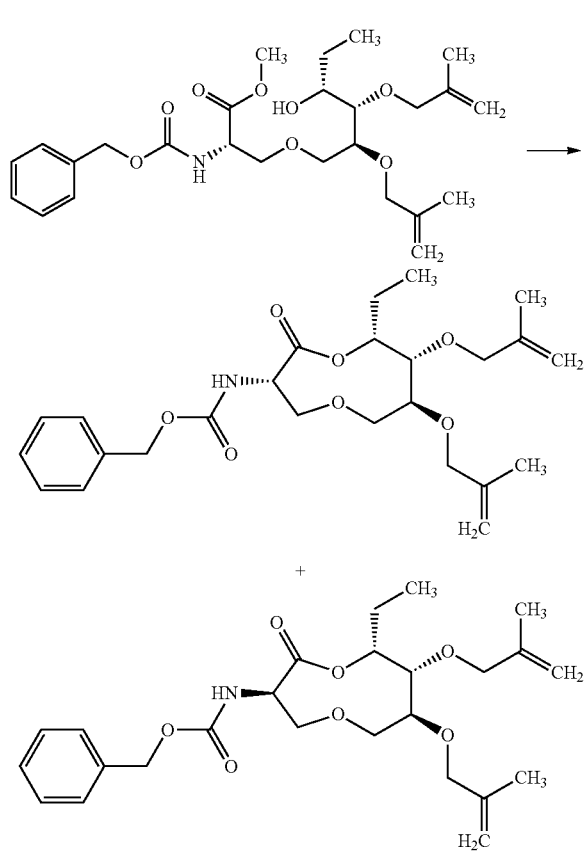

Compounds 90 and 91 were prepared in the same manner as described in Example 3, Step 6 to give the title compounds as pale yellow oils.

Benzyl ((3R,7S,8S,9R)-9-ethyl-7,8-bis((2-methylallyl)oxy)-2-oxo-1,5-dioxonan-3-yl)carbamate (compound 91) (32.0 mg, 33%): IR (neat) 3320, 2969, 2935, 1754, 1722, 1506, 1455, 1200 cm$^{-1}$; $^1$H NMR (400 MHz, CDCl$_3$) δ 7.41-7.26 (m, 5H), 5.74 (d, J=7.5 Hz, 1H), 5.10 (s, 2H), 5.10-5.03 (m, 1H), 4.96 (dd, J=7.9, 0.8 Hz, 2H), 4.89 (d, J=7.8 Hz, 2H), 4.72 (t, J=6.0 Hz, 1H), 4.67-4.63 (m, 1H), 4.08-3.79 (m, 7H), 3.78-3.67 (m, 2H), 3.62 (d, J=12.1 Hz, 1H), 3.45 (ddd, J=6.9, 3.9, 1.4 Hz, 1H), 1.74 (s, 3H), 1.72 (s, 3H), 1.00 (t, J=7.4 Hz, 3H); $^{13}$C NMR (101 MHz, CDCl$_3$) δ 170.76, 155.95, 142.30, 142.06, 136.40, 128.66, 128.27, 128.15, 113.07, 112.78, 78.09, 76.25, 75.88, 73.94, 71.73, 67.09, 55.51, 22.72, 19.76, 19.67, 10.73; ESIMS m/z 462.2 ([M+H]+).

Benzyl ((3R,7S,8S,9R)-9-ethyl-7,8-bis((2-methylallyl)oxy)-2-oxo-1,5-dioxonan-3-yl)carbamate (compound 91) (34.8 mg, 36%): $^1$H NMR (400 MHz, CDCl$_3$) 7.42-7.28 (m, 5H), 5.52-5.37 (m, 1H), 5.11 (s, 2H), 5.01 (ddd, J=9.2, 4.8, 2.8 Hz, 1H), 4.98-4.93 (m, 2H), 4.88 (s, 2H), 4.53 (bs, 1H), 4.16-4.09 (m, 1H), 4.04 (d, J=21.7 Hz, 1H), 4.01 (d, J=22.0 Hz, 1H), 3.93 (dd, J=12.2, 3.3 HZ, 2H), 3.87 (dd, J=11.7, 4.1 Hz, 1H) 3.76 (dd, J=11.8, 1.7 Hz, 1H), 3.70 (dd, J=6.4, 2.7 Hz, 1H), 3.55-3.45 (m, 2H), 1.86-1.74 (m, 2H), 1.74 (s, 3H), 1.72 (s, 3H), 0.98 (t, J=7.4 Hz, 3H); ESIMS m/z 462.2 ([M+H]+).

Example 4

Step 2: Preparation of (3S,7S,8S,9R)-3-amino-9-ethyl-7,8-diisobutoxy-1,5-dioxonan-2-one (compound 122)

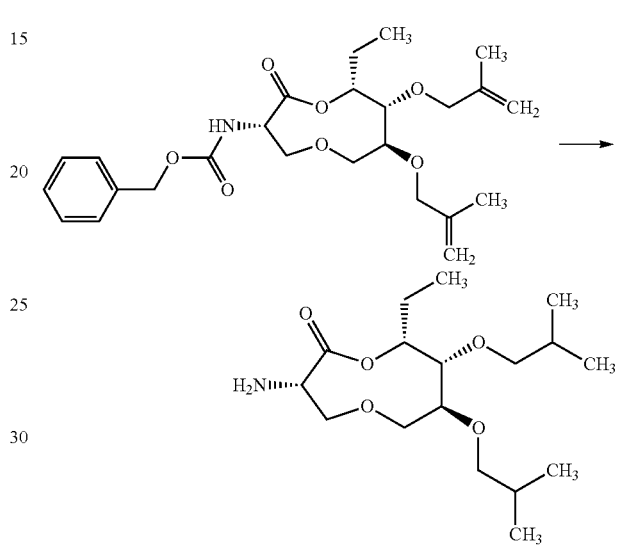

Compound 122 was prepared in the same manner as described in Example 1, Step 5 to give the title compound as a light yellow oil (177 mg, 93%): IR (neat) 2955, 2872, 1745, 1467, 1180, 1081 cm$^{-1}$; $^1$H NMR (400 MHz, CDCl$_3$) δ 4.96 (dt, J=10.1, 3.6 Hz, 1H), 4.07 (dd, J=11.7, 3.5 Hz, 1H), 3.90-3.77 (m, 3H), 3.68 (dd, J=7.1, 3.0 Hz, 1H), 3.63 (dd, J=11.7, 1.7 Hz, 1H), 3.42-3.25 (m, 4H), 3.20 (dd, J=8.8, 6.8 Hz, 1H), 1.91-1.76 (m, 3H), 1.76-1.59 (m, 3H), 1.00 (t, J=7.4 Hz, 3H), 0.89 (ddd, J=6.9, 4.0, 1.6 Hz, 12H); HRMS-ESI (m/z) [M]+ calcd for $C_{17}H_{33}NO_5$, 331.2359; found, 331.2373.

Compound 123 was prepared in the same manner as described in Example 4, Step 2 using compound 91 as starting material.

Example 4

Step 3: Preparation of N-((3S,7S,8S,9R)-9-ethyl-7,8-diisobutoxy-2-oxo-1,5-dioxonan-3-yl)-3-hydroxy-4-methoxypicolinamide (compound 19)

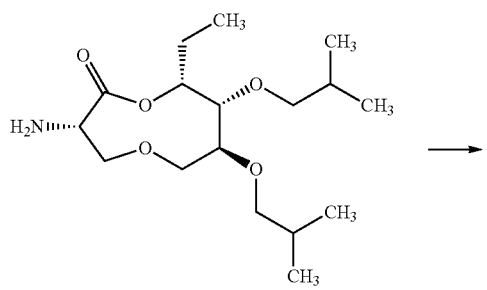

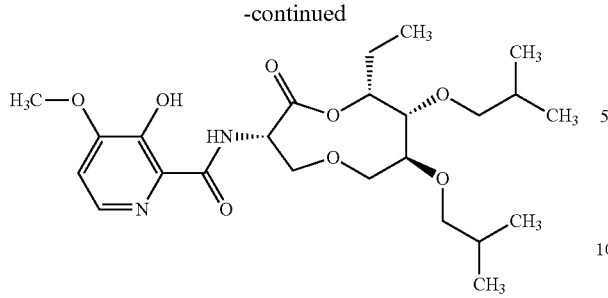

Compound 19 was prepared in the same manner as described in Example 1, Step 6 to give the title compound as a colorless oil (170 mg, 67%): IR (neat) 3369, 2956, 1751, 1650, 1528, 1242, 1082 cm$^{-1}$; $^1$H NMR (400 MHz, CDCl$_3$) δ 12.02 (s, 1H), 8.86 (d, J=8.0 Hz, 1H), 8.00 (d, J=5.2 Hz, 1H), 6.86 (d, J=5.2 Hz, 1H), 5.11-5.02 (m, 2H), 4.17 (dd, J=11.9, 3.6 Hz, 1H), 4.14 (dd, J=11.7, 1.6 Hz, 1H), 3.97 (dd, J=11.7, 5.9 Hz, 1H), 3.94 (s, 3H), 3.78-3.68 (m, 1H), 3.64 (dd, J=11.8, 1.5 Hz, 1H), 3.35 (dtd, J=26.6, 8.9, 6.6 Hz, 4H), 3.21 (dd, J=8.7, 6.8 Hz, 1H), 1.93-1.79 (m, 3H), 1.78-1.65 (m, 1H), 1.02 (t, J=7.4 Hz, 3H), 0.94-0.88 (m, 12H); $^{13}$C NMR (101 MHz, CDCl$_3$) δ 170.17, 169.05, 155.37, 148.79, 140.78, 130.57, 109.59, 79.37, 78.70, 78.33, 75.53, 72.63, 56.19, 53.59, 29.03, 28.85, 22.50, 19.60, 19.53, 19.51, 10.85; HRMS-ESI (m/z) [M]$^+$ calcd for C$_{24}$H$_{38}$N$_2$O$_8$, 482.2628; found, 482.2642.

Compound 22 was prepared in the same manner as described in Example 4, Step 3 using compound 123 as starting material.

Example 5

Steps 1 to 4: Preparation of (S)-methyl 3-((2S,3R)-2,3-bis(benzyloxy)-4-oxobutoxy)-2-((tert-butoxycarbonyl)amino)propanoate

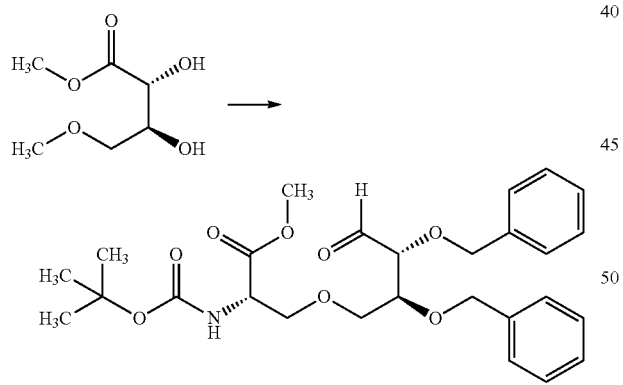

The title compound was prepared in the same manner as described in Example 3, Steps 1 to 4 to give a pale yellow oil (4.85 g, 35% overall yield over four steps): IR (neat) 3380, 2931, 1713, 1498, 1367, 1163 cm$^{-1}$; $^1$H NMR (400 MHz, CDCl$_3$) δ 9.64 (d, J=0.8 Hz, 1H), 7.39-7.22 (m, 10H), 5.34 (d, J=8.7 Hz, 1H), 4.73 (d, J=11.9 Hz, 1H), 4.63-4.49 (m, 3H), 4.46-4.37 (m, 1H), 3.99-3.82 (m, 3H), 3.70 (s, 3H), 3.67-3.57 (m, 3H), 1.46 (s, 9H); $^{13}$C NMR (101 MHz, CDCl$_3$) δ 202.49, 171.05, 155.60, 137.66, 137.20, 128.68, 128.56, 128.32, 128.08, 82.83, 80.18, 78.00, 73.57, 73.09, 71.73, 69.63, 54.06, 52.60, 28.46; HRMS-ESI (m/z) [M]$^+$ calcd for C$_{27}$H$_{35}$NO$_8$, 501.2363; found, 501.2364.

Example 5

Step 5: Preparation of (S)-methyl 3-(((2S,3S,4R)-2,3-bis(benzyloxy)-4-hydroxypentyl)oxy)-2-((tert-butoxycarbonyl)amino)propanoate

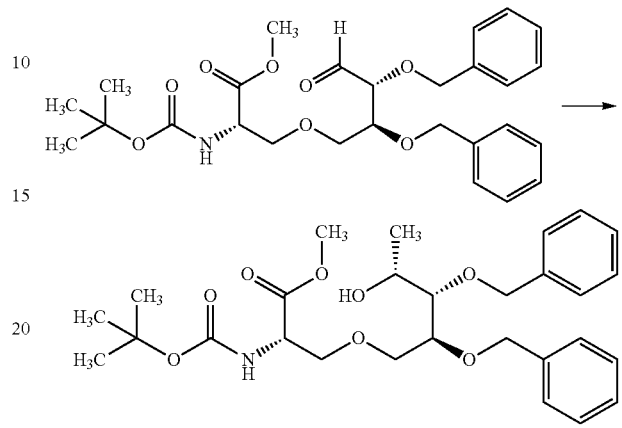

To a solution of (S)-methyl 3-((2S,3R)-2,3-bis(benzyloxy)-4-oxobutoxy)-2-((tert-butoxycarbonyl)amino)propanoate (0.980 g, 1.95 mmol) in DCM (18.61 ml) at −78° C. was added a 3.0 M solution of methylmagnesium bromide in diethyl ether (Et$_2$O) (1.30 ml, 3.91 mmol) and the reaction was stirred at −70° C. for 1 h, warmed slowly to −20° C. over 2 h, and then quenched at −20° C. with H$_2$O. The organic layer was separated and the aqueous layer was extracted with EtOAc. The combined organic phases were washed with brine, dried over MgSO$_4$, filtered, and the filtrate was concentrated and purified by flash chromatography (SiO$_2$, hexanes/EtOAc gradient) to yield the title compound as a colorless oil (0.475 g, 47%): $^1$H NMR (400 MHz, CDCl$_3$) δ 7.37-7.27 (m, 10H), 5.43 (d, J=8.6 Hz, 1H), 4.71 (d, J=14.0 Hz, 1H), 4.69 (d, J=14.4 Hz, 1H), 4.55 (dd, J=11.5, 2.6 Hz, 2H), 4.49-4.41 (m, 1H), 3.96-3.84 (m, 2H), 3.75 (dd, J=10.1, 5.0 Hz, 1H), 3.72 (s, 3H), 3.71-3.63 (m, 3H), 3.32-3.29 (m, 1H), 2.26 (d, J=6.3 Hz, 1H), 1.45 (s, 9H), 1.14 (d, J=6.4 Hz, 3H); $^{13}$C NMR (101 MHz, CDCl$_3$) δ 171.20, 155.58, 138.36, 138.21, 128.59, 128.53, 128.21, 128.07, 128.05, 127.89, 82.88, 80.16, 78.55, 74.94, 73.18, 71.71, 71.34, 67.04, 54.16, 52.58, 28.46, 20.30; ESIMS m/z 516.3 ([M−H]$^-$).

Example 5

Step 6: Preparation of tert-butyl ((3R,7S,8S,9R)-7,8-bis(benzyloxy)-9-methyl-2-oxo-1,5-dioxonan-3-yl)carbamate (compound 172) and tert-butyl ((3S,7S,8S,9R)-7,8-bis(benzyloxy)-9-methyl-2-oxo-1,5-dioxonan-3-yl)carbamate (compound 92)

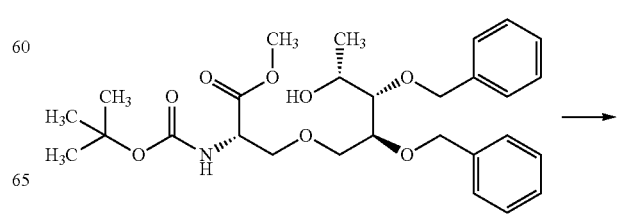

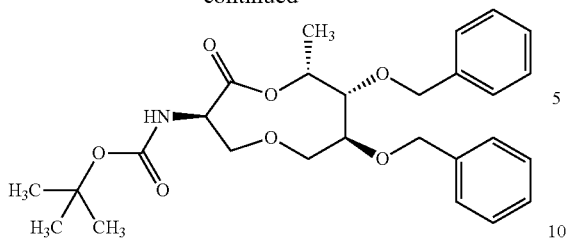

+

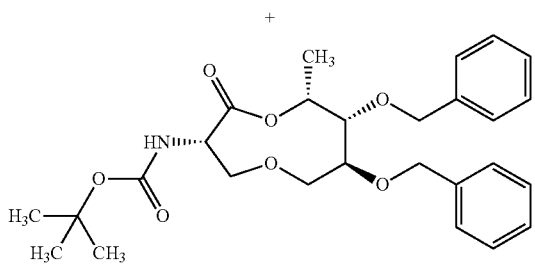

Compounds 172 and 92 were prepared in the same manner as described in Example 3, Step 6 to give the title compounds as colorless oils.

tert-Butyl ((3R,7S,8S,9R)-7,8-bis(benzyloxy)-9-methyl-2-oxo-1,5-dioxonan-3-yl)carbamate (compound 172) (104.0 mg, 36%): ESIMS m/z 386.2 ([M-Boc($C_5H_9O_2$)+2H]$^+$).

tert-Butyl ((3S,7S,8S,9R)-7,8-bis(benzyloxy)-9-methyl-2-oxo-1,5-dioxonan-3-yl)carbamate (compound 92) (89.7 mg, 31%): $^1$H NMR (400 MHz, CDCl$_3$) δ 7.42-7.19 (m, 10H), 5.31-5.19 (m, 1H), 5.18-5.02 (m, 1H), 4.67 (dd, J=16.0, 11.7 Hz, 2H), 4.60-4.52 (m, 1H), 4.51-4.40 (m, 1H), 4.18-4.08 (m, 2H), 3.92 (dd, J=11.7, 3.9 Hz, 1H), 3.85-3.75 (m, 2H), 3.59-3.53 (m, 1H), 3.43 (dd, J=11.5, 5.5 Hz, 1H), 1.44 (s, 9H), 1.36 (d, J=6.8 Hz, 3H); $^{13}$C NMR (101 MHz, CDCl$_3$) δ 169.03, 154.68, 138.23, 138.17, 128.54, 128.53, 128.12, 128.00, 127.97, 127.85, 77.97, 74.40, 73.44, 72.31, 72.14, 71.61, 28.43, 15.64; ESIMS m/z 484.3 ([M−H]$^−$).

Compounds 130 and 131 were prepared in the same manner as described in Example 5, Steps 1 to 6 using (−)-dimethyl D-tartrate as starting material.

Example 5

Step 7: Preparation of (3R,7S,8S,9R)-3-amino-7,8-bis(benzyloxy)-9-methyl-1,5-dioxonan-2-one hydrochloride (compound 124)

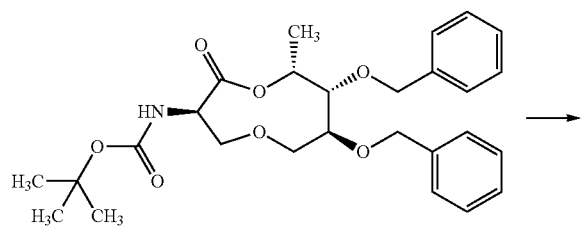

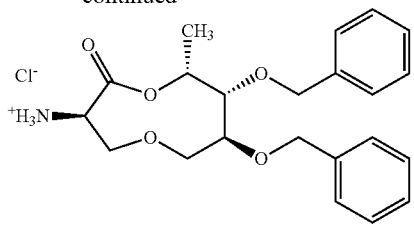

To a solution of tert-butyl ((3R,7S,8S,9R)-7,8-bis(benzyloxy)-9-methyl-2-oxo-1,5-dioxonan-3-yl)carbamate (104.0 mg, 0.214 mmol) in DCM (1.20 mL) was added a 4.0 M solution of HCl in dioxane (1.07 mL, 4.28 mmol) and the reaction was stirred at room temperature for 2 h. The solvent was removed under vacuum and the residue was dried under high vacuum to yield the title compound as an off-white oil (85.0 mg, 94%): IR (neat) 3365, 1636, 1235, 1063 cm$^{−1}$; $^1$H NMR (400 MHz, CDCl$_3$) δ 8.76 (bs, 2H), 7.35-7.20 (m, 10H), 5.30 (s, 1H), 4.69-4.45 (m, 5H), 4.20 (d, J=9.1 Hz, 2H), 3.89-3.75 (m, 2H), 3.59 (d, J=11.1 Hz, 1H), 3.47 (d, J=7.1 Hz, 1H), 1.32 (d, J=6.8 Hz, 3H); HRMS-ESI (m/z) [M]$^+$ calcd for $C_{22}H_{27}NO_5$, 385.1889; found, 385.1890.

Compound 173 was prepared in the same manner as described in Example 5, Step 7 using compound 92 as starting material.

Compounds 188 was prepared in a similar manner as described in Example 5, Step 7 using compound 156 as starting material.

Compounds 133 and 134 were prepared in the same manner as described in Example 5, Step 7 using compounds 130 and 131, respectively as starting materials.

Compound 272 was prepared in the same manner as described in Example 5, Step 7 using compound 241 as starting material.

Example 5

Step 8: Preparation of N-((3R,7S,8S,9R)-7,8-bis(benzyloxy)-9-methyl-2-oxo-1,5-dioxonan-3-yl)-3-hydroxy-4-methoxypicolinamide (compound 30)

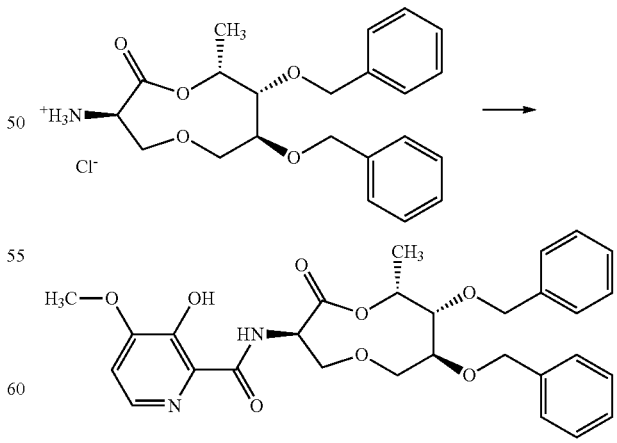

To a mixture of (3R,7S,8S,9R)-3-amino-7,8-bis(benzyloxy)-9-methyl-1,5-dioxonan-2-one hydrochloride (85.0 mg, 0.2015 mmol) and 3-hydroxy-4-methoxypicolinic acid (54.0 mg, 0.321 mmol) in DCM (1.20 mL) was added 4-methylmorpholine (0.141 mL, 1.29 mmol) followed by HATU (135.0 mg, 0.343 mmol) and the mixture was stirred at room temperature for 4 h. The reaction mixture was directly purified by flash chromatography (SiO$_2$, hexanes/EtOAc gradient) to yield the title compound as a colorless oil (65.4 mg, 61%): IR (neat) 3368, 2933, 1748, 1648, 1527, 1242, 1066 cm$^{-1}$; $^1$H NMR (400 MHz, CDCl$_3$) δ 11.98 (s, 1H), 8.86 (d, J=8.0 Hz, 1H), 8.01 (d, J=5.2 Hz, 1H), 7.41-7.27 (m, 10H), 6.86 (d, J=5.2 Hz, 1H), 5.36 (qd, J=6.7, 3.1 Hz, 1H), 5.06 (ddd, J=8.0, 6.1, 1.9 Hz, 1H), 4.71 (d, J=11.4 Hz, 1H), 4.68 (d, J=11.8 Hz, 1H), 4.60 (d, J=11.3 Hz, 1H), 4.58 (d, J=11.8 Hz, 1H), 4.16 (dd, J=12.2, 3.6 Hz, 1H), 4.12 (dd, J=9.4, 2.2 Hz, 2H), 3.98 (dd, J=11.7, 6.1 Hz, 1H), 3.94 (s, 3H), 3.71 (dd, J=11.9, 1.7 Hz, 1H), 3.57-3.50 (m, 1H), 1.38 (d, J=6.8 Hz, 3H); $^{13}$C NMR (101 MHz, CDCl$_3$) δ 169.86, 169.07, 155.41, 148.82, 140.81, 138.27, 138.10, 130.51, 128.58, 128.54, 128.14, 128.05, 128.00, 127.85, 109.64, 78.70, 75.15, 74.37, 72.35, 71.55, 56.21, 53.37, 15.28; HRMS-ESI (m/z) [M]$^+$ calcd for C$_{29}$H$_{32}$N$_2$O$_8$, 536.2159; found, 536.2162.

Compound 49 was prepared in the same manner as described in Example 5, Step 8 using compound 173 as starting material.

Compounds 38 and 39 were prepared in the same manner as described in Example 5, Step 8 using compounds 133 and 134, respectively, as starting materials.

Example 6

Step 1 to 3: Preparation of (S)-methyl 2-(((benzyloxy)carbonyl)-amino)-3-(((2S,3S,4R)-4-hydroxy-2,3,5-tris((2 methylallyl)oxy)pentyl)oxy)propanoate

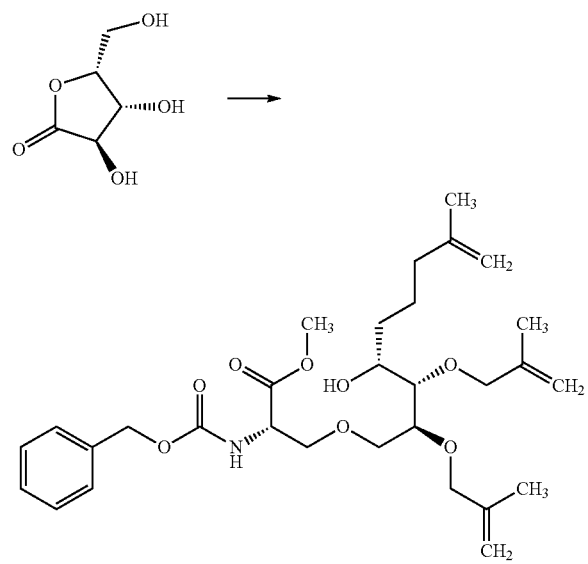

(S)-methyl 2-(((benzyloxy)carbonyl)amino)-3-(((2S,3S,4R)-4-hydroxy-2,3,5-tris((2 methylallyl)oxy)pentyl)oxy)propanoate was prepared starting from D-xylono-1,4-lactone as described in Example 1, Steps 1 to 3: $^1$H NMR (400 MHz, CDCl$_3$) δ 7.42-7.26 (m, 5H), 5.92-5.76 (d, J=8.8 Hz, 1H), 5.22-5.01 (s, 2H), 5.01-4.79 (m, 6H), 4.54-4.43 (m, 1H), 4.10-4.06 (m, 1H), 4.00-3.83 (m, 6H), 3.77-3.72 (s, 3H), 3.72-3.59 (m, 5H), 3.56-3.52 (dd, J=5.2, 2.8 Hz, 1H), 3.47-3.41 (dd, J=6.2, 1.4 Hz, 2H), 2.53-2.43 (d, J=6.8 Hz, 1H), 1.75-1.73 (s, 3H), 1.73-1.70 (s, 6H); $^{13}$C NMR (101 MHz, CDCl$_3$) δ 170.70, 156.09, 142.27, 142.13, 141.96, 136.30, 128.48, 128.45, 128.11, 128.05, 112.52, 112.28, 78.33, 77.76, 76.40, 75.16, 74.75, 71.41, 71.21, 71.11, 69.25, 67.00, 54.50, 52.51, 19.68, 19.54, 19.46; ESIMS m/z 550.3 ([M+H]$^+$).

Example 6

Step 4: Preparation of benzyl (3S,7S,8R,9R)-7,8-bis(2-methylallyloxy)-9-((2-methylallyloxy)methyl)-2-oxo-1,5-dioxonan-3-ylcarbamate (compound 153) and (3R,7S,8R,9R)-7,8-bis(2-methylallyloxy)-9-((2-methylallyloxy)methyl)-2-oxo-1,5-dioxonan-3-ylcarbamate (compound 154)

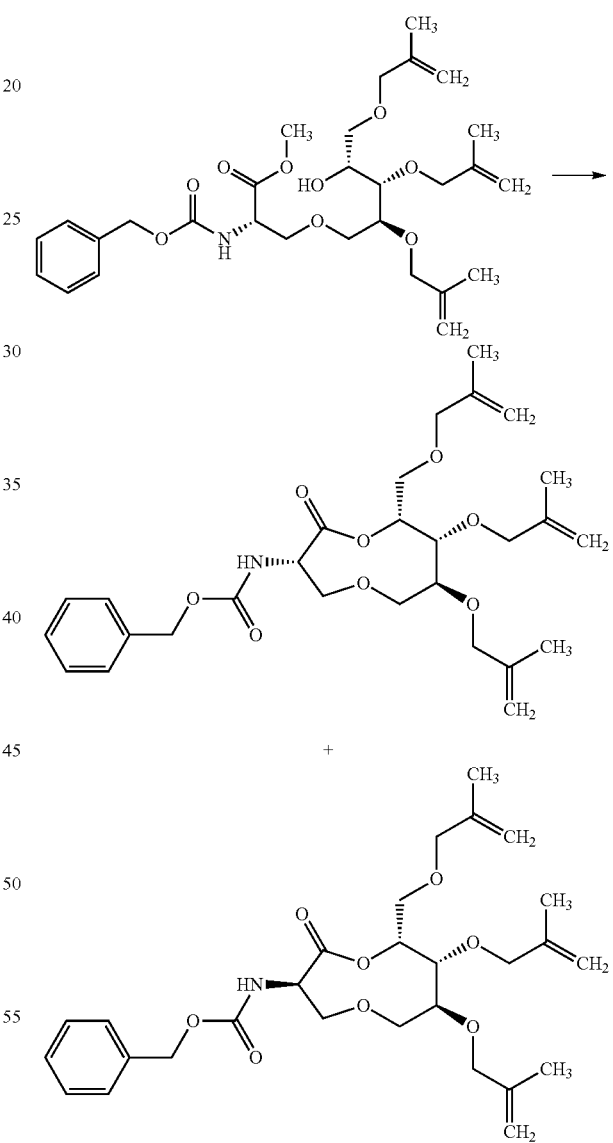

A solution of (S)-2-(benzyloxycarbonylamino)-3-((2S,3S,4R)-4-hydroxy-2,3,5-tris(2-methylallyloxy)pentyloxy)propanoic acid (400 mg, 0.747 mmol) in anhydrous toluene (400 mL) was added to a solution of MNBA (411 mg, 1.195 mmol) and DMAP (547 mg, 4.48 mmol) in toluene (1600 mL) over the course of 3 h via syringe pump. After the addition was complete, the reaction mixture was stirred for 1 h, concentrated, and the residue purified by flash chromatography (SiO$_2$, 200 EtOAc/hexanes) to furnish benzyl (3S,7S,8R,9R)-7,8-bis(2-methylallyloxy)-9-((2-methylallyloxy)methyl)-2-oxo-1,5-dioxonan-3-ylcarbamate (140 mg, 36%) and (3R,7S,8R,9R)-7,8-bis(2-methylallyloxy)-9-((2-methylallyloxy)methyl)-2-oxo-1,5-dioxonan-3-ylcarbamate as white foams (140 mg, 36%).

For (3S,7S,8R,9R)-7,8-bis(2-methylallyloxy)-9-((2-methylallyloxy)methyl)-2-oxo-1,5-dioxonan-3-ylcarbamate (compound 153): $^1$H NMR (400 MHz, CDCl$_3$) δ 7.42-7.27 (m, 6H), 5.74 (d, J=7.7 Hz, 1H), 5.36-5.25 (m, 1H), 5.10 (d, J=1.6 Hz, 2H), 5.00-4.84 (m, 6H), 4.80-4.71 (m, 1H), 4.12 (dd, J=12.0, 3.5 Hz, 1H), 4.09-3.78 (m, 9H), 3.77-3.65 (m, 2H), 3.57-3.45 (m, 1H), 1.78-1.68 (m, 9H); $^{13}$C NMR (101 MHz, CDCl$_3$) δ 170.29, 155.78, 142.14, 141.92, 141.86, 141.74, 136.23, 128.56, 128.51, 128.14, 128.00, 112.95, 112.71, 112.41, 77.22, 76.30, 76.19, 75.77, 75.19, 75.22, 73.82, 67.08, 66.96, 55.29, 19.61, 19.52, 19.45; ESIMS m/z 541.3 ([M+Na]$^+$).

For (3R,7S,8R,9R)-7,8-bis(2-methylallyloxy)-9-((2-methylallyloxy)methyl)-2-oxo-1,5-dioxonan-3-ylcarbamate (compound 154): $^1$H NMR (400 MHz, CDCl$_3$) δ 7.44-7.28 (m, 6H), 5.49 (d, J=9.0 Hz, 1H), 5.24 (td, J=5.7, 3.2 Hz, 1H), 5.09 (s, 2H), 5.00-4.83 (m, 6H), 4.60-4.52 (m, 1H), 4.19 (dd, J=11.6, 6.0 Hz, 1H), 4.04 (t, J=12.7 Hz, 1H), 4.00-3.85 (m, 6H), 3.83-3.77 (m, 1H), 3.76-3.61 (m, 2H), 3.55 (ddd, J=7.0, 3.9, 1.6 Hz, 1H), 3.51-3.38 (m, 1H), 1.74-1.72 (m, 9H). ESIMS m/z 541.2 ([M+Na]$^+$).

Example 6

Step 5: Preparation of (3S,7S,8R,9R)-3-amino-7,8-diisobutoxy-9 (isobutoxy-methyl)-1,5-dioxonan-2-one (compound 189)

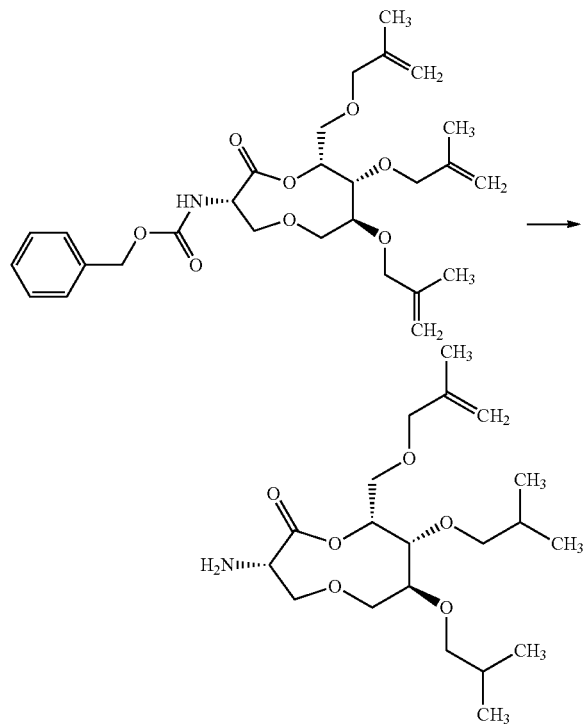

Compound 189 was prepared in the same manner as described in Example 1, step 5 from compound 153 to give a white foam: $^1$H NMR (400 MHz, CDCl$_3$) δ 5.18 (td, J=5.5, 3.3 Hz, 1H), 4.14-4.05 (m, 1H), 3.92-3.80 (m, 2H), 3.76-3.66 (m, 3H), 3.46-3.30 (m, 4H), 3.25 (d, J=6.6 Hz, 2H), 3.23-3.14 (m, 2H), 1.93-1.77 (m, 4H), 0.97-0.83 (m, 19H).

Compound 190 was prepared in the manner as described in Example 6, step 5 starting from compound 154.

Example 6

Step 6: Preparation of N-((3S,7S,8R,9R)-7,8-diisobutoxy-9-(isobutoxymethyl)-2-oxo-1,5-dioxonan-3-yl)-3-hydroxy-4-methoxypicolinamide (compound 15)

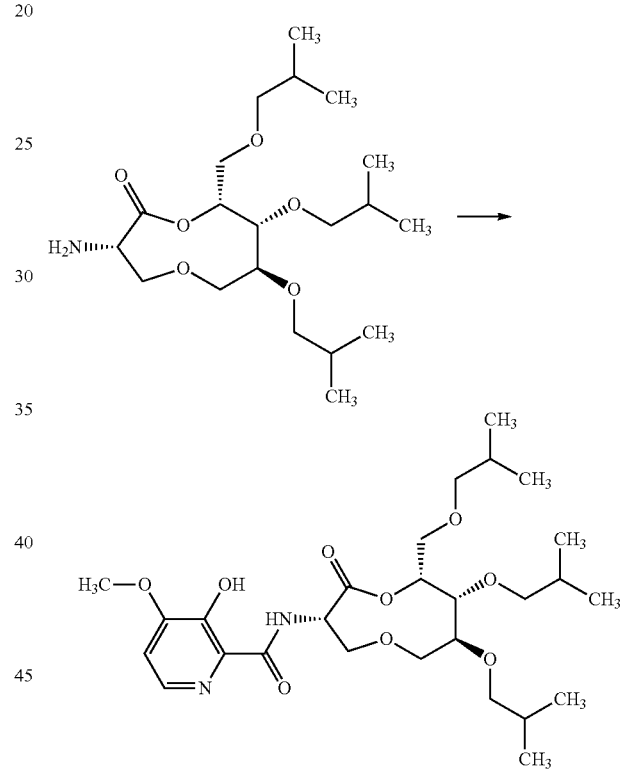

Compound 15 was prepared as described in Example 1, Step 6 starting from compound 189: $^1$H NMR (400 MHz, CDCl$_3$) δ 12.00 (d, J=0.7 Hz, 1H), 8.86 (d, J=8.1 Hz, 1H), 8.01 (d, J=5.2 Hz, 1H), 6.87 (dd, J=5.2, 0.6 Hz, 1H), 5.33-5.23 (m, 1H), 5.09 (ddd, J=7.9, 6.0, 1.7 Hz, 1H), 4.24-4.07 (m, 2H), 3.99 (dd, J=11.7, 6.1 Hz, 1H), 3.93 (s, 3H), 3.92-3.86 (m, 1H), 3.82-3.67 (m, 3H), 3.46-3.39 (m, 2H), 3.34 (td, J=9.1, 6.5 Hz, 2H), 3.27 (d, J=6.6 Hz, 2H), 3.20 (dd, J=8.9, 6.9 Hz, 1H), 1.97-1.79 (m, 3H), 0.96-0.87 (m, 18H); $^{13}$C NMR (101 MHz, CDCl$_3$) δ 169.72, 168.89, 155.24, 148.66, 140.64, 130.39, 109.47, 79.21, 78.31, 76.84, 75.42, 73.40, 72.61, 67.95, 56.05, 53.39, 28.84, 28.70, 28.47, 19.49, 19.39; ESIMS m/z 541.4 ([M+H]$^+$).

Compound 16 was prepared in the same manner as described in Example 6, Step 6 from compound 190.

Example 7

Step 1: Preparation of (S)-methyl 3-(((2S,3S,4S)-2,3-bis(benzyloxy)-4-hydroxypentyl)oxy)-2-((tert-butoxycarbonyl)amino)propanoate

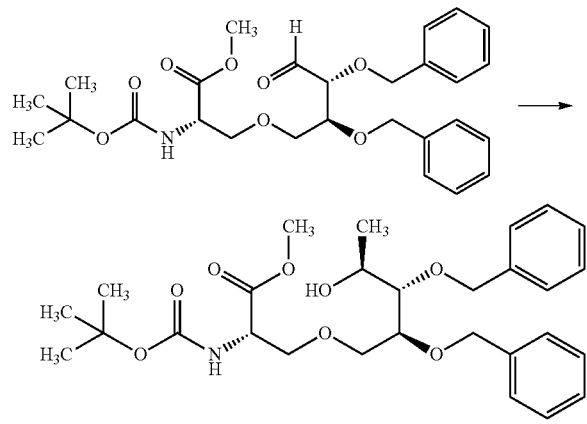

To a solution of (S)-methyl 3-((2S,3R)-2,3-bis(benzyloxy)-4-oxobutoxy)-2-((tert-butoxycarbonyl)amino)propanoate (7.55 g, 15.05 mmol) in DCM (30 ml) and THF (30 ml) at −78° C. was added triisopropoxy(methyl)titanium, 1.0 M in THF (31.6 ml, 31.6 mmol) and the reaction was stirred at −78° C. for 2 h, warmed to −20° C., and stored at −20° C. overnight. The reaction was warmed to 0° C., stirred for 4 h between 0° C. and −10° C., and then quenched at this temperature with saturated aqueous NH$_4$Cl. The reaction mixture was extracted with EtOAc, and the combined extracts were washed with brine, dried over MgSO$_4$, filtered, and concentrated. The crude residue was purified by flash chromatography (SiO$_2$, hexanes/EtOAc) to yield the title compound as a colorless oil (4.59 g, 59%, diastereomer selectivity=6:1): $^1$H NMR (400 MHz, CDCl$_3$) δ 7.45-7.14 (m, 11H), 5.45 (d, J=8.8 Hz, 1H), 4.67 (d, J=11.6 Hz, 1H), 4.61-4.51 (m, 3H), 4.50-4.41 (m, 1H), 3.90 (dd, J=9.4, 3.0 Hz, 1H), 3.84-3.78 (m, 1H), 3.74-3.61 (m, 6H), 3.31 (dd, J=6.8, 4.0 Hz, 1H), 2.85 (d, J=4.5 Hz, 1H), 1.45 (s, 9H), 1.20 (d, J=6.2 Hz, 3H); $^{13}$C NMR (101 MHz, CDCl$_3$) δ 171.04, 155.45, 137.99, 137.76, 128.51, 128.44, 128.12, 128.00, 127.97, 127.87, 81.43, 80.05, 77.91, 73.55, 72.88, 71.60, 70.91, 67.53, 54.00, 52.47, 28.34, 19.89; ESIMS m/z 540.6 ([M+Na]$^+$).

Example 7

Step 2: Preparation of tert-butyl ((3S,7S,8S,9S)-7,8-bis(benzyloxy)-9-methyl-2-oxo-1,5-dioxonan-3-yl)carbamate (compound 93)

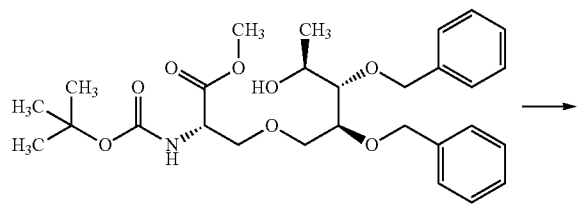

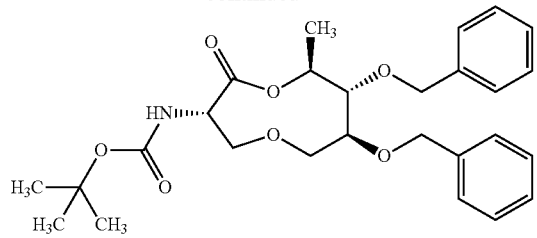

Compound 93 was prepared in the same manner as described in Example 1, Step 4 to give the title compound as an off-white solid (74.5 mg, 73%): mp 69-71° C.; IR (neat) 3349, 2978, 2933, 2876, 1753, 1710, 1497, 1367, 1249, 1161, 1074, 734, 697 cm$^{-1}$; $^1$H NMR (400 MHz, CDCl$_3$) δ 7.38-7.19 (m, 11H), 5.38-5.20 (d, J=7.9 Hz, 1H), 5.08-4.96 (dq, J=8.2, 6.1 Hz, 1H), 4.96-4.88 (d, J=10.8 Hz, 1H), 4.76-4.48 (m, 3H), 4.02-3.85 (dd, J=11.8, 6.3 Hz, 2H), 3.77-3.55 (m, 2H), 3.52-3.34 (m, 2H), 1.48-1.36 (s, 12H); $^{13}$C NMR (101 MHz, CDCl$_3$) δ 171.24, 155.11, 138.11, 137.93, 128.40, 128.38, 127.94, 127.86, 127.74, 84.76, 83.57, 80.17, 75.79, 75.50, 74.90, 72.94, 72.70, 53.72, 28.28, 18.69; ESIMS m/z 508.6 ([M+Na]$^+$).

Example 7

Step 3: Preparation of tert-butyl N-tert-butoxycarbonyl-N-[(3S,7S,8S,9S)-7,8-dibenzyloxy-9-methyl-2-oxo-1,5-dioxonan-3-yl]carbamate (compound 192)

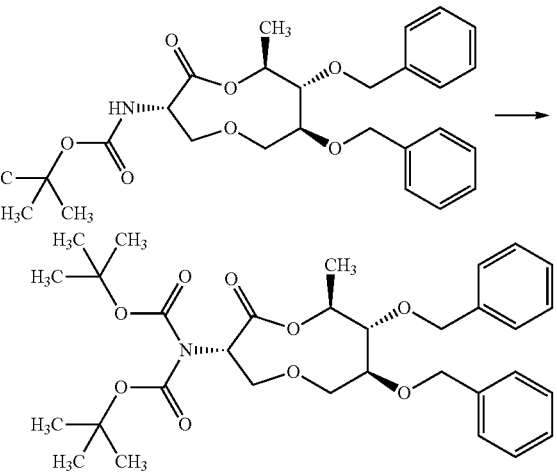

To a solution of tert-butyl ((3S,7S,8S,9S)-7,8-bis(benzyloxy)-9-methyl-2-oxo-1,5-dioxonan-3-yl)carbamate (6.65 g, 13.70 mmol) in anhydrous CH$_3$CN (62 mL) was added DMAP (0.837 g, 6.85 mmol) followed by di-tertibutyl dicarbonate (6.36 ml, 27.4 mmol) at room temperature, and the mixture was stirred overnight at room temperature. The crude residue was purified by flash chromatography (SiO$_2$, hexanes/EtOAc) to yield the title compound as a colorless oil (7.10 g, 89%): $^1$H NMR (400 MHz, CDCl$_3$) δ 7.38-7.23 (m, 10H), 5.24 (dd, J=8.9, 3.9 Hz, 1H), 4.98-4.82 (m, 2H), 4.70-4.54 (m, 3H), 4.26 (dd, J=12.2, 3.9 Hz, 1H), 4.03-3.88 (m, 2H), 3.63 (dd, J=10.9, 7.2 Hz, 1H), 3.58-3.50 (m, 1H), 3.50-3.42 (m, 1H), 1.50 (s, 18H), 1.43 (d, J=6.3 Hz, 3H); ESIMS m/z 609.6 ([M+Na]$^+$).

Example 7

Step 4: Preparation of tert-butyl N-tert-butoxycarbonyl-N-[(3S,7S,8R,9S)-7,8-dihydroxy-9-methyl-2-oxo-1,5-dioxonan-3-yl]carbamate (compound 191)

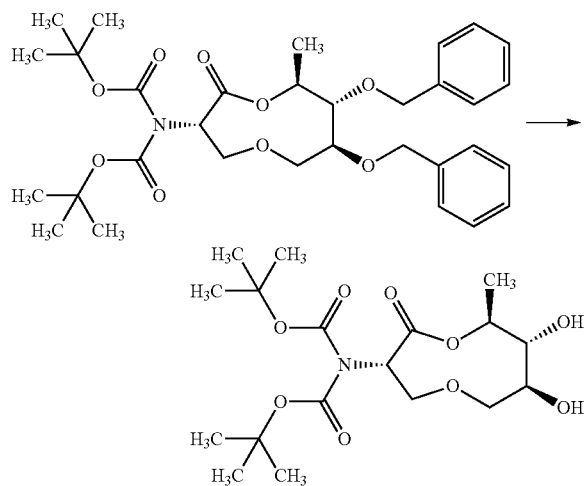

To a solution of tert-butyl N-tert-butoxycarbonyl-N-[(3S,7S,8S,9S)-7,8-dibenzyloxy-9-methyl-2-oxo-1,5-dioxonan-3-yl]carbamate (3.8 g, 6.49 mmol) in EtOAc (10 mL) in a 50 mL high pressure reactor with a stir bar was added 5% Pd/C (500 mg, 0.235 mmol). After the reactor was sealed, it was evacuated and purged with $H_2$ (4x), and then charged to ~600 psi of $H_2$ at room temperature. The reaction mixture was warmed to 45° C. and stirred for 5 h. The reaction mixture was filtered through a pad of Celite® and the filtrate concentrated to yield the title compound as a white foam (2.63 g, 100%): $^1$H NMR (400 MHz, CDCl$_3$) δ 5.25 (dd, J=8.7, 2.8 Hz, 1H), 4.94-4.76 (m, 1H), 4.26 (dd, J=12.3, 2.9 Hz, 1H), 4.06 (dd, J=10.7, 1.3 Hz, 1H), 3.91 (dd, J=12.3, 8.7 Hz, 1H), 3.62-3.54 (m, 1H), 3.54-3.38 (m, 2H), 3.15 (d, J=4.0 Hz, 1H), 2.96 (d, J=3.5 Hz, 1H), 1.51 (s, 18H), 1.46 (d, J=6.3 Hz, 3H); $^{13}$C NMR (101 MHz, CDCl$_3$) δ 168.63, 152.70, 83.18, 79.34, 77.96, 74.40, 74.25, 73.02, 58.54, 27.98, 18.60; ESIMS m/z 428.5 ([M+Na]$^+$).

Example 7

Step 5: Preparation of tert-butyl N-tert-butoxycarbonyl-N-[(3S,7S,8S,9S)-7,8-diallyloxy-9-methyl-2-oxo-1,5-dioxonan-3-yl]carbamate (compound 94)

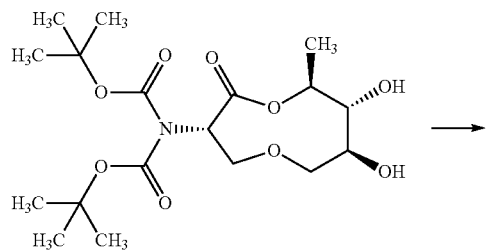

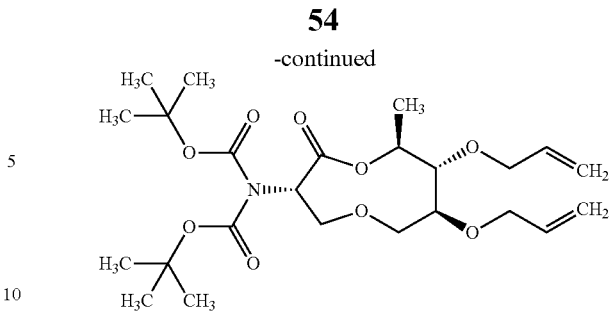

To a stirred solution of tert-butyl N-tert-butoxycarbonyl-N-[(3S,7S,8R,9S)-7,8-dihydroxy-9-methyl-2-oxo-1,5-dioxonan-3-yl]carbamate (170 mg, 0.419 mmol), Pd$_2$(dba)$_3$ (38.4 mg, 0.042 mmol) and dppf (46.5 mg, 0.084 mmol) in anhydrous THF (4.0 mL) was added allyl tert-butyl carbonate (332 mg, 2.096 mmol) and the resulting mixture was warmed to 60° C. and stirred for 1 h. The reaction was concentrated and the residue purified by flash chromatography (SiO$_2$, EtOAc/hexanes) to yield the title compound as a light yellow oil (170 mg, 83%): $^1$H NMR (400 MHz, CDCl$_3$) δ 6.02-5.78 (m, 2H), 5.30-5.10 (m, 5H), 4.81 (dq, J=9.5, 6.3 Hz, 1H), 4.38 (ddd, J=12.2, 5.5, 1.4 Hz, 1H), 4.24 (dd, J=12.1, 4.1 Hz, 1H), 4.17-4.02 (m, 3H), 3.95-3.81 (m, 2H), 3.54 (dd, J=10.9, 7.2 Hz, 1H), 3.41-3.21 (m, 2H), 1.50 (s, 18H), 1.42 (d, J=6.3 Hz, 3H); $^{13}$C NMR (101 MHz, CDCl$_3$) δ 169.00, 152.64, 134.93, 134.80, 116.95, 116.78, 84.63, 83.06, 82.84, 75.93, 74.68, 72.85, 72.62, 71.85, 57.94, 27.97, 18.74; ESIMS m/z 509.2 ([M+Na]$^+$).

Compounds 97, 135 and 136 were prepared in the same manner as described in Example 7, Step 5.

Example 7

Step 6: Preparation of tert-butyl N-tert-butoxycarbonyl-N-[(3S,7S,8S,9S)-9-methyl-2-oxo-7,8-dipropoxy-1,5-dioxonan-3-yl]carbamate (compound 137)

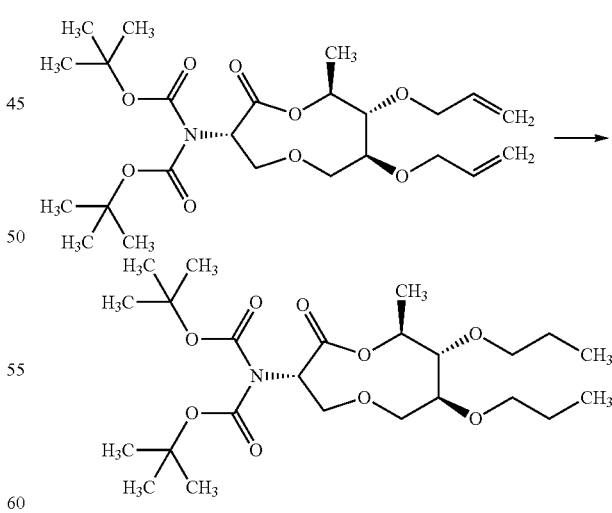

To a solution of tert-butyl N-tert-butoxycarbonyl-N-[(3S,7S,8S,9S)-7,8-diallyloxy-9-methyl-2-oxo-1,5-dioxonan-3-yl]carbamate (170 mg, 0.350 mmol) in EtOAc (3 mL) in a 50 mL high pressure reactor with a stir bar was added 5% Pd/C (20.0 mg, 9.40 μmol). After the reactor was sealed, it was purged with $H_2$ (4x), and charged to ~600 psi with $H_2$ at room temperature. The reaction mixture was warmed to 40° C. and stirred for 2 h. The reaction mixture was filtered through a pad of Celite® and the filtrate concentrated to provide the title compound as a colorless oil (170 mg, 99%): $^1$H NMR (400 MHz, CDCl$_3$) δ 5.21 (dd, J=8.9, 4.2 Hz, 1H), 4.77 (dq, J=9.3, 6.2 Hz, 1H), 4.26 (dd, J=12.1, 4.2 Hz, 1H), 3.92 (dd, J=12.1, 8.9 Hz, 1H), 3.86-3.77 (m, 2H), 3.60-3.41 (m, 4H), 3.29-3.12 (m, 2H), 1.67-1.52 (m, 2H), 1.49 (s, 19H), 1.42 (d, J=6.4 Hz, 3H), 0.92 (td, J=7.4, 2.8 Hz, 7H); $^{13}$C NMR (101 MHz, CDCl$_3$) δ 169.04, 152.59, 84.88, 83.40, 82.95, 75.71, 75.41, 72.78, 72.65, 72.55, 57.88, 27.91, 23.48, 23.27, 18.62, 10.59, 10.57; ESIMS m/z 513.3 ([M+Na]$^+$).

Compounds 98, 138, 141, and 189 were prepared in the same manner as described in Example 7, Step 6.

Compound 240 was prepared in the same manner as described in Example 7, Step 6.

Example 7

Step 7: Preparation of (3S,7S,8S,9S)-9-methyl-2-oxo-7,8-dipropoxy-1,5-dioxonan-3-aminium chloride (compound 139)

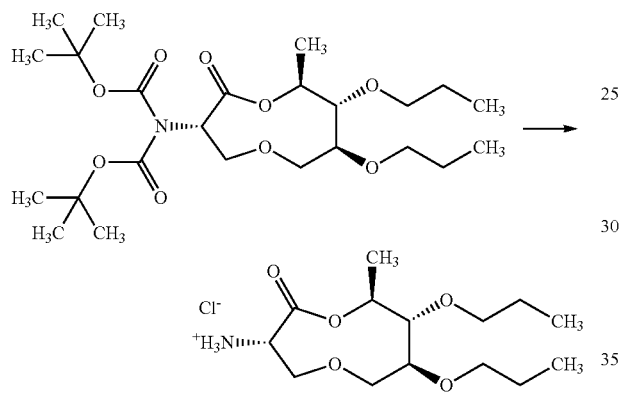

Compound 139 was prepared as described in example 5, step 7: $^1$H NMR (400 MHz, CDCl$_3$) δ 8.67 (s, 3H), 4.91 (dq, J=8.7, 6.2 Hz, 1H), 4.55 (dd, J=6.7, 4.1 Hz, 1H), 4.28 (dd, J=12.8, 4.1 Hz, 1H), 4.05 (dd, J=12.8, 6.7 Hz, 1H), 3.90-3.73 (m, 2H), 3.58-3.38 (m, 4H), 3.23-3.09 (m, 2H), 1.56 (dddd, J=8.6, 7.0, 5.2, 2.4 Hz, 4H), 1.44 (d, J=6.3 Hz, 3H), 0.91 (td, J=7.4, 1.6 Hz, 6H); $^{13}$C NMR (101 MHz, CDCl$_3$) δ 168.56, 84.88, 83.28, 76.08, 75.58, 73.93, 72.69, 70.96, 53.41, 23.50, 23.31, 18.50, 10.63; ESIMS m/z 290.7 ([M+H]$^+$).

Compounds 140, 143 and 175 were prepared in the same manner as described in Example 7, Step 7.

Example 7

Step 8: Preparation of 3-hydroxy-4-methoxy-N-((3S, 7S,8S,9S)-9-methyl-2-oxo-7,8-dipropoxy-1,5-dioxonan-3-yl)picolinamide (compound 58)

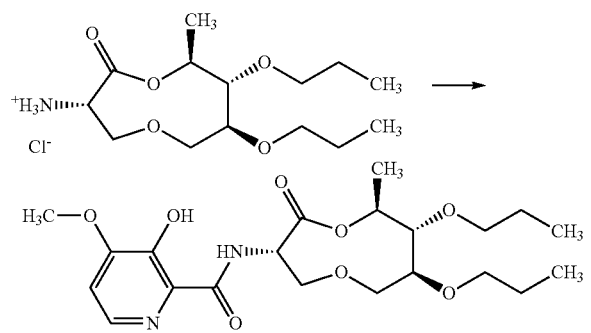

Compound 58 was prepared in the same manner as described in Example 5, Step 8: $^1$H NMR (400 MHz, CDCl$_3$) δ 11.92 (s, 1H), 8.56 (d, J=8.2 Hz, 1H), 8.00 (d, J=5.2 Hz, 1H), 6.87 (d, J=5.2 Hz, 1H), 5.03 (ddd, J=8.2, 6.8, 5.1 Hz, 1H), 4.99-4.89 (m, 1H), 4.07 (dd, J=11.9, 6.8 Hz, 1H), 3.94 (s, 3H), 3.88-3.76 (m, 3H), 3.65-3.43 (m, 4H), 3.26-3.14 (m, 2H), 1.67-1.53 (m, 4H), 1.46 (d, J=6.3 Hz, 3H), 0.92 (td, J=7.4, 3.1 Hz, 6H); $^{13}$C NMR (101 MHz, CDCl$_3$) δ 170.33, 168.99, 155.38, 148.79, 140.66, 130.30, 109.60, 85.00, 83.58, 75.59, 75.38, 73.96, 73.23, 72.74, 56.09, 52.17, 23.53, 23.30, 18.60, 10.65, 10.62; ESIMS m/z 442.1 ([M+H]$^+$).

Compounds 59, 62 and 67 were prepared in the same manner as described in Example 7, Step 8.

Example 8

Step 1: Preparation of (2S,3S,4S)-2,3-bis(benzyloxy)pentane-1,4-diol

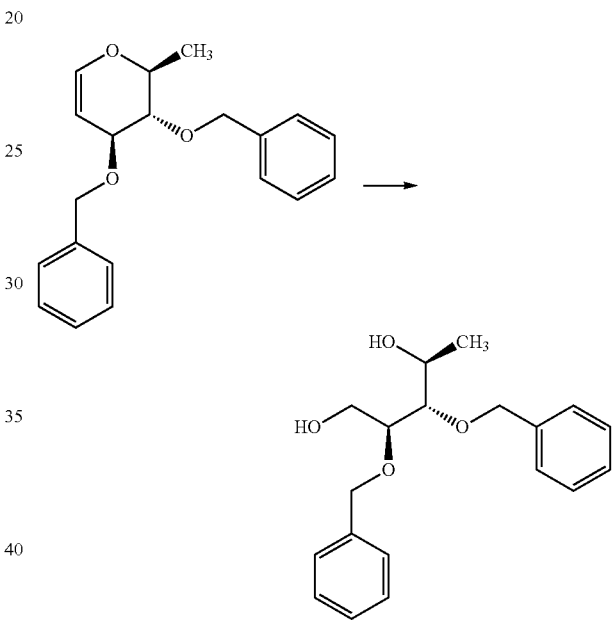

A mixture of (2S,3S,4S)-3,4-bis(benzyloxy)-2-methyl-3,4-dihydro-2H-pyran (0.621 g, 2.00 mmol) and NaHCO$_3$ (17.0 mg, 0.200 mmol) in MeOH (0.22 ml) and DCM (7 mL) was treated with ozone at −78° C. until the solution became light blue in color. The mixture was purged with nitrogen until colorless, diluted with MeOH (7 mL), and treated with a solution of NaBH$_4$ (0.454 g, 12.0 mmol) and NaOAc (0.335 g, 4.08 mmol) in H$_2$O (7 mL). The mixture was slowly warmed to room temperature and stirred for 12 h. The mixture was diluted with EtOAc and washed with H$_2$O. The organic layer was separated and the aqueous layer was extracted with EtOAc. The combined organic phases were washed with brine, dried over MgSO$_4$, filtered, and the filtrate concentrated. The crude residue was purified by flash chromatography (SiO$_2$, hexanes/EtOAc gradient) to yield the title compound as a colorless oil (0.590 g, 93%): IR (neat) 3389, 2876, 1453, 1064, 733, 696 cm$^{-1}$; $^1$H NMR (400 MHz, CDCl$_3$) δ 7.39-7.27 (m, 10H), 4.64 (s, 2H), 4.63 (s, 2H), 4.06-3.97 (m, 1H), 3.92-3.83 (m, 1H), 3.80-3.73 (m, 2H), 3.47 (dd, J=6.2, 4.3 Hz, 1H), 2.92 (d, J=4.9 Hz, 1H), 2.23 (dd, J=6.9, 4.9 Hz, 1H), 1.24 (d, J=6.4 Hz, 3H); $^{13}$C NMR (101 MHz, CDCl$_3$) δ 137.91, 137.71, 128.69, 128.62, 128.23, 128.19, 128.09, 81.72, 79.53, 73.63, 72.78, 67.66, 61.45, 19.74; ESIMS m/z 339.2 ([M+Na]$^+$).

Example 8

Step 2: Preparation of (S)-methyl 3-(((2S,3S,4S)-2,3-bis(benzyloxy)-4-hydroxypentyl)oxy)-2-((tert-butoxycarbonyl)amino)propanoate and (S)-methyl 3-(((2S,3S,4S)-3,4-bis(benzyloxy)-5-hydroxypentan-2-yl)oxy)-2-((tert-butoxycarbonyl)amino)propanoate

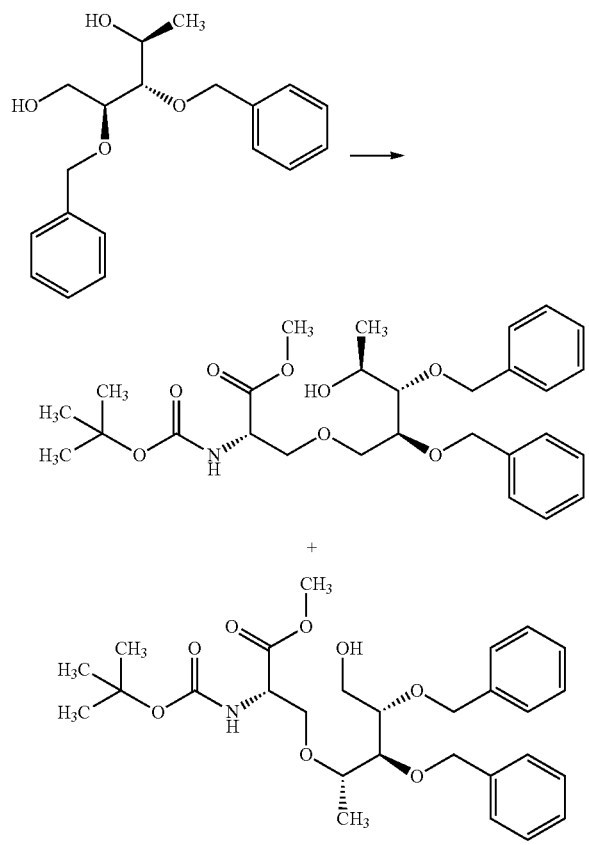

The title compounds were prepared in a similar manner as described in Example 1, Step 3 to give colorless oils.

(S)-Methyl 3-(((2S,3S,4S)-2,3-bis(benzyloxy)-4-hydroxypentyl)oxy)-2-((tert-butoxycarbonyl)amino)propanoate: See Example 7, Step 1

(S)-methyl 3-(((2S,3S,4S)-3,4-bis(benzyloxy)-5-hydroxypentan-2-yl)oxy)-2-((tert-butoxycarbonyl)amino)propanoate: IR (neat) 3439, 2977, 1707, 1497, 1367, 1161, 1062, 734, 698 cm$^{-1}$; $^1$H NMR (400 MHz, CDCl$_3$) δ 7.38-7.24 (m, 10H), 5.36 (d, J=8.6 Hz, 1H), 4.70-4.55 (m, 4H), 4.47-4.36 (m, 1H), 3.80-3.53 (m, 7H), 3.67 (s, 3H), 2.10-2.00 (m, 1H), 1.46 (s, 9H), 1.25 (d, J=6.0 Hz, 3H); ESIMS m/z 540.3 ([M+Na]$^+$).

Example 8

Steps 3 to 5: Preparation of N-((3S,7S,8S,9S)-7,8-bis(benzyloxy)-9-methyl-2-oxo-1,5-dioxonan-3-yl)-3-hydroxy-4-methoxypicolinamide (compound 11)

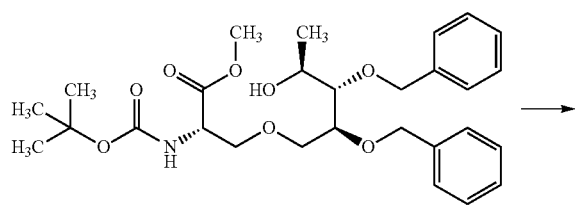

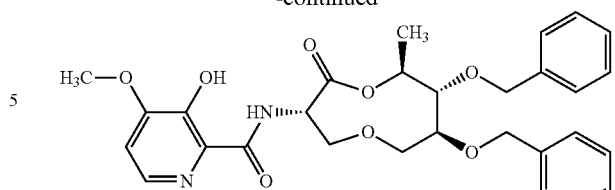

Compound 11 was prepared in three steps: Step 3 was performed in the same manner as described in Example 1, Step 4 to give compound 93 (see Example 7, Step 2); Step 4 was performed in the same manner as described in Example 5, Step 7 to give compound 174; Step 5 was performed in the same manner as described in Example 5, Step 8 to give the title compound as a white solid (137.0 mg, 45% overall yield over three steps): mp 144-146° C.; IR (neat) 3363, 2935, 1749, 1648, 1527, 1263, 1076 cm$^{-1}$; $^1$H NMR (400 MHz, CDCl$_3$) δ 11.93 (s, 1H), 8.69 (d, J=8.1 Hz, 1H), 8.00 (d, J=5.2 Hz, 1H), 7.37-7.25 (m, 10H), 6.87 (d, J=5.2 Hz, 1H), 5.13-5.02 (m, 2H), 4.95 (d, J=10.8 Hz, 1H), 4.70-4.61 (m, 2H), 4.62 (d, J=10.8 Hz, 1H), 4.07 (dd, J=11.9, 6.7 Hz, 1H), 4.02-3.96 (m, 1H), 3.94 (s, 3H), 3.87 (dd, J=11.9, 4.8 Hz, 1H), 3.70 (dd, J=11.3, 6.6 Hz, 1H), 3.56-3.45 (m, 2H), 1.46 (d, J=6.3 Hz, 3H); $^{13}$C NMR (101 MHz, CDCl$_3$) δ 170.31, 169.11, 155.47, 148.87, 140.82, 138.23, 138.06, 130.35, 128.56, 128.54, 128.11, 128.01, 127.91, 109.72, 84.84, 83.68, 75.95, 75.78, 74.38, 73.14, 73.12, 56.23, 52.40, 18.85; ESIMS m/z 537 ([M+H]$^+$); HRMS-ESI (m/z) [M]$^+$ calcd for C$_{29}$H$_{32}$N$_2$O$_8$, 536.2159; found, 536.2150.

Example 9

Step 1: Preparation of (2S,3S,4S)-4-(benzyloxy)-2-methyl-3,4-dihydro-2H-pyran-3-ol and (2S,3R,4S)-3-(benzyloxy)-2-methyl-3,4-dihydro-2H-pyran-4-ol

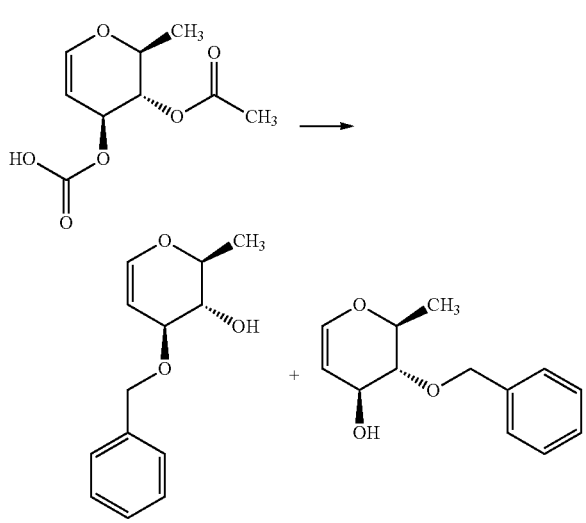

To a stirred solution of (2S,3S,4S)-2-methyl-3,4-dihydro-2H-pyran-3,4-diyl diacetate (20.0 g, 93.0 mmol) in DCM (934 ml) were added (bromomethyl)benzene (11.6 ml, 98.0 mmol), tetrabutylammonium iodide (17.2 g, 46.7 mmol) and a 50% aqueous NaOH solution (49.3 ml, 934 mmol). The resulting mixture was stirred at room temperature for 16 h and then diluted with H₂O. The organic phase was separated and the aqueous layer was extracted with DCM. The combined organic phases were washed with H₂O and brine, dried over Na₂SO₄, filtered, and concentrated to give a colorless oil, which was dissolved in MeOH (150 mL) and treated with potassium carbonate (K₂CO₃; 1.29 g, 9.34 mmol). The reaction mixture was stirred at room temperature for 16 h, concentrated and filtered through a shourt plug of SiO₂ (EtOAc as eluent) to give a pale-yellow filtrate, from which some tetrabutylammonium iodide precipitated out during the filtration. The precipitate was removed by a second filtration and the filtrate was concentrated and purified by flash chromatography (SiO₂, hexanes/EtOAc gradient) to yield the title compounds.

(2S,3S,4S)-4-(Benzyloxy)-2-methyl-3,4-dihydro-2H-pyran-3-ol (0.932 g, 5%) as a light yellow oil: IR (neat) 3416, 2933, 1722, 1645, 1453, 1267, 1049, 735, 698 cm⁻¹; ¹H NMR (400 MHz, CDCl₃) δ 7.42-7.24 (m, 5H), 6.35 (dd, J=6.1, 1.4 Hz, 1H), 4.85 (dd, J=6.2, 2.2 Hz, 1H), 4.70 (d, J=11.7 Hz, 1H), 4.55 (d, J=11.7 Hz, 1H), 4.05 (dt, J=7.0, 1.9 Hz, 1H), 3.89 (dq, J=9.3, 6.3 Hz, 1H), 3.65-3.58 (m, 1H), 2.31 (bs, 1H), 1.38 (d, J=6.4 Hz, 3H); ¹³C NMR (101 MHz, CDCl₃) δ 145.12, 138.42, 128.68, 127.98, 127.96, 99.83, 77.00, 74.59, 72.85, 70.63, 17.29.

(2S,3R,4S)-3-(Benzyloxy)-2-methyl-3,4-dihydro-2H-pyran-4-ol (6.82 g, 33%) as a white solid.

Example 9

Step 2: Preparation of (2S,3S,4S)-4-(benzyloxy)-3-butoxy-2-methyl-3,4-dihydro-2H-pyran To a solution of (2S,3S,4S)-4-(benzyloxy)-2-methyl-3,4-dihydro-2H-pyran-3-ol (0.100 g, 0.454 mmol) in DMF (2.67 ml) at 0° C. was added NaH (45.0 mg, 1.13 mmol, 60% dispersion in mineral oil) and the reaction was stirred for 20 min at 0° C. Tetrabutylammonium iodide (34.0 mg, 0.091 mmol) and 1-iodobutane (0.20 mL, 1.76 mmol) were added and the reaction was stirred at room temperature for 18 h. The reaction was cooled to 0° C., additional NaH in (23.0 mg, 0.575 mmol) and 1-iodobutane (0.10 mL, 0.879 mmol) were added, and the reaction was warmed to 70° C. and stirred for 4 h. The reaction was cooled to room temperature, quenched with H₂O, and extracted with EtOAc. The organic layer was separated and the aqueous layer was further extracted with EtOAc. The combined organic phases were washed with brine, dried over MgSO₄, filtered, and concentrated to yield a pale-yellow oil. Purification of the crude oil by flash chromatography (SiO₂, hexanes/EtOAc gradient) yielded the title compound as a colorless oil (93.0 mg, 74%): IR (neat) 2933, 2871, 1646, 1453, 1239, 1107, 1056, 734, 697 cm⁻¹; ¹H NMR (400 MHz, CDCl₃) δ 7.41-7.24 (m, 5H), 6.34 (dd, J=6.1, 1.3 Hz, 1H), 4.83 (dd, J=6.1, 2.5 Hz, 1H), 4.67 (d, J=11.7 Hz, 1H), 4.59 (d, J=11.7 Hz, 1H), 4.11 (ddd, J=6.5, 2.2, 1.6 Hz, 1H), 3.89 (ddd, J=13.5, 9.3, 6.7 Hz, 1H), 3.83 (dt, J=9.2, 6.5 Hz, 1H), 3.63 (dt, J=9.2, 6.6 Hz, 1H), 3.30 (dd, J=9.0, 6.6 Hz, 1H), 1.64-1.51 (m, 2H), 1.44-1.33 (m, 2H), 1.38 (d, J=6.4 Hz, 3H), 0.92 (t, J=7.4 Hz, 3H); ¹³C NMR (101 MHz, CDCl₃) δ 144.82, 138.69, 128.49, 127.81, 127.69, 100.49, 80.35, 76.53, 74.29, 72.32, 70.83, 32.52, 19.47, 17.53, 14.06; HRMS-ESI (m/z) [M]⁺ calcd for C₁₇H₂₄O₃, 276.1725; found, 276.1710.

Example 9

Steps 3 to 5: Preparation of tert-butyl ((3S,7S,8S,9S)-7-(benzyloxy)-8-butoxy-9-methyl-2-oxo-1,5-dioxonan-3-yl)carbamate (compound 99)

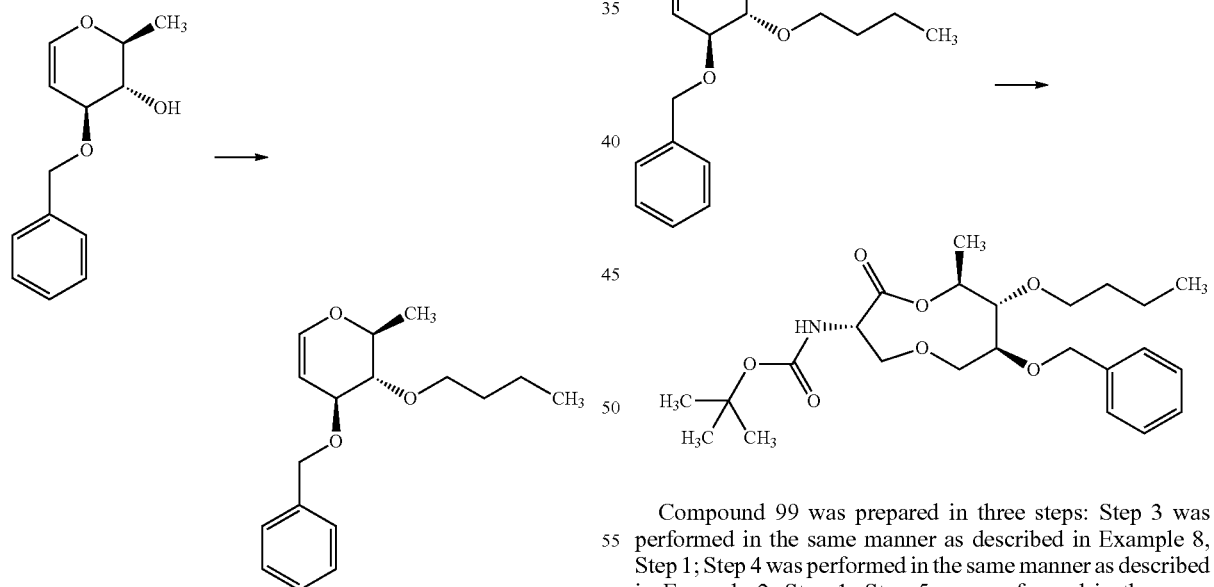

Compound 99 was prepared in three steps: Step 3 was performed in the same manner as described in Example 8, Step 1; Step 4 was performed in the same manner as described in Example 2, Step 1; Step 5 was performed in the same manner as described in Example 1, Step 4 to give the title compound as a white solid (138 mg, 9.6% overall yield over three steps): mp 51-54° C.; ¹H NMR (400 MHz, CDCl₃) δ 7.36-7.25 (m, 5H), 5.32-5.21 (m, 1H), 4.91 (dq, J=9.5, 6.3 Hz, 1H), 4.68-4.60 (m, 1H), 4.62 (s, 2H), 3.96-3.81 (m, 3H), 3.67 (dd, J=11.6, 4.8 Hz, 1H), 3.58 (dd, J=10.8, 7.3 Hz, 1H), 3.50 (dd, J=15.5, 6.9 Hz, 1H), 3.36 (dd, J=12.0, 4.8 Hz, 1H), 3.23 (t, J=9.1 Hz, 1H), 1.60-1.44 (m, 2H), 1.44 (d, J=5.8 Hz, 3H), 1.43 (s, 9H), 1.41-1.22 (m, 2H), 0.88 (t, J=7.3 Hz, 3H); ¹³C NMR (101 MHz, CDCl₃) δ 171.47, 155.24, 138.27, 128.50, 127.88, 127.81, 85.31, 83.48, 80.28, 75.53, 74.86, 74.01, 73.14, 73.03, 53.77, 32.60, 28.42, 19.49, 18.71, 14.11; ESIMS m/z 452.3 ([M+H]⁺).

Example 9

Steps 6 and 7: Preparation of N-((3S,7S,8S,9S)-7-(benzyloxy)-8-butoxy-9-methyl-2-oxo-1,5-dioxonan-3-yl)-3-hydroxy-4-methoxypicolinamide (compound 32)

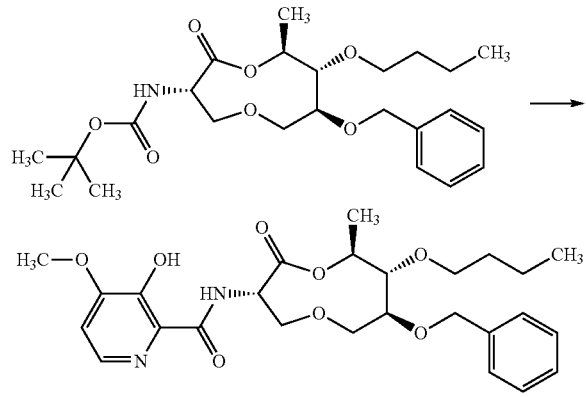

Compound 32 was prepared in two steps: Step 6 was performed in the same manner as described in Example 5, Step 7 to give compound 176; Step 7 was performed in the same manner as described in Example 5, Step 8, to give the title compound as a white solid (84.8 mg, 55% overall yield over two steps): mp 105-107° C.; IR (neat) 3347, 2957, 1732, 1642, 1540, 1435, 1285, 1261, 1206, 1081 cm⁻¹; ¹H NMR (400 MHz, CDCl₃) δ 12.00-11.55 (m, 1H), 8.67 (d, J=8.1 Hz, 1H), 8.00 (d, J=5.2 Hz, 1H), 7.39-7.27 (m, 5H), 6.87 (d, J=5.2 Hz, 1H), 5.04 (ddd, J=8.1, 6.8, 5.0 Hz, 1H), 4.99 (ddd, J=15.8, 7.8, 4.6 Hz, 1H), 4.64 (s, 2H), 4.05 (dd, J=11.9, 6.8 Hz, 1H), 3.94 (s, 3H), 3.94-3.84 (m, 2H), 3.83 (dd, J=11.9, 5.0 Hz, 1H), 3.65 (dd, J=11.2, 7.1 Hz, 1H), 3.52 (dt, J=8.8, 6.8 Hz, 1H), 3.42 (ddd, J=8.4, 7.1, 1.3 Hz, 1H), 3.27 (t, J=9.1 Hz, 1H), 1.59-1.49 (m, 2H), 1.47 (d, J=6.3 Hz, 3H), 1.41-1.27 (m, 2H), 0.89 (t, J=7.4 Hz, 3H); ¹³C NMR (101 MHz, CDCl₃) δ 170.40, 169.09, 155.47, 148.87, 140.81, 138.25, 130.36, 128.52, 127.89, 127.84, 109.71, 85.27, 83.44, 75.66, 74.20, 74.04, 73.32, 73.19, 56.23, 52.31, 32.61, 19.50, 18.72, 14.12; HRMS-ESI (m/z) [M]⁺ calcd for C₂₆H₃₄N₂O₈, 502.2315; found, 502.2324.

Example 10

Steps 1 to 4: Preparation of tert-butyl ((3S,7S,8S, 9S)-8-(benzyloxy)-7-butoxy-9-methyl-2-oxo-1,5-dioxonan-3-yl)carbamate (compound 100)

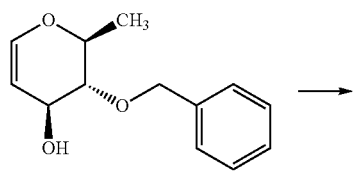

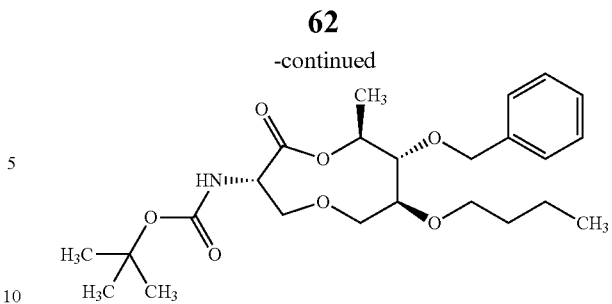

Compound 100 was prepared in four steps: Step 1 was performed in the same manner as described in Example 9, Step 2; Step 2 was performed in the same manner as described in Example 8, Step 1; Step 3 was performed in the same manner as described in Example 2, Step 1, and Step 4 was performed in the same manner as described in Example 1, Step 4 to give the title compound as a colorless oil (1.052 g, 18% overall yield over four steps): IR (neat) 3347, 2932, 1754, 1714, 1498, 1367, 1163, 1094 cm⁻¹; ¹H NMR (400 MHz, CDCl₃) δ 7.38-7.24 (m, 5H), 5.34-5.23 (m, 1H), 5.02-4.91 (m, 1H), 4.93 (d, J=10.8 Hz, 1H), 4.68-4.60 (m, 1H), 4.59 (d, J=10.9 Hz, 1H), 3.92 (dd, J=11.8, 6.7 Hz, 1H), 3.81 (d, J=11.1 Hz, 1H), 3.68 (dd, J=11.7, 4.9 Hz, 1H), 3.60 (t, J=6.7 Hz, 1H), 3.58 (t, J=6.8 Hz, 1H), 3.51 (dt, J=9.1, 6.6 Hz, 1H), 3.37 (t, J=9.0 Hz, 1H), 3.26 (t, J=7.4 Hz, 1H), 1.59-1.49 (m, 2H), 1.43 (s, 9H), 1.41 (d, J=6.3 Hz, 3H), 1.40-1.30 (m, 2H), 0.88 (t, J=7.4 Hz, 3H); ¹³C NMR (101 MHz, CDCl₃) δ 171.43, 155.22, 138.42, 128.49, 128.04, 127.83, 84.76, 83.99, 80.24, 75.84, 75.35, 74.81, 72.82, 70.78, 53.76, 32.31, 28.40, 19.47, 18.82, 14.02; HRMS-ESI (m/z) [M]⁺ calcd for C₂₄H₃₇NO₇, 451.2570; found, 451.2560.

Example 10

Step 5: Preparation of (3S,7S,8S,9S)-3-amino-8-(benzyloxy)-7-butoxy-9-methyl-1,5-dioxonan-2-one hydrochloride (compound 125)

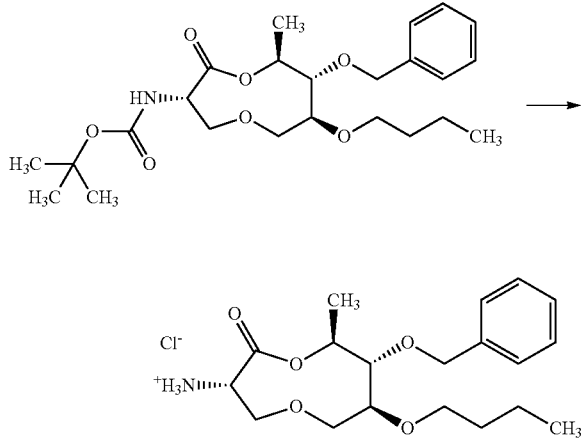 [SMILES: CCCCO[C@H]1COC[C@H](NC(=O)OC(C)(C)C)C(=O)O[C@@H](C)[C@@H]1OCc1ccccc1 ; [Cl-] ; CCCCO[C@H]1COC[C@H]([NH3+])C(=O)O[C@@H](C)[C@@H]1OCc1ccccc1]

Compound 125 was prepared in the same manner as described in Example 5, Step 7 to give the title compound as a white solid (107.2 mg, quantitative): mp 174-177° C.; ¹H NMR (400 MHz, CDCl₃) δ 8.71 (bs, 1H), 7.36-7.25 (m, 5H), 5.04-4.90 (m, 1H), 4.92 (d, J=10.8 Hz, 1H), 4.63-4.47 (m, 2H), 4.39-4.21 (m, 1H), 4.16-3.97 (m, 1H), 3.94-3.79 (m, 1H), 3.64-3.42 (m, 3H), 3.40-3.22 (m, 2H), 1.57-1.45 (m, 2H), 1.44-1.21 (m, 7H), 0.86 (t, J=7.3 Hz, 3H); $^{13}$C NMR (101 MHz, CDCl$_3$) δ 168.62, 138.39, 128.50, 128.06, 127.85, 84.55, 83.65, 76.01, 75.84, 73.82, 71.16, 70.82, 53.59, 32.36, 19.50, 18.76, 14.08; ESIMS m/z 352.2 ([M+H]$^+$).

Example 10

Step 6: Preparation of N-((3S,7S,8S,9S)-8-(benzyloxy)-7-butoxy-9-methyl-2-oxo-1,5-dioxonan-3-yl)-3-hydroxy-4-methoxypicolinamide (compound 33)

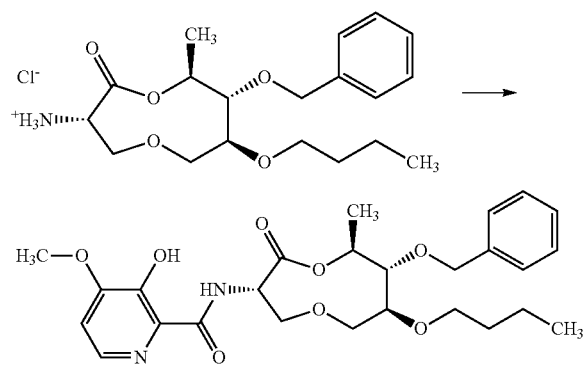

Compound 33 was prepared in the same manner as described in Example 5, Step 8 to give the title compound as a white solid (95.7 mg, 69%): mp 117-119° C.; IR (neat) 3363, 2933, 1749, 1648, 1528, 1243, 1091 cm$^{-1}$; $^1$H NMR (400 MHz, CDCl$_3$) δ 11.93 (s, 1H), 8.67 (d, J=8.1 Hz, 1H), 8.00 (d, J=5.2 Hz, 1H), 7.42-7.26 (m, 5H), 6.87 (d, J=5.2 Hz, 1H), 5.07-4.98 (m, 2H), 4.95 (d, J=10.9 Hz, 1H), 4.61 (d, J=10.9 Hz, 1H), 4.06 (dd, J=11.9, 6.8 Hz, 1H), 3.94 (s, 3H), 3.90-3.79 (m, 2H), 3.69-3.49 (m, 3H), 3.41 (t, J=9.0 Hz, 1H), 3.32 (ddd, J=8.4, 6.9, 1.2 Hz, 1H), 1.59-1.50 (m, 2H), 1.44 (d, J=6.3 Hz, 3H), 1.41-1.29 (m, 2H), 0.89 (t, J=7.4 Hz, 3H); $^{13}$C NMR (101 MHz, CDCl$_3$) δ 170.38, 169.10, 155.47, 148.87, 140.80, 138.40, 130.35, 128.53, 128.09, 127.89, 109.71, 84.72, 83.97, 75.89, 75.51, 74.18, 73.12, 70.86, 56.23, 52.32, 32.34, 19.50, 18.86, 14.05; HRMS-ESI (m/z) [M]$^+$ calcd for C$_{26}$H$_{34}$N$_2$O$_8$, 502.2315; found, 502.2324.

Example 11

Step 1: Preparation of tert-butyl ((3S,7S,8R,9S)-7,8-dihydroxy-9-methyl-2-oxo-1,5-dioxonan-3-yl)carbamate (compound 102)

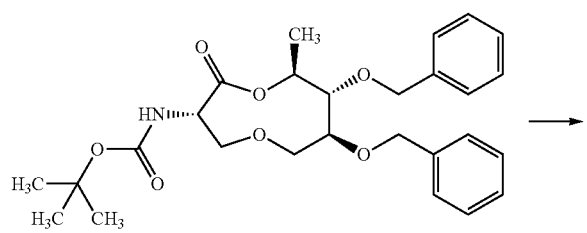

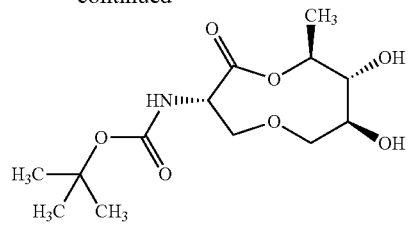

Compound 102 was prepared in the same manner as described in Example 7, Step 4 to give the title compound as a white solid (290 mg, quantitative): IR (neat) 3357, 2979, 1751, 1691, 1523, 1368, 1163, 1047 cm$^{-1}$; $^1$H NMR (400 MHz, CDCl$_3$) δ 5.52 (d, J=7.9 Hz, 1H), 5.02 (dq, J=12.7, 6.3 Hz, 1H), 4.67-4.58 (m, 1H), 4.10-4.01 (m, 1H), 3.93 (dd, J=11.7, 2.6 Hz, 1H), 3.84 (dd, J=11.7, 5.8 Hz, 1H), 3.52-3.36 (m, 3H), 3.08 (bs, 1H), 2.90 (bs, 1H), 1.47 (d, J=6.3 Hz, 3H), 1.43 (s, 9H); $^{13}$C NMR (101 MHz, CDCl$_3$) δ 171.04, 155.49, 80.40, 79.61, 78.32, 76.66, 74.59, 73.06, 54.80, 28.44, 18.74; ESIMS m/z 304.2 ([M–H]$^-$).

Example 11

Step 2: Preparation of (3S,7S,8S,9S)-3-((tert-butoxycarbonyl)amino)-9-methyl-2-oxo-1,5-dioxonane-7,8-diyl bis(2-methylpropanoate) (compound 103)

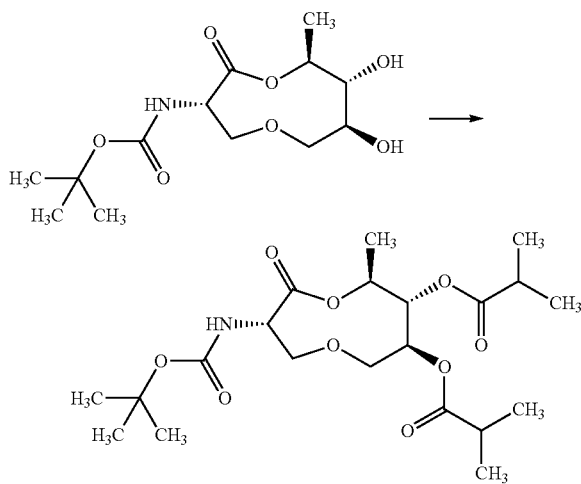

To a solution of tert-butyl ((3S,7S,8R,9S)-7,8-dihydroxy-9-methyl-2-oxo-1,5-dioxonan-3-yl)carbamate (115.0 mg, 0.245 mmol) in pyridine (1.75 mL) was added DMAP (6.40 mg, 0.0520 mmol) followed by isobutyryl chloride (0.10 mL, 0.956 mmol) at 0° C. and the reaction was slowly warmed to room temperature and stirred for 16 h. The reaction mixture was quenched with H$_2$O and the reaction was stirred at room temperature for 30 min and then extracted with Et$_2$O. The phases were separated and the aqueous phase was further extracted with Et$_2$O. The combined organic phases were washed with brine, dried over MgSO$_4$, filtered, and the filtrate was concentrated and purified by flash chromatography (SiO$_2$, hexanes/EtOAc gradient) to yield the title compound as a colorless, thick oil (115 mg, 94%): IR (neat) 3353, 2976, 1742, 1519, 1368, 1251, 1155 cm$^{-1}$; $^1$H NMR (400 MHz, CDCl$_3$) δ 5.41 (d, J=8.2 Hz, 1H), 5.21-5.12 (m, 1H), 5.12-5.04 (m, 1H), 4.92-4.83 (m, 1H), 4.74 (dd, J=13.4, 6.9 Hz, 1H), 3.95 (dd, J=11.7, 7.0 Hz, 1H), 3.80-3.65 (m, 3H), 2.64-2.41 (m, 2H), 1.44 (s, 9H), 1.32 (d, J=6.2 Hz, 3H), 1.20 (d, J=7.0 Hz, 3H), 1.16 (d, J=7.0 Hz, 3H), 1.14 (d, J=7.0 Hz, 3H), 1.10 (d, J=7.0 Hz, 3H); $^{13}$C NMR (101 MHz, CDCl$_3$) δ 175.57, 175.47, 171.37, 155.18, 80.34, 74.52, 74.30, 74.15, 73.35, 71.34, 34.01, 33.91, 28.30, 19.01, 18.88, 18.74, 18.71, 18.03; HRMS-ESI (m/z) [M]$^+$ calcd for C$_{21}$H$_{35}$NO$_9$, 445.2312; found, 445.2322.

Compound 261 was prepared in the same manner as described in Example 11, Step 2 starting from compound 256.

Compound 262 was prepared in the same manner as described in Example 11, Step 2 starting from compound 257.

Example 11

Step 3: Preparation of (3S,7S,8S,9S)-3-amino-9-methyl-2-oxo-1,5-dioxonane-7,8-diyl bis(2-methylpropanoate) hydrochloride (compound 177)

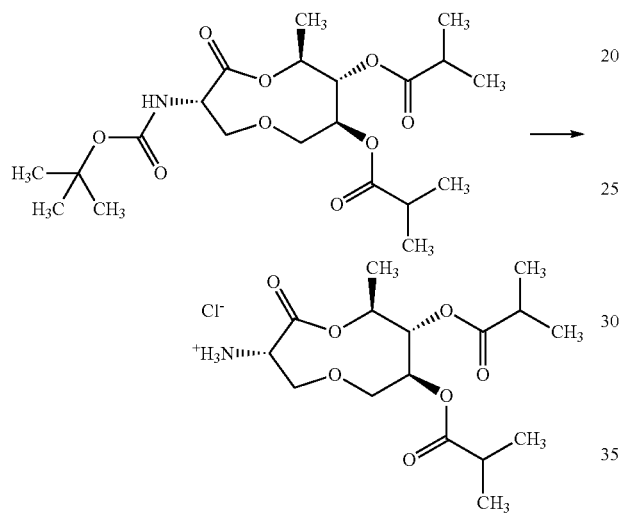

Compound 177 was prepared in the same manner as described in Example 5, Step 7 to give the title compound as a light yellow solid (97.0 mg, quantitative): $^1$H NMR (400 MHz, CDCl$_3$) δ 8.83 (bs, 1H), 5.24-5.12 (m, 2H), 4.88-4.80 (m, 1H), 4.71-4.63 (m, 1H), 4.45 (dd, J=12.9, 3.3 Hz, 1H), 4.12 (dd, J=12.7, 6.5 Hz, 1H), 3.85 (d, J=10.8 Hz, 1H), 3.73 (dd, J=11.9, 7.9 Hz, 1H), 2.57-2.39 (m, 2H), 1.82-1.52 (m, 2H), 1.35 (d, J=5.7 Hz, 3H), 1.16 (d, J=7.0 Hz, 3H), 1.13 (d, J=7.0 Hz, 3H), 1.10 (d, J=7.0 Hz, 3H), 1.09 (d, J=7.0 Hz, 3H); ESIMS m/z 346.7 ([M+H]$^+$).

Example 11

Step 4: Preparation of (3S,7S,8S,9S)-3-(3-hydroxy-4-methoxypicolinamido)-9-methyl-2-oxo-1,5-dioxonane-7,8-diyl bis(2-methylpropanoate) (compound 56)

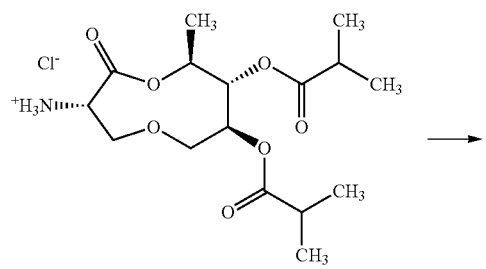

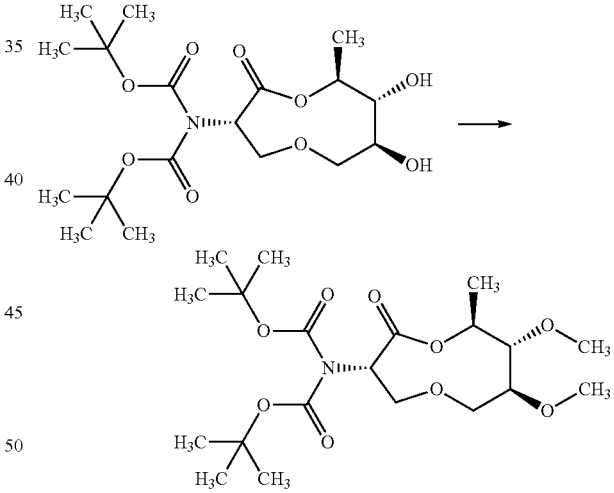

Compound 56 was prepared in the same manner as described in Example 5, Step 8 to give the title compound as a white solid (70.0 mg, 56%): mp 111-113° C.; IR (neat) 3364, 2974, 1738, 1649, 1529, 1242, 1140 cm$^{-1}$; $^1$H NMR (400 MHz, CDCl$_3$) δ 11.85 (s, 1H), 8.64 (d, J=8.3 Hz, 1H), 7.98 (d, J=5.2 Hz, 1H), 6.86 (d, J=5.2 Hz, 1H), 5.22-5.12 (m, 2H), 5.10 (ddd, J=8.2, 7.0, 5.4 Hz, 1H), 4.90 (ddd, J=8.9, 6.5, 2.6 Hz, 1H), 4.07 (dd, J=11.9, 6.9 Hz, 1H), 3.92 (s, 3H), 3.83 (dd, J=11.9, 5.2 Hz, 1H), 3.81-3.72 (m, 2H), 2.57-2.39 (m, 2H), 1.33 (d, J=5.9 Hz, 3H), 1.15 (d, J=7.0 Hz, 3H), 1.13 (d, J=7.0 Hz, 3H), 1.10 (d, J=7.0 Hz, 3H), 1.09 (d, J=7.0 Hz, 3H); $^{13}$C NMR (101 MHz, CDCl$_3$) δ 175.60, 175.50, 170.26, 169.09, 155.46, 148.85, 140.83, 130.20, 109.76, 74.87, 74.19, 73.95, 73.35, 71.71, 56.21, 52.03, 34.08, 33.99, 19.09, 18.98, 18.81, 18.79, 18.11; HRMS-ESI (m/z) [M]$^+$ calcd for C$_{23}$H$_{32}$N$_2$O$_{10}$, 496.2057; found, 496.2063.

Example 12

Step 1: Preparation of tert-butyl N-tert-butoxycarbonyl-N-[(3S,7S,8S,9S)-7,8-dimethoxy-9-methyl-2-oxo-1,5-dioxonan-3-yl]carbamate (compound 104)

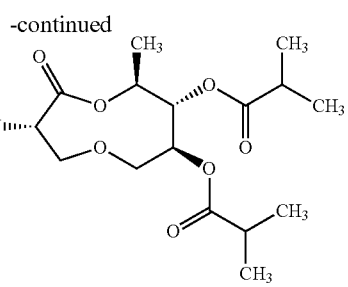

To solution of tert-butyl N-tert-butoxycarbonyl-N-[(3S,7S,8R,9S)-7,8-dihydroxy-9-methyl-2-oxo-1,5-dioxonan-3-yl]carbamate (0.220 g, 0.543 mmol) and Na$_2$SO$_4$ (500 mg) in CH$_2$Cl$_2$ (5.4 mL) at 0° C. was added Proton-Sponge™ (1.63 g, 7.60 mmol) and trimethyloxonium tetrafluoroborate (0.562 g, 3.80 mmol). The reaction mixture was slowly warmed to room temperature and stirred overnight. The reaction mixture was diluted with EtOAc and filtered. The organic layer was washed successively with H$_2$O, 1 M aqueous NaHSO$_4$, and saturated aqueous NaHCO$_3$. The organic layer was dried over MgSO$_4$, filtered, and the filtrate was concentrated and purified by flash chromatography (SiO$_2$, hexanes/EtOAc gradient) to yield the title compound as a colorless oil (133 mg, 57%): IR (neat) 2980, 2935, 1746, 1707, 1367, 1254, 1106 cm$^{-1}$; $^1$H NMR (400 MHz, CDCl$_3$) δ 5.19 (dd, J=8.9, 4.2 Hz, 1H), 4.75 (dq, J=9.4, 6.3 Hz, 1H), 4.23 (dd, J=12.1, 4.2 Hz, 1H), 3.89 (dd, J=12.1, 9.0 Hz, 1H), 3.80 (d, J=10.6 Hz, 1H), 3.56-3.48 (m, 1H), 3.52 (s, 3H), 3.42 (s, 3H), 3.17-3.11 (m, 1H), 3.06 (t, J=9.0 Hz, 1H), 1.48 (s, 18H), 1.40 (d, J=6.3 Hz, 3H); $^{13}$C NMR (101 MHz, CDCl$_3$) δ 169.10, 152.73, 86.77, 85.12, 83.13, 75.07, 72.76, 72.52, 61.21, 58.43, 57.94, 28.03, 18.65; HRMS-ESI (m/z) [M]$^+$ calcd for C$_{20}$H$_{35}$NO$_9$, 433.2312; found, 433.2317.

Example 12

Steps 2 and 3: Preparation of N-((3S,7S,8S,9S)-7,8-dimethoxy-9-methyl-2-oxo-1,5-dioxonan-3-yl)-3-hydroxy-4-methoxypicolinamide (compound 63)

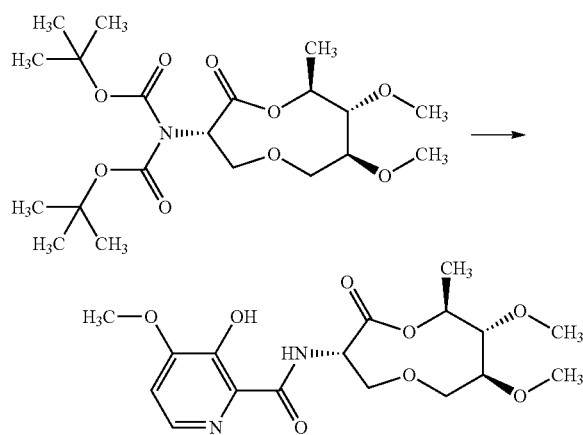

Compound 63 was prepared in two steps: Step 2 was performed in the same manner as described in Example 5, Step 7 to give compound 178; Step 3 was performed in the same manner as described in Example 5, Step 8, to give the title compound as a white solid (82.6 mg, 72%): mp 165-167° C.; IR (neat) 3365, 2982, 1733, 1643, 1535, 1285, 1091 cm$^{-1}$; $^1$H NMR (400 MHz, CDCl$_3$) δ 11.91 (s, 1H), 8.64 (s, 1H), 7.98 (d, J=5.2 Hz, 1H), 6.86 (d, J=5.2 Hz, 1H), 5.02 (ddd, J=8.1, 6.8, 5.1 Hz, 1H), 4.94 (dq, J=8.7, 6.3 Hz, 1H), 4.05 (dd, J=11.9, 6.8 Hz, 1H), 3.92 (s, 3H), 3.81 (d, J=11.8 Hz, 1H), 3.80 (d, J=11.9 Hz, 1H), 3.62-3.57 (m, 1H), 3.55 (s, 3H), 3.44 (s, 3H), 3.16-3.07 (m, 2H), 1.44 (d, J=6.3 Hz, 3H); $^{13}$C NMR (101 MHz, CDCl$_3$) δ 170.38, 169.06, 155.43, 148.82, 140.78, 130.29, 109.69, 86.83, 85.33, 74.75, 74.06, 72.92, 61.35, 58.47, 56.20, 52.23, 18.61; HRMS-ESI (m/z) [M]$^+$ calcd for C$_{17}$H$_{24}$N$_2$O$_8$, 384.1533; found, 384.1532.

Example 13

Step 1: Preparation of tert-butyl N-tert-butoxycarbonyl-N-[(3S,7S,8R,9S)-8-(1,1-dimethylallyloxy)-7-hydroxy-9-methyl-2-oxo-1,5-dioxonan-3-yl]carbamate (compound 105) and tert-butyl N-tert-butoxycarbonyl-N-[(3S,7S,8S,9S)-7-(1,1-dimethylallyloxy)-8-hydroxy-9-methyl-2-oxo-1,5-dioxonan-3-yl]carbamate (compound 106)

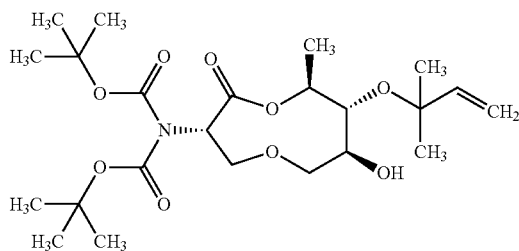

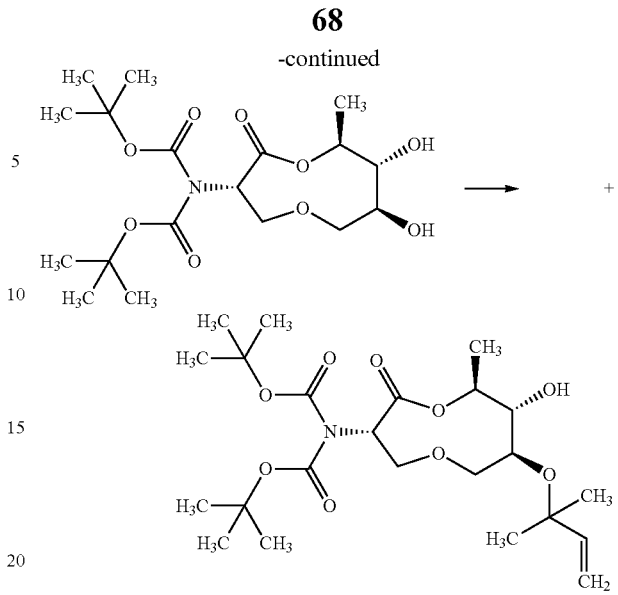

Compounds 105 and 106 were prepared in the same manner as described in Example 7, Step 5 to give the title compounds as pale yellow oils.

tert-Butyl N-tert-butoxycarbonyl-N-[(3S,7S,8R,9S)-8-(1,1-dimethylallyloxy)-7-hydroxy-9-methyl-2-oxo-1,5-dioxonan-3-yl]carbamate (compound 105) (140 mg, 30%): $^1$H NMR (400 MHz, CDCl$_3$) δ 5.81 (dd, J=17.7, 10.6 Hz, 1H), 5.17-5.14 (m, 1H), 4.99-4.86 (m, 2H), 4.19 (dd, J=11.6, 9.1 Hz, 1H), 4.13-4.02 (m, 2H), 3.83-3.71 (m, 2H), 3.55-3.47 (m, 2H), 2.78 (d, J=5.3 Hz, 1H), 1.48 (s, 18H), 1.38 (d, J=6.8 Hz, 3H), 1.27 (s, 3H), 1.23 (s, 3H); $^{13}$C NMR (101 MHz, CDCl$_3$) δ 169.43, 152.53, 143.20, 115.09, 83.16, 77.26, 76.60, 75.75, 74.16, 73.32, 71.73, 58.07, 28.00, 26.74, 26.30, 19.31; ESIMS m/z 496.7 ([M+Na]$^+$).

tert-Butyl N-tert-butoxycarbonyl-N-[(3S,7S,8S,9S)-7-(1,1-dimethylallyloxy)-8-hydroxy-9-methyl-2-oxo-1,5-dioxonan-3-yl]carbamate (compound 106) (200 mg, 43%): $^1$H NMR (400 MHz, CDCl$_3$) δ 5.79 (dd, J=17.8, 10.5 Hz, 1H), 5.18 (dd, J=8.2, 3.4 Hz, 1H), 5.15 (s, 1H), 5.11 (dd, J=5.6, 0.7 Hz, 1H), 4.95 (dq, J=12.9, 6.4 Hz, 1H), 4.14 (dd, J=12.4, 3.4 Hz, 1H), 3.96-3.84 (m, 2H), 3.45 (dd, J=10.6, 7.6 Hz, 1H), 3.41-3.32 (m, 2H), 3.05 (d, J=1.3 Hz, 1H), 1.47 (s, 18H), 1.42 (d, J=6.4 Hz, 3H), 1.29 (s, 3H), 1.26 (s, 3H); $^{13}$C NMR (101 MHz, CDCl$_3$) δ 169.01, 152.64, 142.56, 115.33, 83.07, 79.83, 77.47, 76.46, 74.46, 74.35, 74.01, 58.56, 28.04, 26.82, 25.82, 18.56; ESIMS m/z 496.7 ([M+Na]$^+$).

Example 13

Step 2: Preparation of tert-butyl N-tert-butoxycarbonyl-N-[(3S,7S,8S,9S)-7-(1,1-dimethylallyloxy)-9-methyl-8-(2-methylallyloxy)-2-oxo-1,5-dioxonan-3-yl]carbamate (compound 107)

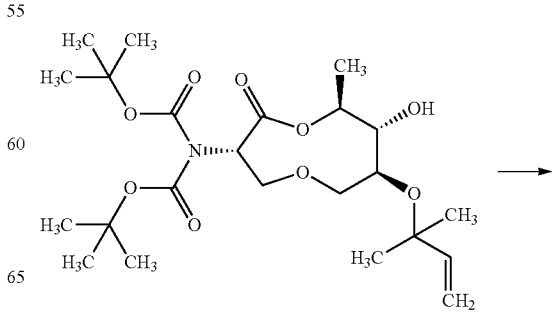

-continued

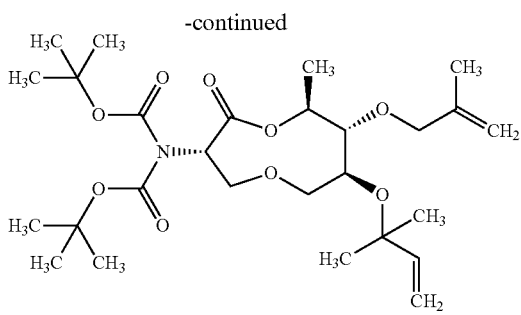

Compound 107 was prepared in the same manner as described in Example 7, Step 5 to give the title compound as a pale yellow oil (210 mg, 59%): $^1$H NMR (400 MHz, CDCl$_3$) δ 5.90 (dd, J=17.9, 10.5 Hz, 1H), 5.17 (dd, J=8.6, 4.1 Hz, 1H), 5.07-5.05 (m, 1H) 5.03 (dd, J=4.9, 1.1 Hz, 1H), 4.96-4.89 (m, 1H), 4.85-4.77 (m, 2H), 4.33 (d, J=12.1 Hz, 1H), 4.13 (dd, J=12.2, 4.1 Hz, 1H), 3.86 (dd, J=12.3, 8.6 Hz, 1H), 3.81 (t, J=11.8 Hz, 2H), 3.48 (dd, J=10.7, 7.2 Hz, 1H), 3.41 (t, J=7.5 Hz, 1H), 3.11 (t, J=8.8 Hz, 1H), 1.70 (s, 3H), 1.46 (s, 18H), 1.38 (d, J=6.3 Hz, 3H), 1.26 (s, 3H), 1.22 (s, 3H); $^{13}$C NMR (101 MHz, CDCl$_3$) δ 169.08, 152.57, 144.07, 142.26, 114.06, 111.66, 84.32, 83.01, 79.73, 77.43, 77.12, 76.01, 73.04, 72.85, 58.13, 28.01, 27.04, 25.68, 19.95, 18.83; ESIMS m/z 550.8 ([M+Na]$^+$).

Compound 109 was prepared in the same manner as described in Example 13, Step 2 using compound 105 as starting material.

Compounds 142 and 144 were prepared in the same manner as described in Example 13, Steps 1 and 2.

Example 13

Step 3: Preparation of tert-butyl N-tert-butoxycarbonyl-N-[(3S,7S,8S,9S)-7-(1,1-dimethylpropoxy)-8-isobutoxy-9-methyl-2-oxo-1,5-dioxonan-3-yl]carbamate (compound 108)

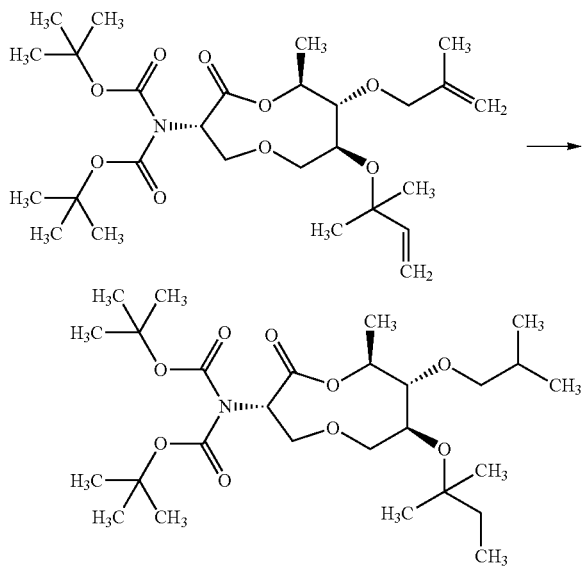

Compound 108 was prepared in the same manner as described in Example 7, Step 6 to give the title compound as a colorless oil (218 mg, 82%): $^1$H NMR (400 MHz, CDCl$_3$) δ 5.18 (dd, J=8.6, 3.8 Hz, 1H), 4.87-4.77 (m, 1H), 4.15 (dd, J=12.3, 3.9 Hz, 1H), 3.87 (dd, J=12.3, 8.6 Hz, 1H), 3.81 (dd, J=10.0, 4.3 Hz, 1H), 3.75 (dd, J=8.5, 5.6 Hz, 1H), 3.54-3.43 (m, 2H), 3.10-2.99 (m, 2H), 1.91-1.72 (m, 1H), 1.48 (s, 18H), 1.47-1.41 (m, 2H), 1.39 (d, J=6.3 Hz, 3H), 1.13 (s, 3H), 1.10 (s, 3H), 0.90 (d, J=6.6 Hz, 3H), 0.85 (t, J=7.5 Hz, 3H), 0.84 (d, J=6.7 Hz, 3H); $^{13}$C NMR (101 MHz, CDCl$_3$) δ 169.10, 152.63, 84.90, 83.01, 81.02, 80.20, 77.56, 75.09, 73.14, 73.07, 58.27, 35.03, 29.04, 28.04, 25.12, 25.00, 19.89, 19.53, 18.97, 9.00; ESIMS m/z 553.4 ([M+Na]$^+$).

Compound 110 was prepared in the same manner as described in Example 13, Step 3 using compound 109 as starting material.

Compounds 145 and 146 were prepared in the same manner as described in Example 13, Step 3.

Example 13

Steps 4 and 5, Method A: Preparation of 3-hydroxy-N-((3S,7S,8S,9S)-8-isobutoxy-9-methyl-2-oxo-7-(tert-pentyloxy)-1,5-dioxonan-3-yl)-4-methoxypicolinamide (compound 71)

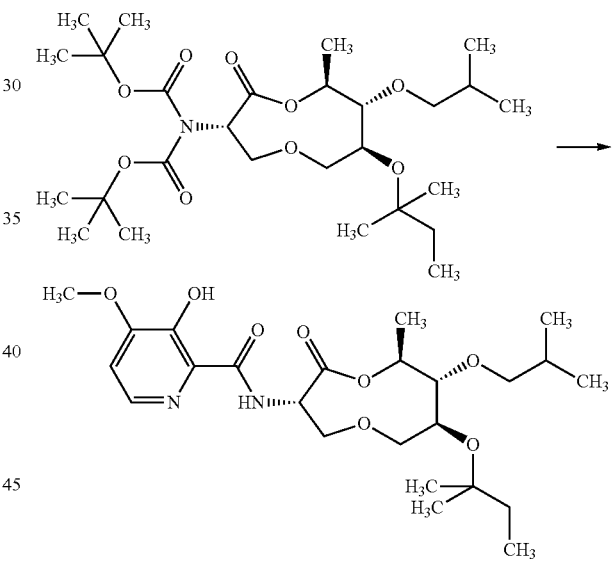

Step 4: To a solution of tert-butyl N-tert-butoxycarbonyl-N-[(3S,7S,8S,9S)-7-(1,1-dimethylpropoxy)-8-isobutoxy-9-methyl-2-oxo-1,5-dioxonan-3-yl]carbamate (165.0 mg, 0.310 mmol) in CH$_2$Cl$_2$ (4.3 mL) was added 2,6-lutidine (0.108 mL, 0.931 mmol) and trimethylsilyl trifluoromethanesulfonate (0.140 mL, 0.776 mmol) and the resulting solution was stirred at room temperature for 2 h. The reaction was treated with MeOH (2 mL), stirred at room temperature overnight, concentrated, and dried under high vacuum to give, (3S,7S,8S,9S)-3-amino-7-(1,1-dimethylpropoxy)-8-isobutoxy-9-methyl-1,5-dioxonan-2-one (Compound 179) as a colorless oil, which was used directly for the coupling reaction.

Step 5: To a mixture of (3S,7S,8S,9S)-3-amino-7-(1,1-dimethylpropoxy)-8-isobutoxy-9-methyl-1,5-dioxonan-2-one and 3-hydroxy-4-methoxypicolinic acid (79.0 mg, 0.466 mmol) in DCM (2.0 mL) were added 4-methylmorpholine (0.205 mL, 1.86 mmol) followed by HATU (189 mg, 0.497 mmol) and the mixture was stirred at room temperature for 16 h. The reaction mixture was directly purified by flash chromatography (SiO$_2$, hexanes/EtOAc gradient) to yield the title compound as a white solid (50.0 mg, 42%): mp 138-140° C.; IR (neat) 3370, 2926, 1750, 1650, 1529, 1243, 1085 cm$^{-1}$; $^1$H NMR (400 MHz, CDCl$_3$) δ 11.98 (s, 1H), 8.73 (d, J=8.0 Hz, 1H), 8.01 (d, J=5.2 Hz, 1H), 6.87 (d, J=5.2 Hz, 1H), 5.08 (dq, J=9.1, 6.3 Hz, 1H), 5.00 (ddd, J=8.1, 6.1, 3.8 Hz, 1H), 4.00 (dd, J=12.1, 6.1 Hz, 1H), 3.94 (s, 3H), 3.95-3.89 (m, 2H), 3.79 (dd, J=8.6, 5.6 Hz, 1H), 3.56-3.45 (m, 2H), 3.07 (dt, J=12.6, 8.4 Hz, 2H), 1.90-1.78 (m, 1H), 1.56-1.43 (m, 2H), 1.45 (d, J=6.4 Hz, 3H), 1.15 (s, 3H), 1.14 (s, 3H), 0.93 (d, J=6.6 Hz, 3H), 0.91-0.85 (m, 6H); $^{13}$C NMR (101 MHz, CDCl$_3$) δ 170.17, 169.09, 155.47, 148.89, 140.79, 130.47, 109.68, 85.26, 81.29, 81.18, 77.82, 75.32, 75.19, 73.37, 56.23, 53.07, 35.01, 29.10, 25.16, 25.08, 19.95, 19.60, 18.97, 9.06; HRMS-ESI (m/z) [M]$^+$ calcd for C$_{24}$H$_{38}$N$_2$O$_8$, 482.2628; found, 482.2631.

Compound 193 was prepared in the same manner as described in Example 13, Step 4 using compound 110 as starting material.

Compound 79 was prepared in the same manner as described in Example 13, Step 5 using compound 193 as starting material.

Example 13

Steps 4 and 5, Method B: Preparation of 3-hydroxy-N-((3S,7S,8R,9S)-7-hydroxy-8-isobutoxy-9-methyl-2-oxo-1,5-dioxonan-3-yl)-4-methoxypicolinamide (compound 72)

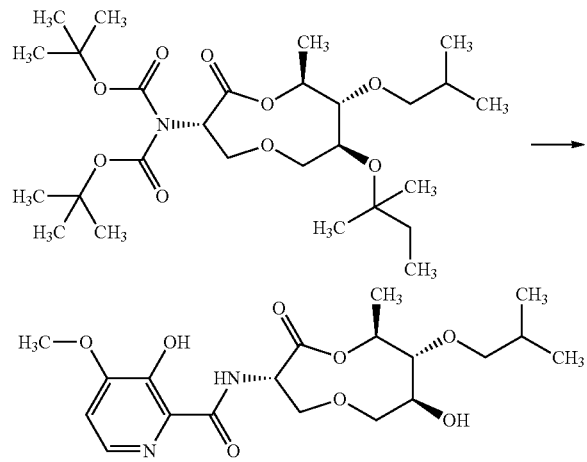

Compound 72 was prepared in the same manner as described in Example 5, Steps 7 and 8 using compound 108 as starting material: $^1$H NMR (400 MHz, CDCl$_3$) δ 11.92 (d, J=0.7 Hz, 1H), 8.75 (d, J=8.2 Hz, 1H), 7.98 (d, J=5.2 Hz, 1H), 6.86 (d, J=5.2 Hz, 1H), 5.12 (dq, J=9.4, 6.4 Hz, 1H), 5.01 (ddd, J=8.2, 5.4, 3.5 Hz, 1H), 4.12 (d, J=11.0 Hz, 1H), 4.07-3.97 (m, 2H), 3.94 (s, 3H), 3.60-3.48 (m, 2H), 3.47-3.43 (m, 2H), 3.14 (dd, J=9.4, 8.4 Hz, 1H), 2.02-1.81 (m, 2H), 1.47 (d, J=6.4 Hz, 3H), 0.97 (dd, J=6.7, 4.0 Hz, 6H); $^{13}$C NMR (101 MHz, CDCl$_3$) δ 169.65, 168.98, 155.31, 148.70, 140.69, 130.23, 109.57, 86.44, 80.31, 79.27, 75.77, 74.17, 72.70, 56.07, 53.09, 29.04, 19.31, 19.21, 18.68; ESIMS m/z 413.1 ([M+H]$^+$).

Compound 74 was prepared in the same manner as described in Example 13, Steps 4 and 5, Method B.

Compound 165 was prepared in the same manner as described in Example 13, Step 4, Method B starting from compound 146.

Compound 166 was prepared in the same manner as described in Example 13, Step 4, Method B starting from compound 145.

Compound 73 was prepared in the same manner as described in Example 13, Step 5, Method B using compound 166 as starting material.

Compound 75 was prepared in the same manner as described in Example 13, Step 5, method B using compound 165 as starting material Compound 70 was prepared in the same manner as described in Example 13, Steps 4 and 5, Method B starting from compound 110.

Compound 211 was prepared in the same manner as described in Example 13, Steps 4 and 5, Method B starting from Compound 239 (by-product).

Example 14

Step 1: Preparation of tert-butyl N-tert-butoxycarbonyl-N-[(3S,7S,8R,9S)-7-hydroxy-9-methyl-2-oxo-8-phenoxy-1,5-dioxonan-3-yl]carbamate (Compound 249) and tert-butyl N-tert-butoxycarbonyl-N-[(3S, 7S,8S,9S)-8-hydroxy-9-methyl-2-oxo-7-phenoxy-1, 5-dioxonan-3-yl]carbamate (Compound 250)

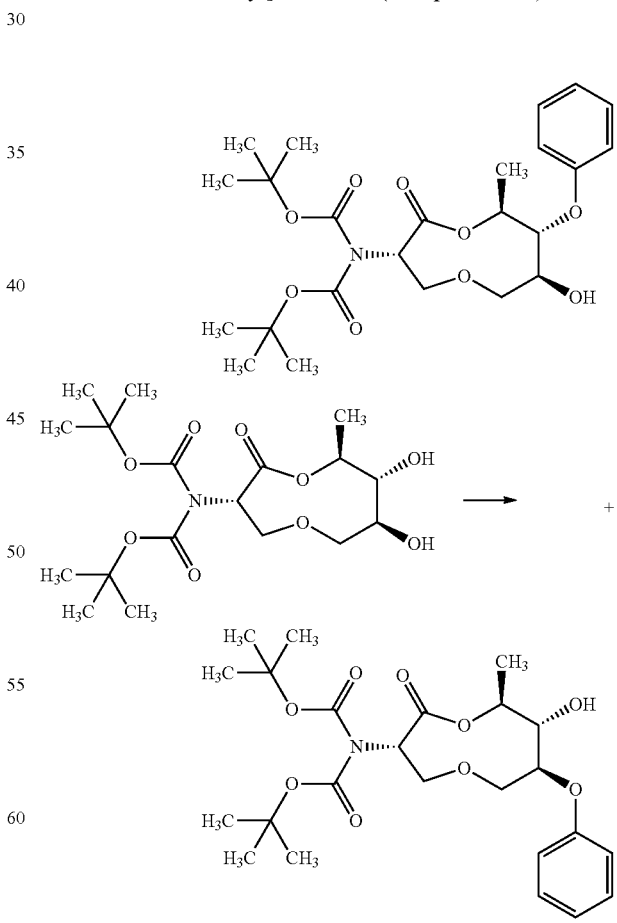

To a stirred solution of tert-butyl N-tert-butoxycarbonyl-N-[(3S,7S,8R,9S)-7,8-dihydroxy-9-methyl-2-oxo-1,5-dioxonan-3-yl]carbamate (484 mg, 1.194 mmol) in DCM (10 ml) was added bis(acetato-O)triphenylbismuth(V) (667 mg, 1.194 mmol) and diacetoxycopper (21.68 mg, 0.119 mmol) in a round bottom flask. The reaction mixture was stirred at room temperature overnight, then purified by flash chromatography (SiO$_2$; EtOAc/hexanes) to provide the title compounds as colorless oils.

tert-Butyl N-tert-butoxycarbonyl-N-[(3S,7S,8R,9S)-7-hydroxy-9-methyl-2-oxo-8-phenoxy-1,5-dioxonan-3-yl]carbamate was isolated as a colorless oil (Compound 249) (380 mg, 66%): $^1$H NMR (400 MHz, CDCl$_3$) δ 7.36-7.20 (m, 2H), 7.05-6.93 (m, 3H), 5.36-5.17 (m, 1H), 5.16-5.00 (m, 1H), 4.34-4.21 (m, 2H), 4.17-4.08 (m, 1H), 3.99 (dd, J=12.2, 8.5 Hz, 1H), 3.93-3.83 (m, 1H), 3.68 (dd, J=11.0, 7.4 Hz, 1H), 2.46 (d, J=3.1 Hz, 1H), 1.51 (s, 18H), 1.34 (d, J=6.4 Hz, 3H); $^{13}$C NMR (101 MHz, CDCl$_3$) δ 168.72, 158.92, 152.61, 129.77, 122.15, 116.26, 84.59, 83.18, 77.53, 73.89, 72.19, 58.22, 27.96, 18.98; ESIMS m/z 505.3 ([M+Na]$^+$).

tert-Butyl N-tert-butoxycarbonyl-N-[(3S,7S,8S,9S)-8-hydroxy-9-methyl-2-oxo-7-phenoxy-1,5-dioxonan-3-yl]carbamate was isolated as a colorless oil (Compound 250) (160 mg, 27.8%): $^1$H NMR (400 MHz, CDCl$_3$) δ 7.33-7.22 (m, 2H), 7.05-6.88 (m, 3H), 5.33 (dd, J=8.7, 2.5 Hz, 1H), 5.03 (dq, J=9.0, 6.3 Hz, 1H), 4.29 (dd, J=12.6, 2.4 Hz, 1H), 4.19 (ddd, J=8.7, 7.6, 1.3 Hz, 1H), 4.11 (dd, J=11.0, 1.3 Hz, 1H), 3.93 (dd, J=12.6, 8.7 Hz, 1H), 3.77 (td, J=8.8, 2.0 Hz, 1H), 3.59 (dd, J=11.0, 7.7 Hz, 1H), 2.99 (d, J=2.1 Hz, 1H), 1.57-1.47 (m, 21H); $^{13}$C NMR (101 MHz, CDCl$_3$) δ 168.42, 156.60, 152.60, 129.73, 121.88, 115.83, 83.19, 80.38, 76.32, 75.91, 74.23, 73.40, 58.41, 27.99, 18.71; ESIMS m/z 505.2 ([M+Na]$^+$).

Compounds 243 and 244 were prepared in the same manner as described in Example 14, Step 1, using tri(4-fluorophenyl)bismuth diacetate.

Compounds 247 and 248 were prepared in the same manner as described in Example 14, Step 1, using tri(4-methylphenyl)bismuth diacetate.

Compounds 249 and 250 were prepared in Example 14, Step 1.

Compounds 256 and 257 were prepared in the same manner as described in Example 14, Step 1, using tri(4-methoxylphenyl)bismuth diacetate.

Example 14

Step 2: Preparation of tert-butyl N-tert-butoxycarbonyl-N-[(3S,7S,8S,9S)-9-methyl-7-(2-methylallyloxy)-2-oxo-8-phenoxy-1,5-dioxonan-3-yl]carbamate (compound 159)

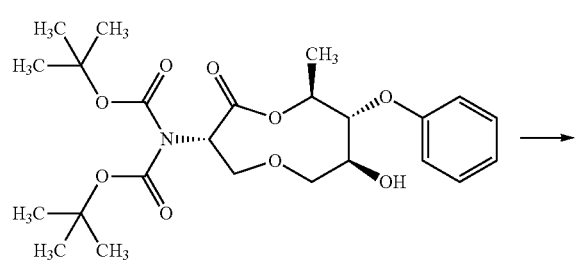

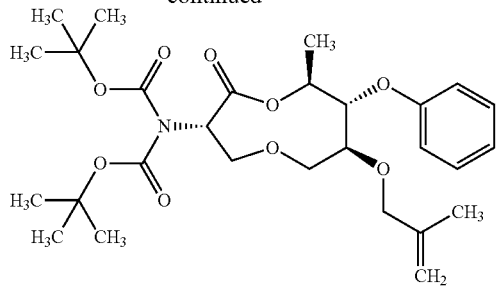

Compound 159 was prepared as described in Example 7, Step 5: $^1$H NMR (400 MHz, CDCl$_3$) δ 7.31-7.19 (m, 2H), 7.05-6.97 (m, 2H), 6.93 (tt, J=7.4, 1.1 Hz, 1H), 5.27 (dd, J=8.9, 4.1 Hz, 1H), 5.04 (dq, J=9.5, 6.3 Hz, 1H), 4.79-4.69 (m, 2H), 4.37-4.24 (m, 2H), 4.03-3.82 (m, 4H), 3.68 (dd, J=11.0, 7.3 Hz, 1H), 3.51 (ddd, J=8.7, 7.3, 1.4 Hz, 1H), 1.52 (s, 18H), 1.49 (s, 3H), 1.37 (d, J=6.3 Hz, 3H); $^{13}$C NMR (101 MHz, CDCl$_3$) δ 169.03, 159.37, 152.63, 141.86, 129.29, 121.18, 116.06, 112.66, 83.15, 83.03, 81.47, 75.52, 74.93, 72.82, 72.46, 57.86, 27.96, 19.41, 18.80; ESIMS m/z 559.4 ([M+Na]$^+$).

Compound 158 was prepared in the same manner as described in Example 14, Step 2 starting from tert-butyl N-tert-butoxycarbonyl-N-[(3S,7S,8S,9S)-8-hydroxy-9-methyl-2-oxo-7-phenoxy-1,5-dioxonan-3-yl]carbamate.

Compound 239 was prepared in the same manner as described in Example 14, Step 2 starting from tert-butyl N-tert-butoxycarbonyl-N-[(3S,7S,8S,9S)-8-hydroxy-9-methyl-2-oxo-7-phenoxy-1,5-dioxonan-3-yl]carbamate.

Example 14

Step 3: Preparation of tert-butyl N-tert-butoxycarbonyl-N-[(3S,7S,8S,9S)-7-isobutoxy-9-methyl-2-oxo-8-phenoxy-1,5-dioxonan-3-yl]carbamate (compound 148)

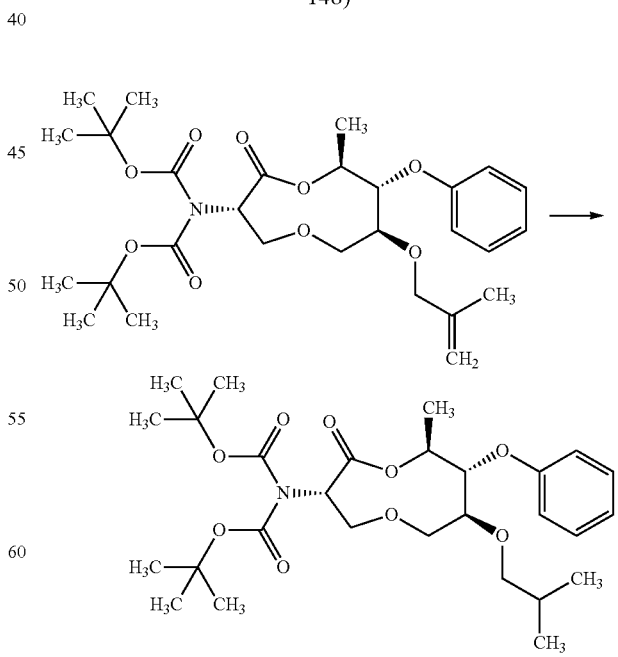

Compound 148 was prepared as described in Example 7, Step 6: $^1$H NMR (400 MHz, CDCl$_3$) δ 7.30-7.18 (m, 2H), 6.99 (dt, J=7.9, 1.0 Hz, 2H), 6.96-6.87 (m, 1H), 5.27 (dd, J=9.0, 4.1 Hz, 1H), 5.10-4.93 (m, 1H), 4.37-4.21 (m, 2H), 4.05-3.88 (m, 2H), 3.64 (dd, J=10.9, 7.5 Hz, 1H), 3.41 (ddd, J=8.9, 7.4, 1.5 Hz, 1H), 3.32-3.23 (m, 1H), 3.23-3.12 (m, 1H), 1.60-1.51 (m, 1H), 1.52 (s, 18H), 1.37 (d, J=6.3 Hz, 3H), 0.66 (dd, J=21.7, 6.7 Hz, 6H); $^{13}$C NMR (101 MHz, CDCl$_3$) δ 169.05, 159.48, 152.64, 129.18, 121.04, 116.07, 83.12, 83.01, 82.48, 78.05, 75.56, 72.81, 72.45, 57.89, 28.61, 27.96, 19.19, 19.07, 18.81; ESIMS m/z 538.8 ([M+H]$^+$).

Compound 149 was prepared in the same manner as described in Example 14, Step 3 starting from compound 158.

Compound 246 was prepared in the same manner as described in Example 14, Steps 2 and 3, starting from compound 243.

Compound 252 was prepared in the same manner as described in Example 14, Steps 2 and 3, starting from compound 250 using tert-butyl cyclopent-2-en-1-yl carbonate.

Compound 253 was prepared in the same manner as described in Example 14, Steps 2 and 3, starting from compound 249 using tert-butyl cyclopent-2-en-1-yl carbonate.

Compound 254 was prepared in the same manner as described in Example 14, Steps 2 and 3, starting from compound 250 using allyl tert-butyl carbonate.

Compound 255 was prepared in the same manner as described in Example 14, Steps 2 and 3, starting from compound 249 using allyl tert-butyl carbonate.

Compound 264 was prepared in the same manner as described in Example 14, Steps 2 and 3, starting from compound 259 using allyl tert-butyl carbonate.

Compound 265 was prepared in the same manner as described in Example 14, Steps 2 and 3, starting from compound 260 using allyl tert-butyl carbonate.

Compound 266 was prepared in the same manner as described in Example 14, Steps 2 and 3, starting from compound 260.

Compound 269 was prepared in the same manner as described in Example 14, Steps 2 and 3, starting from compound 267

Example 14

Step 4: Preparation of (3S,7S,8S,9S)-7-isobutoxy-9-methyl-2-oxo-8-phenoxy-1,5-dioxonan-3-aminium chloride (compound 151)

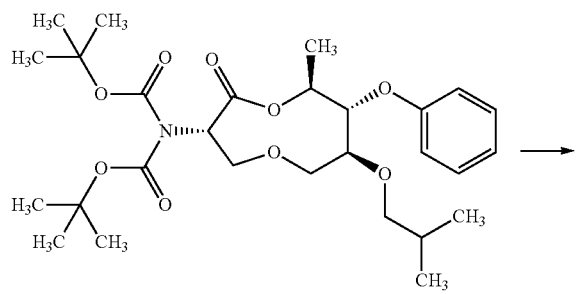

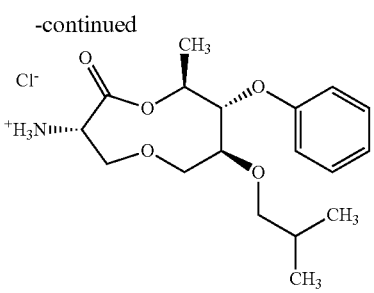

Compound 151 was prepared in the same manner as described in Example 5, Step 7: $^1$H NMR (400 MHz, CDCl$_3$) δ 8.73 (s, 3H), 7.28-7.16 (m, 2H), 7.01-6.87 (m, 3H), 5.17 (dt, J=15.8, 6.2 Hz, 1H), 4.67 (t, J=5.3 Hz, 1H), 4.44-4.31 (m, 1H), 4.27 (t, J=9.0 Hz, 1H), 4.22-4.07 (m, 1H), 3.97 (d, J=10.8 Hz, 1H), 3.70-3.58 (m, 1H), 3.40 (t, J=8.2 Hz, 1H), 3.27 (dd, J=8.8, 6.3 Hz, 1H), 3.16 (dd, J=8.8, 6.3 Hz, 1H), 1.54 (dt, J=13.1, 6.6 Hz, 1H), 1.41 (d, J=6.3 Hz, 3H), 0.67 (d, J=6.7 Hz, 3H), 0.61 (d, J=6.7 Hz, 3H); $^{13}$C NMR (101 MHz, CDCl$_3$) δ 168.69, 159.26, 129.25, 121.24, 115.99, 82.76, 82.29, 78.11, 75.46, 73.58, 70.86, 53.43, 28.60, 19.18, 19.05, 18.67; ESIMS m/z 338.9 ([M+H]$^+$).

Compound 152 was prepared in the same manner as described in Example 14, Step 4.

Compound 275 was prepared in the same manner as described in Example 14, Step 4, starting from compound 246.

Compound 277 was prepared in the same manner as described in Example 14, Step 4, starting from compound 252.

Compound 278 was prepared in the same manner as described in Example 14, Step 4, starting from compound 253.

Compound 279 was prepared in the same manner as described in Example 14, Step 4, starting from compound 254.

Compound 280 was prepared in the same manner as described in Example 14, Step 4, starting from compound 255.

Compound 282 was prepared in the same manner as described in Example 14, Step 4, starting from compound 261.

Compound 283 was prepared in the same manner as described in Example 14, Step 4, starting from compound 262.

Compound 285 was prepared in the same manner as described in Example 14, Step 4, starting from compound 264.

Compound 286 was prepared in the same manner as described in Example 14, Step 4, starting from compound 265.

Compound 287 was prepared in the same manner as described in Example 14, Step 4, starting from compound 266.

Compound 288 was prepared in the same manner as described in Example 14, Step 4, starting from compound 269.

Compound 271 was prepared in the same manner as described in Example 14, Step 4, starting from compound 239.

Example 14

Step 5: Preparation of 3-hydroxy-N-((3S,7S,8S,9S)-7-isobutoxy-9-methyl-2-oxo-8-phenoxy-1,5-dioxonan-3-yl)-4-methoxypicolinamide (compound 82)

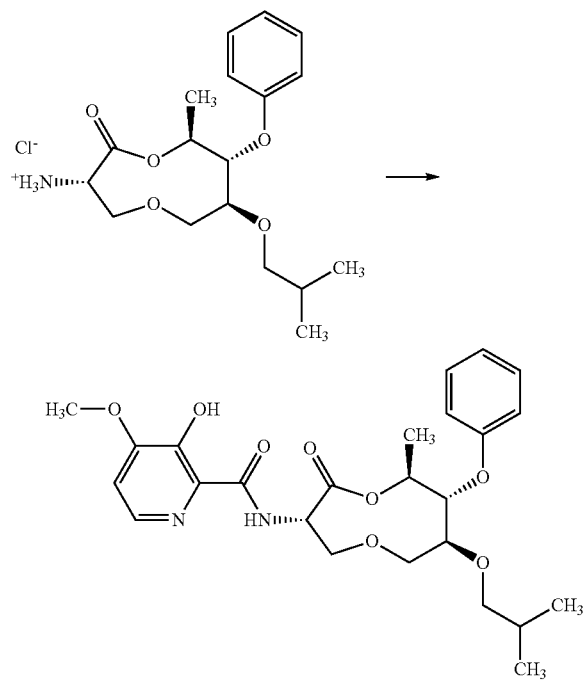

Compound 82 was prepared in the same manner as described in Example 5, Step 8: $^1$H NMR (400 MHz, CDCl$_3$) δ 12.13-11.57 (m, 1H), 8.69 (d, J=8.2 Hz, 1H), 8.00 (d, J=5.2 Hz, 1H), 7.41-7.11 (m, 2H), 7.06-6.97 (m, 2H), 6.97-6.90 (m, 1H), 6.87 (d, J=5.2 Hz, 1H), 5.19 (dq, J=9.4, 6.3 Hz, 1H), 5.10 (ddd, J=8.2, 6.9, 5.2 Hz, 1H), 4.31 (t, J=9.1 Hz, 1H), 4.11 (dd, J=11.9, 6.9 Hz, 1H), 3.94 (s, 3H), 3.91 (d, J=1.6 Hz, 1H), 3.86 (dd, J=11.8, 5.2 Hz, 1H), 3.74 (dd, J=11.1, 7.3 Hz, 1H), 3.40 (ddd, J=8.7, 7.2, 1.6 Hz, 1H), 3.34-3.24 (m, 1H), 3.19 (dd, J=8.9, 6.4 Hz, 1H), 1.59 (dp, J=13.3, 6.6 Hz, 1H), 1.41 (d, J=6.4 Hz, 3H), 0.70 (d, J=6.7 Hz, 3H), 0.65 (d, J=6.7 Hz, 3H); $^{13}$C NMR (101 MHz, CDCl$_3$) δ 170.37, 168.98, 159.41, 155.35, 148.74, 140.70, 130.16, 129.24, 121.20, 116.06, 109.62, 83.01, 82.67, 78.15, 74.80, 73.81, 72.86, 56.09, 52.05, 28.60, 19.19, 19.07, 18.74; ESIMS m/z 489.4 ([M+H]$^+$).

Compound 83 was prepared in the same manner as described in Example 14, Step 5.

Example 15

Step 1: Preparation of tert-butyl N-tert-butoxycarbonyl-N-[(3S,7S,8S,9S)-9-methyl-2-oxo-7,8-diphenoxy-1,5-dioxonan-3-yl]carbamate (compound 147)

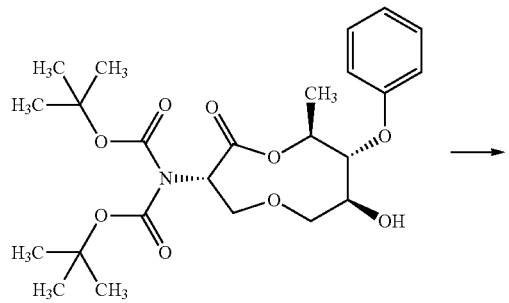

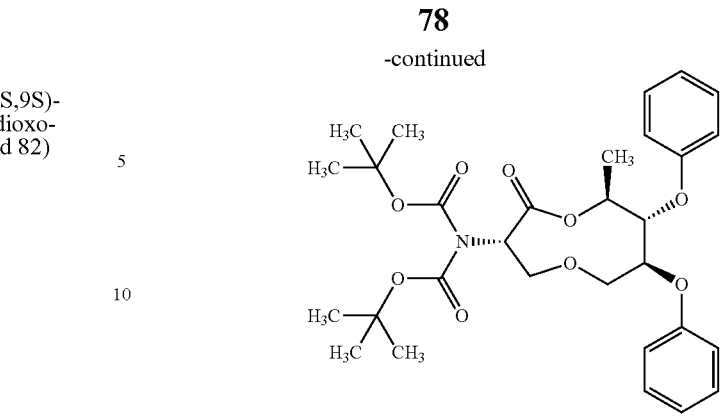

To a solution of tert-butyl N-tert-butoxycarbonyl-N-[(3S,7S,8R,9S)-7-hydroxy-9-methyl-2-oxo-8-phenoxy-1,5-dioxonan-3-yl]carbamate (102 mg, 0.212 mmol) in toluene (1 mL) was added fluorotetraphenylbismuth (227 mg, 0.424 mmol, prepared according to the procedure disclosed in *J. Am. Chem. Soc.* 2003, 125, 10494-10495), diacetoxycopper (7.69 mg, 0.042 mmol) and N-cyclohexyl-N-methylcyclohexanamine (83 mg, 0.424 mmol). The reaction solution was heated to 40° C. for 6 h and then stirred at room temperature overnight. The reaction mixture was purified by flash chromatography (SiO$_2$, hexanes/EtOAc gradient) to yield the title compound as a white solid (95 mg, 80%): $^1$H NMR (400 MHz, CDCl$_3$) δ 7.31-7.20 (m, 2H), 7.20-7.12 (m, 2H), 7.02-6.81 (m, 4H), 6.73 (dt, J=7.8, 1.1 Hz, 2H), 5.34 (dd, J=9.0, 3.6 Hz, 1H), 5.16 (dq, J=9.4, 6.3 Hz, 1H), 4.58-4.45 (m, 1H), 4.41 (ddd, J=8.7, 7.3, 1.3 Hz, 1H), 4.32 (dd, J=12.3, 3.6 Hz, 1H), 4.08 (dd, J=11.1, 1.3 Hz, 1H), 3.98 (dd, J=12.4, 8.9 Hz, 1H), 3.77 (dd, J=11.1, 7.3 Hz, 1H), 1.54 (s, 18H), 1.46 (d, J=6.3 Hz, 3H); $^{13}$C NMR (101 MHz, CDCl$_3$) δ 168.79, 159.50, 157.39, 152.59, 129.37, 129.24, 121.47, 121.23, 116.49, 115.72, 83.25, 82.80, 80.62, 75.45, 73.18, 72.36, 57.95, 28.00, 18.97; ESIMS m/z 559.0 ([M+H]$^+$).

Compound 245 was prepared in the same manner as described in Example 15, Step 1, starting from compound 244 and using tri(4-fluorophenyl)bismuth diacetate.

Compound 251 was prepared in the same manner as described in Example 15, Step 1, starting from compound 247 and using tri(4-methylphenyl)bismuth diacetate.

Compound 258 was prepared in the same manner as described in Example 15, Step 1, starting from compound 257 and using tri(4-methoxyphenyl)bismuth diacetate.

Compound 263 was prepared in two steps from compound 191. Step 1 was performed in the same manner as Example 14, Step 1 using tri(3,5-dimethylphenyl)bismuth diacetate; Step 2 was performed in the same manner as Example 15, Step 1, using tri(3,5-dimethylphenyl)bismuth diacetate.

Example 15

Step 2: Preparation of (3S,7S,8S,9S)-9-methyl-2-oxo-7,8-diphenoxy-1,5-dioxonan-3-aminium chloride (compound 150)

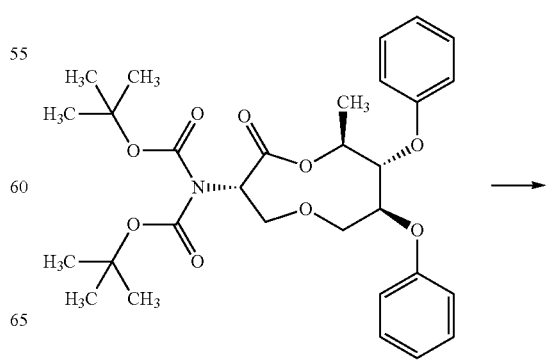

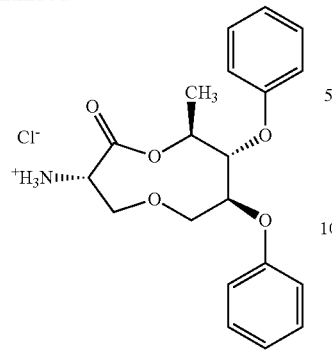

Compound 150 was prepared in a similar manner as described in Example 5, Step 7 to give the title compound as a white solid: mp 227-229° C.; $^1$H NMR (400 MHz, MeOD) δ 7.30-7.21 (m, 2H), 7.21-7.12 (m, 2H), 7.04-6.84 (m, 4H), 6.67 (dt, J=7.8, 1.0 Hz, 2H), 5.53-5.32 (m, 1H), 4.70 (t, J=9.2 Hz, 1H), 4.55 (dd, J=4.2, 3.1 Hz, 1H), 4.29 (ddd, J=9.1, 6.7, 1.0 Hz, 1H), 4.20-4.09 (m, 3H), 4.01-3.83 (m, 1H), 1.50 (d, J=6.3 Hz, 3H); ESIMS m/z 358.7 ([M+H]$^+$).

Compound 274 was prepared in the same manner as described in Example 15, Step 2, starting from compound 245.

Compound 276 was prepared in the same manner as described in Example 15, Step 2, starting from compound 251.

Compound 281 was prepared in the same manner as described in Example 15, Step 2, starting from compound 258.

Compound 284 was prepared in the same manner as described in Example 15, Step 2, starting from compound 263.

Example 15

Step 3: Preparation of 3-hydroxy-4-methoxy-N-((3S, 7S,8S,9S)-9-methyl-2-oxo-7,8-diphenoxy-1,5-dioxonan-3-yl)picolinamide (compound 81)

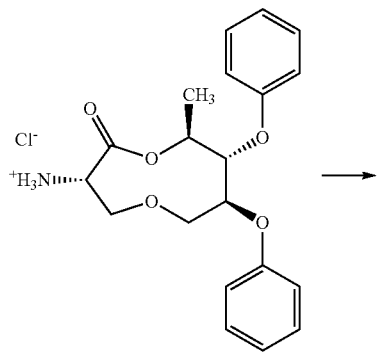

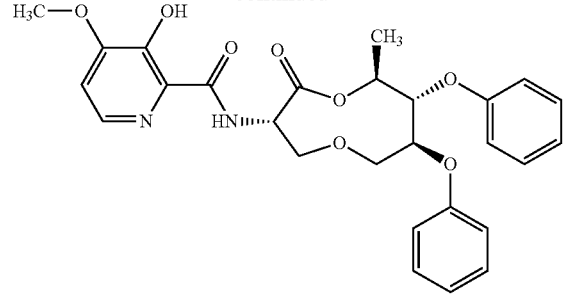

Compound 81 was prepared as described in Example 5, Step 8: $^1$H NMR (400 MHz, CDCl$_3$) δ 11.92 (s, 1H), 8.76 (d, J=8.1 Hz, 1H), 8.02 (d, J=5.2 Hz, 1H), 7.43-7.08 (m, 5H), 7.08-6.80 (m, 5H), 6.73 (dt, J=7.8, 1.1 Hz, 2H), 5.56-5.24 (m, 1H), 5.16 (ddd, J=8.1, 6.6, 4.5 Hz, 1H), 4.70-4.46 (m, 1H), 4.38 (ddd, J=8.7, 7.2, 1.3 Hz, 1H), 4.17-4.03 (m, 1H), 4.02-3.95 (m, 1H), 3.93 (s, 3H), 3.83 (dd, J=11.3, 7.2 Hz, 1H), 1.50 (d, J=6.3 Hz, 3H); $^{13}$C NMR (101 MHz, CDCl$_3$) δ 170.04, 169.04, 159.45, 157.21, 155.39, 148.79, 140.77, 130.15, 129.49, 129.31, 121.62, 121.38, 116.49, 115.59, 109.68, 82.87, 80.51, 75.06, 74.46, 72.54, 56.11, 52.37, 18.88; ESIMS m/z 510.1 ([M+H]$^+$).

Example 16

Step 1: Preparation of tert-butyl ((3S,7S,8S,9S)-7-butoxy-8-hydroxy-9-methyl-2-oxo-1,5-dioxonan-3-yl)carbamate (compound III)

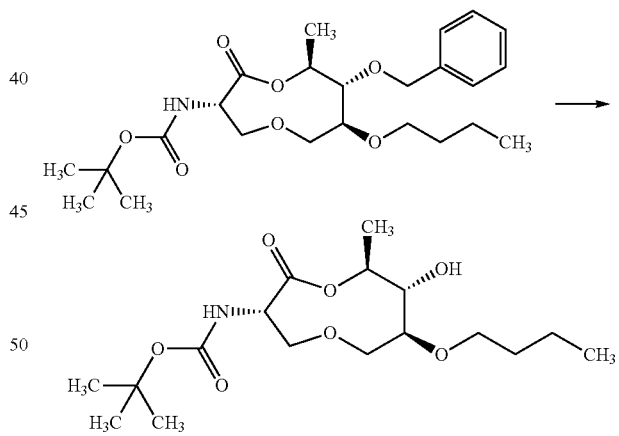

Compound III was prepared in the same manner as described in Example 7, Step 4 to give the title compound as a colorless oil (176 mg, quantitative): IR (neat) 3323, 2960, 2933, 2874, 1755, 1710, 1521, 1367, 1248, 1164, 1084 cm$^{-1}$; $^1$H NMR (400 MHz, CDCl$_3$) δ 5.41 (d, J=7.1 Hz, 1H), 5.08 (dq, J=9.3, 6.3 Hz, 1H), 4.66-4.56 (m, 1H), 4.07 (d, J=12.0 Hz, 1H), 4.02 (d, J=13.5 Hz, 1H), 3.81 (dd, J=11.9, 5.6 Hz, 1H), 3.65 (dt, J=9.3, 6.6 Hz, 1H), 3.44-3.34 (m, 3H), 3.17 (s, 1H), 3.08-3.01 (m, 1H), 1.59-1.49 (m, 2H), 1.46 (d, J=6.3 Hz, 3H), 1.44 (s, 9H), 1.41-1.31 (m, 2H), 0.91 (t, J=7.4 Hz, 3H); HRMS-ESI (m/z) [M]$^+$ calcd for C$_{17}$H$_{31}$NO$_7$, 361.2101; found, 361.2107.

Example 16

Step 2: Preparation of (3S,6S,7S,8S)-8-butoxy-3-((tert-butoxycarbonyl)amino)-6-methyl-4-oxo-1,5-dioxonan-7-yl isobutyrate (compound 113)

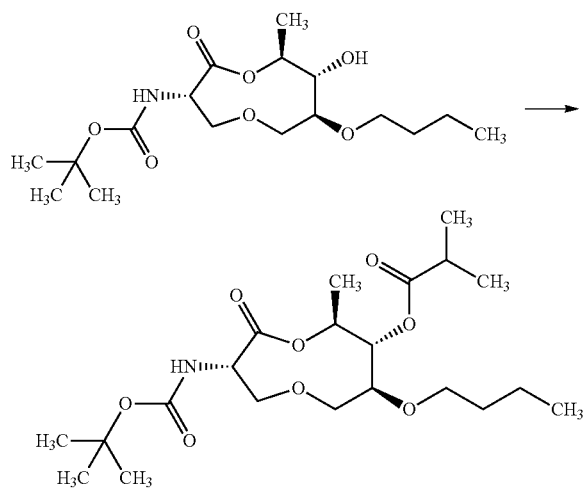

Compound 113 was prepared in the same manner as described in Example 11, Step 2 to give the title compound as a white solid (98.9 mg, 83%): mp 69-71° C.; IR (neat) 3364, 2967, 2935, 2876, 1745, 1717, 1517, 1367, 1153, 1096 cm$^{-1}$; $^1$H NMR (400 MHz, CDCl$_3$) δ 5.34 (d, J=7.9 Hz, 1H), 5.12-4.99 (m, 1H), 4.93 (t, J=9.4 Hz, 1H), 4.71-4.63 (m, 1H), 3.94-3.85 (m, 2H), 3.77 (dd, J=11.7, 3.7 Hz, 1H), 3.59-3.45 (m, 2H), 3.30 (dt, J=9.1, 6.6 Hz, 1H), 3.17 (t, J=7.9 Hz, 1H), 2.53 (hept, J=7.0 Hz, 1H), 1.41 (s, 9H), 1.28 (d, J=6.3 Hz, 3H), 1.30-1.20 (m, 2H), 1.19-1.13 (m, 8H), 0.84 (t, J=7.3 Hz, 3H); $^{13}$C NMR (101 MHz, CDCl$_3$) δ 175.77, 171.28, 155.23, 80.88, 80.29, 75.79, 75.70, 75.30, 71.49, 70.49, 54.10, 34.18, 32.00, 28.37, 19.30, 19.16, 18.84, 18.28, 13.94; HRMS-ESI (m/z) [M]$^+$ calcd for C$_{21}$H$_{37}$NO$_8$, 431.2519; found, 431.2524.

Compound 114 was prepared in the same manner as described in Example 16, Step 2 using compound III as starting material.

Example 16

Step 3: Preparation of (3S,6S,7S,8S)-3-amino-8-butoxy-6-methyl-4-oxo-1,5-dioxonan-7-yl isobutyrate hydrochloride (compound 180)

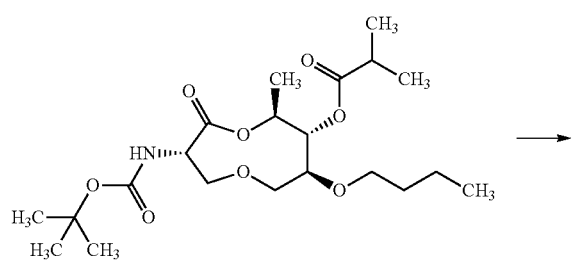

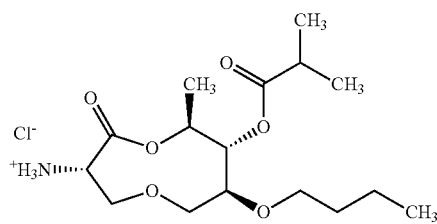

Compound 180 was prepared in the same manner as described in Example 5, Step 7 to give the title compound as a light yellow solid (83.5 mg, quantitative): ESIMS m/z 332.8 ([M+H]$^+$).

Compound 181 was prepared in the same manner as described in Example 16, Step 3 using compound 114 as starting material.

Example 16

Step 4: Preparation of (3S,6S,7S,8S)-8-butoxy-3-(3-hydroxy-4-methoxypicolinamido)-6-methyl-4-oxo-1,5-dioxonan-7-yl isobutyrate (compound 46)

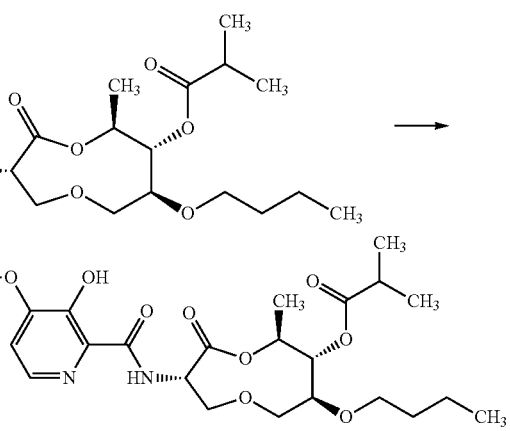

Compound 46 was prepared in the same manner as described in Example 5, Step 8 to give the title compound as a colorless oil (71.8 mg, 66%): IR (neat) 3367, 2935, 2875, 1739, 1649, 1528, 1481, 1242, 1182, 1145, 1093 cm$^{-1}$; $^1$H NMR (400 MHz, CDCl$_3$) δ 11.90 (s, 1H), 8.68 (d, J=8.1 Hz, 1H), 7.98 (d, J=5.2 Hz, 1H), 6.86 (d, J=5.2 Hz, 1H), 5.14 (dq, J=9.8, 6.4 Hz, 1H), 5.07 (ddd, J=8.1, 6.5, 4.2 Hz, 1H), 4.98 (t, J=9.4 Hz, 1H), 4.04 (dd, J=11.9, 6.5 Hz, 1H), 3.97 (dd, J=11.3, 1.1 Hz, 1H), 3.95-3.89 (m, 1H), 3.92 (s, 3H), 3.61 (dd, J=11.4, 7.6 Hz, 1H), 3.52 (dt, J=9.1, 6.6 Hz, 1H), 3.33 (dt, J=9.1, 6.6 Hz, 1H), 3.23 (ddd, J=8.9, 7.6, 1.3 Hz, 1H), 2.56 (hept, J=7.0 Hz, 1H), 1.49-1.38 (m, 2H), 1.32 (d, J=6.3 Hz, 3H), 1.32-1.24 (m, 2H), 1.19 (d, J=7.0 Hz, 3H), 1.17 (d, J=7.0 Hz, 3H), 0.86 (t, J=7.3 Hz, 3H); $^{13}$C NMR (101 MHz, CDCl$_3$) δ 175.79, 170.21, 169.06, 155.46, 148.86, 140.77, 130.28, 109.71, 80.84, 75.91, 75.76, 74.72, 71.79, 70.55, 56.20, 52.63, 34.20, 32.02, 19.33, 19.18, 18.87, 18.31, 13.96; HRMS-ESI (m/z) [M]$^+$ calcd for C$_{23}$H$_{34}$N$_2$O$_9$, 482.2264; found, 482.2266.

Compound 66 was prepared in the same manner as described in Example 16, Step 4 using compound 181 as starting material.

Example 17

Step 1: Preparation of tert-butyl N-[(3S,7S,8S,9S)-8-benzyloxy-7-butoxy-9-methyl-2-oxo-1,5-dioxonan-3-yl]-N-tert-butoxycarbonylcarbamate (compound 101)

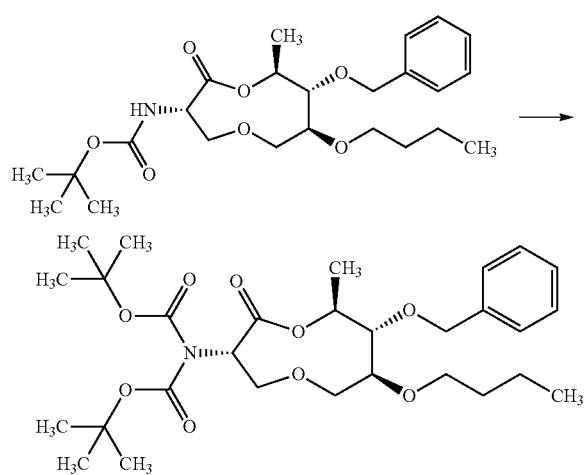

Compound 101 was prepared in the same manner as described in Example 7, Step 3 to give the title compound as a colorless oil (562 mg, 92%): IR (neat) 2932, 1766, 1709, 1367, 1256, 1147, 1122 cm$^{-1}$; $^1$H NMR (400 MHz, CDCl$_3$) δ 7.40-7.23 (m, 5H), 5.23 (dd, J=8.9, 4.1 Hz, 1H), 4.94 (d, J=10.9 Hz, 1H), 4.85 (dq, J=9.1, 6.3 Hz, 1H), 4.60 (d, J=10.9 Hz, 1H), 4.25 (dd, J=12.1, 4.1 Hz, 1H), 3.92 (dd, J=12.2, 8.9 Hz, 1H), 3.85 (d, J=10.7 Hz, 1H), 3.65-3.48 (m, 3H), 3.42-3.30 (m, 2H), 1.61-1.45 (m, 2H), 1.50 (s, 18H), 1.41 (d, J=6.3 Hz, 3H), 1.38-1.28 (m, 2H), 0.88 (t, J=7.4 Hz, 3H); HRMS-ESI (m/z) [M]$^+$ calcd for C$_{29}$H$_{45}$NO$_9$, 551.3094; found, 551.3109

Example 17

Step 2: Preparation of tert-butyl N-tert-butoxycarbonyl-N-[(3S,7S,8S,9S)-7-butoxy-8-hydroxy-9-methyl-2-oxo-1,5-dioxonan-3-yl]carbamate (compound 112)

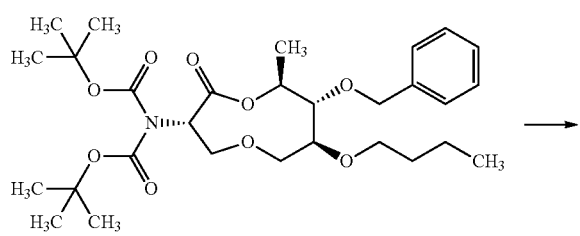

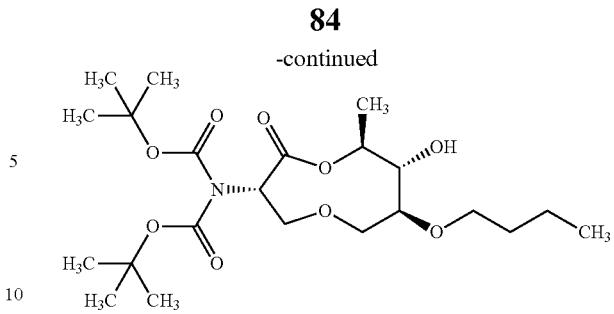

Compound 112 was prepared in the same manner as described in Example 7, Step 4 to give the title compound as a colorless oil (403.3 mg, 86%): IR (neat) 3536, 2979, 2934, 2875, 1764, 1747, 1706, 1366, 1246, 1147, 1121, 1088, 1049 cm$^{-1}$; $^1$H NMR (400 MHz, CDCl$_3$) δ 5.27 (dd, J=8.8, 2.4 Hz, 1H), 4.91 (dq, J=9.2, 6.3 Hz, 1H), 4.27 (dd, J=12.4, 2.4 Hz, 1H), 4.08 (dd, J=10.9, 0.8 Hz, 1H), 3.90 (dd, J=12.4, 8.8 Hz, 1H), 3.66 (dt, J=9.4, 6.6 Hz, 1H), 3.46-3.36 (m, 3H), 3.22-3.14 (m, 1H), 3.11 (d, J=1.1 Hz, 1H), 1.57-1.51 (m, 2H), 1.51 (s, 18H), 1.45 (d, J=6.3 Hz, 3H), 1.40-1.29 (m, 2H), 0.91 (t, J=7.4 Hz, 3H); $^{13}$C NMR (101 MHz, CDCl$_3$) δ 168.42, 152.63, 82.95, 82.47, 76.64, 76.60, 74.41, 73.34, 69.79, 58.57, 31.80, 27.93, 19.25, 18.69, 13.81; HRMS-ESI (m/z) [M]$^+$ calcd for C$_{22}$H$_{39}$NO$_9$, 461.2625; found, 461.2632.

Example 17

Step 3: Preparation of tert-butyl N-tert-butoxycarbonyl-N-[(3S,7S,8S,9S)-7-butoxy-8-methoxy-9-methyl-2-oxo-1,5-dioxonan-3-yl]carbamate (compound 115)

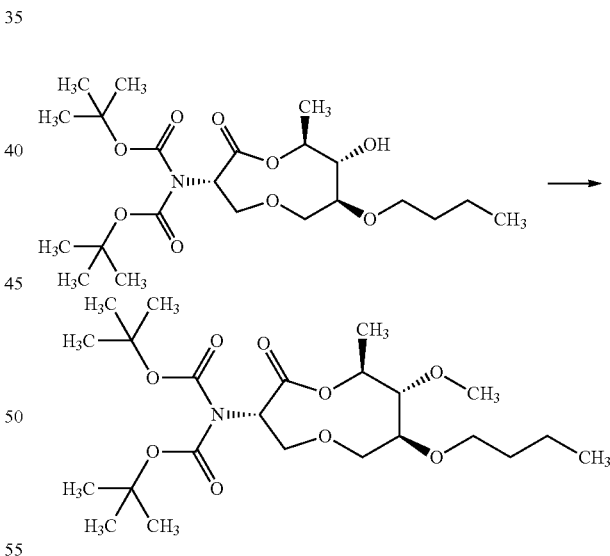

Compound 115 was prepared in the same manner as described in Example 12, Step 1 to give the title compound as a colorless oil (78.7 mg, 76%): IR (neat) 2979, 2933, 2875, 1765, 1747, 1707, 1367, 1243, 1106 cm$^{-1}$; $^1$H NMR (400 MHz, CDCl$_3$) δ 5.20 (dd, J=9.0, 4.1 Hz, 1H), 4.73 (dq, J=9.7, 6.3 Hz, 1H), 4.22 (dd, J=12.1, 4.1 Hz, 1H), 3.88 (dd, J=12.1, 9.0 Hz, 1H), 3.80 (dd, J=10.7, 0.6 Hz, 1H), 3.62-3.43 (m, 3H), 3.53 (s, 3H), 3.24-3.17 (m, 1H), 3.08-3.01 (m, 2H), 1.57-1.45 (m, 2H), 1.48 (s, 18H), 1.40 (d, J=6.3 Hz, 3H), 1.39-1.28 (m, 2H), 0.88 (t, J=7.4 Hz, 3H); $^{13}$C NMR (101 MHz, CDCl$_3$) δ 169.12, 152.73, 86.80, 83.43, 83.12, 75.78, 72.79, 72.64,

Example 17

Steps 4 and 5: Preparation of N-((3S,7S,8S,9S)-7-butoxy-8-methoxy-9-methyl-2-oxo-1,5-dioxonan-3-yl)-3-hydroxy-4-methoxypicolinamide (compound 36)

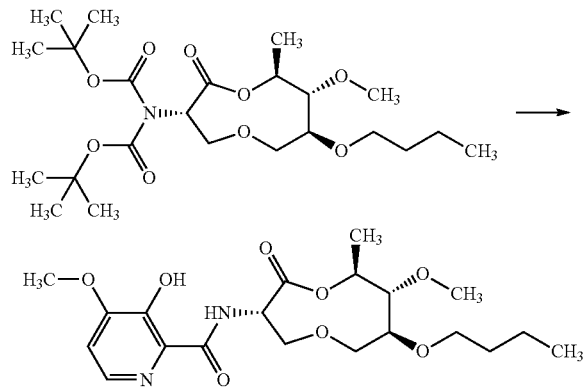

Compound 36 was prepared in two steps: Step 4 was performed in the same manner as described in Example 5, Step 7 to give compound 182; Step 5 was performed in the same manner as described in Example 5, Step 8, to give the title compound as a white solid (52.1 mg, 63%): mp 118-120° C.; IR (neat) 3366, 2933, 1742, 1650, 1529, 1244, 1103 cm$^{-1}$; $^1$H NMR (400 MHz, CDCl$_3$) δ 11.91 (s, 1H), 8.65 (d, J=8.1 Hz, 1H), 7.97 (d, J=5.2 Hz, 1H), 6.85 (d, J=5.2 Hz, 1H), 5.02 (ddd, J=8.1, 6.8, 5.1 Hz, 1H), 4.92 (dq, J=9.4, 6.3 Hz, 1H), 4.03 (dd, J=11.9, 6.8 Hz, 1H), 3.92 (s, 3H), 3.84-3.76 (m, 2H), 3.62-3.55 (m, 2H), 3.55 (s, 3H), 3.50 (dt, J=9.1, 6.6 Hz, 1H), 3.19 (ddd, J=8.4, 7.1, 1.3 Hz, 1H), 3.09 (t, J=9.0 Hz, 1H), 1.62-1.48 (m, 2H), 1.44 (d, J=6.3 Hz, 3H), 1.42-1.30 (m, 2H), 0.90 (t, J=7.4 Hz, 3H); $^{13}$C NMR (101 MHz, CDCl$_3$) δ 170.38, 169.05, 155.42, 148.81, 140.77, 130.29, 109.68, 86.84, 83.62, 75.34, 74.02, 73.03, 70.82, 61.56, 56.19, 52.24, 32.25, 19.43, 18.64, 13.99; HRMS-ESI (m/z) [M]$^+$ calcd for C$_{20}$H$_{30}$N$_2$O$_8$, 426.2002; found, 426.2039.

Example 18

Step 1: Preparation of tert-butyl N-[(3S,7S,8S,9S)-8-allyloxy-7-butoxy-9-methyl-2-oxo-1,5-dioxonan-3-yl]-N-tert-butoxycarbonyl-carbamate (compound 116)

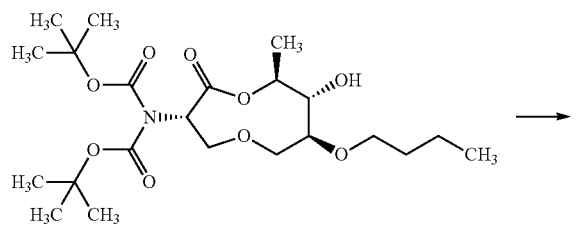

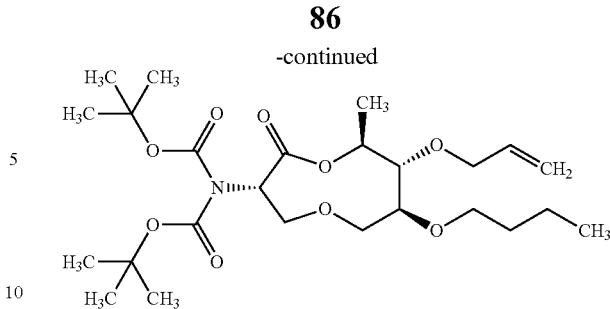

Compound 116 was prepared in the same manner as described in Example 7, Step 5 to give the title compound as a pale yellow oil (102.0 mg, 94%): IR (neat) 2979, 2933, 1765, 1708, 1367, 1244, 1121, 1098 cm$^{-1}$; $^1$H NMR (400 MHz, CDCl$_3$) δ 5.89 (ddt, J=16.2, 10.4, 5.7 Hz, 1H), 5.27-5.17 (m, 2H), 5.13 (dd, J=10.4, 1.7 Hz, 1H), 4.78 (dq, J=12.6, 6.2 Hz, 1H), 4.36 (ddt, J=12.1, 5.4, 1.3 Hz, 1H), 4.22 (dd, J=12.1, 4.1 Hz, 1H), 4.10-4.03 (m, 1H), 3.89 (dd, J=12.2, 9.0 Hz, 1H), 3.81 (d, J=10.8 Hz, 1H), 3.60-3.44 (m, 3H), 3.29-3.17 (m, 2H), 1.57-1.45 (m, 2H), 1.48 (s, 18H), 1.40 (d, J=6.3 Hz, 3H), 1.38-1.27 (m, 2H), 0.88 (t, J=7.4 Hz, 3H); $^{13}$C NMR (101 MHz, CDCl$_3$) δ 169.13, 152.73, 135.04, 116.82, 84.57, 83.62, 83.13, 75.87, 74.70, 72.87, 72.72, 70.76, 58.00, 32.30, 28.05, 19.42, 18.85, 14.02; HRMS-ESI (m/z) [M]$^+$ calcd for C$_{25}$H$_{43}$NO$_9$, 501.2938; found, 501.2955.

Example 18

Steps 2 and 3: Preparation of N-((3S,7S,8S,9S)-8-(allyloxy)-7-butoxy-9-methyl-2-oxo-1,5-dioxonan-3-yl)-3-hydroxy-4-methoxypicolinamide (compound 43)

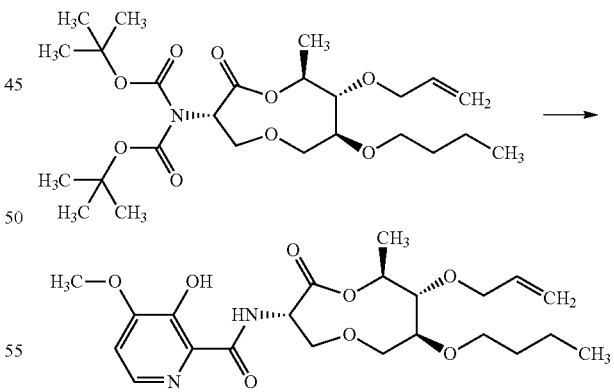

Compound 43 was prepared in two steps: Step 2 was performed in the same manner as described in Example 5, Step 7 to give compound 183; Step 3 was performed in the same manner as described in Example 5, Step 8, to give the title compound as an off-white solid (77.4 mg, 60%): mp 101-103° C.; IR (neat) 3335, 2931, 1745, 1640, 1534, 1281, 1092 cm$^{-1}$; $^1$H NMR (400 MHz, CDCl$_3$) δ 11.92 (s, 1H), 8.66 (d, J=8.1 Hz, 1H), 7.98 (d, J=5.2 Hz, 1H), 6.85 (d, J=5.2 Hz, 1H), 5.91 (ddt, J=16.2, 10.4, 5.8 Hz, 1H), 5.25 (ddd, J=17.2, 3.2, 1.6 Hz, 1H), 5.15 (ddd, J=10.4, 2.7, 1.1 Hz, 1H), 5.02 (ddd, J=8.1, 6.8, 5.0 Hz, 1H), 4.99-4.92 (m, 1H), 4.38 (ddt, J=12.2, 5.5, 1.3 Hz, 1H), 4.13-4.05 (m, 1H), 4.03 (dd, J=11.9, 6.8 Hz, 1H), 3.92 (s, 3H), 3.86-3.76 (m, 2H), 3.64-3.54 (m, 2H), 3.49 (dt, J=9.2, 6.6 Hz, 1H), 3.31-3.19 (m, 2H), 1.59-1.48 (m, 2H), 1.44 (d, J=6.4 Hz, 3H), 1.40-1.28 (m, 2H), 0.89 (t, J=7.4 Hz, 3H); $^{13}$C NMR (101 MHz, CDCl$_3$) δ 170.37, 169.05, 155.42, 148.81, 140.77, 134.92, 130.29, 117.01, 109.68, 84.56, 83.77, 75.44, 74.78, 74.08, 73.10, 70.87, 56.18, 52.25, 32.26, 19.42, 18.77, 14.02; HRMS-ESI (m/z) [M]$^+$ calcd for C$_{22}$H$_{32}$N$_2$O$_8$, 452.2159; found, 452.2166.

Compound 171 was prepared in the same manner as described in Example 18, Step 2 using compound 187 as starting material.

Compound 9 was prepared in the same manner as described in Example 18, Step 3 using compound 171 as starting material.

Example 18

Step 4: Preparation of N-((3S,7S,8S,9S)-7-butoxy-9-methyl-2-oxo-8-propoxy-1,5-dioxonan-3-yl)-3-hydroxy-4-methoxypicolinamide (compound 44)

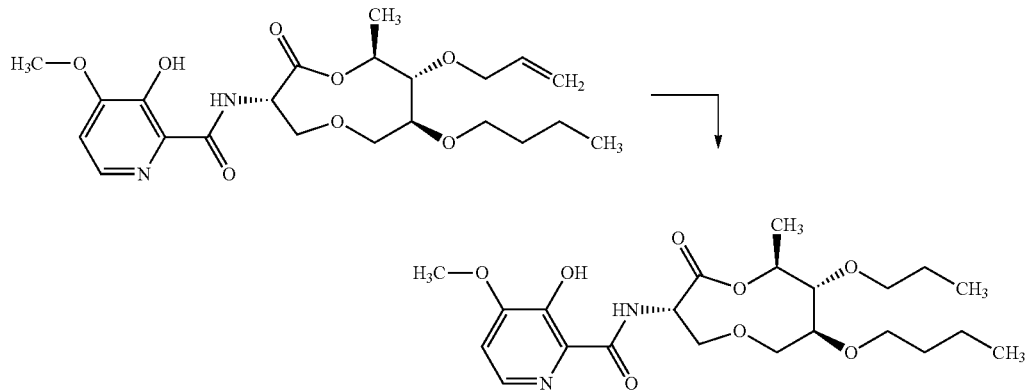

Compound 44 was prepared in the same manner as described in Example 7, Step 6 to give the title compound as a white solid (64.4 mg, 99%): mp 110-112° C.; IR (neat) 3366, 2933, 1750, 1649, 1529, 1245, 1095 cm$^{-1}$; $^1$H NMR (400 MHz, CDCl$_3$) δ 11.93 (s, 1H), 8.66 (d, J=8.1 Hz, 1H), 7.99 (d, J=5.2 Hz, 1H), 6.86 (d, J=5.2 Hz, 1H), 5.02 (ddd, J=8.1, 6.9, 5.2 Hz, 1H), 4.95 (dq, J=12.6, 6.3 Hz, 1H), 4.04 (dd, J=11.9, 6.8 Hz, 1H), 3.93 (s, 3H), 3.86-3.76 (m, 3H), 3.64-3.54 (m, 2H), 3.49 (tt, J=8.7, 6.7 Hz, 2H), 3.24-3.16 (m, 2H), 1.65-1.49 (m, 4H), 1.45 (d, J=6.3 Hz, 3H), 1.41-1.30 (m, 2H), 0.92 (t, J=7.4 Hz, 3H), 0.91 (t, J=7.3 Hz, 3H); $^{13}$C NMR (101 MHz, CDCl$_3$) δ 170.46, 169.08, 155.46, 148.85, 140.79, 130.34, 109.69, 85.05, 83.70, 75.72, 75.39, 74.01, 73.32, 70.90, 56.22, 52.23, 32.31, 23.64, 19.45, 18.71, 14.04, 10.79; HRMS-ESI (m/z) [M]$^+$ calcd for C$_{22}$H$_{34}$N$_2$O$_8$, 454.2315; found, 454.2326.

Compound 10 was prepared in the same manner as described in Example 18, Step 4 using compound 9 as starting material.

Example 19

Step 1: Preparation of tert-butyl N-tert-butoxycarbonyl-N-[(3S,7S,8S,9S)-7-butoxy-9-methyl-8-(2-methylallyloxy)-2-oxo-1,5-dioxonan-3-yl]carbamate (compound 117)

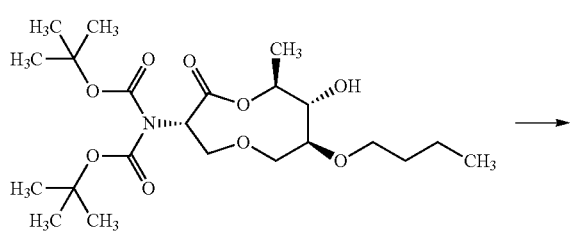

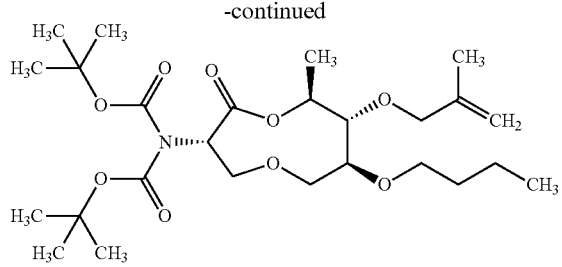

-continued

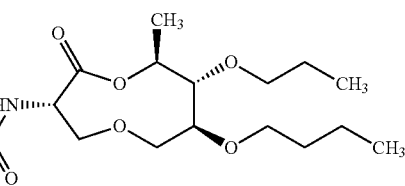

Compound 117 was prepared in the same manner as described in Example 7, Step 5 to give the title compound as a pale yellow oil (79.6 mg, 71%): IR (neat) 2978, 2933, 2874, 1765, 1709, 1456, 1367, 1244, 1147, 1120, cm$^{-1}$; $^1$H NMR (400 MHz, CDCl$_3$) δ 5.21 (dd, J=8.9, 4.1 Hz, 1H), 4.96-4.92 (m, 1H), 4.86-4.77 (m, 2H), 4.30 (d, J=11.6 Hz, 1H), 4.23 (dd, J=12.1, 4.1 Hz, 1H), 3.95-3.86 (m, 2H), 3.81 (d, J=10.8 Hz, 1H), 3.60-3.44 (m, 3H), 3.30-3.20 (m, 2H), 1.73 (s, 3H), 1.55-1.45 (m, 2H), 1.49 (s, 18H), 1.42 (d, J=6.3 Hz, 3H), 1.38-1.28 (m, 2H), 0.88 (t, J=7.4 Hz, 3H); $^{13}$C NMR (101 MHz, CDCl$_3$) δ 169.17, 152.77, 142.55, 111.93, 84.92, 83.69, 83.17, 77.66, 75.85, 72.88, 72.75, 70.76, 58.03, 32.36, 28.08, 19.95, 19.47, 18.86, 14.06; HRMS-ESI (m/z) [M]$^+$ calcd for C$_{26}$H$_{45}$NO$_9$, 515.3094; found, 515.3101.

Example 19

Steps 2 and 3: Preparation of N-((3S,7S,8S,9S)-7-butoxy-8-(2-chloro-2-methylpropoxy)-9-methyl-2-oxo-1,5-dioxonan-3-yl)-3-hydroxy-4-methoxypicolinamide (compound 87) and N-((3S,7S,8S,9S)-7-butoxy-8-hydroxy-9-methyl-2-oxo-1,5-dioxonan-3-yl)-3-hydroxy-4-methoxypicolinamide (compound 42)

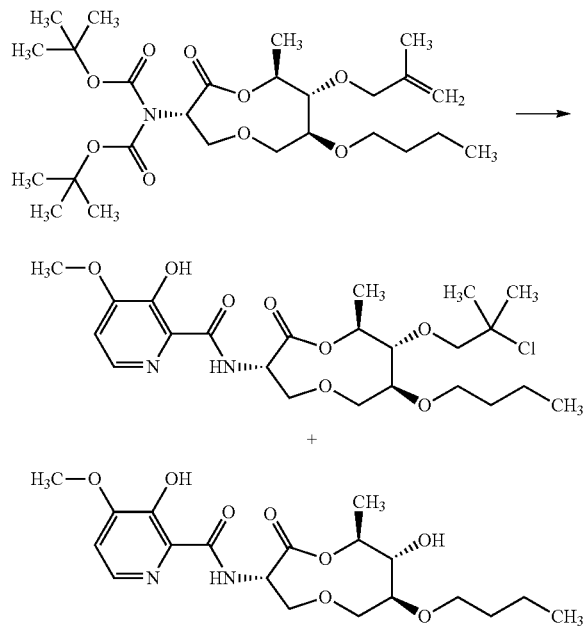

Compounds 87 and 42 were prepared in two steps: Step 2 was performed in the same manner as described in Example 5, Step 7 to give compounds 184 and 185; Step 3 was performed in the same manner as described in Example 5, Step 8, to give the title compounds.

N-((3S,7S,8S,9S)-7-Butoxy-8-(2-chloro-2-methylpropoxy)-9-methyl-2-oxo-1,5-dioxonan-3-yl)-3-hydroxy-4-methoxypicolinamide (compound 87) was isolated as an amber solid (5.8 mg, 4.4%): mp 115-117° C.; IR (neat) 3364, 2932, 1751, 1650, 1529, 1244, 1094 cm$^{-1}$; $^1$H NMR (400 MHz, CDCl$_3$) δ 11.92 (s, 1H), 8.67 (d, J=8.1 Hz, 1H), 8.02-7.98 (m, 1H), 6.87 (d, J=5.2 Hz, 1H), 5.08-4.99 (m, 2H), 4.05 (dd, J=11.9, 6.8 Hz, 1H), 4.00 (d, J=9.3 Hz, 1H), 3.94 (s, 3H), 3.82 (dt, J=10.7, 5.4 Hz, 2H), 3.66-3.45 (m, 4H), 3.32-3.23 (m, 2H), 1.58 (s, 3H), 1.56 (s, 3H), 1.57-1.50 (m, 2H), 1.50 (d, J=6.3 Hz, 3H), 1.41-1.29 (m, 2H), 0.91 (t, J=7.3 Hz, 3H); $^{13}$C NMR (101 MHz, CDCl$_3$) δ 170.36, 169.10, 155.50, 148.89, 140.81, 130.36, 109.73, 84.87, 83.89, 82.38, 75.30, 74.18, 73.05, 70.57, 68.04, 56.24, 52.31, 32.34, 29.65, 29.51, 19.51, 18.97, 14.08; HRMS-ESI (m/z) [M]$^+$ calcd for C$_{23}$H$_{35}$ClN$_2$O$_8$, 502.2082; found, 502.2090.

N-((3S,7S,8S,9S)-7-Butoxy-8-hydroxy-9-methyl-2-oxo-1,5-dioxonan-3-yl)-3-hydroxy-4-methoxypicolinamide (compound 42) was isolated as an off-white oil (20.5 mg, 19%): IR (neat) 3370, 2933, 1750, 1648, 1529, 1244, 1088 cm$^{-1}$; $^1$H NMR (400 MHz, CDCl$_3$) δ 11.96-11.93 (m, 1H), 8.79 (d, J=7.8 Hz, 1H), 8.01 (d, J=5.2 Hz, 1H), 6.87 (d, J=5.2 Hz, 1H), 5.14 (dq, J=9.3, 6.3 Hz, 1H), 5.01 (ddd, J=7.9, 5.7, 2.2 Hz, 1H), 4.18-4.06 (m, 2H), 3.98-3.90 (m, 1H), 3.94 (s, 3H), 3.66 (dt, J=9.3, 6.6 Hz, 1H), 3.48-3.38 (m, 3H), 3.20 (s, 1H), 3.15-3.07 (m, 1H), 1.60-1.51 (m, 2H), 1.49 (d, J=6.3 Hz, 3H), 1.41-1.29 (m, 2H), 0.91 (t, J=7.4 Hz, 3H); $^{13}$C NMR (101 MHz, CDCl$_3$) δ 169.62, 169.15, 155.48, 148.89, 140.83, 130.45, 109.71, 82.72, 77.79, 77.36, 76.62, 73.73, 70.15, 56.24, 53.63, 31.90, 19.44, 18.90, 13.96; HRMS-ESI (m/z) [M]$^+$ calcd for C$_{19}$H$_{28}$N$_2$O$_8$, 412.1846; found, 412.1849.

Example 20

Step 1: Preparation of tert-butyl N-tert-butoxycarbonyl-N-[(3S,7S,8S,9S)-7-butoxy-8-(2-hydroxyethoxy)-9-methyl-2-oxo-1,5-dioxonan-3-yl]carbamate (compound 164)

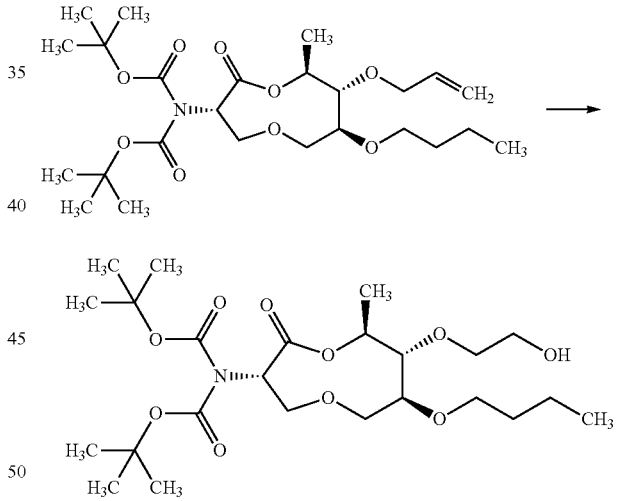

Compound 164 was prepared in the same manner as described in Example 8, Step 1 to give the title compound as a colorless oil (170 mg, 84%): IR (neat) 2934, 1745, 1707, 1457, 1367, 1254, 1120 cm$^{-1}$; $^1$H NMR (400 MHz, CDCl$_3$) δ 5.22 (dd, J=8.9, 3.9 Hz, 1H), 4.80 (dq, J=8.9, 6.3 Hz, 1H), 4.24 (dd, J=12.2, 3.9 Hz, 1H), 3.95-3.79 (m, 3H), 3.78-3.68 (m, 2H), 3.66-3.45 (m, 4H), 3.45-3.38 (m, 1H), 3.39-3.23 (m, 2H), 1.61-1.50 (m, 2H), 1.49 (s, 18H), 1.44 (d, J=6.3 Hz, 3H), 1.40-1.26 (m, 2H), 0.89 (t, J=7.4 Hz, 3H); $^{13}$C NMR (101 MHz, CDCl$_3$) δ 169.06, 152.76, 85.77, 83.22, 83.05, 75.57, 75.51, 73.09, 73.00, 70.54, 62.93, 58.04, 31.86, 28.07, 19.32, 18.80, 13.99; HRMS-ESI (m/z) [M]$^+$ calcd for C$_{24}$H$_{43}$NO$_{10}$, 505.2887; found, 505.2900.

Example 20

Step 2: Preparation of tert-butyl N-tert-butoxycarbonyl-N-[(3S,7S,8S,9S)-7-butoxy-8-(2-methoxyethoxy)-9-methyl-2-oxo-1,5-dioxonan-3-yl]carbamate (compound 163)

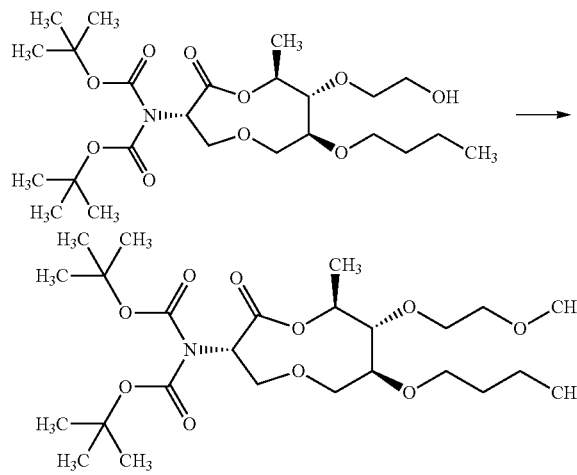

Compound 163 was prepared in the same manner as described in Example 12, Step 1 to give the title compound as a colorless oil (192.0 mg, 79%): IR (neat) 2933, 2875, 1764, 1747, 1708, 1456, 1367, 1243, 1099 cm$^{-1}$; $^1$H NMR (400 MHz, CDCl$_3$) δ 5.19 (dd, J=9.0, 4.1 Hz, 1H), 4.79 (dq, J=9.2, 6.3 Hz, 1H), 4.20 (dd, J=12.2, 4.1 Hz, 1H), 3.98 (ddd, J=10.6, 5.2, 3.8 Hz, 1H), 3.88 (dd, J=12.2, 9.0 Hz, 1H), 3.79 (d, J=10.7 Hz, 1H), 3.73-3.65 (m, 1H), 3.60-3.43 (m, 5H), 3.34 (s, 3H), 3.28-3.15 (m, 2H), 1.55-1.44 (m, 2H), 1.47 (s, 18H), 1.42 (d, J=6.3 Hz, 3H), 1.38-1.26 (m, 2H), 0.87 (t, J=7.4 Hz, 3H); $^{13}$C NMR (101 MHz, CDCl$_3$) δ 169.06, 152.69, 85.55, 83.49, 83.10, 75.76, 72.96, 72.85, 72.70, 72.34, 70.62, 59.02, 57.95, 32.28, 28.02, 19.41, 18.67, 14.01; HRMS-ESI (m/z) [M]$^+$ calcd for C$_{25}$H$_{45}$NO$_{10}$, 519.3043; found, 519.3026.

Example 20

Step 3: Preparation of (3S,7S,8S,9S)-3-amino-7-butoxy-8-(2-methoxyethoxy)-9-methyl-1,5-dioxonan-2-one hydrochloride (compound 169)

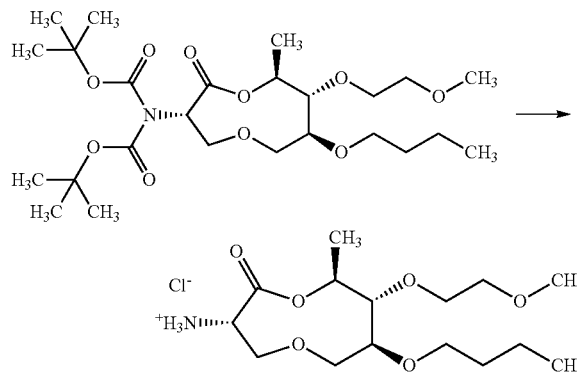

Compound 169 was prepared in the same manner as described in Example 5, Step 7 to give the title compound as a light yellow oil (130 mg, quantitative): ESIMS m/z 319 ([M]$^+$).

Example 20

Step 4: Preparation of N-((3S,7S,8S,9S)-7-butoxy-8-(2-methoxyethoxy)-9-methyl-2-oxo-1,5-dioxonan-3-yl)-3-hydroxy-4-methoxypicolinamide (compound 52)

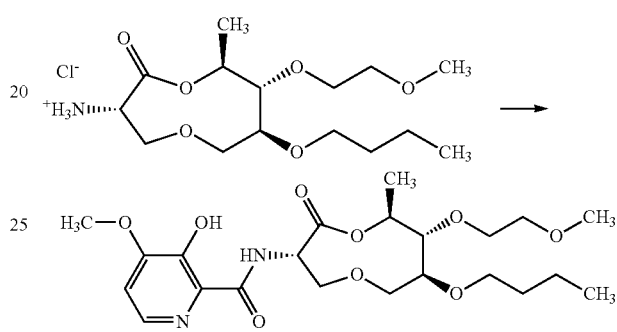

Compound 52 was prepared in the same manner as described in Example 5, Step 8 to give the title compound as a white solid (107.0 mg, 62%): mp 75-77° C.; IR (neat) 3367, 2933, 1750, 1649, 1529, 1282, 1094 cm$^{-1}$; $^1$H NMR (400 MHz, CDCl$_3$) δ 11.92-11.89 (m, 1H), 8.65 (d, J=8.1 Hz, 1H), 7.97 (d, J=5.2 Hz, 1H), 6.85 (d, J=5.2 Hz, 1H), 5.04-4.94 (m, 2H), 4.06-3.96 (m, 2H), 3.92 (s, 3H), 3.84-3.77 (m, 2H), 3.75-3.68 (m, 1H), 3.61-3.44 (m, 5H), 3.36 (s, 3H), 3.27-3.19 (m, 2H), 1.58-1.48 (m, 2H), 1.46 (d, J=6.3 Hz, 3H), 1.40-1.27 (m, 2H), 0.89 (t, J=7.4 Hz, 3H); $^{13}$C NMR (101 MHz, CDCl$_3$) δ 170.31, 169.04, 155.40, 148.79, 140.75, 130.28, 109.67, 85.60, 83.64, 75.38, 74.07, 73.09, 73.06, 72.34, 70.75, 59.04, 56.17, 52.23, 32.25, 19.41, 18.60, 14.01; HRMS-ESI (m/z) [M]$^+$ calcd for C$_{22}$H$_{34}$N$_2$O$_9$, 470.2264; found, 470.2264.

Example 21

Step 1: Preparation of tert-butyl N-tert-butoxycarbonyl-N-[(3S,7S,8S,9S)-7-butoxy-9-methyl-2-oxo-8-(2-oxoethoxy)-1,5-dioxonan-3-yl]carbamate (compound 119)

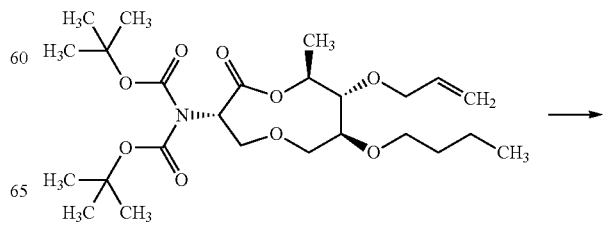

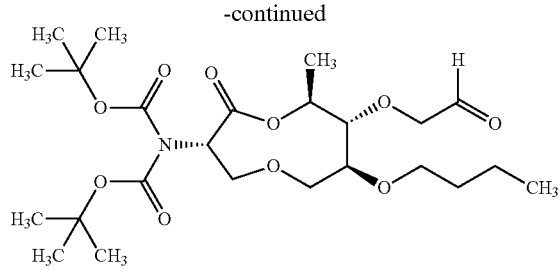

A mixture of tert-butyl N-[(3S,7S,8S,9S)-8-allyloxy-7-butoxy-9-methyl-2-oxo-1,5-dioxonan-3-yl]-N-tert-butoxycarbonylcarbamate (0.350 g, 0.698 mmol) and NaHCO$_3$ (5.86 mg, 0.070 mmol) in MeOH (0.21 ml) and DCM (6.8 ml) was treated with ozone at −78° C. until the solution became light blue in color. The mixture was purged with nitrogen until colorless and quenched by the addition of DMS (0.10 ml, 1.40 mmol). The reaction mixture was slowly warmed to room temperature and stirred for 20 h. The mixture was concentrated and purified by flash chromatography on (SiO$_2$, hexanes/EtOAc gradient) to yield the title compound as a colorless oil (320 mg, 91%): IR (neat) 2934, 2876, 1743, 1706, 1367, 1253, 1121, 1096 cm$^{-1}$; $^1$H NMR (400 MHz, CDCl$_3$) δ 9.63 (s, 1H), 5.18 (dd, J=8.9, 3.8 Hz, 1H), 4.84 (dq, J=9.4, 6.3 Hz, 1H), 4.39 (dd, J=17.9, 0.9 Hz, 1H), 4.22 (dd, J=17.8, 0.5 Hz, 1H), 4.19 (dd, J=12.2, 3.8 Hz, 1H), 3.91-3.75 (m, 2H), 3.57-3.42 (m, 2H), 3.37 (dt, J=9.2, 6.5 Hz, 1H), 3.29 (dd, J=7.9, 6.9 Hz, 1H), 3.21 (t, J=9.0 Hz, 1H), 1.52-1.40 (m, 2H), 1.45 (s, 18H), 1.41 (d, J=6.3 Hz, 3H), 1.30-1.19 (m, 2H), 0.83 (t, J=7.3 Hz, 3H); $^{13}$C NMR (101 MHz, CDCl$_3$) δ 200.51, 168.79, 152.61, 86.19, 83.52, 83.08, 79.09, 75.35, 72.95, 71.99, 70.03, 57.92, 32.02, 27.94, 19.29, 18.84, 13.85; HRMS-ESI (m/z) [M]$^+$ calcd for C$_{24}$H$_{41}$NO$_{10}$, 503.2730; found, 503.2727.

Compound 95 was prepared in the same manner as described in Example 21, Step 1 using compound 94 as starting material.

Example 21

Step 2: Preparation of tert-butyl N-tert-butoxycarbonyl-N-[(3S,7S,8S,9S)-7-butoxy-8-(2,2-difluoroethoxy)-9-methyl-2-oxo-1,5-dioxonan-3-yl]carbamate (compound 120)

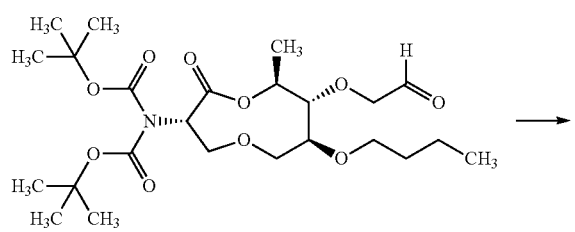

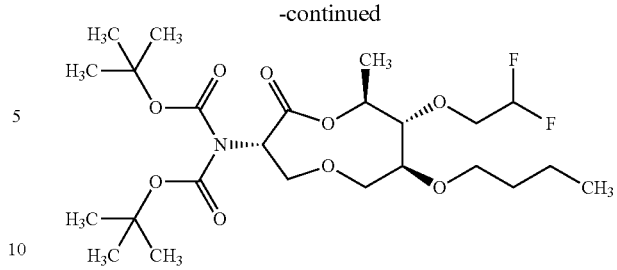

To a solution of tert-butyl N-tert-butoxycarbonyl-N-[(3S,7S,8S,9S)-7-butoxy-9-methyl-2-oxo-8-(2-oxoethoxy)-1,5-dioxonan-3-yl]carbamate (0.130 g, 0.258 mmol) in DCM (1.50 mL) at 0° C. was added a solution of Deoxo-Fluor® (0.10 ml, 0.542 mmol) in DCM (1.0 mL) dropwise at 0° C., and the reaction mixture was then stirred at 0° C. for 1 h. The mixture was concentrated and purified by flash chromatography (SiO$_2$, hexanes/EtOAc gradient) to yield the title compound as a colorless oil (89.0 mg, 66%): IR (neat) 2980, 2395, 2877, 1747, 1708, 1367, 1254, 1120 cm$^{-1}$; $^1$H NMR (400 MHz, CDCl$_3$) δ 5.81 (tdd, J=55.1, 4.7, 3.4 Hz, 1H), 5.21 (dd, J=9.0, 3.8 Hz, 1H), 4.80 (dq, J=12.6, 6.2 Hz, 1H), 4.23 (dd, J=12.2, 3.8 Hz, 1H), 4.13-3.99 (m, 1H), 3.92-3.71 (m, 3H), 3.56 (dt, J=9.1, 6.8 Hz, 1H), 3.52-3.40 (m, 2H), 3.29-3.19 (m, 2H), 1.56-1.45 (m, 2H), 1.48 (s, 18H), 1.41 (d, J=6.3 Hz, 3H), 1.38-1.26 (m, 2H), 0.89 (t, J=7.4 Hz, 3H); $^{13}$C NMR (101 MHz, CDCl$_3$) δ 168.92, 152.72, 114.35 (t, J=241.7 Hz), 86.15, 83.55, 83.20, 75.56, 73.03, 72.78 (t, J=27.6 Hz), 72.17, 70.36, 58.01, 32.19, 28.04, 19.40, 18.71, 13.97; HRMS-ESI (m/z) [M]$^+$ calcd for C$_{24}$H$_{41}$F$_2$NO$_9$, 525.2749; found, 525.2723.

Compound 96 was prepared in the same manner as described in Example 21, Step 2 using compound 95 as starting material.

Example 21

Step 3: Preparation of (3S,7S,8S,9S)-3-amino-7-butoxy-8-(2,2-difluoroethoxy)-9-methyl-1,5-dioxonan-2-one hydrochloride (compound 167)

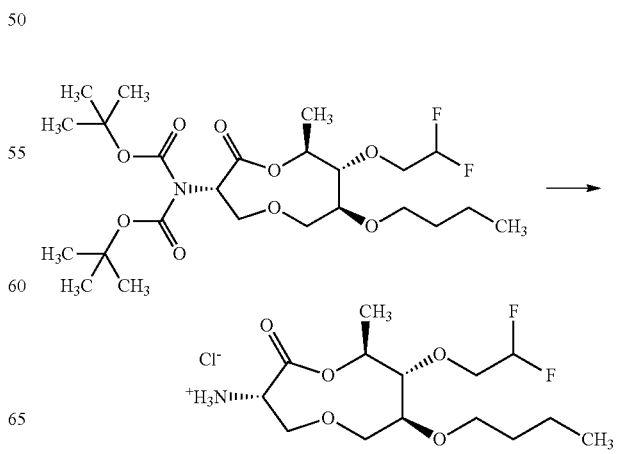

Compound 167 was prepared in the same manner as described in Example 5, Step 7 to give the title compound as a white solid (142 mg, quantitative): ESIMS m/z 326.7 ([M+H]+).

Example 21

Step 4: Preparation of N-((3S,7S,8S,9S)-7-butoxy-8-(2,2-difluoroethoxy)-9-methyl-2-oxo-1,5-dioxonan-3-yl)-3-hydroxy-4-methoxypicolinamide (compound 53)

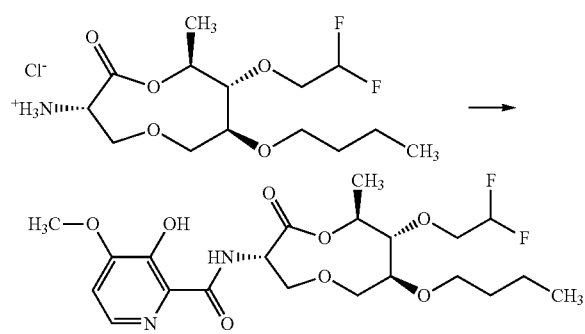

Compound 53 was prepared in the same manner as described in Example 5, Step 8 to give the title compound as a white solid (94.4 mg, 50%): mp 127-129° C.; IR (neat) 3356, 2958, 1736, 1643, 1536, 1262, 1091 cm$^{-1}$; $^1$H NMR (400 MHz, CDCl$_3$) δ 11.90 (s, 1H), 8.66 (d, J=8.0 Hz, 1H), 7.97 (d, J=5.2 Hz, 1H), 6.85 (d, J=5.2 Hz, 1H), 5.83 (tdd, J=55.1, 4.7, 3.3 Hz, 1H), 5.07-4.93 (m, 2H), 4.14-4.01 (m, 1H), 4.02 (dd, J=12.0, 6.7 Hz, 1H), 3.92 (s, 3H), 3.88-3.72 (m, 3H), 3.62-3.51 (m, 2H), 3.45 (dt, J=9.1, 6.6 Hz, 1H), 3.31-3.19 (m, 2H), 1.58-1.48 (m, 2H), 1.45 (d, J=6.3 Hz, 3H), 1.39-1.28 (m, 2H), 0.90 (t, J=7.4 Hz, 3H); $^{13}$C NMR (101 MHz, CDCl$_3$) δ 170.17, 169.05, 155.44, 148.82, 140.78, 130.24, 114.30 (t, J=241.7 Hz), 109.69, 86.19, 83.72, 75.28, 74.31, 72.79 (t, J=27.6 Hz), 72.51, 70.45, 56.19, 52.33, 32.13, 19.39, 18.64, 13.96; HRMS-ESI (m/z) [M]$^+$ calcd for C$_{21}$H$_{30}$F$_2$N$_2$O$_8$, 476.1970; found, 476.1978.

Example 22

Step 1: Preparation of tert-butyl N-tert-butoxycarbonyl-N-[(3S,7S,8S,9S)-7-butoxy-8-isobutoxy-9-methyl-2-oxo-1,5-dioxonan-3-yl]carbamate (compound 118)

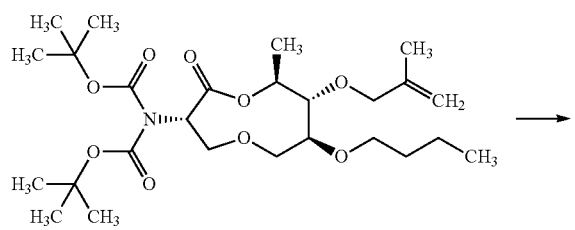

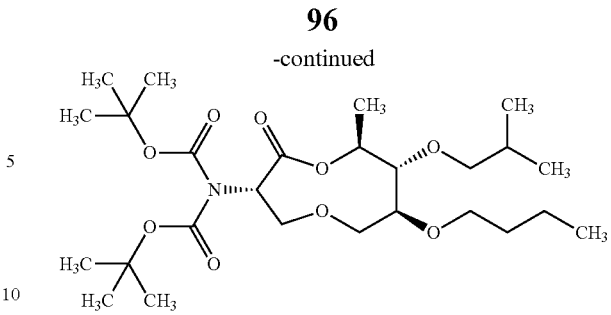

Compound 118 was prepared in the same manner as described in Example 7, Step 6 to give the title compound as a colorless oil (112 mg, 70%): IR (neat) 3313, 1637, 1367 cm$^{-1}$; $^1$H NMR (400 MHz, CDCl$_3$) δ 5.20 (dd, J=8.9, 4.2 Hz, 1H), 4.78 (dq, J=9.4, 6.3 Hz, 1H), 4.23 (dd, J=12.1, 4.2 Hz, 1H), 3.90 (dd, J=12.1, 9.0 Hz, 1H), 3.80 (d, J=10.6 Hz, 1H), 3.66 (dd, J=8.4, 6.1 Hz, 1H), 3.60-3.42 (m, 3H), 3.26-3.18 (m, 2H), 3.18-3.10 (m, 1H), 1.87-1.74 (m, 1H), 1.56-1.44 (m, 2H), 1.49 (s, 18H), 1.40 (d, J=6.3 Hz, 3H), 1.39-1.28 (m, 2H), 0.93-0.84 (m, 9H); $^{13}$C NMR (101 MHz, CDCl$_3$) δ 169.21, 152.77, 84.93, 83.58, 83.13, 80.65, 75.88, 72.92, 72.85, 70.74, 58.02, 32.36, 29.26, 28.08, 19.69, 19.51, 19.48, 18.83, 14.06; HRMS-ESI (m/z) [M]$^+$ calcd for C$_{26}$H$_{47}$NO$_9$, 517.3521; found, 517.3527.

Example 22

Steps 2 and 3: Preparation of N-((3S,7S,8S,9S)-7-butoxy-8-isobutoxy-9-methyl-2-oxo-1,5-dioxonan-3-yl)-3-hydroxy-4-methoxypicolinamide (compound 48)

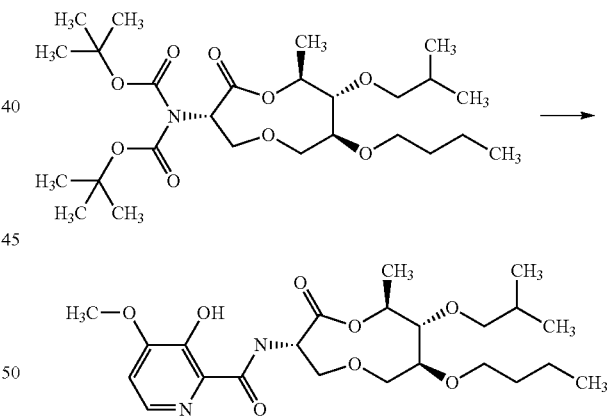

Compound 48 was prepared in two steps: Step 2 was performed in the same manner as described in Example 5, Step 7 to give compound 168; Step 3 was performed in the same manner as described in Example 5, Step 8 to give the title compound as a light yellow solid (61.5 mg, 62%): mp 104-106° C.; IR (neat) 3367, 2956, 1749, 1649, 1528, 1281, 1092 cm$^{-1}$; $^1$H NMR (400 MHz, CDCl$_3$) δ 11.92 (s, 1H), 8.65 (d, J=8.1 Hz, 1H), 7.97 (d, J=5.2 Hz, 1H), 6.85 (d, J=5.2 Hz, 1H), 5.01 (ddd, J=8.0, 6.9, 5.2 Hz, 1H), 4.94 (dq, J=12.6, 6.2 Hz, 1H), 4.03 (dd, J=11.9, 6.8 Hz, 1H), 3.91 (s, 3H), 3.82-3.75 (m, 2H), 3.66 (dd, J=8.4, 6.2 Hz, 1H), 3.64-3.44 (m, 3H), 3.24 (dd, J=8.4, 6.9 Hz, 1H), 3.21-3.13 (m, 2H), 1.88-1.74 (m, 1H), 1.57-1.47 (m, 2H), 1.43 (d, J=6.3 Hz, 3H), 1.40-1.29 (m, 2H), 0.94-0.83 (m, 9H); $^{13}$C NMR (101 MHz, CDCl$_3$) δ 170.44, 169.04, 155.41, 148.80, 140.75, 130.29, 109.66, 84.93, 83.70, 80.71, 75.29, 73.92, 73.29, 70.79, 56.17, 52.18, 32.28, 29.21, 19.64, 19.48, 19.44, 18.71, 14.02; HRMS-ESI (m/z) [M]$^+$ calcd for C$_{23}$H$_{36}$N$_2$O$_8$, 468.2472; found, 468.2497.

Example 23

Preparation of (2-((3S,7S,8S,9S)-7,8-diisobutoxy-9-methyl-2-oxo-1,5-dioxonan-3-ylcarbamoyl)-4-methoxypyridin-3-yloxy)methyl (compound 3)

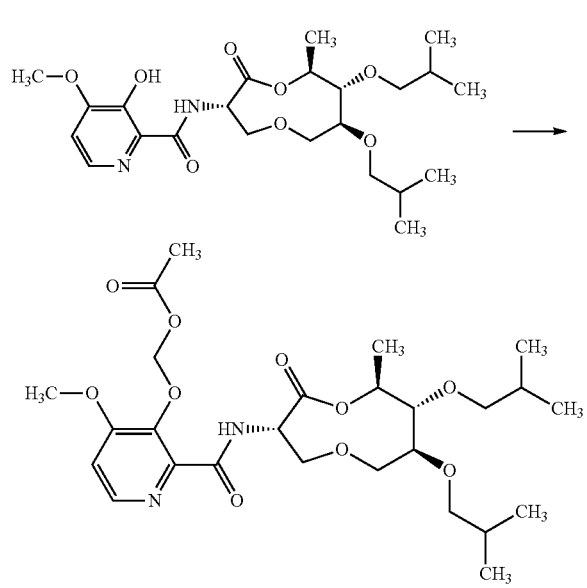

A mixture of N-((3S,7S,8S,9S)-7,8-diisobutoxy-9-methyl-2-oxo-1,5-dioxonan-3-yl)-3-hydroxy-4-methoxypicolinamide (58 mg, 0.124 mmol), Na$_2$CO$_3$ (17.06 mg, 0.161 mmol) and NaI (3.71 mg, 0.025 mmol) in acetone (1 mL) was stirred at room temperature. Bromomethyl acetate (0.016 mL, 0.155 mmol) was then added slowly. The resulting reaction mixture was stirred at 50° C. overnight. The solvent was removed and the crude residue was purified via flash chromatography (SiO$_2$) to afford the title compound as a white foam (41 mg, 61%): $^1$H NMR (400 MHz, CDCl$_3$) δ 8.53 (d, J=7.9 Hz, 1H), 8.29 (d, J=5.3 Hz, 1H), 6.95 (d, J=5.4 Hz, 1H), 5.79-5.69 (m, 2H), 5.13-5.01 (m, 1H), 5.01-4.88 (m, 1H), 4.04 (dd, J=7.9, 3.9 Hz, 1H), 3.91 (s, 3H), 3.83-3.74 (m, 2H), 3.71 (dd, J=8.4, 6.1 Hz, 1H), 3.65-3.56 (m, 1H), 3.37-3.13 (m, 5H), 2.07 (s, 3H), 1.91-1.73 (m, 2H), 1.45 (d, J=6.3 Hz, 3H), 0.97-0.87 (m, 12H); $^{13}$C NMR (101 MHz, CDCl$_3$) δ 170.95, 170.30, 163.28, 160.25, 145.84, 143.97, 142.20, 109.73, 89.47, 84.86, 83.81, 80.60, 77.72, 75.07, 74.18, 73.03, 56.23, 52.49, 29.13, 28.90, 20.90, 19.61, 19.48, 19.39, 18.67; ESIMS m/z 540.5 ([M+H]$^+$).

Compounds 2, 6, 7, 12, 13, 14, 17, 18, 23, 20, 24, 28, 29, 31, 51, 34, 35, 37, 40, 41, 45, 47, 50, 54, 55, 57, 60, 65, 64, 68, 69, 76, 77, 78, 80, 84, 85, 86, 214, 215, 216, 217, 218, 220, 221, 222, 223, 224, 226, 228, and 231 were prepared in the same manner as described in Example 23 from the corresponding 3-hydroxy picolinamides.

Example 24

Preparation of tert-butyl N-tert-butoxycarbonyl-N-[(3S,7S,8S,9S)-8-hydroxy-9-methyl-2-oxo-7-(4-trifluoromethylphenoxy)-1,5-dioxonan-3-yl]carbamate (compound 259) and tert-butyl N-tert-butoxycarbonyl-N-[(3S,7S,8R,9S)-7-hydroxy-9-methyl-2-oxo-8-(4-trifluoromethylphenoxy)-1,5-dioxonan-3-yl]carbamate (compound 260)

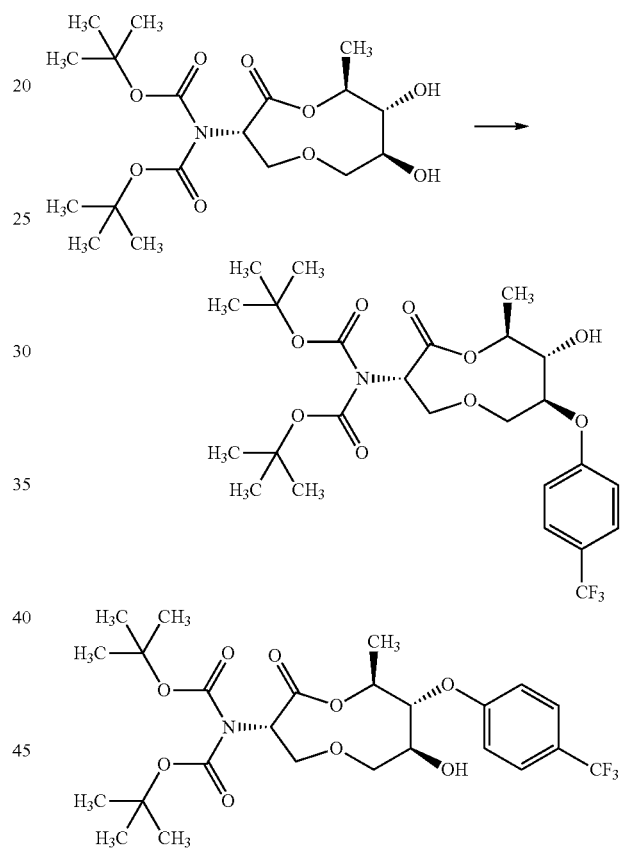

To a stirred solution of tris(4-(trifluoromethyl)phenyl)bismuthine (1.67 g, 2.59 mmol) in DCM (3.5 mL) and THF (3.5 mL) cooled in an ice bath was added 32% peracetic acid in acetic acid, (0.61 mL, 2.94 mmol). The solution was warmed to room temperature and stirred for 20 min. To the reaction was added tert-butyl N-tert-butoxycarbonyl-N-[(3S,7S,8R,9S)-7,8-dihydroxy-9-methyl-2-oxo-1,5-dioxonan-3-yl]carbamate (0.70 g, 1.73 mmol) and diacetoxycopper (63 mg, 0.345 mmol). The reaction mixture was warmed to 45° C. and stirred for 18 h. The reaction was cooled to room temperature and filtered through Celite®, washing with DCM (5 mL). The filtrate was concentrated and purified by flash chromatography (SiO$_2$; EtOAc/Hexanes) to provide the title compounds.

tert-butyl N-tert-butoxycarbonyl-N-[(3S,7S,8S,9S)-8-hydroxy-9-methyl-2-oxo-7-(4-trifluoromethylphenoxy)-1,5-dioxonan-3-yl]carbamate was isolated as a white solid (152 mg, 16%): $^1$H NMR (400 MHz, CDCl$_3$) δ 7.59-7.52 (m, 2H), 7.03 (d, J=8.6 Hz, 2H), 5.39-5.28 (m, 1H), 5.06 (dq, J=8.9, 6.3 Hz, 1H), 4.34-4.21 (m, 2H), 4.06 (dd, J=11.2, 1.3 Hz, 1H), 3.94 (dd, J=12.7, 8.5 Hz, 1H), 3.80 (t, J=8.7 Hz, 1H), 3.64 (dd, J=11.2, 7.4 Hz, 1H), 2.87 (s, 1H), 1.53 (s, 21H); $^{13}$C NMR (101 MHz, CDCl$_3$) δ 168.30, 159.10, 152.61, 127.21, 127.18, 127.14, 127.10, 125.55, 124.15, 123.82, 122.86, 115.66, 83.27, 80.62, 76.11, 75.90, 74.35, 73.36, 58.38, 27.99, 27.95, 18.69; ESIMS m/z 572 ([M+Na]$^+$).

tert-butyl N-tert-butoxycarbonyl-N-[(3S,7S,8R,9S)-7-hydroxy-9-methyl-2-oxo-8-(4-trifluoromethylphenoxy)-1,5-dioxonan-3-yl]carbamate was isolated as a white solid (456 mg, 48%): $^1$H NMR (400 MHz, CDCl$_3$) δ 7.59-7.52 (m, 2H), 7.13-7.06 (m, 2H), 5.26 (dd, J=8.5, 4.1 Hz, 1H), 5.09 (dq, J=8.7, 6.4 Hz, 1H), 4.37-4.29 (m, 2H), 4.09 (dd, J=12.1, 1.5 Hz, 1H), 4.00 (dd, J=12.2, 8.6 Hz, 1H), 3.91 (ddd, J=8.5, 7.3, 1.4 Hz, 1H), 3.72 (dd, J=11.1, 7.3 Hz, 1H), 2.33 (bs, 1H), 1.52 (s, 18H), 1.35 (d, J=6.4 Hz, 3H); $^{13}$C NMR (101 MHz, CDCl$_3$) δ 168.72, 161.29, 152.63, 127.25, 127.21, 127.17, 127.13, 116.13, 84.48, 83.24, 77.25, 73.80, 73.68, 71.79, 58.08, 27.95, 18.90; ESIMS m/z 572 ([M+Na]$^+$).

Compounds 267 and 268 were prepared in the same manner as described in Example 24 using tri(3-chlorophenyl) bismuth diacetate.

Example 25

Preparation of N-((3S,7S,8S,9S)-7,8-bis(isopentyloxy)-9-methyl-2-oxo-1,5-dioxonan-3-yl)-3-hydroxy-4-methoxypicolinamide (Compound 210)

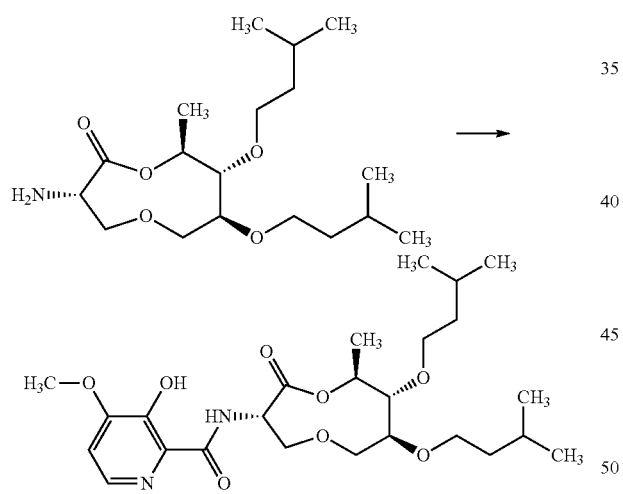

(3S,7S,8S,9S)-3-amino-7,8-bis(isopentyloxy)-9-methyl-1,5-dioxonan-2-one (130 mg, 0.376 mmol) and 3-hydroxy-4-methoxypicolinic acid (70.0 mg, 0.414 mmol) were diluted with DCM (3763 µl). PyBOP (215 mg, 0.414 mmol) was added, followed by N-ethyl-N-isopropylpropan-2-amine (216 µl, 1.242 mmol), and the mixture was stirred at room temperature until thin layer chromatography (TLC) indicated complete consumption of starting material. The reaction mixture was purified by column chromatography (SiO$_2$; hexanes/EtOAc) to furnish the title compound (79.1 mg, 0.159 mmol, 42.3% yield) as a white solid: mp 61-70° C.; IR (thin film) 3530, 3371, 2955, 2873, 1750, 1649, 1529, 1262 cm$^{-1}$; $^1$H NMR (400 MHz, CDCl$_3$) δ 11.94 (s, 1H), 8.67 (d, J=8.1 Hz, 1H), 8.01-7.98 (m, 1H), 6.87 (d, J=5.2 Hz, 1H), 5.04 (ddd, J=8.2, 6.8, 5.0 Hz, 1H), 5.01-4.89 (m, 1H), 4.05 (dd, J=11.9, 6.8 Hz, 1H), 3.94 (s, 3H), 3.92-3.85 (m, 1H), 3.85-3.78 (m, 2H), 3.66-3.58 (m, 2H), 3.57-3.48 (m, 2H), 3.26-3.14 (m, 2H), 1.69 (dp, J=13.4, 6.7 Hz, 2H), 1.51-1.38 (m, 7H), 0.90 (dt, J=6.2, 2.7 Hz, 12H); $^{13}$C NMR (101 MHz, CDCl$_3$) δ 170.30, 168.94, 155.32, 148.72, 140.66, 130.22, 109.56, 85.02, 83.63, 75.28, 73.94, 73.17, 72.48, 69.35, 56.09, 52.12, 39.23, 38.95, 24.96, 22.91, 22.67, 22.62, 22.50, 18.59; HRMS-ESI (m/z) [M+Na]$^+$ calcd for C$_{25}$H$_{40}$N$_2$NaO$_8$, 519.2677, found 519.2687.

Compound 194 was prepared in the same manner as described in Example 25, starting from compound 288.

Compound 195 was prepared in the same manner as described in Example 25, starting from compound 287.

Compound 196 was prepared in the same manner as described in Example 25, starting from compound 286.

Compound 197 was prepared in the same manner as described in Example 25, starting from compound 285.

Compound 199 was prepared in the same manner as described in Example 25, starting from compound 283.

Compound 200 was prepared in the same manner as described in Example 25, starting from compound 282.

Compound 202 was prepared in the same manner as described in Example 25, starting from compound 280.

Compound 203 was prepared in the same manner as described in Example 25, starting from compound 279.

Compound 204 was prepared in the same manner as described in Example 25, starting from compound 278.

Compound 205 was prepared in the same manner as described in Example 25, starting from compound 277.

Compound 207 was prepared in the same manner as described in Example 25, starting from compound 275.

Compound 198 was prepared in the same manner as described in Example 25, starting from compound 284.

Compound 201 was prepared in the same manner as described in Example 25, starting from compound 281.

Compound 206 was prepared in the same manner as described in Example 25, starting from compound 276.

Compound 208 was prepared in the same manner as described in Example 25, starting from compound 274.

Compound 212 was prepared in the same manner as described in Example 25, starting from compound 271.

Example 26

Preparation of 2-(((3S,7S,8S,9S)-7,8-diisobutoxy-9-methyl-2-oxo-1,5-dioxonan-3-yl)carbamoyl)-4-methoxypyridin-3-yl 3-methoxypropanoate (compound 237)

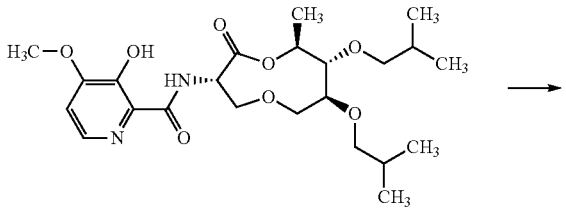

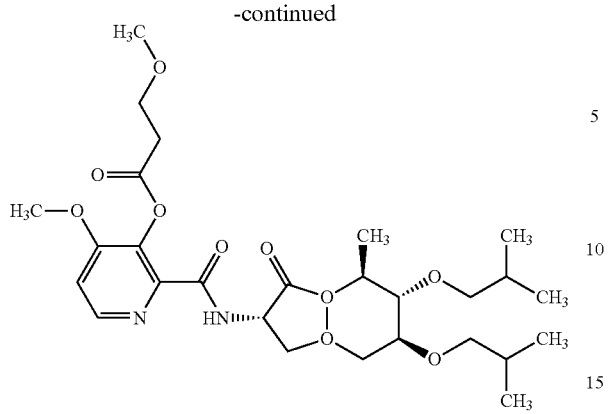

A reaction flask was charged with N-((3S,7S,8S,9S)-7,8-diisobutoxy-9-methyl-2-oxo-1,5-dioxonan-3-yl)-3-hydroxy-4-methoxypicolinamide (97 mg, 0.207 mmol), DMAP (40.1 mg, 0.328 mmol), and DCM. 3-Methoxypropanoyl chloride (22.5 μl, 0.207 mmol) was added and the colorless solution was stirred at room temperature under $N_2$ overnight. The reaction mixture was concentrated and purified by column chromatography ($SiO_2$, hexanes/EtOAc gradient) to afford the title compound (108.5 mg, 94% yield) as a sticky orange oil: IR (thin film) 3375, 2955, 2873, 1753, 1677, 1507, 1088 cm$^{-1}$; $^1$H NMR (400 MHz, CDCl$_3$) δ 8.67 (d, J=8.2 Hz, 1H), 8.38-8.30 (m, 1H), 7.00 (dd, J=5.7, 1.8 Hz, 1H), 5.08-4.98 (m, 1H), 4.93 (ddt, J=12.2, 8.4, 4.1 Hz, 1H), 4.00 (tt, J=7.2, 3.4 Hz, 1H), 3.93-3.84 (m, 3H), 3.85-3.64 (m, 5H), 3.64-3.55 (m, 1H), 3.41 (d, J=1.5 Hz, 3H), 3.33-3.12 (m, 5H), 2.97 (t, J=6.6 Hz, 2H), 1.82 (tt, J=12.9, 6.0 Hz, 2H), 1.43 (dd, J=6.3, 1.7 Hz, 3H), 0.97-0.85 (m, 12H); $^{13}$C NMR (101 MHz, CDCl$_3$) δ 170.85, 169.37, 162.67, 159.42, 146.81, 141.19, 137.38, 109.88, 84.82, 83.75, 80.56, 77.70, 74.88, 74.07, 72.99, 67.58, 58.80, 56.32, 52.13, 34.61, 29.11, 28.87, 19.58, 19.46, 19.37, 18.63; ESIMS m/z 555 ([M+H]$^+$).

Compounds 235 was prepared in the same manner as described in Example 26 from the corresponding 3-hydroxy picolinamides.

Example 27

Preparation of ((2-(((3S,7S,8S,9S)-8-(3-chlorophenoxy)-7-isobutoxy-9-methyl-2-oxo-1,5-dioxonan-3-yl)carbamoyl)-4-methoxypyridin-3-yl)oxy)methyl 2-ethoxyacetate

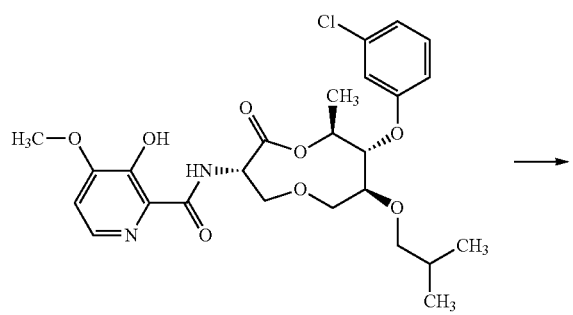

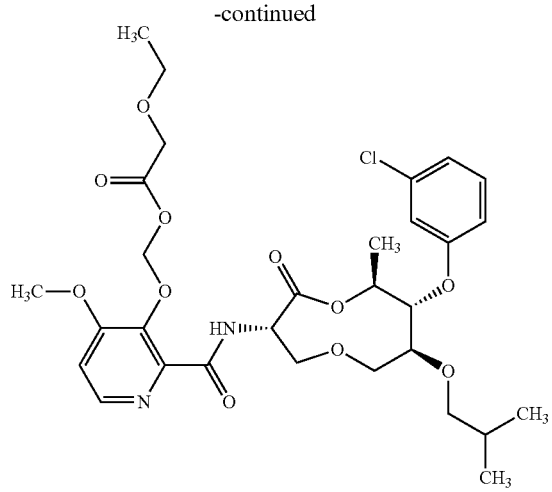

To a solution of N-((3S,7S,8S,9S)-8-(3-chlorophenoxy)-7-isobutoxy-9-methyl-2-oxo-1,5-dioxonan-3-yl)-3-hydroxy-4-methoxypicolinamide (85 mg, 0.163 mmol) in acetone (2.0 mL) was added Na$_2$CO$_3$ (34.5 mg, 0.325 mmol), NaI (4.87 mg, 0.033 mmol), and chloromethyl 2-ethoxyacetate (37.2 mg, 0.244 mmol). The reaction was warmed to 45° C. and stirred for 16 h. The reaction was then concentrated and the residue purified by flash chromatography (SiO$_2$; EtOAc/Hexanes) to give the title compound as a white foam (72.2 mg, 69.5%): $^1$H NMR (400 MHz, CDCl$_3$) δ 8.56 (d, J=8.0 Hz, 1H), 8.29 (d, J=5.4 Hz, 1H), 7.17 (t, J=8.2 Hz, 1H), 7.04 (t, J=2.2 Hz, 1H), 6.96 (d, J=5.4 Hz, 1H), 6.95-6.87 (m, 2H), 5.82 (s, 2H), 5.23-5.06 (m, 2H), 4.25 (t, J=9.1 Hz, 1H), 4.10 (s, 2H), 3.91 (s, 4H), 3.82 (dd, J=11.8, 5.3 Hz, 1H), 3.71 (dd, J=11.1, 7.4 Hz, 1H), 3.59 (q, J=7.0 Hz, 2H), 3.37 (ddd, J=8.9, 7.4, 1.6 Hz, 1H), 3.29 (dd, J=8.8, 6.3 Hz, 1H), 3.15 (dd, J=8.8, 6.4 Hz, 1H), 1.67-1.51 (m, 2H), 1.39 (d, J=6.3 Hz, 3H), 1.23 (t, J=7.0 Hz, 3H), 0.68 (dd, J=18.4, 6.7 Hz, 6H); $^{13}$C NMR (101 MHz, CDCl$_3$) δ 170.88, 170.06, 163.23, 160.17, 145.87, 143.98, 141.92, 134.59, 129.98, 121.38, 116.68, 114.41, 109.87, 89.44, 83.42, 82.64, 78.00, 74.36, 74.08, 72.30, 67.80, 67.20, 56.25, 52.32, 28.62, 19.16, 19.06, 18.72, 15.01; HRMS-FAB (m/z) [M+H]$^+$ calcd for C$_{30}$H$_{39}$ClN$_2$O$_{11}$, 639.2315; found, 639.2320.

Compounds 219, 225, 227, and 230 were prepared in the same manner as described in Example 27 from the corresponding 3-hydroxy picolinamides.

Example 28

Preparation of 2-(((3S,7S,8S,9S)-7,8-bis(4-fluorophenoxy)-9-methyl-2-oxo-1,5-dioxonan-3-yl)carbamoyl)-4-methoxypyridin-3-yl acetate (compound 229)

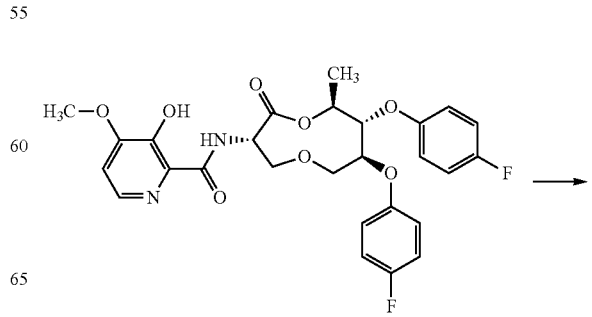

-continued

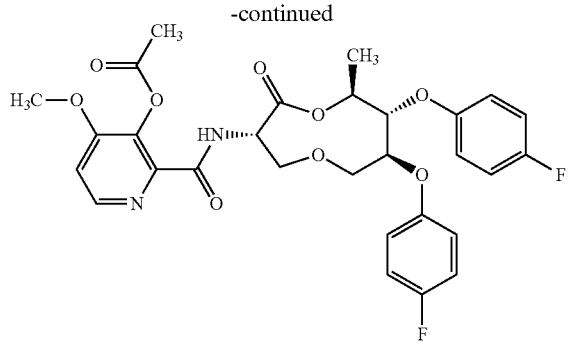

To a solution of N-((3S,7S,8S,9S)-7,8-bis(4-fluorophenoxy)-9-methyl-2-oxo-1,5-dioxonan-3-yl)-3-hydroxy-4-methoxypicolinamide (54 mg, 0.099 mmol) in DCM (0.5 mL) was added TEA (0.028 mL, 0.198 mmol), DMAP (6.1 mg, 0.050 mmol), and acetyl chloride (0.011 ml, 0.149 mmol). The reaction was warmed to 40° C. for and stirred for 14 h. The reaction was then concentrated and the crude residue purified by flash chromatography (SiO$_2$, EtOAc/Hexanes) to give the title compound as a white foam (46.5 mg, 80%): IR (thin film) 3372, 2939, 1765, 1676 cm$^{-1}$; $^1$H NMR (400 MHz, CDCl$_3$) δ 8.78 (d, J=8.2 Hz, 1H), 8.37 (d, J=5.4 Hz, 1H), 7.03 (d, J=5.5 Hz, 1H), 6.98-6.86 (m, 6H), 6.74-6.61 (m, 2H), 5.33-5.24 (m, 1H), 5.14 (m, 1H), 4.36 (t, J=9.2 Hz, 1H), 4.30-4.22 (m, 1H), 4.10-3.99 (m, 2H), 3.92 (s, 3H), 3.92-3.87 (m, 1H), 3.79 (dd, J=11.2, 7.3 Hz, 1H), 2.40 (s, 3H), 1.48 (d, J=6.4 Hz, 3H); HRMS-FAB (m/z) [M+H]$^+$ calcd for C29H28F2N2O9, 587.1836; found, 587.1838.

Compounds 232, 236, and 238 were prepared in the same manner as described in Example 28 from the corresponding 3-hydroxy picolinamides.

Example A

Evaluation of Fungicidal Activity: Leaf Blotch of Wheat (*Mycosphaerella Graminicola*; Anamorph: *Septoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B

Evaluation of Fungicidal Activity: Wheat Brown Rust (*Puccinia Triticina*; Synonym: *Puccinia recondita* f. Sp. *Tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C

Evaluation of Fungicidal Activity: Wheat Glume Blotch (*Leptosphaeria nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D

Evaluation of Fungicidal Activity: Apple Scab (*Venturia inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% RH for 48 hr, and then moved to a greenhouse set at 20° C. for disease to develop. Fungicide formulation, application and disease assessment on the sprayed leaves followed the procedures as described in the Example A.

Example E

Evaluation of Fungicidal Activity: Grape Powdery Mildew (*Uncinula necator*; Bayer Code UNCINE)

Grape seedlings (variety Carignane) were grown in soil-less Metro mix, with one plant per pot, and used in the test when approximately one month old. Plants were inoculated 24 hr after fungicide treatment by shaking spores from infected leaves over test plants. Plants were maintained in a greenhouse set at 20° C. until disease was fully developed.

Fungicide formulation, application and disease assessment on the sprayed leaves followed the procedures as described in the Example A.

Example F

Evaluation of Fungicidal Activity: Powdery Mildew of Cucumber (*Erysiphe cichoracearum*; Bayer Code ERYSCI)

Cucumber seedlings (variety Bush Pickle) were grown in soil-less Metro mix, with one plant per pot, and used in the test when 12 to 14 days old. Plants were inoculated with a spore suspension 24 hr following fungicide treatments. After inoculation the plants remained in the greenhouse set at 20° C. until disease was fully expressed. Fungicide formulation, application and disease assessment on the sprayed leaves followed the procedures as described in the Example A.

Example G

Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example H

Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 2 days prior to or 1 day after fungicide treatments. Plants were incubated for 24 h in a dark dew room at 22° C. and 100% RH then transferred to a growth room at 23° C. for disease to develop. Disease severity was assessed on the sprayed leaves.

Example I

Evaluation of Fungicidal Activity: Wheat Powdery Mildew (*Blumeria graminis* f.sp. *tritici*; Synonym: *Erysiphe graminis* f.sp. *tritici*; Bayer Code ERYSGT)

Wheat plants (variety Yuma) were grown from seed in a greenhouse in 50% mineral soil/50% soil-less Metro mix until the first leaf was fully emerged, with 7-10 seedlings per pot. These plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example J

Evaluation of Fungicidal Activity: Barley Powdery Mildew (*Blumeria graminis* f.sp. *hordei*; Synonym: *Erysiphe graminis* f.sp. *hordei*; Bayer Code ERYSGH)

Barley seedlings (variety Harrington) were propagated in soil-less Metro mix, with each pot having 8 to 12 plants, and used in the test when first leaf was fully emerged. Test plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example K

Evaluation of Fungicidal Activity: Barley Scald (*Rhyncosporium secalis*; Bayer Code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 20° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example L

Evaluation of Fungicidal Activity: Rice Blast (*Magnaporthe grisea*; Anamorph: *Pyricularia oryzae*; Bayer Code PYRIOR)

Rice seedlings (variety Japonica) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example M

Evaluation of Fungicidal Activity: Tomato Early Blight (*Alternaria solani*; Bayer Code ALTESO)

Tomato plants (variety Outdoor girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a growth room at 22° C. for disease to develop. F TABLE 1-continued Compound Structure and Appearance

| Compound Number | Appearance | Structure |
|---|---|---|
| 3 | Glassy Solid | 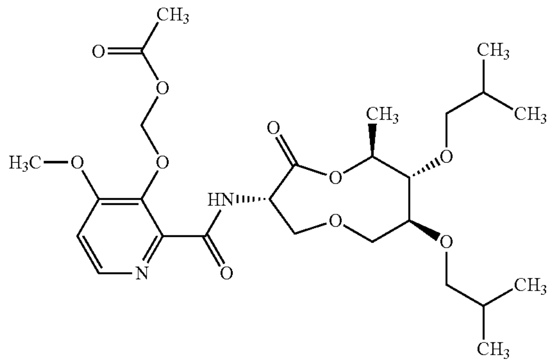 [SMILES: COc1ccnc(C(=O)N[C@H]2COC[C@H](OCC(C)C)[C@@H](OCC(C)C)[C@H](C)OC2=O)c1OCOC(C)=O] |
| 4 | White Solid | 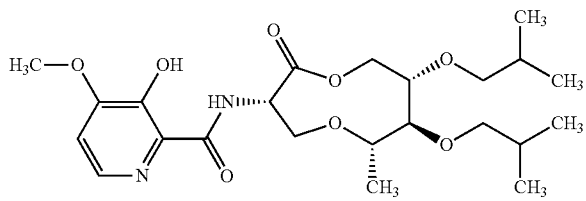 [SMILES: COc1ccnc(C(=O)N[C@H]2CO[C@@H](C)[C@H](OCC(C)C)[C@@H](OCC(C)C)COC2=O)c1O] |
| 5 | White Foam | 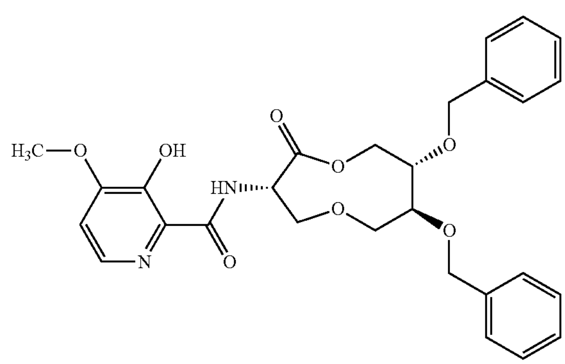 [SMILES: COc1ccnc(C(=O)N[C@H]2COC[C@H](OCc3ccccc3)[C@@H](OCc3ccccc3)COC2=O)c1O] |
| 6 | White Sticky Solid | 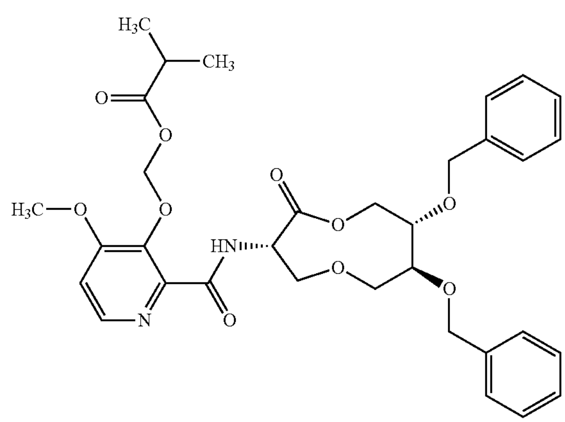 [SMILES: COc1ccnc(C(=O)N[C@H]2COC[C@H](OCc3ccccc3)[C@@H](OCc3ccccc3)COC2=O)c1OCOC(=O)C(C)C] |

TABLE 1-continued

Compound Structure and Appearance

| Compound Number | Appearance | Structure |
|---|---|---|
| 7 | Sticky Solid | 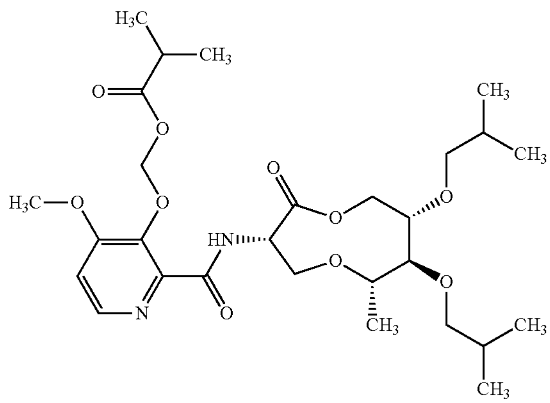 [SMILES: COc1ccnc(C(=O)N[C@H]2CO[C@@H](C)[C@H](OCC(C)C)[C@@H](OCC(C)C)COC2=O)c1OCOC(=O)C(C)C] |
| 8 | White Solid | 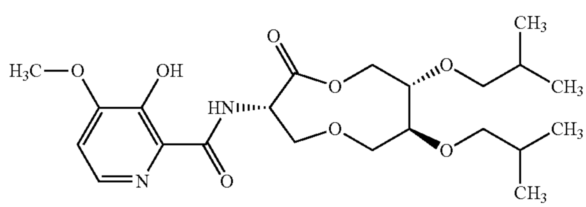 [SMILES: COc1ccnc(C(=O)N[C@H]2COC[C@H](OCC(C)C)[C@@H](OCC(C)C)COC2=O)c1O] |
| 9 | White Solid | 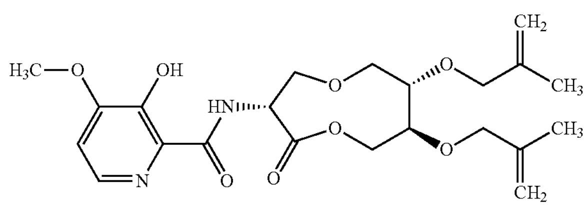 [SMILES: C=C(C)CO[C@H]1COC[C@@H](NC(=O)c2nccc(OC)c2O)C(=O)OC[C@@H]1OCC(=C)C] |
| 10 | White Solid | 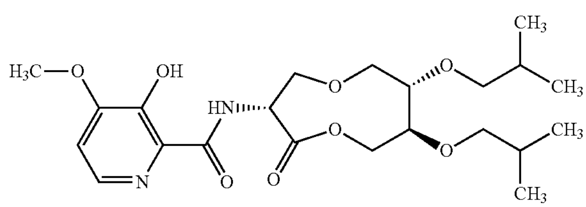 [SMILES: COc1ccnc(C(=O)N[C@@H]2COC[C@H](OCC(C)C)[C@@H](OCC(C)C)COC2=O)c1O] |
| 11 | White Solid | 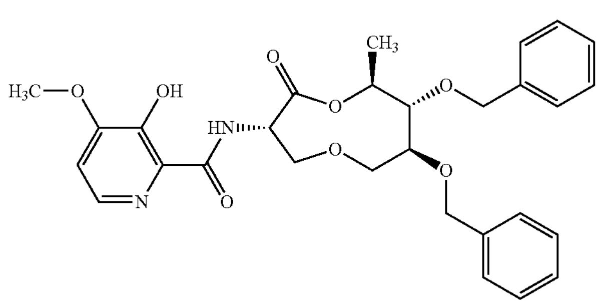 [SMILES: COc1ccnc(C(=O)N[C@H]2COC[C@H](OCc3ccccc3)[C@@H](OCc3ccccc3)[C@H](C)OC2=O)c1O] |

TABLE 1-continued

Compound Structure and Appearance

| Compound Number | Appearance | Structure |
|---|---|---|
| 12 | Colorless Oil | 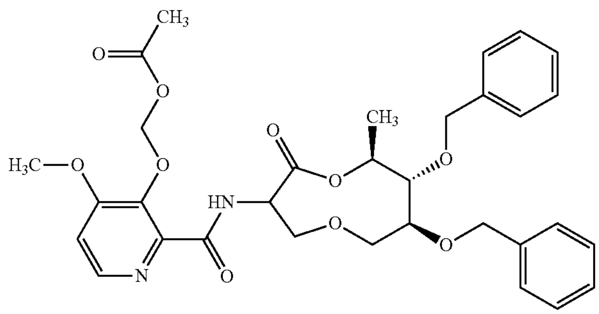 [SMILES: COc1ccnc(C(=O)NC2COC[C@H](OCc3ccccc3)[C@@H](OCc3ccccc3)[C@H](C)OC2=O)c1OCOC(C)=O] |
| 13 | White Solid | 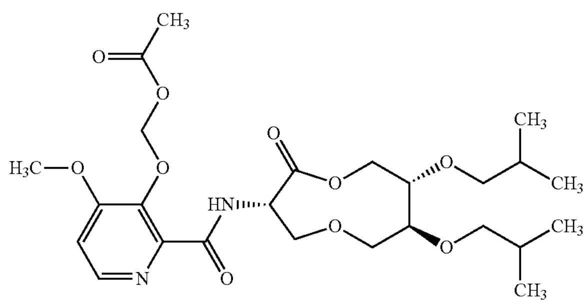 [SMILES: COc1ccnc(C(=O)N[C@H]2COC[C@H](OCC(C)C)[C@@H](OCC(C)C)COC2=O)c1OCOC(C)=O] |
| 14 | Oil | 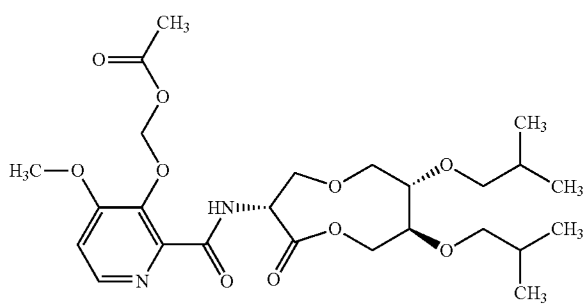 [SMILES: COc1ccnc(C(=O)N[C@@H]2COC[C@H](OCC(C)C)[C@@H](OCC(C)C)COC2=O)c1OCOC(C)=O] |
| 15 | Colorless Viscous Oil | 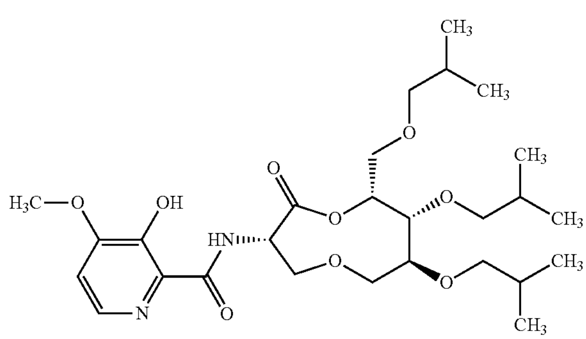 [SMILES: COc1ccnc(C(=O)N[C@H]2COC[C@H](OCC(C)C)[C@@H](OCC(C)C)[C@@H](COCC(C)C)OC2=O)c1O] |

TABLE 1-continued
Compound Structure and Appearance
| Compound Number | Appearance | Structure |
|---|---|---|
| 16 | Colorless Viscous Oil | 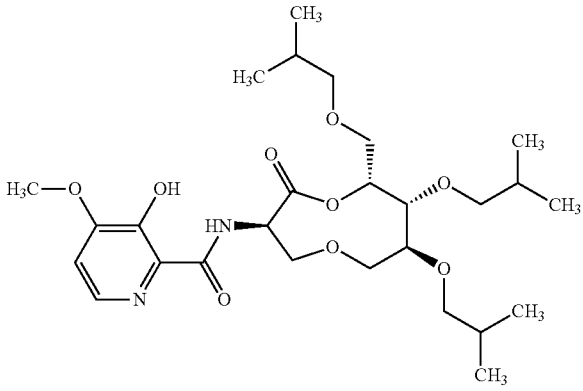 [SMILES: COc1ccnc(C(=O)N[C@@H]2COC[C@H](OCC(C)C)[C@@H](OCC(C)C)[C@@H](COCC(C)C)OC2=O)c1O] |
| 17 | Colorless Viscous Oil | 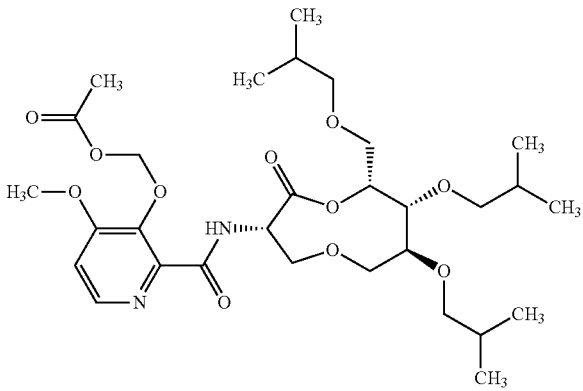 [SMILES: COc1ccnc(C(=O)N[C@H]2COC[C@H](OCC(C)C)[C@@H](OCC(C)C)[C@@H](COCC(C)C)OC2=O)c1OCOC(C)=O] |
| 18 | Colorless Viscous Oil | 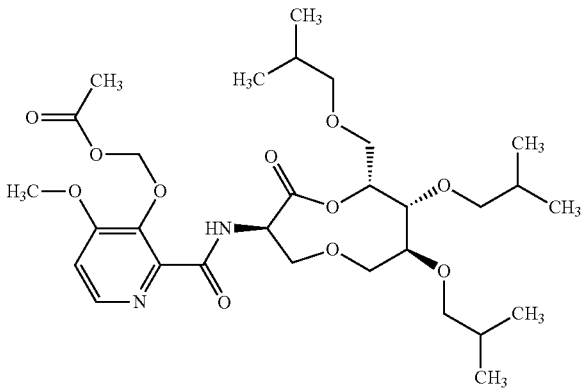 [SMILES: COc1ccnc(C(=O)N[C@@H]2COC[C@H](OCC(C)C)[C@@H](OCC(C)C)[C@@H](COCC(C)C)OC2=O)c1OCOC(C)=O] |
| 19 | Colorless Oil | 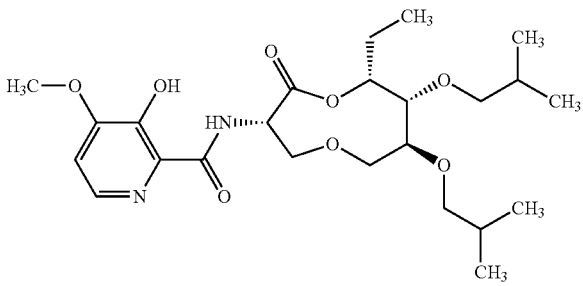 [SMILES: CC[C@H]1OC(=O)[C@@H](NC(=O)c2nccc(OC)c2O)COC[C@H](OCC(C)C)[C@H]1OCC(C)C] |

TABLE 1-continued
Compound Structure and Appearance
| Compound Number | Appearance | Structure |
|---|---|---|
| 20 | Light Yellow Oil | 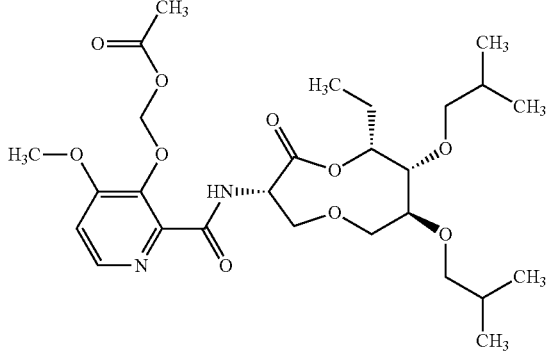 [SMILES: CC[C@H]1OC(=O)[C@@H](NC(=O)c2nccc(OC)c2OCOC(C)=O)COC[C@H](OCC(C)C)[C@H]1OCC(C)C] |
| 21 | White Solid | 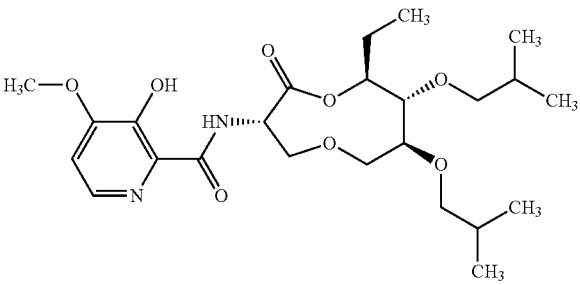 [SMILES: CC[C@@H]1OC(=O)[C@@H](NC(=O)c2nccc(OC)c2O)COC[C@H](OCC(C)C)[C@H]1OCC(C)C] |
| 22 | Colorless Oil | 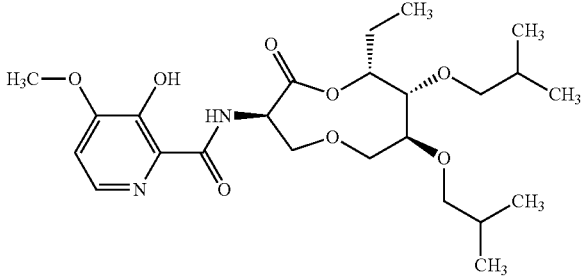 [SMILES: CC[C@H]1OC(=O)[C@H](NC(=O)c2nccc(OC)c2O)COC[C@H](OCC(C)C)[C@H]1OCC(C)C] |
| 23 | Light Yellow Oil | 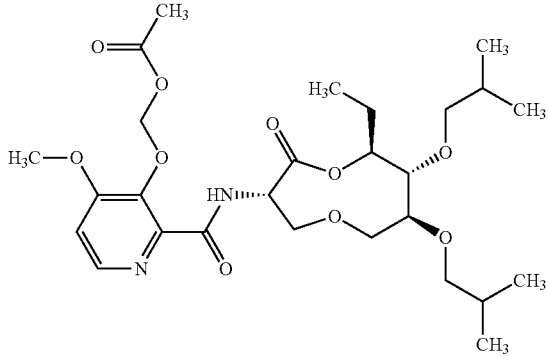 [SMILES: CC[C@@H]1OC(=O)[C@@H](NC(=O)c2nccc(OC)c2OCOC(C)=O)COC[C@H](OCC(C)C)[C@H]1OCC(C)C] |

TABLE 1-continued

Compound Structure and Appearance

| Compound Number | Appearance | Structure |
|---|---|---|
| 24 | Colorless Oil | 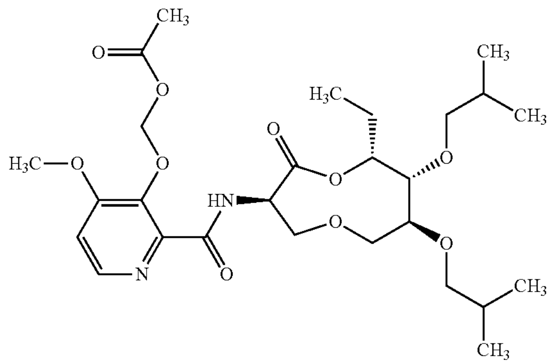 [SMILES: CC[C@H]1OC(=O)[C@H](NC(=O)c2nccc(OC)c2OCOC(C)=O)COC[C@H](OCC(C)C)[C@H]1OCC(C)C] |
| 25 | White Solid | 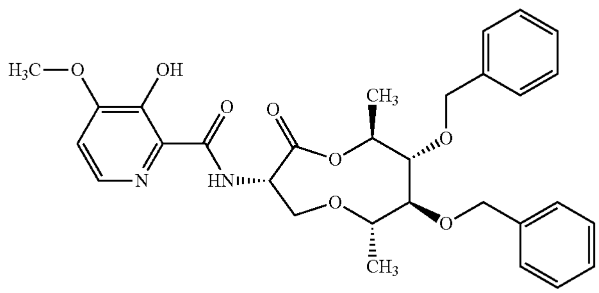 [SMILES: COc1ccnc(C(=O)N[C@H]2CO[C@@H](C)[C@H](OCc3ccccc3)[C@@H](OCc3ccccc3)[C@H](C)OC2=O)c1O] |
| 26 | White Solid | 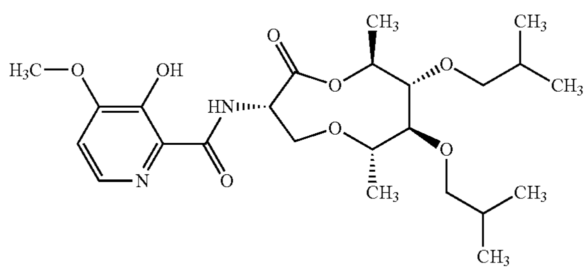 [SMILES: COc1ccnc(C(=O)N[C@H]2CO[C@@H](C)[C@H](OCC(C)C)[C@@H](OCC(C)C)[C@H](C)OC2=O)c1O] |
| 27 | White Solid | 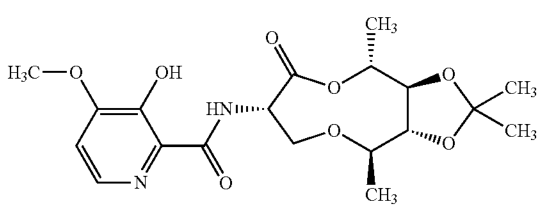 |
| 28 | White Solid | 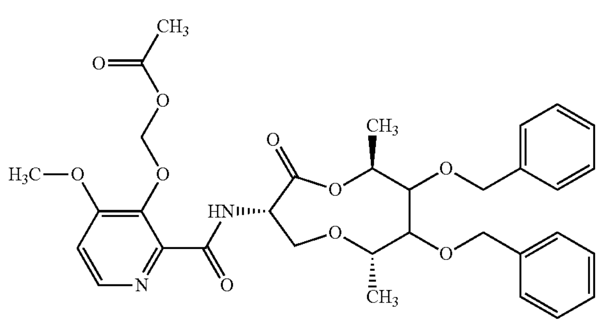 [SMILES: COc1ccnc(C(=O)N[C@H]2CO[C@@H](C)C(OCc3ccccc3)C(OCc3ccccc3)[C@H](C)OC2=O)c1OCOC(C)=O] |

TABLE 1-continued

Compound Structure and Appearance

| Compound Number | Appearance | Structure |
|---|---|---|
| 29 | White Solid | 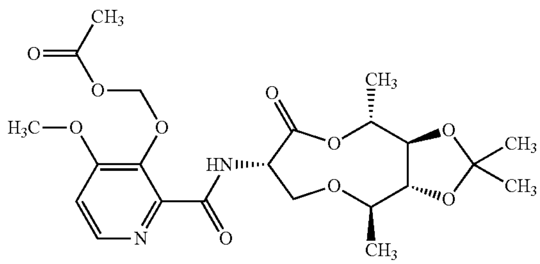 |
| 30 | Colorless Oil | 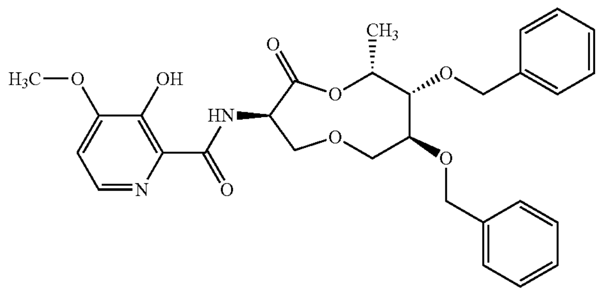 [SMILES: COc1ccnc(C(=O)N[C@@H]2COC[C@H](OCc3ccccc3)[C@@H](OCc3ccccc3)[C@@H](C)OC2=O)c1O] |
| 31 | Colorless Oil | 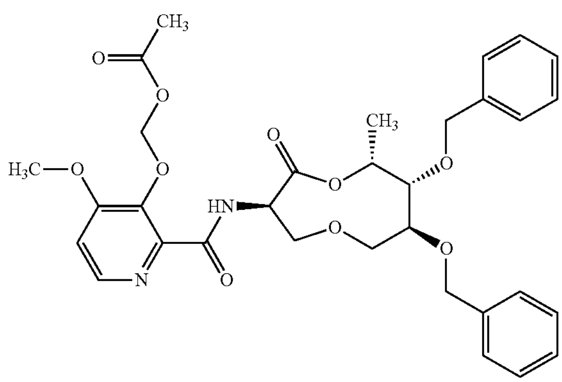 [SMILES: COc1ccnc(C(=O)N[C@@H]2COC[C@H](OCc3ccccc3)[C@@H](OCc3ccccc3)[C@@H](C)OC2=O)c1OCOC(C)=O] |
| 32 | White Solid | 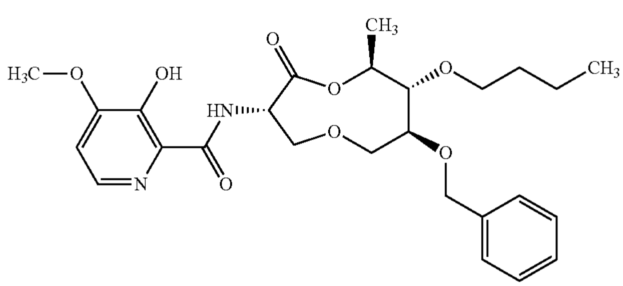 [SMILES: CCCCO[C@H]1[C@H](C)OC(=O)[C@@H](NC(=O)c2nccc(OC)c2O)COC[C@@H]1OCc1ccccc1] |
| 33 | White Solid | 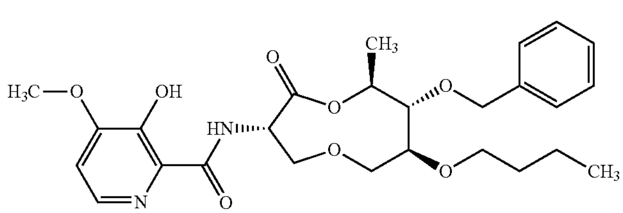 [SMILES: CCCCO[C@H]1COC[C@H](NC(=O)c2nccc(OC)c2O)C(=O)O[C@@H](C)[C@@H]1OCc1ccccc1] |

TABLE 1-continued

Compound Structure and Appearance

| Compound Number | Appearance | Structure |
|---|---|---|
| 34 | Light Yellow Oil | 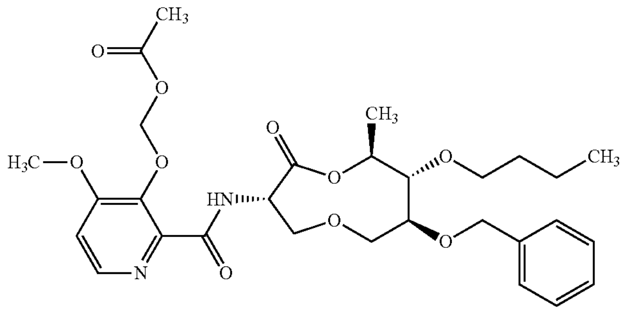 [SMILES: CCCCO[C@H]1[C@H](C)OC(=O)[C@@H](NC(=O)c2nccc(OC)c2OCOC(C)=O)COC[C@@H]1OCc1ccccc1] |
| 35 | Light Yellow Oil | 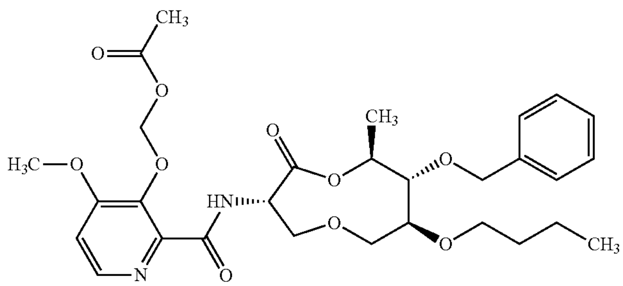 [SMILES: CCCCO[C@H]1COC[C@H](NC(=O)c2nccc(OC)c2OCOC(C)=O)C(=O)O[C@@H](C)[C@@H]1OCc1ccccc1] |
| 36 | White Solid | 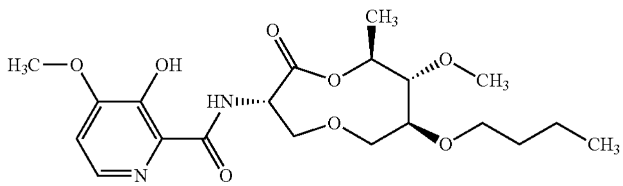 [SMILES: CCCCO[C@H]1COC[C@H](NC(=O)c2nccc(OC)c2O)C(=O)O[C@@H](C)[C@@H]1OC] |
| 37 | Light Yellow Oil | 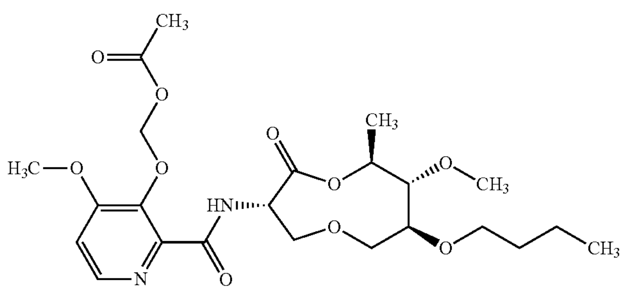 [SMILES: CCCCO[C@H]1COC[C@H](NC(=O)c2nccc(OC)c2OCOC(C)=O)C(=O)O[C@@H](C)[C@@H]1OC] |
| 38 | White Solid | 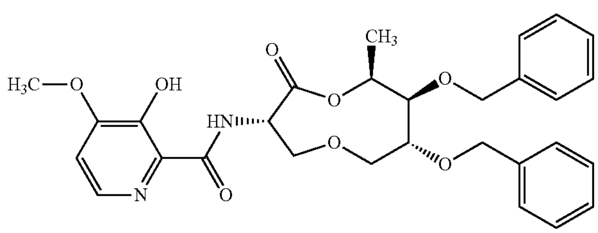 [SMILES: COc1ccnc(C(=O)N[C@H]2COC[C@@H](OCc3ccccc3)[C@H](OCc3ccccc3)[C@H](C)OC2=O)c1O] |
| 39 | White Solid | 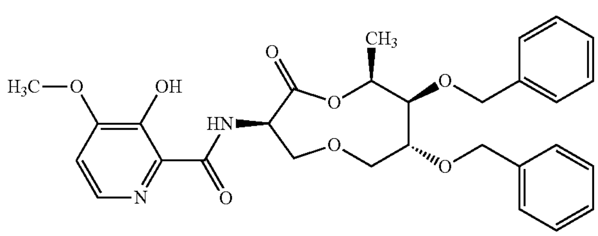 [SMILES: COc1ccnc(C(=O)N[C@@H]2COC[C@@H](OCc3ccccc3)[C@H](OCc3ccccc3)[C@H](C)OC2=O)c1O] |

TABLE 1-continued

Compound Structure and Appearance

| Compound Number | Appearance | Structure |
|---|---|---|
| 40 | White Solid | 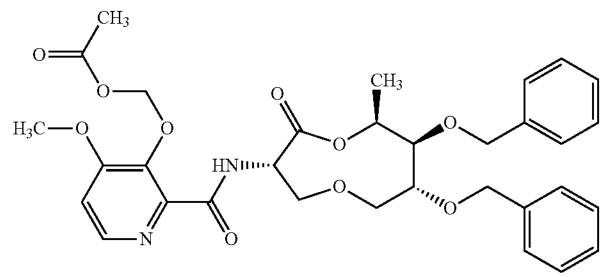 [SMILES: COc1ccnc(C(=O)N[C@H]2COC[C@@H](OCc3ccccc3)[C@H](OCc3ccccc3)[C@H](C)OC2=O)c1OCOC(C)=O] |
| 41 | White Solid | 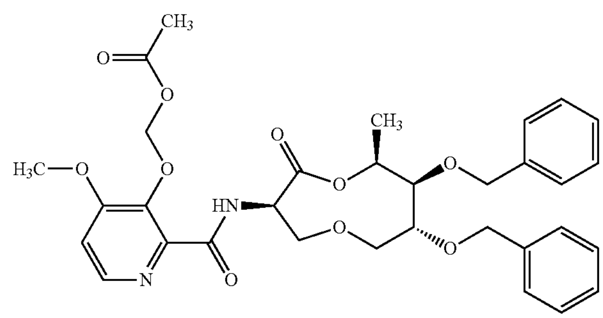 [SMILES: COc1ccnc(C(=O)N[C@@H]2COC[C@@H](OCc3ccccc3)[C@H](OCc3ccccc3)[C@H](C)OC2=O)c1OCOC(C)=O] |
| 42 | Off-White Oil | 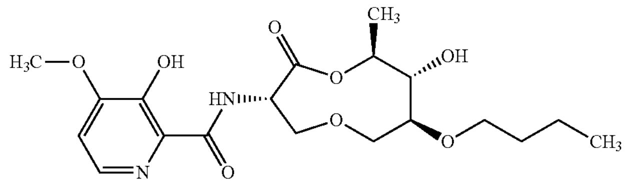 [SMILES: CCCCO[C@H]1COC[C@H](NC(=O)c2nccc(OC)c2O)C(=O)O[C@@H](C)[C@@H]1O] |
| 43 | Off-White Solid | 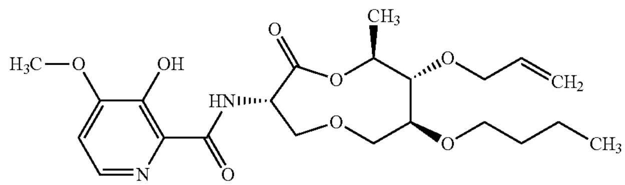 [SMILES: C=CCO[C@H]1[C@H](C)OC(=O)[C@@H](NC(=O)c2nccc(OC)c2O)COC[C@@H]1OCCCC] |
| 44 | White Solid | 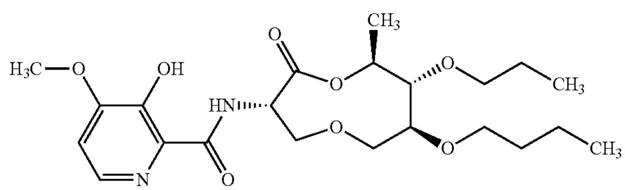 [SMILES: CCCCO[C@H]1COC[C@H](NC(=O)c2nccc(OC)c2O)C(=O)O[C@@H](C)[C@@H]1OCCC] |
| 45 | Colorless Oil | 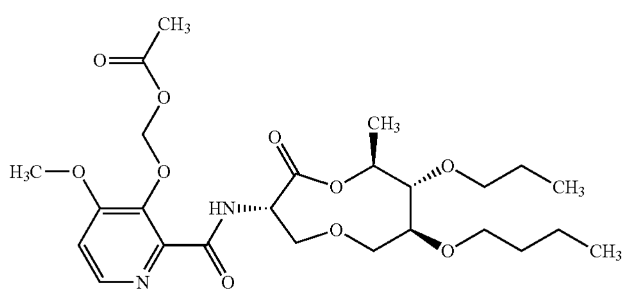 [SMILES: CCCCO[C@H]1COC[C@H](NC(=O)c2nccc(OC)c2OCOC(C)=O)C(=O)O[C@@H](C)[C@@H]1OCCC] |

TABLE 1-continued

Compound Structure and Appearance

| Compound Number | Appearance | Structure |
|---|---|---|
| 46 | Colorless Oil | 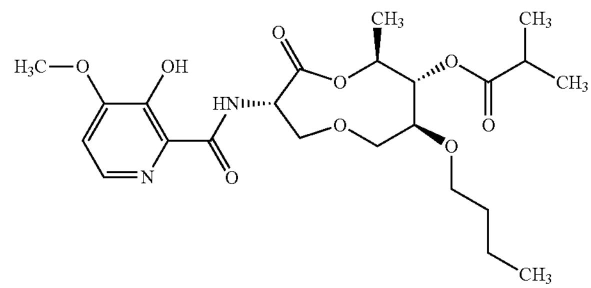 [SMILES: CCCCO[C@H]1COC[C@H](NC(=O)c2nccc(OC)c2O)C(=O)O[C@@H](C)[C@@H]1OC(=O)C(C)C] |
| 47 | Light Yellow Oil | 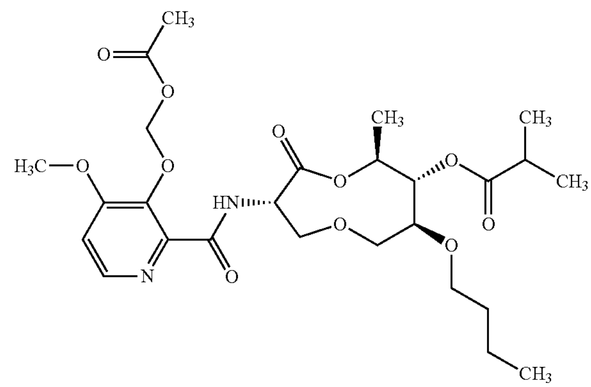 [SMILES: CCCCO[C@H]1COC[C@H](NC(=O)c2nccc(OC)c2OCOC(C)=O)C(=O)O[C@@H](C)[C@@H]1OC(=O)C(C)C] |
| 48 | Light Yellow Solid | 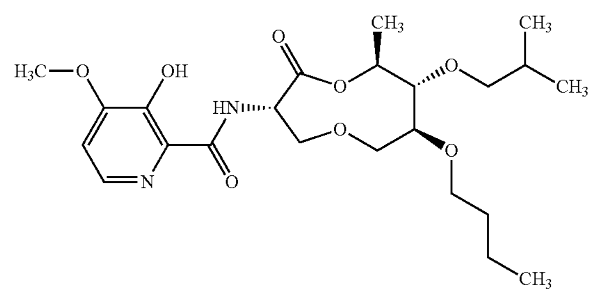 [SMILES: CCCCO[C@H]1COC[C@H](NC(=O)c2nccc(OC)c2O)C(=O)O[C@@H](C)[C@@H]1OCC(C)C] |
| 49 | Colorless Oil | 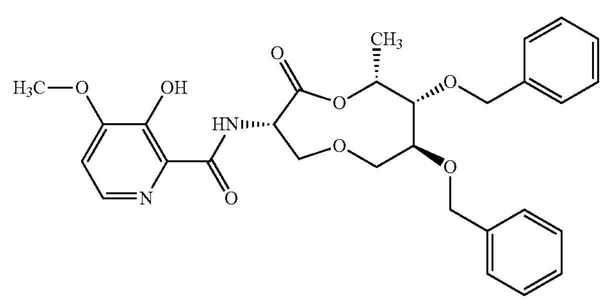 [SMILES: COc1ccnc(C(=O)N[C@H]2COC[C@H](OCc3ccccc3)[C@@H](OCc3ccccc3)[C@@H](C)OC2=O)c1O] |
| 50 | Colorless Oil | 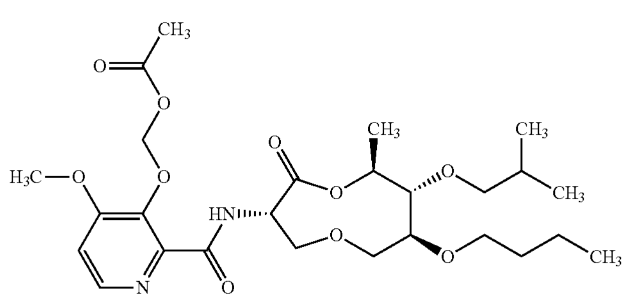 [SMILES: CCCCO[C@H]1COC[C@H](NC(=O)c2nccc(OC)c2OCOC(C)=O)C(=O)O[C@@H](C)[C@@H]1OCC(C)C] |

TABLE 1-continued
Compound Structure and Appearance
| Compound Number | Appearance | Structure |
|---|---|---|
| 51 | Light Yellow Oil | 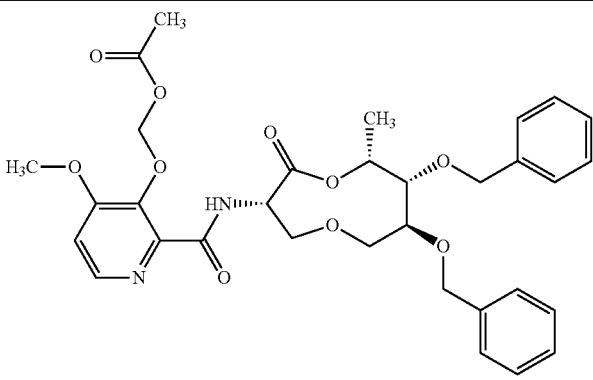 |
| 52 | White Solid | 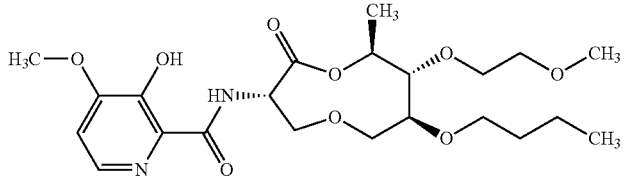 |
| 53 | White Solid | 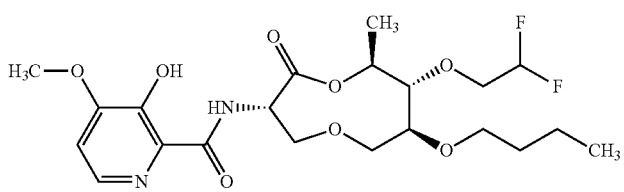 [SMILES: CCCCO[C@H]1COC[C@H](NC(=O)c2nccc(OC)c2O)C(=O)O[C@@H](C)[C@@H]1OCC(F)F] |
| 54 | Colorless Oil | 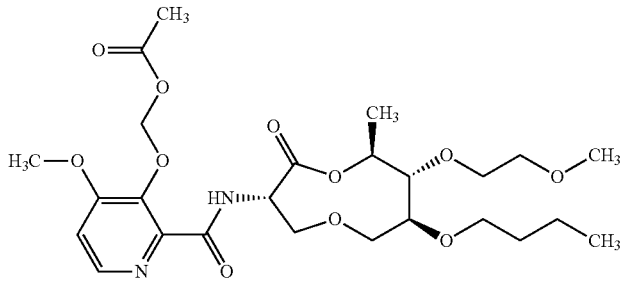 |
| 55 | Colorless Oil | 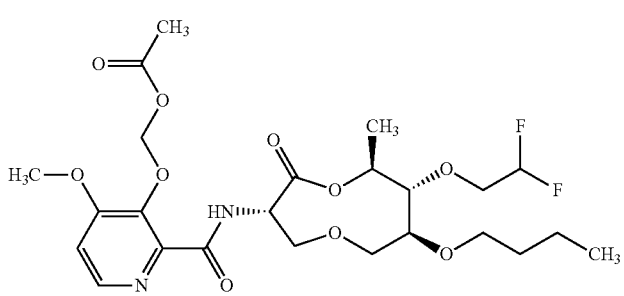 [SMILES: CCCCO[C@H]1COC[C@H](NC(=O)c2nccc(OC)c2OCOC(C)=O)C(=O)O[C@@H](C)[C@@H]1OCC(F)F] |

TABLE 1-continued
Compound Structure and Appearance
| Compound Number | Appearance | Structure |
|---|---|---|
| 56 | White Solid | 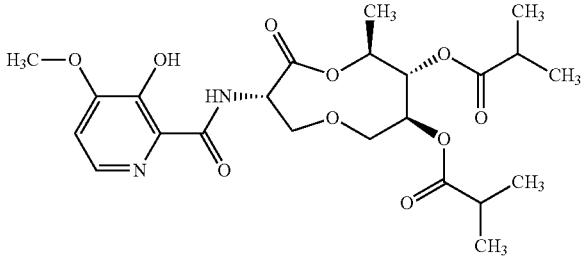 [SMILES: COc1ccnc(C(=O)N[C@H]2COC[C@H](OC(=O)C(C)C)[C@@H](OC(=O)C(C)C)[C@H](C)OC2=O)c1O] |
| 57 | Colorless Oil | 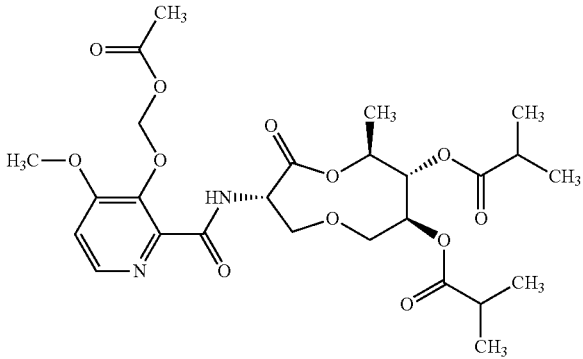 [SMILES: COc1ccnc(C(=O)N[C@H]2COC[C@H](OC(=O)C(C)C)[C@@H](OC(=O)C(C)C)[C@H](C)OC2=O)c1OCOC(C)=O] |
| 58 | White Solid | 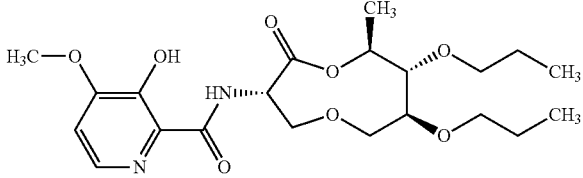 [SMILES: CCCO[C@H]1[C@H](C)OC(=O)[C@@H](NC(=O)c2nccc(OC)c2O)COC[C@@H]1OCCC] |
| 59 | Colorless Oil | 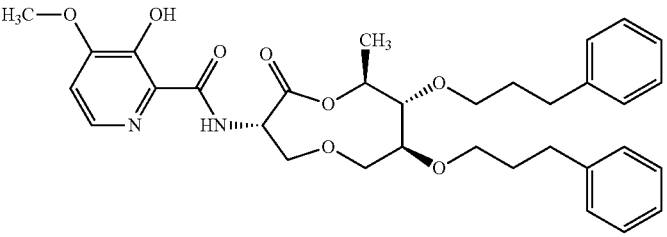 [SMILES: COc1ccnc(C(=O)N[C@H]2COC[C@H](OCCCc3ccccc3)[C@@H](OCCCc3ccccc3)[C@H](C)OC2=O)c1O] |
| 60 | Light Yellow Oil | 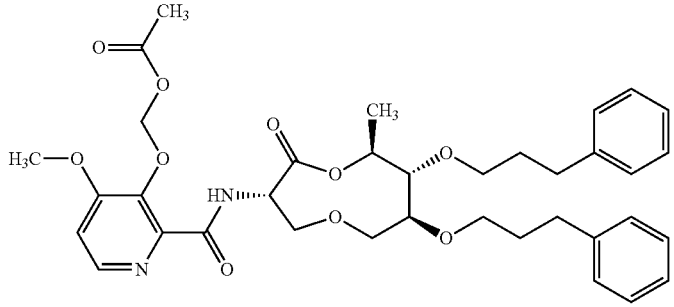 [SMILES: COc1ccnc(C(=O)N[C@H]2COC[C@H](OCCCc3ccccc3)[C@@H](OCCCc3ccccc3)[C@H](C)OC2=O)c1OCOC(C)=O] |

TABLE 1-continued
Compound Structure and Appearance
| Compound Number | Appearance | Structure |
|---|---|---|
| 61 | White Solid | 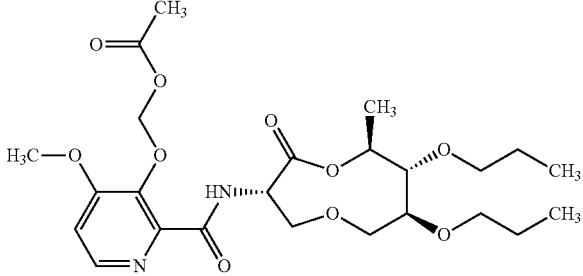 [SMILES: CCCO[C@H]1[C@H](C)OC(=O)[C@@H](NC(=O)c2nccc(OC)c2OCOC(C)=O)COC[C@@H]1OCCC] |
| 62 | White Solid | 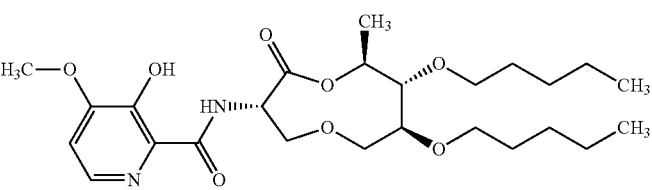 [SMILES: CCCCCO[C@H]1[C@H](C)OC(=O)[C@@H](NC(=O)c2nccc(OC)c2O)COC[C@@H]1OCCCCC] |
| 63 | White Solid | 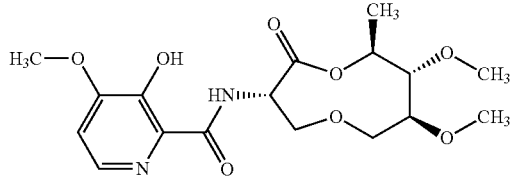 |
| 64 | Thick Oil | 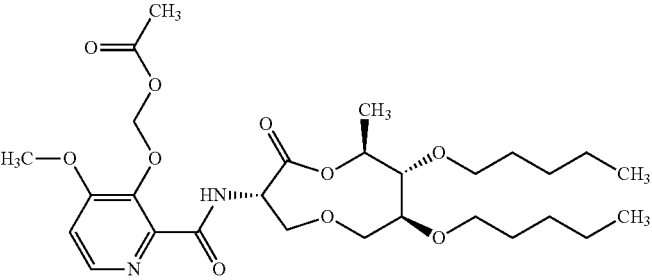 [SMILES: CCCCCO[C@H]1[C@H](C)OC(=O)[C@@H](NC(=O)c2nccc(OC)c2OCOC(C)=O)COC[C@@H]1OCCCCC] |
| 65 | Light Yellow Oil | 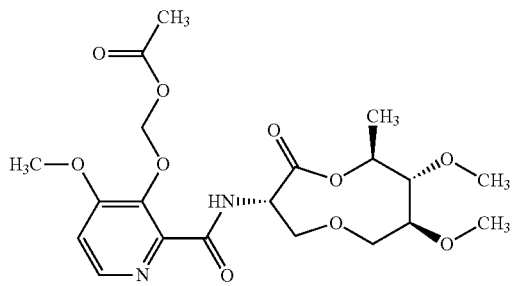 |
| 66 | Colorless Oil | 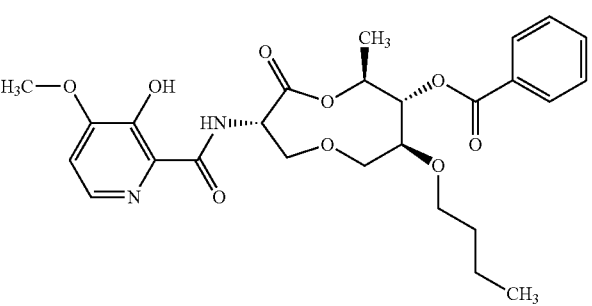 [SMILES: CCCCO[C@H]1COC[C@H](NC(=O)c2nccc(OC)c2O)C(=O)O[C@@H](C)[C@@H]1OC(=O)c1ccccc1] |

TABLE 1-continued

Compound Structure and Appearance

| Compound Number | Appearance | Structure |
|---|---|---|
| 67 | White Solid | 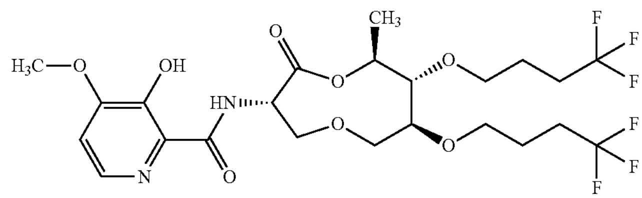 [SMILES: COc1ccnc(C(=O)N[C@H]2COC[C@H](OCCCC(F)(F)F)[C@@H](OCCCC(F)(F)F)[C@H](C)OC2=O)c1O] |
| 68 | Little Yellow Oil | 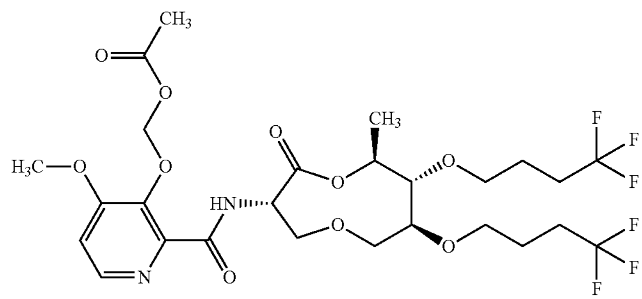 [SMILES: COc1ccnc(C(=O)N[C@H]2COC[C@H](OCCCC(F)(F)F)[C@@H](OCCCC(F)(F)F)[C@H](C)OC2=O)c1OCOC(C)=O] |
| 69 | Colorless Oil | 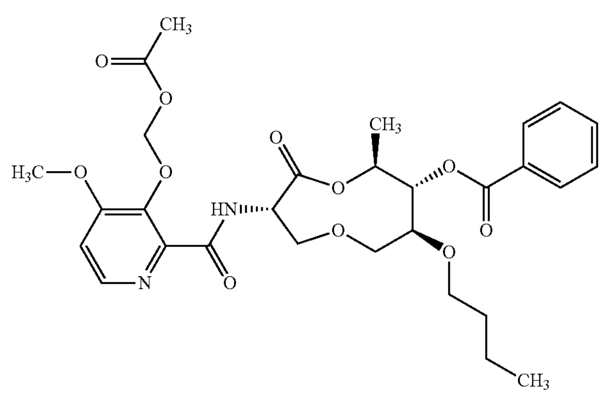 [SMILES: CCCCO[C@H]1COC[C@H](NC(=O)c2nccc(OC)c2OCOC(C)=O)C(=O)O[C@@H](C)[C@@H]1OC(=O)c1ccccc1] |
| 70 | White Solid | 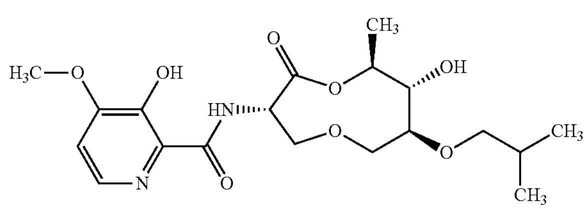 [SMILES: COc1ccnc(C(=O)N[C@H]2COC[C@H](OCC(C)C)[C@@H](O)[C@H](C)OC2=O)c1O] |
| 71 | White Solid | 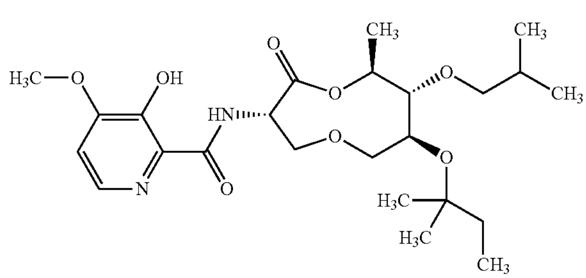 [SMILES: CCC(C)(C)O[C@H]1COC[C@H](NC(=O)c2nccc(OC)c2O)C(=O)O[C@@H](C)[C@@H]1OCC(C)C] |

TABLE 1-continued
Compound Structure and Appearance
| Compound Number | Appearance | Structure |
|---|---|---|
| 72 | White Solid | 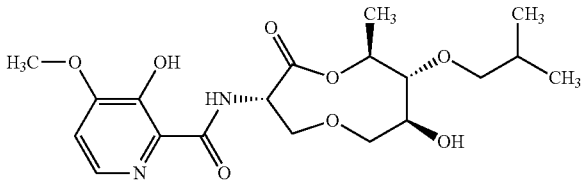 [SMILES: COc1ccnc(C(=O)N[C@H]2COC[C@H](O)[C@@H](OCC(C)C)[C@H](C)OC2=O)c1O] |
| 73 | White Solid | 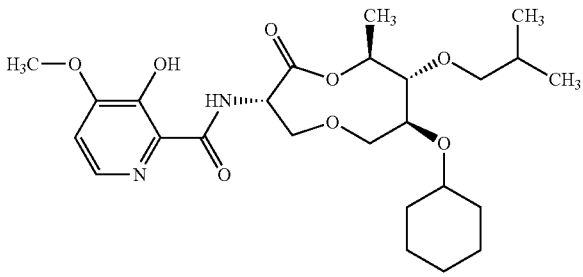 [SMILES: COc1ccnc(C(=O)N[C@H]2COC[C@H](OC3CCCCC3)[C@@H](OCC(C)C)[C@H](C)OC2=O)c1O] |
| 74 | Thick Colorless Oil | 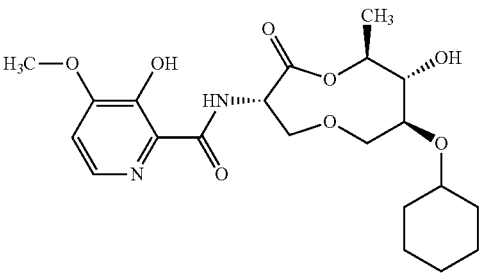 [SMILES: COc1ccnc(C(=O)N[C@H]2COC[C@H](OC3CCCCC3)[C@@H](O)[C@H](C)OC2=O)c1O] |
| 75 | White Solid | 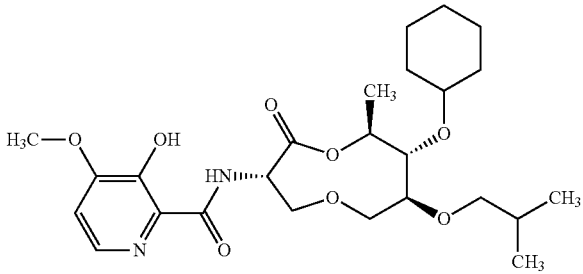 [SMILES: COc1ccnc(C(=O)N[C@H]2COC[C@H](OCC(C)C)[C@@H](OC3CCCCC3)[C@H](C)OC2=O)c1O] |
| 76 | Colorless Oil | 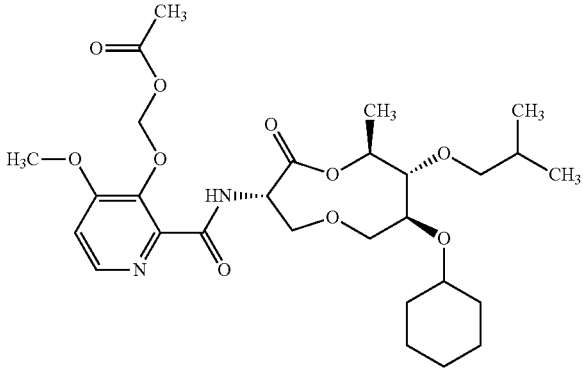 [SMILES: COc1ccnc(C(=O)N[C@H]2COC[C@H](OC3CCCCC3)[C@@H](OCC(C)C)[C@H](C)OC2=O)c1OCOC(C)=O] |

TABLE 1-continued
Compound Structure and Appearance
| Compound Number | Appearance | Structure |
|---|---|---|
| 77 | Colorless Oil | 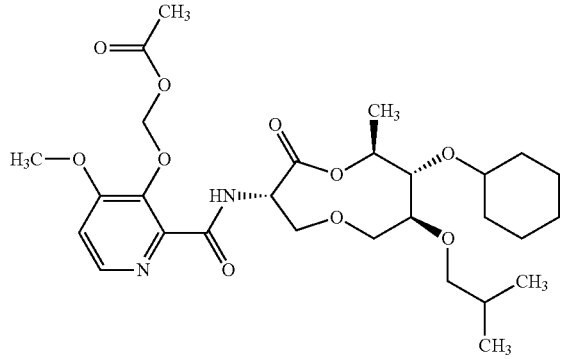 [SMILES: COc1ccnc(C(=O)N[C@H]2COC[C@H](OCC(C)C)[C@@H](OC3CCCCC3)[C@H](C)OC2=O)c1OCOC(C)=O] |
| 78 | Colorless Oil | 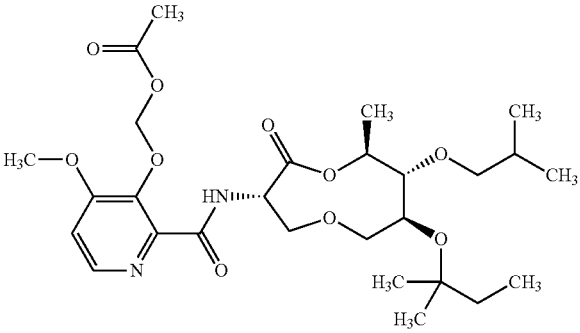 [SMILES: CCC(C)(C)O[C@H]1COC[C@H](NC(=O)c2nccc(OC)c2OCOC(C)=O)C(=O)O[C@@H](C)[C@@H]1OCC(C)C] |
| 79 | Colorless Oil | 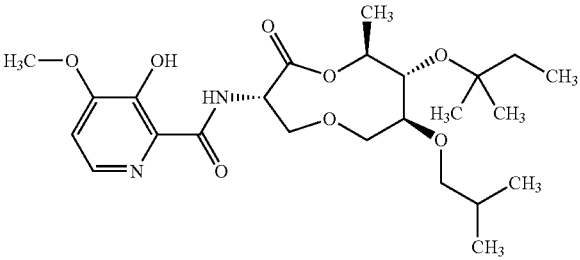 [SMILES: CCC(C)(C)O[C@H]1[C@H](C)OC(=O)[C@@H](NC(=O)c2nccc(OC)c2O)COC[C@@H]1OCC(C)C] |
| 80 | Colorless Oil | 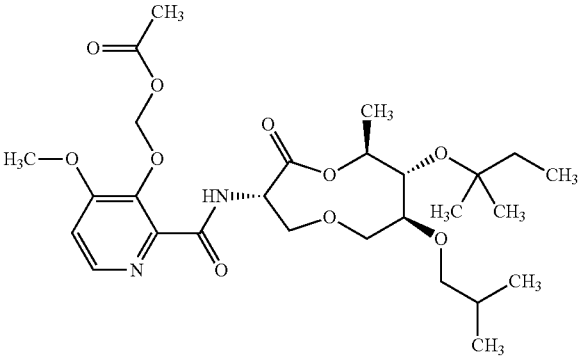 [SMILES: CCC(C)(C)O[C@H]1[C@H](C)OC(=O)[C@@H](NC(=O)c2nccc(OC)c2OCOC(C)=O)COC[C@@H]1OCC(C)C] |

TABLE 1-continued

Compound Structure and Appearance

| Compound Number | Appearance | Structure |
|---|---|---|
| 81 | White Foam | 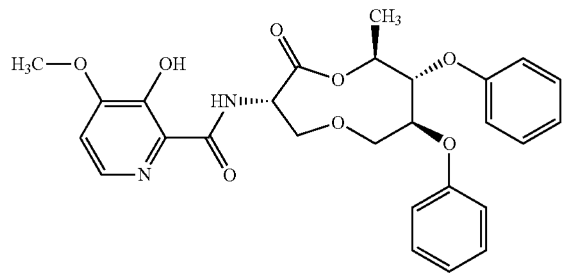 [SMILES: COc1ccnc(C(=O)N[C@H]2COC[C@H](Oc3ccccc3)[C@@H](Oc3ccccc3)[C@H](C)OC2=O)c1O] |
| 82 | White Solid | 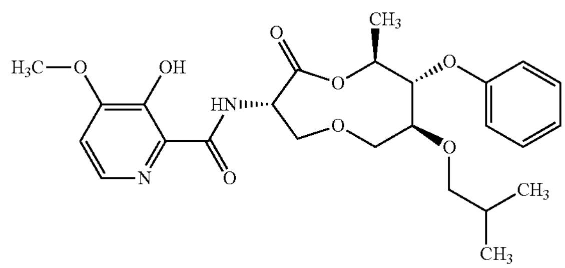 [SMILES: COc1ccnc(C(=O)N[C@H]2COC[C@H](OCC(C)C)[C@@H](Oc3ccccc3)[C@H](C)OC2=O)c1O] |
| 83 | White Solid | 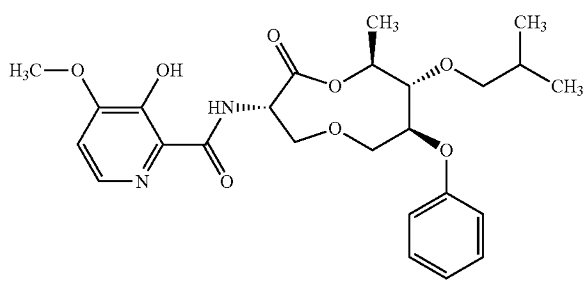 [SMILES: COc1ccnc(C(=O)N[C@H]2COC[C@H](Oc3ccccc3)[C@@H](OCC(C)C)[C@H](C)OC2=O)c1O] |
| 84 | Colorless Oil | 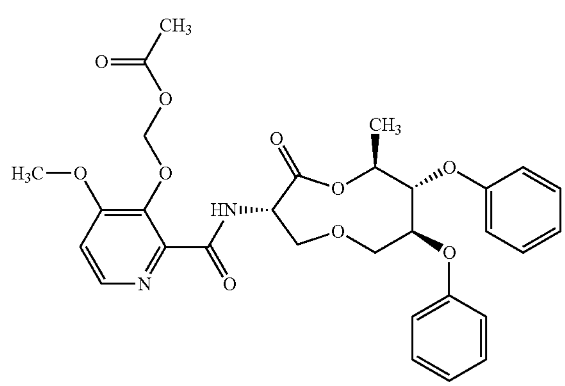 [SMILES: COc1ccnc(C(=O)N[C@H]2COC[C@H](Oc3ccccc3)[C@@H](Oc3ccccc3)[C@H](C)OC2=O)c1OCOC(C)=O] |

TABLE 1-continued

Compound Structure and Appearance

| Compound Number | Appearance | Structure |
|---|---|---|
| 85 | Colorless Oil | 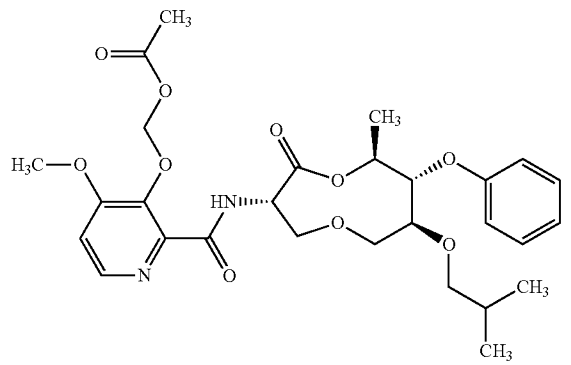 [SMILES: COc1ccnc(C(=O)N[C@H]2COC[C@H](OCC(C)C)[C@@H](Oc3ccccc3)[C@H](C)OC2=O)c1OCOC(C)=O] |
| 86 | Colorless Oil | 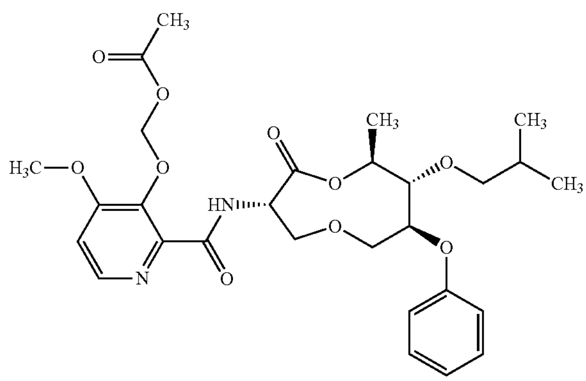 [SMILES: COc1ccnc(C(=O)N[C@H]2COC[C@H](Oc3ccccc3)[C@@H](OCC(C)C)[C@H](C)OC2=O)c1OCOC(C)=O] |
| 87 | Amber Solid | 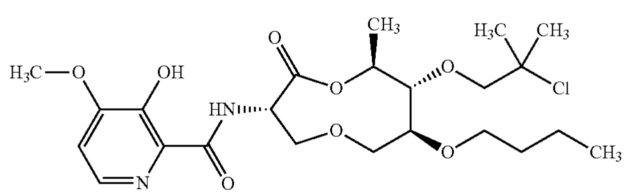 [SMILES: CCCCO[C@H]1COC[C@H](NC(=O)c2nccc(OC)c2O)C(=O)O[C@@H](C)[C@@H]1OCC(C)(C)Cl] |
| 88 | White Solid | 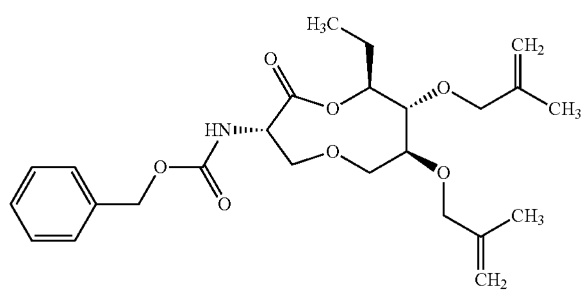 [SMILES: C=C(C)CO[C@@H]1[C@@H](OCC(=C)C)COC[C@H](NC(=O)OCc2ccccc2)C(=O)O[C@H]1CC] |
| 89 | Colorless Oil | 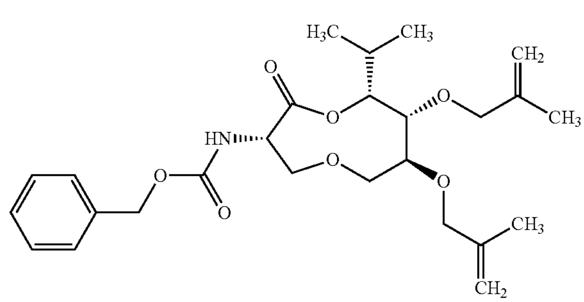 [SMILES: C=C(C)CO[C@@H]1[C@@H](OCC(=C)C)COC[C@H](NC(=O)OCc2ccccc2)C(=O)O[C@@H]1C(C)C] |

TABLE 1-continued

Compound Structure and Appearance

| Compound Number | Appearance | Structure |
|---|---|---|
| 90 | Pale Yellow Oil | 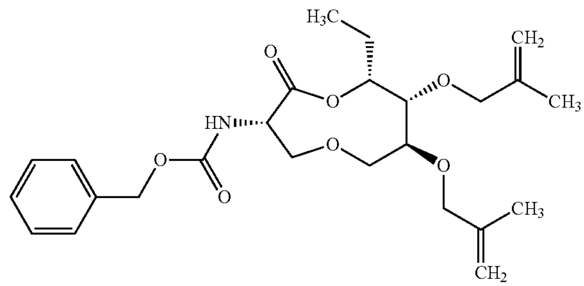 [SMILES: C=C(C)CO[C@@H]1[C@@H](OCC(=C)C)COC[C@H](NC(=O)OCc2ccccc2)C(=O)O[C@@H]1CC] |
| 91 | Pale Yellow Oil | 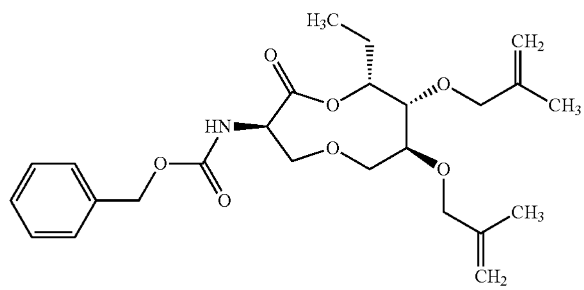 [SMILES: C=C(C)CO[C@@H]1[C@@H](OCC(=C)C)COC[C@@H](NC(=O)OCc2ccccc2)C(=O)O[C@@H]1CC] |
| 92 | Colorless Oil | 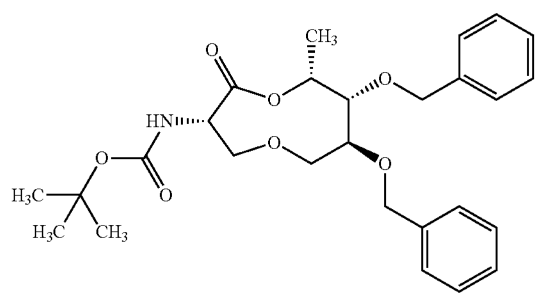 [SMILES: C[C@H]1OC(=O)[C@@H](NC(=O)OC(C)(C)C)COC[C@H](OCc2ccccc2)[C@H]1OCc1ccccc1] |
| 93 | Off-White Solid | 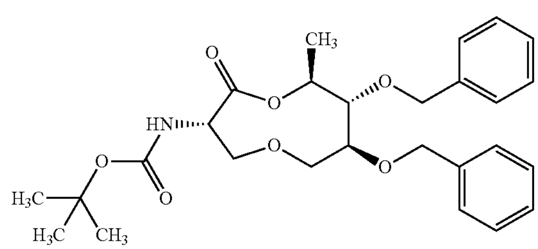 [SMILES: C[C@@H]1OC(=O)[C@@H](NC(=O)OC(C)(C)C)COC[C@H](OCc2ccccc2)[C@H]1OCc1ccccc1] |
| 94 | Colorless Oil | 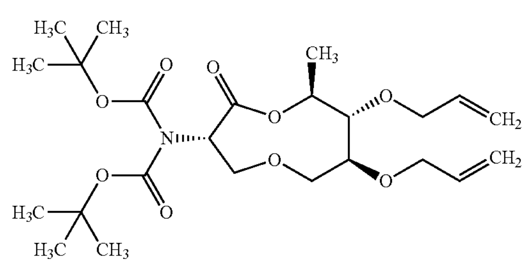 [SMILES: C=CCO[C@H]1[C@H](C)OC(=O)[C@@H](N(C(=O)OC(C)(C)C)C(=O)OC(C)(C)C)COC[C@@H]1OCC=C] |

TABLE 1-continued

Compound Structure and Appearance

| Compound Number | Appearance | Structure |
|---|---|---|
| 95 | Colorless Oil | 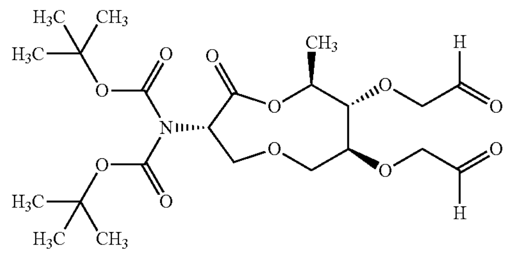 [SMILES: C[C@@H]1OC(=O)[C@@H](N(C(=O)OC(C)(C)C)C(=O)OC(C)(C)C)COC[C@H](OCC=O)[C@H]1OCC=O] |
| 96 | Colorless Oil | 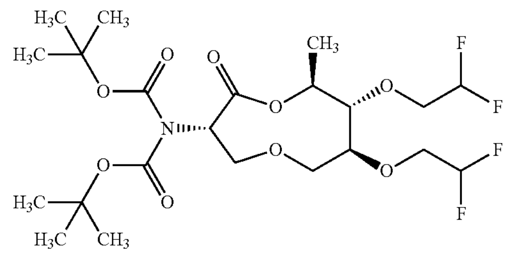 |
| 97 | Light Yellow Oil | 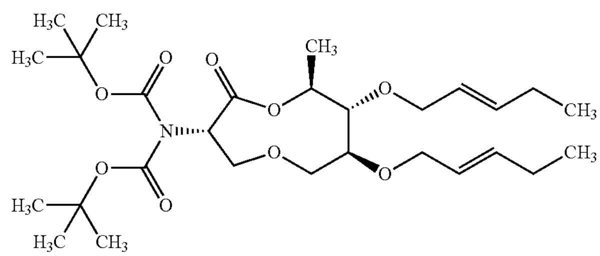 [SMILES: CC/C=C/CO[C@H]1[C@H](C)OC(=O)[C@@H](N(C(=O)OC(C)(C)C)C(=O)OC(C)(C)C)COC[C@@H]1OC/C=C/CC] |
| 98 | Colorless Oil | 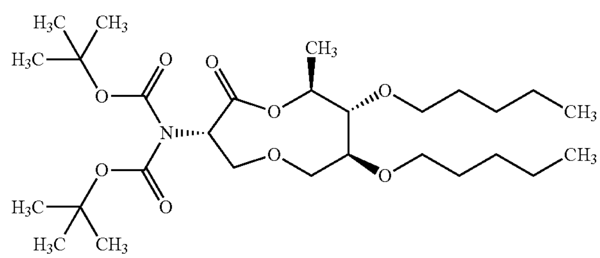 [SMILES: CCCCCO[C@H]1[C@H](C)OC(=O)[C@@H](N(C(=O)OC(C)(C)C)C(=O)OC(C)(C)C)COC[C@@H]1OCCCCC] |
| 99 | White Solid | 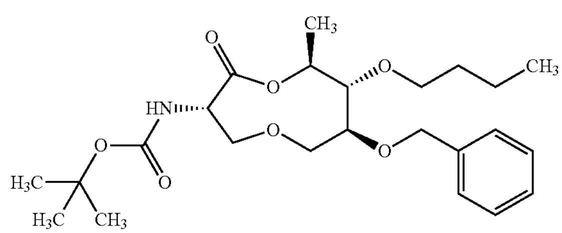 [SMILES: CCCCO[C@H]1[C@H](C)OC(=O)[C@@H](NC(=O)OC(C)(C)C)COC[C@@H]1OCc1ccccc1] |
| 100 | Colorless Oil | 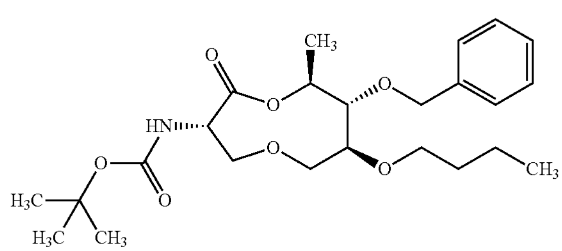 [SMILES: CCCCO[C@H]1COC[C@H](NC(=O)OC(C)(C)C)C(=O)O[C@@H](C)[C@@H]1OCc1ccccc1] |

TABLE 1-continued
Compound Structure and Appearance
| Compound Number | Appearance | Structure |
|---|---|---|
| 101 | Colorless Oil | 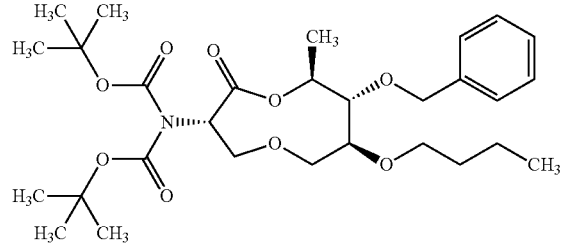 [SMILES: CCCCO[C@H]1COC[C@H](N(C(=O)OC(C)(C)C)C(=O)OC(C)(C)C)C(=O)O[C@@H](C)[C@@H]1OCc1ccccc1] |
| 102 | White Gummy Solid | 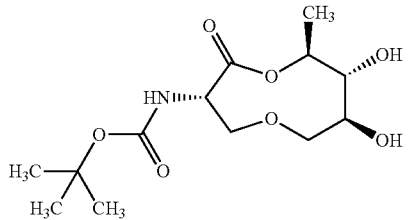 [SMILES: C[C@@H]1OC(=O)[C@@H](NC(=O)OC(C)(C)C)COC[C@H](O)[C@H]1O] |
| 103 | Colorless, Thick Oil | 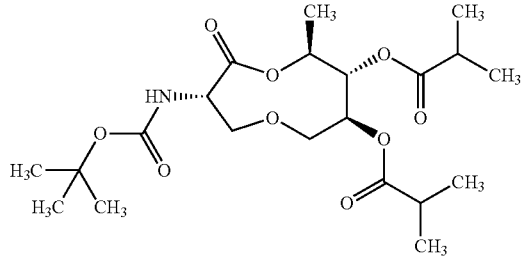 [SMILES: CC(C)C(=O)O[C@H]1[C@H](C)OC(=O)[C@@H](NC(=O)OC(C)(C)C)COC[C@@H]1OC(=O)C(C)C] |
| 104 | Colorless Oil | 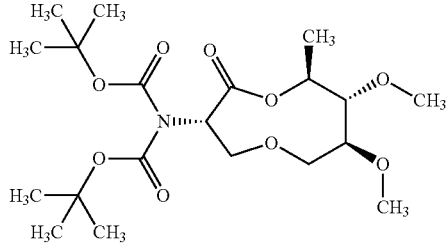 [SMILES: CO[C@H]1[C@H](C)OC(=O)[C@@H](N(C(=O)OC(C)(C)C)C(=O)OC(C)(C)C)COC[C@@H]1OC] |
| 105 | Light Yellow Oil | 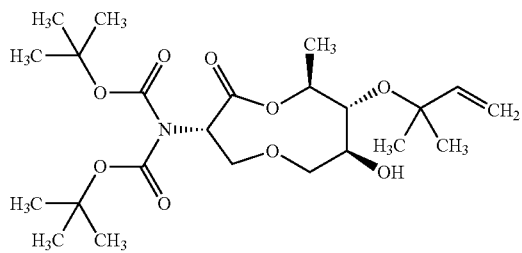 [SMILES: C=CC(C)(C)O[C@H]1[C@H](C)OC(=O)[C@@H](N(C(=O)OC(C)(C)C)C(=O)OC(C)(C)C)COC[C@@H]1O] |

TABLE 1-continued

Compound Structure and Appearance

| Compound Number | Appearance | Structure |
|---|---|---|
| 106 | Light Yellow Oil | 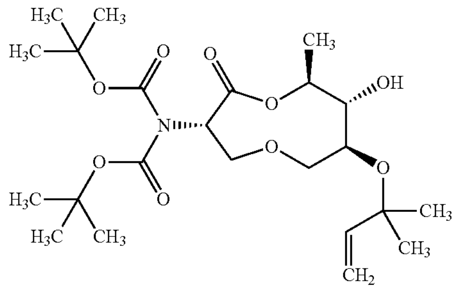 [SMILES: C=CC(C)(C)O[C@H]1COC[C@H](N(C(=O)OC(C)(C)C)C(=O)OC(C)(C)C)C(=O)O[C@@H](C)[C@@H]1O] |
| 107 | Colorless Oil | 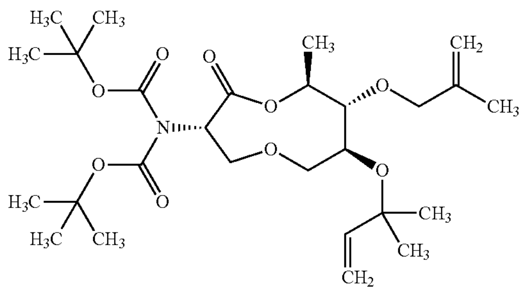 [SMILES: C=CC(C)(C)O[C@H]1COC[C@H](N(C(=O)OC(C)(C)C)C(=O)OC(C)(C)C)C(=O)O[C@@H](C)[C@@H]1OCC(=C)C] |
| 108 | Colorless Oil | 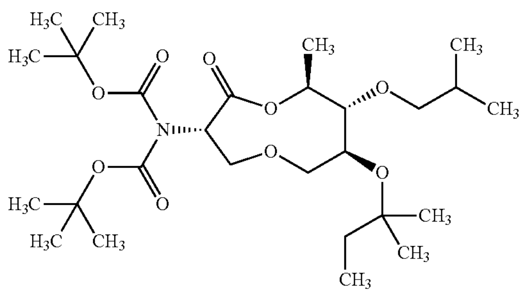 [SMILES: CCC(C)(C)O[C@H]1COC[C@H](N(C(=O)OC(C)(C)C)C(=O)OC(C)(C)C)C(=O)O[C@@H](C)[C@@H]1OCC(C)C] |
| 109 | Colorless Oil | 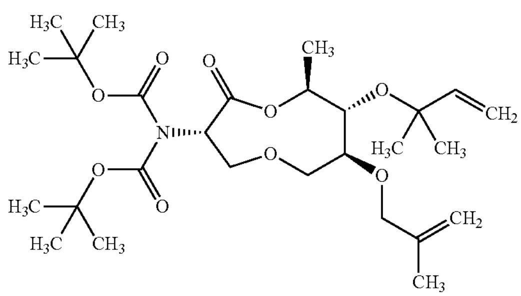 [SMILES: C=CC(C)(C)O[C@H]1[C@H](C)OC(=O)[C@@H](N(C(=O)OC(C)(C)C)C(=O)OC(C)(C)C)COC[C@@H]1OCC(=C)C] |
| 110 | Colorless Oil | 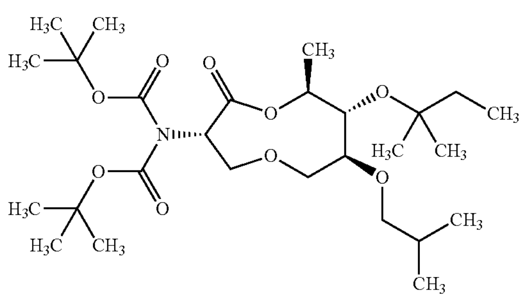 [SMILES: CCC(C)(C)O[C@H]1[C@H](C)OC(=O)[C@@H](N(C(=O)OC(C)(C)C)C(=O)OC(C)(C)C)COC[C@@H]1OCC(C)C] |

TABLE 1-continued
Compound Structure and Appearance
| Compound Number | Appearance | Structure |
|---|---|---|
| 111 | Colorless Oil | 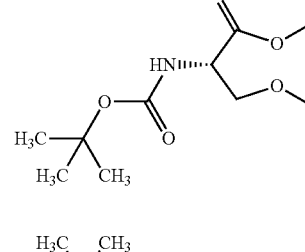 |
| 112 | Colorless Oil | 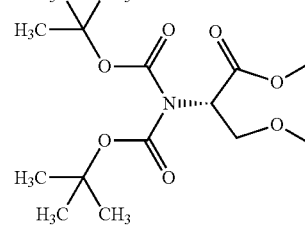 |
| 113 | White Solid | 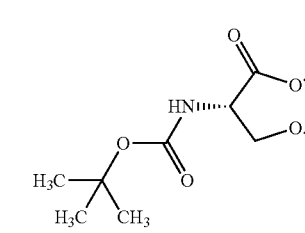 |
| 114 | White Solid | 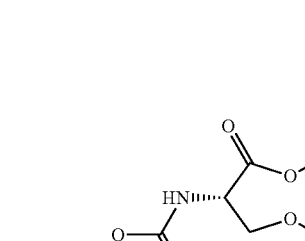 |
| 115 | Colorless Oil | 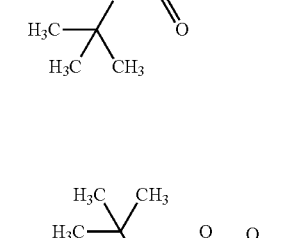 |

TABLE 1-continued
Compound Structure and Appearance
| Compound Number | Appearance | Structure |
|---|---|---|
| 116 | Light Yellow Oil | 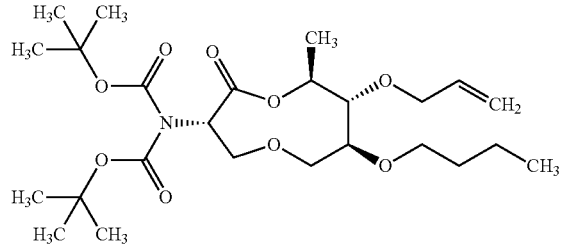 |
| 117 | Light Yellow Oil | 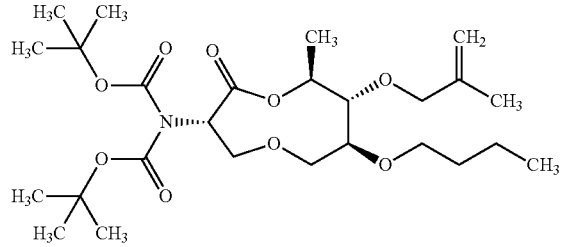 |
| 118 | Colorless Oil | 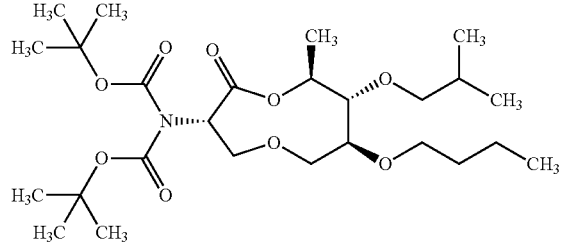 [SMILES: CCCCO[C@H]1COC[C@H](N(C(=O)OC(C)(C)C)C(=O)OC(C)(C)C)C(=O)O[C@@H](C)[C@@H]1OCC(C)C] |
| 119 | Colorless Oil | 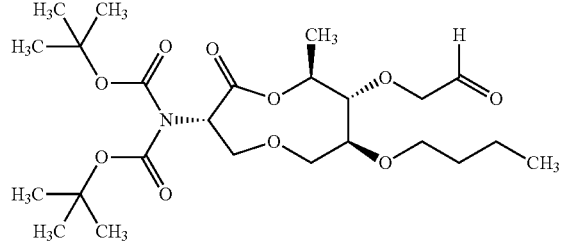 [SMILES: CCCCO[C@H]1COC[C@H](N(C(=O)OC(C)(C)C)C(=O)OC(C)(C)C)C(=O)O[C@@H](C)[C@@H]1OCC=O] |
| 120 | Colorless Oil | 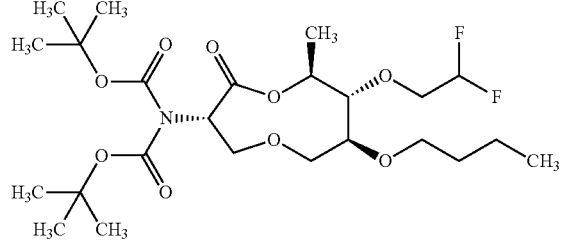 [SMILES: CCCCO[C@H]1COC[C@H](N(C(=O)OC(C)(C)C)C(=O)OC(C)(C)C)C(=O)O[C@@H](C)[C@@H]1OCC(F)F] |
| 121 | Colorless Oil | 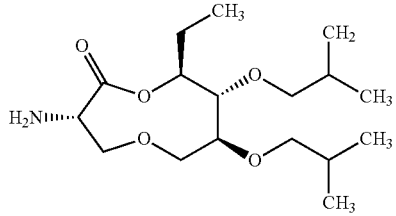 [SMILES: CC[C@@H]1OC(=O)[C@@H](N)COC[C@H](OCC(C)C)[C@H]1OCC(C)C] |

TABLE 1-continued
Compound Structure and Appearance
| Compound Number | Appearance | Structure |
|---|---|---|
| 122 | Light Yellow Oil | 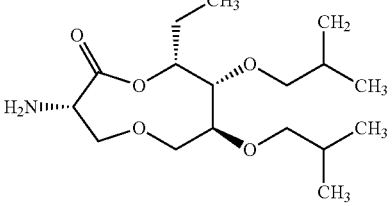 |
| 123 | Colorless Oil | 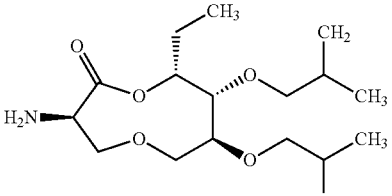 |
| 124 | Off-White Oil | 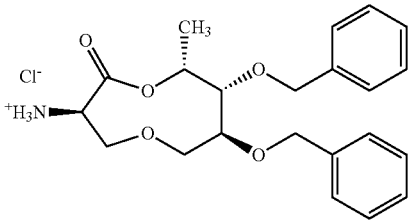 [SMILES: [Cl-] ; C[C@H]1OC(=O)[C@H]([NH3+])COC[C@H](OCc2ccccc2)[C@H]1OCc1ccccc1] |
| 125 | White Solid | 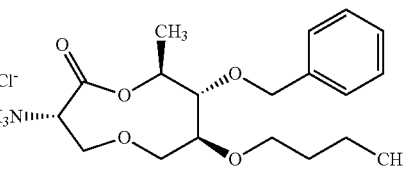 |
| 126 | White Solid | 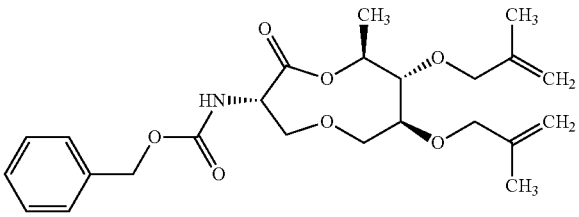 [SMILES: C=C(C)CO[C@H]1[C@H](C)OC(=O)[C@@H](NC(=O)OCc2ccccc2)COC[C@@H]1OCC(=C)C] |
| 127 | White Solid | 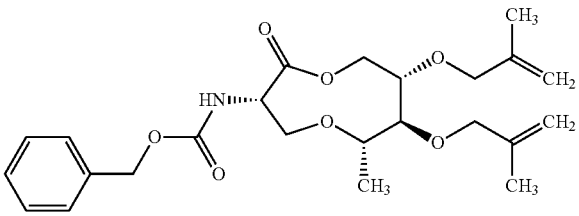 [SMILES: C=C(C)CO[C@H]1[C@H](C)OC[C@H](NC(=O)OCc2ccccc2)C(=O)OC[C@@H]1OCC(=C)C] |
| 128 | White Foam | 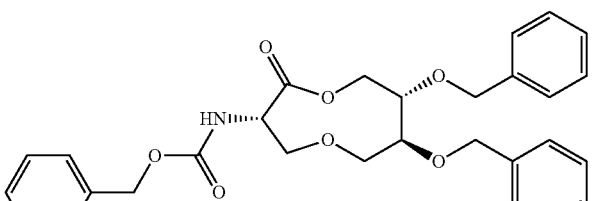 |

TABLE 1-continued
Compound Structure and Appearance
| Compound Number | Appearance | Structure |
|---|---|---|
| 129 | Off-White Solid | 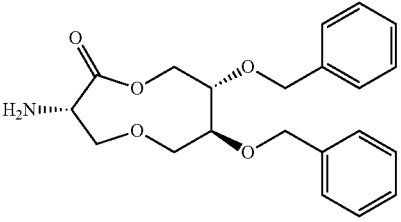 [SMILES: N[C@H]1COC[C@H](OCc2ccccc2)[C@@H](OCc2ccccc2)COC1=O] |
| 130 | Colorless Oil | 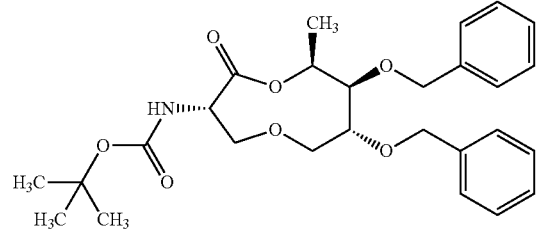 [SMILES: C[C@@H]1OC(=O)[C@@H](NC(=O)OC(C)(C)C)COC[C@@H](OCc2ccccc2)[C@@H]1OCc1ccccc1] |
| 131 | Colorless Oil | 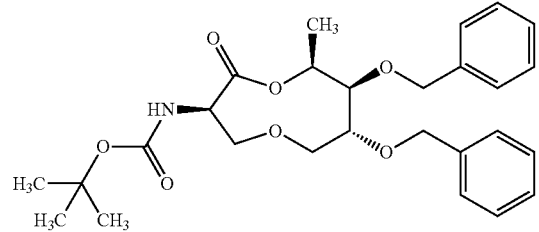 [SMILES: C[C@@H]1OC(=O)[C@H](NC(=O)OC(C)(C)C)COC[C@@H](OCc2ccccc2)[C@@H]1OCc1ccccc1] |
| 132 | Colorless Solid | 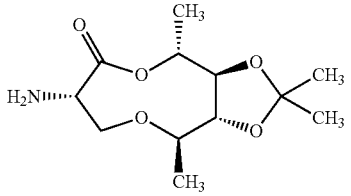 [SMILES: C[C@H]1OC[C@H](N)C(=O)O[C@H](C)[C@H]2OC(C)(C)O[C@@H]21] |
| 133 | Colorless Oil | 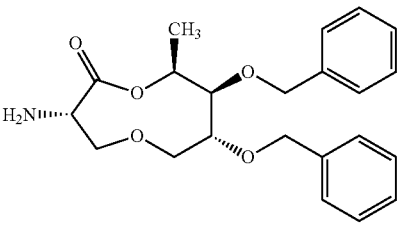 [SMILES: C[C@@H]1OC(=O)[C@@H](N)COC[C@@H](OCc2ccccc2)[C@@H]1OCc1ccccc1] |
| 134 | Colorless Oil | 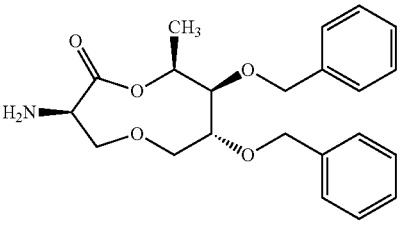 [SMILES: C[C@@H]1OC(=O)[C@H](N)COC[C@@H](OCc2ccccc2)[C@@H]1OCc1ccccc1] |

TABLE 1-continued
Compound Structure and Appearance
| Compound Number | Appearance | Structure |
|---|---|---|
| 135 | White Foam | 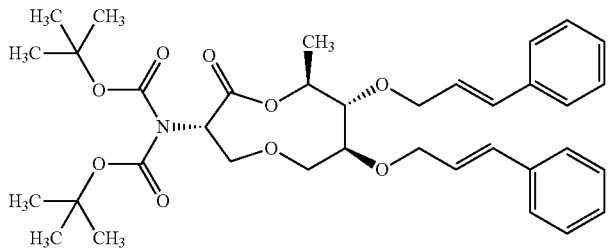 |
| 136 | Light Yellow Oil | 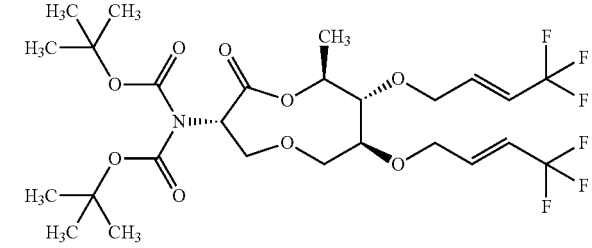 [SMILES: C[C@@H]1OC(=O)[C@@H](N(C(=O)OC(C)(C)C)C(=O)OC(C)(C)C)COC[C@H](OC/C=C/C(F)(F)F)[C@H]1OC/C=C/C(F)(F)F] |
| 137 | Colorless Oil | 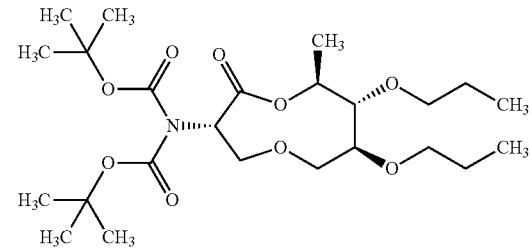 [SMILES: CCCO[C@H]1[C@H](C)OC(=O)[C@@H](N(C(=O)OC(C)(C)C)C(=O)OC(C)(C)C)COC[C@@H]1OCCC] |
| 138 | Colorless Oil | 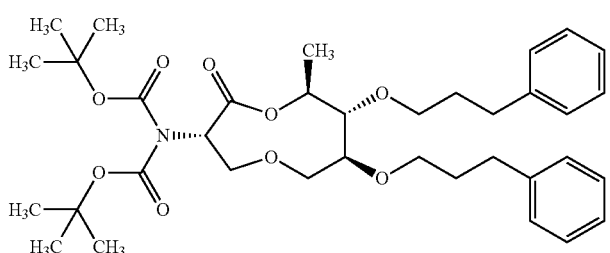 |
| 139 | White Solid | 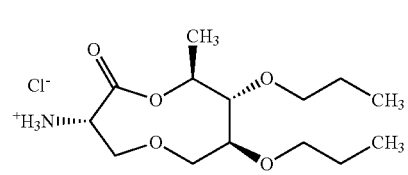 [SMILES: [Cl-] ; CCCO[C@H]1[C@H](C)OC(=O)[C@@H]([NH3+])COC[C@@H]1OCCC] |
| 140 | White Foam | 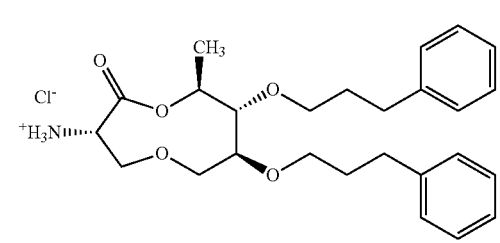 [SMILES: [Cl-] ; C[C@@H]1OC(=O)[C@@H]([NH3+])COC[C@H](OCCCc2ccccc2)[C@H]1OCCCc1ccccc1] |

TABLE 1-continued
Compound Structure and Appearance
| Compound Number | Appearance | Structure |
|---|---|---|
| 141 | Colorless Oil | 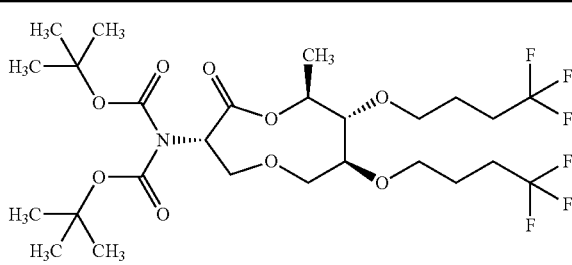 |
| 142 | Colorless Oil | 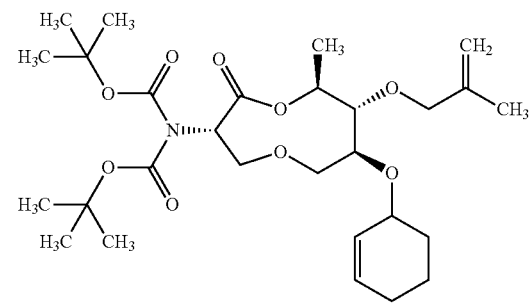 [SMILES: C=C(C)CO[C@H]1[C@H](C)OC(=O)[C@@H](N(C(=O)OC(C)(C)C)C(=O)OC(C)(C)C)COC[C@@H]1OC1C=CCCC1] |
| 143 | Yellow Solid | 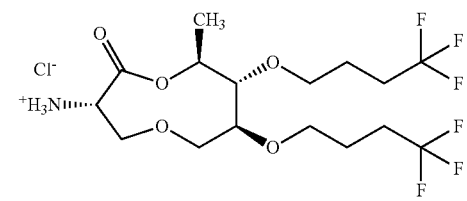 [SMILES: [Cl-] ; C[C@@H]1OC(=O)[C@@H]([NH3+])COC[C@H](OCCCC(F)(F)F)[C@H]1OCCCC(F)(F)F] |
| 144 | Colorless Oil | 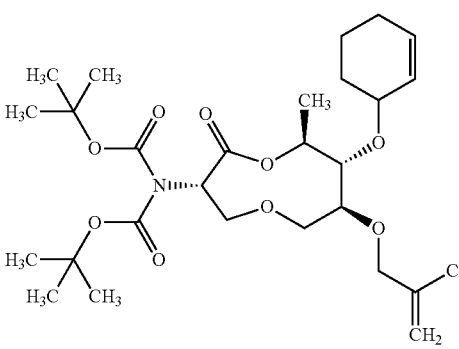 |
| 145 | Colorless Oil | 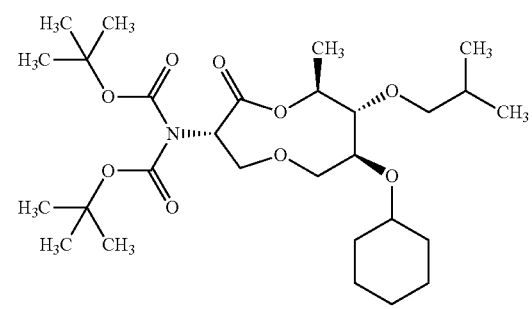 [SMILES: CC(C)CO[C@H]1[C@H](C)OC(=O)[C@@H](N(C(=O)OC(C)(C)C)C(=O)OC(C)(C)C)COC[C@@H]1OC1CCCCC1] |

TABLE 1-continued

Compound Structure and Appearance

| Compound Number | Appearance | Structure |
|---|---|---|
| 146 | Colorless Oil | 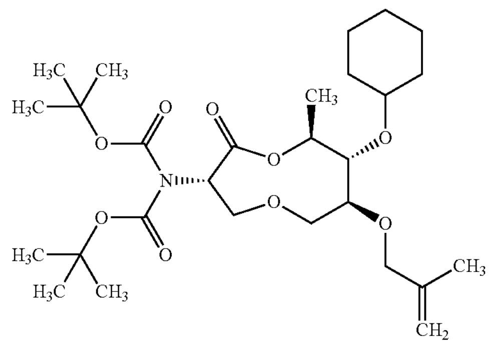 [SMILES: C=C(C)CO[C@H]1COC[C@H](N(C(=O)OC(C)(C)C)C(=O)OC(C)(C)C)C(=O)O[C@@H](C)[C@@H]1OC1CCCCC1] |
| 147 | White Solid | 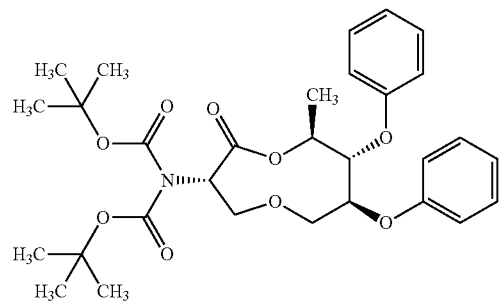 [SMILES: C[C@@H]1OC(=O)[C@@H](N(C(=O)OC(C)(C)C)C(=O)OC(C)(C)C)COC[C@H](Oc2ccccc2)[C@H]1Oc1ccccc1] |
| 148 | Colorless Oil | 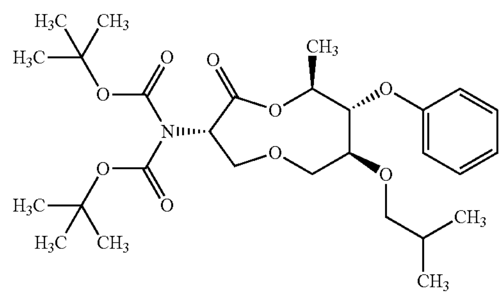 [SMILES: CC(C)CO[C@H]1COC[C@H](N(C(=O)OC(C)(C)C)C(=O)OC(C)(C)C)C(=O)O[C@@H](C)[C@@H]1Oc1ccccc1] |
| 149 | Colorless Oil | 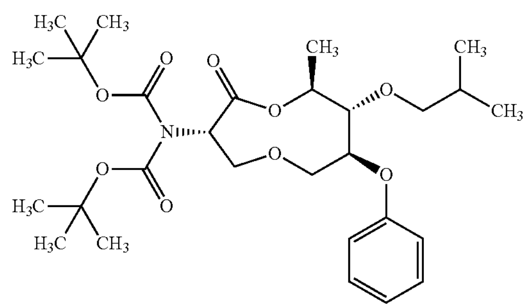 [SMILES: CC(C)CO[C@H]1[C@H](C)OC(=O)[C@@H](N(C(=O)OC(C)(C)C)C(=O)OC(C)(C)C)COC[C@@H]1Oc1ccccc1] |
| 150 | White Solid | 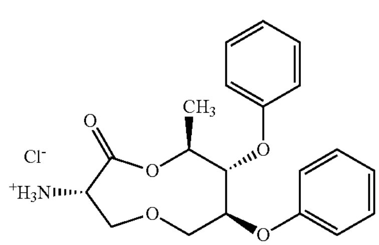 [SMILES: [Cl-] ; C[C@@H]1OC(=O)[C@@H]([NH3+])COC[C@H](Oc2ccccc2)[C@H]1Oc1ccccc1] |

TABLE 1-continued

Compound Structure and Appearance

| Compound Number | Appearance | Structure |
|---|---|---|
| 151 | White Solid | 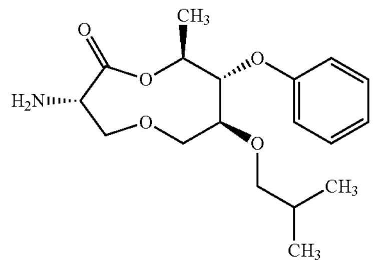 [SMILES: CC(C)CO[C@H]1COC[C@H](N)C(=O)O[C@@H](C)[C@@H]1Oc1ccccc1] |
| 152 | White Solid | 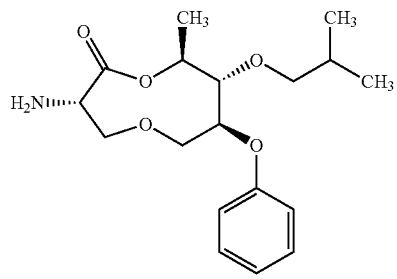 [SMILES: CC(C)CO[C@H]1[C@H](C)OC(=O)[C@@H](N)COC[C@@H]1Oc1ccccc1] |
| 153 | White Foam | 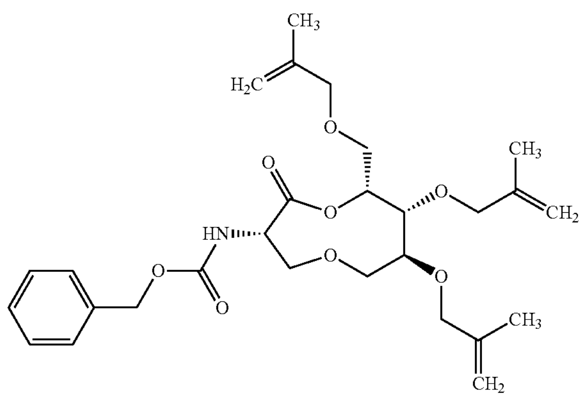 [SMILES: C=C(C)COC[C@H]1OC(=O)[C@@H](NC(=O)OCc2ccccc2)COC[C@H](OCC(=C)C)[C@H]1OCC(=C)C] |
| 154 | White Foam | 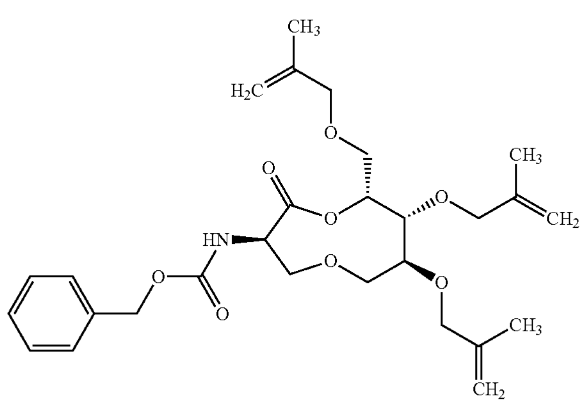 [SMILES: C=C(C)COC[C@H]1OC(=O)[C@H](NC(=O)OCc2ccccc2)COC[C@H](OCC(=C)C)[C@H]1OCC(=C)C] |

TABLE 1-continued
Compound Structure and Appearance
| Compound Number | Appearance | Structure |
|---|---|---|
| 155 | White Foam | 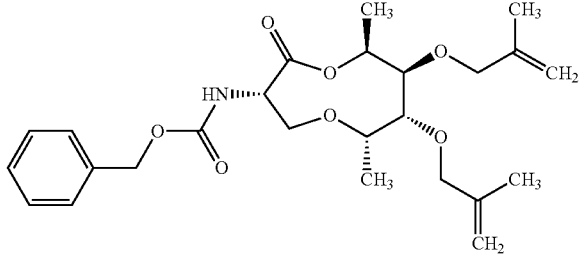 [SMILES: C=C(C)CO[C@H]1[C@H](OCC(=C)C)[C@H](C)OC(=O)[C@@H](NC(=O)OCc2ccccc2)CO[C@H]1C] |
| 156 | White Foam | 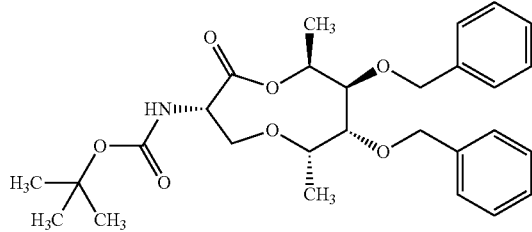 [SMILES: C[C@@H]1OC[C@H](NC(=O)OC(C)(C)C)C(=O)O[C@@H](C)[C@@H](OCc2ccccc2)[C@@H]1OCc1ccccc1] |
| 157 | White Foam | 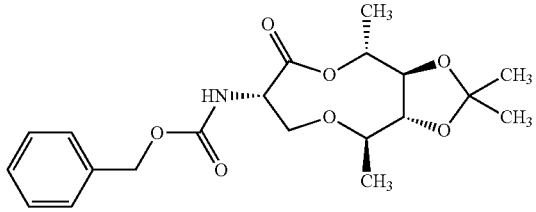 [SMILES: C[C@H]1OC[C@H](NC(=O)OCc2ccccc2)C(=O)O[C@H](C)[C@H]2OC(C)(C)O[C@@H]21] |
| 158 | White Foam | 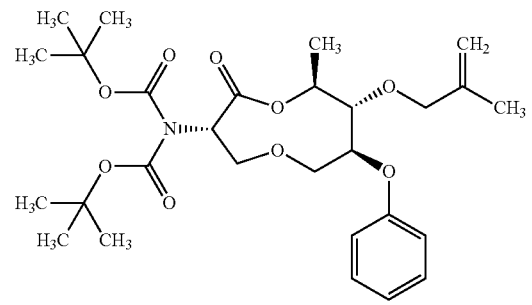 [SMILES: C=C(C)CO[C@H]1[C@H](C)OC(=O)[C@@H](N(C(=O)OC(C)(C)C)C(=O)OC(C)(C)C)COC[C@@H]1Oc1ccccc1] |
| 159 | White Foam | 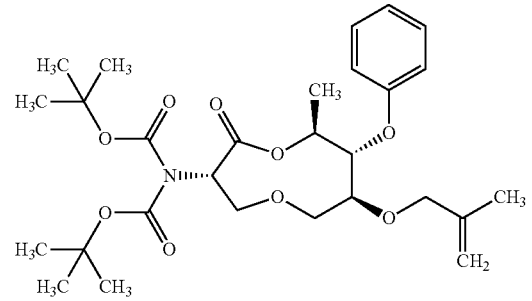 [SMILES: C=C(C)CO[C@H]1COC[C@H](N(C(=O)OC(C)(C)C)C(=O)OC(C)(C)C)C(=O)O[C@@H](C)[C@@H]1Oc1ccccc1] |

TABLE 1-continued

Compound Structure and Appearance

| Compound Number | Appearance | Structure |
|---|---|---|
| 160 | White Solid | 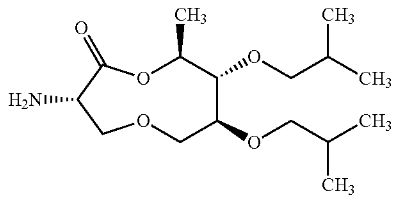 [SMILES: CC(C)CO[C@H]1[C@H](C)OC(=O)[C@@H](N)COC[C@@H]1OCC(C)C] |
| 161 | — | 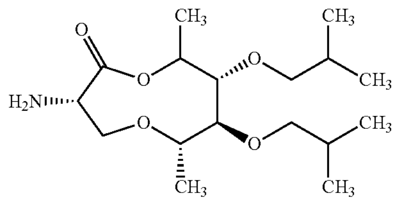 [SMILES: CC(C)CO[C@H]1[C@H](C)OC[C@H](N)C(=O)OC(C)[C@@H]1OCC(C)C] |
| 162 | White Solid | 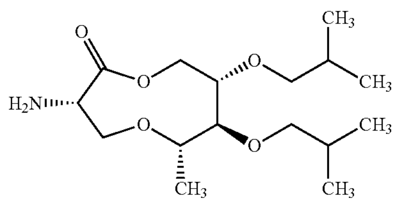 [SMILES: CC(C)CO[C@H]1[C@H](C)OC[C@H](N)C(=O)OC[C@@H]1OCC(C)C] |
| 163 | Colorless Oil | 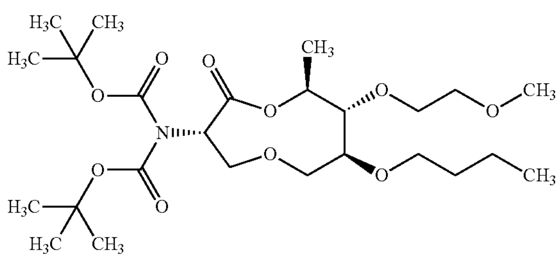 [SMILES: CCCCO[C@H]1COC[C@H](N(C(=O)OC(C)(C)C)C(=O)OC(C)(C)C)C(=O)O[C@@H](C)[C@@H]1OCCOC] |
| 164 | Colorless Oil | 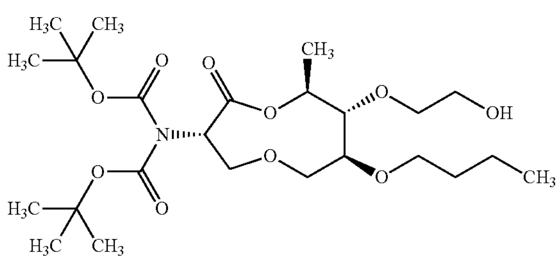 [SMILES: CCCCO[C@H]1COC[C@H](N(C(=O)OC(C)(C)C)C(=O)OC(C)(C)C)C(=O)O[C@@H](C)[C@@H]1OCCO] |
| 165 | White Solid | 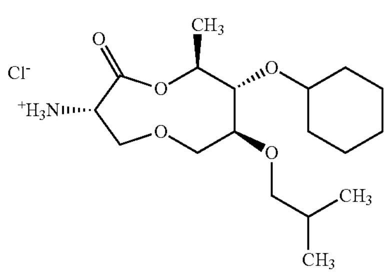 [SMILES: [Cl-] ; CC(C)CO[C@H]1COC[C@H]([NH3+])C(=O)O[C@@H](C)[C@@H]1OC1CCCCC1] |

TABLE 1-continued

Compound Structure and Appearance

| Compound Number | Appearance | Structure |
|---|---|---|
| 166 | White Solid | 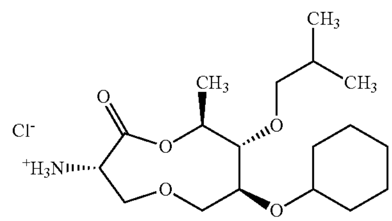 [SMILES: [Cl-] ; CC(C)CO[C@H]1[C@H](C)OC(=O)[C@@H]([NH3+])COC[C@@H]1OC1CCCCC1] |
| 167 | White Solid | 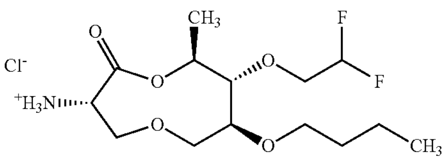 [SMILES: [Cl-] ; CCCCO[C@H]1COC[C@H]([NH3+])C(=O)O[C@@H](C)[C@@H]1OCC(F)F] |
| 168 | Off-White Solid | 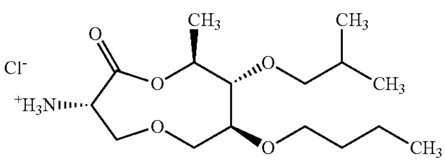 [SMILES: [Cl-] ; CCCCO[C@H]1COC[C@H]([NH3+])C(=O)O[C@@H](C)[C@@H]1OCC(C)C] |
| 169 | Light Yellow Oil | 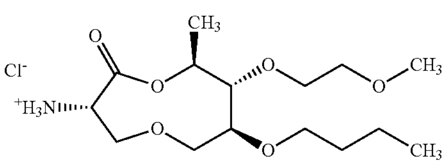 [SMILES: [Cl-] ; CCCCO[C@H]1COC[C@H]([NH3+])C(=O)O[C@@H](C)[C@@H]1OCCOC] |
| 170 | Clear Oil | 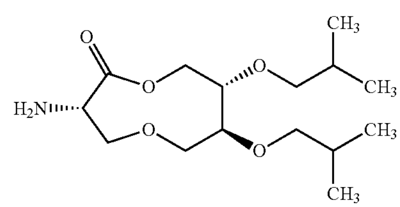 [SMILES: CC(C)CO[C@H]1COC[C@H](N)C(=O)OC[C@@H]1OCC(C)C] |
| 171 | Clear Oil | 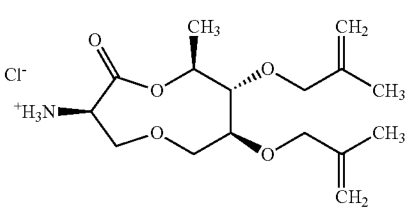 [SMILES: [Cl-] ; C=C(C)CO[C@H]1[C@H](C)OC(=O)[C@H]([NH3+])COC[C@@H]1OCC(=C)C] |
| 172 | Colorless Oil | 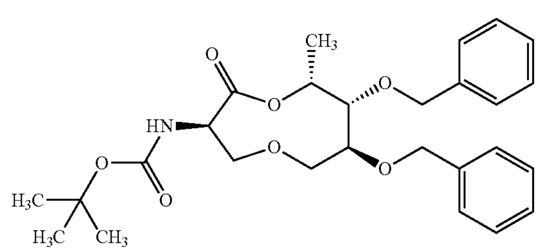 [SMILES: C[C@H]1OC(=O)[C@H](NC(=O)OC(C)(C)C)COC[C@H](OCc2ccccc2)[C@H]1OCc1ccccc1] |

TABLE 1-continued

Compound Structure and Appearance

| Compound Number | Appearance | Structure |
|---|---|---|
| 173 | Off-White Solid | 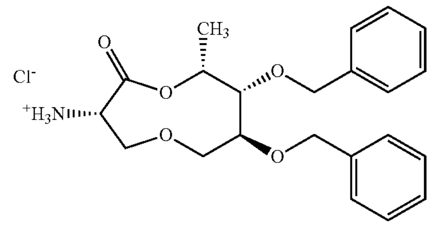 [SMILES: [Cl-] ; C[C@H]1OC(=O)[C@@H]([NH3+])COC[C@H](OCc2ccccc2)[C@H]1OCc1ccccc1] |
| 174 | Off-White Solid | 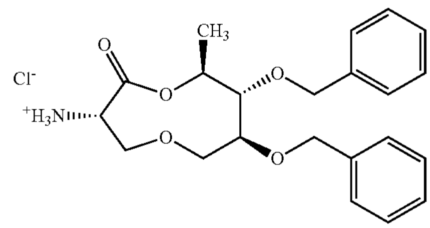 [SMILES: [Cl-] ; C[C@@H]1OC(=O)[C@@H]([NH3+])COC[C@H](OCc2ccccc2)[C@H]1OCc1ccccc1] |
| 175 | Crystalline Colorless Solid | 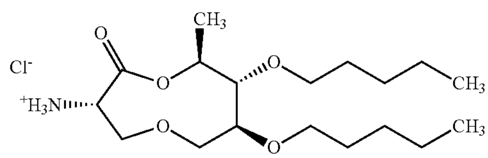 [SMILES: [Cl-] ; CCCCCO[C@H]1[C@H](C)OC(=O)[C@@H]([NH3+])COC[C@@H]1OCCCCC] |
| 176 | White Solid | 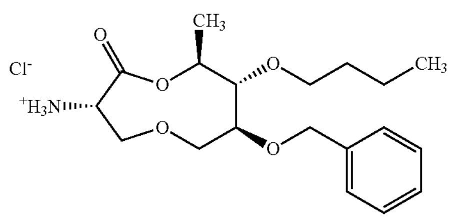 [SMILES: [Cl-] ; CCCCO[C@H]1[C@H](C)OC(=O)[C@@H]([NH3+])COC[C@@H]1OCc1ccccc1] |
| 177 | Light Yellow Solid | 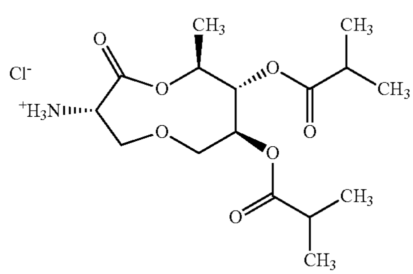 [SMILES: [Cl-] ; CC(C)C(=O)O[C@H]1[C@H](C)OC(=O)[C@@H]([NH3+])COC[C@@H]1OC(=O)C(C)C] |
| 178 | White Solid | 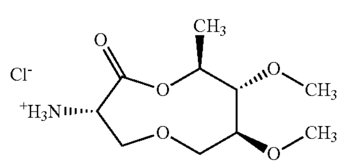 [SMILES: [Cl-] ; CO[C@H]1[C@H](C)OC(=O)[C@@H]([NH3+])COC[C@@H]1OC] |
| 179 | Colorless Oil | 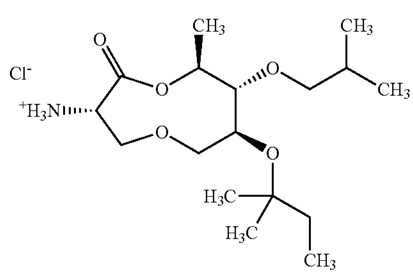 [SMILES: [Cl-] ; CCC(C)(C)O[C@H]1COC[C@H]([NH3+])C(=O)O[C@@H](C)[C@@H]1OCC(C)C] |

TABLE 1-continued

Compound Structure and Appearance

| Compound Number | Appearance | Structure |
|---|---|---|
| 180 | Light Yellow Solid | 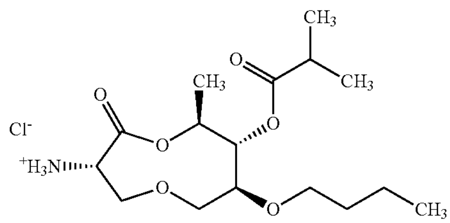 [SMILES: [Cl-] ; CCCCO[C@H]1COC[C@H]([NH3+])C(=O)O[C@@H](C)[C@@H]1OC(=O)C(C)C] |
| 181 | White Solid | 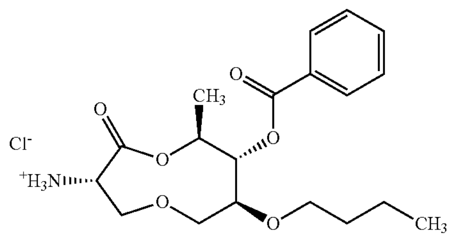 [SMILES: [Cl-] ; CCCCO[C@H]1COC[C@H]([NH3+])C(=O)O[C@@H](C)[C@@H]1OC(=O)c1ccccc1] |
| 182 | White Solid | 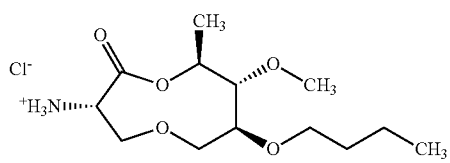 [SMILES: [Cl-] ; CCCCO[C@H]1COC[C@H]([NH3+])C(=O)O[C@@H](C)[C@@H]1OC] |
| 183 | Off-White Solid | 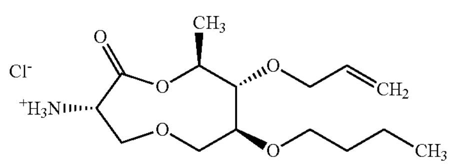 [SMILES: [Cl-] ; C=CCO[C@H]1[C@H](C)OC(=O)[C@@H]([NH3+])COC[C@@H]1OCCCC] |
| 184 | Off-White Solid | 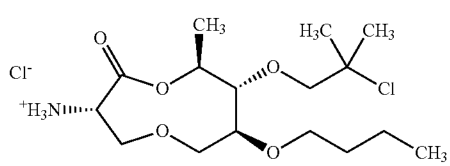 [SMILES: [Cl-] ; CCCCO[C@H]1COC[C@H]([NH3+])C(=O)O[C@@H](C)[C@@H]1OCC(C)(C)Cl] |
| 185 | Off-White Solid | 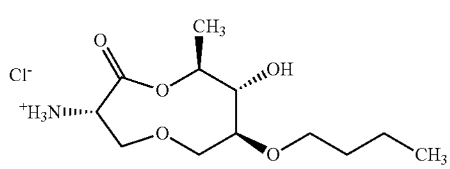 [SMILES: [Cl-] ; CCCCO[C@H]1COC[C@H]([NH3+])C(=O)O[C@@H](C)[C@@H]1O] |
| 186 | White Solid | 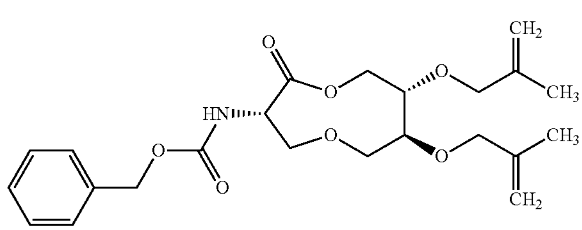 [SMILES: C=C(C)CO[C@H]1COC[C@H](NC(=O)OCc2ccccc2)C(=O)OC[C@@H]1OCC(=C)C] |

TABLE 1-continued
Compound Structure and Appearance
| Compound Number | Appearance | Structure |
|---|---|---|
| 187 | Clear Oil | 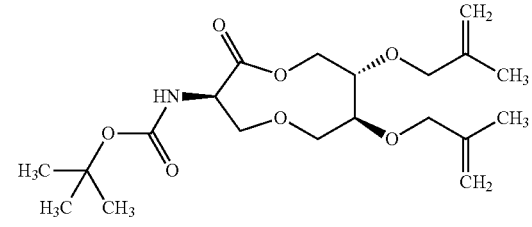 [SMILES: C=C(C)CO[C@H]1COC[C@@H](NC(=O)OC(C)(C)C)C(=O)OC[C@@H]1OCC(=C)C] |
| 188 | — | 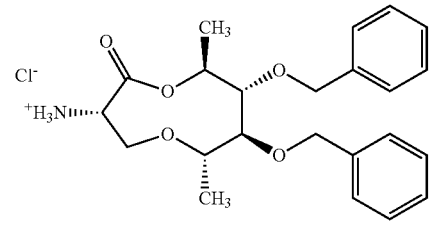 [SMILES: [Cl-] ; C[C@@H]1OC[C@H]([NH3+])C(=O)O[C@@H](C)[C@H](OCc2ccccc2)[C@H]1OCc1ccccc1] |
| 189 | — | 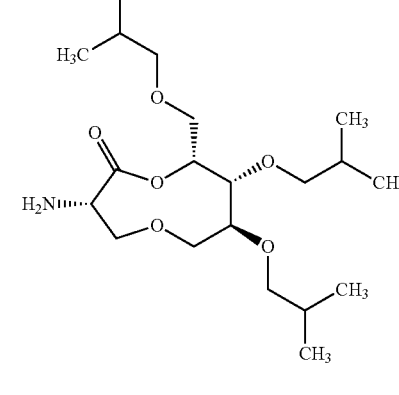 |
| 190 | — | 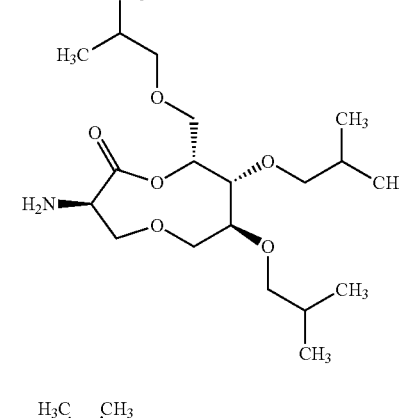 |
| 191 | White Foam | 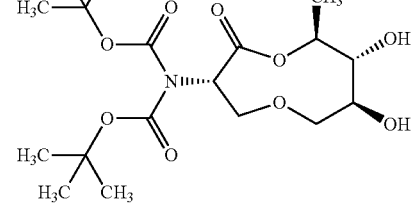 |

TABLE 1-continued
Compound Structure and Appearance
| Compound Number | Appearance | Structure |
|---|---|---|
| 192 | Colorless Oil | 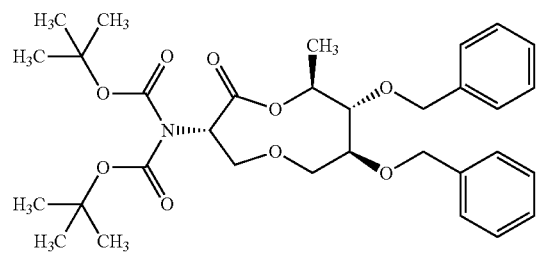 [SMILES: C[C@@H]1OC(=O)[C@@H](N(C(=O)OC(C)(C)C)C(=O)OC(C)(C)C)COC[C@H](OCc2ccccc2)[C@H]1OCc1ccccc1] |
| 193 | — | 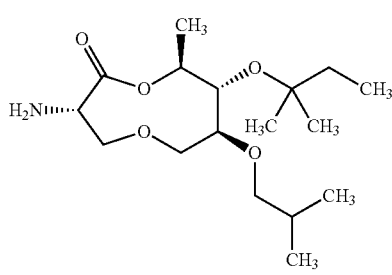 [SMILES: CCC(C)(C)O[C@H]1[C@H](C)OC(=O)[C@@H](N)COC[C@@H]1OCC(C)C] |
| 194 | White Foam | 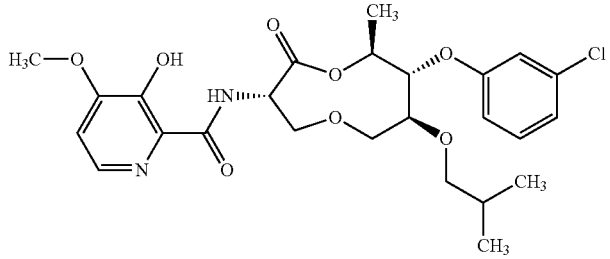 [SMILES: COc1ccnc(C(=O)N[C@H]2COC[C@H](OCC(C)C)[C@@H](Oc3cccc(Cl)c3)[C@H](C)OC2=O)c1O] |
| 195 | White Foam | 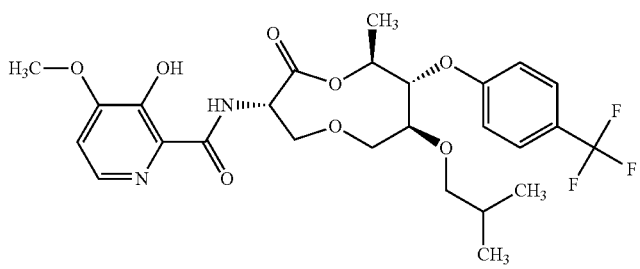 [SMILES: COc1ccnc(C(=O)N[C@H]2COC[C@H](OCC(C)C)[C@@H](Oc3ccc(C(F)(F)F)cc3)[C@H](C)OC2=O)c1O] |
| 196 | White Solid | 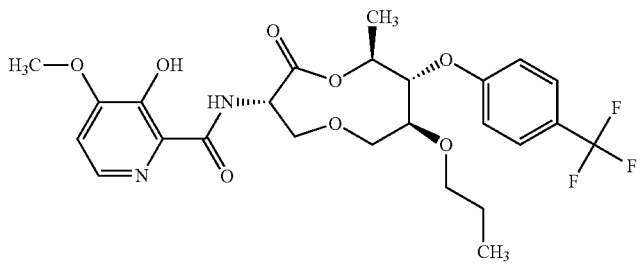 [SMILES: CCCO[C@H]1COC[C@H](NC(=O)c2nccc(OC)c2O)C(=O)O[C@@H](C)[C@@H]1Oc1ccc(C(F)(F)F)cc1] |

TABLE 1-continued
Compound Structure and Appearance
| Compound Number | Appearance | Structure |
|---|---|---|
| 197 | White Foam | 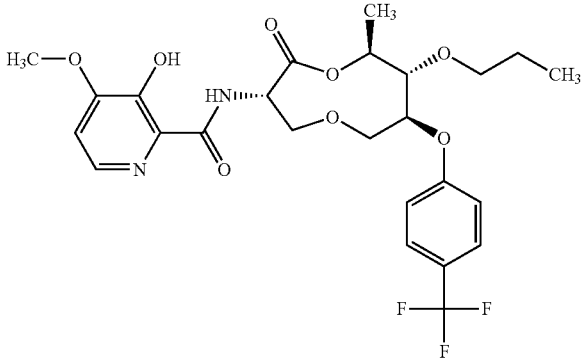 [SMILES: CCCO[C@H]1[C@H](C)OC(=O)[C@@H](NC(=O)c2nccc(OC)c2O)COC[C@@H]1Oc1ccc(C(F)(F)F)cc1] |
| 198 | White Foam | 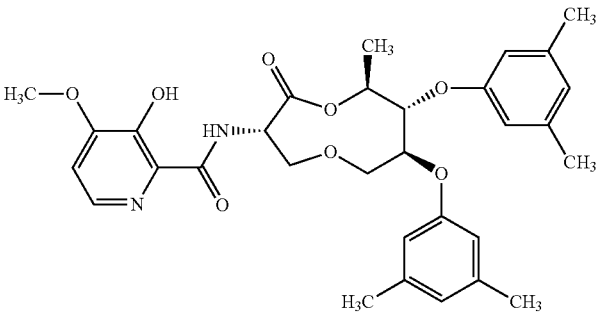 |
| 199 | White Foam | 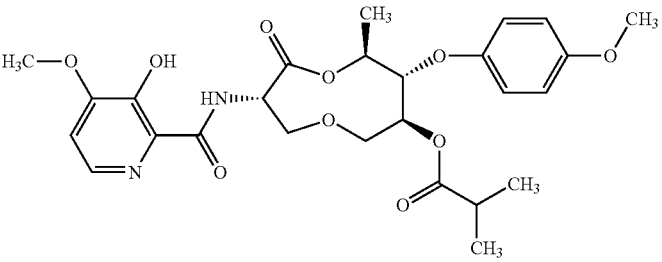 |
| 200 | Colorless Glass | 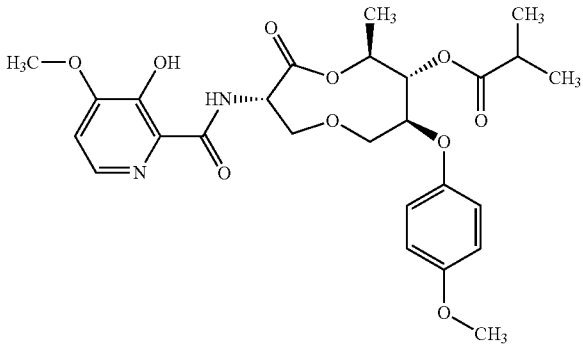 [SMILES: COc1ccc(O[C@H]2COC[C@H](NC(=O)c3nccc(OC)c3O)C(=O)O[C@@H](C)[C@@H]2OC(=O)C(C)C)cc1] |

TABLE 1-continued
Compound Structure and Appearance
| Compound Number | Appearance | Structure |
|---|---|---|
| 201 | White Foam | 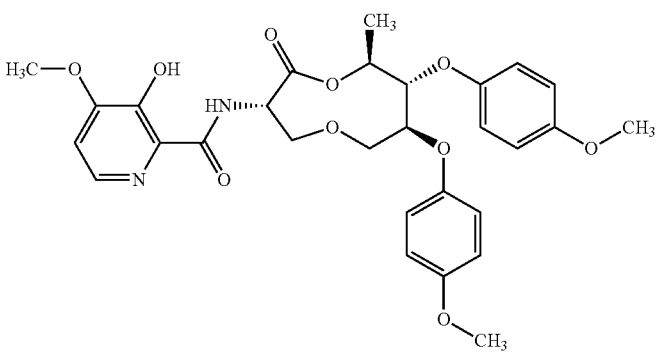 |
| 202 | White Solid | 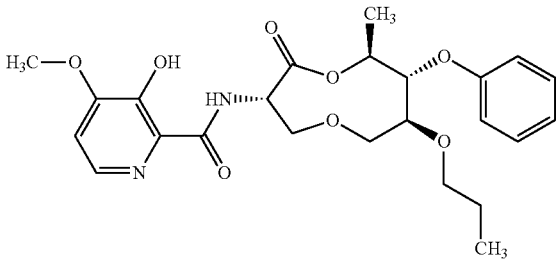 [SMILES: CCCO[C@H]1COC[C@H](NC(=O)c2nccc(OC)c2O)C(=O)O[C@@H](C)[C@@H]1Oc1ccccc1] |
| 203 | White Solid | 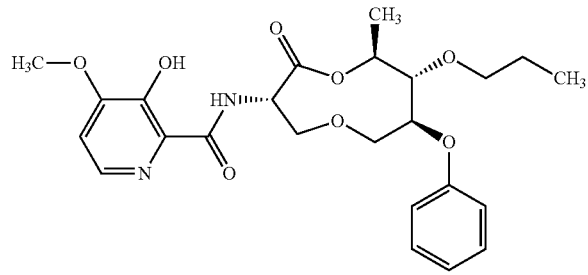 [SMILES: CCCO[C@H]1[C@H](C)OC(=O)[C@@H](NC(=O)c2nccc(OC)c2O)COC[C@@H]1Oc1ccccc1] |
| 204 | White Solid | 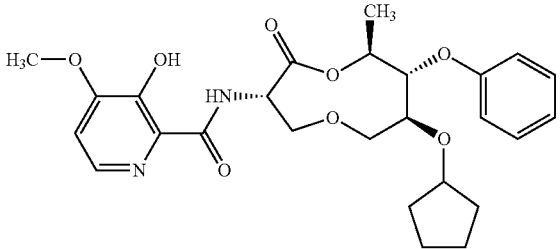 [SMILES: COc1ccnc(C(=O)N[C@H]2COC[C@H](OC3CCCC3)[C@@H](Oc3ccccc3)[C@H](C)OC2=O)c1O] |
| 205 | White Solid | 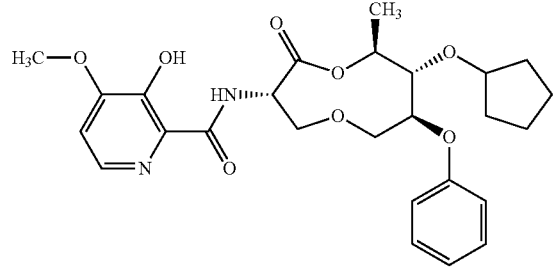 [SMILES: COc1ccnc(C(=O)N[C@H]2COC[C@H](Oc3ccccc3)[C@@H](OC3CCCC3)[C@H](C)OC2=O)c1O] |

TABLE 1-continued

Compound Structure and Appearance

| Compound Number | Appearance | Structure |
|---|---|---|
| 206 | White Foam | 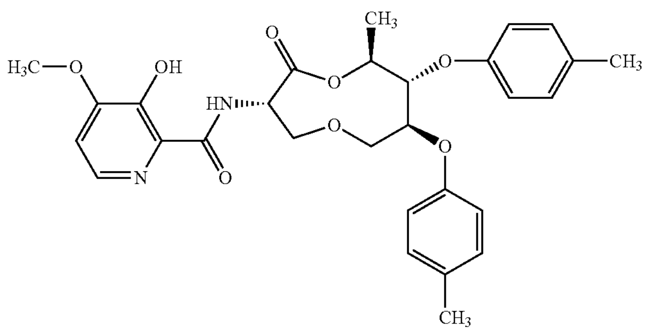 |
| 207 | White Solid | 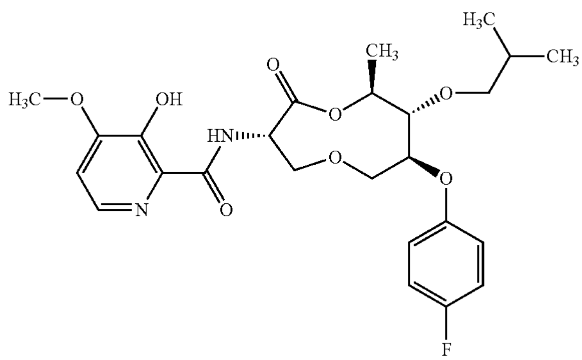 [SMILES: COc1ccnc(C(=O)N[C@H]2COC[C@H](Oc3ccc(F)cc3)[C@@H](OCC(C)C)[C@H](C)OC2=O)c1O] |
| 208 | White Solid | 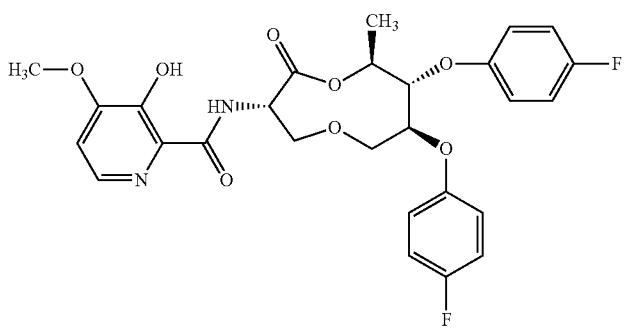 [SMILES: COc1ccnc(C(=O)N[C@H]2COC[C@H](Oc3ccc(F)cc3)[C@@H](Oc3ccc(F)cc3)[C@H](C)OC2=O)c1O] |
| 209 | White Solid | 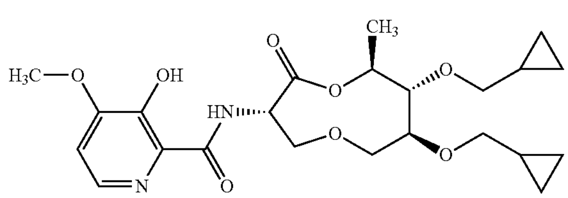 [SMILES: COc1ccnc(C(=O)N[C@H]2COC[C@H](OCC3CC3)[C@@H](OCC3CC3)[C@H](C)OC2=O)c1O] |
| 210 | White Solid | 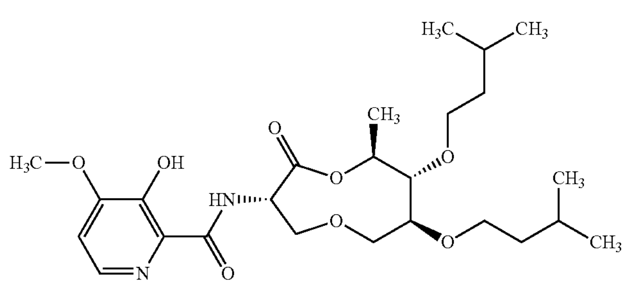 [SMILES: COc1ccnc(C(=O)N[C@H]2COC[C@H](OCCC(C)C)[C@@H](OCCC(C)C)[C@H](C)OC2=O)c1O] |

TABLE 1-continued
Compound Structure and Appearance
| Compound Number | Appearance | Structure |
|---|---|---|
| 211 | Pale Yellow Oil | 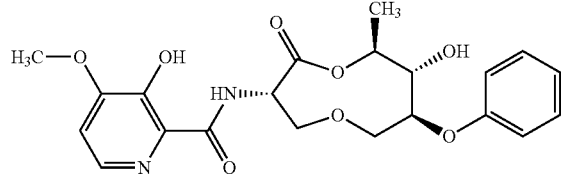 [SMILES: COc1ccnc(C(=O)N[C@H]2COC[C@H](Oc3ccccc3)[C@@H](O)[C@H](C)OC2=O)c1O] |
| 212 | Pale Yellow Oil | 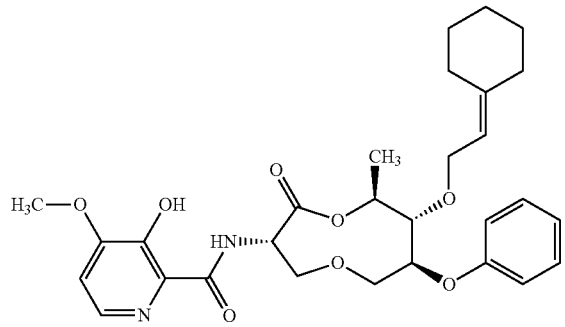 [SMILES: COc1ccnc(C(=O)N[C@H]2COC[C@H](Oc3ccccc3)[C@@H](OCC=C3CCCCC3)[C@H](C)OC2=O)c1O] |
| 213 | White Foam | 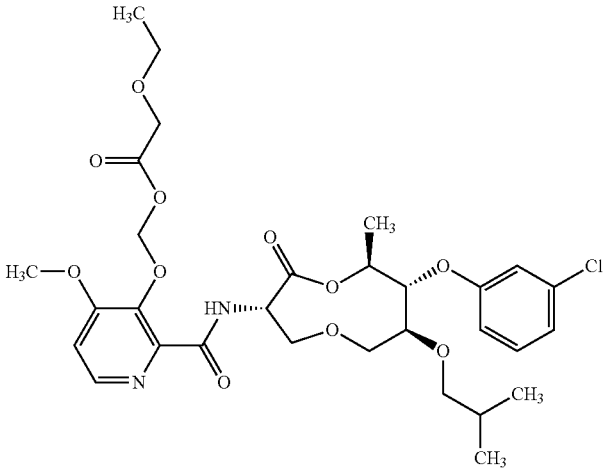 [SMILES: CCOCC(=O)OCOc1c(OC)ccnc1C(=O)N[C@H]1COC[C@H](OCC(C)C)[C@@H](Oc2cccc(Cl)c2)[C@H](C)OC1=O] |
| 214 | White Foam | 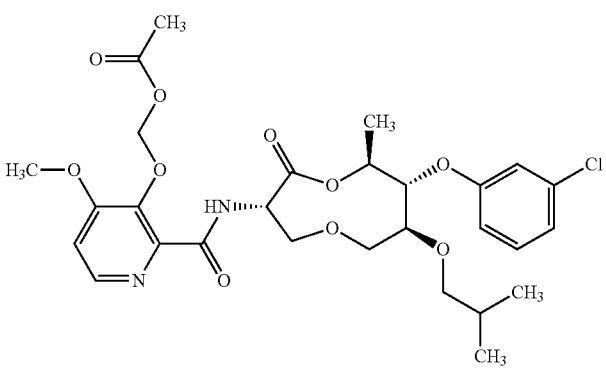 [SMILES: COc1ccnc(C(=O)N[C@H]2COC[C@H](OCC(C)C)[C@@H](Oc3cccc(Cl)c3)[C@H](C)OC2=O)c1OCOC(C)=O] |

TABLE 1-continued
Compound Structure and Appearance
| Compound Number | Appearance | Structure |
|---|---|---|
| 215 | White Foam | 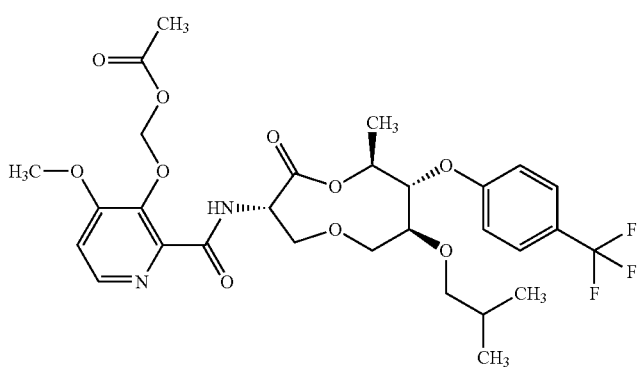 [SMILES: COc1ccnc(C(=O)N[C@H]2COC[C@H](OCC(C)C)[C@@H](Oc3ccc(C(F)(F)F)cc3)[C@H](C)OC2=O)c1OCOC(C)=O] |
| 216 | White Foam | 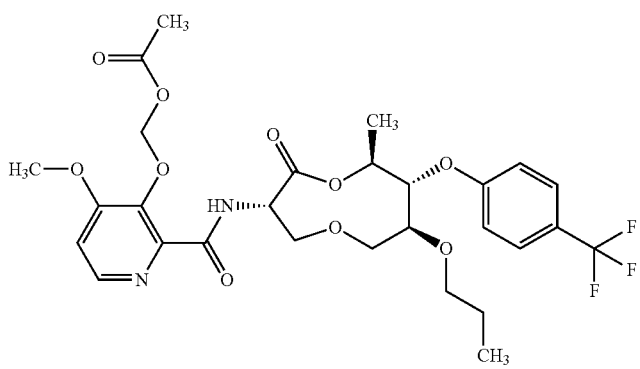 [SMILES: CCCO[C@H]1COC[C@H](NC(=O)c2nccc(OC)c2OCOC(C)=O)C(=O)O[C@@H](C)[C@@H]1Oc1ccc(C(F)(F)F)cc1] |
| 217 | White Foam | 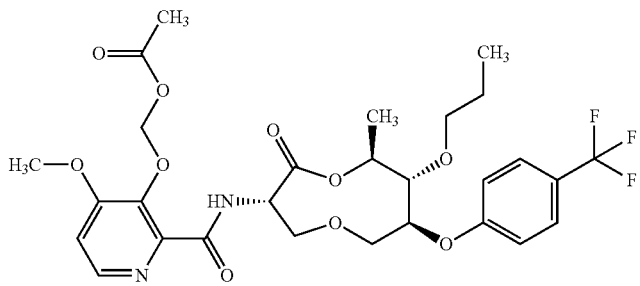 [SMILES: CCCO[C@H]1[C@H](C)OC(=O)[C@@H](NC(=O)c2nccc(OC)c2OCOC(C)=O)COC[C@@H]1Oc1ccc(C(F)(F)F)cc1] |
| 218 | White Foam | 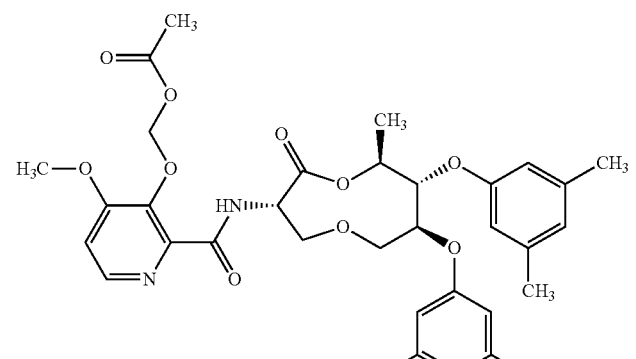 |

TABLE 1-continued

Compound Structure and Appearance

| Compound Number | Appearance | Structure |
|---|---|---|
| 219 | White Foam | 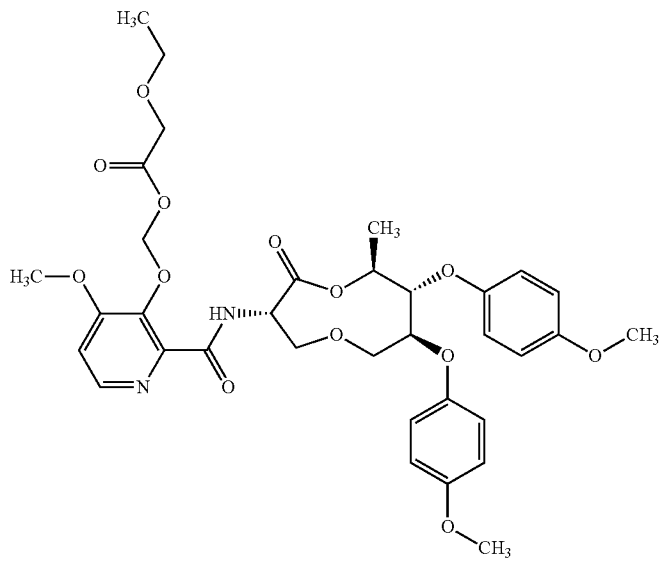 |
| 220 | White Foam | 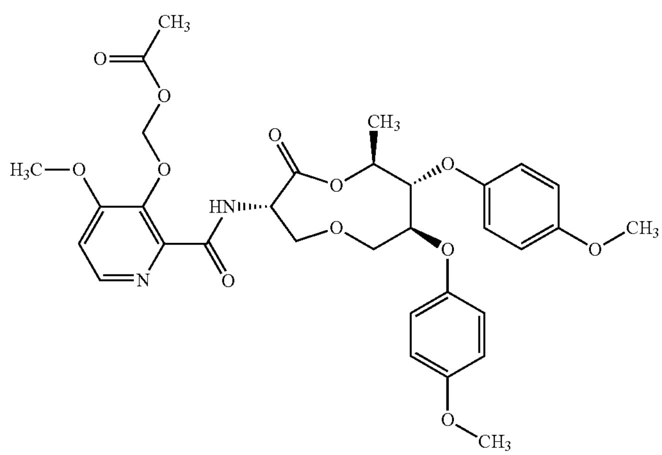 |
| 221 | White Foam | 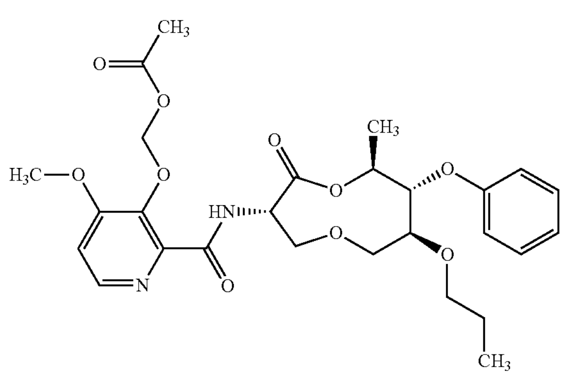 [SMILES: CCCO[C@H]1COC[C@H](NC(=O)c2nccc(OC)c2OCOC(C)=O)C(=O)O[C@@H](C)[C@@H]1Oc1ccccc1] |

TABLE 1-continued
Compound Structure and Appearance
| Compound Number | Appearance | Structure |
|---|---|---|
| 222 | Light Yellow Foam | 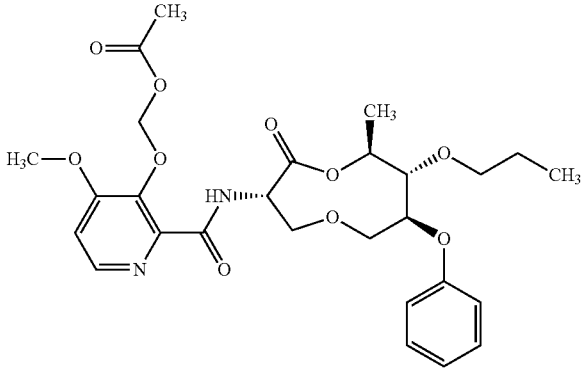 [SMILES: CCCO[C@H]1[C@H](C)OC(=O)[C@@H](NC(=O)c2nccc(OC)c2OCOC(C)=O)COC[C@@H]1Oc1ccccc1] |
| 223 | White Foam | 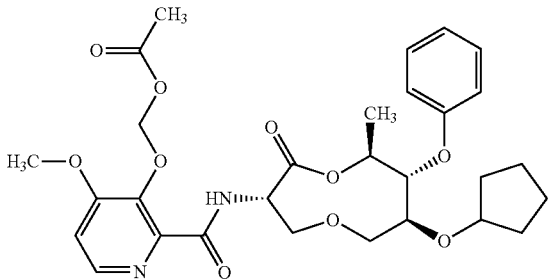 [SMILES: COc1ccnc(C(=O)N[C@H]2COC[C@H](OC3CCCC3)[C@@H](Oc3ccccc3)[C@H](C)OC2=O)c1OCOC(C)=O] |
| 224 | White Foam | 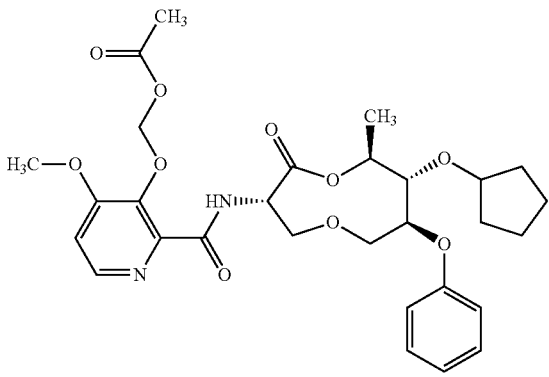 [SMILES: COc1ccnc(C(=O)N[C@H]2COC[C@H](Oc3ccccc3)[C@@H](OC3CCCC3)[C@H](C)OC2=O)c1OCOC(C)=O] |

TABLE 1-continued
| Compound Number | Appearance | Structure |
|---|---|---|
| 225 | White Foam | 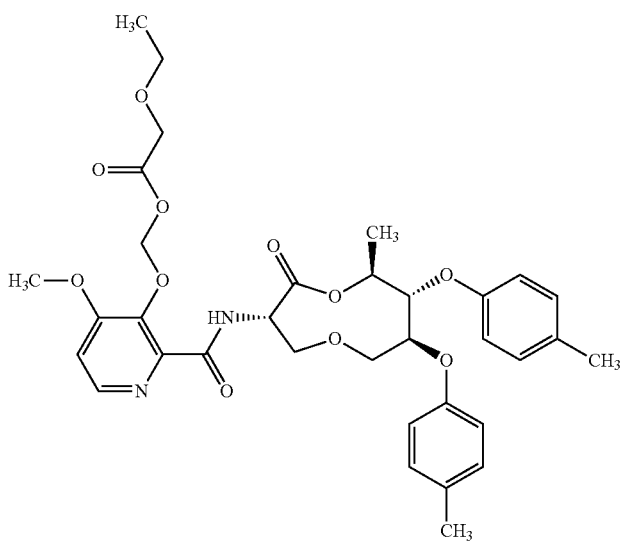 |
| 226 | White Foam | 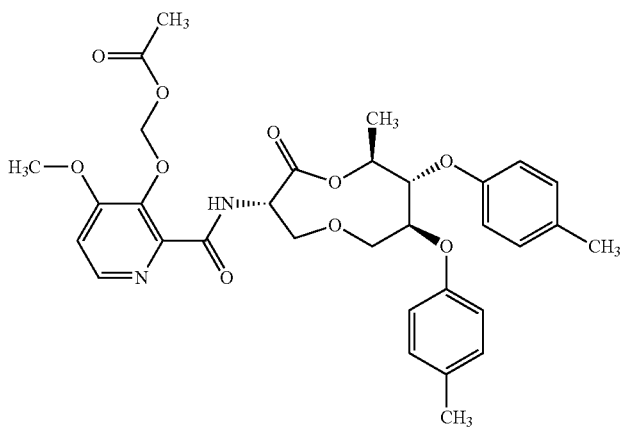 |
| 227 | Colorless Oil | 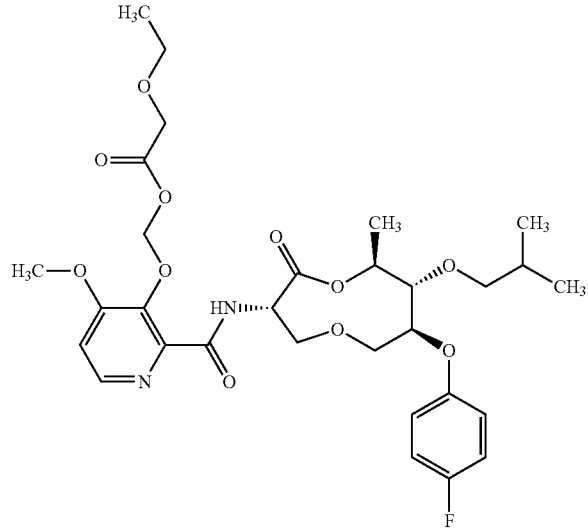 [SMILES: CCOCC(=O)OCOc1c(OC)ccnc1C(=O)N[C@H]1COC[C@H](Oc2ccc(F)cc2)[C@@H](OCC(C)C)[C@H](C)OC1=O] |

TABLE 1-continued
Compound Structure and Appearance
| Compound Number | Appearance | Structure |
|---|---|---|
| 228 | Clear Oil | 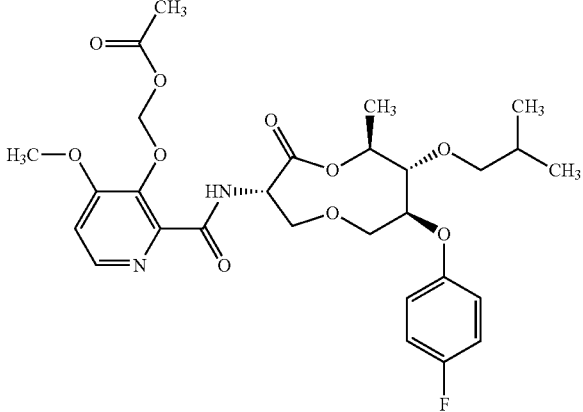 [SMILES: COc1ccnc(C(=O)N[C@H]2COC[C@H](Oc3ccc(F)cc3)[C@@H](OCC(C)C)[C@H](C)OC2=O)c1OCOC(C)=O] |
| 229 | White Foam | 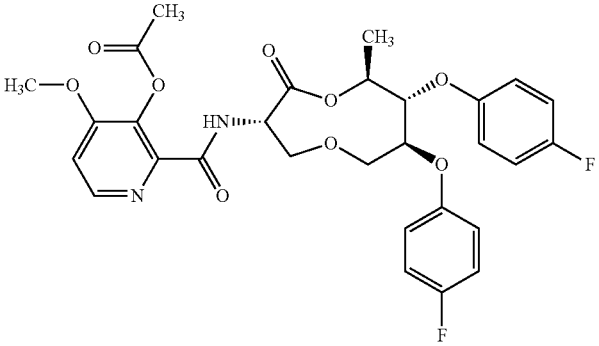 [SMILES: COc1ccnc(C(=O)N[C@H]2COC[C@H](Oc3ccc(F)cc3)[C@@H](Oc3ccc(F)cc3)[C@H](C)OC2=O)c1OC(C)=O] |
| 230 | White Foam | 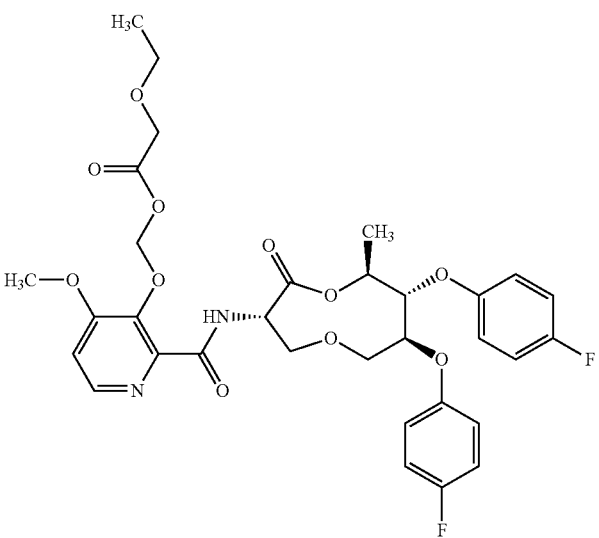 [SMILES: CCOCC(=O)OCOc1c(OC)ccnc1C(=O)N[C@H]1COC[C@H](Oc2ccc(F)cc2)[C@@H](Oc2ccc(F)cc2)[C@H](C)OC1=O] |

TABLE 1-continued
Compound Structure and Appearance
| Compound Number | Appearance | Structure |
|---|---|---|
| 231 | White Foam | 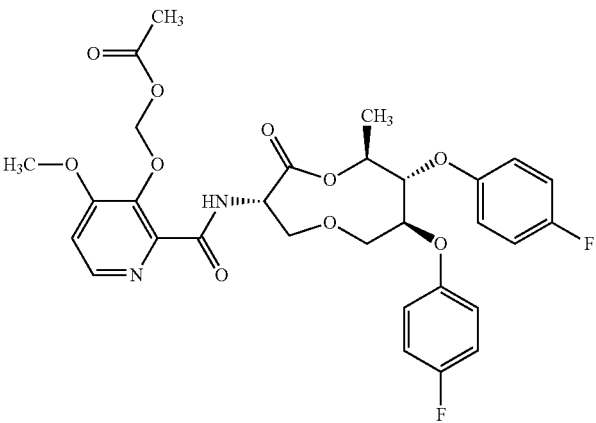 [SMILES: COc1ccnc(C(=O)N[C@H]2COC[C@H](Oc3ccc(F)cc3)[C@@H](Oc3ccc(F)cc3)[C@H](C)OC2=O)c1OCOC(C)=O] |
| 232 | White Solid | 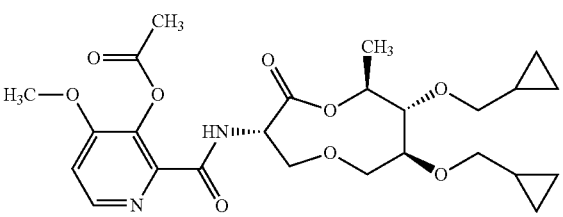 [SMILES: COc1ccnc(C(=O)N[C@H]2COC[C@H](OCC3CC3)[C@@H](OCC3CC3)[C@H](C)OC2=O)c1OC(C)=O] |
| 233 | Colorless Oil | 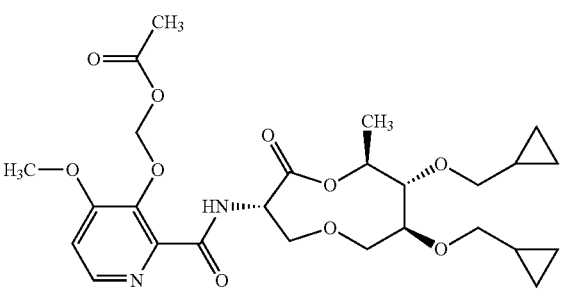 [SMILES: COc1ccnc(C(=O)N[C@H]2COC[C@H](OCC3CC3)[C@@H](OCC3CC3)[C@H](C)OC2=O)c1OCOC(C)=O] |
| 234 | White Solid | 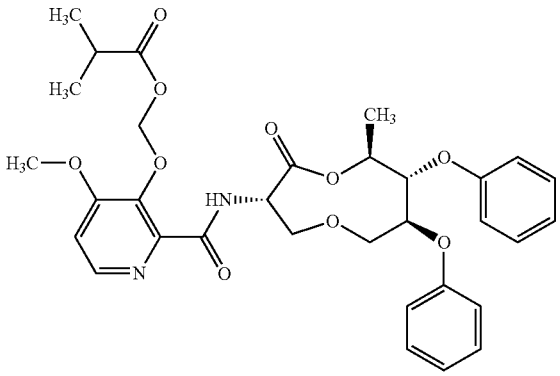 [SMILES: COc1ccnc(C(=O)N[C@H]2COC[C@H](Oc3ccccc3)[C@@H](Oc3ccccc3)[C@H](C)OC2=O)c1OCOC(=O)C(C)C] |

TABLE 1-continued
Compound Structure and Appearance
| Compound Number | Appearance | Structure |
|---|---|---|
| 235 | Yellow-White Solid | 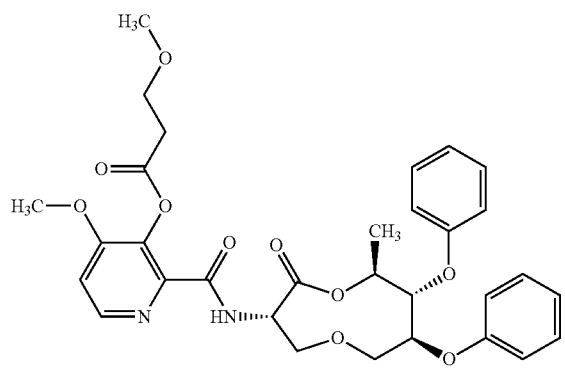 [SMILES: COCCC(=O)Oc1c(OC)ccnc1C(=O)N[C@H]1COC[C@H](Oc2ccccc2)[C@@H](Oc2ccccc2)[C@H](C)OC1=O] |
| 236 | White Solid | 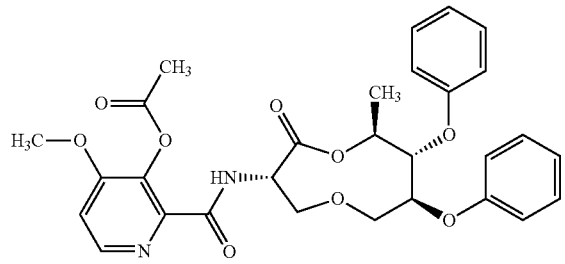 [SMILES: COc1ccnc(C(=O)N[C@H]2COC[C@H](Oc3ccccc3)[C@@H](Oc3ccccc3)[C@H](C)OC2=O)c1OC(C)=O] |
| 237 | Sticky Orange Oil | 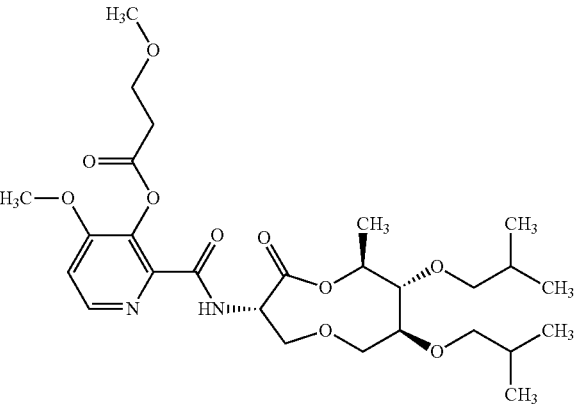 [SMILES: COCCC(=O)Oc1c(OC)ccnc1C(=O)N[C@H]1COC[C@H](OCC(C)C)[C@@H](OCC(C)C)[C@H](C)OC1=O] |
| 238 | White Solid | 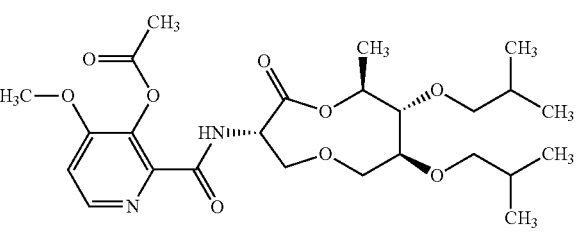 [SMILES: COc1ccnc(C(=O)N[C@H]2COC[C@H](OCC(C)C)[C@@H](OCC(C)C)[C@H](C)OC2=O)c1OC(C)=O] |

TABLE 1-continued

Compound Structure and Appearance

| Compound Number | Appearance | Structure |
|---|---|---|
| 239 | Light Amber Foam | 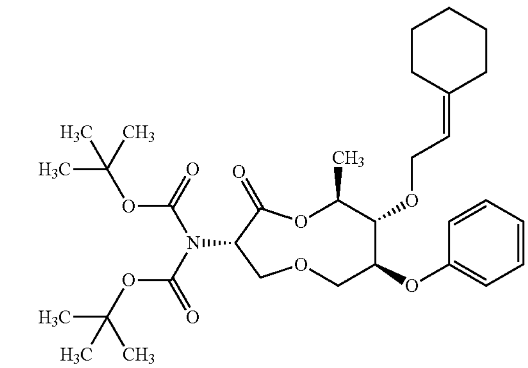 [SMILES: C[C@@H]1OC(=O)[C@@H](N(C(=O)OC(C)(C)C)C(=O)OC(C)(C)C)COC[C@H](Oc2ccccc2)[C@H]1OCC=C1CCCCC1] |
| 240 | Colorless Oil | 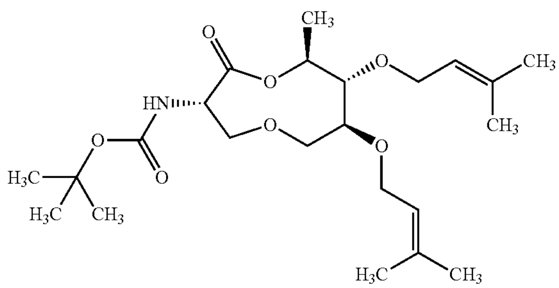 [SMILES: CC(C)=CCO[C@H]1[C@H](C)OC(=O)[C@@H](NC(=O)OC(C)(C)C)COC[C@@H]1OCC=C(C)C] |
| 241 | Colorless Oil | 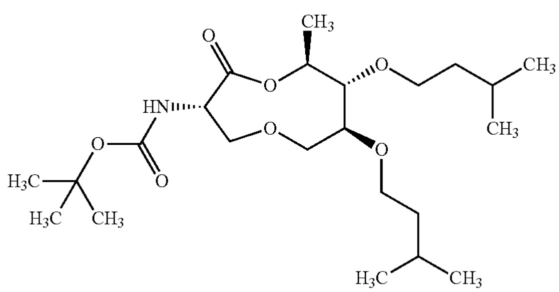 [SMILES: CC(C)CCO[C@H]1[C@H](C)OC(=O)[C@@H](NC(=O)OC(C)(C)C)COC[C@@H]1OCCC(C)C] |
| 242 | Colorless Oil | 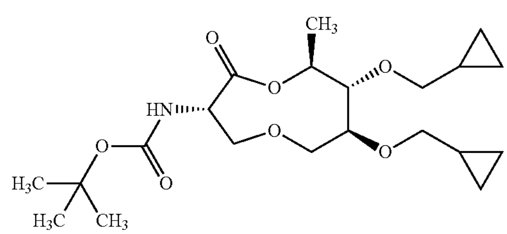 [SMILES: C[C@@H]1OC(=O)[C@@H](NC(=O)OC(C)(C)C)COC[C@H](OCC2CC2)[C@H]1OCC1CC1] |
| 243 | Colorless Oil | 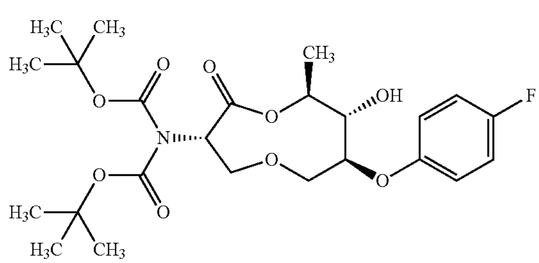 [SMILES: C[C@@H]1OC(=O)[C@@H](N(C(=O)OC(C)(C)C)C(=O)OC(C)(C)C)COC[C@H](Oc2ccc(F)cc2)[C@H]1O] |

TABLE 1-continued
Compound Structure and Appearance
| Compound Number | Appearance | Structure |
|---|---|---|
| 244 | White Solid | 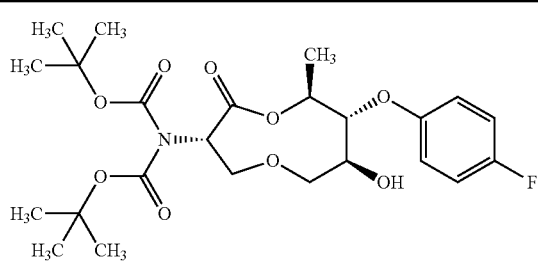 |
| 245 | White Solid | 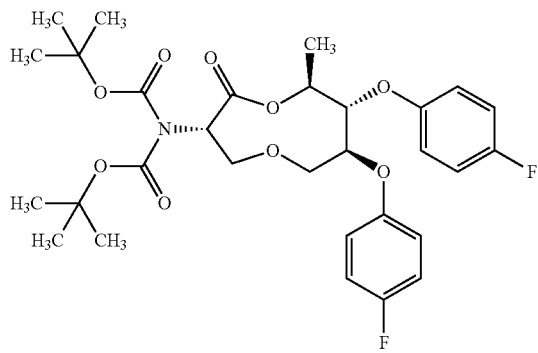 [SMILES: C[C@@H]1OC(=O)[C@@H](N(C(=O)OC(C)(C)C)C(=O)OC(C)(C)C)COC[C@H](Oc2ccc(F)cc2)[C@H]1Oc1ccc(F)cc1] |
| 246 | White Solid | 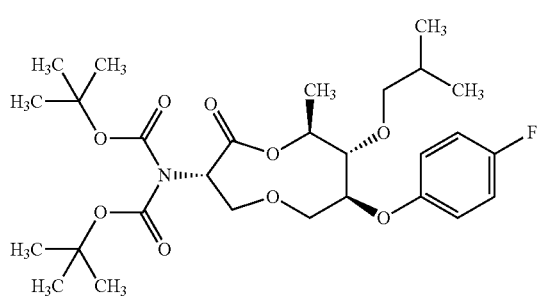 [SMILES: CC(C)CO[C@H]1[C@H](C)OC(=O)[C@@H](N(C(=O)OC(C)(C)C)C(=O)OC(C)(C)C)COC[C@@H]1Oc1ccc(F)cc1] |
| 247 | Colorless Oil | 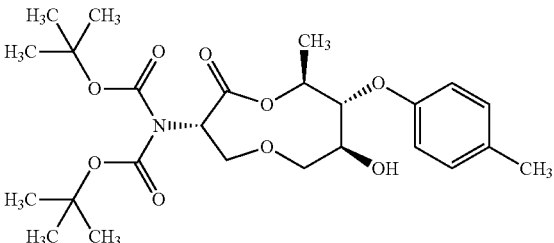 |
| 248 | Colorless Oil | 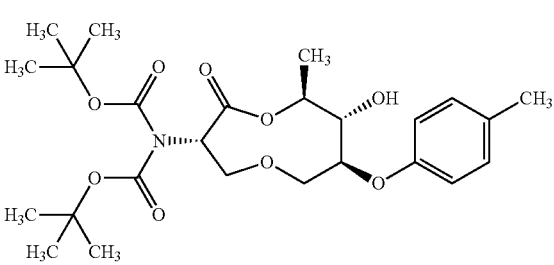 |

TABLE 1-continued
Compound Structure and Appearance
| Compound Number | Appearance | Structure |
|---|---|---|
| 249 | White Solid | 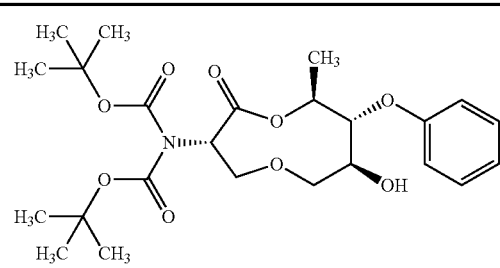 |
| 250 | White Foam | 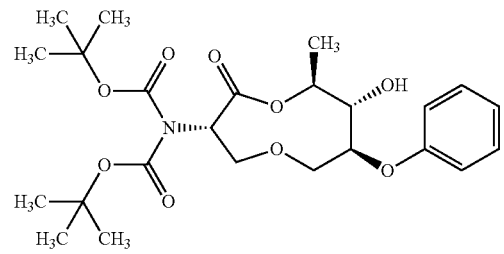 [SMILES: C[C@@H]1OC(=O)[C@@H](N(C(=O)OC(C)(C)C)C(=O)OC(C)(C)C)COC[C@H](Oc2ccccc2)[C@H]1O] |
| 251 | White Solid | 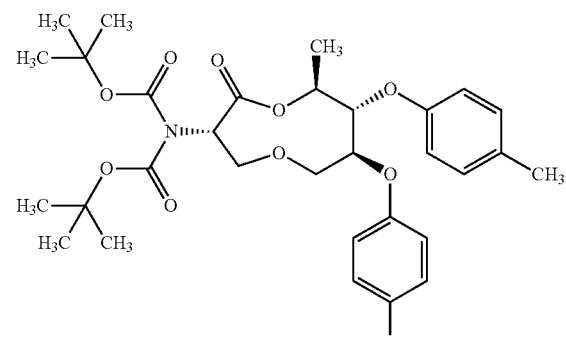 |
| 252 | Colorless Oil | 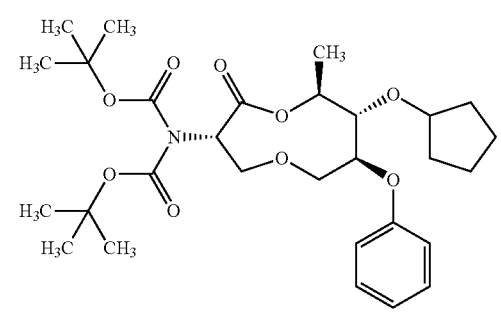 [SMILES: C[C@@H]1OC(=O)[C@@H](N(C(=O)OC(C)(C)C)C(=O)OC(C)(C)C)COC[C@H](Oc2ccccc2)[C@H]1OC1CCCC1] |
| 253 | Colorless Oil | 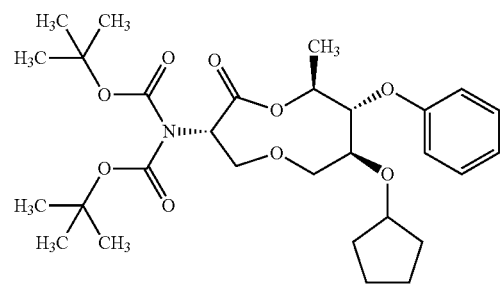 [SMILES: C[C@@H]1OC(=O)[C@@H](N(C(=O)OC(C)(C)C)C(=O)OC(C)(C)C)COC[C@H](OC2CCCC2)[C@H]1Oc1ccccc1] |

TABLE 1-continued

Compound Structure and Appearance

| Compound Number | Appearance | Structure |
|---|---|---|
| 254 | Colorless Oil | 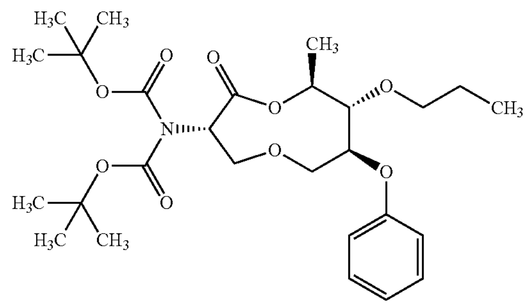 [SMILES: CCCO[C@H]1[C@H](C)OC(=O)[C@@H](N(C(=O)OC(C)(C)C)C(=O)OC(C)(C)C)COC[C@@H]1Oc1ccccc1] |
| 255 | Colorless Oil | 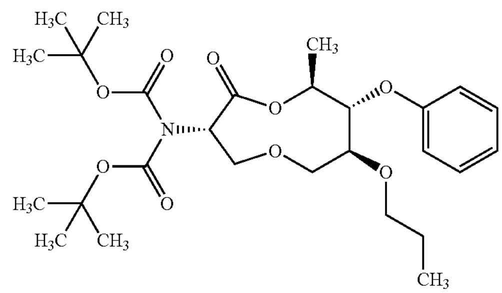 [SMILES: CCCO[C@H]1COC[C@H](N(C(=O)OC(C)(C)C)C(=O)OC(C)(C)C)C(=O)O[C@@H](C)[C@@H]1Oc1ccccc1] |
| 256 | Colorless Oil | 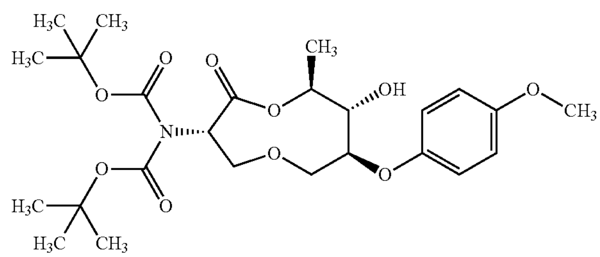 [SMILES: COc1ccc(O[C@H]2COC[C@H](N(C(=O)OC(C)(C)C)C(=O)OC(C)(C)C)C(=O)O[C@@H](C)[C@@H]2O)cc1] |
| 257 | White Solid | 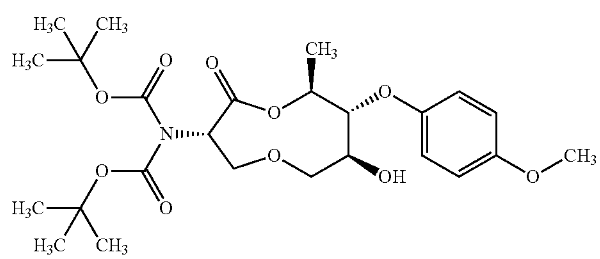 [SMILES: COc1ccc(O[C@H]2[C@H](C)OC(=O)[C@@H](N(C(=O)OC(C)(C)C)C(=O)OC(C)(C)C)COC[C@@H]2O)cc1] |
| 258 | White Solid | 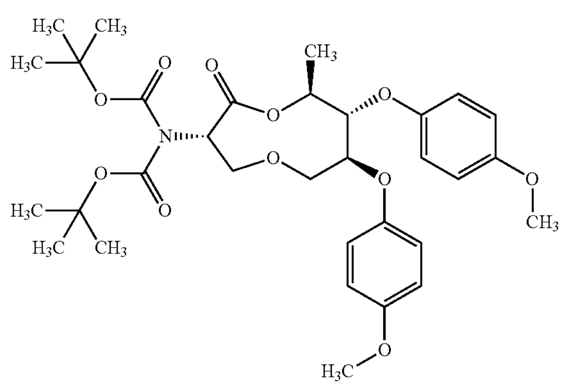 [SMILES: COc1ccc(O[C@H]2[C@H](C)OC(=O)[C@@H](N(C(=O)OC(C)(C)C)C(=O)OC(C)(C)C)COC[C@@H]2Oc2ccc(OC)cc2)cc1] |

TABLE 1-continued
Compound Structure and Appearance
| Compound Number | Appearance | Structure |
|---|---|---|
| 259 | White Solid | 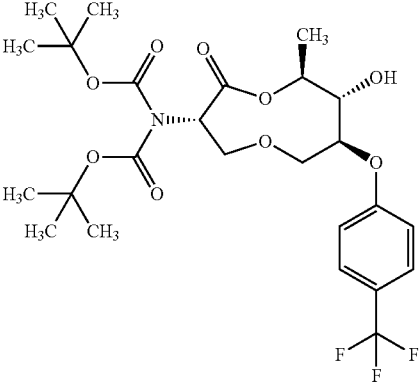 [SMILES: C[C@@H]1OC(=O)[C@@H](N(C(=O)OC(C)(C)C)C(=O)OC(C)(C)C)COC[C@H](Oc2ccc(C(F)(F)F)cc2)[C@H]1O] |
| 260 | White Solid | 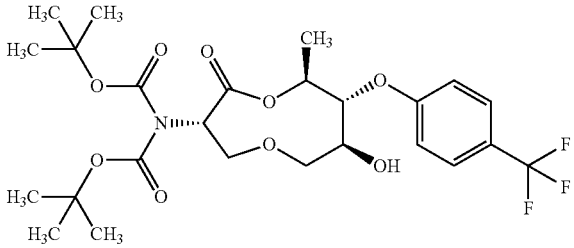 [SMILES: C[C@@H]1OC(=O)[C@@H](N(C(=O)OC(C)(C)C)C(=O)OC(C)(C)C)COC[C@H](O)[C@H]1Oc1ccc(C(F)(F)F)cc1] |
| 261 | Colorless Oil | 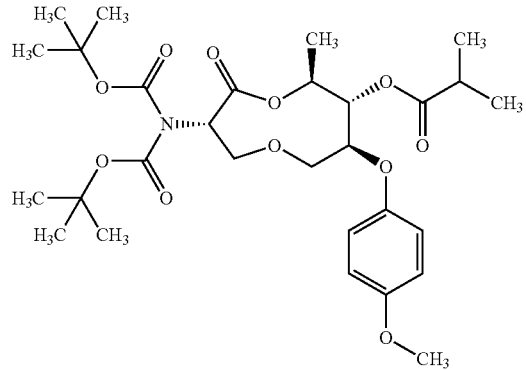 [SMILES: COc1ccc(O[C@H]2COC[C@H](N(C(=O)OC(C)(C)C)C(=O)OC(C)(C)C)C(=O)O[C@@H](C)[C@@H]2OC(=O)C(C)C)cc1] |
| 262 | Colorless Oil | 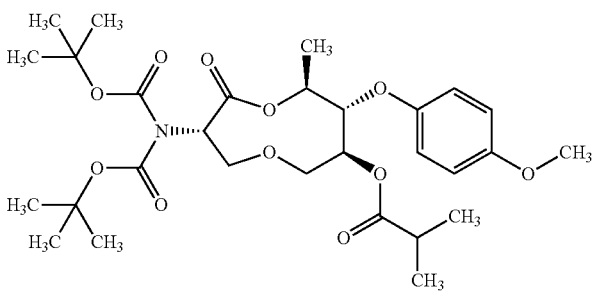 [SMILES: COc1ccc(O[C@H]2[C@H](C)OC(=O)[C@@H](N(C(=O)OC(C)(C)C)C(=O)OC(C)(C)C)COC[C@@H]2OC(=O)C(C)C)cc1] |

TABLE 1-continued

Compound Structure and Appearance

| Compound Number | Appearance | Structure |
|---|---|---|
| 263 | White Solid. | 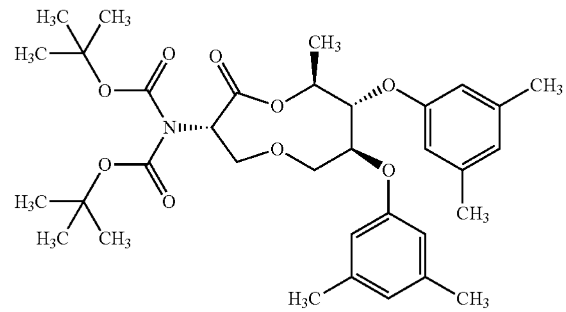 [SMILES: Cc1cc(C)cc(O[C@H]2[C@H](C)OC(=O)[C@@H](N(C(=O)OC(C)(C)C)C(=O)OC(C)(C)C)COC[C@@H]2Oc2cc(C)cc(C)c2)c1] |
| 264 | Yellow Oil | 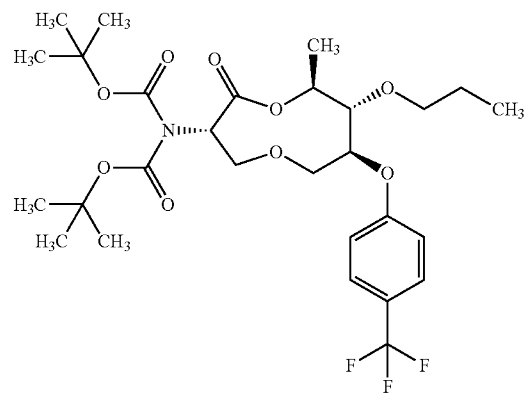 [SMILES: CCCO[C@H]1[C@H](C)OC(=O)[C@@H](N(C(=O)OC(C)(C)C)C(=O)OC(C)(C)C)COC[C@@H]1Oc1ccc(C(F)(F)F)cc1] |
| 265 | Colorless Oil | 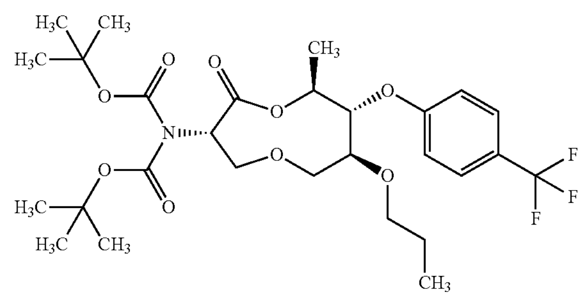 [SMILES: CCCO[C@H]1COC[C@H](N(C(=O)OC(C)(C)C)C(=O)OC(C)(C)C)C(=O)O[C@@H](C)[C@@H]1Oc1ccc(C(F)(F)F)cc1] |
| 266 | Colorless Oil | 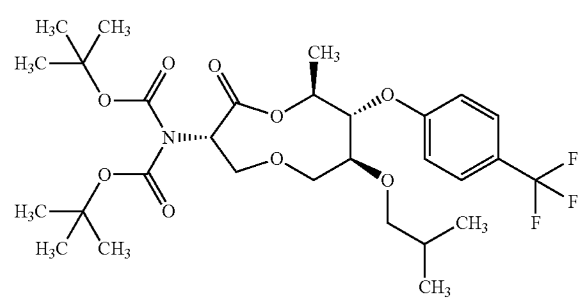 [SMILES: CC(C)CO[C@H]1COC[C@H](N(C(=O)OC(C)(C)C)C(=O)OC(C)(C)C)C(=O)O[C@@H](C)[C@@H]1Oc1ccc(C(F)(F)F)cc1] |
| 267 | Oil | 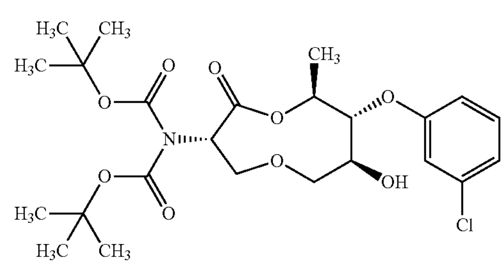 [SMILES: C[C@@H]1OC(=O)[C@@H](N(C(=O)OC(C)(C)C)C(=O)OC(C)(C)C)COC[C@H](O)[C@H]1Oc1cccc(Cl)c1] |

TABLE 1-continued
Compound Structure and Appearance
| Compound Number | Appearance | Structure |
|---|---|---|
| 268 | Oil | 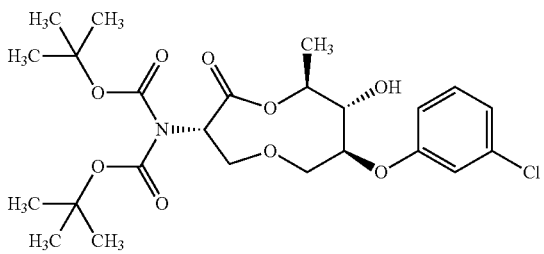 [SMILES: C[C@@H]1OC(=O)[C@@H](N(C(=O)OC(C)(C)C)C(=O)OC(C)(C)C)COC[C@H](Oc2cccc(Cl)c2)[C@H]1O] |
| 269 | Colorless Oil | 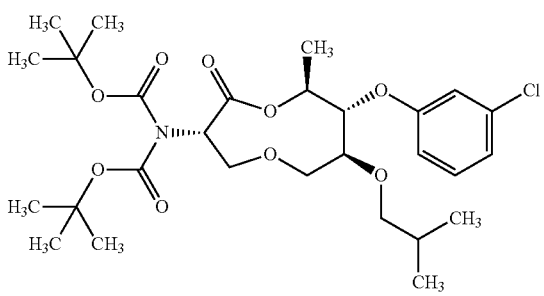 [SMILES: CC(C)CO[C@H]1COC[C@H](N(C(=O)OC(C)(C)C)C(=O)OC(C)(C)C)C(=O)O[C@@H](C)[C@@H]1Oc1cccc(Cl)c1] |
| 270 | White Solid | 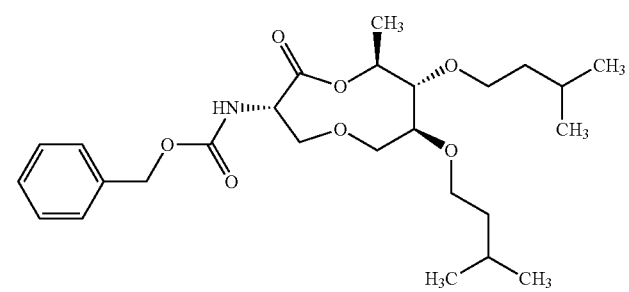 [SMILES: CC(C)CCO[C@H]1[C@H](C)OC(=O)[C@@H](NC(=O)OCc2ccccc2)COC[C@@H]1OCCC(C)C] |
| 271 | Yellow Oil | 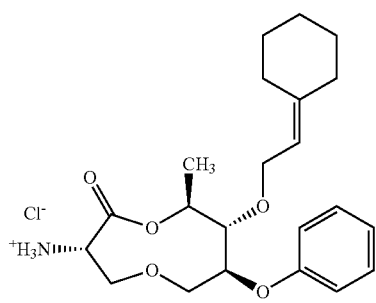 [SMILES: [Cl-] ; C[C@@H]1OC(=O)[C@@H]([NH3+])COC[C@H](Oc2ccccc2)[C@H]1OCC=C1CCCCC1] |
| 272 | Sticky Yellow Solid | 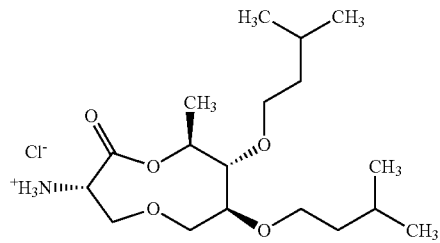 |

TABLE 1-continued
Compound Structure and Appearance
| Compound Number | Appearance | Structure |
|---|---|---|
| 273 | White Solid | 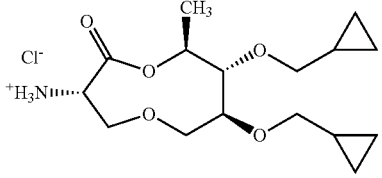 [SMILES: [Cl-] ; C[C@@H]1OC(=O)[C@@H]([NH3+])COC[C@H](OCC2CC2)[C@H]1OCC1CC1] |
| 274 | White Solid | 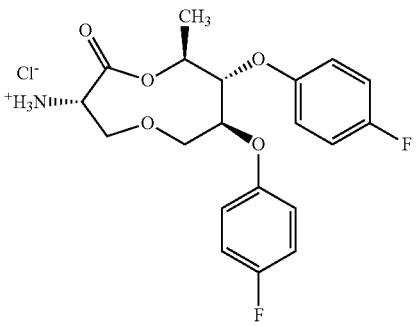 [SMILES: [Cl-] ; C[C@@H]1OC(=O)[C@@H]([NH3+])COC[C@H](Oc2ccc(F)cc2)[C@H]1Oc1ccc(F)cc1] |
| 275 | White Solid | 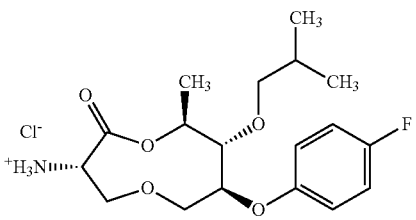 [SMILES: [Cl-] ; CC(C)CO[C@H]1[C@H](C)OC(=O)[C@@H]([NH3+])COC[C@@H]1Oc1ccc(F)cc1] |
| 276 | White Solid | 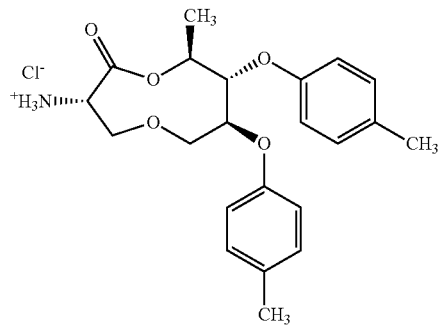 [SMILES: [Cl-] ; Cc1ccc(O[C@H]2[C@H](C)OC(=O)[C@@H]([NH3+])COC[C@@H]2Oc2ccc(C)cc2)cc1] |
| 277 | White Solid | 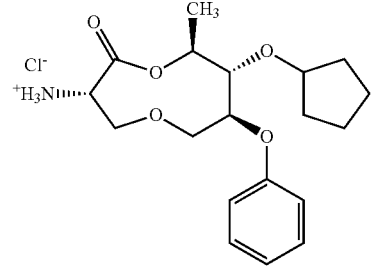 [SMILES: [Cl-] ; C[C@@H]1OC(=O)[C@@H]([NH3+])COC[C@H](Oc2ccccc2)[C@H]1OC1CCCC1] |

TABLE 1-continued

Compound Structure and Appearance

| Compound Number | Appearance | Structure |
|---|---|---|
| 278 | Clear Glass | 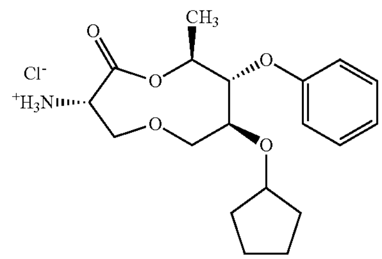 [SMILES: [Cl-] ; C[C@@H]1OC(=O)[C@@H]([NH3+])COC[C@H](OC2CCCC2)[C@H]1Oc1ccccc1] |
| 279 | White Solid | 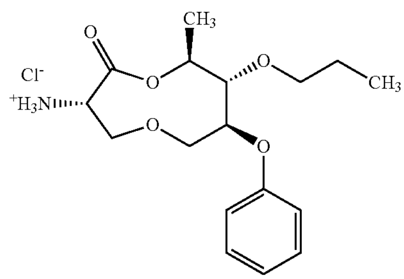 [SMILES: [Cl-] ; CCCO[C@H]1[C@H](C)OC(=O)[C@@H]([NH3+])COC[C@@H]1Oc1ccccc1] |
| 280 | White Solid | 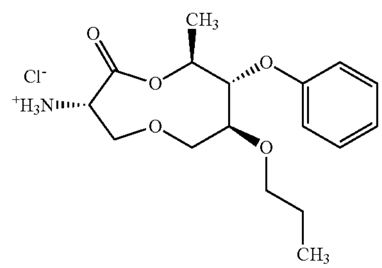 [SMILES: [Cl-] ; CCCO[C@H]1COC[C@H]([NH3+])C(=O)O[C@@H](C)[C@@H]1Oc1ccccc1] |
| 281 | White Solid | 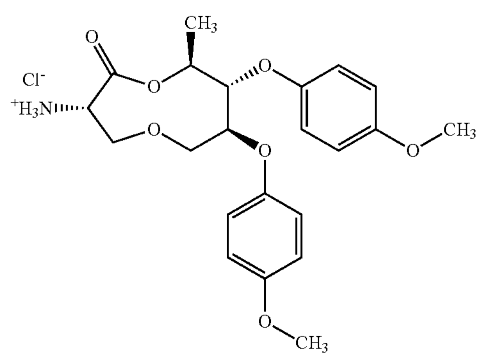 [SMILES: [Cl-] ; COc1ccc(O[C@H]2[C@H](C)OC(=O)[C@@H]([NH3+])COC[C@@H]2Oc2ccc(OC)cc2)cc1] |
| 282 | White Solid | 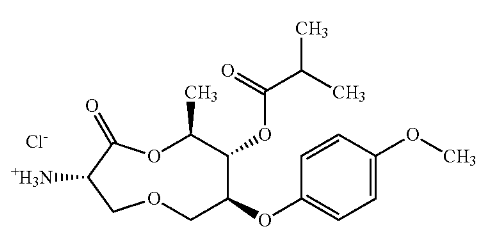 [SMILES: [Cl-] ; COc1ccc(O[C@H]2COC[C@H]([NH3+])C(=O)O[C@@H](C)[C@@H]2OC(=O)C(C)C)cc1] |

TABLE 1-continued
Compound Structure and Appearance
| Compound Number | Appearance | Structure |
|---|---|---|
| 283 | White Solid | 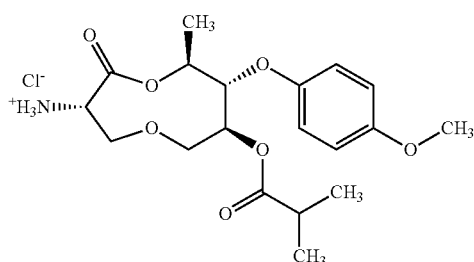 |
| 284 | White Solid | 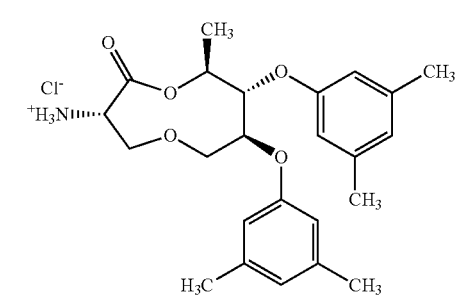 [SMILES: [Cl-] ; Cc1cc(C)cc(O[C@H]2[C@H](C)OC(=O)[C@@H]([NH3+])COC[C@@H]2Oc2cc(C)cc(C)c2)c1] |
| 285 | Off-White Solid | 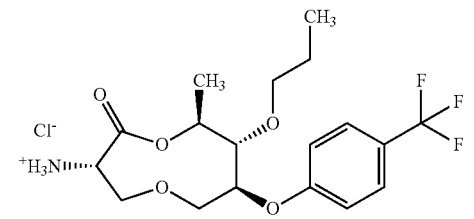 [SMILES: [Cl-] ; CCCO[C@H]1[C@H](C)OC(=O)[C@@H]([NH3+])COC[C@@H]1Oc1ccc(C(F)(F)F)cc1] |
| 286 | White Solid | 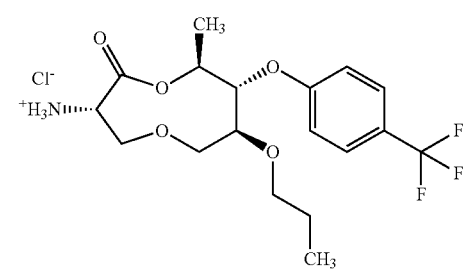 [SMILES: [Cl-] ; CCCO[C@H]1COC[C@H]([NH3+])C(=O)O[C@@H](C)[C@@H]1Oc1ccc(C(F)(F)F)cc1] |
| 287 | White Solid | 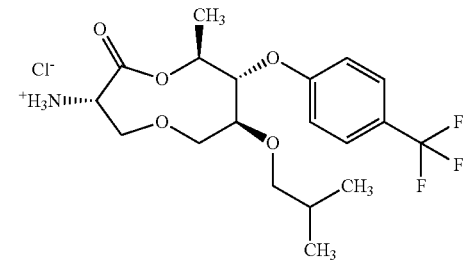 [SMILES: [Cl-] ; CC(C)CO[C@H]1COC[C@H]([NH3+])C(=O)O[C@@H](C)[C@@H]1Oc1ccc(C(F)(F)F)cc1] |

TABLE 1-continued

Compound Structure and Appearance

| Compound Number | Appearance | Structure |
|---|---|---|
| 288 | White Solid | (structure shown: lactone ring with CH₃ group, bearing an ammonium chloride substituent, a (3-chlorophenoxy) group, and an isobutoxy group) |

TABLE 2

Analytical Data

| Compound Number | MP (° C.) | IR (cm⁻¹) | MASS | ¹H NMR* | ¹³C NMR* |
|---|---|---|---|---|---|
| 1 | 111-113 | — | ESIMS m/z 469.4 ([M + H]⁺) | ¹H NMR (CDCl₃) δ 11.95 (s, 1H), 8.68 (d, J = 8.0 Hz, 1H), 8.00 (d, J = 5.2 Hz, 1H), 6.87 (d, J = 5.2 Hz, 1H), 5.10-5.00 (m, 1H), 4.97 (dt, J = 12.6, 6.3 Hz, 1H), 4.10-4.01 (m, 1H), 3.94 (s, 3H), 3.87-3.78 (m, 2H), 3.71 (dd, J = 8.4, 6.1 Hz, 1H), 3.66-3.57 (m, 1H), 3.38-3.28 (m, 2H), 3.28-3.17 (m, 3H), 1.90-1.76 (m, 2H), 1.45 (t, J = 5.8 Hz, 3H), 0.98-0.88 (m, 12H) | ¹³C NMR (CDCl₃) δ 170.33, 168.95, 155.38, 148.76, 140.66, 130.23, 109.58, 84.84, 83.75, 80.60, 77.74, 75.32, 73.97, 73.23, 56.11, 52.19, 29.13, 28.89, 19.60, 19.48, 19.47, 19.39, 18.66 |
| 2 | — | — | ESIMS m/z 569.5 ([M + H]⁺) | ¹H NMR (CDCl₃) δ 8.59 (d, J = 7.9 Hz, 1H), 8.27 (t, J = 4.6 Hz, 1H), 6.94 (d, J = 5.4 Hz, 1H), 5.76 (q, J = 6.4 Hz, 2H), 5.13-5.01 (m, 1H), 5.01-4.87 (m, 1H), 4.08-4.00 (m, 1H), 3.89 (s, 3H), 3.83-3.74 (m, 2H), 3.71 (dd, J = 8.4, 6.1 Hz, 1H), 3.67-3.57 (m, 1H), 3.37-3.27 (m, 2H), 3.27-3.14 (m, 3H), 2.54 (hept, J = 7.0 Hz, 1H), 1.91-1.76 (m, 2H), 1.45 (d, J = 6.3 Hz, 3H), 1.14 (d, J = 7.0 Hz, 6H), 0.96-0.87 (m, 12H) | ¹³C NMR (CDCl₃) δ 176.25, 170.96, 163.23, 160.22, 145.67, 144.18, 141.82, 109.66, 89.78, 84.82, 83.78, 80.57, 77.68, 74.91, 74.09, 72.99, 56.14, 52.39, 33.85, 29.10, 28.86, 19.57, 19.45, 19.44, 19.36, 18.67, 18.63 |
| 3 | — | — | ESIMS m/z 540.5 ([M]⁺) | ¹H NMR (CDCl₃) δ 8.53 (d, J = 7.9 Hz, 1H), 8.29 (d, J = 5.3 Hz, 1H), 6.95 (d, J = 5.4 Hz, 1H), 5.79-5.69 (m, 2H), 5.13-5.01 (m, 1H), 5.01-4.88 (m, 1H), 4.04 (dd, J = 7.9, 3.9 Hz, 1H), 3.91 (s, 3H), 3.83-3.74 (m, 2H), 3.71 (dd, J = 8.4, 6.1 Hz, 1H), 3.65-3.56 (m, 1H), 3.37-3.13 (m, 5H), 2.07 (s, 3H), 1.91-1.73 (m, 2H), 1.45 (d, J = 6.3 Hz, 3H), 0.97-0.87 (m, 12H) | ¹³C NMR (CDCl₃) δ 170.95, 170.30, 163.28, 160.25, 145.84, 143.97, 142.20, 109.73, 89.47, 84.86, 83.81, 80.60, 77.72, 75.07, 74.18, 73.03, 56.23, 52.49, 29.13, 28.90, 20.90, 19.61, 19.48, 19.39, 18.67 |

TABLE 2-continued

Analytical Data

| Compound Number | MP (°C.) | IR (cm$^{-1}$) | MASS | $^1$H NMR* | $^{13}$C NMR* |
|---|---|---|---|---|---|
| 4 | — | — | ESIMS m/z 469.4 ([M + H]$^+$) | $^1$H NMR (CDCl$_3$) δ 11.96 (d, J = 0.6 Hz, 1H), 8.68 (dd, J = 8.2, 5.1 Hz, 1H), 7.99 (d, J = 5.1 Hz, 1H), 6.87 (dd, J = 5.3, 1.3 Hz, 1H), 5.15-4.98 (m, 1H), 4.71 (dd, J = 11.5, 8.3 Hz, 1H), 4.20-4.14 (m, 1H), 4.12 (d, J = 7.1 Hz, 1H), 4.10-4.03 (m, 1H), 3.94 (s, 3H), 3.89-3.78 (m, 1H), 3.68-3.61 (m, 1H), 3.54 (dd, J = 8.5, 6.1 Hz, 1H), 3.47 (ddd, J = 8.3, 7.0, 3.4 Hz, 1H), 3.36 (d, J = 6.5 Hz, 2H), 3.02 (dd, J = 8.3, 7.0 Hz, 1H), 1.91-1.75 (m, 2H), 1.24 (d, J = 6.2 Hz, 3H), 1.00-0.84 (m, 12H) | $^{13}$C NMR (CDCl$_3$) δ 171.47, 168.93, 155.30, 148.71, 140.61, 130.24, 109.54, 84.89, 80.90, 80.55, 80.39, 78.39, 71.45, 64.45, 56.08, 52.21, 29.09, 28.84, 19.62, 19.43, 19.37, 17.64 |
| 5 | — | — | ESIMS m/z 524.1 ([M]$^+$) | $^1$H NMR (CDCl$_3$) δ 11.90 (d, J = 0.6 Hz, 1H), 8.61 (d, J = 8.2 Hz, 1H), 8.49 (d, J = 5.2 Hz, 1H), 7.43-7.24 (m, 11H), 6.86 (d, J = 5.2 Hz, 1H), 5.03 (ddd, J = 8.2, 6.8, 6.0 Hz, 1H), 4.80-4.62 (m, 5H), 4.21-4.07 (m, 2H), 3.93 (s, 3H), 3.85 (s, 1H), 3.79-3.65 (m, 2H), 3.55-3.47 (m, 1H) | $^{13}$C NMR (CDCl$_3$) δ 170.83, 168.92, 155.37, 148.76, 140.66, 137.97, 137.94, 130.17, 128.48, 128.43, 127.91, 127.89, 127.87, 127.81, 109.61, 81.52, 79.29, 73.80, 73.44, 73.24, 72.97, 63.91, 56.10, 52.25 |
| 6 | — | — | ESIMS m/z 623.4 ([M + H]$^+$) | $^1$H NMR (CDCl$_3$) δ 8.54 (d, J = 7.9 Hz, 1H), 8.26 (d, J = 5.3 Hz, 1H), 7.44-7.24 (m, 10H), 6.94 (d, J = 5.4 Hz, 1H), 5.75 (q, J = 6.4 Hz, 2H), 5.15-5.01 (m, 1H), 4.84-4.59 (m, 5H), 4.22-4.05 (m, 2H), 3.89 (s, J = 7.2 Hz, 3H), 3.84 (dd, J = 10.9, 6.8 Hz, 2H), 3.78-3.61 (m, 2H), 3.50 (dd, J = 10.6, 4.0 Hz, 1H), 2.63-2.45 (m, 1H), 1.14 (d, J = 7.0 Hz, 6H) | $^{13}$C NMR (CDCl$_3$) δ 176.27, 171.46, 163.14, 160.23, 145.63, 144.25, 141.69, 138.03, 138.01, 128.45, 128.40, 127.90, 127.86, 127.85, 127.75, 109.68, 89.76, 81.78, 79.45, 73.91, 73.64, 73.08, 72.99, 63.88, 56.15, 52.51, 33.85, 18.67 |
| 7 | — | — | ESIMS m/z 569.7 ([M + H]$^+$) | $^1$H NMR (CDCl$_3$) δ 8.60 (d, J = 7.9 Hz, 1H), 8.27 (d, J = 5.4 Hz, 1H), 7.27 (s, 1H), 6.94 (d, J = 5.5 Hz, 1H), 5.79-5.72 (m, 2H), 5.12-5.02 (m, 1H), 4.66 (dd, J = 11.4, 8.8 Hz, 1H), 4.17-4.04 (m, 1H), 3.89 (s, 3H), 3.80-3.74 (m, 1H), 3.66 (dd, J = 8.2, 6.2 Hz, 1H), 3.55 (dd, J = 8.4, 6.1 Hz, 1H), 3.47 (ddd, J = 8.8, 7.4, 3.5 Hz, 1H), 3.41-3.34 (m, 2H), 3.26-3.21 (m, 1H), 2.99 (dd, J = 8.3, 7.4 Hz, 1H), 2.54 (hept, J = 7.0 Hz, 1H), 1.89-1.75 (m, 2H), 1.22 (d, J = 6.2 Hz, 3H), 1.14 (d, J = 7.0 Hz, 6H), 0.96-0.86 (m, 12H) | $^{13}$C NMR (CDCl$_3$) δ 176.24, 172.19, 163.23, 160.24, 145.64, 144.20, 141.79, 109.64, 89.83, 85.05, 81.04, 80.57, 80.02, 78.49, 71.51, 64.42, 56.14, 52.40, 33.86, 29.11, 28.87, 19.64, 19.45, 19.43, 19.36, 18.68, 17.38 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 8 | 94-108 | — | HRMS-ESI (m/z) [M + H]$^+$ calcd for C$_{22}$H$_{34}$N$_2$O$_8$, 455.2388; found, 455.2374 | $^1$H NMR (CDCl$_3$) δ 11.93 (s, 1H), 8.59 (d, J = 8.2 Hz, 1H), 8.00 (d, J = 5.2 Hz, 1H), 6.87 (d, J = 5.2 Hz, 1H), 5.13-4.87 (m, 1H), 4.67 (dd, J = 11.4, 9.4 Hz, 1H), 4.24-4.08 (m, 2H), 3.94 (s, 3H), 3.79-3.70 (m, 2H), 3.70-3.57 (m, 2H), 3.49-3.27 (m, 4H), 3.28-3.14 (m, 1H), 1.94-1.74 (m, 2H), 0.98-0.83 (m, 12H) | — |
| 9 | 115-118 | — | HRMS-ESI (m/z) [M + H]$^+$ calcd for C$_{22}$H$_{30}$N$_2$O$_8$, 451.2075; found, 451.2089 | $^1$H NMR (CDCl$_3$) δ 11.99 (s, 1H), 8.84 (d, J = 8.0 Hz, 1H), 8.01 (d, J = 5.2 Hz, 1H), 6.87 (d, J = 5.2 Hz, 1H), 5.16-5.03 (m, 2H), 5.03-4.84 (m, 4H), 4.22-3.96 (m, 8H), 3.94 (s, 3H), 3.89-3.79 (m, 1H), 3.75-3.65 (m, 1H), 3.50-3.40 (m, 1H), 1.76 (d, J = 6.5 Hz, 6H) | — |
| 10 | 92-97 | — | HRMS-ESI (m/z) [M + H]$^+$ calcd for C$_{22}$H$_{34}$N$_2$O$_8$, 455.2388; found, 455.2437 | $^1$H NMR (CDCl$_3$) δ 11.99 (s, 1H), 8.91-8.74 (m, 1H), 8.04-7.97 (m, 1H), 6.88-6.86 (m, 1H), 5.12-4.96 (m, 2H), 4.28-4.05 (m, 2H), 4.03-3.88 (m, 2H), 3.94 (s, 3H), 3.85-3.60 (m, 3H), 3.49-3.14 (m, 4H), 1.97-1.76 (m, 2H), 1.00-0.79 (m, 12H) | — |
| 11 | 144-146 | (Neat) 3363, 2935, 1749, 1648, 1527, 1263, 1076 | HRMS-ESI (m/z) [M]$^+$ calcd for C$_{29}$H$_{32}$N$_2$O$_8$, 536.2159; found, 536.2150 | $^1$H NMR (CDCl$_3$) δ 11.93 (s, 1H), 8.69 (d, J = 8.1 Hz, 1H), 8.00 (d, J = 5.2 Hz, 1H), 7.37-7.25 (m, 10H), 6.87 (d, J = 5.2 Hz, 1H), 5.13-5.02 (m, 2H), 4.95 (d, J = 10.8 Hz, 1H), 4.70-4.61 (m, 2H), 4.62 (d, J = 10.8 Hz, 1H), 4.07 (dd, J = 11.9, 6.7 Hz, 1H), 4.02-3.96 (m, 1H), 3.94 (s, 3H), 3.87 (dd, J = 11.9, 4.8 Hz, 1H), 3.70 (dd, J = 11.3, 6.6 Hz, 1H), 3.56-3.45 (m, 2H), 1.46 (d, J = 6.3 Hz, 3H) | $^{13}$C NMR (CDCl$_3$) δ 170.31, 169.11, 155.47, 148.87, 140.82, 138.23, 138.06, 130.35, 128.56, 128.54, 128.11, 128.01, 127.91, 109.72, 84.84, 83.68, 75.95, 75.78, 74.38, 73.14, 73.12, 56.23, 52.40, 18.85 |
| 12 | — | (Neat) 3382, 2920, 1753, 1677, 1504, 1202, 1090 | HRMS-ESI (m/z) [M]$^+$ calcd for C$_{32}$H$_{36}$N$_2$O$_{10}$, 608.2370; found, 608.2374. | $^1$H NMR (CDCl$_3$) δ 8.55 (d, J = 7.9 Hz, 1H), 8.29 (d, J = 5.4 Hz, 1H), 7.38-7.21 (m, 10H), 6.95 (d, J = 5.4 Hz, 1H), 5.79-5.67 (m, 2H), 5.13-5.00 (m, 2H), 4.94 (d, J = 10.8 Hz, 1H), 4.70-4.58 (m, 3H), 4.07 (dd, J = 11.9, 6.8 Hz, 1H), 3.98 (d, J = 10.7 Hz, 1H), 3.91 (s, 3H), 3.83 (dd, J = 11.9, 4.9 Hz, 1H), 3.70 (dd, J = 11.2, 6.7 Hz, 1H), 3.57-3.42 (m, 2H), 2.07 (s, 3H), 1.45 (d, J = 6.3 Hz, 3H) | $^{13}$C NMR (CDCl$_3$) δ 170.95, 170.39, 163.42, 160.38, 145.96, 144.12, 142.31, 138.32, 138.14, 128.55, 128.53, 128.10, 128.01, 127.88, 109.87, 89.60, 84.91, 83.78, 75.96, 75.49, 74.58, 73.13, 72.93, 56.34, 52.70, 21.02, 18.87 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 13 | 58-64 | — | HRMS-ESI (m/z) [M + H]$^+$ calcd for C$_{25}$H$_{38}$N$_2$O$_{10}$, 527.2599; found, 527.2657 | $^1$H NMR (CDCl$_3$) δ 8.46 (d, J = 8.0 Hz, 1H), 8.28 (d, J = 5.3 Hz, 1H), 6.96 (d, J = 5.4 Hz, 1H), 5.80-5.66 (m, 2H), 5.14-5.01 (m, 1H), 4.69-4.58 (m, 1H), 4.20-4.05 (m, 2H), 3.91 (s, 3H), 3.76-3.69 (m, 2H), 3.67-3.57 (m, 2H), 3.49-3.41 (m, 1H), 3.41-3.27 (m, 3H), 3.27-3.17 (m, 1H), 2.07 (s, 3H), 1.91-1.75 (m, 2H), 0.97-0.83 (m, 12H) | — |
| 14 | — | — | HRMS-ESI (m/z) [M + H]$^+$ calcd for C$_{25}$H$_{38}$N$_2$O$_{10}$, 527.2599; found, 527.2592 | $^1$H NMR (CDCl$_3$) δ 8.76-8.63 (m, 1H), 8.33-8.24 (m, 1H), 6.96-6.94 (m, 1H), 5.79-5.67 (m, 2H), 5.12-5.04 (m, 1H), 4.23-4.05 (m, 2H), 4.02-3.85 (m, 2H), 3.91 (s, 3H); 3.85-3.76 (m, 1H), 3.76-3.54 (m, 2H), 3.51-3.27 (m, 4H), 3.25-3.20 (m, 1H), 2.07 (s, 3H), 1.94-1.76 (m, 2H), 0.99-0.85 (m, 12H) | — |
| 15 | — | — | ESIMS m/z 541.4 ([M + H]$^+$) | $^1$H NMR (CDCl$_3$) δ 12.00 (d, J = 0.7 Hz, 1H), 8.86 (d, J = 8.1 Hz, 1H), 8.01 (d, J = 5.2 Hz, 1H), 6.87 (dd, J = 5.2, 0.6 Hz, 1H), 5.33-5.23 (m, 1H), 5.09 (ddd, J = 7.9, 6.0, 1.7 Hz, 1H), 4.24-4.07 (m, 2H), 3.99 (dd, J = 11.7, 6.1 Hz, 1H), 3.93 (s, 3H), 3.92-3.86 (m, 1H), 3.82-3.67 (m, 3H), 3.46-3.39 (m, 2H), 3.34 (td, J = 9.1, 6.5 Hz, 2H), 3.27 (d, J = 6.6 Hz, 2H), 3.20 (dd, J = 8.9, 6.9 Hz, 1H), 1.97-1.79 (m, 3H), 0.96-0.87 (m, 18H) | $^{13}$C NMR (CDCl$_3$) δ 169.72, 168.89, 155.24, 148.66, 140.64, 130.39, 109.47, 79.21, 78.31, 76.84, 75.42, 73.40, 72.61, 67.95, 56.05, 53.39, 28.84, 28.70, 28.47, 19.49, 19.39 |
| 16 | — | — | ESIMS m/z 541.3 ([M + H]$^+$) | $^1$H NMR (400 MHz, CDCl$_3$) δ 12.00 (d, J = 0.6 Hz, 1H), 8.61 (d, J = 8.7 Hz, 1H), 7.95 (d, J = 5.2 Hz, 1H), 6.92-6.81 (m, 1H), 5.20 (td, J = 5.6, 3.1 Hz, 1H), 4.94 (ddd, J = 8.7, 6.2, 5.2 Hz, 1H), 4.30 (dd, J = 11.6, 6.3 Hz, 1H), 4.06-3.99 (m, 1H), 3.95 (s, 4H), 3.91-3.84 (m, 2H), 3.76 (qd, J = 10.2, 5.5 Hz, 2H), 3.58 (dd, J = 11.6, 5.1 Hz, 1H), 3.54-3.46 (m, 1H), 3.44 (dd, J = 8.9, 6.4 Hz, 1H), 3.34 (td, J = 8.8, 6.5 Hz, 2H), 3.29-3.24 (m, 2H), 3.24-3.16 (m, 1H), 1.87 (tt, J = 13.3, 6.6 Hz, 3H), 1.03-0.78 (m, 20H) | $^{13}$C NMR (CDCl$_3$) δ 168.47, 167.68, 155.44, 148.87, 140.46, 140.42, 130.31, 109.55, 79.11, 78.34, 78.30, 73.76, 72.63, 68.03, 56.10, 54.44, 28.94, 28.70, 28.52, 19.37, 19.35 |
| 17 | — | — | ESIMS m/z 613.4 ([M + H]$^+$) | $^1$H NMR (CDCl$_3$) δ 8.73 (d, J = 7.9 Hz, 1H), 8.29 (d, J = 5.4 Hz, 1H), 6.94 (d, J = 5.4 Hz, 1H), 5.73 (d, J = 0.7 Hz, 2H), 5.25 (q, J = 4.6 Hz, 1H), 5.12 (ddd, J = 7.9, 6.1, 1.9 Hz, 1H), 4.22-4.06 (m, 2H), | $^{13}$C NMR (CDCl3) δ 170.32, 170.25, 163.20, 160.19, 145.81, 143.89, 142.33, 109.60, 89.50, 79.20, 78.31, 76.80, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 3.97 (dd, J = 11.7, 6.1 Hz, 1H), 3.91 (s, 4H), 3.80-3.67 (m, 3H), 3.45-3.38 (m, 2H), 3.34 (dt, J = 9.0, 6.9 Hz, 2H), 3.26 (d, J = 6.6 Hz, 2H), 3.20 (dd, J = 8.8, 6.9 Hz, 1H), 2.06 (s, 3H), 1.86 (tdd, J = 13.2, 6.6, 4.0 Hz, 3H), 0.98-0.83 (m, 18H) | 75.70, 73.26, 67.96, 56.17, 53.64, 28.85, 28.70, 28.48, 20.88, 19.49, 19.39, 19.37 |
| 18 | — | — | ESIMS m/z 613.4 ([M + H]$^+$) | $^1$H NMR (CDCl$_3$) δ 8.52 (d, J = 8.6 Hz, 1H), 8.23 (d, J = 5.3 Hz, 1H), 6.95 (d, J = 5.4 Hz, 1H), 5.73 (s, 2H), 5.19 (dt, J = 5.4, 2.7 Hz, 1H), 4.95 (ddd, J = 8.4, 6.3, 5.0 Hz, 1H), 4.29 (dd, J = 11.7, 6.3 Hz, 1H), 4.06-3.96 (m, 1H), 3.91 (s, 4H), 3.90-3.84 (m, 2H), 3.75 (ddt, J = 15.9, 10.2, 5.3 Hz, 3H), 3.55 (dd, J = 11.7, 5.0 Hz, 1H), 3.51-3.40 (m, 2H), 3.34 (td, J = 9.1, 6.4 Hz, 2H), 3.29-3.17 (m, 4H), 2.07 (s, 3H), 1.86 (dqd, J = 12.8, 6.6, 1.6 Hz, 3H), 1.01-0.78 (m, 18H) | $^{13}$C NMR (CDCl$_3$) δ 170.33, 168.22, 162.66, 160.35, 145.55, 144.31, 142.16, 109.68, 89.55, 79.24, 79.09, 78.26, 73.61, 72.90, 71.06, 68.05, 56.21, 54.83, 28.93, 28.70, 28.51, 20.87, 19.48, 19.40, 19.37, 19.35, 19.33 |
| 19 | — | (Neat) 3369, 2956, 1751, 1650, 1528, 1242, 1082 | HRMS-ESI (m/z) [M]$^+$ calcd for C$_{24}$H$_{38}$N$_2$O$_8$, 482.2628; found, 482.2642 | $^1$H NMR (CDCl$_3$) δ 12.02 (s, 1H), 8.86 (d, J = 8.0 Hz, 1H), 8.00 (d, J = 5.2 Hz, 1H), 6.86 (d, J = 5.2 Hz, 1H), 5.11-5.02 (m, 2H), 4.17 (dd, J = 11.9, 3.6 Hz, 1H), 4.14 (dd, J = 11.7, 1.6 Hz, 1H), 3.97 (dd, J = 11.7, 5.9 Hz, 1H), 3.94 (s, 3H), 3.78-3.68 (m, 1H), 3.64 (dd, J = 11.8, 1.5 Hz, 1H), 3.35 (dtd, J = 26.6, 8.9, 6.6 Hz, 4H), 3.21 (dd, J = 8.7, 6.8 Hz, 1H), 1.93-1.79 (m, 3H), 1.78-1.65 (m, 1H), 1.02 (t, J = 7.4 Hz, 3H), 0.94-0.88 (m, 12H) | $^{13}$C NMR (CDCl$_3$) δ 170.17, 169.05, 155.37, 148.79, 140.78, 130.57, 109.59, 79.37, 78.70, 78.33, 75.53, 72.63, 56.19, 53.59, 29.03, 28.85, 22.50, 19.60, 19.53, 19.51, 10.85 |
| 20 | — | (Neat) 2956, 1753, 1678, 1504, 1202, 1082 | HRMS-ESI (m/z) [M]$^+$ calcd for C$_{27}$H$_{42}$N$_2$O$_{10}$, 554.2839; found, 554.2841 | $^1$H NMR (CDCl$_3$) δ 8.73 (d, J = 7.7 Hz, 1H), 8.28 (d, J = 5.4 Hz, 1H), 6.94 (d, J = 5.4 Hz, 1H), 6.01-5.44 (m, 2H), 5.09 (ddd, J = 7.7, 6.0, 1.6 Hz, 1H), 5.04 (dt, J = 9.9, 3.2 Hz, 1H), 4.15 (dd, J = 11.9, 3.6 Hz, 1H), 4.11 (dd, J = 11.8, 1.7 Hz, 1H), 3.95 (dd, J = 11.7, 6.0 Hz, 1H), 3.90 (s, 3H), 3.80-3.71 (m, 1H), 3.63 (dd, J = 11.8, 1.6 Hz, 1H), 3.47-3.26 (m, 4H), 3.21 (dd, J = 8.7, 6.8 Hz, 1H), 2.06 (s, 3H), 1.94-1.76 (m, 3H), 1.77-1.62 (m, 1H), 1.02 (t, J = 7.4 Hz, 3H), 0.95-0.81 (m, 12H) | $^{13}$C NMR (CDCl$_3$) δ 170.79, 170.40, 163.40, 160.35, 145.96, 144.05, 142.53, 109.74, 89.68, 79.36, 78.60, 78.53, 76.96, 75.79, 56.31, 53.84, 29.04, 28.85, 21.02, 19.61, 19.53, 19.51, 10.87 |

TABLE 2-continued

Analytical Data

| Compound Number | MP (°C.) | IR (cm$^{-1}$) | MASS | $^1$H NMR* | $^{13}$C NMR* |
|---|---|---|---|---|---|
| 21 | 119-121 | — | HRMS-ESI (m/z) [M]$^+$ calcd for $C_{24}H_{38}N_2O_8$, 482.2628; found, 482.2647 | $^1$H NMR (CDCl$_3$) δ 11.95 (s, 1H), 8.73 (d, J = 8.0 Hz, 1H), 8.00 (d, J = 5.2 Hz, 1H), 6.86 (d, J = 5.2 Hz, 1H), 5.03 (ddd, J = 8.0, 6.3, 4.2 Hz, 1H), 4.93 (td, J = 8.8, 2.9 Hz, 1H), 4.04 (dd, J = 12.0, 6.3 Hz, 1H), 3.94 (s, 3H), 3.89 (dd, J = 12.0, 4.0 Hz, 1H), 3.85 (d, J = 12.0 Hz, 1H), 3.71 (dd, J = 8.4, 6.2 Hz, 1H), 3.58 (dd, J = 11.6, 6.0 Hz, 1H), 3.37-3.14 (m, 5H), 2.03 (dqd, J = 14.9, 7.5, 2.9 Hz, 1H), 1.81 (dp, J = 13.2, 6.6 Hz, 2H), 1.72-1.59 (m, 1H), 0.97 (t, J = 7.4 Hz, 3H), 0.93-0.86 (m, 12H) | $^{13}$C NMR (151 MHz, CDCl$_3$) δ 170.53, 169.10, 155.49, 148.90, 140.81, 130.47, 109.71, 84.19, 83.34, 80.50, 77.84, 77.76, 76.80, 74.99, 56.23, 52.79, 29.26, 29.01, 25.30, 19.72, 19.62, 19.60, 19.53, 9.64 |
| 22 | — | (Neat) 2956, 1749, 1651, 1526, 1262, 1083 | HRMS-ESI (m/z) [M]$^+$ calcd for $C_{24}H_{38}N_2O_8$, 482.2628; found, 482.2660 | $^1$H NMR (CDCl$_3$) δ 12.00 (s, 1H), 8.60 (s, 1H), 7.95 (d, J = 5.2 Hz, 1H), 6.86 (d, J = 5.3 Hz, 1H), 4.99 (ddd, J = 9.3, 4.7, 2.8 Hz, 1H), 4.87 (dt, J = 8.8, 5.6 Hz, 1H), 4.23 (dd, J = 11.6, 6.0 Hz, 1H), 3.97 (dd, J = 11.5, 4.2 Hz, 1H), 3.93 (s, 3H), 3.79 (dd, J = 11.5, 1.6 Hz, 1H), 3.65 (dd, J = 6.4, 2.5 Hz, 1H), 3.59 (dd, J = 11.6, 5.3 Hz, 1H), 3.46-3.37 (m, 2H), 3.31 (ddd, J = 21.1, 8.7, 6.5 Hz, 2H), 3.20 (dd, J = 8.8, 6.8 Hz, 1H), 1.94-1.72 (m, 4H), 1.00 (t, J = 7.4 Hz, 3H), 0.94 (d, J = 3.1 Hz, 3H), 0.92 (d, J = 3.1 Hz, 3H), 0.89 (d, J = 4.1 Hz, 3H), 0.87 (d, J = 4.1 Hz, 3H) | $^{13}$C NMR (CDCl$_3$) δ 168.56, 168.39, 155.59, 148.99, 140.56, 130.37, 109.63, 79.24, 79.17, 78.29, 77.39, 72.70, 71.21, 56.22, 54.57, 29.11, 28.80, 23.16, 19.54, 19.47, 10.71 |
| 23 | — | (Neat) 2956, 1756, 1679, 1506, 1202, 1097 | HRMS-ESI (m/z) [M]$^+$ calcd for $C_{27}H_{42}N_2O_{10}$, 554.2839; found, 554.2863 | $^1$H NMR (CDCl$_3$) δ 8.59 (d, J = 7.8 Hz, 1H), 8.27 (d, J = 5.4 Hz, 1H), 6.94 (d, J = 5.4 Hz, 1H), 5.82-5.57 (m, 2H), 5.05 (ddd, J = 7.7, 6.4, 4.3 Hz, 1H), 4.91 (td, J = 8.8, 2.9 Hz, 1H), 4.02 (dd, J = 11.9, 6.4 Hz, 1H), 3.90 (s, 3H), 3.86 (dd, J = 11.9, 4.2 Hz, 1H), 3.84 (d, J = 11.7 Hz, 1H), 3.70 (dd, J = 8.4, 6.1 Hz, 1H), 3.56 (dd, J = 11.6, 6.1 Hz, 1H), 3.35-3.13 (m, 5H), 2.06 (s, 3H), 1.80 (dtd, J = 8.3, 6.6, 1.6 Hz, 2H), 1.64 (ddd, J = 21.8, 14.9, 7.6 Hz, 2H), 0.96 (t, J = 7.4 Hz, 3H), 0.93-0.84 (m, 12H) | $^{13}$C NMR (CDCl$_3$) δ 171.06, 170.37, 163.38, 160.34, 145.93, 144.08, 142.38, 109.82, 89.58, 84.23, 83.32, 80.45, 77.70, 77.52, 76.65, 75.27, 56.32, 53.07, 29.24, 28.98, 25.29, 20.99, 19.70, 19.60, 19.58, 19.50, 9.59 |
| 24 | — | (Neat) 2956, 1755, 1680, 1502, 1203, 1085 | HRMS-ESI (m/z) [M]$^+$ calcd for $C_{27}H_{42}N_2O_{10}$, 554.2839; found, 554.2842 | $^1$H NMR (CDCl$_3$) δ 8.49 (d, J = 8.6 Hz, 1H), 8.25 (d, J = 5.4 Hz, 1H), 6.95 (d, J = 5.4 Hz, 1H), 5.73 (s, 2H), 4.98 (ddd, J = 9.5, 4.3, 3.1 Hz, 1H), 4.90 (dt, J = 8.6, 5.5 Hz, 1H), 4.24 (dd, J = 11.6, 6.0 Hz, 1H), 3.96 (dd, J = 11.5, | $^{13}$C NMR (CDCl$_3$) δ 170.49, 168.91, 162.84, 160.47, 145.77, 144.39, 142.38, 109.79, 89.67, 79.20, 79.17, 78.64, 77.33, 73.04, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 4.0 Hz, 1H), 3.91 (s, 3H), 3.80 (dd, J = 11.4, 1.6 Hz, 1H), 3.68 (dd, J = 6.6, 2.8 Hz, 1H), 3.57 (dd, J = 11.7, 5.2 Hz, 1H), 3.45-3.37 (m, 2H), 3.31 (ddd, J = 22.5, 8.8, 6.5 Hz, 2H), 3.20 (dd, J = 8.8, 6.9 Hz, 1H), 2.07 (s, 3H), 1.94-1.69 (m, 4H), 1.01 (t, J = 7.4 Hz, 3H), 0.93 (d, J = 3.1 Hz, 3H), 0.91 (d, J = 3.1 Hz, 3H), 0.90 (d, J = 4.8 Hz, 3H), 0.88 (d, J = 4.8 Hz, 3H) | 71.28, 56.35, 55.00, 29.12, 28.84, 23.05, 21.02, 19.60, 19.52, 10.75 |
| 25 | — | — | ESIMS m/z 551.3 ([M + H]$^+$) | $^1$H NMR (CDCl$_3$) δ 11.96 (s, 1H), 8.73 (d, J = 8.1 Hz, 1H), 8.00 (d, J = 5.2 Hz, 1H), 7.39-7.18 (m, 10H), 6.87 (d, J = 5.2 Hz, 1H), 5.16 (dq, J = 8.3, 6.4 Hz, 1H), 5.07 (ddd, J = 8.3, 6.9, 4.5 Hz, 1H), 4.85 (d, J = 11.1 Hz, 1H), 4.74 (d, J = 10.9 Hz, 1H), 4.61 (dd, J = 15.6, 11.0 Hz, 2H), 4.11 (dd, J = 12.0, 6.9 Hz, 1H), 3.94 (s, 3H), 3.89 (dd, J = 12.0, 4.5 Hz, 1H), 3.81 (t, J = 6.6 Hz, 1H), 3.45 (t, J = 8.2 Hz, 1H), 3.37 (dd, J = 8.0, 6.9 Hz, 1H), 1.47 (d, J = 6.5 Hz, 3H), 1.29 (d, J = 6.4 Hz, 3H) | $^{13}$C NMR (CDCl$_3$) δ 170.61, 168.98, 155.32, 148.73, 140.66, 138.13, 138.05, 130.26, 128.41, 128.37, 128.28, 127.77, 127.72, 127.67, 109.56, 86.10, 84.78, 81.83, 75.91, 75.18, 73.38, 71.93, 56.08, 52.28, 18.64, 17.43 |
| 26 | — | — | ESIMS m/z 483.7 ([M + H]$^+$) | $^1$H NMR (CDCl$_3$) δ 11.97 (s, 1H), 8.71 (d, J = 8.2 Hz, 1H), 8.00 (d, J = 5.4 Hz, 1H), 6.87 (d, J = 5.3 Hz, 1H), 5.11-4.96 (m, 2H), 4.09 (dd, J = 12.0, 7.0 Hz, 1H), 3.94 (s, 3H), 3.84 (dd, J = 12.0, 4.6 Hz, 1H), 3.78-3.50 (m, 3H), 3.31-3.19 (m, 3H), 3.15 (t, J = 8.4 Hz, 1H), 3.06 (t, J = 7.5 Hz, 1H), 1.83 (dtd, J = 13.1, 6.9, 3.8 Hz, 2H), 1.45 (d, J = 6.4 Hz, 3H), 1.21 (d, J = 6.4 Hz, 3H), 0.91 (dt, J = 14.6, 6.0 Hz, 12H) | $^{13}$C NMR (CDCl$_3$) δ 170.69, 168.94, 155.30, 148.71, 140.63, 130.29, 109.53, 86.09, 85.32, 81.91, 80.92, 80.25, 73.76, 71.72, 56.08, 52.25, 29.22, 29.13, 19.75, 19.64, 19.45, 19.37, 18.60, 17.21 |
| 27 | — | — | ESIMS m/z 411.6 ([M + H]$^+$) | $^1$H NMR (CDCl$_3$) δ 12.32-11.65 (m, 1H), 8.66 (d, J = 8.6 Hz, 1H), 8.01 (d, J = 5.2 Hz, 1H), 6.88 (d, J = 5.2 Hz, 1H), 4.88-4.72 (m, 2H), 4.09-3.98 (m, 2H), 3.94 (s, 3H), 3.90-3.80 (m, 1H), 3.80-3.72 (m, 2H), 1.64 (d, J = 6.5 Hz, 3H), 1.37 (d, J = 3.7 Hz, 6H), 1.34 (d, J = 6.4 Hz, 3H) | $^{13}$C NMR (CDCl$_3$) δ 170.56, 168.82, 155.35, 148.78, 140.65, 130.29, 109.54, 109.30, 81.92, 80.88, 77.96, 77.36, 77.04, 76.73, 65.93, 56.08, 54.07, 26.75, 26.57, 18.34, 16.73 |
| 28 | — | — | ESIMS m/z 623.8 ([M + H]$^+$) | $^1$H NMR (CDCl$_3$) δ 8.59 (d, J = 7.9 Hz, 1H), 8.28 (d, J = 5.4 Hz, 1H), 7.42-7.19 (m, 10H), 6.95 (d, J = 5.4 Hz, 1H), 5.74 (s, 2H), 5.19-5.03 (m, 2H), 4.85 (d, J = 11.1 Hz, 1H), 4.75 (d, J = 10.8 Hz, 1H), 4.61 (dd, J = 13.2, 10.9 Hz, | $^{13}$C NMR (CDCl$_3$) δ 171.29, 170.26, 163.31, 160.24, 145.82, 143.96, 142.16, 138.18, 138.11, 128.40, 128.36, 127.76, 127.70, 127.65, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 2H), 4.12 (dd, J = 12.0, 7.1 Hz, 1H), 3.91 (s, 3H), 3.83 (dt, J = 12.6, 5.8 Hz, 2H), 3.45 (t, J = 8.4 Hz, 1H), 3.35 (t, J = 7.6 Hz, 1H), 2.07 (s, 3H), 1.47 (d, J = 6.3 Hz, 3H), 1.28 (d, J = 6.4 Hz, 3H) | 127.50, 109.70, 89.50, 86.21, 84.92, 81.30, 75.97, 75.27, 73.22, 71.97, 56.20, 52.48, 20.88, 18.69, 17.30 |
| 29 | — | — | ESIMS m/z 506.0 ([M + Na]$^+$) | $^1$H NMR (CDCl$_3$) δ 8.53 (d, J = 8.3 Hz, 1H), 8.30 (d, J = 5.4 Hz, 1H), 6.96 (d, J = 5.4 Hz, 1H), 5.73 (s, 2H), 4.84 (dt, J = 8.3, 3.3 Hz, 1H), 4.74 (s, 1H), 4.08-3.97 (m, 2H), 3.91 (s, 3H), 3.86 (dd, J = 9.2, 6.8 Hz, 1H), 3.81-3.71 (m, 2H), 2.07 (s, 3H), 1.64 (d, J = 6.5 Hz, 3H), 1.37 (d, J = 4.1 Hz, 6H), 1.33 (d, J = 6.5 Hz, 3H) | $^{13}$C NMR (CDCl$_3$) δ 171.10, 170.28, 163.15, 160.26, 145.83, 144.06, 142.28, 109.66, 109.28, 89.52, 81.83, 80.94, 77.84, 66.10, 56.19, 54.46, 26.77, 26.59, 20.87, 18.38, 16.71 |
| 30 | — | (Neat) 3368, 2933, 1748, 1648, 1527, 1242, 1066 | HRMS-ESI (m/z) [M]$^+$ calcd for C$_{29}$H$_{32}$N$_2$O$_8$, 536.2159; found, 536.2162 | $^1$H NMR (CDCl$_3$) δ 11.98 (s, 1H), 8.86 (d, J = 8.0 Hz, 1H), 8.01 (d, J = 5.2 Hz, 1H), 7.41-7.27 (m, 10H), 6.86 (d, J = 5.2 Hz, 1H), 5.36 (qd, J = 6.7, 3.1 Hz, 1H), 5.06 (ddd, J = 8.0, 6.1, 1.9 Hz, 1H), 4.71 (d, J = 11.4 Hz, 1H), 4.68 (d, J = 11.8 Hz, 1H), 4.60 (d, J = 11.3 Hz, 1H), 4.58 (d, J = 11.8 Hz, 1H), 4.16 (dd, J = 12.2, 3.6 Hz, 1H), 4.12 (dd, J = 9.4, 2.2 Hz, 2H), 3.98 (dd, J = 11.7, 6.1 Hz, 1H), 3.94 (s, 3H), 3.71 (dd, J = 11.9, 1.7 Hz, 1H), 3.57-3.50 (m, 1H), 1.38 (d, J = 6.8 Hz, 3H) | $^{13}$C NMR (CDCl$_3$) δ 169.86, 169.07, 155.41, 148.82, 140.81, 138.27, 138.10, 130.51, 128.58, 128.54, 128.14, 128.05, 128.00, 127.85, 109.64, 78.70, 75.15, 74.37, 72.35, 71.55, 56.21, 53.37, 15.28 |
| 31 | — | (Neat) 3380, 2931, 1752, 1677, 1504, 1203, 1068 | HRMS-ESI (m/z) [M]$^+$ calcd for C$_{32}$H$_{36}$N$_2$O$_{10}$, 608.2370; found, 608.2375 | $^1$H NMR (CDCl$_3$) δ 8.73 (d, J = 7.7 Hz, 1H), 8.29 (d, J = 5.3 Hz, 1H), 7.48-7.16 (m, 10H), 6.94 (d, J = 5.4 Hz, 1H), 5.77-5.69 (m, 2H), 5.41-5.30 (m, 1H), 5.09 (ddd, J = 7.8, 6.2, 1.9 Hz, 1H), 4.71 (d, J = 15.8 Hz, 1H), 4.68 (d, J = 16.1 Hz, 1H), 4.61 (d, J = 11.4 Hz, 1H), 4.58 (d, J = 11.8 Hz, 1H), 4.19-4.07 (m, 3H), 3.97 (dd, J = 11.7, 6.1 Hz, 1H), 3.90 (s, 3H), 3.70 (dd, J = 11.8, 1.7 Hz, 1H), 3.58-3.49 (m, 1H), 2.06 (s, 3H), 1.37 (d, J = 6.8 Hz, 3H) | $^{13}$C NMR (CDCl$_3$) δ 170.43, 170.39, 163.37, 160.33, 145.96, 144.03, 142.39, 138.33, 138.20, 128.53, 128.49, 128.07, 127.97, 127.78, 109.77, 89.61, 78.63, 75.39, 74.32, 72.36, 71.33, 56.31, 53.64, 21.01, 15.15 |
| 32 | 105-107 | (Neat) 3347, 2957, 1732, 1642, 1540, 1206, 1081 | HRMS-ESI (m/z) [M]$^+$ calcd for C$_{26}$H$_{34}$N$_2$O$_8$, 502.2315; found, 502.2324 | $^1$H NMR (CDCl$_3$) δ 12.00-11.55 (m, 1H), 8.67 (d, J = 8.1 Hz, 1H), 8.00 (d, J = 5.2 Hz, 1H), 7.39-7.27 (m, 5H), 6.87 (d, J = 5.2 Hz, 1H), 5.04 (ddd, J = 8.1, 6.8, 5.0 Hz, 1H), 4.99 (ddd, J = 15.8, 7.8, 4.6 Hz, 1H), 4.64 (s, 2H), 4.05 (dd, J = 11.9, 6.8 Hz, 1H), 3.94 (s, 3H), 3.94-3.84 (m, 2H), 3.83 (dd, J = 11.9, 5.0 Hz, 1H), 3.65 (dd, J = 11.2, | $^{13}$C NMR (CDCl$_3$) δ 170.40, 169.09, 155.47, 148.87, 140.81, 138.25, 130.36, 128.52, 127.89, 127.84, 109.71, 85.27, 83.44, 75.66, 74.20, 74.04, 73.32, 73.19, 56.23, 52.31, 32.61, 19.50, 18.72, 14.12 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 7.1 Hz, 1H), 3.52 (dt, J = 8.8, 6.8 Hz, 1H), 3.42 (ddd, J = 8.4, 7.1, 1.3 Hz, 1H), 3.27 (t, J = 9.1 Hz, 1H), 1.59-1.49 (m, 2H), 1.47 (d, J = 6.3 Hz, 3H), 1.41-1.27 (m, 2H), 0.89 (t, J = 7.4 Hz, 3H) | |
| 33 | 117-119 | (Neat) 3363, 2933, 1749, 1648, 1528, 1243, 1091 | HRMS-ESI (m/z) [M]$^+$ calcd for C$_{26}$H$_{34}$N$_2$O$_8$, 502.2315; found, 502.2324 | $^1$H NMR (CDCl$_3$) δ 11.93 (s, 1H), 8.67 (d, J = 8.1 Hz, 1H), 8.00 (d, J = 5.2 Hz, 1H), 7.42-7.26 (m, 5H), 6.87 (d, J = 5.2 Hz, 1H), 5.07-4.98 (m, 2H), 4.95 (d, J = 10.9 Hz, 1H), 4.61 (d, J = 10.9 Hz, 1H), 4.06 (dd, J = 11.9, 6.8 Hz, 1H), 3.94 (s, 3H), 3.90-3.79 (m, 2H), 3.69-3.49 (m, 3H), 3.41 (t, J = 9.0 Hz, 1H), 3.32 (ddd, J = 8.4, 6.9, 1.2 Hz, 1H), 1.59-1.50 (m, 2H), 1.44 (d, J = 6.3 Hz, 3H), 1.41-1.29 (m, 2H), 0.89 (t, J = 7.4 Hz, 3H) | $^{13}$C NMR (CDCl$_3$) δ 170.38, 169.10, 155.47, 148.87, 140.80, 138.40, 130.35, 128.53, 128.09, 127.89, 109.71, 84.72, 83.97, 75.89, 75.51, 74.18, 73.12, 70.86, 56.23, 52.32, 32.34, 19.50, 18.86, 14.05 |
| 34 | — | (Neat) 3373, 2933, 1753, 1677, 1504, 1201, 1093 | HRMS-ESI (m/z) [M]$^+$ calcd for C$_{29}$H$_{38}$N$_2$O$_{10}$, 574.2526; found, 574.2538 | $^1$H NMR (CDCl$_3$) δ 8.53 (d, J = 7.9 Hz, 1H), 8.27 (d, J = 5.4 Hz, 1H), 7.37-7.22 (m, 5H), 6.94 (d, J = 5.4 Hz, 1H), 5.88-5.54 (m, 2H), 5.06 (td, J = 6.9, 5.2 Hz, 1H), 4.95 (dq, J = 9.5, 6.3 Hz, 1H), 4.63 (s, 2H), 4.04 (dd, J = 11.9, 6.9 Hz, 1H), 3.94-3.83 (m, 2H), 3.90 (s, 3H), 3.79 (dd, J = 11.8, 5.1 Hz, 1H), 3.64 (dd, J = 11.1, 7.2 Hz, 1H), 3.52 (dt, J = 8.7, 6.9 Hz, 1H), 3.40 (ddd, J = 7.9, 7.3, 1.1 Hz, 1H), 3.26 (t, J = 9.1 Hz, 1H), 2.06 (s, 3H), 1.63-1.45 (m, 2H), 1.45 (d, J = 6.3 Hz, 3H), 1.41-1.26 (m, 2H), 0.88 (t, J = 7.4 Hz, 3H) | $^{13}$C NMR (CDCl$_3$) δ 171.01, 170.37, 163.38, 160.35, 145.93, 144.08, 142.26, 138.29, 129.14, 128.48, 127.86, 127.78, 109.84, 89.55, 85.26, 83.50, 75.33, 74.35, 73.99, 73.13, 73.08, 56.31, 52.56, 32.58, 20.97, 19.46, 18.69, 14.08 |
| 35 | — | (Neat) 3373, 2933, 1752, 1676, 1503, 1200, 1091 | HRMS-ESI (m/z) [M]$^+$ calcd for C$_{29}$H$_{38}$N$_2$O$_{10}$, 574.2526; found, 574.2529 | $^1$H NMR (CDCl$_3$) δ 8.53 (d, J = 7.9 Hz, 1H), 8.27 (d, J = 5.4 Hz, 1H), 7.40-7.25 (m, 5H), 6.94 (d, J = 5.4 Hz, 1H), 5.92-5.45 (m, 2H), 5.06 (ddd, J = 7.7, 6.9, 5.2 Hz, 1H), 4.99 (ddd, J = 9.8, 6.4, 3.3 Hz, 1H), 4.94 (d, J = 10.8 Hz, 1H), 4.60 (d, J = 10.9 Hz, 1H), 4.05 (dd, J = 11.9, 6.9 Hz, 1H), 3.90 (s, 3H), 3.84 (dd, J = 11.1, 1.0 Hz, 1H), 3.79 (dd, J = 11.8, 5.1 Hz, 1H), 3.69-3.48 (m, 3H), 3.40 (t, J = 9.0 Hz, 1H), 3.30 (ddd, J = 8.4, 7.1, 1.2 Hz, 1H), 2.06 (s, 3H), 1.60-1.49 (m, 2H), 1.42 (d, J = 6.3 Hz, 3H), 1.40-1.29 (m, 2H); 0.88 (t, J = 7.4 Hz, 3H) | $^{13}$C NMR (CDCl$_3$) δ 170.97, 170.35, 163.37, 160.33, 145.91, 144.07, 142.23, 138.43, 128.48, 128.04, 127.82, 109.84, 89.53, 84.73, 83.99, 75.85, 75.17, 74.32, 72.88, 70.79, 56.31, 52.56, 32.31, 20.97, 19.46, 18.83, 14.01 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 36 | 118-120 | (Neat) 3366, 2933, 1742, 1650, 1529, 1244, 1103 | HRMS-ESI (m/z) [M]$^+$ calcd for C$_{20}$H$_{30}$N$_2$O$_8$, 426.2002; found, 426.2039 | $^1$H NMR (CDCl$_3$) δ 11.91 (s, 1H), 8.65 (d, J = 8.1 Hz, 1H), 7.97 (d, J = 5.2 Hz, 1H), 6.85 (d, J = 5.2 Hz, 1H), 5.02 (ddd, J = 8.1, 6.8, 5.1 Hz, 1H), 4.92 (dq, J = 9.4, 6.3 Hz, 1H), 4.03 (dd, J = 11.9, 6.8 Hz, 1H), 3.92 (s, 3H), 3.84-3.76 (m, 2H), 3.62-3.55 (m, 2H), 3.55 (s, 3H), 3.50 (dt, J = 9.1, 6.6 Hz, 1H), 3.19 (ddd, J = 8.4, 7.1, 1.3 Hz, 1H), 3.09 (t, J = 9.0 Hz, 1H), 1.62-1.48 (m, 2H), 1.44 (d, J = 6.3 Hz, 3H), 1.42-1.30 (m, 2H), 0.90 (t, J = 7.4 Hz, 3H) | $^{13}$C NMR (CDCl$_3$) δ 170.38, 169.05, 155.42, 148.81, 140.77, 130.29, 109.68, 86.84, 83.62, 75.34, 74.02, 73.03, 70.82, 61.56, 56.19, 52.24, 32.25, 19.43, 18.64, 13.99 |
| 37 | — | (Neat) 3371, 2933, 1754, 1671, 1505, 1201, 1103 | HRMS-ESI (m/z) [M]$^+$ calcd for C$_{23}$H$_{34}$N$_2$O$_{10}$, 498.2213; found, 498.2218 | $^1$H NMR (CDCl$_3$) δ 8.52 (d, J = 7.8 Hz, 1H), 8.28 (d, J = 5.4 Hz, 1H), 6.95 (d, J = 5.4 Hz, 1H), 5.85-5.57 (m, 2H), 5.06 (td, J = 7.0, 5.2 Hz, 1H), 4.90 (dq, J = 9.4, 6.3 Hz, 1H), 4.04 (dd, J = 11.8, 6.9 Hz, 1H), 3.90 (s, 3H), 3.84-3.73 (m, 2H), 3.64-3.56 (m, 3H), 3.56 (s, 3H), 3.50 (dt, J = 9.2, 6.6 Hz, 1H), 3.19 (ddd, J = 8.5, 7.3, 1.2 Hz, 1H), 3.09 (t, J = 9.1 Hz, 1H), 2.06 (s, 2H), 1.60-1.49 (m, 2H), 1.44 (d, J = 6.3 Hz, 3H), 1.42-1.31 (m, 2H), 0.91 (t, J = 7.3 Hz, 3H) | $^{13}$C NMR (CDCl$_3$) δ 171.04, 170.40, 163.39, 160.36, 145.95, 144.11, 142.25, 109.86, 89.58, 86.91, 83.71, 75.10, 74.26, 72.87, 70.85, 61.60, 56.34, 52.56, 32.30, 21.01, 19.47, 18.68, 14.03 |
| 38 | — | — | ESIMS m/z 537.8. ([M − H]$^-$) | $^1$H NMR (CDCl$_3$) δ 11.98 (s, 1H), 8.86 (d, J = 8.0 Hz, 1H), 8.01 (d, J = 5.2 Hz, 1H), 7.41-7.27 (m, 10H), 6.86 (d, J = 5.2 Hz, 1H), 5.36 (qd, J = 6.7, 3.1 Hz, 1H), 5.06 (ddd, J = 8.0, 6.1, 1.9 Hz, 1H), 4.71 (d, J = 11.4 Hz, 1H), 4.68 (d, J = 11.8 Hz, 1H), 4.60 (d, J = 11.3 Hz, 1H), 4.58 (d, J = 11.8 Hz, 1H), 4.16 (dd, J = 12.2, 3.6 Hz, 1H), 4.12 (dd, J = 9.4, 2.2 Hz, 2H), 3.98 (dd, J = 11.7, 6.1 Hz, 1H), 3.94 (s, 3H), 3.71 (dd, J = 11.9, 1.7 Hz, 1H), 3.57-3.50 (m, 1H), 1.38 (d, J = 6.8 Hz, 3H) | $^{13}$C NMR (CDCl$_3$) δ 169.86, 169.07, 155.41, 148.82, 140.81, 138.27, 138.10, 130.51, 128.58, 128.54, 128.14, 128.05, 128.00, 127.85, 109.64, 78.70, 75.15, 74.37, 72.35, 71.55, 56.21, 53.37, 15.28 |
| 39 | — | — | HRMS-ESI (m/z) [M]$^+$ calcd for C$_{29}$H$_{32}$N$_2$O$_8$, 536.2159; found, 536.2165 | $^1$H NMR (CDCl$_3$) δ 11.96 (s, 1H), 8.51 (d, J = 8.6 Hz, 1H), 7.93 (d, J = 5.2 Hz, 1H), 7.38-7.27 (m, 10H), 6.87 (d, J = 5.2 Hz, 1H), 5.30 (qd, J = 6.7, 3.2 Hz, 1H), 4.92 (dt, J = 8.8, 6.1 Hz, 1H), 4.71 (d, J = 11.6 Hz, 1H), 4.69 (d, J = 11.8 Hz, 1H), 4.61 (d, J = 11.6 Hz, 1H), 4.58 (d, J = 11.9 Hz, 1H), 4.30 (dd, J = 11.5, | $^{13}$C NMR (CDCl$_3$) δ 168.67, 168.06, 155.61, 149.01, 140.67, 138.24, 138.22, 130.34, 128.54, 127.99, 127.93, 127.87, 109.71, 79.48, 77.33, 74.36, 72.82, 72.29, 71.97, 71.81, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 6.3 Hz, 1H), 4.05 (dd, J = 11.6, 3.9 Hz, 1H), 3.94 (s, 3H), 3.91-3.82 (m, 2H), 3.64-3.54 (m, 2H), 1.41 (d, J = 6.8 Hz, 3H) | 56.26, 54.38, 15.68 |
| 40 | — | — | ESIMS m/z 609.8 ([M + H]$^+$) | $^1$H NMR (CDCl$_3$) δ 8.73 (d, J = 7.7 Hz, 1H), 8.29 (d, J = 5.3 Hz, 1H), 7.48-7.16 (m, 10H), 6.94 (d, J = 5.4 Hz, 1H), 5.77-5.69 (m, 2H), 5.41-5.30 (m, 1H), 5.09 (ddd, J = 7.8, 6.2, 1.9 Hz, 1H), 4.71 (d, J = 15.8 Hz, 1H), 4.68 (d, J = 16.1 Hz, 1H), 4.61 (d, J = 11.4 Hz, 1H), 4.58 (d, J = 11.8 Hz, 1H), 4.19-4.07 (m, 3H), 3.97 (dd, J = 11.7, 6.1 Hz, 1H), 3.90 (s, 3H), 3.70 (dd, J = 11.8, 1.7 Hz, 1H), 3.58-3.49 (m, 1H), 2.06 (s, 3H), 1.37 (d, J = 6.8 Hz, 3H) | $^{13}$C NMR (CDCl$_3$) δ 170.43, 170.39, 163.37, 160.33, 145.96, 144.03, 142.39, 138.33, 138.20, 128.53, 128.49, 128.07, 127.97, 127.78, 109.77, 89.61, 78.63, 75.39, 74.32, 72.36, 71.33, 56.31, 53.64, 21.01, 15.15 |
| 41 | — | — | ESIMS m/z 609.8 ([M + H]$^+$) | $^1$H NMR (CDCl$_3$) δ 8.44 (d, J = 8.5 Hz, 1H), 8.20 (d, J = 5.4 Hz, 1H), 7.37-7.27 (m, 10H), 6.94 (d, J = 5.4 Hz, 1H), 5.72 (s, 2H), 5.28 (qd, J = 6.7, 3.3 Hz, 1H), 4.93 (dt, J = 8.5, 5.9 Hz, 1H), 4.71 (d, J = 11.5 Hz, 1H), 4.69 (d, J = 11.8 Hz, 1H), 4.60 (d, J = 11.5 Hz, 1H), 4.58 (d, J = 11.9 Hz, 1H), 4.29 (dd, J = 11.6, 6.3 Hz, 1H), 4.02 (dd, J = 11.6, 3.8 Hz, 1H), 3.91 (s, 3H), 3.90-3.82 (m, 2H), 3.62-3.59 (m, 1H), 3.56 (dd, J = 11.7, 5.7 Hz, 1H), 2.06 (s, 3H), 1.41 (d, J = 6.8 Hz, 3H) | $^{13}$C NMR (CDCl$_3$) δ 170.49, 168.56, 162.86, 160.47, 145.80, 144.42, 142.18, 138.34, 128.52, 128.00, 127.89, 127.83, 109.84, 89.66, 79.49, 74.35, 73.05, 72.28, 71.80, 71.64, 56.36, 54.84, 21.02, 15.65 |
| 42 | — | (Neat) 3370, 2933, 1750, 1648, 1529, 1244, 1088 | HRMS-ESI (m/z) [M]$^+$ calcd for C$_{19}$H$_{28}$N$_2$O$_8$, 412.1846; found, 412.1849 | $^1$H NMR (CDCl$_3$) δ 11.96-11.93 (m, 1H), 8.79 (d, J = 7.8 Hz, 1H), 8.01 (d, J = 5.2 Hz, 1H), 6.87 (d, J = 5.2 Hz, 1H), 5.14 (dq, J = 9.3, 6.3 Hz, 1H), 5.01 (ddd, J = 7.9, 5.7, 2.2 Hz, 1H), 4.18-4.06 (m, 2H), 3.98-3.90 (m, 1H), 3.94 (s, 3H), 3.66 (dt, J = 9.3, 6.6 Hz, 1H), 3.48-3.38 (m, 3H), 3.20 (s, 1H), 3.15-3.07 (m, 1H), 1.60-1.51 (m, 2H), 1.49 (d, J = 6.3 Hz, 3H), 1.41-1.29 (m, 2H), 0.91 (t, J = 7.4 Hz, 3H) | $^{13}$C NMR (CDCl$_3$) δ 169.62, 169.15, 155.48, 148.89, 140.83, 130.45, 109.71, 82.72, 77.79, 77.36, 76.62, 73.73, 70.15, 56.24, 53.63, 31.90, 19.44, 18.90, 13.96 |
| 43 | 101-103 | (Neat) 3335, 2931, 1745, 1640, 1534, 1281, 1029 | HRMS-ESI (m/z) [M]$^+$ calcd for C$_{22}$H$_{32}$N$_2$O$_8$, 452.2159; found, 452.2166 | $^1$H NMR (CDCl$_3$) δ 11.92 (s, 1H), 8.66 (d, J = 8.1 Hz, 1H), 7.98 (d, J = 5.2 Hz, 1H), 6.85 (d, J = 5.2 Hz, 1H), 5.91 (ddt, J = 16.2, 10.4, 5.8 Hz, 1H), 5.25 (ddd, J = 17.2, 3.2, 1.6 Hz, 1H), 5.15 (ddd, J = 10.4, 2.7, 1.1 Hz, 1H), 5.02 (ddd, J = 8.1, 6.8, 5.0 Hz, 1H), | $^{13}$C NMR (CDCl$_3$) δ 170.37, 169.05, 155.42, 148.81, 140.77, 134.92, 130.29, 117.01, 109.68, 84.56, 83.77, 75.44, 74.78, 74.08, 73.10, 70.87, 56.18, 52.25, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 4.99-4.92 (m, 1H), 4.38 (ddt, J = 12.2, 5.5, 1.3 Hz, 1H), 4.13-4.05 (m, 1H), 4.03 (dd, J = 11.9, 6.8 Hz, 1H), 3.92 (s, 3H), 3.86-3.76 (m, 2H), 3.64-3.54 (m, 2H), 3.49 (dt, J = 9.2, 6.6 Hz, 1H), 3.31-3.19 (m, 2H), 1.59-1.48 (m, 2H), 1.44 (d, J = 6.4 Hz, 3H), 1.40-1.28 (m, 2H), 0.89 (t, J = 7.4 Hz, 3H) | 32.26, 19.42, 18.77, 14.02 |
| 44 | 110-112 | (Neat) 3366, 2933, 1750, 1649, 1529, 1245, 1095 | HRMS-ESI (m/z) [M]$^+$ calcd for C$_{22}$H$_{34}$N$_2$O$_8$, 454.2315; found, 454.2326 | $^1$H NMR (CDCl$_3$) δ 11.93 (s, 1H), 8.66 (d, J = 8.1 Hz, 1H), 7.99 (d, J = 5.2 Hz, 1H), 6.86 (d, J = 5.2 Hz, 1H), 5.02 (ddd, J = 8.1, 6.9, 5.2 Hz, 1H), 4.95 (dq, J = 12.6, 6.3 Hz, 1H), 4.04 (dd, J = 11.9, 6.8 Hz, 1H), 3.93 (s, 3H), 3.86-3.76 (m, 3H), 3.64-3.54 (m, 2H), 3.49 (tt, J = 8.7, 6.7 Hz, 2H), 3.24-3.16 (m, 2H), 1.65-1.49 (m, 4H), 1.45 (d, J = 6.3 Hz, 3H), 1.41-1.30 (m, 2H), 0.92 (t, J = 7.4 Hz, 3H), 0.91 (t, J = 7.3 Hz, 3H) | $^{13}$C NMR (CDCl$_3$) δ 170.46, 169.08, 155.46, 148.85, 140.79, 130.34, 109.69, 85.05, 83.70, 75.72, 75.39, 74.01, 73.32, 70.90, 56.22, 52.23, 32.31, 23.64, 19.45, 18.71, 14.04, 10.79 |
| 45 | — | (Neat) 3376, 2933, 1754, 1678, 1506, 1202, 1099 | HRMS-ESI (m/z) [M]$^+$ calcd for C$_{25}$H$_{38}$N$_2$O$_{10}$, 526.2526; found, 526.2536 | $^1$H NMR (CDCl$_3$) δ 8.52 (d, J = 7.9 Hz, 1H), 8.28 (d, J = 5.4 Hz, 1H), 6.94 (d, J = 5.4 Hz, 1H), 5.76-5.68 (m, 2H), 5.09-5.02 (m, 1H), 4.92 (dq, J = 12.6, 6.3 Hz, 1H), 4.04 (dd, J = 11.8, 6.9 Hz, 1H), 3.91 (s, 3H), 3.87-3.72 (m, 3H), 3.64-3.54 (m, 2H), 3.49 (dq, J = 8.7, 6.8 Hz, 2H), 3.23-3.15 (m, 2H), 2.06 (s, 3H), 1.60-1.49 (m, 4H), 1.44 (d, J = 6.3 Hz, 3H), 1.41-1.30 (m, 2H), 0.92 (t, J = 7.4 Hz, 3H), 0.91 (t, J = 7.3 Hz, 3H) | $^{13}$C NMR (CDCl$_3$) δ 171.10, 170.41, 163.39, 160.37, 145.94, 144.11, 142.28, 109.84, 89.59, 85.09, 83.76, 75.72, 75.11, 74.21, 73.13, 70.89, 56.34, 52.52, 32.33, 23.66, 21.02, 19.47, 18.73, 14.06, 10.80 |
| 46 | — | (Neat) 3367, 2935, 1739, 1649, 1528, 1242, 1093 | HRMS-ESI (m/z) [M]$^+$ calcd for C$_{23}$H$_{34}$N$_2$O$_9$, 482.2264; found, 482.2266 | $^1$H NMR (CDCl$_3$) δ 11.90 (s, 1H), 8.68 (d, J = 8.1 Hz, 1H), 7.98 (d, J = 5.2 Hz, 1H), 6.86 (d, J = 5.2 Hz, 1H), 5.14 (dq, J = 9.8, 6.4 Hz, 1H), 5.07 (ddd, J = 8.1, 6.5, 4.2 Hz, 1H), 4.98 (t, J = 9.4 Hz, 1H), 4.04 (dd, J = 11.9, 6.5 Hz, 1H), 3.97 (dd, J = 11.3, 1.1 Hz, 1H), 3.95-3.89 (m, 1H), 3.92 (s, 3H), 3.61 (dd, J = 11.4, 7.6 Hz, 1H), 3.52 (dt, J = 9.1, 6.6 Hz, 1H), 3.33 (dt, J = 9.1, 6.6 Hz, 1H), 3.23 (ddd, J = 8.9, 7.6, 1.3 Hz, 1H), 2.56 (hept, J = 7.0 Hz, 1H), 1.49-1.38 (m, 2H), 1.32 (d, J = 6.3 Hz, 3H), 1.32-1.24 (m, 2H), 1.19 (d, J = 7.0 Hz, 3H), 1.17 (d, J = 7.0 Hz, 3H), 0.86 (t, J = 7.3 Hz, 3H) | $^{13}$C NMR (CDCl$_3$) δ 175.79, 170.21, 169.06, 155.46, 148.86, 140.77, 130.28, 109.71, 80.84, 75.91, 75.76, 74.72, 71.79, 70.55, 56.20, 52.63, 34.20, 32.02, 19.33, 19.18, 18.87, 18.31, 13.96 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 47 | — | (Neat) 3370, 2935, 1739, 1676, 1505, 1199, 1093 | HRMS-ESI (m/z) [M]$^+$ calcd for C$_{26}$H$_{38}$N$_2$O$_{11}$, 554.2476; found, 554.2484 | $^1$H NMR (CDCl$_3$) δ 8.56 (d, J = 7.8 Hz, 1H), 8.28 (d, J = 5.4 Hz, 1H), 6.95 (d, J = 5.4 Hz, 1H), 5.78-5.68 (m, 2H), 5.17-5.05 (m, 2H), 4.98 (t, J = 9.4 Hz, 1H), 4.04 (dd, J = 11.9, 6.6 Hz, 1H), 3.96 (dd, J = 11.2, 0.8 Hz, 1H), 3.93-3.87 (m, 1H), 3.91 (s, 3H), 3.62 (dd, J = 11.3, 7.7 Hz, 1H), 3.53 (dt, J = 9.1, 6.6 Hz, 1H), 3.33 (dt, J = 9.1, 6.6 Hz, 1H), 3.27-3.18 (m, 1H), 2.56 (hept, J = 7.0 Hz, 1H), 2.06 (s, 3H), 1.50-1.40 (m, 2H), 1.32 (d, J = 6.3 Hz, 3H), 1.32-1.22 (m, 2H), 1.19 (d, J = 7.0 Hz, 3H), 1.18 (d, J = 7.0 Hz, 3H), 0.87 (t, J = 7.3 Hz, 3H) | $^{13}$C NMR (CDCl$_3$) δ 175.83, 170.85, 170.39, 163.39, 160.38, 145.92, 144.17, 142.19, 109.87, 89.57, 75.82, 75.64, 74.96, 71.60, 70.53, 56.34, 52.93, 34.23, 32.05, 21.00, 19.35, 19.22, 18.90, 18.35, 13.99 |
| 48 | 104-106 | (Neat) 3367, 2956, 1749, 1649, 1528, 1281, 1092 | HRMS-ESI (m/z) [M]$^+$ calcd for C$_{23}$H$_{36}$N$_2$O$_8$, 468.2472; found, 468.2497 | $^1$H NMR (CDCl$_3$) δ 11.92 (s, 1H), 8.65 (d, J = 8.1 Hz, 1H), 7.97 (d, J = 5.2 Hz, 1H), 6.85 (d, J = 5.2 Hz, 1H), 5.01 (ddd, J = 8.0, 6.9, 5.2 Hz, 1H), 4.94 (dq, J = 12.6, 6.2 Hz, 1H), 4.03 (dd, J = 11.9, 6.8 Hz, 1H), 3.91 (s, 3H), 3.82-3.75 (m, 2H), 3.66 (dd, J = 8.4, 6.2 Hz, 1H), 3.64-3.44 (m, 3H), 3.24 (dd, J = 8.4, 6.9 Hz, 1H), 3.21-3.13 (m, 2H), 1.88-1.74 (m, 1H), 1.57-1.47 (m, 2H), 1.43 (d, J = 6.3 Hz, 3H), 1.40-1.29 (m, 2H), 0.94-0.83 (m, 9H) | $^{13}$C NMR (CDCl$_3$) δ 170.44, 169.04, 155.41, 148.80, 140.75, 130.29, 109.66, 84.93, 83.70, 80.71, 75.29, 73.92, 73.29, 70.79, 56.17, 52.18, 32.28, 29.21, 19.64, 19.48, 19.44, 18.71, 14.02 |
| 49 | — | (Neat) 3359, 2929, 1745, 1649, 1525, 1261, 1065 | HRMS-ESI (m/z) [M]$^+$ calcd for C$_{29}$H$_{32}$N$_2$O$_8$, 536.2159; found, 536.2165 | $^1$H NMR (CDCl$_3$) δ 11.96 (s, 1H), 8.51 (d, J = 8.6 Hz, 1H), 7.93 (d, J = 5.2 Hz, 1H), 7.38-7.27 (m, 10H), 6.87 (d, J = 5.2 Hz, 1H), 5.30 (qd, J = 6.7, 3.2 Hz, 1H), 4.92 (dt, J = 8.8, 6.1 Hz, 1H), 4.71 (d, J = 11.6 Hz, 1H), 4.69 (d, J = 11.8 Hz, 1H), 4.61 (d, J = 11.6 Hz, 1H), 4.58 (d, J = 11.9 Hz, 1H), 4.30 (dd, J = 11.5, 6.3 Hz, 1H), 4.05 (dd, J = 11.6, 3.9 Hz, 1H), 3.94 (s, 3H), 3.91-3.82 (m, 2H), 3.64-3.54 (m, 2H), 1.41 (d, J = 6.8 Hz, 3H) | $^{13}$C NMR (CDCl$_3$) δ 168.67, 168.06, 155.61, 149.01, 140.67, 138.24, 138.22, 130.34, 128.54, 127.99, 127.93, 127.87, 109.71, 79.48, 77.33, 74.36, 72.82, 72.29, 71.97, 71.81, 56.26, 54.38, 15.68 |
| 50 | — | (Neat) 3372, 2956, 1751, 1675, 1505, 1200, 1093 cm$^{-1}$ | HRMS-ESI (m/z) [M]$^+$ calcd for C$_{26}$H$_{40}$N$_2$O$_{10}$, 540.2683; found, 540.2690 | $^1$H NMR (CDCl$_3$) δ 8.52 (d, J = 7.8 Hz, 1H), 8.27 (d, J = 5.3 Hz, 1H), 6.94 (d, J = 5.4 Hz, 1H), 5.76-5.68 (m, 2H), 5.05 (td, J = 7.0, 5.4 Hz, 1H), 4.92 (dq, J = 12.7, 6.3 Hz, 1H), 4.04 (dd, J = 11.8, 6.9 Hz, 1H), 3.90 (s, 3H), 3.81-3.73 (m, 2H), 3.68 (dd, J = 8.4, 6.2 Hz, 1H), 3.63-3.44 (m, 3H), 3.25 (dd, J = 8.4, 6.9 Hz, 1H), | $^{13}$C NMR (CDCl$_3$) δ 171.09, 170.39, 163.38, 160.36, 145.93, 144.10, 142.27, 109.84, 89.58, 85.00, 83.80, 80.75, 75.09, 74.19, 73.14, 70.82, 56.33, 52.52, 32.33, 29.26, 21.01, 19.69, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 3.23-3.12 (m, 2H), 2.06 (s, 3H), 1.88-1.75 (m, 1H), 1.57-1.47 (m, 2H), 1.43 (d, J = 6.3 Hz, 3H), 1.40-1.29 (m, 2H), 0.96-0.85 (m, 9H) | 19.53, 19.48, 18.77, 14.06 |
| 51 | — | (Neat) 3369, 2925, 1749, 1677, 1499, 1202, 1064 | HRMS-ESI (m/z) [M]$^+$ calcd for C$_{32}$H$_{36}$N$_2$O$_{10}$, 608.2370; found, 608.2377 | $^1$H NMR (CDCl$_3$) δ 8.44 (d, J = 8.5 Hz, 1H), 8.20 (d, J = 5.4 Hz, 1H), 7.37-7.27 (m, 10H), 6.94 (d, J = 5.4 Hz, 1H), 5.72 (s, 2H), 5.28 (qd, J = 6.7, 3.3 Hz, 1H), 4.93 (dt, J = 8.5, 5.9 Hz, 1H), 4.71 (d, J = 11.5 Hz, 1H), 4.69 (d, J = 11.8 Hz, 1H), 4.60 (d, J = 11.5 Hz, 1H), 4.58 (d, J = 11.9 Hz, 1H), 4.29 (dd, J = 11.6, 6.3 Hz, 1H), 4.02 (dd, J = 11.6, 3.8 Hz, 1H), 3.91 (s, 3H), 3.90-3.82 (m, 2H), 3.62-3.59 (m, 1H), 3.56 (dd, J = 11.7, 5.7 Hz, 1H), 2.06 (s, 3H), 1.41 (d, J = 6.8 Hz, 3H) | $^{13}$C NMR (CDCl$_3$) δ 170.49, 168.56, 162.86, 160.47, 145.80, 144.42, 142.18, 138.34, 128.52, 128.00, 127.89, 127.83, 109.84, 89.66, 79.49, 74.35, 73.05, 72.28, 71.80, 71.64, 56.36, 54.84, 21.02, 15.65 |
| 52 | 75-77 | (Neat) 3367, 2933, 1750, 1649, 1529, 1282, 1094 | HRMS-ESI (m/z) [M]$^+$ calcd for C$_{22}$H$_{34}$N$_2$O$_9$, 470.2264; found, 470.2264 | $^1$H NMR (CDCl$_3$) δ 11.92-11.89 (m, 1H), 8.65 (d, J = 8.1 Hz, 1H), 7.97 (d, J = 5.2 Hz, 1H), 6.85 (d, J = 5.2 Hz, 1H), 5.04-4.94 (m, 2H), 4.06-3.96 (m, 2H), 3.92 (s, 3H), 3.84-3.77 (m, 2H), 3.75-3.68 (m, 1H), 3.61-3.44 (m, 5H), 3.36 (s, 3H), 3.27-3.19 (m, 2H), 1.58-1.48 (m, 2H), 1.46 (d, J = 6.3 Hz, 3H), 1.40-1.27 (m, 2H), 0.89 (t, J = 7.4 Hz, 3H) | $^{13}$C NMR (CDCl$_3$) δ 170.31, 169.04, 155.40, 148.79, 140.75, 130.28, 109.67, 85.60, 83.64, 75.38, 74.07, 73.09, 73.06, 72.34, 70.75, 59.04, 56.17, 52.23, 32.25, 19.41, 18.60, 14.01 |
| 53 | 127-129 | (Neat) 3356, 2958, 1736, 1643, 1536, 1262, 1091 | HRMS-ESI (m/z) [M]$^+$ calcd for C$_{21}$H$_{30}$F$_2$N$_2$O$_8$, 476.1970; found, 476.1978 | $^1$H NMR (CDCl$_3$) δ 11.90 (s, 1H), 8.66 (d, J = 8.0 Hz, 1H), 7.97 (d, J = 5.2 Hz, 1H), 6.85 (d, J = 5.2 Hz, 1H), 5.83 (tdd, J = 55.1 (H-F), 4.7, 3.3 Hz, 1H), 5.07-4.93 (m, 2H), 4.14-4.01 (m, 1H), 4.02 (dd, J = 12.0, 6.7 Hz, 1H), 3.92 (s, 3H), 3.88-3.72 (m, 3H), 3.62-3.51 (m, 2H), 3.45 (dt, J = 9.1, 6.6 Hz, 1H), 3.31-3.19 (m, 2H), 1.58-1.48 (m, 2H), 1.45 (d, J = 6.3 Hz, 3H), 1.39-1.28 (m, 2H), 0.90 (t, J = 7.4 Hz, 3H) | $^{13}$C NMR (CDCl$_3$) δ 170.17, 169.05, 155.44, 148.82, 140.78, 130.24, 114.30 (t, J = 241.7 Hz), 109.69, 86.19, 83.72, 75.28, 74.31, 72.79 (t, J = 27.6 Hz), 72.51, 70.45, 56.19, 52.33, 32.13, 19.39, 18.64, 13.96 |
| 54 | — | (Neat) 3381, 2953, 1755, 1678, 1507, 1202, 1095 | HRMS-ESI (m/z) [M]$^+$ calcd for C$_{25}$H$_{38}$N$_2$O$_{11}$, 542.2476; found, 542.2487 | $^1$H NMR (CDCl$_3$) δ 8.51 (d, J = 7.9 Hz, 1H), 8.26 (d, J = 5.3 Hz, 1H), 6.93 (d, J = 5.4 Hz, 1H), 5.73-5.67 (m, 2H), 5.04 (td, J = 7.0, 5.2 Hz, 1H), 4.95 (dq, J = 9.1, 6.2 Hz, 1H), 4.05-3.97 (m, 2H), 3.89 (s, 3H), 3.81-3.67 (m, 3H), 3.62-3.45 (m, 5H), 3.36 (s, 3H), 3.26-3.19 (m, 2H), 2.04 (s, 3H), 1.56-1.48 (m, 2H), 1.45 (d, J = 6.3 Hz, 3H), 1.39-1.27 (m, 2H), 0.89 (t, J = 7.4 Hz, 3H) | $^{13}$C NMR (CDCl$_3$) δ 170.94, 170.34, 163.34, 160.31, 145.90, 144.04, 142.20, 109.82, 89.52, 85.62, 83.69, 75.05, 74.25, 73.05, 72.90, 72.35, 70.73, 59.03, 56.30, 52.50, 32.26, 20.96, 19.41, 18.61, 14.01 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 55 | — | (Neat) 3372, 2934, 1752, 1675, 1505, 1201, 1094 | HRMS-ESI (m/z) [M]$^+$ calcd for $C_{24}H_{34}F_2N_2O_{10}$, 548.2182; found, 548.2194. | $^1$H NMR (CDCl$_3$) δ 8.53 (d, J = 7.9 Hz, 1H), 8.27 (d, J = 5.4 Hz, 1H), 6.94 (d, J = 5.4 Hz, 1H), 5.83 (tdd, J = 55.7 (H-F), 4.7, 3.3 Hz, 1H), 5.74-5.68 (m, 2H), 5.08-5.01 (m, 1H), 4.96 (dq, J = 12.7, 6.3 Hz, 1H), 4.14-4.02 (m, 1H), 4.01 (dd, J = 11.9, 6.8 Hz, 1H), 3.89 (s, 3H), 3.85-3.70 (m, 3H), 3.60-3.52 (m, 2H), 3.45 (dt, J = 9.1, 6.6 Hz, 1H), 3.30-3.18 (m, 2H), 2.05 (s, 3H), 1.57-1.47 (m, 2H), 1.44 (d, J = 6.3 Hz, 3H), 1.39-1.27 (m, 2H), 0.90 (t, J = 7.4 Hz, 3H) | $^{13}$C NMR (CDCl$_3$) δ 170.80, 170.36, 163.37, 160.34, 145.92, 144.09, 142.17, 114.31 (t, J = 240.8 Hz), 109.86, 89.52, 86.23, 83.77, 74.96, 74.51, 72.81 (t, J = 27.8 Hz), 72.32, 70.44, 56.32, 52.61, 32.15, 20.97, 19.40, 18.66, 13.97 |
| 56 | 111-113 | (Neat) 3364, 2974, 1738, 1649, 1529, 1242, 1140 | HRMS-ESI (m/z) [M]$^+$ calcd for $C_{23}H_{32}N_2O_{10}$, 496.2057; found, 496.2063 | $^1$H NMR (CDCl$_3$) δ 11.85 (s, 1H), 8.64 (d, J = 8.3 Hz, 1H), 7.98 (d, J = 5.2 Hz, 1H), 6.86 (d, J = 5.2 Hz, 1H), 5.22-5.12 (m, 2H), 5.10 (ddd, J = 8.2, 7.0, 5.4 Hz, 1H), 4.90 (ddd, J = 8.9, 6.5, 2.6 Hz, 1H), 4.07 (dd, J = 11.9, 6.9 Hz, 1H), 3.92 (s, 3H), 3.83 (dd, J = 11.9, 5.2 Hz, 1H), 3.81-3.72 (m, 2H), 2.57-2.39 (m, 2H), 1.33 (d, J = 5.9 Hz, 3H), 1.15 (d, J = 7.0 Hz, 3H), 1.13 (d, J = 7.0 Hz, 3H), 1.10 (d, J = 7.0 Hz, 3H), 1.09 (d, J = 7.0 Hz, 3H) | $^{13}$C NMR (CDCl$_3$) δ 175.60, 175.50, 170.26, 169.09, 155.46, 148.85, 140.83, 130.20, 109.76, 74.87, 74.19, 73.95, 73.35, 71.71, 56.21, 52.03, 34.08, 33.99, 19.09, 18.98, 18.81, 18.79, 18.11 |
| 57 | — | (Neat) 3374, 2976, 1739, 1677, 1505, 1197, 1141 | HRMS-ESI (m/z) [M]$^+$ calcd for $C_{26}H_{36}N_2O_{12}$, 568.2268; found, 568.2272 | $^1$H NMR (CDCl$_3$) δ 8.53 (d, J = 8.0 Hz, 1H), 8.28 (d, J = 5.4 Hz, 1H), 6.96 (d, J = 5.4 Hz, 1H), 5.79-5.64 (m, 2H), 5.18-5.08 (m, 2H), 4.91 (ddd, J = 9.1, 7.0, 2.2 Hz, 1H), 4.07 (dd, J = 11.8, 7.0 Hz, 1H), 3.91 (s, 3H), 3.85-3.71 (m, 3H), 2.57-2.38 (m, 2H), 2.06 (s, 3H), 1.33 (d, J = 6.0 Hz, 3H), 1.16 (d, J = 7.0 Hz, 3H), 1.13 (d, J = 7.0 Hz, 3H), 1.11 (d, J = 7.0 Hz, 4H), 1.10 (d, J = 7.0 Hz, 3H) | $^{13}$C NMR (CDCl$_3$) δ 175.65, 175.57, 170.89, 170.41, 163.41, 160.36, 145.97, 144.12, 142.10, 109.93, 89.52, 74.66, 74.26, 74.20, 73.43, 71.51, 56.36, 52.37, 34.12, 34.02, 21.01, 19.13, 19.01, 18.84, 18.82, 18.15 |
| 58 | — | — | ESIMS m/z 442.1 ([M + H]$^+$) | $^1$H NMR (CDCl$_3$) δ 11.92 (s, 1H), 8.56k (d, J = 8.2 Hz, 1H), 8.00 (d, J = 5.2 Hz, 1H), 6.87 (d, J = 5.2 Hz, 1H), 5.03 (ddd, J = 8.2, 6.8, 5.1 Hz, 1H), 4.99-4.89 (m, 1H), 4.07 (dd, J = 11.9, 6.8 Hz, 1H), 3.94 (s, 3H), 3.88-3.76 (m, 3H), 3.65-3.43 (m, 4H), 3.26-3.14 (m, 2H), 1.67-1.53 (m, 4H), 1.46 (d, J = 6.3 Hz, 3H), 0.92 (td, J = 7.4, 3.1 Hz, 6H); | $^{13}$C NMR (CDCl$_3$) δ 170.33, 168.99, 155.38, 148.79, 140.66, 130.30, 109.60, 85.00, 83.58, 75.59, 75.38, 73.96, 73.23, 72.74, 56.09, 52.17, 23.53, 23.30, 18.60, 10.65, 10.62 |
| 59 | — | — | ESIMS m/z 593.5 ([M + H]$^+$) | $^1$H NMR (CDCl$_3$) δ 11.92 (d, J = 0.7 Hz, 1H), 8.66 (d, J = 8.1 Hz, 1H), 7.99 (d, J = 5.2 Hz, 1H), 7.37-7.21 (m, 4H), | $^{13}$C NMR (CDCl$_3$) δ 170.29, 168.97, 155.36, 148.77, 141.89, 141.78, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 7.21-7.10 (m, 6H), 6.86 (d, J = 5.2 Hz, 1H), 5.15-4.89 (m, 2H), 4.05 (dd, J = 11.9, 6.8 Hz, 1H), 3.99-3.86 (m, 4H), 3.85-3.75 (m, 2H), 3.69-3.45 (m, 4H), 3.27-3.18 (m, 2H), 2.78-2.56 (m, 4H), 2.02-1.79 (m, 4H), 1.46 (d, J = 6.3 Hz, 3H) | 140.64, 130.27, 128.36, 128.34, 128.30, 125.83, 125.81, 109.59, 85.12, 83.72, 75.23, 73.98, 73.35, 73.10, 70.15, 56.07, 52.16, 32.50, 32.38, 31.97, 31.65, 18.66 |
| 60 | — | — | ESIMS m/z 665.5 ([M + H]$^+$) | $^1$H NMR (CDCl$_3$) δ 8.51 (d, J = 7.9 Hz, 1H), 8.27 (d, J = 5.3 Hz, 1H), 7.36-7.21 (m, 4H), 7.21-7.11 (m, 6H), 6.94 (d, J = 5.4 Hz, 1H), 5.82-5.65 (m, 2H), 5.06 (ddd, J = 8.0, 6.8, 5.2 Hz, 1H), 4.95 (dq, J = 9.0, 6.0 Hz, 1H), 4.05 (dd, J = 11.8, 6.9 Hz, 1H), 3.97-3.85 (m, 4H), 3.85-3.70 (m, 2H), 3.67-3.54 (m, 3H), 3.50 (dt, J = 9.2, 6.4 Hz, 1H), 3.29-3.16 (m, 2H), 2.74-2.57 (m, 4H), 2.06 (s, 3H), 1.97-1.78 (m, 4H), 1.45 (d, J = 6.3 Hz, 3H) | $^{13}$C NMR (CDCl$_3$) δ 170.94, 170.22, 163.28, 160.26, 145.80, 143.99, 142.24, 141.94, 141.83, 128.38, 128.35, 128.32, 125.83, 125.81, 109.73, 89.47, 85.15, 83.79, 74.94, 74.18, 73.37, 72.91, 70.13, 56.20, 52.46, 32.52, 32.40, 32.00, 31.67, 20.85, 18.69 |
| 61 | — | — | ESIMS m/z 513.2 ([M + H]$^+$) | $^1$H NMR (CDCl$_3$) δ 8.51 (d, J = 7.9 Hz, 1H), 8.28 (d, J = 5.3 Hz, 1H), 6.95 (d, J = 5.4 Hz, 1H), 5.83-5.62 (m, 2H), 5.06 (ddd, J = 8.0, 6.9, 5.2 Hz, 1H), 5.00-4.82 (m, 1H), 4.05 (dd, J = 11.8, 6.9 Hz, 1H), 3.91 (s, 3H), 3.88-3.72 (m, 3H), 3.64-3.42 (m, 4H), 3.26-3.17 (m, 2H), 2.06 (s, 3H), 1.58 (dddd, J = 10.9, 7.1, 3.9, 2.2 Hz, 4H), 1.45 (d, J = 6.3 Hz, 3H), 0.92 (td, J = 7.4, 3.8 Hz, 6H) | $^{13}$C NMR (CDCl$_3$) δ 170.96, 170.27, 163.26, 160.22, 145.81, 143.96, 142.14, 109.72, 89.44, 84.95, 83.60, 75.58, 75.00, 74.07, 72.99, 72.68, 56.20, 52.39, 23.51, 23.28, 20.87, 18.59, 10.65, 10.63 |
| 62 | 89-91 | (Neat) 3365, 2931, 1751, 1646, 1529, 1265, 1096 | HRMS-ESI (m/z) [M]$^+$ calcd for C$_{25}$H$_{40}$N$_2$O$_8$, 496.2785; found, 496.2791 | $^1$H NMR (CDCl$_3$) δ 11.93 (s, 1H), 8.65 (d, J = 8.1 Hz, 1H), 7.98 (d, J = 5.2 Hz, 1H), 6.86 (d, J = 5.2 Hz, 1H), 5.02 (ddd, J = 8.1, 6.9, 5.2 Hz, 1H), 4.94 (dq, J = 12.5, 6.2 Hz, 1H), 4.04 (dd, J = 11.9, 6.8 Hz, 1H), 3.93 (s, 3H), 3.89-3.74 (m, 3H), 3.65-3.43 (m, 4H), 3.24-3.15 (m, 2H), 1.62-1.48 (m, 4H), 1.45 (d, J = 6.3 Hz, 3H), 1.38-1.21 (m, 8H), 0.94-0.82 (m, 6H) | $^{13}$C NMR (CDCl$_3$) δ 170.45, 169.07, 155.45, 148.84, 140.78, 130.33, 109.69, 85.08, 83.69, 75.38, 74.19, 74.00, 73.31, 71.22, 56.21, 52.22, 30.19, 29.93, 28.49, 28.48, 22.73, 22.67, 18.71, 14.17 |
| 63 | 165-167 | (Neat) 3365, 2982, 1733, 1643, 1535, 1285, 1091 | HRMS-ESI (m/z) [M]$^+$ calcd for C$_{17}$H$_{24}$N$_2$O$_8$, 384.1533; found, 384.1532 | $^1$H NMR (CDCl$_3$) δ 11.91 (s, 1H), 8.64 (s, 1H), 7.98 (d, J = 5.2 Hz, 1H), 6.86 (d, J = 5.2 Hz, 1H), 5.02 (ddd, J = 8.1, 6.8, 5.1 Hz, 1H), 4.94 (dq, J = 8.7, 6.3 Hz, 1H), 4.05 (dd, J = 11.9, 6.8 Hz, 1H), 3.92 (s, 3H), 3.81 (d, J = 11.8 Hz, 1H), 3.80 (d, J = 11.9 Hz, 1H), 3.62-3.57 (m, 1H), 3.55 (s, 3H), 3.44 (s, 3H), 3.16-3.07 (m, 2H), 1.44 (d, J = 6.3 Hz, 3H) | $^{13}$C NMR (CDCl$_3$) δ 170.38, 169.06, 155.43, 148.82, 140.78, 130.29, 109.69, 86.83, 85.33, 74.75, 74.06, 72.92, 61.35, 58.47, 56.20, 52.23, 18.61 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 64 | — | (Neat) 3372, 2931, 1753, 1677, 1505, 1201, 1096 | HRMS-ESI (m/z) [M]$^+$ calcd for C$_{28}$H$_{44}$N$_2$O$_{10}$, 568.2996; found, 568.3011 | $^1$H NMR (CDCl$_3$) δ 8.52 (d, J = 7.9 Hz, 1H), 8.28 (d, J = 5.4 Hz, 1H), 6.94 (d, J = 5.4 Hz, 1H), 5.79-5.67 (m, 2H), 5.05 (td, J = 7.0, 5.3 Hz, 1H), 4.91 (dq, J = 12.5, 6.2 Hz, 1H), 4.04 (dd, J = 11.8, 6.9 Hz, 1H), 3.90 (s, 3H), 3.89-3.72 (m, 3H), 3.63-3.45 (m, 4H), 3.23-3.14 (m, 2H), 2.06 (s, 3H), 1.62-1.49 (m, 4H), 1.44 (d, J = 6.3 Hz, 3H), 1.38-1.23 (m, 8H), 0.95-0.81 (m, 6H) | $^{13}$C NMR (CDCl$_3$) δ 171.09, 170.40, 163.38, 160.36, 145.94, 144.11, 142.28, 109.84, 89.59, 85.12, 83.75, 75.10, 74.20, 73.12, 71.21, 56.34, 52.52, 30.21, 29.95, 28.51, 28.50, 22.75, 22.68, 21.01, 18.73, 14.18 |
| 65 | — | (Neat) 3370, 2935, 1752, 1676, 1506, 1203, 1100 | HRMS-ESI (m/z) [M]$^+$ calcd for C$_{20}$H$_{28}$N$_2$O$_{10}$, 456.1744; found, 456.1752 | $^1$H NMR (CDCl$_3$) δ 8.51 (d, J = 7.9 Hz, 1H), 8.26 (d, J = 5.4 Hz, 1H), 6.94 (d, J = 5.4 Hz, 1H), 5.74-5.68 (m, 2H), 5.04 (ddd, J = 7.8, 6.9, 5.3 Hz, 1H), 4.91 (dq, J = 8.9, 6.3 Hz, 1H), 4.04 (dd, J = 11.8, 6.9 Hz, 1H), 3.89 (s, 3H), 3.83-3.73 (m, 2H), 3.63-3.56 (m, 1H), 3.54 (s, 3H), 3.43 (s, 3H), 3.15-3.05 (m, 2H), 2.05 (s, 3H), 1.43 (d, J = 6.3 Hz, 3H) | $^{13}$C NMR (CDCl$_3$) δ 171.00, 170.36, 163.36, 160.33, 145.92, 144.07, 142.20, 109.84, 89.53, 86.86, 85.39, 74.47, 74.24, 72.72, 61.36, 58.45, 56.31, 52.51, 20.98, 18.61 |
| 66 | — | (Neat) 3366, 2934, 1725, 1649, 1529, 1265, 1097 cm$^{-1}$ | HRMS-ESI (m/z) [M]$^+$ calcd for C$_{26}$H$_{32}$N$_2$O$_9$, 516.2108; found, 516.2108 | $^1$H NMR (CDCl$_3$) δ 11.93-11.92 (m, 1H), 8.73 (d, J = 8.1 Hz, 1H), 8.08-8.03 (m, 2H), 8.02 (d, J = 5.2 Hz, 1H), 7.61-7.56 (m, 1H), 7.49-7.43 (m, 2H), 6.88 (d, J = 5.2 Hz, 1H), 5.38-5.30 (m, 1H), 5.30-5.22 (m, 1H), 5.13 (ddd, J = 8.1, 6.4, 4.0 Hz, 1H), 4.16-3.97 (m, 3H), 3.95 (s, 3H), 3.69 (dd, J = 11.4, 7.7 Hz, 1H), 3.54 (dt, J = 9.2, 6.3 Hz, 1H), 3.39 (ddd, J = 8.9, 7.8, 1.4 Hz, 1H), 3.30 (dt, J = 9.2, 6.6 Hz, 1H), 1.42 (d, J = 6.2 Hz, 3H), 1.32-1.23 (m, 2H), 1.15-0.97 (m, 2H), 0.63 (t, J = 7.4 Hz, 3H) | $^{13}$C NMR (CDCl$_3$) δ 170.26, 169.13, 165.59, 155.52, 148.93, 140.82, 133.34, 130.35, 129.98, 129.88, 128.58, 109.75, 81.13, 76.95, 76.33, 75.03, 71.87, 70.95, 56.25, 52.83, 31.87, 19.14, 18.50, 13.72 |
| 67 | — | — | ESIMS m/z 577.7 ([M + H]$^+$) | $^1$H NMR (CDCl$_3$) δ 11.9 (m, 1H), 8.67 (d, J = 8.2 Hz, 1H), 8.00 (d, J = 5.2 Hz, 1H), 6.88 (d, J = 5.2 Hz, 1H), 5.15-4.78 (m, 2H), 4.05 (dd, J = 12.0, 6.7 Hz, 1H), 3.94 (s, 3H), 3.91-3.75 (m, 3H), 3.71-3.46 (m, 4H), 3.29-3.13 (m, 2H), 2.29-2.06 (m, 4H), 1.89-1.72 (m, 4H), 1.45 (d, J = 6.3 Hz, 3H) | $^{13}$C NMR (CDCl$_3$) δ 170.17, 168.97, 155.36, 148.75, 140.70, 130.16, 127.2 (q, J = 276 Hz), 127.1 (q, J = 276 Hz), 109.61, 85.01, 83.76, 75.10, 74.15, 72.71, 71.92, 68.67, 56.09, 52.17, 30.72 (q, J = 29 Hz), 30.71 (q, J = 29 Hz), 23.0 (q, J = 3 Hz), 22.88 (q, J = 3 Hz), 18.59 |
| 68 | — | — | ESIMS m/z 650.3 ([M + H]$^+$) | $^1$H NMR (CDCl$_3$) δ 8.53 (d, J = 7.9 Hz, 1H), 8.29 (d, J = 5.4 Hz, 1H), 6.96 (d, J = 5.4 Hz, 1H), 5.89-5.61 (m, 2H), | $^{13}$C NMR (CDCl$_3$) δ 170.82, 170.29, 163.29, 160.26, 145.84, 144.00, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 5.06 (ddd, J = 7.9, 6.7, 5.0 Hz, 1H), 4.94 (ddd, J = 12.3, 9.0, 6.0 Hz, 1H), 4.04 (dd, J = 11.9, 6.8 Hz, 1H), 3.91 (s, 3H), 3.87 (dt, J = 9.0, 6.2 Hz, 1H), 3.83-3.75 (m, 2H), 3.68-3.57 (m, 3H), 3.57-3.48 (m, 1H), 3.26-3.12 (m, 2H), 2.27-2.09 (m, 4H), 2.07 (s, 3H), 1.89-1.76 (m, 4H), 1.44 (d, J = 6.3 Hz, 3H) | 142.08, 127.1 (q, J = 275 Hz), 127.0 (q, J = 275 Hz), 109.78, 89.42, 85.04, 83.82, 74.80, 74.33, 72.53, 71.92, 68.65, 56.22, 52.47, 30.71, J = 28 Hz), 30.70 (q, J = 28 Hz), 23.02 (q, J = 3 Hz), 22.79 (q, J = 3 Hz), 20.87, 18.62 |
| 69 | — | (Neat) 3372, 2934, 1725, 1676, 1505, 1266, 1145 | HRMS-ESI (m/z) [M]$^+$ calcd for C$_{29}$H$_{36}$N$_2$O$_{11}$, 588.2319; found, 588.2329 | $^1$H NMR (CDCl$_3$) δ 8.59 (d, J = 7.8 Hz, 1H), 8.28 (d, J = 5.3 Hz, 1H), 8.09-8.00 (m, 2H), 7.60-7.54 (m, 1H), 7.48-7.41 (m, 2H), 6.95 (d, J = 5.4 Hz, 1H), 5.77-5.69 (m, 2H), 5.30-5.21 (m, 2H), 5.14 (ddd, J = 7.8, 6.6, 4.2 Hz, 1H), 4.07 (dd, J = 11.9, 6.5 Hz, 1H), 4.02 (dd, J = 11.2, 1.1 Hz, 1H), 3.94 (dd, J = 11.8, 4.2 Hz, 1H), 3.90 (s, 3H), 3.68 (dd, J = 11.3, 7.8 Hz, 1H), 3.52 (dt, J = 9.2, 6.3 Hz, 1H), 3.39-3.34 (m, 1H), 3.28 (dt, J = 9.2, 6.6 Hz, 1H), 2.06 (s, 3H), 1.40 (d, J = 6.0 Hz, 3H), 1.31-1.17 (m, 2H), 1.16-0.94 (m, 2H), 0.60 (t, J = 7.4 Hz, 3H) | $^{13}$C NMR (CDCl$_3$) δ 170.84, 170.37, 165.54, 163.39, 160.35, 145.92, 144.14, 142.17, 133.26, 129.98, 129.82, 128.51, 109.87, 89.53, 81.15, 76.94, 75.92, 75.12, 71.59, 70.83, 56.32, 53.04, 31.83, 20.97, 19.09, 18.45, 13.66 |
| 70 | — | — | ESIMS m/z 413 ([M + H]$^+$) | $^1$H NMR (CDCl$_3$) δ 11.95 (d, J = 0.6 Hz, 1H), 8.80 (d, J = 7.9 Hz, 1H), 8.01 (d, J = 5.2 Hz, 1H), 6.88 (dd, J = 5.3, 0.7 Hz, 1H), 5.15 (dq, J = 9.3, 6.3 Hz, 1H), 5.02 (ddd, J = 7.9, 5.6, 2.2 Hz, 1H), 4.21-4.07 (m, 2H), 4.01-3.90 (m, 4H), 3.52-3.37 (m, 3H), 3.28-3.16 (m, 2H), 3.11 (ddd, J = 9.1, 7.3, 1.1 Hz, 1H), 1.85 (dp, J = 13.3, 6.7 Hz, 1H), 1.49 (d, J = 6.3 Hz, 3H), 0.91 (dd, J = 6.7, 3.9 Hz, 6H) | $^{13}$C NMR (CDCl$_3$) δ 169.47, 168.98, 155.31, 148.71, 140.69, 130.26, 109.56, 82.64, 77.56, 77.14, 76.90, 76.46, 73.57, 56.08, 53.47, 28.59, 19.31, 19.26, 18.73 |
| 71 | 138-140 | (Neat) 3370, 2926, 1750, 1650, 1529, 1243, 1085 | HRMS-ESI (m/z) [M]$^+$ calcd for C$_{24}$H$_{38}$N$_2$O$_8$, 482.2628; found, 482.2631 | $^1$H NMR (CDCl$_3$) δ 11.98 (s, 1H), 8.73 (d, J = 8.0 Hz, 1H), 8.01 (d, J = 5.2 Hz, 1H), 6.87 (d, J = 5.2 Hz, 1H), 5.08 (dq, J = 9.1, 6.3 Hz, 1H), 5.00 (ddd, J = 8.1, 6.1, 3.8 Hz, 1H), 4.00 (dd, J = 12.1, 6.1 Hz, 1H), 3.94 (s, 3H), 3.95-3.89 (m, 2H), 3.79 (dd, J = 8.6, 5.6 Hz, 1H), 3.56-3.45 (m, 2H), 3.07 (dt, J = 12.6, 8.4 Hz, 2H), 1.90-1.78 (m, 1H), 1.56-1.43 (m, 2H), 1.45 (d, J = 6.4 Hz, 3H), 1.15 (s, 3H), 1.14 (s, 3H), 0.93 (d, J = 6.6 Hz, 3H), 0.91-0.85 (m, 6H) | $^{13}$C NMR (CDCl$_3$) δ 170.17, 169.09, 155.47, 148.89, 140.79, 130.47, 109.68, 85.26, 81.29, 81.18, 77.82, 75.32, 75.19, 73.37, 56.23, 53.07, 35.01, 29.10, 25.16, 25.08, 19.95, 19.60, 18.97, 9.06 |

TABLE 2-continued

Analytical Data

| Compound Number | MP (°C.) | IR (cm⁻¹) | MASS | $^1$H NMR* | $^{13}$C NMR* |
|---|---|---|---|---|---|
| 72 | 121-124 | — | ESIMS m/z 413.1 ([M + H]⁺) | $^1$H NMR (CDCl$_3$) δ 11.92 (d, J = 0.7 Hz, 1H), 8.75 (d, J = 8.2 Hz, 1H), 7.98 (d, J = 5.2 Hz, 1H), 6.86 (d, J = 5.2 Hz, 1H), 5.12 (dq, J = 9.4, 6.4 Hz, 1H), 5.01 (ddd, J = 8.2, 5.4, 3.5 Hz, 1H), 4.12 (d, J = 11.0 Hz, 1H), 4.07-3.97 (m, 2H), 3.94 (s, 3H), 3.60-3.48 (m, 2H), 3.47-3.43 (m, 2H), 3.14 (dd, J = 9.4, 8.4 Hz, 1H), 2.02-1.81 (m, 2H), 1.47 (d, J = 6.4 Hz, 3H), 0.97 (dd, J = 6.7, 4.0 Hz, 6H) | $^{13}$C NMR (CDCl$_3$) δ 169.65, 168.98, 155.31, 148.70, 140.69, 130.23, 109.57, 86.44, 80.31, 79.27, 75.77, 74.17, 72.70, 56.07, 53.09, 29.04, 19.31, 19.21, 18.68 |
| 73 | 122-125 | — | ESIMS m/z 495.6 ([M + H]⁺) | $^1$H NMR (CDCl$_3$) δ 12.17-11.64 (m, 1H), 8.67 (d, J = 8.2 Hz, 1H), 8.00 (d, J = 5.2 Hz, 1H), 6.87 (d, J = 5.2 Hz, 1H), 5.04 (ddd, J = 8.2, 6.8, 4.9 Hz, 1H), 4.96 (dq, J = 9.3, 6.3 Hz, 1H), 4.04 (dd, J = 11.9, 6.9 Hz, 1H), 3.94 (s, 3H), 3.88-3.71 (m, 3H), 3.60 (dd, J = 10.9, 7.2 Hz, 1H), 3.48-3.31 (m, 2H), 3.26-3.11 (m, 2H), 2.08-1.67 (m, 5H), 1.59-1.49 (m, 1H), 1.46 (d, J = 6.3 Hz, 3H), 1.36-1.09 (m, 5H), 0.91 (dd, J = 13.5, 6.7 Hz, 6H) | $^{13}$C NMR (CDCl$_3$) δ 170.33, 168.94, 155.33, 148.73, 140.65, 130.24, 109.56, 84.91, 80.88, 80.42, 78.13, 73.88, 73.35, 56.09, 52.15, 33.29, 32.39, 29.13, 25.73, 24.39, 24.32, 19.64, 19.41, 18.67 |
| 74 | — | — | ESIMS m/z 461.9 ([M + Na]⁺) | $^1$H NMR (CDCl$_3$) δ 11.96 (d, J = 0.7 Hz, 1H), 8.80 (d, J = 7.8 Hz, 1H), 8.01 (d, J = 5.2 Hz, 1H), 6.88 (d, J = 5.2 Hz, 1H), 5.15 (dq, J = 9.2, 6.3 Hz, 1H), 5.02 (ddd, J = 7.9, 5.6, 2.2 Hz, 1H), 4.20-4.00 (m, 2H), 4.00-3.89 (m, 3H), 3.56-3.33 (m, 3H), 3.33-3.21 (m, 1H), 1.96 (d, J = 10.8 Hz, 1H), 1.90-1.79 (m, 1H), 1.73 (dd, J = 9.2, 4.0 Hz, 2H), 1.59-1.52 (m, 1H), 1.49 (d, J = 6.3 Hz, 3H), 1.38-1.09 (m, 5H) | $^{13}$C NMR (CDCl$_3$) δ 169.53, 168.98, 155.33, 148.73, 140.69, 130.28, 109.56, 80.02, 79.09, 76.79, 76.45, 73.62, 56.09, 53.50, 33.59, 31.75, 25.49, 24.29, 24.12, 18.80 |
| 75 | — | — | ESIMS m/z 495.6 ([M + H]⁺) | $^1$H NMR (CDCl$_3$) δ 11.94 (d, J = 0.6 Hz, 1H), 8.67 (d, J = 8.1 Hz, 1H), 8.00 (d, J = 5.2 Hz, 1H), 6.87 (dd, J = 5.2, 0.7 Hz, 1H), 5.02 (ddd, J = 8.2, 6.7, 4.9 Hz, 1H), 4.94 (dq, J = 9.4, 6.4 Hz, 1H), 4.07 (dd, J = 11.9, 6.7 Hz, 1H), 3.94 (s, 3H), 3.87-3.76 (m, 2H), 3.64 (dd, J = 11.3, 6.5 Hz, 2H), 3.43 (dd, J = 9.4, 8.4 Hz, 1H), 3.37-3.25 (m, 2H), 3.19 (ddd, J = 8.2, 6.5, 1.3 Hz, 1H), 2.05-1.90 (m, 2H), 1.89-1.68 (m, 3H), 1.56 (d, J = 9.6 Hz, 1H), 1.45 (d, J = 6.4 Hz, 3H), 1.33-1.09 (m, 5H), 0.91 (dd, J = 6.7, 3.7 Hz, 6H) | $^{13}$C NMR (CDCl$_3$) δ 170.30, 168.95, 155.32, 148.72, 140.66, 130.24, 109.56, 84.40, 80.64, 79.54, 77.53, 75.43, 74.08, 73.48, 56.08, 52.21, 33.57, 32.56, 28.90, 25.72, 24.74, 24.57, 19.50, 19.43, 18.90 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 76 | — | — | ESIMS m/z 567.8 ([M + H]$^+$) | $^1$H NMR (CDCl$_3$) δ 8.53 (d, J = 7.9 Hz, 1H), 8.28 (d, J = 5.4 Hz, 1H), 6.95 (d, J = 5.4 Hz, 1H), 5.93-5.60 (m, 2H), 5.20-4.99 (m, 1H), 4.92 (dq, J = 9.5, 6.3 Hz, 1H), 4.03 (dd, J = 11.8, 7.0 Hz, 1H), 3.91 (s, 3H), 3.85-3.73 (m, 3H), 3.59 (dd, J = 10.9, 7.3 Hz, 1H), 3.48-3.30 (m, 2H), 3.26-3.09 (m, 2H), 2.07 (s, 3H), 2.01-1.87 (m, 2H), 1.87-1.77 (m, 1H), 1.77-1.68 (m, 2H), 1.60-1.48 (m, 1H), 1.44 (d, J = 6.3 Hz, 3H), 1.35-1.13 (m, 5H), 0.91 (dd, J = 13.5, 6.7 Hz, 6H) | $^{13}$C NMR (CDCl$_3$) δ 170.96, 170.27, 163.25, 160.22, 145.80, 143.96, 142.16, 109.70, 89.45, 84.90, 80.87, 80.48, 78.08, 76.45, 74.05, 73.15, 56.19, 52.41, 33.30, 32.39, 29.13, 25.73, 24.40, 24.33, 20.87, 19.65, 19.41, 18.67 |
| 77 | — | — | ESIMS m/z 568.4 ([M + H]$^+$) | $^1$H NMR (CDCl$_3$) δ 8.53 (d, J = 7.9 Hz, 1H), 8.28 (d, J = 5.4 Hz, 1H), 6.95 (d, J = 5.4 Hz, 1H), 5.84-5.49 (m, 2H), 5.05 (ddd, J = 8.0, 6.8, 5.1 Hz, 1H), 4.91 (dq, J = 9.4, 6.4 Hz, 1H), 4.06 (dd, J = 11.9, 6.8 Hz, 1H), 3.91 (s, 3H), 3.78 (ddd, J = 11.9, 3.5, 2.1 Hz, 2H), 3.69-3.58 (m, 2H), 3.42 (dd, J = 9.5, 8.5 Hz, 1H), 3.36-3.25 (m, 2H), 3.17 (ddd, J = 8.3, 6.6, 1.3 Hz, 1H), 2.07 (s, 3H), 2.04-1.90 (m, 2H), 1.88-1.69 (m, 3H), 1.56 (d, J = 10.4 Hz, 1H), 1.44 (d, J = 6.4 Hz, 3H), 1.29-1.09 (m, 5H), 0.90 (dd, J = 6.7, 3.6 Hz, 6H) | $^{13}$C NMR (CDCl$_3$) δ 170.91, 170.27, 163.25, 160.21, 145.80, 143.94, 142.16, 109.70, 89.44, 84.45, 80.66, 79.54, 77.51, 75.15, 74.27, 73.25, 56.19, 52.49, 33.58, 32.58, 28.90, 25.72, 24.75, 24.57, 20.87, 19.49, 19.42, 18.91 |
| 78 | — | (Neat) 3377, 2967, 1755, 1679, 1506, 1203, 1085 | HRMS-ESI (m/z) [M]$^+$ calcd for C$_{27}$H$_{42}$N$_2$O$_{10}$, 554.2839; found, 554.2837 | $^1$H NMR (CDCl$_3$) δ 8.58 (d, J = 7.8 Hz, 1H), 8.28 (d, J = 5.4 Hz, 1H), 6.94 (d, J = 5.4 Hz, 1H), 5.75-5.68 (m, 2H), 5.10-4.95 (m, 2H), 3.98 (dd, J = 12.0, 6.3 Hz, 1H), 3.90 (s, 3H), 3.90-3.85 (m, 2H), 3.78 (dd, J = 8.5, 5.6 Hz, 1H), 3.55-3.43 (m, 2H), 3.06 (dt, J = 14.7, 8.5 Hz, 2H), 2.05 (s, 3H), 1.90-1.76 (m, 1H), 1.55-1.44 (m, 2H), 1.43 (d, J = 6.4 Hz, 3H), 1.14 (s, 3H), 1.12 (s, 3H), 0.92 (d, J = 6.6 Hz, 3H), 0.90-0.83 (m, 6H) | $^{13}$C NMR (CDCl$_3$) δ 170.77, 170.39, 163.38, 160.33, 145.94, 144.05, 142.39, 109.79, 89.58, 85.21, 81.16, 80.92, 77.73, 75.35, 73.14, 56.31, 53.28, 35.00, 29.07, 25.14, 25.04, 20.99, 19.92, 19.57, 18.95, 9.03 |
| 79 | — | — | ESIMS m/z 506.2 ([M + Na]$^+$) | $^1$H NMR (CDCl$_3$) δ 11.87 (d, J = 0.6 Hz, 1H), 8.60-8.37 (m, 1H), 7.84 (d, J = 5.2 Hz, 1H), 6.71 (d, J = 5.3 Hz, 1H), 5.04-4.94 (m, 1H), 4.81 (dt, J = 8.2, 5.7 Hz, 1H), 4.07 (dd, J = 11.5, 5.9 Hz, 1H), 3.79 (s, 3H), 3.72-3.62 (m, 2H), 3.61-3.52 (m, 2H), 3.21-3.08 (m, 2H), 3.08-3.00 (m, 1H), 1.83-1.61 (m, 1H), 1.38 (qd, J = 7.4, 2.3 Hz, 2H), | $^{13}$C NMR (CDCl$_3$) δ 169.91, 168.23, 154.59, 148.00, 139.96, 139.86, 129.67, 108.79, 82.49, 76.93, 76.89, 75.23, 74.93, 72.99, 55.36, 51.90, 34.51, 28.01, 24.72, 24.67, 18.88, 18.77, 18.15, 8.21 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 80 | — | — | ESIMS m/z 556.4 ([M + H]$^+$) | 1.30 (d, J = 6.7 Hz, 3H), 1.01 (d, J = 4.9 Hz, 5H), 0.82-0.71 (m, 10H) $^1$H NMR (CDCl$_3$) δ 8.38 (d, J = 7.9 Hz, 1H), 8.13 (d, J = 5.4 Hz, 1H), 6.80 (d, J = 5.4 Hz, 1H), 5.68-5.47 (m, 2H), 4.94 (t, J = 6.7 Hz, 1H), 4.84 (dt, J = 7.9, 5.8 Hz, 1H), 4.05 (dd, J = 11.5, 6.0 Hz, 1H), 3.84-3.71 (m, 3H), 3.72-3.58 (m, 2H), 3.58-3.49 (m, 1H), 3.25-3.06 (m, 2H), 3.06-2.97 (m, 1H), 1.92 (s, 3H), 1.70 (tt, J = 13.5, 6.7 Hz, 1H), 1.38 (qd, J = 7.5, 4.8 Hz, 2H), 1.29 (d, J = 6.8 Hz, 3H), 1.01 (d, J = 3.8 Hz, 6H), 0.83-0.67 (m, 10H) | $^{13}$C NMR (CDCl$_3$) δ 171.21, 170.30, 163.21, 160.21, 145.81, 145.74, 143.94, 109.63, 89.48, 83.23, 77.59, 77.57, 75.84, 75.56, 74.09, 73.99, 56.17, 52.90, 35.30, 28.71, 25.49, 25.45, 20.88, 19.61, 19.47, 18.94, 8.92 |
| 81 | — | — | ESIMS m/z 532.2 ([M + Na$^+$) | $^1$H NMR (CDCl$_3$) δ 11.92 (s, 1H), 8.76 (d, J = 8.1 Hz, 1H), 8.02 (d, J = 5.2 Hz, 1H), 7.43-7.08 (m, 5H), 7.08-6.80 (m, 5H), 6.73 (dt, J = 7.8, 1.1 Hz, 2H), 5.56-5.24 (m, 1H), 5.16 (ddd, J = 8.1, 6.6, 4.5 Hz, 1H), 4.70-4.46 (m, 1H), 4.38 (ddd, J = 8.7, 7.2, 1.3 Hz, 1H), 4.17-4.03 (m, 1H), 4.02-3.95 (m, 1H), 3.93 (s, 3H), 3.83 (dd, J = 11.3, 7.2 Hz, 1H), 1.50 (d, J = 6.3 Hz, 3H) | $^{13}$C NMR (CDCl$_3$) δ 170.04, 169.04, 159.45, 157.21, 155.39, 148.79, 140.77, 130.15, 129.49, 129.31, 121.62, 121.38, 116.49, 115.59, 109.68, 82.87, 80.51, 75.06, 74.46, 72.54, 56.11, 52.37, 18.88 |
| 82 | 117-119 | — | ESIMS m/z 489.4 ([M + H]$^+$) | $^1$H NMR (CDCl$_3$) δ 12.13-11.57 (m, 1H), 8.69 (d, J = 8.2 Hz, 1H), 8.00 (d, J = 5.2 Hz, 1H), 7.41-7.11 (m, 2H), 7.06-6.97 (m, 2H), 6.97-6.90 (m, 1H), 6.87 (d, J = 5.2 Hz, 1H), 5.19 (dq, J = 9.4, 6.3 Hz, 1H), 5.10 (ddd, J = 8.2, 6.9, 5.2 Hz, 1H), 4.31 (t, J = 9.1 Hz, 1H), 4.11 (dd, J = 11.9, 6.9 Hz, 1H), 3.94 (s, 3H), 3.91 (d, J = 1.6 Hz, 1H), 3.86 (dd, J = 11.8, 5.2 Hz, 1H), 3.74 (dd, J = 11.1, 7.3 Hz, 1H), 3.40 (ddd, J = 8.7, 7.2, 1.6 Hz, 1H), 3.34-3.24 (m, 1H), 3.19 (dd, J = 8.9, 6.4 Hz, 1H), 1.59 (dp, J = 13.3, 6.6 Hz, 1H), 1.41 (d, J = 6.4 Hz, 3H), 0.70 (d, J = 6.7 Hz, 3H), 0.65 (d, J = 6.7 Hz, 3H) | $^{13}$C NMR (CDCl$_3$) δ 170.37, 168.98, 159.41, 155.35, 148.74, 140.70, 130.16, 129.24, 121.20, 116.06, 109.62, 83.01, 82.67, 78.15, 74.80, 73.81, 72.86, 56.09, 52.05, 28.60, 19.19, 19.07, 18.74 |
| 83 | 112-113 | — | ESIMS m/z 489.8 ([M + H]$^+$) | $^1$H NMR (CDCl$_3$) δ 11.94 (d, J = 0.6 Hz, 1H), 8.73 (d, J = 8.1 Hz, 1H), 8.01 (d, J = 5.2 Hz, 1H), 7.41-7.15 (m, 2H), 7.06-6.62 (m, 4H), 5.27-4.89 (m, 2H), 4.23 (ddd, J = 8.5, 7.1, 1.3 Hz, 1H), 4.05 (dd, J = 12.0, 6.7 Hz, 1H), 3.99-3.86 (m, 5H), 3.76-3.62 (m, 2H), | $^{13}$C NMR (CDCl$_3$) δ 170.07, 168.99, 157.34, 155.35, 148.75, 140.72, 130.18, 129.55, 121.16, 115.58, 109.62, 84.42, 81.11, 80.64, 75.35, 74.34, 72.87, 56.09, |

TABLE 2-continued

Analytical Data

| Compound Number | MP (° C.) | IR (cm⁻¹) | MASS | ¹H NMR* | ¹³C NMR* |
|---|---|---|---|---|---|
| | | | | 3.45 (dd, J = 9.5, 8.7 Hz, 1H), 3.33 (dd, J = 8.4, 6.5 Hz, 1H), 1.73 (tt, J = 13.2, 6.8 Hz, 1H), 1.51 (d, J = 6.3 Hz, 3H), 0.84 (d, J = 6.7 Hz, 3H), 0.80 (d, J = 6.7 Hz, 3H) | 52.35, 28.98, 19.41, 19.34, 18.72 |
| 84 | — | — | ESIMS m/z 581.4 ([M + H]⁺) | ¹H NMR (CDCl₃) δ 8.62 (d, J = 7.9 Hz, 1H), 8.32 (d, J = 5.4 Hz, 1H), 7.35-7.13 (m, 5H), 7.09-6.85 (m, 5H), 6.73 (dt, J = 7.8, 1.0 Hz, 2H), 5.85-5.69 (m, 2H), 5.41-5.24 (m, 1H), 5.18 (ddd, J = 7.8, 6.7, 4.6 Hz, 1H), 4.51 (t, J = 9.1 Hz, 1H), 4.37 (ddd, J = 8.7, 7.4, 1.3 Hz, 1H), 4.17-4.02 (m, 1H), 3.98-3.90 (m, 4H), 3.83 (dd, J = 11.2, 7.3 Hz, 1H), 2.08 (s, 3H) 1.49 (d, J = 6.3 Hz, 3H) | ¹³C NMR (CDCl₃) δ 170.64, 170.29, 163.34, 160.26, 159.48, 157.25, 145.87, 144.01, 142.08, 129.45, 129.28, 121.55, 121.32, 116.48, 115.59, 109.80, 89.41, 82.88, 80.58, 74.71, 74.63, 72.36, 56.23, 52.62, 20.88, 18.88 |
| 85 | — | — | ESIMS m/z 561.1 ([M + H]⁺) | ¹H NMR (CDCl₃) δ 8.55 (d, J = 7.9 Hz, 1H), 8.29 (d, J = 5.3 Hz, 1H), 7.29-7.21 (m, 2H), 7.03-6.90 (m, 4H), 5.83-5.66 (m, 2H), 5.21-5.04 (m, 2H), 4.30 (dd, J = 9.5, 8.7 Hz, 1H), 4.10 (dd, J = 11.9, 7.0 Hz, 1H), 3.95-3.88 (m, 4H), 3.82 (dd, J = 11.8, 5.3 Hz, 1H), 3.73 (dd, J = 11.0, 7.4 Hz, 1H), 3.38 (ddd, J = 8.8, 7.4, 1.6 Hz, 1H), 3.33-3.24 (m, 1H), 3.24-3.13 (m, 1H), 2.07 (s, 3H), 1.58 (dp, J = 13.3, 6.6 Hz, 1H), 1.40 (d, J = 6.3 Hz, 3H), 0.70 (d, J = 6.7 Hz, 3H), 0.64 (d, J = 6.6 Hz, 3H) | ¹³C NMR (CDCl₃) δ 170.98, 170.29, 163.28, 160.24, 159.45, 145.82, 143.99, 142.09, 129.23, 121.14, 116.06, 109.76, 89.42, 83.04, 82.72, 78.14, 74.56, 74.03, 72.67, 56.21, 52.35, 28.60, 20.88, 19.19, 19.07, 18.76 |
| 86 | — | — | ESIMS m/z 562.4 ([M + H]⁺) | ¹H NMR (CDCl₃) δ 8.58 (d, J = 7.9 Hz, 1H), 8.30 (d, J = 5.4 Hz, 1H), 7.37-7.09 (m, 2H), 7.04-6.80 (m, 4H), 5.87-5.66 (m, 2H), 5.22-4.95 (m, 2H), 4.22 (ddd, J = 8.6, 7.2, 1.3 Hz, 1H), 4.04 (dd, J = 12.0, 6.8 Hz 1H), 4.00-3.82 (m, 5H), 3.78-3.63 (m, 2H), 3.44 (dd, J = 9.6, 8.7 Hz, 1H), 3.32 (dd, J = 8.4, 6.5 Hz, 1H), 2.07 (s, 3H), 1.84-1.67 (m, 1H), 1.50 (d, J = 6.3 Hz, 3H), 0.83 (d, J = 6.7 Hz, 3H), 0.79 (d, J = 6.7 Hz, 3H) | ¹³C NMR (CDCl₃) δ 170.69, 170.28, 163.30, 160.23, 157.39, 145.85, 143.96, 142.14, 129.52, 121.10, 115.60, 109.75, 89.42, 84.43, 81.18, 80.62, 74.99, 74.52, 72.69, 56.21, 52.61, 28.99, 20.87, 19.41, 19.34, 18.72 |
| 87 | 115-117 | (Neat) 3364, 2932, 1751, 1650, 1529, 1244, 1094 | HRMS-ESI (m/z) [M]⁺ calcd for C₂₃H₃₅ClN₂O₈, 502.2082; found, 502.2090 | ¹H NMR (CDCl₃) δ 11.92 (s, 1H), 8.67 (d, J = 8.1 Hz, 1H), 8.02-7.98 (m, 1H), 6.87 (d, J = 5.2 Hz, 1H), 5.08-4.99 (m, 2H), 4.05 (dd, J = 11.9, 6.8 Hz, 1H), 4.00 (d, J = 9.3 Hz, 1H), 3.94 (s, 3H), 3.82 (dt, J = 10.7, 5.4 Hz, 2H), 3.66-3.45 (m, 4H), 3.32-3.23 (m, 2H), 1.58 (s, 3H), 1.56 (s, 3H), | ¹³C NMR (CDCl₃) δ 170.36, 169.10, 155.50, 148.89, 140.81, 130.36, 109.73, 84.87, 83.89, 82.38, 75.30, 74.18, 73.05, 70.57, 68.04, 56.24, 52.31, 32.34, 29.65, 29.51, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 1.57-1.50 (m, 2H), 1.50 (d, J = 6.3 Hz, 3H), 1.41-1.29 (m, 2H), 0.91 (t, J = 7.3 Hz, 3H) | 19.51, 18.97, 14.08 |
| 88 | 108-110 | 3288, 2925, 2879, 1752, 1689, 1555, 1330, 1197 | ESIMS m/z 462.3 ([M + H]$^+$) | $^1$H NMR (CDCl$_3$) δ 7.41-7.27 (m, 5H), 5.60 (d, J = 7.5 Hz, 1H), 5.10 (s, 2H), 4.98-4.88 (m, 3H), 4.88-4.81 (m, 2H), 4.74-4.64 (m, 1H), 4.33 (d, J = 11.8 Hz, 1H), 3.96 (s, 2H), 3.95-3.80 (m, 4H), 3.53 (dd, J = 11.9, 6.0 Hz, 1H), 3.38-3.25 (m, 2H), 2.07-1.95 (m, 1H), 1.72 (d, J = 4.7 Hz, 6H), 1.72-1.61 (m, 1H), 0.96 (t, J = 7.4 Hz, 3H) | $^{13}$C NMR (CDCl$_3$) δ 171.00, 155.85, 142.43, 142.12, 136.25, 128.69, 128.36, 128.23, 112.41, 112.00, 83.44, 83.36, 75.92, 74.66, 67.24, 54.84, 25.32, 19.91, 19.78, 9.61 |
| 89 | — | (Neat) 2961, 2926, 1755, 1721, 1504, 1455, 1334, 1244, 1200, 1062 | HRMS-ESI (m/z) [M]$^+$ calcd for C$_{26}$H$_{37}$NO$_7$, 475.2570; found, 475.2593 | $^1$H NMR (CDCl$_3$) δ 7.39-7.27 (m, 5H), 5.76 (d, J = 7.3 Hz, 1H), 5.10 (s, 2H), 4.99-4.87 (m, 5H), 4.74-4.67 (m, 1H), 4.19-3.74 (m, 8H), 3.68 (d, J = 12.7 Hz, 1H), 3.50 (dd, J = 6.3, 4.6 Hz, 1H), 2.27-2.12 (m, 1H), 1.76 (s, 3H), 1.72 (s, 3H), 1.01 (d, J = 6.7 Hz, 3H), 0.98 (d, J = 6.7 Hz, 3H) | $^{13}$C NMR (CDCl$_3$) δ 170.52, 155.96, 142.22, 141.86, 136.45, 128.63, 128.23, 128.17, 113.42, 112.76, 79.45, 77.69, 76.73, 75.73, 74.84, 73.31, 70.03, 67.03, 55.78, 28.68, 19.83, 19.73, 19.63, 19.60 |
| 90 | — | (Neat) 3320, 2969, 2935, 1754, 1722, 1506, 1455, 1200 | ESIMS m/z 462.2 ([M + H]$^+$) | $^1$H NMR (CDCl$_3$) δ 7.41-7.26 (m, 5H), 5.74 (d, J = 7.5 Hz, 1H), 5.10 (s, 2H), 5.10-5.03 (m, 1H), 4.96 (dd, J = 7.9, 0.8 Hz, 2H), 4.89 (d, J = 7.8 Hz, 2H), 4.72 (t, J = 6.0 Hz, 1H), 4.67-4.63 (m, 1H), 4.08-3.79 (m, 7H), 3.78-3.67 (m, 2H), 3.62 (d, J = 12.1 Hz, 1H), 3.45 (ddd, J = 6.9, 3.9, 1.4 Hz, 1H), 1.74 (s, 3H), 1.72 (s, 3H), 1.00 (t, J = 7.4 Hz, 3H) | $^{13}$C NMR (CDCl$_3$) δ 170.76, 155.95, 142.30, 142.06, 136.40, 128.66, 128.27, 128.15, 113.07, 112.78, 78.09, 76.25, 75.88, 73.94, 71.73, 67.09, 55.51, 22.72, 19.76, 19.67, 10.73 |
| 91 | — | — | ESIMS m/z 462.2 ([M + H]$^+$) | $^1$H NMR (CDCl$_3$) δ 7.42-7.28 (m, 5H), 5.52-5.37 (m, 1H), 5.11 (s, 2H), 5.01 (ddd, J = 9.2, 4.8, 2.8 Hz, 1H), 4.98-4.93 (m, 2H), 4.88 (s, 2H), 4.53 (bs, 1H), 4.16-4.09 (m, 1H), 4.04 (d, J = 21.7 Hz, 1H), 4.01 (d, J = 22.0 Hz, 1H), 3.93 (dd, J = 12.2, 3.3 Hz, 2H), 3.87 (dd, J = 11.7, 4.1 Hz, 1H), 3.76 (dd, J = 11.8, 1.7 Hz, 1H), 3.70 (dd, J = 6.4, 2.7 Hz, 1H), 3.55-3.45 (m, 2H), 1.86-1.74 (m, 2H), 1.74 (s, 3H), 1.72 (s, 3H), 0.98 (t, J = 7.4 Hz, 3H) | |
| 92 | — | — | ESIMS m/z 484.3 ([M − H]$^-$) | $^1$H NMR (CDCl$_3$) δ 7.42-7.19 (m, 10H), 5.31-5.19 (m, 1H), 5.18-5.02 (m, 1H), 4.67 (dd, J = 16.0, 11.7 Hz, 2H), 4.60-4.52 (m, 1H), 4.51-4.40 (m, 1H), 4.18-4.08 (m, 2H), 3.92 (dd, J = 11.7, | $^{13}$C NMR (CDCl$_3$) δ 169.03, 154.68, 138.23, 138.17, 128.54, 128.53, 128.12, 128.00, 127.97, 127.85, 77.97, 74.40, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 3.9 Hz, 1H), 3.85-3.75 (m, 2H), 3.59-3.53 (m, 1H), 3.43 (dd, J = 11.5, 5.5 Hz, 1H), 1.44 (s, 9H), 1.36 (d, J = 6.8 Hz, 3H) | 73.44, 72.31, 72.14, 71.61, 28.43, 15.64 |
| 93 | 69-71 | (Neat) 3349, 2978, 2933, 2876, 1753, 1710, 1497, 1367, 1249, 1161, 1074, 734, 697 | ESIMS m/z 508.6 ([M + Na]$^+$) | $^1$H NMR (CDCl$_3$) δ 7.38-7.19 (m, 11H), 5.38-5.20 (d, J = 7.9 Hz, 1H), 5.08-4.96 (dq, J = 8.2, 6.1 Hz, 1H), 4.96-4.88 (d, J = 10.8 Hz, 1H), 4.76-4.48 (m, 3H), 4.02-3.85 (dd, J = 11.8, 6.3 Hz, 2H), 3.77-3.55 (m, 2H), 3.52-3.34 (m, 2H), 1.48-1.36 (s, 12H) | $^{13}$C NMR (CDCl$_3$) δ 171.24, 155.11, 138.11, 137.93, 128.40, 128.38, 127.94, 127.86, 127.74, 84.76, 83.57, 80.17, 75.79, 75.50, 74.90, 72.94, 72.70, 53.72, 28.28, 18.69 |
| 94 | — | — | ESIMS m/z 509.2 ([M + Na]$^+$) | $^1$H NMR (CDCl$_3$) δ 6.02-5.78 (m, 2H), 5.30-5.10 (m, 5H), 4.81 (dq, J = 9.5, 6.3 Hz, 1H), 4.38 (ddd, J = 12.2, 5.5, 1.4 Hz, 1H), 4.24 (dd, J = 12.1, 4.1 Hz, 1H), 4.17-4.02 (m, 3H), 3.95-3.81 (m, 2H), 3.54 (dd, J = 10.9, 7.2 Hz, 1H), 3.41-3.21 (m, 2H), 1.50 (s, 18H), 1.42 (d, J = 6.3 Hz, 3H) | $^{13}$C NMR (CDCl$_3$) δ 169.00, 152.64, 134.93, 134.80, 116.95, 116.78, 84.63, 83.06, 82.84, 75.93, 74.68, 72.85, 72.62, 71.85, 57.94, 27.97, 18.74 |
| 95 | — | (Neat) 3440, 2980, 2935, 1740, 1705, 1367, 1253, 1120 | HRMS-ESI (m/z) [M]$^+$ calcd for C$_{22}$H$_{35}$NO$_{11}$, 489.2210; found, 489.2210 | $^1$H NMR (CDCl$_3$) δ 9.64 (s, 1H), 9.61 (s, 1H), 5.22 (dd, J = 8.8, 3.8 Hz, 1H), 4.97-4.86 (m, 1H), 4.51 (d, J = 18.0 Hz, 1H), 4.34 (d, J = 18.1 Hz, 1H), 4.29-4.19 (m, 2H), 3.91 (dd, J = 11.7, 8.1 Hz, 3H), 3.58 (dd, J = 11.4, 7.1 Hz, 1H), 3.49-3.42 (m, 1H), 3.40-3.33 (m, 1H), 1.49 (s, 18H), 1.47 (d, J = 6.3 Hz, 3H) | $^{13}$C NMR (CDCl$_3$) δ 199.32, 198.53, 168.72, 152.76, 86.24, 84.89, 83.33, 79.40, 76.11, 75.14, 73.28, 72.00, 58.01, 28.09, 18.91 |
| 96 | — | (Neat) 2982, 2938, 1743, 1705, 1367, 1246, 1104 | HRMS-ESI (m/z) [M]$^+$ calcd for C$_{22}$H$_{35}$F$_4$NO$_9$, 533.2248; found, 533.2252 | $^1$H NMR (CDCl$_3$) δ 6.01-5.66 (m, 2H), 5.24 (dd, J = 8.9, 3.7 Hz, 1H), 4.84 (dq, J = 9.5, 6.3 Hz, 1H), 4.27 (dd, J = 12.3, 3.7 Hz, 1H), 4.13-3.98 (m, 1H), 3.96-3.87 (m, 2H), 3.86-3.67 (m, 3H), 3.55 (dd, J = 11.3, 7.3 Hz, 1H), 3.42-3.35 (m, 1H), 3.29 (t, J = 9.2 Hz, 1H), 1.50 (s, 18H), 1.44 (d, J = 6.3 Hz, 3H) | |
| 97 | — | (Neat) 3351, 2978, 2934, 1745, 1707, 1367, 1252, 1121 | HRMS-ESI (m/z) [M]$^+$ calcd for C$_{28}$H$_{47}$NO$_9$, 541.3251; found, 541.3244 | $^1$H NMR (CDCl$_3$) δ 5.79-5.66 (m, 2H), 5.60-5.48 (m, 2H), 5.20 (dd, J = 8.9, 4.2 Hz, 1H), 4.78 (dq, J = 9.4, 6.3 Hz, 1H), 4.31 (ddd, J = 11.1, 6.2, 0.8 Hz, 1H), 4.22 (dd, J = 12.1, 4.2 Hz, 1H), 4.16-3.98 (m, 3H), 3.89 (dd, J = 12.1, 8.9 Hz, 1H), 3.83 (d, J = 10.9 Hz, 1H), 3.52 (dd, J = 10.9, 7.2 Hz, 1H), 3.35-3.28 (m, 1H), 3.24 (t, J = 9.0 Hz, 1H), | $^{13}$C NMR (CDCl$_3$) δ 169.19, 152.75, 129.10, 128.51, 125.64, 125.50, 84.48, 83.15, 82.72, 76.04, 74.65, 72.86, 71.92, 58.03, 28.08, 25.38, 18.90, 13.42, 13.39 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 2.12-1.99 (m, 4H), 1.49 (s, 18H), 1.41 (d, J = 6.3 Hz, 3H), 1.02-0.95 (m, 6H) | |
| 98 | — | (Neat) 2933, 1766, 1710, 1367, 1256, 1148, 1122 | HRMS-ESI (m/z) [M]$^+$ calcd for C$_{28}$H$_{51}$NO$_9$, 545.3564; found, 545.3568 | $^1$H NMR (CDCl$_3$) δ 5.20 (dd, J = 9.0, 4.1 Hz, 1H), 4.76 (dq, J = 9.3, 6.3 Hz, 1H), 4.22 (dd, J = 12.1, 4.1 Hz, 1H), 3.93-3.76 (m, 3H), 3.60-3.43 (m, 4H), 3.24-3.11 (m, 2H), 1.60-1.48 (m, 4H), 1.49 (s, 18H), 1.40 (d, J = 6.3 Hz, 3H), 1.37-1.21 (m, 8H), 0.93-0.81 (m, 6H) | $^{13}$C NMR (CDCl$_3$) δ 169.20, 152.76, 85.05, 83.54, 83.14, 75.89, 74.07, 72.91, 72.84, 71.11, 58.01, 30.21, 29.97, 28.50, 28.07, 22.73, 22.68, 18.79, 14.16 |
| 99 | 51-54 | — | ESIMS m/z 452.3 ([M + H]$^+$) | $^1$H NMR (CDCl$_3$) δ 7.36-7.25 (m, 5H), 5.32-5.21 (m, 1H), 4.91 (dq, J = 9.5, 6.3 Hz, 1H), 4.68-4.60 (m, 1H), 4.62 (s, 2H), 3.96-3.81 (m, 3H), 3.67 (dd, J = 11.6, 4.8 Hz, 1H), 3.58 (dd, J = 10.8, 7.3 Hz, 1H), 3.50 (dd, J = 15.5, 6.9 Hz, 1H), 3.36 (dd, J = 12.0, 4.8 Hz, 1H), 3.23 (t, J = 9.1 Hz, 1H), 1.60-1.44 (m, 2H), 1.44 (d, J = 5.8 Hz, 3H), 1.43 (s, 9H), 1.41-1.22 (m, 2H), 0.88 (t, J = 7.3 Hz, 3H) | $^{13}$C NMR (CDCl$_3$) δ 171.47, 155.24, 138.27, 128.50, 127.88, 127.81, 85.31, 83.48, 80.28, 75.53, 74.86, 74.01, 73.14, 73.03, 53.77, 32.60, 28.42, 19.49, 18.71, 14.11 |
| 100 | — | (Neat) 3347, 2932, 1754, 1714, 1498, 1367, 1163, 1094 | HRMS-ESI (m/z) [M]$^+$ calcd for C$_{24}$H$_{37}$NO$_7$, 451.2570; found, 451.2560 | $^1$H NMR (CDCl$_3$) δ 7.38-7.24 (m, 5H), 5.34-5.23 (m, 1H), 5.02-4.91 (m, 1H), 4.93 (d, J = 10.8 Hz, 1H), 4.68-4.60 (m, 1H), 4.59 (d, J = 10.9 Hz, 1H), 3.92 (dd, J = 11.8, 6.7 Hz, 1H), 3.81 (d, J = 11.1 Hz, 1H), 3.68 (dd, J = 11.7, 4.9 Hz, 1H), 3.60 (t, J = 6.7 Hz, 1H), 3.58 (t, J = 6.8 Hz, 1H), 3.51 (dt, J = 9.1, 6.6 Hz, 1H), 3.37 (t, J = 9.0 Hz, 1H), 3.26 (t, J = 7.4 Hz, 1H), 1.59-1.49 (m, 2H), 1.43 (s, 9H), 1.41 (d, J = 6.3 Hz, 3H), 1.40-1.30 (m, 2H), 0.88 (t, J = 7.4 Hz, 3H) | $^{13}$C NMR (CDCl$_3$) δ 171.43, 155.22, 138.42, 128.49, 128.04, 127.83, 84.76, 83.99, 80.24, 75.84, 75.35, 74.81, 72.82, 70.78, 53.76, 32.31, 28.40, 19.47, 18.82, 14.02 |
| 101 | — | (Neat) 2932, 1766, 1709, 1367, 1256, 1147, 1122 | HRMS-ESI (m/z) [M]$^+$ calcd for C$_{29}$H$_{45}$NO$_9$, 551.3094; found, 551.3109 | $^1$H NMR (CDCl$_3$) δ 7.40-7.23 (m, 5H), 5.23 (dd, J = 8.9, 4.1 Hz, 1H), 4.94 (d, J = 10.9 Hz, 1H), 4.85 (dq, J = 9.1, 6.3 Hz, 1H), 4.60 (d, J = 10.9 Hz, 1H), 4.25 (dd, J = 12.1, 4.1 Hz, 1H), 3.92 (dd, J = 12.2, 8.9 Hz, 1H), 3.85 (d, J = 10.7 Hz, 1H), 3.65-3.48 (m, 3H), 3.42-3.30 (m, 2H), 1.61-1.45 (m, 2H), 1.50 (s, 18H), 1.41 (d, J = 6.3 Hz, 3H), 1.38-1.28 (m, 2H), 0.88 (t, J = 7.4 Hz, 3H) | — |
| 102 | — | (Neat) 3357, 2979, 1751, 1691, | ESIMS m/z 304.2 ([M − H]$^-$) | $^1$H NMR (CDCl$_3$) δ 5.52 (d, J = 7.9 Hz, 1H), 5.02 (dq, J = 12.7, 6.3 Hz, 1H), 4.67-4.58 (m, 1H), 4.10-4.01 (m, 1H), | $^{13}$C NMR (CDCl$_3$) δ 171.04, 155.49, 80.40, 79.61, 78.32, 76.66, |

TABLE 2-continued

Analytical Data

| Compound Number | MP (°C.) | IR (cm$^{-1}$) | MASS | $^1$H NMR* | $^{13}$C NMR* |
|---|---|---|---|---|---|
| | | 1523, 1368, 1163, 1047 | | 3.93 (dd, J = 11.7, 2.6 Hz, 1H), 3.84 (dd, J = 11.7, 5.8 Hz, 1H), 3.52-3.36 (m, 3H), 3.08 (bs, 1H), 2.90 (bs, 1H), 1.47 (d, J = 6.3 Hz, 3H), 1.43 (s, 9H) | 74.59, 73.06, 54.80, 28.44, 18.74 |
| 103 | — | (Neat) 3353, 2976, 1742, 1519, 1368, 1251, 1155 | HRMS-ESI (m/z) [M]$^+$ calcd for C$_{21}$H$_{35}$NO$_9$, 445.2312; found, 445.2322 | $^1$H NMR (CDCl$_3$) δ 5.41 (d, J = 8.2 Hz, 1H), 5.21-5.12 (m, 1H), 5.12-5.04 (m, 1H), 4.92-4.83 (m, 1H), 4.74 (dd, J = 13.4, 6.9 Hz, 1H), 3.95 (dd, J = 11.7, 7.0 Hz, 1H), 3.80-3.65 (m, 3H), 2.64-2.41 (m, 2H), 1.44 (s, 9H), 1.32 (d, J = 6.2 Hz, 3H), 1.20 (d, J = 7.0 Hz, 3H), 1.16 (d, J = 7.0 Hz, 3H), 1.14 (d, J = 7.0 Hz, 3H), 1.10 (d, J = 7.0 Hz, 3H) | $^{13}$C NMR (CDCl$_3$) δ 175.57, 175.47, 171.37, 155.18, 80.34, 74.52, 74.30, 74.15, 73.35, 71.34, 34.01, 33.91, 28.30, 19.01, 18.88, 18.74, 18.71, 18.03 |
| 104 | — | (Neat) 2980, 2935, 1746, 1707, 1367, 1254, 1106 | HRMS-ESI (m/z) [M]$^+$ calcd for C$_{20}$H$_{35}$NO$_9$, 433.2312; found, 433.2317 | $^1$H NMR (CDCl$_3$) δ 5.19 (dd, J = 8.9, 4.2 Hz, 1H), 4.75 (dq, J = 9.4, 6.3 Hz, 1H), 4.23 (dd, J = 12.1, 4.2 Hz, 1H), 3.89 (dd, J = 12.1, 9.0 Hz, 1H), 3.80 (d, J = 10.6 Hz, 1H), 3.56-3.48 (m, 1H), 3.52 (s, 3H), 3.42 (s, 3H), 3.17-3.11 (m, 1H), 3.06 (t, J = 9.0 Hz, 1H), 1.48 (s, 18H), 1.40 (d, J = 6.3 Hz, 3H) | $^{13}$C NMR (CDCl$_3$) δ 169.10, 152.73, 86.77, 85.12, 83.13, 75.07, 72.76, 72.52, 61.21, 58.43, 57.94, 28.03, 18.65 |
| 105 | — | — | ESIMS m/z 496.7 ([M + Na]$^+$) | $^1$H NMR (CDCl$_3$) δ 5.81 (dd, J = 17.7, 10.6 Hz, 1H), 5.17-5.14 (m, 1H), 4.99-4.86 (m, 2H), 4.19 (dd, J = 11.6, 9.1 Hz, 1H), 4.13-4.02 (m, 2H), 3.83-3.71 (m, 2H), 3.55-3.47 (m, 2H), 2.78 (d, J = 5.3 Hz, 1H), 1.48 (s, 18H), 1.38 (d, J = 6.8 Hz, 3H), 1.27 (s, 3H), 1.23 (s, 3H) | $^{13}$C NMR (CDCl$_3$) δ 169.43, 152.53, 143.20, 115.09, 83.16, 77.26, 76.60, 75.75, 74.16, 73.32, 71.73, 58.07, 28.00, 26.74, 26.30, 19.31 |
| 106 | — | — | ESIMS m/z 496.7 ([M + Na]$^+$) | $^1$H NMR (CDCl$_3$) δ 5.79 (dd, J = 17.8, 10.5 Hz, 1H), 5.18 (dd, J = 8.2, 3.4 Hz, 1H), 5.15 (s, 1H), 5.11 (dd, J = 5.6, 0.7 Hz, 1H), 4.95 (dq, J = 12.9, 6.4 Hz, 1H), 4.14 (dd, J = 12.4, 3.4 Hz, 1H), 3.96-3.84 (m, 2H), 3.45 (dd, J = 10.6, 7.6 Hz, 1H), 3.41-3.32 (m, 2H), 3.05 (d, J = 1.3 Hz, 1H), 1.47 (s, 18H), 1.42 (d, J = 6.4 Hz, 3H), 1.29 (s, 3H), 1.26 (s, 3H) | $^{13}$C NMR (CDCl$_3$) δ 169.01, 152.64, 142.56, 115.33, 83.07, 79.83, 77.47, 76.46, 74.46, 74.35, 74.01, 58.56, 28.04, 26.82, 25.82, 18.56 |
| 107 | — | — | ESIMS m/z 550.8 ([M + Na]$^+$) | $^1$H NMR (CDCl$_3$) δ 5.90 (dd, J = 17.9, 10.5 Hz, 1H), 5.17 (dd, J = 8.6, 4.1 Hz, 1H), 5.07-5.05 (m, 1H) 5.03 (dd, J = 4.9, 1.1 Hz, 1H) 4.96-4.89 (m, 1H), 4.85-4.77 (m, 2H), 4.33 (d, J = 12.1 Hz, 1H), 4.13 (dd, J = 12.2, 4.1 Hz, 1H), 3.86 (dd, J = 12.3, 8.6 Hz, 1H), 3.81 (t, J = 11.8 Hz, 2H), 3.48 (dd, J = 10.7, 7.2 Hz, | $^{13}$C NMR (CDCl$_3$) δ 169.08, 152.57, 144.07, 142.26, 114.06, 111.66, 84.32, 83.01, 79.73, 77.43, 77.12, 76.01, 73.04, 72.85, 58.13, 28.01, 27.04, 25.68, 19.95, 18.83 |

TABLE 2-continued

Analytical Data

| Compound Number | MP (° C.) | IR (cm⁻¹) | MASS | ¹H NMR* | ¹³C NMR* |
|---|---|---|---|---|---|
| | | | | 1H), 3.41 (t, J = 7.5 Hz, 1H), 3.11 (t, J = 8.8 Hz, 1H), 1.70 (s, 3H), 1.46 (s, 18H), 1.38 (d, J = 6.3 Hz, 3H), 1.26 (s, 3H), 1.22 (s, 3H) | |
| 108 | — | — | ESIMS m/z 553.4 ([M + Na]⁺) | ¹H NMR (CDCl₃) δ 5.18 (dd, J = 8.6, 3.8 Hz, 1H), 4.87-4.77 (m, 1H), 4.15 (dd, J = 12.3, 3.9 Hz, 1H), 3.87 (dd, J = 12.3, 8.6 Hz, 1H), 3.81 (dd, J = 10.0, 4.3 Hz, 1H), 3.75 (dd, J = 8.5, 5.6 Hz, 1H), 3.54-3.43 (m, 2H), 3.10-2.99 (m, 2H), 1.91-1.72 (m, 1H), 1.48 (s, 18H), ), 1.47-1.41 (m, 2H), 1.39 (d, J = 6.3 Hz, 3H), 1.13 (s, 3H), 1.10 (s, 3H), 0.90 (d, J = 6.6 Hz, 3H), 0.85 (t, J = 7.5 Hz, 3H), 0.84 (d, J = 6.7 Hz, 3H) | ¹³C NMR (CDCl₃) δ 169.10, 152.63, 84.90, 83.01, 81.02, 80.20, 77.56, 75.09, 73.14, 73.07, 58.27, 35.03, 29.04, 28.04, 25.12, 25.00, 19.89, 19.53, 18.97, 9.00 |
| 109 | — | — | ESIMS m/z 550.8 ([M + Na]⁺) | ¹H NMR (CDCl₃) δ 5.92 (dd, J = 17.6, 10.8 Hz, 1H), 5.14-5.06 (m, 2H), 5.06-5.00 (m, 1H), 4.97-4.91 (m, 2H), 4.89-4.81 (m, 1H), 4.16 (dd, J = 12.1, 8.1 Hz, 1H), 4.03 (dd, J = 11.6, 7.0 Hz, 1H), 3.99-3.94 (m, 1H), 3.93-3.81 (m, 2H), 3.73-3.67 (m, 1H), 3.56-3.51 (m, 1H), 3.21 (td, J = 6.6, 1.6 Hz, 1H), 1.72 (s, 3H), 1.52-1.45 (m, 21H), 1.39 (d, J = 6.7 Hz, 3H), 1.27 (s, 3H) | ¹³C NMR (CDCl₃) δ 169.59, 152.73, 152.62, 144.07, 142.20, 114.19, 112.54, 83.00, 80.59, 77.04, 76.10, 75.42, 74.38, 73.22, 58.15, 28.06, 26.69, 26.52, 19.77, 18.71 |
| 110 | — | — | ESIMS m/z 555.5 ([M + Na]⁺) | ¹H NMR (CDCl₃) δ 5.05 (t, J = 7.3 Hz, 1H), 4.94-4.84 (m, 1H), 4.17 (dd, J = 11.6, 7.5 Hz, 1H), 4.04 (dd, J = 11.6, 7.1 Hz, 1H), 3.88 (dd, J = 12.3, 5.9 Hz, 1H), 3.69-3.61 (m, 2H), 3.27 (d, J = 6.7 Hz, 2H), 3.19-3.12 (m, 1H), 1.92-1.74 (m, 1H), 1.52-1.47 (m, 20H), 1.41 (d, J = 6.7 Hz, 3H), 1.13 (s, 3H), 1.12 (s, 3H), 0.92-0.84 (m, 9H) | ¹³C NMR (CDCl₃) δ 169.70, 152.68, 83.00, 82.98, 75.49, 75.39, 73.27, 73.13, 58.15, 35.30, 28.79, 28.07, 25.59, 25.53, 19.70, 19.63, 18.86, 8.99 |
| 111 | — | (Neat) 3323, 2960, 2933, 2874, 1755, 1710, 1521, 1367, 1248, 1164, 1084 | HRMS-ESI (m/z) [M]⁺ calcd for C₁₇H₃₁NO₇, 361.2101; found, 361.2107 | ¹H NMR (CDCl₃) δ 5.41 (d, J = 7.1 Hz, 1H), 5.08 (dq, J = 9.3, 6.3 Hz, 1H), 4.66-4.56 (m, 1H), 4.07 (d, J = 12.0 Hz, 1H), 4.02 (d, J = 13.5 Hz, 1H), 3.81 (dd, J = 11.9, 5.6 Hz, 1H), 3.65 (dt, J = 9.3, 6.6 Hz, 1H), 3.44-3.34 (m, 3H), 3.17 (s, 1H), 3.08-3.01 (m, 1H), ), 1.59-1.49 (m, 2H), 1.46 (d, J = 6.3 Hz, 3H), 1.44 (s, 9H), 1.41-1.31 (m, 2H), 0.91 (t, J = 7.4 Hz, 3H) | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 112 | — | (Neat) 3536, 2979, 2934, 2875, 1764, 1747, 1706, 1366, 1246, 1147, 1121, 1088, 1049 | HRMS-ESI (m/z) [M]$^+$ calcd for C$_{22}$H$_{39}$NO$_9$, 461.2625; found, 461.2632 | $^1$H NMR (CDCl$_3$) δ 5.27 (dd, J = 8.8, 2.4 Hz, 1H), 4.91 (dq, J = 9.2, 6.3 Hz, 1H), 4.27 (dd, J = 12.4, 2.4 Hz, 1H), 4.08 (dd, J = 10.9, 0.8 Hz, 1H), 3.90 (dd, J = 12.4, 8.8 Hz, 1H), 3.66 (dt, J = 9.4, 6.6 Hz, 1H), 3.46-3.36 (m, 3H), 3.22-3.14 (m, 1H), 3.11 (d, J = 1.1 Hz, 1H), 1.57-1.51 (m, 2H), 1.51 (s, 18H), 1.45 (d, J = 6.3 Hz, 3H), 1.40-1.29 (m, 2H), 0.91 (t, J = 7.4 Hz, 3H) | $^{13}$C NMR (CDCl$_3$) δ 168.42, 152.63, 82.95, 82.47, 76.64, 76.60, 74.41, 73.34, 69.79, 58.57, 31.80, 27.93, 19.25, 18.69, 13.81 |
| 113 | 69-71 | (Neat) 3364, 2967, 2935, 2876, 1745, 1717, 1517, 1367, 1153, 1096 | HRMS-ESI (m/z) [M]$^+$ calcd for C$_{21}$H$_{37}$NO$_8$, 431.2519; found, 431.2524 | $^1$H NMR (CDCl$_3$) δ 5.34 (d, J = 7.9 Hz, 1H), 5.12-4.99 (m, 1H), 4.93 (t, J = 9.4 Hz, 1H), 4.71-4.63 (m, 1H), 3.94-3.85 (m, 2H), 3.77 (dd, J = 11.7, 3.7 Hz, 1H), 3.59-3.45 (m, 2H), 3.30 (dt, J = 9.1, 6.6 Hz, 1H), 3.17 (t, J = 7.9 Hz, 1H), 2.53 (hept, J = 7.0 Hz, 1H), 1.41 (s, 9H), 1.28 (d, J = 6.3 Hz, 3H), 1.30-1.20 (m, 2H), 1.19-1.13 (m, 8H), 0.84 (t, J = 7.3 Hz, 3H) | $^{13}$C NMR (CDCl$_3$) δ 175.77, 171.28, 155.23, 80.88, 80.29, 75.79, 75.70, 75.30, 71.49, 70.49, 54.10, 34.18, 32.00, 28.37, 19.30, 19.16, 18.84, 18.28, 13.94 |
| 114 | 97-99 | (Neat) 3339, 2959, 2933, 1716, 1513, 1367, 1257, 1162, 1095, 710 | HRMS-ESI (m/z) [M]$^+$ calcd for C$_{24}$H$_{35}$NO$_8$, 465.2363; found, 465.2380 | $^1$H NMR (CDCl$_3$) δ 8.13-7.98 (m, 2H), 7.59-7.51 (m, 1H), 7.47-7.40 (m, 2H), 5.41 (d, J = 7.8 Hz, 1H), 5.30-5.16 (m, 2H), 4.78-4.66 (m, 1H), 4.02-3.90 (m, 2H), 3.83 (dd, J = 11.7, 3.7 Hz, 1H), 3.62 (dd, J = 11.0, 7.9 Hz, 1H), 3.50 (dt, J = 9.2, 6.3 Hz, 1H), 3.32 (t, J = 7.8 Hz, 1H), 3.26 (dt, J = 9.1, 6.6 Hz, 1H), 1.43 (s, 9H), 1.37 (d, J = 6.0 Hz, 3H), 1.29-1.18 (m, 2H), 1.12-0.93 (m, 2H), 0.59 (t, J = 7.4 Hz, 3H) | $^{13}$C NMR (CDCl$_3$) δ 171.27, 165.48, 155.23, 133.46, 133.23, 130.17, 129.92, 129.77, 128.47, 81.09, 80.27, 76.90, 75.94, 75.45, 71.48, 70.78, 54.20, 31.78, 28.35, 19.04, 18.39, 13.62 |
| 115 | — | (Neat) 2979, 2933, 2875, 1765, 1747, 1707, 1367, 1243, 1106 | HRMS-ESI (m/z) [M]$^+$ calcd for C$_{23}$H$_{41}$NO$_9$, 475.2781; found, 475.2784 | $^1$H NMR (CDCl$_3$) δ 5.20 (dd, J = 9.0, 4.1 Hz, 1H), 4.73 (dq, J = 9.7, 6.3 Hz, 1H), 4.22 (dd, J = 12.1, 4.1 Hz, 1H), 3.88 (dd, J = 12.1, 9.0 Hz, 1H), 3.80 (dd, J = 10.7, 0.6 Hz, 1H), 3.62-3.43 (m, 3H), 3.53 (s, 3H), 3.24-3.17 (m, 1H), 3.08-3.01 (m, 1H), 1.57-1.45 (m, 2H), 1.48 (s, 18H), 1.40 (d, J = 6.3 Hz, 3H), 1.39-1.28 (m, 2H), 0.88 (t, J = 7.4 Hz, 3H) | $^{13}$C NMR (CDCl$_3$) δ 169.12, 152.73, 86.80, 83.43, 83.12, 75.78, 72.79, 72.64, 70.71, 61.45, 57.97, 32.29, 28.03, 19.43, 18.69, 13.99 |
| 116 | — | (Neat) 2979, 2933, 1765, 1708, 1367, | HRMS-ESI (m/z) [M]$^+$ calcd for C$_{25}$H$_{43}$NO$_9$, 501.2938; | $^1$H NMR (CDCl$_3$) δ 5.89 (ddt, J = 16.2, 10.4, 5.7 Hz, 1H), 5.27-5.17 (m, 2H), 5.13 (dd, J = 10.4, 1.7 Hz, 1H), 4.78 (dq, J = 12.6, 6.2 Hz, 1H), | $^{13}$C NMR (CDCl$_3$) δ 169.13, 152.73, 135.04, 116.82, 84.57, 83.62, 83.13, 75.87, |

TABLE 2-continued

Analytical Data

| Compound Number | MP (°C.) | IR (cm$^{-1}$) | MASS | $^1$H NMR* | $^{13}$C NMR* |
|---|---|---|---|---|---|
| | | 1244, 1121, 1098 | found, 501.2955 | 4.36 (ddt, J = 12.1, 5.4, 1.3 Hz, 1H), 4.22 (dd, J = 12.1, 4.1 Hz, 1H), 4.10-4.03 (m, 1H), 3.89 (dd, J = 12.2, 9.0 Hz, 1H), 3.81 (d, J = 10.8 Hz, 1H), 3.60-3.44 (m, 3H), 3.29-3.17 (m, 2H), 1.57-1.45 (m, 2H), 1.48 (s, 18H), 1.40 (d, J = 6.3 Hz, 3H), 1.38-1.27 (m, 2H), 0.88 (t, J = 7.4 Hz, 3H) | 74.70, 72.87, 72.72, 70.76, 58.00, 32.30, 28.05, 19.42, 18.85, 14.02 |
| 117 | — | (Neat) 2978, 2933, 2874, 1765, 1709, 1456, 1367, 1244, 1147, 1120, | HRMS-ESI (m/z) [M]$^+$ calcd for C$_{26}$H$_{45}$NO$_9$, 515.3094; found, 515.3101 | $^1$H NMR (CDCl$_3$) δ 5.21 (dd, J = 8.9, 4.1 Hz, 1H), 4.96-4.92 (m, 1H), 4.86-4.77 (m, 2H), 4.30 (d, J = 11.6 Hz, 1H), 4.23 (dd, J = 12.1, 4.1 Hz, 1H), 3.95-3.86 (m, 2H), 3.81 (d, J = 10.8 Hz, 1H), 3.60-3.44 (m, 3H), 3.30-3.20 (m, 2H), 1.73 (s, 3H), 1.55-1.45 (m, 2H), 1.49 (s, 18H), 1.42 (d, J = 6.3 Hz, 3H), 1.38-1.28 (m, 2H), 0.88 (t, J = 7.4 Hz, 3H) | $^{13}$C NMR (CDCl$_3$) δ 169.17, 152.77, 142.55, 111.93, 84.92, 83.69, 83.17, 77.66, 75.85, 72.88, 72.75, 70.76, 58.03, 32.36, 28.08, 19.95, 19.47, 18.86, 14.06 |
| 118 | — | (Neat) 3313, 1637, 1367 | HRMS-ESI (m/z) [M]$^+$ calcd for C$_{26}$H$_{47}$NO$_9$, 517.3521; found, 517.3527 | $^1$H NMR (CDCl$_3$) δ 5.20 (dd, J = 8.9, 4.2 Hz, 1H), 4.78 (dq, J = 9.4, 6.3 Hz, 1H), 4.23 (dd, J = 12.1, 4.2 Hz, 1H), 3.90 (dd, J = 12.1, 9.0 Hz, 1H), 3.80 (d, J = 10.6 Hz, 1H), 3.66 (dd, J = 8.4, 6.1 Hz, 1H), 3.60-3.42 (m, 3H), 3.26-3.18 (m, 2H), 3.18-3.10 (m, 1H), 1.87-1.74 (m, 1H), 1.56-1.44 (m, 2H), 1.49 (s, 18H), 1.40 (d, J = 6.3 Hz, 3H), 1.39-1.28 (m, 2H), 0.93-0.84 (m, 9H) | $^{13}$C NMR (CDCl$_3$) δ 169.21, 152.77, 84.93, 83.58, 83.13, 80.65, 75.88, 72.92, 72.85, 70.74, 58.02, 32.36, 29.26, 28.08, 19.69, 19.51, 19.48, 18.83, 14.06 |
| 119 | — | (Neat) 2934, 2876, 1743, 1706, 1367, 1253, 1121, 1096 | HRMS-ESI (m/z) [M]$^+$ calcd for C$_{24}$H$_{41}$NO$_{10}$, 503.2730; found, 503.2727 | $^1$H NMR (CDCl$_3$) δ 9.63 (s, 1H), 5.18 (dd, J = 8.9, 3.8 Hz, 1H), 4.84 (dq, J = 9.4, 6.3 Hz, 1H), 4.39 (dd, J = 17.9, 0.9 Hz, 1H), 4.22 (dd, J = 17.8, 0.5 Hz, 1H), 4.19 (dd, J = 12.2, 3.8 Hz, 1H), 3.91-3.75 (m, 2H), 3.57-3.42 (m, 2H), 3.37 (dt, J = 9.2, 6.5 Hz, 1H), 3.29 (dd, J = 7.9, 6.9 Hz, 1H), 3.21 (t, J = 9.0 Hz, 1H), 1.52-1.40 (m, 2H), 1.45 (s, 18H), 1.41 (d, J = 6.3 Hz, 3H), 1.30-1.19 (m, 2H), 0.83 (t, J = 7.3 Hz, 3H) | $^{13}$C NMR (CDCl$_3$) δ 200.51, 168.79, 152.61, 86.19, 83.52, 83.08, 79.09, 75.35, 72.95, 71.99, 70.03, 57.92, 32.02, 27.94, 19.29, 18.84, 13.85 |
| 120 | — | (Neat) 2980, 2395, 2877, 1747, 1708, 1367, 1254, 1120 | HRMS-ESI (m/z) [M]$^+$ calcd for C$_{24}$H$_{41}$F$_2$NO$_9$, 525.2749; found, 525.2723 | $^1$H NMR (CDCl$_3$) δ 5.81 (tdd, J = 55.1 (H-F), 4.7, 3.4 Hz, 1H), 5.21 (dd, J = 9.0, 3.8 Hz, 1H), 4.80 (dq, J = 12.6, 6.2 Hz, 1H), 4.23 (dd, J = 12.2, 3.8 Hz, 1H), 4.13-3.99 (m, 1H), 3.92-3.71 (m, 3H), 3.56 (dt, J = 9.1, 6.8 Hz, 1H), 3.52-3.40 (m, 2H), 3.29-3.19 (m, 2H), | $^{13}$C NMR (CDCl$_3$) δ 168.92, 152.72, 114.35 (t, J = 241.7 Hz), 86.15, 83.55, 83.20, 75.56, 73.03, 72.78 (t, J = 27.6 Hz), 72.17, 70.36, 58.01, 32.19, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 1.56-1.45 (m, 2H), 1.48 (s, 18H), 1.41 (d, J = 6.3 Hz, 3H), 1.38-1.26 (m, 2H),, 0.89 (t, J = 7.4 Hz, 3H) | 28.04, 19.40, 18.71, 13.97 |
| 121 | — | (Neat) 3364, 2954, 2873, 1742, 1467, 1183, 1094 | HRMS-ESI (m/z) [M]$^+$ calcd for C$_{17}$H$_{33}$NO$_5$, 331.2359; found, 331.2350 | $^1$H NMR (CDCl$_3$) δ 4.79 (td, J = 8.8, 3.1 Hz, 1H), 3.92 (dd, J = 11.7, 6.8 Hz, 1H), 3.78 (t, J = 6.4 Hz, 1H), 3.68 (dd, J = 8.4, 6.1 Hz, 1H), 3.62 (d, J = 3.7 Hz, 2H), 3.45 (dd, J = 11.7, 6.0 Hz, 1H), 3.36-3.13 (m, 5H), 2.08-1.95 (m, 1H), 1.88-1.74 (m, 2H), 1.72-1.58 (m, 3H), 0.97 (t, J = 7.4 Hz, 3H), 0.92-0.86 (m, 12H) | |
| 122 | — | (Neat) 2955, 2872, 1745, 1467, 1180, 1081 | HRMS-ESI (m/z) [M]$^+$ calcd for C$_{17}$H$_{33}$NO$_5$, 331.2359; found, 331.2373 | $^1$H NMR (CDCl$_3$) δ 4.96 (dt, J = 10.1, 3.6 Hz, 1H), 4.07 (dd, J = 11.7, 3.5 Hz, 1H), 3.90-3.77 (m, 3H), 3.68 (dd, J = 7.1, 3.0 Hz, 1H), 3.63 (dd, J = 11.7, 1.7 Hz, 1H), 3.42-3.25 (m, 4H), 3.20 (dd, J = 8.8, 6.8 Hz, 1H), 1.91-1.76 (m, 3H), 1.76-1.59 (m, 3H), 1.00 (t, J = 7.4 Hz, 3H), 0.89 (ddd, J = 6.9, 4.0, 1.6 Hz, 12H) | — |
| 123 | — | (Neat) 2955, 2873, 1744, 1228, 1084 | HRMS-ESI (m/z) [M]$^+$ calcd for C$_{17}$H$_{33}$NO$_5$, 331.2359; found, 331.2367 | $^1$H NMR (CDCl$_3$) δ 4.99-4.94 (m, 1H), 4.17-4.08 (m, 2H), 3.92 (dd, J = 11.8, 3.8 Hz, 1H), 3.88-3.80 (m, 1H), 3.77 (d, J = 10.4 Hz, 1H), 3.65 (dt, J = 8.0, 4.0 Hz, 1H), 3.67-3.54 (m, 2H), 3.44-3.36 (m, 2H), 3.28 (ddd, J = 13.3, 8.8, 6.6 Hz, 2H), 3.19 (dd, J = 8.8, 6.8 Hz, 1H), 1.92-1.72 (m, 4H), 1.02 (t, J = 7.4 Hz, 3H), 0.95-0.83 (m, 12H) | — |
| 124 | — | (Neat) 3365, 1636, 1235, 1063 | HRMS-ESI (m/z) [M]$^+$ calcd for C$_{22}$H$_{27}$NO$_5$, 385.1889; found, 385.1890 | $^1$H NMR (CDCl$_3$) δ 8.76 (bs, 2H), 7.35-7.20 (m, 10H), 5.30 (s, 1H), 4.69-4.45 (m, 5H), 4.20 (d, J = 9.1 Hz, 2H), 3.89-3.75 (m, 2H), 3.59 (d, J = 11.1 Hz, 1H), 3.47 (d, J = 7.1 Hz, 1H), 1.32 (d, J = 6.8 Hz, 3H) | — |
| 125 | 174-177 | — | ESIMS m/z 352.2 ([M + H]$^+$) | $^1$H NMR (CDCl$_3$) δ 8.71 (bs, 1H), 7.36-7.25 (m, 5H), 5.04-4.90 (m, 1H), 4.92 (d, J = 10.8 Hz, 1H), 4.63-4.47 (m, 2H), 4.39-4.21 (m, 1H), 4.16-3.97 (m, 1H), 3.94-3.79 (m, 1H), 3.64-3.42 (m, 3H), 3.40-3.22 (m, 2H), 1.57-1.45 (m, 2H), 1.44-1.21 (m, 7H), 0.86 (t, J = 7.3 Hz, 3H) | $^{13}$C NMR (CDCl$_3$) δ 168.62, 138.39, 128.50, 128.06, 127.85, 84.55, 83.65, 76.01, 75.84, 73.82, 71.16, 70.82, 53.59, 32.36, 19.50, 18.76, 14.08 |
| 126 | 90-91 | — | ESIMS m/z 470.3 ([M + Na]$^+$) | $^1$H NMR (CDCl$_3$) δ 7.40-7.28 (m, 5H), 5.55 (d, J = 7.7 Hz, 1H), 5.10 (s, 2H), 5.01-4.91 (m, 3H), 4.85 (d, J = 1.2 Hz, 2H), 4.69 (dd, J = 12.1, 6.7 Hz, 1H), 4.32 (d, J = 11.7 Hz, | $^{13}$C NMR (CDCl$_3$) δ 170.85, 155.71, 142.26, 142.02, 136.10, 128.57, 128.25, 128.11, 112.33, 112.02, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 1H), 3.99-3.89 (m, 4H), 3.85 (d, J = 11.3 Hz, 1H), 3.74 (dd, J = 11.9, 4.5 Hz, 1H), 3.60-3.51 (m, 1H), 3.33-3.23 (m, 2H), 1.72 (d, J = 6.2 Hz, 6H), 1.44 (d, J = 6.3 Hz, 3H) | 84.95, 83.01, 77.63, 75.87, 74.89, 74.66, 72.86, 67.14, 54.26, 19.81, 19.66, 18.63, 0.03 |
| 127 | 79-81 | — | ESIMS m/z 471.1 ([M + Na]$^+$) | $^1$H NMR (CDCl$_3$) δ 7.40-7.29 (m, 5H), 5.57 (d, J = 7.9 Hz, 1H), 5.10 (s, 2H), 5.02-4.92 (m, 3H), 4.91-4.83 (m, 2H), 4.82-4.65 (m, 2H), 4.17-3.87 (m, 5H), 3.84-3.77 (m, 1H), 3.68-3.59 (m, 1H), 3.56 (td, J = 7.0, 3.3 Hz, 1H), 3.12 (dd, J = 8.2, 6.6 Hz, 1H), 1.85-1.66 (m, 6H), 1.23 (d, J = 6.2 Hz, 3H) | — |
| 128 | — | — | ESIMS m/z 506.3 ([M + H]$^+$) | $^1$H NMR (CDCl$_3$) δ 7.37-7.24 (m, 15H), 5.54 (d, J = 8.0 Hz, 1H), 5.11 (s, 2H), 4.80-4.61 (m, 6H), 4.09 (dd, J = 11.5, 3.9 Hz, 1H), 3.99 (dd, J = 11.5, 6.7 Hz, 1H), 3.78 (dt, J = 8.4, 3.8 Hz, 2H), 3.72-3.63 (m, 1H), 3.56 (dd, J = 11.5, 6.0 Hz, 1H), 3.49-3.39 (m, 1H) | $^{13}$C NMR (CDCl$_3$) δ 171.66, 155.61, 138.01, 137.98, 136.10, 128.59, 128.50, 128.45, 128.28, 128.15, 127.91, 127.89, 127.82, 81.63, 79.43, 73.96, 73.80, 73.26, 72.96, 67.17, 63.80, 54.10 |
| 129 | — | — | ESIMS m/z 372.9 ([M + H]$^+$) | $^1$H NMR (CDCl$_3$) δ 7.79-6.92 (m, 10H), 4.79-4.53 (m, 6H), 4.14 (dd, J = 11.4, 3.6 Hz, 1H), 3.97 (dd, J = 11.4, 7.2 Hz, 1H), 3.87-3.74 (m, 3H), 3.73-3.56 (m, 2H), 3.45 (ddd, J = 7.8, 6.0, 1.8 Hz, 1H), 3.25 (dd, J = 11.5, 7.9 Hz, 1H) | $^{13}$C NMR (CDCl$_3$) δ 175.95, 138.09, 138.04, 128.46, 128.40, 128.00, 127.88, 127.85, 127.74, 81.49, 79.46, 75.01, 73.66, 72.75, 71.53, 63.47, 54.33 |
| 130 | — | — | ESIMS m/z 506.8 ([M + Na]$^+$) | $^1$H NMR (CDCl$_3$) δ 7.44-7.12 (m, 10H), 5.24 (qd, J = 6.7, 3.3 Hz, 1H), 5.20-5.06 (m, 1H), 4.76-4.52 (m, 4H), 4.21-4.06 (m, 1H), 3.92 (dd, J = 11.8, 4.0 Hz, 1H), 3.85-3.76 (m, 2H), 3.56 (dd, J = 4.7, 2.1 Hz, 1H), 3.43 (dd, J = 11.6, 5.8 Hz, 1H), 1.43 (s, 9H), 1.36 (d, J = 6.7 Hz, 3H) | $^{13}$C NMR (CDCl$_3$) δ 168.91, 154.56, 138.04, 137.96, 128.36, 128.34, 127.95, 127.82, 127.79, 127.67, 77.72, 74.18, 73.11, 72.11, 71.87, 71.35, 55.72, 28.25 |
| 131 | — | — | ESIMS m/z 487.1 ([M + H]$^+$) | $^1$H NMR (CDCl$_3$) δ 7.40-7.23 (m, 10H), 5.48 (d, J = 7.7 Hz, 1H), 5.31 (qd, J = 7.0, 3.3 Hz, 1H), 4.73-4.62 (m, 2H), 4.61-4.50 (m, 2H), 4.14-4.05 (m, 1H), 4.00 (dd, J = 11.6, 2.0 Hz, 1H), 3.84 (dd, J = 11.6, 5.9 Hz, 2H), 3.65 (dd, J = 12.0, 1.9 Hz, 1H), 3.54-3.45 (m, 1H), 1.43 (s, 9H), 1.34 (d, J = 6.8 Hz, 3H) | $^{13}$C NMR (CDCl$_3$) δ 170.72, 155.29, 138.20, 137.98, 128.43, 128.39, 128.03, 127.91, 127.78, 127.69, 79.90, 78.53, 76.59, 75.54, 74.15, 72.07, 71.06, 54.80, 28.34 |
| 132 | — | — | ESIMS m/z 260.1 ([M + H]$^+$) | $^1$H NMR (CDCl$_3$) δ 4.92 (dq, J = 9.3, 6.4 Hz, 1H), 4.03 (dd, J = 10.3, 4.4 Hz, 1H), 3.78 (dd, J = 9.3, | $^{13}$C NMR (CDCl$_3$) δ 174.41, 108.61, 83.25, 81.95, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 6.7 Hz, 1H), 3.70-3.52 (m, 3H), 3.39 (dd, J = 10.3, 6.3 Hz, 1H), 1.65 (s, 2H), 1.53 (d, J = 6.5 Hz, 3H), 1.35 (s, 6H), 1.29 (d, J = 6.0 Hz, 3H) | 79.84, 74.17, 71.40, 57.27, 26.77, 26.49, 18.48, 17.89 |
| 133 | — | — | ESIMS m/z 386.9 ([M + H]$^+$) | $^1$H NMR (CDCl$_3$) δ 8.77 (s, 3H), 7.54-6.95 (m, 10H), 5.29 (d, J = 7.4 Hz, 1H), 4.63-4.47 (m, 5H), 4.44 (s, 1H), 4.21-4.09 (m, 1H), 3.92-3.84 (m, 1H), 3.80-3.73 (m, 1H), 3.68-3.53 (m, 2H), 3.49-3.37 (m, 1H), 1.29 (d, J = 6.6 Hz, 3H) | $^{13}$C NMR (CDCl$_3$) δ 167.90, 137.94, 137.75, 128.45, 128.39, 128.13, 127.92, 127.80, 161.65, 54.29, 42.92, 20.91 |
| 134 | — | — | ESIMS m/z 386.3 ([M + H]$^+$) | $^1$H NMR (CDCl$_3$) δ 8.89 (s, 3H), 7.41-7.10 (m, 10H), 5.21 (d, J = 7.9 Hz, 1H), 4.66 (d, J = 11.4 Hz, 1H), 4.60-4.44 (m, 3H), 4.23-4.11 (m, 1H), 4.03 (t, J = 10.3 Hz, 2H), 3.86 (d, J = 6.9 Hz, 1H), 3.79-3.72 (m, 1H), 3.68-3.52 (m, 2H), 1.37 (d, J = 6.6 Hz, 3H) | $^{13}$C NMR (CDCl$_3$) δ 165.18, 137.87, 137.53, 128.49, 128.40, 128.27, 128.05, 127.85, 127.78, 74.35, 72.80, 72.47, 72.25, 71.77, 71.12, 61.69, 54.70, 15.32 |
| 135 | — | — | ESIMS m/z 661.8 ([M + Na]$^+$) | $^1$H NMR (CDCl$_3$) δ 7.43-7.15 (m, 10H), 6.65-6.51 (m, 2H), 6.29 (dtd, J = 16.1, 6.0, 4.2 Hz, 2H), 5.23 (dd, J = 8.9, 4.2 Hz, 1H), 4.93-4.77 (m, 1H), 4.56 (ddd, J = 12.3, 6.0, 1.5 Hz, 1H), 4.41-4.17 (m, 4H), 4.01-3.84 (m, 2H), 3.60 (dd, J = 11.0, 7.2 Hz, 1H), 3.45 (ddd, J = 8.5, 7.1, 1.4 Hz, 1H), 3.40-3.31 (m, 1H), 1.50 (s, 18H), 1.47 (d, J = 6.3 Hz, 3H) | $^{13}$C NMR (CDCl$_3$) δ 169.03, 152.65, 132.35, 132.15, 128.53, 127.64, 126.53, 126.51, 126.20, 126.07, 84.59, 83.07, 82.96, 74.28, 72.85, 72.66, 71.54, 57.92, 27.96, 18.81 |
| 136 | — | — | ESIMS m/z 644.2 ([M + Na]$^+$) | $^1$H NMR (CDCl$_3$) δ 6.48-6.28 (m, 2H), 5.87 (dddt, J = 15.4, 8.7, 6.5, 2.0 Hz, 2H), 5.24 (dd, J = 8.9, 3.7 Hz, 1H), 4.97-4.75 (m, 1H), 4.52-4.38 (m, 1H), 4.32-4.13 (m, 4H), 3.98-3.82 (m, 2H), 3.56 (dd, J = 11.2, 7.2 Hz, 1H), 3.49-3.35 (m, 1H), 3.35-3.25 (m, 1H), 1.51 (s, 18H), 1.43 (d, J = 6.3 Hz, 3H) | $^{13}$C NMR (CDCl$_3$) δ 168.72, 152.68, 136.51-136.07 (q, J = 6.1 Hz), 136.27 (q, J = 6.1 Hz), 122.99 (q, J = 269.1 Hz), 122.92 (q, J = 269.1 Hz), 118.80 (q, J = 34.3 Hz), 118.51 (q, J = 34.3 Hz), 85.42, 83.62, 83.20, 75.78, 73.19, 72.03, 71.34, 68.35, 57.97, 27.98, 18.67 |
| 137 | — | — | ESIMS m/z 513.3 ([M + Na]$^+$) | $^1$H NMR (CDCl$_3$) δ 5.21 (dd, J = 8.9, 4.2 Hz, 1H), 4.77 (dq, J = 9.3, 6.2 Hz, 1H), 4.26 (dd, J = 12.1, 4.2 Hz, 1H), 3.92 (dd, J = 12.1, 8.9 Hz, 1H), 3.86-3.77 (m, 2H), 3.60-3.41 (m, 4H), 3.29-3.12 (m, 2H), 1.67-1.52 (m, 2H), 1.49 (s, 19H), 1.42 (d, J = 6.4 Hz, 3H), 0.92 (td, J = 7.4, 2.8 Hz, 7H) | $^{13}$C NMR (CDCl$_3$) δ 169.04, 152.59, 84.88, 83.40, 82.95, 75.71, 75.41, 72.78, 72.65, 72.55, 57.88, 27.91, 23.48, 23.27, 18.62, 10.59, 10.57 |
| 138 | — | — | ESIMS m/z 664.2 ([M + Na]$^+$) | $^1$H NMR (CDCl$_3$) δ 7.34-7.20 (m, 4H), 7.20-7.11 (m, 6H), 5.21 (dd, J = 8.9, 4.3 Hz, 1H), 4.80 (dq, J = 9.1, 6.3 Hz, 1H), | $^{13}$C NMR (CDCl$_3$) δ 169.07, 152.66, 141.97, 141.89, 128.38, 128.34, |

TABLE 2-continued

Analytical Data

| Compound Number | MP (°C.) | IR (cm$^{-1}$) | MASS | $^1$H NMR* | $^{13}$C NMR* |
|---|---|---|---|---|---|
|  |  |  |  | 4.23 (dd, J = 12.1, 4.3 Hz, 1H), 4.00-3.84 (m, 2H), 3.80 (dd, J = 11.1, 1.4 Hz, 1H), 3.65-3.44 (m, 4H), 3.30-3.15 (m, 2H), 2.73-2.58 (m, 4H), 1.95-1.77 (m, 4H), 1.50 (s, 18H), 1.43 (d, J = 6.3 Hz, 3H) | 128.32, 125.81, 125.79, 85.06, 83.59, 83.04, 75.51, 73.25, 72.73, 72.68, 70.07, 57.90, 32.53, 32.43, 32.02, 31.72, 27.97, 18.75 |
| 139 | — | — | ESIMS m/z 290.7 ([M + H]$^+$) | $^1$H NMR (CDCl$_3$) δ 8.67 (s, 3H), 4.91 (dq, J = 8.7, 6.2 Hz, 1H), 4.55 (dd, J = 6.7, 4.1 Hz, 1H), 4.28 (dd, J = 12.8, 4.1 Hz, 1H), 4.05 (dd, J = 12.8, 6.7 Hz, 1H), 3.90-3.73 (m, 2H), 3.58-3.38 (m, 4H), 3.23-3.09 (m, 2H), 1.56 (dddd, J = 8.6, 7.0, 5.2, 2.4 Hz, 4H), 1.44 (d, J = 6.3 Hz, 3H), 0.91 (td, J = 7.4, 1.6 Hz, 6H) | $^{13}$C NMR (CDCl$_3$) δ 168.56, 84.88, 83.28, 76.08, 75.58, 73.93, 72.69, 70.96, 53.41, 23.50, 23.31, 18.50, 10.63 |
| 140 | — | — | ESIMS m/z 442.9 ([M + H]$^+$) | $^1$H NMR (CDCl$_3$) δ 8.72 (s, 3H), 7.36-7.19 (m, 4H), 7.19-7.06 (m, 6H), 5.04-4.85 (m, 1H), 4.53 (s, 1H), 4.29 (d, J = 12.3 Hz, 1H), 4.04 (dd, J = 12.7, 6.3 Hz, 1H), 3.94-3.80 (m, 2H), 3.81-3.73 (m, 1H), 3.68-3.61 (m, 1H), 3.61-3.42 (m, 3H), 3.27-3.09 (m, 2H), 2.73-2.55 (m, 3H), 2.07-1.73 (m, 4H), 1.44 (d, J = 6.2 Hz, 3H) | $^{13}$C NMR (CDCl$_3$) δ 168.44, 141.83, 128.36, 128.30, 125.84, 85.03, 83.43, 73.88, 73.44, 71.17, 70.21, 61.74, 53.48, 32.49, 32.43, 31.96, 31.74, 18.59 |
| 141 | — | — | ESIMS m/z 647.4 ([M + Na]$^+$) | $^1$H NMR (CDCl$_3$) δ 5.21 (dd, J = 8.8, 4.1 Hz, 1H), 4.87-4.71 (m, 1H), 4.25 (dd, J = 12.2, 4.1 Hz, 1H), 3.91 (dd, J = 12.2, 8.8 Hz, 1H), 3.88-3.76 (m, 2H), 3.67-3.48 (m, 4H), 3.29-3.22 (m, 1H), 3.22-3.13 (m, 1H), 2.29-2.06 (m, 4H), 1.88-1.73 (m, 4H), 1.50 (s, 18H), 1.41 (d, J = 6.3 Hz, 3H) | $^{13}$C NMR (CDCl$_3$) δ 168.91, 152.66, 127.14 (q, J = 275.5 Hz), 127.11 (d, J = 276.8 Hz), 84.94, 83.56, 83.13, 75.36, 72.87, 72.34, 71.79, 68.58, 57.86, 30.76 (q, J = 29.4 Hz), 30.73 (q, J = 28.3 Hz), 27.95, 23.02 (q, J = 3.0 Hz), 22.80 (q, J = 3.0 Hz), 18.68 |
| 142 | — | — | ESIMS m/z 563.5 ([M + Na]$^+$) | $^1$H NMR (400 MHz, CDCl$_3$, as mixture of diastereomers) δ 5.92-5.64 (m, 2H), 5.24 (ddd, J = 9.0, 3.9, 2.4 Hz, 1H), 5.01-4.90 (m, 1H), 4.90-4.77 (m, 2H), 4.37 (dd, J = 11.8, 5.2 Hz, 1H), 4.24 (ddd, J = 12.2, 4.0, 3.2 Hz, 1H), 4.12-4.00 (m, 1H), 4.00-3.82 (m, 4H), 3.55 (ddd, J = 10.6, 7.6, 6.4 Hz, 1H), 3.46 (dddd, J = 8.8, 7.5, 3.2, 1.2 Hz, 1H), 3.23 (ddd, J = 9.7, 8.5, 4.8 Hz, 1H), 2.18-1.83 (m, 2H), 1.80-1.70 (m, 6H), 1.51 (s, | $^{13}$C NMR (101 MHz, CDCl$_3$ as mixture of diastereomers,) δ 169.05, 152.62, 152.60, 142.27, 131.12, 130.82, 128.00, 127.54, 111.66, 111.41, 84.99, 84.44, 83.03, 81.30, 81.00, 77.61, 77.57, 73.66, 72.84, 72.78, 72.75, 72.73, 72.28, 57.94, 28.91, 28.25, 27.94, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 18H), 1.43 (d, J = 6.3 Hz, 3H) | 25.24, 25.19, 19.84, 19.81, 19.08, 18.90, 18.76, 18.74 |
| 143 | — | — | ESIMS m/z 426.04 ([M + H]$^+$) | $^1$H NMR (CDCl$_3$) δ 8.65 (s, 3H), 4.93 (s, 1H), 4.57 (s, 1H), 4.32 (s, 1H), 4.21-3.96 (m, 1H), 3.96-3.80 (m, 2H), 3.67-3.42 (m, 4H), 3.18 (dt, J = 14.7, 4.4 Hz, 2H), 2.31-2.04 (m, 4H), 1.93-1.68 (m, 4H), 1.43 (d, J = 5.4 Hz, 3H) | — |
| 144 | — | — | ESIMS m/z 562.8 ([M + Na]$^+$) | $^1$H NMR (400 MHz, CDCl$_3$ as mixture of diastereomers) δ 5.88-5.74 (m, 2H), 5.21 (dt, J = 8.6, 4.3 Hz, 1H), 4.96 (tt, J = 1.8, 1.0 Hz, 1H), 4.91-4.74 (m, 2H), 4.28 (s, 1H), 4.26-4.17 (m, 1H), 4.02-3.89 (m, 3H), 3.81 (ddd, J = 21.8, 11.3, 1.3 Hz, 1H), 3.60 (ddd, J = 13.4, 11.3, 6.7 Hz, 1H), 3.46 (ddd, J = 21.6, 9.5, 8.5 Hz, 1H), 3.36-3.25 (m, 1H), 2.09-1.85 (m, 2H), 1.84-1.67 (m, 6H), 1.53-1.47 (m, 18H), 1.45 (dd, J = 6.3, 4.5 Hz, 3H) | — |
| 145 | — | — | ESIMS m/z 567.5 ([M + Na]$^+$) | $^1$H NMR (CDCl$_3$) δ 5.22 (dd, J = 9.0, 4.0 Hz, 1H), 4.78 (dq, J = 9.7, 6.3 Hz, 1H), 4.22 (dd, J = 12.2, 4.0 Hz, 1H), 3.90 (dd, J = 12.2, 9.0 Hz, 1H), 3.83-3.71 (m, 2H), 3.52 (dd, J = 10.8, 7.3 Hz, 1H), 3.46-3.35 (m, 2H), 3.23-3.07 (m, 2H), 2.02-1.86 (m, 2H), 1.86-1.76 (m, 1H), 1.76-1.60 (m, 3H), 1.50 (s, 18H), 1.42 (d, J = 6.3 Hz, 3H), 1.31-1.10 (m, 5H), 0.90 (dd, J = 13.8, 6.7 Hz, 6H) | $^{13}$C NMR (CDCl$_3$) δ 169.10, 152.62, 84.78, 83.00, 80.77, 80.32, 77.75, 72.95, 72.64, 57.92, 33.39, 32.33, 29.12, 27.94, 25.75, 24.43, 24.33, 19.65, 19.41, 18.75 |
| 146 | — | — | ESIMS m/z 566.8 ([M + Na]$^+$) | $^1$H NMR (CDCl$_3$) δ 5.21 (dd, J = 8.8, 4.3 Hz, 1H), 4.75 (dq, J = 9.5, 6.3 Hz, 1H), 4.22 (dd, J = 12.1, 4.3 Hz, 1H), 3.92 (dd, J = 12.2, 8.8 Hz, 1H), 3.77 (dd, J = 11.1, 1.3 Hz, 1H), 3.71-3.61 (m, 2H), 3.57 (dd, J = 11.2, 6.7 Hz, 1H), 3.40 (dd, J = 9.5, 8.5 Hz, 2H), 3.35-3.24 (m, 3H), 3.24-3.14 (m, 1H), 2.95-2.84 (m, 1H), 2.76-2.64 (m, 1H), 2.03-1.89 (m, 2H), 1.87-1.59 (m, 4H), 1.50 (s, 18H), 1.46-1.38 (m, 3H), 1.28-1.09 (m, 5H), 0.90 (dd, J = 6.7, 3.9 Hz, 6H) | $^{13}$C NMR (CDCl$_3$) δ 169.07, 152.61, 84.32, 83.01, 80.53, 79.44, 77.42, 73.11, 72.68, 57.86, 44.51, 39.23, 33.59, 32.62, 29.73, 28.92, 28.28, 27.94, 25.73, 24.75, 24.58, 19.50, 19.44, 18.99 |
| 147 | — | — | ESIMS m/z 559.0 ([M + H]$^+$) | $^1$H NMR (CDCl$_3$) δ 7.31-7.20 (m, 2H), 7.20-7.12 (m, 2H), 7.02-6.81 (m, 4H), 6.73 (dt, J = 7.8, 1.1 Hz, 2H), 5.34 (dd, J = 9.0, | $^{13}$C NMR (CDCl$_3$) δ 168.79, 159.50, 157.39, 152.59, 129.37, 129.24, |

TABLE 2-continued

Analytical Data

| Compound Number | MP (° C.) | IR (cm⁻¹) | MASS | ¹H NMR* | ¹³C NMR* |
|---|---|---|---|---|---|
| | | | | 3.6 Hz, 1H), 5.16 (dq, J = 9.4, 6.3 Hz, 1H), 4.58-4.45 (m, 1H), 4.41 (ddd, J = 8.7, 7.3, 1.3 Hz, 1H), 4.32 (dd, J = 12.3, 3.6 Hz, 1H), 4.08 (dd, J = 11.1, 1.3 Hz, 1H), 3.98 (dd, J = 12.4, 8.9 Hz, 1H), 3.77 (dd, J = 11.1, 7.3 Hz, 1H), 1.54 (s, 18H), 1.46 (d, J = 6.3 Hz, 3H) | 121.47, 121.23, 116.49, 115.72, 83.25, 82.80, 80.62, 75.45, 73.18, 72.36, 57.95, 28.00, 18.97 |
| 148 | — | — | ESIMS m/z 538.8 ([M + H]⁺) | ¹H NMR (CDCl₃) δ 7.30-7.18 (m, 2H), 6.99 (dt, J = 7.9, 1.0 Hz, 2H), 6.96-6.87 (m, 1H), 5.27 (dd, J = 9.0, 4.1 Hz, 1H), 5.10-4.93 (m, 1H), 4.37-4.21 (m, 2H), 4.05-3.88 (m, 2H), 3.64 (dd, J = 10.9, 7.5 Hz, 1H), 3.41 (ddd, J = 8.9, 7.4, 1.5 Hz, 1H), 3.32-3.23 (m, 1H), 3.23-3.12 (m, 1H), 1.60-1.51 (m, overlapping, m, 1H), 1.52 (s, 18H), 1.37 (d, J = 6.3 Hz, 3H), 0.66 (dd, J = 21.7, 6.7 Hz, 6H) | ¹³C NMR (CDCl₃) δ 169.05, 159.48, 152.64, 129.18, 121.04, 116.07, 83.12, 83.01, 82.48, 78.05, 75.56, 72.81, 72.45, 57.89, 28.61, 27.96, 19.19, 19.07, 18.81 |
| 149 | — | — | ESIMS m/z 538.8 ([M + H]⁺) | ¹H NMR (CDCl₃) δ 7.32-7.21 (m, 2H), 6.98-6.88 (m, 3H), 5.28 (dd, J = 8.9, 3.7 Hz, 1H), 4.92 (dq, J = 9.7, 6.2 Hz, 1H), 4.30-4.21 (m, 2H), 4.00-3.85 (m, 2H), 3.72-3.60 (m, 2H), 3.43 (dd, J = 9.7, 8.7 Hz, 1H), 3.30 (dd, J = 8.4, 6.6 Hz, 1H), 1.75-1.65 (m, 1H), 1.52 (s, 18H), 1.48 (d, J = 6.3 Hz, 3H), 0.82 (d, J = 6.7 Hz, 3H), 0.78 (d, J = 6.7 Hz, 3H) | ¹³C NMR (CDCl₃) δ 168.87, 157.52, 152.59, 129.44, 128.49, 121.02, 115.72, 84.32, 83.14, 81.24, 80.56, 75.61, 73.01, 72.67, 57.94, 28.98, 27.97, 19.42, 19.33, 18.80 |
| 150 | 227-229 | — | ESIMS m/z 358.7 ([M + H]⁺) | ¹H NMR (400 MHz, MeOD) δ 7.30-7.21 (m, 2H), 7.21-7.12 (m, 2H), 7.04-6.84 (m, 4H), 6.67 (dt, J = 7.8, 1.0 Hz, 2H), 5.53-5.32 (m, 1H), 4.70 (t, J = 9.2 Hz, 1H), 4.55 (dd, J = 4.2, 3.1 Hz, 1H), 4.29 (ddd, J = 9.1, 6.7, 1.0 Hz, 1H), 4.20-4.09 (m, 3H), 4.01-3.83 (m, 1H), 1.50 (d, J = 6.3 Hz, 3H) | — |
| 151 | — | — | ESIMS m/z 338.9 ([M + H]⁺) | ¹H NMR (CDCl₃) δ 8.73 (s, 3H), 7.28-7.16 (m, 2H), 7.01-6.87 (m, 3H), 5.17 (dt, J = 15.8, 6.2 Hz, 1H), 4.67 (t, J = 5.3 Hz, 1H), 4.44-4.31 (m, 1H), 4.27 (t, J = 9.0 Hz, 1H), 4.22-4.07 (m, 1H), 3.97 (d, J = 10.8 Hz, 1H), 3.70-3.58 (m, 1H), 3.40 (t, J = 8.2 Hz, 1H), 3.27 (dd, J = 8.8, 6.3 Hz, 1H), 3.16 (dd, J = 8.8, 6.3 Hz, 1H), 1.54 (dt, J = 13.1, 6.6 Hz, 1H), 1.41 (d, J = 6.3 Hz, 3H), 0.67 (d, J = 6.7 Hz, 3H), 0.61 (d, J = 6.7 Hz, 3H) | ¹³C NMR (CDCl₃) δ 168.69, 159.26, 129.25, 121.24, 115.99, 82.76, 82.29, 78.11, 75.46, 73.58, 70.86, 53.43, 28.60, 19.18, 19.05, 18.67 |

TABLE 2-continued

Analytical Data

| Compound Number | MP (° C.) | IR (cm⁻¹) | MASS | ¹H NMR* | ¹³C NMR* |
|---|---|---|---|---|---|
| 152 | — | — | ESIMS m/z 338.7 ([M + H]⁺) | — | — |
| 153 | — | — | ESIMS m/z 541.3 ([M + Na]⁺) | ¹H NMR (CDCl₃) δ 7.42-7.27 (m, 6H), 5.74 (d, J = 7.7 Hz, 1H), 5.36-5.25 (m, 1H), 5.10 (d, J = 1.6 Hz, 2H), 5.00-4.84 (m, 6H), 4.80-4.71 (m, 1H), 4.12 (dd, J = 12.0, 3.5 Hz, 1H), 4.09-3.78 (m, 9H), 3.77-3.65 (m, 2H), 3.57-3.45 (m, 1H), 1.78-1.68 (m, 9H) | ¹³C NMR (CDCl₃) δ 170.29, 155.78, 142.14, 141.92, 141.86, 141.74, 136.23, 128.56, 128.51, 128.14, 128.00, 112.95, 112.71, 112.41, 77.22, 76.30, 76.19, 75.77, 75.19, 75.22, 73.82, 67.08, 66.96, 55.29, 19.61, 19.52, 19.45 |
| 154 | — | — | ESIMS m/z 541.2 ([M + Na]⁺) | ¹H NMR (CDCl₃) δ 7.44-7.28 (m, 6H), 5.49 (d, J = 9.0 Hz, 1H), 5.24 (td, J = 5.7, 3.2 Hz, 1H), 5.09 (s, 2H), 5.00-4.83 (m, 6H), 4.60-4.52 (m, 1H), 4.19 (dd, J = 11.6, 6.0 Hz, 1H) 4.04 (t, J = 12.7 Hz, 1H), 4.00-3.85 (m, 6H), 3.83-3.77 (m, 1H), 3.76-3.61 (m, 2H), 3.55 (ddd, J = 7.0, 3.9, 1.6 Hz, 1H), 3.51-3.38 (m, 1H), 1.74-1.72 (m, 9H) | — |
| 155 | — | — | ESIMS m/z 484.2 ([M + Na]⁺) | ¹H NMR (CDCl₃) δ 7.40-7.28 (m, 5H), 5.57 (d, J = 8.0 Hz, 1H), 5.11 (s, 2H), 4.94 (qd, J = 2.1, 1.0 Hz, 2H), 4.85 (td, J = 2.3, 1.3 Hz, 2H) 4.67 (s, 1H), 4.52 (t, J = 4.0 Hz, 1H), 4.21 (d, J = 11.8 Hz, 2H), 3.98 (dd, J = 11.2, 4.9 Hz, 1H), 3.86 (dd, J = 11.9, 10.5 Hz, 2H), 3.75 (dq, J = 8.7, 6.4 Hz, 1H), 3.63 (dd, J = 11.2, 2.8 Hz, 1H), 3.50 (t, J = 7.6 Hz, 1H), 3.26 (dd, J = 8.8, 5.8 Hz, 1H), 1.72 (dt, J = 2.4, 1.1 Hz, 6H), 1.62 (d, J = 6.7 Hz, 3H), 1.26 (d, J = 6.4 Hz, 3H) | ¹³C NMR (CDCl₃) δ 170.10, 155.51, 142.15, 142.10, 136.09, 128.55, 128.25, 128.13, 112.17, 112.07, 82.31, 81.16, 78.80, 76.94, 67.42, 67.12, 55.95, 19.82, 19.75, 18.58, 16.50 |
| 156 | — | — | ESIMS m/z 400.2 ([M + H]⁺) | ¹H NMR (CDCl₃) δ 7.37-7.19 (m, 10H), 5.31 (d, J = 8.0 Hz, 1H), 5.08 (dq, J = 8.4, 6.4 Hz, 1H), 4.83 (d, J = 11.2 Hz, 1H), 4.76-4.70 (m, 1H), 4.67 (td, J = 7.4, 4.7 Hz, 1H), 4.58 (t, J = 11.7 Hz, 2H), 4.05-3.92 (m, 1H), 3.79-3.67 (m, 2H), 3.41 (t, J = 8.3 Hz, 1H), 3.36-3.25 (m, 1H), 1.47-1.41 (m, 12H), 1.27 (d, J = 6.2 Hz, 3H) | ¹³C NMR (CDCl₃) δ 171.73, 155.17, 138.15, 138.08, 128.40, 128.35, 128.34, 128.26, 128.13, 127.76, 127.75, 127.71, 127.66, 127.53, 86.14, 84.87, 81.40, 80.11, 75.90, 75.19, 73.13, 72.46, 53.66, 28.30, 18.65, 17.34 |
| 157 | — | — | ESIMS m/z 416.8 ([M + Na]⁺) | ¹H NMR (CDCl₃) δ 7.50-7.27 (m, 5H), 5.60 (d, J = 8.5 Hz, 1H), 5.11 (d, J = 2.7 Hz, 2H), 4.76 (d, J = 8.7 Hz, 1H), 4.46 (d, J = 8.6 Hz, 1H), 4.00-3.85 (m, 2H), | ¹³C NMR (CDCl₃) δ 171.27, 155.59, 136.12, 128.54, 128.24, 128.13, 109.33, 80.62, 77.57, 67.11, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 3.85-3.75 (m, 1H), 3.75-3.54 (m, 2H), 1.59 (d, J = 6.5 Hz, 3H), 1.35 (d, J = 2.7 Hz, 6H), 1.31 (d, J = 6.4 Hz, 3H) | 65.67, 56.15, 26.73, 26.52, 18.29, 16.53 |
| 158 | — | — | ESIMS m/z 559.3 ([M + Na]$^+$) | $^1$H NMR (CDCl$_3$) δ 7.30-7.20 (m, 2H), 6.99-6.87 (m, 3H), 5.29 (dd, J = 8.9, 3.7 Hz, 1H), 5.02-4.90 (m, 1H), 4.87 (dq, J = 2.2, 1.2 Hz, 1H), 4.83-4.74 (m, 1H), 4.39-4.20 (m, 3H), 4.02-3.87 (m, 3H), 3.67 (dd, J = 11.0, 7.3 Hz, 1H), 3.52 (dd, J = 9.7, 8.7 Hz, 1H), 1.65 (t, J = 1.2 Hz, 3H), 1.52 (s, 18H), 1.49 (d, J = 6.3 Hz, 3H) | $^{13}$C NMR (CDCl$_3$) δ 168.81, 157.35, 152.57, 142.17, 129.48, 121.14, 115.75, 112.41, 84.29, 83.14, 81.39, 77.76, 75.44, 72.98, 72.49, 57.90, 27.96, 19.79, 18.84 |
| 159 | — | — | ESIMS m/z 559.4 ([M + Na]$^+$) | $^1$H NMR (CDCl$_3$) δ 7.31-7.19 (m, 2H), 7.05-6.97 (m, 2H), 6.93 (tt, J = 7.4, 1.1 Hz, 1H), 5.27 (dd, J = 8.9, 4.1 Hz, 1H), 5.04 (dq, J = 9.5, 6.3 Hz, 1H), 4.79-4.69 (m, 2H), 4.37-4.24 (m, 2H), 4.03-3.82 (m, 4H), 3.68 (dd, J = 11.0, 7.3 Hz, 1H), 3.51 (ddd, J = 8.7, 7.3, 1.4 Hz, 1H), 1.52 (s, 18H), 1.49 (s, 3H), 1.37 (d, J = 6.3 Hz, 3H) | $^{13}$C NMR (CDCl$_3$) δ 169.03, 159.37, 152.63, 141.86, 129.29, 121.18, 116.06, 112.66, 83.15, 83.03, 81.47, 75.52, 74.93, 72.82, 72.46, 57.86, 27.96, 19.41, 18.80 |
| 160 | m 144-146° C. | — | ESIMS m/z 318.8 ([M + H]$^+$) | $^1$H NMR (CDCl$_3$) δ 4.82 (dq, J = 8.5, 6.3 Hz, 1H), 3.97-3.84 (m, 1H), 3.78 (t, J = 7.0 Hz, 1H), 3.72-3.53 (m, 3H), 3.44-3.29 (m, 2H), 3.29-3.12 (m, 4H), 1.82 (ttd, J = 13.4, 6.5, 2.5 Hz, 2H), 1.42 (d, J = 6.3 Hz, 3H), 0.99-0.78 (m, 12H) | $^{13}$C NMR (CDCl$_3$) δ 175.66, 84.70, 83.85, 80.55, 77.57, 74.90, 72.72, 72.70, 29.11, 28.87, 19.58, 19.48, 19.45, 19.38, 18.61 |
| 161 | — | — | — | $^1$H NMR (CDCl$_3$) δ 4.84 (dq, J = 8.8, 6.4 Hz, 1H), 3.99-3.86 (m, 1H), 3.78 (dd, J = 7.4, 6.1 Hz, 1H), 3.68 (dd, J = 7.2, 6.1 Hz, 1H), 3.61 (dd, J = 8.3, 5.8 Hz, 1H), 3.55 (dd, J = 8.5, 5.9 Hz, 1H), 3.42 (dd, J = 11.8, 6.2 Hz, 1H), 3.22 (ddd, J = 8.5, 7.3, 2.0 Hz, 2H), 3.15-3.06 (m, 1H), 2.98 (dd, J = 8.2, 7.4 Hz, 1H), 1.81 (p, J = 6.8 Hz, 4H), 1.42 (d, J = 6.4 Hz, 3H), 1.19 (d, J = 6.4 Hz, 3H), 0.90 (ddd, J = 15.4, 6.7, 3.7 Hz, 12H). | — |
| 162 | — | — | ESIMS m/z 318.8 ([M + H]$^+$) | $^1$H NMR (300 MHz, CDCl$_3$) δ 4.53 (dd, J = 11.2, 9.0 Hz, 1H), 4.10 (dd, J = 11.2, 3.6 Hz, 1H), 3.75-3.49 (m, 2H), 3.47-3.10 (m, 5H), 2.96 (t, J = 7.8 Hz, 1H), 1.81 (dt, J = 13.3, 6.6 Hz, 2H), 1.22 (d, J = 5.9 Hz, 3H), 1.04-0.77 (m, 16H) | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 163 | — | (Neat) 2933, 2875, 1764, 1747, 1708, 1456, 1367, 1243, 1099 | HRMS-ESI (m/z) [M]$^+$ calcd for C$_{25}$H$_{45}$NO$_{10}$, 519.3043; found, 519.3026 | $^1$H NMR (CDCl$_3$) δ 5.19 (dd, J = 9.0, 4.1 Hz, 1H), 4.79 (dq, J = 9.2, 6.3 Hz, 1H), 4.20 (dd, J = 12.2, 4.1 Hz, 1H), 3.98 (ddd, J = 10.6, 5.2, 3.8 Hz, 1H), 3.88 (dd, J = 12.2, 9.0 Hz, 1H), 3.79 (d, J = 10.7 Hz, 1H), 3.73-3.65 (m, 1H), 3.60-3.43 (m, 5H), 3.34 (s, 3H), 3.28-3.15 (m, 2H), 1.55-1.44 (m, 2H), 1.47 (s, 18H), 1.42 (d, J = 6.3 Hz, 3H), 1.38-1.26 (m, 2H), 0.87 (t, J = 7.4 Hz, 3H) | $^{13}$C NMR (CDCl$_3$) δ 169.06, 152.69, 85.55, 83.49, 83.10, 75.76, 72.96, 72.85, 72.70, 72.34, 70.62, 59.02, 57.95, 32.28, 28.02, 19.41, 18.67, 14.01 |
| 164 | — | (Neat) 2934, 1745, 1707, 1457, 1367, 1254, 1120 | HRMS-ESI (m/z) [M]$^+$ calcd for C$_{24}$H$_{43}$NO$_{10}$, 505.2887; found, 505.2900 | $^1$H NMR (CDCl$_3$) δ 5.22 (dd, J = 8.9, 3.9 Hz, 1H), 4.80 (dq, J = 8.9, 6.3 Hz, 1H), 4.24 (dd, J = 12.2, 3.9 Hz, 1H), 3.95-3.79 (m, 3H), 3.78-3.68 (m, 2H), 3.66-3.45 (m, 4H), 3.45-3.38 (m, 1H), 3.39-3.23 (m, 2H), 1.61-1.50 (m, 2H), 1.49 (s, 18H), 1.44 (d, J = 6.3 Hz, 3H), 1.40-1.26 (m, 2H), 0.89 (t, J = 7.4 Hz, 3H) | $^{13}$C NMR (CDCl$_3$) δ 169.06, 152.76, 85.77, 83.22, 83.05, 75.57, 75.51, 73.09, 73.00, 70.54, 62.93, 58.04, 31.86, 28.07, 19.32, 18.80, 13.99 |
| 167 | — | — | ESIMS m/z 326.7 ([M + H]$^+$) | — | — |
| 169 | — | — | ESIMS m/z 319 ([M]$^+$) | — | — |
| 170 | — | — | ESIMS m/z 304.6 ([M + H]$^+$) | — | — |
| 172 | — | — | ESIMS m/z 386.2 ([M − Boc + 2H]$^+$) | — | — |
| 177 | — | — | ESIMS m/z 346.7 ([M + H]$^+$) | $^1$H NMR (CDCl$_3$) δ 8.83 (bs, 1H), 5.24-5.12 (m, 2H), 4.88-4.80 (m, 1H), 4.71-4.63 (m, 1H), 4.45 (dd, J = 12.9, 3.3 Hz, 1H), 4.12 (dd, J = 12.7, 6.5 Hz, 1H), 3.85 (d, J = 10.8 Hz, 1H), 3.73 (dd, J = 11.9, 7.9 Hz, 1H), 2.57-2.39 (m, 2H), 1.82-1.52 (m, 2 H), 1.35 (d, J = 5.7 Hz, 3H), 1.16 (d, J = 7.0 Hz, 3H), 1.13 (d, J = 7.0 Hz, 3H), 1.10 (d, J = 7.0 Hz, 3H), 1.09 (d, J = 7.0 Hz, 3H) | — |
| 180 | — | — | ESIMS m/z 332.8 ([M + H]$^+$) | — | — |
| 186 | 66-68 | — | ESIMS m/z 456.19 ([M + Na]$^+$) | $^1$H NMR (CDCl$_3$) δ 7.42-7.29 (m, 5H), 5.48 (d, J = 7.9 Hz, 1H), 5.10 (s, 2H), 4.96 (s, 2H), 4.89 (s, 2H), 4.69 (dd, J = 11.5, 8.8 Hz, 2H), 4.12 (dd, J = 11.5, 3.8 Hz, 1H), 4.09-3.96 (m, 5H), 3.69 (ddt, J = 12.4, 8.7, 4.5 Hz, 3H), 3.56 (dd, J = 11.5, 6.0 Hz, 1H), 3.33 (t, J = 6.2 Hz, 1H), 1.73 (s, 6H) | — |

TABLE 2-continued

Analytical Data

| Compound Number | MP (° C.) | IR (cm⁻¹) | MASS | ¹H NMR* | ¹³C NMR* |
|---|---|---|---|---|---|
| 187 | — | — | ESIMS m/z 422.22 ([M + Na]⁺) | ¹H NMR (CDCl₃) δ 5.46 (d, J = 7.7 Hz, 1H), 5.05-4.94 (m, 3H), 4.90 (d, J = 12.7 Hz, 2H), 4.71-4.61 (m, 2H), 4.14-4.07 (m, 2H), 4.05-3.92 (m, 4H), 3.87 (td, J = 10.9, 6.1 Hz, 1H), 3.78 (td, J = 6.6, 2.6 Hz, 1H), 3.65 (dd, J = 12.1, 1.3 Hz, 1H), 3.44-3.38 (m, 1H), 1.74 (d, J = 8.7 Hz, 6H), 1.43 (s, 9H) | ¹³C NMR (CDCl₃) δ 170.89, 155.22, 142.05, 141.87, 112.88, 112.66, 79.94, 78.02, 77.22, 75.78, 75.67, 74.69, 73.73, 71.35, 62.99, 54.95, 28.30, 19.55 |
| 188 | — | — | — | ¹H NMR (CDCl₃) δ 8.66 (s, 2H), 7.35-7.15 (m, 10H), 5.16 (t, J = 7.0 Hz, 1H), 4.77 (d, J = 11.1 Hz, 1H), 4.67 (d, J = 10.9 Hz, 1H), 4.62-4.50 (m, 3H), 4.32 (d, J = 12.7 Hz, 1H), 4.09 (dd, J = 13.0, 6.6 Hz, 1H), 3.81-3.60 (m, 1H), 3.36 (dt, J = 22.9, 7.6 Hz, 2H), 1.43 (d, J = 6.3 Hz, 3H), 1.26 (d, J = 6.1 Hz, 3H). | — |
| 189 | — | — | — | ¹H NMR (CDCl₃) δ 5.18 (td, J = 5.5, 3.3 Hz, 1H), 4.14-4.05 (m, 1H), 3.92-3.80 (m, 2H), 3.76-3.66 (m, 3H), 3.46-3.30 (m, 4H), 3.25 (d, J = 6.6 Hz, 2H), 3.23-3.14 (m, 2H), 1.93-1.77 (m, 4H), 0.97-0.83 (m, 19H) | — |
| 190 | — | — | — | ¹H NMR (CDCl₃) δ 5.16 (td, J = 5.3, 3.6 Hz, 1H), 4.20 (dd, J = 10.8, 6.8 Hz, 1H), 3.81 (dd, J = 7.5, 3.6 Hz, 1H), 3.77-3.62 (m, 4H), 3.44-3.35 (m, 2H), 3.35-3.28 (m, 2H), 3.25 (dd, J = 6.6, 0.8 Hz, 2H), 3.22-3.13 (m, 2H), 1.94-1.77 (m, 4H), 0.95-0.83 (m, 19H) | — |
| 191 | — | — | ESIMS m/z 428.5 ([M + Na]⁺) | ¹H NMR (CDCl₃) δ 5.25 (dd, J = 8.7, 2.8 Hz, 1H), 4.94-4.76 (m, 1H), 4.26 (dd, J = 12.3, 2.9 Hz, 1H), 4.06 (dd, J = 10.7, 1.3 Hz, 1H), 3.91 (dd, J = 12.3, 8.7 Hz, 1H), 3.62-3.54 (m, 1H), 3.54-3.38 (m, 2H), 3.15 (d, J = 4.0 Hz, 1H), 2.96 (d, J = 3.5 Hz, 1H), 1.51 (s, 18H), 1.46 (d, J = 6.3 Hz, 3H) | ¹³C NMR (CDCl₃) δ 168.63, 152.70, 83.18, 79.34, 77.96, 74.40, 74.25, 73.02, 58.54, 27.98, 18.60 |
| 192 | — | — | ESIMS m/z 609.6 ([M + Na]⁺) | ¹H NMR (CDCl₃) δ 7.38-7.23 (m, 10H), 5.24 (dd, J = 8.9, 3.9 Hz, 1H), 4.98-4.82 (m, 2H), 4.70-4.54 (m, 3H), 4.26 (dd, J = 12.2, 3.9 Hz, 1H), 4.03-3.88 (m, 2H), 3.63 (dd, J = 10.9, 7.2 Hz, 1H), 3.58-3.50 (m, 1H), 3.50-3.42 (m, 1H), 1.50 (s, 18H), 1.43 (d, J = 6.3 Hz, 3H) | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 194 | — | (Thin Film) 3364, 2955, 2874, 1752, 1649 | HRMS-FAB (m/z) [M + H]$^+$ calcd for C$_{25}$H$_{31}$ClN$_2$O$_8$, 523.1842; found, 523.1848 | $^1$H NMR (CDCl$_3$) δ 11.91 (d, J = 0.7 Hz, 1H), 8.68 (d, J = 8.2 Hz, 1H), 8.01 (d, J = 5.2 Hz, 1H), 7.17 (t, J = 8.1 Hz, 1H), 7.04 (t, J = 2.2 Hz, 1H), 6.93 (ddd, J = 8.0, 2.0, 0.9 Hz, 1H), 6.91-6.86 (m, 2H), 5.18 (dq, J = 9.6, 6.3 Hz, 1H), 5.10 (ddd, J = 8.2, 6.8, 5.1 Hz, 1H), 4.25 (t, J = 9.1 Hz, 1H), 4.16-4.05 (m, 1H), 4.00-3.89 (m, 4H), 3.87 (dd, J = 11.9, 5.1 Hz, 1H), 3.72 (dd, J = 11.1, 7.4 Hz, 1H), 3.38 (ddd, J = 8.8, 7.3, 1.5 Hz, 1H), 3.30 (dd, J = 8.8, 6.4 Hz, 1H), 3.16 (dd, J = 8.8, 6.4 Hz, 1H), 1.67-1.50 (m, 1H), 1.41 (d, J = 6.3 Hz, 3H), 0.69 (dd, J = 17.9, 6.7 Hz, 6H) | $^{13}$C NMR (CDCl$_3$) δ 170.27, 168.98, 160.14, 155.37, 148.76, 140.70, 134.61, 130.16, 129.99, 121.43, 116.66, 114.42, 109.63, 83.40, 82.59, 78.02, 74.66, 73.92, 72.49, 56.10, 52.06, 28.62, 19.16, 19.05, 18.72 |
| 195 | — | (Thin Film) 3369, 2957, 2876, 1752, 1650 | HRMS-FAB (m/z) [M + H]$^+$ calcd for C$_{26}$H$_{31}$F$_3$N$_2$O$_8$, 557.2105; found, 557.2115 | $^1$H NMR (CDCl$_3$) δ 11.90 (d, J = 0.6 Hz, 1H), 8.68 (d, J = 8.2 Hz, 1H), 8.01 (d, J = 5.2 Hz, 1H), 7.58-7.44 (m, 2H), 7.07 (dd, J = 8.8, 0.9 Hz, 2H), 6.88 (dd, J = 5.3, 0.7 Hz, 1H), 5.21 (dq, J = 9.4, 6.3 Hz, 1H), 5.11 (ddd, J = 8.2, 6.9, 5.1 Hz, 1H), 4.35 (t, J = 9.1 Hz, 1H), 4.11 (dd, J = 11.9, 6.9 Hz, 1H), 4.00-3.91 (m, 4H), 3.88 (dd, J = 11.9, 5.1 Hz, 1H), 3.73 (dd, J = 11.2, 7.3 Hz, 1H), 3.40 (ddd, J = 8.8, 7.4, 1.5 Hz, 1H), 3.29 (dd, J = 8.9, 6.3 Hz, 1H), 3.13 (dd, J = 8.9, 6.4 Hz, 1H), 1.54 (hept, J = 6.6 Hz, 1H), 1.40 (d, J = 6.3 Hz, 3H), 0.67 (d, J = 6.7 Hz, 3H), 0.62 (d, J = 6.7 Hz, 3H) | $^{13}$C NMR (CDCl$_3$) δ 170.25, 168.99, 161.79, 155.38, 148.77, 140.71, 130.14, 126.73, 126.69, 115.91, 109.64, 83.01, 82.57, 78.02, 74.65, 73.96, 72.38, 56.11, 52.06, 28.56, 19.10, 18.98, 18.69 |
| 196 | — | (Thin Film) 3331, 2944, 2884, 1737, 1646 | HRMS-FAB (m/z) [M + H]$^+$ calcd for C$_{25}$H$_{29}$F$_3$N$_2$O$_8$, 543.1949; found, 543.1957 | $^1$H NMR (CDCl$_3$) δ 11.90 (s, 1H), 8.68 (d, J = 8.2 Hz, 1H), 8.01 (d, J = 5.2 Hz, 1H), 7.60-7.47 (m, 2H), 7.08 (d, J = 8.6 Hz, 2H), 6.88 (d, J = 5.2 Hz, 1H), 5.20 (dq, J = 9.5, 6.3 Hz, 1H), 5.11 (ddd, J = 8.2, 6.9, 5.3 Hz, 1H), 4.35 (t, J = 9.1 Hz, 1H), 4.11 (dd, J = 11.8, 7.0 Hz, 1H), 3.97-3.89 (m, 4H), 3.86 (dd, J = 11.8, 5.3 Hz, 1H), 3.74 (dd, J = 11.1, 7.4 Hz, 1H), 3.52-3.38 (m, 2H), 3.31 (dt, J = 9.1, 6.6 Hz, 1H), 1.40 (d, J = 6.3 Hz, 3H), 1.38-1.24 (m, 2H), 0.66 (t, J = 7.4 Hz, 3H) | $^{13}$C NMR (CDCl$_3$) δ 170.31, 169.00, 161.84, 155.39, 148.78, 140.71, 130.14, 126.79, 126.75, 126.71, 115.98, 109.64, 83.22, 82.34, 74.57, 73.80, 72.99, 72.38, 56.10, 51.98, 22.92, 18.69, 10.27 |
| 197 | — | (Thin Film) 3365, 2939, 2879, 1751, 1649 | HRMS-FAB (m/z) [M + H]$^+$ calcd for C$_{25}$H$_{29}$F$_3$N$_2$O$_8$, 543.1949; found, 543.1957 | $^1$H NMR (CDCl$_3$) δ 11.91 (s, 1H), 8.75 (d, J = 8.1 Hz, 1H), 8.03 (d, J = 5.2 Hz, 1H), 7.62-7.46 (m, 2H), 6.99 (dd, J = 8.8, 0.9 Hz, 2H), 6.89 (d, J = 5.2 Hz, 1H), 5.19-5.04 (m, 2H), 4.27 (ddd, J = 8.5, 7.0, 1.2 Hz, 1H), 4.05 (dd, | $^{13}$C NMR (CDCl$_3$) δ 169.89, 169.00, 159.91, 155.39, 148.79, 140.73, 130.16, 127.07, 127.03, 126.99, 126.95, 115.41, 109.63, 84.47, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | J = 12.1, 6.5 Hz, 1H), 4.01-3.91 (m, 5H), 3.85-3.68 (m, 2H), 3.59-3.42 (m, 2H), 1.52 (d, J = 6.3 Hz, 3H), 1.51-1.42 (m, 2H), 0.82 (t, J = 7.4 Hz, 3H) | 81.33, 77.22, 75.76, 75.74, 74.77, 72.70, 56.11, 52.46, 23.36, 18.63, 10.56 |
| 198 | — | (Thin Film) 3363, 2919, 1753, 1649 | HRMS-FAB (m/z) [M + H]$^+$ calcd for C$_{31}$H$_{36}$N$_2$O$_8$, 565.2544; found, 565.2549 | $^1$H NMR (CDCl$_3$) δ 11.93 (d, J = 0.6 Hz, 1H), 8.74 (d, J = 8.2 Hz, 1H), 8.02 (d, J = 5.2 Hz, 1H), 6.88 (d, J = 5.2 Hz, 1H), 6.61 (d, J = 1.3 Hz, 3H), 6.59-6.53 (m, 1H), 6.41-6.29 (m, 2H), 5.29 (dq, J = 9.4, 6.3 Hz, 1H), 5.15 (ddd, J = 8.3, 6.8, 4.7 Hz, 1H), 4.46 (t, J = 9.0 Hz, 1H), 4.32 (ddd, J = 8.7, 7.2, 1.4 Hz, 1H), 4.11 (dd, J = 11.9, 6.9 Hz, 1H), 4.03 (dd, J = 11.3, 1.3 Hz, 1H), 3.94 (s, 3H), 3.95-3.91 (m, 1H), 3.81 (dd, J = 11.2, 7.3 Hz, 1H), 2.27 (s, 6H), 2.23 (s, 6H), 1.50 (d, J = 6.3 Hz, 3H) | $^{13}$C NMR (CDCl$_3$) δ 170.13, 169.01, 159.55, 157.31, 155.39, 148.80, 140.73, 139.17, 138.92, 130.19, 123.37, 123.15, 114.47, 113.45, 109.64, 82.89, 80.39, 74.62, 74.16, 72.78, 56.11, 52.22, 21.42, 21.40, 18.92 |
| 199 | — | (Thin Film) 3335, 2938, 2838, 1745, 1644, 1506 | HRMS-FAB (m/z) [M + H]$^+$ Calcd for C$_{26}$H$_{32}$N$_2$O$_{10}$, 533.213; found, 533.2142 | $^1$H NMR (CDCl$_3$) δ 11.89 (d, J = 0.7 Hz, 1H), 8.69 (d, J = 8.3 Hz, 1H), 8.01 (d, J = 5.2 Hz, 1H), 6.92-6.85 (m, 3H), 6.84-6.78 (m, 2H), 5.25 (dq, J = 9.4, 6.3 Hz, 1H), 5.11 (ddd, J = 8.3, 6.9, 5.4 Hz, 1H), 5.05 (ddd, J = 8.8, 6.6, 2.0 Hz, 1H), 4.39 (t, J = 9.1 Hz, 1H), 4.12 (dd, J = 11.9, 6.9 Hz, 1H), 3.94 (s, 3H), 3.90-3.78 (m, 3H), 3.77 (s, 3H), 2.23 (hept, J = 7.0 Hz, 1H), 1.44 (d, J = 6.4 Hz, 3H), 0.96 (d, J = 7.0 Hz, 3H), 0.88 (d, J = 7.0 Hz, 3H) | $^{13}$C NMR (CDCl$_3$) δ 175.56, 170.14, 169.00, 155.33, 154.30, 152.98, 148.71, 140.74, 130.09, 116.58, 114.54, 109.65, 81.64, 75.01, 74.81, 73.81, 72.83, 56.09, 55.70, 51.90, 33.79, 18.76, 18.64, 18.44 |
| 200 | — | (Thin Film) 3364, 2939, 2838, 1740, 1506 | HRMS-FAB (m/z) [M + H]$^+$ calcd for C$_{26}$H$_{32}$N$_2$O$_{10}$, 533.213; found, 533.2138 | $^1$H NMR (CDCl$_3$) δ 11.91 (s, 1H), 8.75 (d, J = 8.1 Hz, 1H), 8.02 (d, J = 5.2 Hz, 1H), 6.89 (d, J = 5.2 Hz, 1H), 6.87-6.73 (m, 4H), 5.35-5.20 (m, 2H), 5.14 (ddd, J = 8.1, 6.1, 3.9 Hz, 1H), 4.23-3.99 (m, 4H), 3.95 (s, 3H), 3.75 (s, 3H), 3.74-3.70 (m, 1H), 2.47 (hept, J = 7.0 Hz, 1H), 1.40 (d, J = 5.8 Hz, 3H), 1.10 (dd, J = 15.3, 7.0 Hz, 6H) | $^{13}$C NMR (CDCl$_3$) δ 175.85, 169.89, 168.99, 155.39, 154.26, 151.07, 148.80, 140.71, 130.17, 116.33, 114.75, 109.64, 78.98, 75.80, 75.15, 75.07, 71.35, 56.11, 55.68, 52.71, 34.04, 18.91, 18.23 |
| 201 | — | (Thin Film) 3364, 2938, 2835, 1751, 1649 | HRMS-FAB (m/z) [M + H]$^+$ calcd for C$_{29}$H$_{32}$N$_2$O$_{10}$, 569.2130; found, 569.2133 | $^1$H NMR (CDCl$_3$) δ 11.92 (s, 1H), 8.73 (d, J = 8.2 Hz, 1H), 8.01 (d, J = 5.2 Hz, 1H), 7.05-6.91 (m, 2H), 6.87 (d, J = 5.2 Hz, 1H), 6.83-6.70 (m, 6H), 5.30 (dq, J = 9.3, 6.3 Hz, 1H), 5.13 (ddd, J = 8.2, 6.7, 4.7 Hz, 1H), 4.35 (t, J = 9.1 Hz, 1H), 4.23 (ddd, J = 8.7, 7.0, 1.3 Hz, 1H), 4.16-4.00 (m, 2H), | $^{13}$C NMR (CDCl$_3$) δ 170.10, 169.01, 155.36, 154.36, 154.34, 153.74, 151.45, 148.77, 140.73, 130.15, 117.64, 116.97, 114.64, 114.38, 109.65, 84.13, 81.78, 74.75, 74.21, 72.64, |

TABLE 2-continued

Analytical Data

| Compound Number | MP (° C.) | IR (cm⁻¹) | MASS | ¹H NMR* | ¹³C NMR* |
|---|---|---|---|---|---|
| | | | | 3.95-3.91 (m, 4H), 3.80 (dd, J = 11.3, 7.1 Hz, 1H), 3.76 (s, 3H), 3.72 (s, 3H), 1.50 (d, J = 6.3 Hz, 3H) | 56.10, 55.65, 52.24, 18.93 |
| 202 | — | — | HRMS-FAB (m/z) [M + H]⁺ calcd for $C_{24}H_{30}N_2O_8$, 475.2075; found, 475.2088 | ¹H NMR (CDCl3) δ 11.92 (d, J = 0.6 Hz, 1H), 8.68 (d, J = 8.2 Hz, 1H), 8.00 (d, J = 5.2 Hz, 1H), 7.33-7.20 (m, 2H), 7.07-6.98 (m, 2H), 6.95 (tt, J = 7.4, 1.1 Hz, 1H), 6.87 (dd, J = 5.2, 0.7 Hz, 1H), 5.18 (dq, J = 9.5, 6.3 Hz, 1H), 5.10 (ddd, J = 8.2, 7.0, 5.4 Hz, 1H), 4.31 (dd, J = 9.5, 8.6 Hz, 1H), 4.11 (dd, J = 11.8, 7.0 Hz, 1H), 3.94 (s, 3H), 3.90 (dd, J = 11.0, 1.6 Hz, 1H), 3.83 (dd, J = 11.8, 5.4 Hz, 1H), 3.74 (dd, J = 11.1, 7.3 Hz, 1H), 3.49 (dt, J = 9.0, 6.6 Hz, 1H), 3.44-3.33 (m, 2H), 1.42 (d, J = 6.3 Hz, 3H), 1.40-1.29 (m, 2H), 0.69 (t, J = 7.4 Hz, 3H) | ¹³C NMR (CDCl₃) δ 170.42, 168.98, 159.47, 155.35, 148.74, 140.69, 130.16, 129.27, 121.26, 116.14, 109.62, 83.24, 82.45, 74.74, 73.68, 73.12, 72.85, 56.09, 51.96, 22.99, 18.75, 10.34 |
| 203 | — | — | HRMS-FAB (m/z) [M + H]⁺ calcd for $C_{24}H_{30}N_2O_8$, 475.2075; found, 475.2085 | ¹H NMR (CDCl₃) δ 11.93 (s, 1H), 8.72 (d, J = 8.1 Hz, 1H), 8.02 (d, J = 5.2 Hz, 1H), 7.38-7.20 (m, 2H), 7.04-6.89 (m, 3H), 6.88 (d, J = 5.2 Hz, 1H), 5.16-5.04 (m, 2H), 4.22 (ddd, J = 8.7, 7.1, 1.3 Hz, 1H), 4.05 (dd, J = 12.0, 6.7 Hz, 1H), 4.00-3.89 (m, 5H), 3.85 (dt, J = 8.8, 6.6 Hz, 1H), 3.71 (dd, J = 11.3, 7.1 Hz, 1H), 3.54 (dt, J = 8.8, 6.7 Hz, 1H), 3.46 (dd, J = 9.6, 8.8 Hz, 1H), 1.59-1.41 (m, 5H), 0.83 (t, J = 7.4 Hz, 3H) | ¹³C NMR (CDCl₃) δ 170.04, 168.99, 157.43, 155.35, 148.76, 140.71, 130.20, 129.56, 121.20, 115.62, 109.61, 84.52, 81.17, 75.64, 75.35, 74.37, 72.85, 56.10, 52.33, 23.41, 18.68, 10.60 |
| 204 | — | — | HRMS-FAB (m/z) [M + H]⁺ calcd for $C_{26}H_{32}N_2O_8$, 501.2231; found, 501.2246 | ¹H NMR (CDCl₃) δ 11.92 (s, 1H), 8.68 (d, J = 8.2 Hz, 1H), 8.01 (d, J = 5.2 Hz, 1H), 7.36-7.15 (m, 2H), 7.04-6.98 (m, 2H), 6.93 (tt, J = 7.2, 1.1 Hz, 1H), 6.88 (d, J = 5.2 Hz, 1H), 5.23-5.14 (m, 1H), 5.14-5.06 (m, 1H), 4.28 (t, J = 9.1 Hz, 1H), 4.11 (dd, J = 11.8, 7.1 Hz, 1H), 4.03 (ddd, J = 8.6, 5.0, 3.6 Hz, 1H), 3.94 (s, 3H), 3.88 (dd, J = 11.1, 1.7 Hz, 1H), 3.83 (dd, J = 11.8, 5.5 Hz, 1H), 3.73 (dd, J = 11.0, 7.5 Hz, 1H), 3.48 (ddd, J = 8.9, 7.3, 1.6 Hz, 1H), 1.63-1.49 (m, 2H), 1.46-1.35 (m, 7H), 1.37-1.26 (m, 2H) | ¹³C NMR (CDCl₃) δ 170.14, 168.99, 157.40, 155.35, 148.75, 140.71, 130.20, 129.56, 121.14, 115.59, 109.61, 84.26, 82.20, 81.24, 75.47, 74.34, 73.27, 56.10, 52.32, 32.96, 32.32, 23.13, 18.80 |
| 205 | — | — | HRMS-FAB (m/z) [M + H]⁺ calcd for $C_{26}H_{32}N_2O_8$, 501.2231; found, 501.2243 | ¹H NMR (CDCl₃) δ 11.93 (d, J = 0.6 Hz, 1H), 8.72 (d, J = 8.1 Hz, 1H), 8.01 (d, J = 5.2 Hz, 1H), 7.32-7.24 (m, 2H), 6.99-6.90 (m, 3H), 6.88 (dd, J = 5.3, 0.6 Hz, 1H), 5.13-5.01 (m, 2H), 4.41-4.32 (m, 1H), 4.18 (ddd, J = 8.4, | ¹³C NMR (CDCl₃) δ 170.14, 168.99, 157.40, 155.35, 148.75, 140.71, 130.20, 129.56, 121.14, 115.59, 109.61, 84.26, 82.20, 81.24, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 6.8, 1.2 Hz, 1H), 4.06 (dd, J = 12.0, 6.7 Hz, 1H), 3.94 (m, 4H), 3.89 (dd, J = 12.0, 4.6 Hz, 1H), 3.73 (dd, J = 11.4, 6.8 Hz, 1H), 3.60 (dd, J = 9.5, 8.6 Hz, 1H), 1.74-1.57 (m, 6H), 1.52 (m, J = 6.4 Hz, 4H), 1.48-1.40 (m, 1H) | 75.47, 74.34, 73.27, 56.10, 52.32, 32.96, 32.32, 23.13, 18.80 |
| 206 | — | (Thin Film) 3361, 2938, 1750, 1648, 1577, 1506 | HRMS-FAB (m/z) [M + H]$^+$ calcd for C$_{29}$H$_{32}$N$_2$O$_8$, 537.2231; found, 537.2243. | $^1$H NMR (CDCl$_3$) δ 11.92 (d, J = 0.6 Hz, 1H), 8.74 (d, J = 8.1 Hz, 1H), 8.02 (d, J = 5.2 Hz, 1H), 7.08-7.02 (m, 2H), 7.02-6.97 (m, 2H), 6.94-6.85 (m, 3H), 6.69-6.64 (m, 2H), 5.31 (dq, J = 9.4, 6.3 Hz, 1H), 5.14 (ddd, J = 8.1, 6.7, 4.6 Hz, 1H), 4.43 (t, J = 9.1 Hz, 1H), 4.30 (ddd, J = 8.6, 7.1, 1.3 Hz, 1H), 4.13-4.02 (m, 2H), 3.97-3.91 (m, 4H), 3.80 (dd, J = 11.3, 7.2 Hz, 1H), 2.28 (s, 3H), 2.24 (s, 3H), 1.49 (d, J = 6.3 Hz, 3H) | $^{13}$C NMR (CDCl$_3$) δ 170.07, 169.02, 157.50, 155.38, 155.23, 148.78, 140.74, 130.86, 130.69, 130.17, 129.93, 129.76, 116.44, 115.65, 109.65, 83.30, 80.89, 74.88, 74.32, 72.68, 56.11, 52.29, 20.53, 20.48, 18.90 |
| 207 | 127 | (Thin Film) 3376, 2955, 1733, 1642, 1506 | HRMS-FAB (m/z) [M + H]$^+$ calcd for C$_{25}$H$_{31}$F$_1$N$_2$O$_8$, 507.2137; found, 507.2147 | $^1$H NMR (CDCl$_3$) δ 11.92 (d, J = 0.6 Hz, 1H), 8.72 (d, J = 8.1 Hz, 1H), 8.02 (d, J = 5.2 Hz, 1H), 7.05-6.91 (m, 2H), 6.91-6.80 (m, 3H), 5.19-5.03 (m, 2H), 4.17-4.08 (m, 1H), 4.05 (dd, J = 12.1, 6.6 Hz, 1H), 4.00-3.91 (m, 5H), 3.75-3.62 (m, 2H), 3.43 (t, J = 9.2 Hz, 1H), 3.32 (dd, J = 8.4, 6.5 Hz, 1H), 1.73 (hept, J = 6.7 Hz, 1H), 1.51 (d, J = 6.3 Hz, 3H), 0.82 (dd, J = 15.4, 6.7 Hz, 6H) | — |
| 208 | 170-172 | (Thin Film) 3150.6, 3097.8, 2932.5, 2886.2, 1755.4, 1650.2 | HRMS-FAB (m/z) [M + H]$^+$ calcd for C$_{27}$H$_{26}$F$_2$N$_2$O$_8$, 545.173; found, 545.1729 | $^1$H NMR (CDCl$_3$) δ 11.89 (d, J = 0.6 Hz, 1H), 8.74 (d, J = 8.1 Hz, 1H), 8.04 (d, J = 5.2 Hz, 1H), 7.03-6.82 (m, 7H), 6.76-6.62 (m, 2H), 5.33 (dq, J = 9.4, 6.3 Hz, 1H), 5.14 (m, 1H), 4.38 (t, J = 9.1 Hz, 1H), 4.27 (ddd, J = 8.7, 7.1, 1.3 Hz, 1H), 4.15-4.02 (m, 2H), 3.99 (d, J = 4.4 Hz, 1H), 3.96 (s, 3H), 3.81 (dd, J = 11.4, 7.1 Hz, 1H), 1.50 (d, J = 6.4 Hz, 3H) | — |
| 209 | 114-117 | — | ESIMS m/z 465 ([M + H]$^+$) | $^1$H NMR (CDCl$_3$) δ 11.72 (s, 1H), 8.46 (d, J = 8.2 Hz, 1H), 7.78 (d, J = 5.2 Hz, 1H), 6.66 (d, J = 5.2 Hz, 1H), 4.83 (ddd, J = 8.3, 6.9, 5.1 Hz, 1H), 4.80-4.75 (m, 1H), 3.83 (dd, J = 11.9, 6.9 Hz, 1H), 3.73 (s, 3H), 3.67-3.53 (m, 3H), 3.40 (dd, J = 11.1, 6.7 Hz, 1H), 3.27-3.14 (m, 3H), 3.10-3.00 (m, 2H), 1.27 (d, J = 6.3 Hz, 3H), 0.95-0.78 (m, 2H), 0.40-0.28 (m, 4H), 0.08--0.06 (m, 4H) | $^{13}$C NMR (CDCl$_3$) δ 170.26, 168.93, 155.28, 148.67, 140.65, 130.14, 109.56, 84.60, 83.26, 78.74, 75.81, 75.36, 73.81, 73.11, 56.06, 52.05, 18.59, 11.07, 10.91, 3.21, 3.15, 2.93, 2.84 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 210 | 61-70 | (Thin Film) 3530, 3371, 2955, 2873, 1750, 1649, 1529, 1262 | HRMS-ESI (m/z) [M + Na]$^+$ calcd for C$_{25}$H$_{40}$N$_2$NaO$_8$, 519.2677, found, 519.2687 | $^1$H NMR (CDCl$_3$) δ 11.94 (s, 1H), 8.67 (d, J = 8.1 Hz, 1H), 8.01-7.98 (m, 1H), 6.87 (d, J = 5.2 Hz, 1H), 5.04 (ddd, J = 8.2, 6.8, 5.0 Hz, 1H), 5.01-4.89 (m, 1H), 4.05 (dd, J = 11.9, 6.8 Hz, 1H), 3.94 (s, 3H), 3.92-3.85 (m, 1H), 3.85-3.78 (m, 2H), 3.66-3.58 (m, 1H), 3.57-3.48 (m, 2H), 3.26-3.14 (m, 2H), 1.69 (dp, J = 13.4, 6.7 Hz, 2H), 1.51-1.38 (m, 7H), 0.90 (dt, J = 6.2, 2.7 Hz, 12H) | $^{13}$C NMR (CDCl$_3$) δ 170.30, 168.94, 155.32, 148.72, 140.66, 130.22, 109.56, 85.02, 83.63, 75.28, 73.94, 73.17, 72.48, 69.35, 56.09, 52.12, 39.23, 38.95, 24.96, 22.91, 22.67, 22.62, 22.50, 18.59 |
| 211 | — | (Thin Film) 3364, 2926, 1750, 1649, 1530, 1482, 1242 | ESIMS m/z 433.1 ([M + H]$^+$) | $^1$H NMR (CDCl$_3$) δ 11.94 (s, 1H), 8.83 (d, J = 7.9 Hz, 1H), 8.04 (d, J = 5.2 Hz, 1H), 7.37-7.27 (m, 2H), 7.01 (t, J = 7.4 Hz, 1H), 6.97-6.87 (m, 3H), 5.31-5.21 (m, 1H), 5.09 (ddd, J = 8.0, 5.9, 2.5 Hz, 1H), 4.22-4.06 (m, 4H), 3.99 (dd, J = 12.2, 5.9 Hz, 1H), 3.95 (s, 3H), 3.78 (t, J = 9.1 Hz, 1H), 3.58 (dd, J = 11.9, 7.1 Hz, 1H), 1.56 (d, J = 6.4 Hz, 3H); | — |
| 212 | — | (Thin Film) 3367, 2925, 1752, 1650, 1530, 1242 | ESIMS m/z 541.2 ([M + H]$^+$) | $^1$H NMR (CDCl$_3$) δ 11.93 (s, 1H), 8.73 (t, J = 7.0 Hz, 1H), 8.02 (dd, J = 5.2, 2.1 Hz, 1H), 7.32-7.25 (m, 2H), 6.99-6.86 (m, 4H), 5.16-5.04 (m, 2H), 4.30-4.00 (m, 4H), 4.00-3.82 (m, 2H), 3.95 (s, 3H), 3.80-3.59 (m, 2H), 3.55-3.38 (m, 1H), 2.17-2.01 (m, 2H), 2.01-1.77 (m, 2H), 1.73-1.38 (m, 9H) | — |
| 213 | — | (Thin Film) 3375, 2956, 2875, 1753, 1677 | HRMS-FAB (m/z) [M + H]$^+$ calcd for C$_{30}$H$_{39}$ClN$_2$O$_{11}$, 639.2315; found, 639.232 | $^1$H NMR (CDCl$_3$) δ 8.56 (d, J = 8.0 Hz, 1H), 8.29 (d, J = 5.4 Hz, 1H), 7.17 (t, J = 8.2 Hz, 1H), 7.04 (t, J = 2.2 Hz, 1H), 6.96 (d, J = 5.4 Hz, 1H), 6.95-6.87 (m, 2H), 5.82 (s, 2H), 5.23-5.06 (m, 2H), 4.25 (t, J = 9.1 Hz, 1H), 4.10 (s, 2H), 3.91 (s, 4H), 3.82 (dd, J = 11.8, 5.3 Hz, 1H), 3.71 (dd, J = 11.1, 7.4 Hz, 1H), 3.59 (q, J = 7.0 Hz, 2H), 3.37 (ddd, J = 8.9, 7.4, 1.6 Hz, 1H), 3.29 (dd, J = 8.8, 6.3 Hz, 1H), 3.15 (dd, J = 8.8, 6.4 Hz, 1H), 1.67-1.51 (m, 2H), 1.39 (d, J = 6.3 Hz, 3H), 1.23 (t, J = 7.0 Hz, 3H), 0.68 (dd, J = 18.4, 6.7 Hz, 6H) | $^{13}$C NMR (CDCl$_3$) δ 170.88, 170.06, 163.23, 160.17, 145.87, 143.98, 141.92, 134.59, 129.98, 121.38, 116.68, 114.41, 109.87, 89.44, 83.42, 82.64, 78.00, 74.36, 74.08, 72.30, 67.80, 67.20, 56.25, 52.32, 28.62, 19.16, 19.06, 18.72, 15.01 |
| 214 | — | (Thin Film) 3376, 2955, 2874, 1753, 1677 | HRMS-FAB (m/z) [M + H]$^+$ calcd for C$_{28}$H$_{35}$ClN$_2$O$_{10}$, 595.2053; found, 595.2066 | $^1$H NMR (CDCl$_3$) δ 8.55 (d, J = 7.9 Hz, 1H), 8.29 (d, J = 5.4 Hz, 1H), 7.17 (t, J = 8.1 Hz, 1H), 7.04 (t, J = 2.2 Hz, 1H), 6.96 (d, J = 5.4 Hz, 1H), 6.94-6.87 (m, 2H), 5.78-5.70 (m, 2H), 5.21-5.08 (m, 2H), 4.25 (t, J = 9.1 Hz, 1H), 4.16-4.05 (m, 1H), | $^{13}$C NMR (CDCl$_3$) δ 170.90, 170.27, 163.27, 160.25, 160.18, 145.82, 144.03, 142.05, 134.59, 129.98, 121.37, 116.68, 114.41, 109.77, 89.43, 83.41, |

TABLE 2-continued

Analytical Data

| Compound Number | MP (°C.) | IR (cm$^{-1}$) | MASS | $^1$H NMR* | $^{13}$C NMR* |
|---|---|---|---|---|---|
| | | | | 3.94-3.88 (m, 4H), 3.83 (dd, J = 11.8, 5.3 Hz, 1H), 3.72 (dd, J = 11.0, 7.4 Hz, 1H), 3.37 (ddd, J = 8.8, 7.5, 1.6 Hz, 1H), 3.29 (dd, J = 8.8, 6.3 Hz, 1H), 3.15 (dd, J = 8.9, 6.4 Hz, 1H), 2.07 (s, 3H), 1.59 (dq, J = 13.2, 6.6 Hz, 1H), 1.39 (d, J = 6.3 Hz, 3H), 0.68 (dd, J = 18.2, 6.7 Hz, 6H) | 82.64, 77.99, 74.35, 74.09, 72.28, 56.21, 52.34, 28.62, 20.87, 19.16, 19.05, 18.73 |
| 215 | — | (Thin Film) 3377, 2956, 2876, 1754, 1678 | HRMS-FAB (m/z) [M + H]$^+$ calcd for C$_{29}$H$_{35}$F$_3$N$_2$O$_{10}$, 629.2317; found, 629.2327 | $^1$H NMR (CDCl$_3$) δ 8.55 (d, J = 7.9 Hz, 1H), 8.30 (d, J = 5.3 Hz, 1H), 7.56-7.47 (m, 2H), 7.07 (d, J = 8.6 Hz, 2H), 6.97 (d, J = 5.4 Hz, 1H), 5.78-5.70 (m, 2H), 5.24-5.09 (m, 2H), 4.34 (t, J = 9.1 Hz, 1H), 4.10 (dd, J = 11.8, 7.0 Hz, 1H), 3.96-3.88 (m, 4H), 3.83 (dd, J = 11.8, 5.3 Hz, 1H), 3.77-3.69 (m, 1H), 3.39 (ddd, J = 8.9, 7.3, 1.4 Hz, 1H), 3.28 (dd, J = 8.8, 6.3 Hz, 1H), 3.12 (dd, J = 8.9, 6.4 Hz, 1H), 2.08 (s, 3H), 1.61-1.47 (m, 1H), 1.39 (d, J = 6.3 Hz, 3H), 0.64 (dd, J = 22.7, 6.7 Hz, 6H) | — |
| 216 | — | (Thin Film) 3376, 2937, 2879, 1754, 1677 | HRMS-FAB (m/z) [M + H]$^+$ calcd for C$_{28}$H$_{33}$F$_3$N$_2$O$_{10}$, 615.216; found, 615.2167 | $^1$H NMR (CDCl$_3$) δ 8.54 (d, J = 8.0 Hz, 1H), 8.29 (d, J = 5.3 Hz, 1H), 7.56-7.47 (m, 2H), 7.09 (dd, J = 7.8, 1.6 Hz, 2H), 6.97 (d, J = 5.4 Hz, 1H), 5.78-5.70 (m, 2H), 5.23-5.09 (m, 2H), 4.34 (dd, J = 9.6, 8.6 Hz, 1H), 4.11 (dd, J = 11.8, 7.0 Hz, 1H), 3.94-3.87 (m, 4H), 3.82 (dd, J = 11.8, 5.5 Hz, 1H), 3.73 (dd, J = 11.0, 7.5 Hz, 1H), 3.48 (dt, J = 9.1, 6.6 Hz, 1H), 3.41 (ddd, J = 8.9, 7.5, 1.6 Hz, 1H), 3.30 (dt, J = 9.1, 6.6 Hz, 1H), 2.08 (s, 3H), 1.39 (d, J = 6.3 Hz, 3H), 1.36-1.22 (m, 2H), 0.65 (t, J = 7.4 Hz, 3H) | $^{13}$C NMR (CDCl$_3$) δ 170.95, 170.26, 163.28, 161.89, 160.26, 145.81, 144.05, 142.02, 126.77, 126.73, 126.69, 115.98, 109.79, 89.42, 83.23, 82.40, 74.25, 73.95, 72.95, 72.17, 56.21, 52.25, 22.92, 20.86, 18.69, 10.27 |
| 217 | — | (Thin Film) 3374, 2938, 2879, 1753, 1677 | HRMS-FAB (m/z) [M + H]$^+$ calcd for C$_{28}$H$_{33}$F$_3$N$_2$O$_{10}$, 615.216; found, 615.2156 | $^1$H NMR (CDCl$_3$) δ 8.61 (d, J = 7.9 Hz, 1H), 8.31 (d, J = 5.3 Hz, 1H), 7.54 (d, J = 9.0 Hz, 2H), 7.03-6.94 (m, 3H), 5.74 (d, J = 1.0 Hz, 2H), 5.19-5.05 (m, 2H), 4.26 (ddd, J = 8.6, 7.1, 1.2 Hz, 1H), 4.04 (dd, J = 12.0, 6.6 Hz, 1H), 3.99-3.88 (m, 5H), 3.83-3.68 (m, 2H), 3.53 (dt, J = 8.8, 6.6 Hz, 1H), 3.46 (t, J = 9.2 Hz, 1H), 2.07 (s, 3H), 1.51 (d, J = 6.3 Hz, 3H), 1.49-1.37 (m, 2H), 0.81 (t, J = 7.4 Hz, 3H) | $^{13}$C NMR (CDCl$_3$) δ 170.52, 170.25, 163.32, 160.25, 159.97, 145.86, 144.00, 142.08, 127.00, 126.96, 115.42, 109.78, 89.40, 84.46, 81.40, 75.71, 75.36, 74.89, 72.51, 56.22, 52.71, 23.36, 20.86, 18.63, 10.55 |
| 218 | — | (Thin Film) 3373, 2921, 1753, 1678 | ESIMS m/z 637 ([M + H]$^+$) | $^1$H NMR (CDCl$_3$) δ 8.59 (d, J = 8.0 Hz, 1H), 8.32 (d, J = 5.4 Hz, 1H), 6.97 (d, J = 5.4 Hz, 1H), 6.61 (d, J = 1.1 Hz, 3H), 6.56 (tt, J = 1.6, 0.7 Hz, 1H), | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 6.41-6.30 (m, 2H), 5.76-5.73 (d, J = 1.2 Hz, 2H), 5.25 (dq, J = 9.4, 6.3 Hz, 1H), 5.17 (ddd, J = 7.8, 6.9, 4.9 Hz, 1H), 4.45 (t, J = 9.1 Hz, 1H), 4.31 (ddd, J = 8.6, 7.4, 1.4 Hz, 1H), 4.16-4.06 (m, 1H), 4.01 (dt, J = 11.2, 2.2 Hz, 1H), 3.92 (s, 3H), 3.92-3.85 (m, 1H), 3.85-3.77 (m, 1H), 2.27 (s,, 6H), 2.22 (s, 6H), 2.08 (s, 3H), 1.49 (d, J = 6.3 Hz, 3H) | |
| 219 | — | (Thin Film) 3375, 2937, 1751, 1677, 1503 | HRMS-FAB (m/z) [M + H]$^+$ calcd for C$_{34}$H$_{40}$N$_2$O$_{13}$, 685.2603; found, 685.261 | $^1$H NMR (CDCl$_3$) δ 8.60 (d, J = 7.9 Hz, 1H), 8.30 (d, J = 5.4 Hz, 1H), 7.02-6.91 (m, 3H), 6.86-6.67 (m, 6H), 5.82 (s, 2H), 5.27 (dq, J = 9.4, 6.3 Hz, 1H), 5.14 (ddd, J = 7.9, 6.8, 4.9 Hz, 1H), 4.34 (t, J = 9.1 Hz, 1H), 4.23 (ddd, J = 8.7, 7.2, 1.3 Hz, 1H), 4.17-4.05 (m, 3H), 4.02 (dd, J = 11.3, 1.4 Hz, 1H), 3.91 (s, 3H), 3.88 (dd, J = 11.9, 4.9 Hz, 1H), 3.80 (dd, J = 11.2, 7.2 Hz, 1H), 3.76 (s, 3H), 3.73 (s, 3H), 3.59 (q, J = 7.0 Hz, 2H), 1.50 (s, 3H), 1.23 (t, J = 7.0 Hz, 3H) | $^{13}$C NMR (CDCl$_3$) δ 170.70, 170.05, 163.26, 160.17, 154.33, 154.31, 153.78, 151.51, 145.90, 143.96, 141.93, 117.63, 116.98, 114.62, 114.38, 109.90, 89.41, 84.14, 81.85, 74.43, 74.37, 72.46, 67.79, 67.20, 56.26, 55.66, 52.48, 18.94, 15.01 |
| 220 | — | (Thin Film) 3375, 2938, 2835, 1752, 1677, 1502 | HRMS-FAB (m/z) [M + H]$^+$ calcd for C$_{32}$H$_{36}$N$_2$O$_{12}$, 641.2341; found, 641.2349 | $^1$H NMR (CDCl$_3$) δ 8.59 (d, J = 7.9 Hz, 1H), 8.31 (d, J = 5.4 Hz, 1H), 7.02-6.91 (m, 3H), 6.85-6.68 (m, 6H), 5.74 (d, J = 1.3 Hz, 2H), 5.27 (dq, J = 9.3, 6.3 Hz, 1H), 5.16 (ddd, J = 8.0, 6.8, 4.9 Hz, 1H), 4.34 (t, J = 9.1 Hz, 1H), 4.23 (ddd, J = 8.7, 7.2, 1.3 Hz, 1H), 4.09 (dd, J = 12.0, 6.9 Hz, 1H), 4.02 (dd, J = 11.2, 1.4 Hz, 1H), 3.92 (s, 3H), 3.88 (dd, J = 11.9, 4.9 Hz, 1H), 3.80 (dd, J = 11.2, 7.3 Hz, 1H), 3.77 (s, 3H), 3.73 (s, 3H), 2.07 (s, 3H), 1.49 (d, J = 6.3 Hz, 3H) | $^{13}$C NMR (CDCl$_3$) δ 170.72, 170.27, 163.31, 160.25, 154.33, 154.30, 153.79, 151.52, 145.85, 144.02, 142.07, 117.64, 116.98, 114.63, 114.38, 109.79, 89.42, 84.14, 81.85, 74.42, 74.39, 72.46, 56.22, 55.67, 52.50, 20.88, 18.95 |
| 221 | — | (Thin Film) 3374, 2935, 2877, 1751, 1676, 1492 | HRMS-FAB (m/z) [M + H]$^+$ calcd for C$_{27}$H$_{34}$N$_2$O$_{10}$, 547.2286; found, 547.2312 | $^1$H NMR (CDCl$_3$) δ 8.55 (d, J = 8.0 Hz, 1H), 8.29 (d, J = 5.4 Hz, 1H), 7.31-7.20 (m, 2H), 7.07-6.99 (m, 2H), 6.99-6.90 (m, 2H), 5.78-5.69 (m, 2H), 5.21-5.08 (m, 2H), 4.30 (dd, J = 9.6, 8.5 Hz, 1H), 4.17-4.06 (m, 1H), 3.91 (s, 3H), 3.89 (dd, J = 11.1, 1.7 Hz, 1H), 3.77 (ddd, J = 22.7, 11.4, 6.5 Hz, 2H), 3.48 (dt, J = 9.0, 6.6 Hz, 1H), 3.44-3.32 (m, 2H), 2.07 (s, 3H), 1.41 (d, J = 6.3 Hz, 3H), 1.38-1.29 (m, 2H), 0.68 (t, J = 7.4 Hz, 3H) | $^{13}$C NMR (CDCl$_3$) δ 171.04, 170.27, 163.27, 160.25, 159.52, 145.81, 144.02, 142.06, 129.26, 121.20, 116.14, 109.76, 89.43, 83.27, 82.51, 74.46, 73.87, 73.10, 72.65, 56.21, 52.24, 22.98, 20.87, 18.76, 10.34 |
| 222 | — | (Thin Film) 3374, 2920, | HRMS-FAB (m/z) [M + H]$^+$ calcd for | $^1$H NMR (CDCl$_3$) δ 8.59 (d, J = 7.9 Hz, 1H), 8.30 (d, J = 5.4 Hz, 1H), 7.32-7.23 (m, 2H), | $^{13}$C NMR (CDCl$_3$) δ 170.69, 170.27, 163.29, 160.24, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | 2877, 1751, 1676, 1494 | C$_{27}$H$_{34}$N$_2$O$_{10}$, 547.2286; found, 547.2301 | 7.01-6.89 (m, 4H), 5.74 (d, J = 1.2 Hz, 2H), 5.17-5.03 (m, 2H), 4.21 (ddd, J = 8.6, 7.3, 1.3 Hz, 1H), 4.04 (dd, J = 12.0, 6.8 Hz, 1H), 3.94 (d, J = 11.1, 1H), 3.92 (s, 3H), 3.90-3.80 (m, 2H), 3.71 (dd, J = 11.1, 7.3 Hz, 1H), 3.54 (dt, J = 8.7, 6.7 Hz, 1H), 3.46 (dd, J = 9.6, 8.7 Hz, 1H), 2.07 (s, 3H), 1.57-1.43 (m, 5H), 0.83 (t, J = 7.4 Hz, 3H) | 157.49, 145.85, 143.99, 142.13, 129.54, 121.15, 115.64, 109.75, 89.44, 84.52, 81.24, 75.62, 74.95, 74.50, 72.66, 56.21, 52.58, 23.41, 20.87, 18.68, 10.59 |
| 223 | — | (Thin Film) 3375, 2943, 1751, 1675, 1587, 1492 | HRMS-FAB (m/z) [M + H]$^+$ calcd for C$_{29}$H$_{37}$N$_2$O$_{10}$, 573.2443; found, 573.2463 | $^1$H NMR (CDCl$_3$) δ 8.55 (d, J = 7.9 Hz, 1H), 8.29 (d, J = 5.3 Hz, 1H), 7.30-7.19 (m, 2H), 7.05-6.98 (m, 2H), 6.98-6.90 (m, 2H), 5.79-5.70 (m, 2H), 5.20-5.08 (m, 2H), 4.27 (dd, J = 9.6, 8.6 Hz, 1H), 4.10 (dd, J = 11.8, 7.1 Hz, 1H), 4.02 (ddd, J = 8.6, 5.1, 3.6 Hz, 1H), 3.92 (s, 3H), 3.86 (dd, J = 10.8, 1.6 Hz, 1H), 3.79 (dd, J = 11.8, 5.6 Hz, 1H), 3.73 (dd, J = 10.8, 7.5 Hz, 1H), 3.47 (ddd, J = 9.0, 7.5, 1.6 Hz, 1H), 2.07 (s, 3H), 1.61-1.51 (m, 2H), 1.47-1.35 (m, 7H), 1.29 (m, 2H) | $^{13}$C NMR (CDCl$_3$) δ 171.06, 170.27, 163.26, 160.25, 159.48, 145.80, 144.02, 142.13, 129.16, 121.00, 115.92, 109.75, 89.44, 82.68, 81.65, 80.05, 74.87, 73.79, 72.72, 56.21, 52.21, 32.94, 31.70, 23.31, 22.99, 20.88, 18.81 |
| 224 | — | (Thin Film) 3375, 2946, 2874, 1751, 1676, 1494 | HRMS-FAB (m/z) [M + H]$^+$ calcd for C$_{29}$H$_{36}$N$_2$O$_{10}$, 573.2443; found, 573.2469 | $^1$H NMR (CDCl$_3$) δ 8.58 (d, J = 7.9 Hz, 1H), 8.30 (d, J = 5.3 Hz, 1H), 7.34-7.21 (m, 3H), 7.00-6.86 (m, 4H), 5.74 (d, J = 1.4 Hz, 2H), 5.11 (ddd, J = 7.9, 6.7, 4.8 Hz, 1H), 5.03 (dq, J = 9.4, 6.4 Hz, 1H), 4.35 (m, 1H), 4.17 (ddd, J = 8.4, 6.8, 1.3 Hz, 1H), 4.06 (dd, J = 12.0, 6.8 Hz, 1H), 3.95-3.89 (m, 4H), 3.85 (dd, J = 12.0, 4.8 Hz, 1H), 3.73 (dd, J = 11.2, 6.9 Hz, 1H), 3.59 (dd, J = 9.5, 8.6 Hz, 1H), 2.07 (s, 3H), 1.72-1.56 (m, 6H), 1.51 (d, J = 6.4 Hz, 3H), 1.47-1.39 (m, 1H) | $^{13}$C NMR (CDCl$_3$) δ 170.77, 170.26, 163.28, 160.23, 157.44, 145.83, 143.98, 142.12, 129.52, 121.07, 115.60, 109.74, 89.43, 84.23, 82.20, 81.30, 75.08, 74.48, 73.07, 56.21, 52.56, 32.96, 32.32, 23.13, 20.87, 18.82 |
| 225 | — | — | HRMS-FAB (m/z) [M + H]$^+$ calcd for C$_{34}$H$_{40}$N$_2$O$_{11}$, 653.2705; found, 653.2727 | $^1$H NMR (CDCl$_3$) δ 8.61 (d, J = 7.9 Hz, 1H), 8.30 (d, J = 5.4 Hz, 1H), 7.10-7.02 (m, 2H), 7.02-6.94 (m, 3H), 6.94-6.87 (m, 2H), 6.72-6.62 (m, 2H), 5.82 (s, 2H), 5.28 (dq, J = 9.4, 6.3 Hz, 1H), 5.15 (ddd, J = 8.0, 6.8, 4.8 Hz, 1H), 4.42 (t, J = 9.1 Hz, 1H), 4.30 (ddd, J = 8.7, 7.3, 1.3 Hz, 1H), 4.14-4.05 (m, 3H), 4.03 (dd, J = 11.3, 1.3 Hz, 1H), 3.95-3.86 (m, 4H), 3.81 (dd, J = 11.2, 7.3 Hz, 1H), 3.59 (q, J = 7.0 Hz, 2H), 2.28 (s, 3H), 2.23 (s, 3H), 1.48 (d, J = 6.3 Hz, 3H), 1.23 (t, J = 7.0 Hz, 3H) | $^{13}$C NMR (CDCl$_3$) δ 170.68, 170.06, 163.27, 160.18, 157.53, 155.27, 145.91, 143.98, 141.94, 130.80, 130.63, 129.90, 129.74, 116.43, 115.66, 109.89, 89.43, 83.30, 80.95, 74.53, 74.45, 72.49, 67.80, 67.21, 56.26, 52.52, 20.52, 20.46, 18.90, 15.02 |

TABLE 2-continued

Analytical Data

| Compound Number | MP (° C.) | IR (cm⁻¹) | MASS | ¹H NMR* | ¹³C NMR* |
|---|---|---|---|---|---|
| 226 | — | — | HRMS-FAB (m/z) [M + H]⁺ calcd for $C_{32}H_{36}N_2O_{10}$, 609.2443; found, 609.2469 | ¹H NMR (CDCl₃) δ 8.60 (d, J = 7.9 Hz, 1H), 8.31 (d, J = 5.4 Hz, 1H), 7.09-7.02 (m, 2H), 7.02-6.94 (m, 3H), 6.94-6.87 (m, 2H), 6.71-6.62 (m, 2H), 5.74 (d, J = 1.2 Hz, 2H), 5.28 (dq, J = 9.4, 6.3 Hz, 1H), 5.16 (ddd, J = 8.0, 6.8, 4.8 Hz, 1H), 4.42 (t, J = 9.1 Hz, 1H), 4.30 (ddd, J = 8.7, 7.3, 1.3 Hz, 1H), 4.14-4.05 (m, 1H), 4.03 (dd, J = 11.2, 1.3 Hz, 1H), 3.95-3.86 (m, 4H), 3.81 (dd, J = 11.2, 7.3 Hz, 1H), 2.28 (s, 3H), 2.23 (s, 3H), 2.07 (s, 3H), 1.48 (d, J = 6.3 Hz, 3H) | ¹³C NMR (CDCl₃) δ 170.70, 170.27, 163.31, 160.25, 157.53, 155.27, 145.85, 144.02, 142.08, 130.79, 130.62, 129.89, 129.73, 116.43, 115.65, 109.78, 89.42, 83.30, 80.95, 74.52, 74.47, 72.49, 56.22, 52.54, 20.88, 20.51, 20.46, 18.89 |
| 227 | — | (Thin Film) 3377, 2927, 1750, 1676, 1502 | HRMS-FAB (m/z) [M + H]⁺ calcd for $C_{30}H_{39}F_1N_2O_{11}$, 623.2611; found, 623.2626 | ¹H NMR (CDCl₃) δ 8.59 (d, J = 7.9 Hz, 1H), 8.30 (d, J = 5.4 Hz, 1H), 7.04-6.91 (m, 3H), 6.92-6.79 (m, 2H), 5.81 (s, 2H), 5.16-5.03 (m, 2H), 4.17-4.08 (m, 3H), 4.03 (dd, J = 12.0, 6.7 Hz, 1H), 3.96-3.89 (m, 4H), 3.87 (dd J = 12.0, 4.6 Hz, 1H), 3.75-3.63 (m, 2H), 3.59 (q, J = 7.0 Hz, 2H), 3.42 (dd, J = 9.6, 8.8 Hz, 1H), 3.32 (dd, J = 8.4, 6.5 Hz, 1H), 1.73 (hept, J = 6.6 Hz, 1H), 1.50 (d, J = 6.3 Hz, 3H), 1.23 (t, J = 7.0 Hz, 3H), 0.82 (dd, J = 15.7, 6.7 Hz, 6H) | ¹³C NMR (CDCl₃) δ 170.62, 170.04, 163.24, 160.16, 158.66, 156.28, 153.57, 153.55, 145.89, 143.94, 141.97, 116.79, 116.71, 116.00, 115.77, 109.85, 89.42, 84.44, 82.22, 80.67, 75.06, 74.61, 72.63, 67.79, 67.19, 56.25, 52.59, 29.00, 19.40, 19.35, 18.69, 15.00 |
| 228 | — | (Thin Film) 3376, 2956, 1753, 1678, 1503 | HRMS-FAB (m/z) [M + H]⁺ calcd for $C_{28}H_{35}F_1N_2O_{10}$, 579.2349; found, 579.2366 | ¹H NMR (CDCl₃) δ 8.58 (d, J = 7.9 Hz, 1H), 8.30 (d, J = 5.4 Hz, 1H), 7.04-6.91 (m, 3H), 6.91-6.81 (m, 2H), 5.74 (d, J = 1.1 Hz, 2H), 5.18-5.00 (m, 2H), 4.12 (ddd, J = 8.6, 7.1, 1.2 Hz, 1H), 4.04 (dd, J = 12.0, 6.7 Hz, 1H), 3.97-3.83 (m, 5H), 3.74-3.62 (m, 2H), 3.42 (dd, J = 9.6, 8.7 Hz, 1H), 3.32 (dd, J = 8.4, 6.5 Hz, 1H), 2.07 (s, 3H), 1.73 (hept, J = 6.6 Hz, 1H), 1.50 (d, J = 6.3 Hz, 3H), 0.82 (dd, J = 15.6, 6.7 Hz, 6H) | ¹³C NMR (CDCl₃) δ 170.64, 170.26, 163.29, 160.24, 145.84, 143.99, 142.10, 116.79, 116.71, 116.00, 115.77, 109.75, 89.42, 84.43, 82.22, 80.67, 75.04, 74.62, 72.62, 56.21, 52.61, 29.00, 20.87, 19.40, 19.35, 18.70 |
| 229 | — | (Thin Film) 3372, 2939, 1765, 1676 | HRMS-FAB (m/z) [M + H]⁺ calcd for $C_{29}H_{28}F_2N_2O_9$, 587.1836; found, 587.1838 | ¹H NMR (CDCl₃) δ 8.78 (d, J = 8.2 Hz, 1H), 8.37 (d, J = 5.4 Hz, 1H), 7.03 (d, J = 5.5 Hz, 1H), 6.98-6.86 (m, 6H), 6.74-6.61 (m, 2H), 5.33-5.24 (m, 1H), 5.14 (m, 1H), 4.36 (t, J = 9.2 Hz, 1H), 4.30-4.22 (m, 1H), 4.10-3.99 (m, 2H), 3.92 (s, 3H), 3.92-3.87 (m, 1H), 3.79 (dd, J = 11.2, 7.3 Hz, 1H), 2.40 (s, 3H), 1.48 (d, J = 6.4 Hz, 3H) | — |

TABLE 2-continued

Analytical Data

| Compound Number | MP (°C.) | IR (cm⁻¹) | MASS | ¹H NMR* | ¹³C NMR* |
|---|---|---|---|---|---|
| 230 | — | (Thin Film) 3372, 2926, 1753, 1676 | HRMS-FAB (m/z) [M + H]⁺ calcd for $C_{32}H_{34}F_2N_2O_{11}$, 661.2203; found, 661.2217 | ¹H NMR (CDCl₃) δ 8.61 (d, J = 7.9 Hz, 1H), 8.31 (d, J = 5.4 Hz, 1H), 7.01-6.86 (m, 7H), 6.72-6.64 (m, 2H), 5.82 (s, 2H), 5.30 (dq, J = 9.4, 6.4 Hz, 1H), 5.19-5.12 (m, 1H), 4.38 (t, J = 9.2 Hz, 1H), 4.26 (t, J = 7.9 Hz, 1H), 4.14-4.05 (m, 3H), 4.02 (d, J = 11.3 Hz, 1H), 3.97-3.88 (m, 4H), 3.81 (dd, J = 11.3, 7.2 Hz, 1H), 3.59 (q, J = 7.0 Hz, 2H), 1.49 (d, J = 6.3 Hz, 3H), 1.24 (t, J = 7.0 Hz, 3H) | — |
| 231 | — | (Thin Film) 2928, 1752, 1676, 1500 | HRMS-FAB (m/z) [M + H]⁺ calcd for $C_{30}H_{30}F_2N_2O_{10}$, 617.1941; found, 617.1929 | ¹H NMR (CDCl₃) δ 8.61 (d, J = 7.9 Hz, 1H), 8.31 (d, J = 5.4 Hz, 1H), 7.03-6.84 (m, 7H), 6.74-6.62 (m, 2H), 5.74 (d, J = 1.1 Hz, 2H), 5.29 (m, 1H), 5.17 (ddd, J = 7.9, 6.7, 4.7 Hz, 1H), 4.38 (t, J = 9.1 Hz, 1H), 4.31-4.22 (m, 1H), 4.09 (dd, J = 12.0, 6.8 Hz, 1H), 4.02 (dd, J = 11.3, 1.3 Hz, 1H), 3.99-3.87 (m, 4H), 3.81 (dd, J = 11.3, 7.3 Hz, 1H), 2.08 (s, 3H), 1.49 (d, J = 6.3 Hz, 3H) | — |
| 232 | 54-60 | — | ESIMS m/z 507 ([M + H]⁺) | ¹H NMR (CDCl₃) δ 8.68 (d, J = 8.2 Hz, 1H), 8.31 (d, J = 5.4 Hz, 1H), 6.99 (d, J = 5.5 Hz, 1H), 5.03 (ddd, J = 8.3, 7.1, 5.3 Hz, 1H), 4.92 (dq, J = 9.0, 6.3 Hz, 1H), 3.99 (dd, J = 11.8, 7.0 Hz, 1H), 3.88 (s, 3H), 3.83-3.69 (m, 3H), 3.57 (dd, J = 10.9, 7.0 Hz, 1H), 3.45-3.33 (m, 3H), 3.28-3.17 (m, 2H), 2.37 (s, 3H), 1.44 (d, J = 6.3 Hz, 3H), 1.13-0.95 (m, 2H), 0.59-0.45 (m, 4H), 0.26-0.12 (m, 4H) | ¹³C NMR (CDCl₃) δ 170.80, 168.81, 162.72, 159.40, 146.77, 141.09, 137.51, 109.91, 84.63, 83.30, 78.75, 75.85, 74.95, 73.94, 72.94, 56.29, 52.05, 20.70, 18.59, 11.08, 10.92, 3.21, 3.16, 2.93, 2.84 |
| 233 | — | — | ESIMS m/z 537 ([M + H]⁺) | ¹H NMR (CDCl₃) δ 8.31 (d, J = 7.9 Hz, 1H), 8.06 (d, J = 5.3 Hz, 1H), 6.75 (d, J = 5.4 Hz, 1H), 5.55-5.47 (m, 2H), 4.85 (td, J = 7.3, 5.2 Hz, 1H), 4.73 (dq, J = 8.4, 6.3 Hz, 1H), 3.82 (dd, J = 11.8, 7.0 Hz, 1H), 3.70 (s, 3H), 3.64-3.53 (m, 3H), 3.39 (dd, J = 10.9, 6.8 Hz, 1H), 3.25-3.13 (m, 3H), 3.10-2.98 (m, 2H), 1.85 (s, 3H), 1.26 (d, J = 6.3 Hz, 3H), 0.93-0.77 (m, 2H), 0.39-0.25 (m, 4H), −0.01 (ddt, J = 9.2, 6.0, 4.7 Hz, 4H) | ¹³C NMR (CDCl₃) δ 170.88, 170.22, 163.23, 160.19, 145.79, 143.91, 142.06, 109.73, 89.38, 84.61, 83.31, 78.72, 75.79, 75.03, 73.98, 72.90, 56.19, 52.31, 20.84, 18.59, 11.07, 10.91, 3.20, 3.14, 2.92, 2.83 |
| 234 | 68-75 | (Thin Film) 3372, 2978, 2938, 1750, 1678, 1493, 1227 | HRMS-ESI (m/z) [M + H]⁺ calcd for $C_{32}H_{37}N_2O_{10}$, 609.2443; found, 609.2450 | ¹H NMR (CDCl₃) δ 8.67 (d, J = 6.5 Hz, 1H), 8.36 (s, 1H), 7.27-7.09 (m, 4H), 7.08-6.82 (m, 5H), 6.82-6.64 (m, 2H), 5.79 (s, 2H), 5.36-5.27 (m, 1H), 5.21-5.13 (m, 1H), 4.51 (t, J = 9.1 Hz, 1H), 4.37 (t, J = 7.9 Hz, 1H), | ¹³C NMR (CDCl₃) δ 176.27, 170.59, 159.46, 157.24, 129.44, 129.27, 121.55, 121.31, 116.48, 115.59, 89.70, 82.86, 80.56, 74.64, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 4.14-4.00 (m, 2H), 3.99-3.89 (m, 4H), 3.83 (dd, J = 11.1, 7.3 Hz, 1H), 2.56 (p, J = 7.0 Hz, 1H), 1.49 (d, J = 6.3 Hz, 3H), 1.14 (d, J = 6.9 Hz, 6H) | 74.56, 72.38, 56.42, 52.67, 33.85, 18.88, 18.69 |
| 235 | 58-66 | (Thin Film) 3372, 2934, 1758, 1678, 1587, 1492, 1200 | HRMS-ESI (m/z) [M + H]$^+$ calcd for C$_{31}$H$_{35}$N$_2$O$_{10}$, 595.2286; found, 595.2297 | $^1$H NMR (CDCl$_3$) δ 8.77 (d, J = 8.1 Hz, 1H), 8.37 (d, J = 5.2 Hz, 1H), 7.36-7.15 (m, 4H), 7.05-6.86 (m, 5H), 6.73 (d, J = 7.8 Hz, 2H), 5.31 (dq, J = 9.5, 6.3 Hz, 1H), 5.15 (ddd, J = 8.2, 6.8, 4.7 Hz, 1H), 4.50 (t, J = 9.1 Hz, 1H), 4.37 (ddd, J = 8.8, 7.4, 1.3 Hz, 1H), 4.14-4.00 (m, 2H), 3.91 (s, 3H), 3.90-3.86 (m, 1H), 3.85-3.78 (m, 3H), 3.41 (s, 3H), 2.98 (t, J = 6.5 Hz, 2H), 1.48 (d, J = 6.3 Hz, 3H) | $^{13}$C NMR (CDCl$_3$) δ 176.27, 170.59, 159.46, 157.24, 129.44, 129.27, 121.55, 121.31, 116.48, 115.59, 89.70, 82.86, 80.56, 74.64, 74.56, 72.38, 56.42, 52.67, 33.85, 18.88, 18.69 |
| 236 | 85-95 | (Thin Film) 3371, 2940, 1769, 1678, 1493 | HRMS-ESI (m/z) [M + H]$^+$ calcd for C$_{29}$H$_{31}$N$_2$O$_9$, 551.2024; found, 551.2033 | $^1$H NMR (CDCl$_3$) δ 8.79 (s, 1H), 8.38 (s, 1H), 7.34-7.15 (m, 4H), 7.06-6.86 (m, 5H), 6.76-6.69 (m, 2H), 5.37-5.25 (m, 1H), 5.15 (td, J = 7.2, 4.6 Hz, 1H), 4.50 (t, J = 9.1 Hz, 1H), 4.37 (dd, J = 8.8, 7.1 Hz, 1H), 4.12-4.01 (m, 2H), 3.92 (s, 3H), 3.92-3.86 (m, 1H), 3.82 (dd, J = 11.2, 7.4 Hz, 1H), 2.40 (s, 3H), 1.48 (d, J = 6.3 Hz, 3H) | $^{13}$C NMR (CDCl$_3$) δ 170.53, 168.85, 159.47, 157.24, 146.83, 129.45, 129.27, 121.54, 121.31, 116.49, 115.58, 110.00, 99.99, 82.87, 80.54, 74.57, 72.36, 56.34, 52.34, 20.73, 18.88 |
| 237 | — | (Thin Film) 3375, 2955, 2873, 1753, 1677, 1507, 1088 | ESIMS m/z 555 ([M + H]$^+$) | $^1$H NMR (CDCl$_3$) δ 8.67 (d, J = 8.2 Hz, 1H), 8.38-8.30 (m, 1H), 7.00 (dd, J = 5.7, 1.8 Hz, 1H), 5.08-4.98 (m, 1H), 4.93 (ddt, J = 12.2, 8.4, 4.1 Hz, 1H), 4.00 (tt, J = 7.2, 3.4 Hz, 1H), 3.93-3.84 (m, 3H), 3.85-3.64 (m, 5H), 3.64-3.55 (m, 1H), 3.41 (d, J = 1.5 Hz, 3H), 3.33-3.12 (m, 5H), 2.97 (t, J = 6.6 Hz, 2H), 1.82 (tt, J = 12.9, 6.0 Hz, 2H), 1.43 (dd, J = 6.3, 1.7 Hz, 3H), 0.97-0.85 (m, 12H) | $^{13}$C NMR (CDCl$_3$) δ 170.85, 169.37, 162.67, 159.42, 146.81, 141.19, 137.38, 109.88, 84.82, 83.75, 80.56, 77.70, 74.88, 74.07, 72.99, 67.58, 58.80, 56.32, 52.13, 34.61, 29.11, 28.87, 19.58, 19.46, 19.37, 18.63 |
| 238 | 118-120 | (Thin Film) 3384, 2954, 2873, 1760, 1748, 1675, 1512, 1092 | HRMS-ESI (m/z) [M + H]$^+$ calcd for C$_{25}$H$_{39}$N$_2$O$_9$, 511.2650; found, 511.2652 | $^1$H NMR (CDCl$_3$) δ 8.70 (d, J = 8.2 Hz, 1H), 8.34 (d, J = 5.4 Hz, 1H), 7.00 (d, J = 5.5 Hz, 1H), 5.09-4.87 (m, 2H), 4.02 (dd, J = 11.9, 6.9 Hz, 1H), 3.91 (s, 3H), 3.84-3.66 (m, 3H), 3.65-3.52 (m, 1H), 3.37-3.12 (m, 5H), 2.39 (s, 3H), 1.82 (dh, J = 13.2, 6.6 Hz, 2H), 1.44 (d, J = 6.3 Hz, 3H), 0.97-0.84 (m, 12H) | $^{13}$C NMR (CDCl$_3$) δ 170.82, 168.83, 162.73, 159.41, 146.76, 141.17, 137.53, 109.89, 84.83, 83.75, 80.57, 77.71, 74.95, 74.10, 73.00, 56.29, 52.17, 29.11, 28.88, 20.72, 19.58, 19.46, 19.45, 19.37, 18.64 |
| 239 | — | (Thin Film) 2931, 1765, 1708, | HRMS-FAB (m/z) [M + H]$^+$ calcd for C$_{32}$H$_{47}$NO$_9$, | $^1$H NMR (CDCl$_3$) δ 7.29-7.21 (m, 2H), 6.97-6.90 (m, 3H), 5.29 (dd, J = 8.9, 3.8 Hz, 1H), 5.24-5.17 (m, 1H), 4.97-4.86 (m, | $^{13}$C NMR (CDCl$_3$) δ 168.83, 157.55, 152.56, 145.41, 129.46, 121.08, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | 1367, 1240 | 589.3251; found, 589.3265 | 1H), 4.36 (dd, J = 10.8, 7.1 Hz, 1H), 4.32-4.21 (m, 2H), 4.15 (dd, J = 10.9, 7.6 Hz, 1H), 4.00-3.87 (m, 2H), 3.66 (dd, J = 11.0, 7.3 Hz, 1H), 3.50 (dd, J = 9.7, 8.8 Hz, 1H), 2.17-1.99 (m, 4H), 1.59-1.38 (m, 6H), 1.51 (s, 18H), 1.49 (d, J = 6.3 Hz, 3H) | 117.47, 115.76, 83.20, 83.13, 81.41, 75.57, 72.96, 72.65, 69.01, 57.88, 37.04, 28.86, 28.27, 27.73, 26.66, 18.87 |
| 240 | — | — | ESIMS m/z 464 ([M + Na]$^+$) | $^1$H NMR (CDCl$_3$) δ 5.41-5.22 (m, 3H), 4.88 (dq, J = 8.8, 6.2 Hz, 1H), 4.64 (q, J = 6.8 Hz, 1H), 4.37 (dd, J = 10.8, 7.1 Hz, 1H), 4.13-3.99 (m, 3H), 3.98-3.83 (m, 1H), 3.80 (d, J = 11.0 Hz, 1H), 3.69-3.62 (m, 1H), 3.55 (dd, J = 11.1, 6.3 Hz, 1H), 3.29-3.17 (m, 2H), 1.78-1.72 (m, 6H), 1.71-1.64 (m, 6H), 1.46-1.41 (m, 12H) | $^{13}$C NMR (CDCl$_3$) δ 171.39, 137.14, 136.86, 121.12, 121.00, 84.38, 82.85, 80.13, 77.02, 76.71, 75.24, 74.51, 72.90, 70.29, 67.43, 60.39, 53.53, 28.28, 25.79, 25.78, 18.64, 18.03, 17.99, 14.21 |
| 241 | — | (Thin Film) 3352, 2956, 2930, 2872, 1754, 1715, 1367, 1164, 1095 | HRMS-ESI (m/z) [M + H]$^+$ calcd for C$_{23}$H$_{44}$NO$_7$, 446.3112; found, 446.3212 | $^1$H NMR (CDCl$_3$) δ 5.33 (t, J = 7.2 Hz, 1H), 4.87 (dq, J = 9.4, 6.1 Hz, 1H), 4.64 (td, J = 7.1, 4.7 Hz, 1H), 3.98-3.79 (m, 2H), 3.76 (d, J = 11.0 Hz, 1H), 3.72-3.45 (m, 4H), 3.19-3.11 (m, 2H), 1.75-1.58 (m, 2H), 1.47-1.39 (m, 16H), 1.32-1.19 (m, 1H), 0.92-0.86 (m, 12H) | $^{13}$C NMR (CDCl$_3$) δ 171.38, 155.09, 85.06, 83.68, 80.13, 74.60, 72.88, 72.45, 69.29, 53.56, 39.22, 38.93, 28.28, 25.00, 24.94, 22.90, 22.65, 22.61, 22.58, 22.49, 18.58 |
| 242 | — | — | ESIMS m/z 436 ([M + Na]$^+$) | $^1$H NMR (CDCl$_3$) δ 5.26 (d, J = 8.8 Hz, 1H), 4.88 (dq, J = 8.9, 6.2 Hz, 1H), 4.62 (td, J = 7.3, 5.2 Hz, 1H), 3.88 (dd, J = 11.8, 6.7 Hz, 1H), 3.74 (dt, J = 9.8, 7.5 Hz, 2H), 3.62 (dd, J = 11.8, 5.1 Hz, 1H), 3.58-3.48 (m, 1H), 3.44-3.29 (m, 3H), 3.25-3.12 (m, 2H), 1.45-1.37 (m, 12H), 1.11-0.94 (m, 2H), 0.56-0.45 (m, 4H), 0.17 (ddt, J = 9.3, 6.0, 4.7 Hz, 4H) | $^{13}$C NMR (CDCl$_3$) δ 171.35, 155.08, 84.65, 83.29, 80.09, 78.71, 75.78, 75.15, 74.43, 72.84, 53.47, 28.25, 18.53, 11.06, 10.90, 3.19, 3.14, 2.92, 2.82 |
| 243 | — | — | ESIMS m/z 522 ([M + Na]$^+$) | $^1$H NMR (CDCl$_3$) δ 7.02-6.93 (m, 2H), 6.93-6.86 (m, 2H), 5.31 (dd, J = 8.6, 2.4 Hz, 1H), 5.04 (dq, J = 8.9, 6.3 Hz, 1H), 4.27 (dd, J = 12.6, 2.4 Hz, 1H), 4.17-4.05 (m, 2H), 3.93 (dd, J = 12.6, 8.6 Hz, 1H), 3.75 (td, J = 8.8, 2.1 Hz, 1H), 3.58 (dd, J = 11.1, 7.6 Hz, 1H), 2.94 (d, J = 2.1 Hz, 1H), 1.52 (s, 21H) | $^{13}$C NMR (CDCl$_3$) δ 168.35, 152.62, 117.17, 117.09, 116.26, 116.03, 83.19, 81.37, 76.29, 75.89, 74.32, 73.33, 58.41, 27.99, 18.72 |
| 244 | — | — | ESIMS m/z 522 ([M + Na]$^+$) | $^1$H NMR (CDCl$_3$) δ 7.03-6.91 (m, 4H), 5.25 (dd, J = 8.5, 4.0 Hz, 1H), 5.12-5.02 (m, 1H), 4.31 (dd, J = 12.2, 4.0 Hz, 1H), 4.20-4.07 (m, 2H), 3.99 (dd, J = 12.1, 8.5 Hz, 1H), 3.87 (td, J = 6.2, 5.1, 3.4 Hz, 1H), 3.68 (dd, J = 11.2, 7.4 Hz, | $^{13}$C NMR (CDCl$_3$) δ 168.70, 159.08, 156.68, 155.09, 155.06, 152.63, 117.59, 117.51, 116.27, 116.04, 85.69, 83.19, 73.85, 71.99, |

TABLE 2-continued

Analytical Data

| Compound Number | MP (°C.) | IR (cm⁻¹) | MASS | ¹H NMR* | ¹³C NMR* |
|---|---|---|---|---|---|
| | | | | 1H), 2.38 (d, J = 3.3 Hz, 1H), 1.52 (d, J = 2.6 Hz, 18H), 1.35 (d, J = 6.4 Hz, 3H) | 58.17, 27.96, 19.01 |
| 245 | — | — | ESIMS m/z 616 ([M + Na]⁺) | ¹H NMR (CDCl₃) δ 6.98-6.82 (m, 6H), 6.72-6.65 (m, 2H), 5.33 (dd, J = 8.9, 3.6 Hz, 1H), 5.13 (dq, J = 9.2, 6.3 Hz, 1H), 4.45-4.26 (m, 3H), 4.05 (dd, J = 11.2, 1.0 Hz, 1H), 3.98 (dd, J = 12.4, 8.9 Hz, 1H), 3.75 (dd, J = 11.1, 7.0 Hz, 1H), 1.53 (s, 18H), 1.46 (d, J = 6.3 Hz, 3H) | ¹³C NMR (CDCl₃) δ 168.69, 156.38, 155.54, 153.44, 153.41, 152.61, 117.54, 117.46, 116.92, 116.84, 115.91, 115.76, 115.68, 115.53, 83.76, 83.28, 81.62, 75.41, 73.22, 72.11, 57.91, 27.98, 18.95 |
| 246 | 108 | — | ESIMS m/z 578 ([M + Na]⁺) | ¹H NMR (CDCl₃) δ 6.98-6.90 (m, 2H), 6.91-6.83 (m, 2H), 5.27 (dd, J = 8.8, 3.6 Hz, 1H), 4.91 (dq, J = 9.8, 6.2 Hz, 1H), 4.26 (dd, J = 12.3, 3.6 Hz, 1H), 4.15 (dd, J = 8.7, 7.2 Hz, 1H), 3.98-3.87 (m, 2H), 3.69-3.60 (m, 2H), 3.40 (t, J = 9.2 Hz, 1H), 3.30 (dd, J = 8.4, 6.6 Hz, 1H), 1.78-1.65 (m, 1H), 1.51 (s, 18H), 1.47 (d, J = 6.3 Hz, 3H), 0.82 (d, J = 6.7 Hz, 3H), 0.78 (d, J = 6.7 Hz, 3H) | — |
| 247 | — | — | ESIMS m/z 518 ([M + Na]⁺) | ¹H NMR (CDCl₃) δ 7.12-7.05 (m, 2H), 6.95-6.88 (m, 2H), 5.25 (dd, J = 8.5, 3.9 Hz, 1H), 5.06 (dq, J = 8.9, 6.4 Hz, 1H), 4.30 (dd, J = 12.2, 3.9 Hz, 1H), 4.19 (t, J = 8.8 Hz, 1H), 4.16-4.08 (m, 1H), 3.99 (dd, J = 12.2, 8.5 Hz, 1H), 3.90-3.81 (m, 1H), 3.67 (dd, J = 11.1, 7.4 Hz, 1H), 2.42 (d, J = 2.9 Hz, 1H), 2.29 (s, 3H), 1.52 (s, 18H), 1.34 (d, J = 6.4 Hz, 3H) | ¹³C NMR (CDCl₃) δ 168.70, 156.86, 152.61, 131.56, 130.20, 116.13, 84.88, 83.16, 73.91, 72.23, 58.24, 27.96, 20.48, 19.00 |
| 248 | — | — | ESIMS m/z 440 ([M − C₄H₉+ 2H]⁺) | ¹H NMR (CDCl₃) δ 7.11-7.05 (m, 2H), 6.87-6.80 (m, 2H), 5.32 (dd, J = 8.8, 2.5 Hz, 1H), 5.03 (dq, J = 9.0, 6.3 Hz, 1H), 4.26 (dd, J = 12.5, 2.5 Hz, 1H), 4.18-4.07 (m, 2H), 3.92 (dd, J = 12.6, 8.8 Hz, 1H), 3.75 (td, J = 8.8, 2.0 Hz, 1H), 3.57 (dd, J = 11.0, 7.7 Hz, 1H), 2.98 (d, J = 1.9 Hz, 1H), 2.28 (s, 3H), 1.52 (s, 21H) | ¹³C NMR (CDCl₃) δ 168.44, 154.46, 152.59, 131.27, 130.15, 115.75, 83.17, 80.57, 76.35, 75.86, 74.19, 73.40, 58.40, 27.99, 20.48, 18.71 |
| 249 | 110-112 | — | ESIMS m/z 504 ([M + Na]⁺) | ¹H NMR (CDCl₃) δ 7.33-7.27 (m, 2H), 7.04-6.97 (m, 3H), 5.26 (dd, J = 8.5, 3.9 Hz, 1H), 5.08 (dq, J = 8.9, 6.4 Hz, 1H), 4.31 (dd, J = 12.2, 4.0 Hz, 1H), 4.26 (t, J = 8.7 Hz, 1H), 4.14-4.11 (m, 1H), 3.99 (dd, J = 12.2, 8.5 Hz, 1H), 3.88 (dddd, J = 8.6, 7.5, 3.1, 1.3 Hz, 1H), 3.68 (dd, J = 11.0, | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 7.4 Hz, 1H), 2.42 (d, J = 3.1 Hz, 1H), 1.52 (s, 18H), 1.35 (d, J = 6.4 Hz, 3H) | |
| 250 | — | — | ESIMS m/z 504 ([M + Na]$^+$) | $^1$H NMR (CDCl$_3$) δ 7.33-7.26 (m, 2H), 7.04-6.92 (m, 3H), 5.32 (dd, J = 8.7, 2.4 Hz, 1H), 5.05 (dq, J = 9.0, 6.3 Hz, 1H), 4.27 (dd, J = 12.5, 2.4 Hz, 1H), 4.23-4.16 (m, 1H), 4.16-4.08 (m, 1H), 3.93 (dd, J = 12.6, 8.7 Hz, 1H), 3.77 (td, J = 8.8, 2.0 Hz, 1H), 3.59 (dd, J = 11.0, 7.7 Hz, 1H), 2.97 (d, J = 2.0 Hz, 1H), 1.53 (s, 18H), 1.52 (d, J = 1.9 Hz, 3H) | — |
| 251 | — | — | ESIMS m/z 608 ([M + Na]$^+$) | $^1$H NMR (CDCl$_3$) δ 7.07-7.01 (m, 2H), 7.00-6.95 (m, 2H), 6.93-6.86 (m, 2H), 6.70-6.64 (m, 2H), 5.33 (dd, J = 8.9, 3.8 Hz, 1H), 5.12 (dq, J = 9.4, 6.3 Hz, 1H), 4.41 (t, J = 9.1 Hz, 1H), 4.37-4.26 (m, 2H), 4.05 (dd, J = 11.0, 1.3 Hz, 1H), 3.97 (dd, J = 12.3, 8.9 Hz, 1H), 3.75 (dd, J = 11.0, 7.3 Hz, 1H), 2.27 (s, 3H), 2.23 (s, 3H), 1.53 (s, 18H), 1.45 (d, J = 6.3 Hz, 3H) | $^{13}$C NMR (CDCl$_3$) δ 168.86, 157.56, 155.41, 152.59, 130.69, 130.51, 129.82, 129.70, 116.45, 115.75, 83.23, 83.21, 80.98, 77.38, 77.06, 76.74, 75.31, 73.04, 72.47, 57.92, 27.99, 20.52, 20.46, 18.98 |
| 252 | — | — | ESIMS m/z 572 ([M + Na]$^+$) | $^1$H NMR (CDCl$_3$) δ 7.31-7.22 (m, 2H), 6.97-6.89 (m, 3H), 5.33-5.23 (m, 1H), 4.86 (dq, J = 9.5, 6.3 Hz, 1H), 4.35 (ddd, J = 7.4, 4.2, 2.0 Hz, 1H), 4.28-4.18 (m, 2H), 3.98-3.87 (m, 2H), 3.69 (dd, J = 11.2, 6.9 Hz, 1H), 3.58 (dd, J = 9.6, 8.6 Hz, 1H), 1.73-1.54 (m, 5H), 1.51 (s, 20H), 1.48 (d, J = 6.3 Hz, 3H), 1.46-1.33 (m, 1H) | $^{13}$C NMR (CDCl$_3$) δ 168.93, 157.56, 152.57, 129.44, 120.99, 115.70, 84.14, 83.10, 82.04, 81.39, 75.62, 73.09, 72.91, 57.88, 32.96, 32.32, 27.96, 23.12, 18.89 |
| 253 | — | — | ESIMS m/z 572 ([M + Na]$^+$) | $^1$H NMR (CDCl$_3$) δ 7.27-7.19 (m, 2H), 6.98 (m, 2H), 6.95-6.87 (m, 1H), 5.27 (dd, J = 9.1, 4.2 Hz, 1H), 5.01 (dq, J = 9.7, 6.3 Hz, 1H), 4.40-4.21 (m, 2H), 4.02 (td, J = 5.1, 2.6 Hz, 1H), 3.96 (dd, J = 12.2, 9.2 Hz, 1H), 3.92-3.86 (m, 1H), 3.78-3.72 (m, 1H), 3.64 (dd, J = 10.8, 7.5 Hz, 1H), 3.54-3.45 (m, 1H), 1.85 (m, 1H), 1.52 (s, 18H), 1.47-1.33 (m, 6H), 1.32-1.24 (m, 3H) | $^{13}$C NMR (CDCl$_3$) δ 169.11, 159.51, 152.62, 129.10, 120.90, 115.92, 83.09, 82.64, 81.36, 79.83, 75.97, 72.60, 72.47, 57.80, 32.97, 31.66, 27.95, 23.34, 23.00, 18.86 |
| 254 | — | — | ESIMS m/z 546 ([M + Na]$^+$) | $^1$H NMR (CDCl$_3$) δ 7.30-7.22 (m, 2H), 6.98-6.89 (m, 3H), 5.29 (dd, J = 8.9, 3.7 Hz, 1H), 4.91 (dq, J = 9.7, 6.2 Hz, 1H), 4.30-4.22 (m, 2H), 3.99-3.88 (m, 2H), 3.82 (dt, J = 8.8, 6.6 Hz, 1H), 3.66 (dd, J = 11.0, 7.2 Hz, 1H), 3.52 (dt, J = 8.7, 6.7 Hz, 1H), 3.44 (dd, J = 9.7, 8.7 Hz, 1H), | $^{13}$C NMR (CDCl$_3$) δ 168.85, 157.62, 152.57, 129.45, 121.06, 115.75, 84.42, 83.12, 81.31, 75.60, 75.54, 73.00, 72.65, 57.92, 27.97, 23.41, 18.76, 10.59 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 1.52 (s, 18H), 1.50-1.43 (m, 5H), 0.81 (t, J = 7.4 Hz, 3H) | |
| 255 | — | — | ESIMS m/z 546 ([M + Na]$^+$) | $^1$H NMR (CDCl$_3$) δ 7.29-7.20 (m, 2H), 7.03-6.98 (m, 2H), 6.93 (tt, J = 7.3, 1.0 Hz, 1H), 5.27 (dd, J = 9.0, 4.2 Hz, 1H), 5.02 (dq, J = 9.6, 6.3 Hz, 1H), 4.34-4.24 (m, 2H), 4.02-3.88 (m, 2H), 3.65 (dd, J = 10.9, 7.4 Hz, 1H), 3.52-3.40 (m, 2H), 3.36 (dt, J = 9.0, 6.6 Hz, 1H), 1.52 (s, 18H), 1.38 (d, J = 6.3 Hz, 3H), 1.36-1.24 (m, 2H), 0.67 (t, J = 7.4 Hz, 3H) | $^{13}$C NMR (CDCl$_3$) δ 169.07, 159.54, 152.64, 129.20, 121.09, 116.13, 83.25, 83.09, 82.29, 75.59, 73.01, 72.72, 72.40, 57.84, 27.95, 22.99, 18.81, 10.33 |
| 256 | — | — | ESIMS m/z 534 ([M + Na]$^+$) | $^1$H NMR (CDCl$_3$) δ 6.96-6.84 (m, 2H), 6.84-6.76 (m, 2H), 5.31 (dd, J = 8.7, 2.5 Hz, 1H), 5.02 (dq, J = 9.1, 6.3 Hz, 1H), 4.26 (dd, J = 12.5, 2.5 Hz, 1H), 4.15-4.03 (m, 2H), 3.91 (dd, J = 12.6, 8.7 Hz, 1H), 3.81-3.69 (m, 4H), 3.55 (dd, J = 10.8, 7.6 Hz, 1H), 3.10 (d, J = 2.0 Hz, 1H), 1.52 (s, 21H) | $^{13}$C NMR (CDCl$_3$) δ 168.43, 154.66, 152.58, 150.61, 117.16, 114.80, 83.11, 81.43, 76.35, 75.78, 74.15, 73.33, 58.40, 55.67, 27.97, 18.72 |
| 257 | — | — | ESIMS m/z 534 ([M + H]$^+$) | $^1$H NMR (CDCl$_3$) δ 6.98-6.91 (m, 2H), 6.85-6.78 (m, 2H), 5.24 (dd, J = 8.5, 4.0 Hz, 1H), 5.05 (dq, J = 8.8, 6.3 Hz, 1H), 4.30 (dd, J = 12.2, 4.0 Hz, 1H), 4.16-4.06 (m, 2H), 3.98 (dd, J = 12.2, 8.5 Hz, 1H), 3.84 (dddd, J = 8.6, 7.4, 3.1, 1.3 Hz, 1H), 3.76 (s, 3H), 3.66 (dd, J = 11.0, 7.4 Hz, 1H), 2.61 (d, J = 3.1 Hz, 1H), 1.51 (s, 18H), 1.34 (d, J = 6.4 Hz, 3H) | $^{13}$C NMR (CDCl$_3$) δ 168.70, 154.68, 153.06, 152.59, 117.42, 114.76, 85.73, 83.10, 77.55, 73.86, 73.83, 72.19, 58.21, 55.64, 27.94, 19.02 |
| 258 | — | — | ESIMS m/z 640 ([M + Na]$^+$) | $^1$H NMR (CDCl$_3$) δ 6.97-6.91 (m, 2H), 6.81-6.76 (m, 2H), 6.73 (s, 4H), 5.32 (dd, J = 8.9, 3.8 Hz, 1H), 5.11 (dq, J = 9.3, 6.3 Hz, 1H), 4.38-4.22 (m, 3H), 4.08-4.02 (m, 1H), 3.97 (dd, J = 12.3, 9.0 Hz, 1H), 3.78-3.74 (m, 4H), 3.72 (s, 3H), 1.53 (s, 18H), 1.47 (d, J = 6.3 Hz, 3H) | $^{13}$C NMR (CDCl$_3$) δ 168.87, 154.27, 154.25, 153.80, 152.59, 151.65, 117.63, 117.10, 114.54, 114.34, 84.06, 83.20, 81.88, 75.20, 72.96, 72.42, 57.87, 55.65, 27.98, 19.02. |
| 259 | — | — | ESIMS m/z 572 ([M + Na]$^+$) | $^1$H NMR (CDCl$_3$) δ 7.59-7.52 (m, 2H), 7.03 (d, J = 8.6 Hz, 2H), 5.39-5.28 (m, 1H), 5.06 (dq, J = 8.9, 6.3 Hz, 1H), 4.34-4.21 (m, 2H), 4.06 (dd, J = 11.2, 1.3 Hz, 1H), 3.94 (dd, J = 12.7, 8.5 Hz, 1H), 3.80 (t, J = 8.7 Hz, 1H), 3.64 (dd, J = 11.2, 7.4 Hz, 1H), 2.87 (s, 1H), 1.53 (s, 21H) | $^{13}$C NMR (CDCl$_3$) δ 168.30, 159.10, 152.61, 127.21, 127.18, 127.14, 127.10, 125.55, 124.15, 123.82, 122.86, 115.66, 83.27, 80.62, 76.11, 75.90, 74.35, 73.36, 58.38, 27.99, 27.95, 18.69 |
| 260 | — | — | ESIMS m/z 572 ([M + Na]$^+$) | $^1$H NMR (CDCl$_3$) δ 7.59-7.52 (m, 2H), 7.13-7.06 (m, 2H), 5.26 (dd, J = 8.5, 4.1 Hz, 1H), 5.09 (dq, J = 8.7, 6.4 Hz, 1H), | $^{13}$C NMR (CDCl$_3$) δ 168.72, 161.29, 152.63, 127.25, 127.21, 127.17, |

TABLE 2-continued

Analytical Data

| Compound Number | MP (° C.) | IR (cm⁻¹) | MASS | ¹H NMR* | ¹³C NMR* |
|---|---|---|---|---|---|
| | | | | 4.37-4.29 (m, 2H), 4.09 (dd, J = 12.1, 1.5 Hz, 1H), 4.00 (dd, J = 12.2, 8.6 Hz, 1H), 3.91 (ddd, J = 8.5, 7.3, 1.4 Hz, 1H), 3.72 (dd, J = 11.1, 7.3 Hz, 1H), 2.33 (bs, 1H), 1.52 (s, 18H), 1.35 (d, J = 6.4 Hz, 3H) | 127.13, 116.13, 84.48, 83.24, 77.25, 73.80, 73.68, 71.79, 58.08, 27.95, 18.90, −0.01 |
| 261 | — | — | ESIMS m/z 426 ([M − C₄H₉ + 2H]⁺) | ¹H NMR (CDCl₃) δ 6.78 (s, 4H), 5.33 (dd, J = 8.9, 3.1 Hz, 1H), 5.24 (dd, J = 9.9, 9.1 Hz, 1H), 5.08 (dq, J = 9.9, 6.2 Hz, 1H), 4.30 (dd, J = 12.3, 3.1 Hz, 1H), 4.18 (ddd, J = 9.1, 7.8, 1.3 Hz, 1H), 4.09 (dd, J = 11.1, 1.3 Hz, 1H), 3.96 (dd, J = 12.4, 8.9 Hz, 1H), 3.75 (s, 3H), 3.68 (dd, J = 11.0, 7.8 Hz, 1H), 2.44 (p, J = 7.0 Hz, 1H), 1.53 (s, 18H), 1.36 (d, J = 6.2 Hz, 3H), 1.09 (d, J = 7.0 Hz, 3H), 1.05 (d, J = 7.0 Hz, 3H) | ¹³C NMR (CDCl₃) δ 175.92, 168.72, 154.18, 152.56, 151.32, 116.51, 114.63, 83.20, 79.10, 75.91, 75.13, 73.63, 71.19, 58.19, 55.68, 34.04, 27.98, 18.91, 18.87, 18.27 |
| 262 | — | — | ESIMS m/z 526 ([M − C₄H₉ + 2H]⁺) | ¹H NMR (CDCl₃) δ 6.90-6.83 (m, 2H), 6.82-6.76 (m, 2H), 5.29 (dd, J = 8.8, 4.4 Hz, 1H), 5.14-5.01 (m, 2H), 4.38 (t, J = 9.2 Hz, 1H), 4.28 (dd, J = 12.1, 4.4 Hz, 1H), 3.97 (dd, J = 12.2, 8.9 Hz, 1H), 3.85-3.77 (m, 2H), 3.76 (s, 3H), 2.20 (hept, J = 7.0 Hz, 1H), 1.52 (s, 18H), 1.41 (d, J = 6.3 Hz, 3H), 0.94 (d, J = 7.0 Hz, 3H), 0.86 (d, J = 7.0 Hz, 3H) | ¹³C NMR (CDCl₃) δ 175.52, 168.89, 154.21, 153.01, 152.51, 116.57, 114.50, 83.29, 81.55, 75.11, 72.50, 57.59, 55.69, 33.78, 27.95, 18.78, 18.73, 18.44 |
| 263 | — | — | ESIMS m/z 636 ([M + Na]⁺) | ¹H NMR (CDCl₃) δ 6.60 (m, 3H), 6.55 (m, 1H), 6.40-6.31 (m, 2H), 5.35 (dd, J = 9.1, 3.7 Hz, 1H), 5.11 (dq, J = 9.4, 6.3 Hz, 1H), 4.44 (t, J = 9.1 Hz, 1H), 4.38-4.27 (m, 2H), 4.04 (dd, J = 11.0, 1.3 Hz, 1H), 3.97 (dd, J = 12.3, 9.1 Hz, 1H), 3.75 (dd, J = 11.0, 7.3 Hz, 1H), 2.26 (s, 6H), 2.20 (s, 6H), 1.54 (s, 18H), 1.46 (d, J = 6.3 Hz, 3H) | ¹³C NMR (CDCl₃) δ 168.88, 159.63, 157.44, 152.57, 139.04, 138.85, 123.26, 122.97, 114.52, 113.46, 83.23, 82.83, 80.46, 75.29, 73.05, 72.49, 57.90, 28.01, 21.42, 21.36, 19.00 |
| 264 | — | — | ESIMS m/z 614 ([M + Na]⁺) | ¹H NMR (CDCl₃) δ 7.55-7.48 (m, 2H), 7.03-6.97 (m, 2H), 5.29 (dd, J = 8.7, 3.4 Hz, 1H), 4.93 (dq, J = 9.6, 6.2 Hz, 1H), 4.37-4.25 (m, 2H), 4.00-3.88 (m, 2H), 3.76 (dt, J = 8.7, 6.5 Hz, 1H), 3.68 (dd, J = 11.2, 7.2 Hz, 1H), 3.57-3.40 (m, 2H), 1.52 (s, 18H), 1.48 (d, J = 6.2 Hz, 3H), 1.48-1.39 (m, 2H), 0.80 (t, J = 7.4 Hz, 3H) | ¹³C NMR (CDCl₃) δ 168.66, 160.10, 152.60, 128.48, 126.91, 126.87, 115.50, 84.34, 83.19, 81.40, 75.99, 75.62, 73.37, 72.58, 57.99, 27.97, 23.36, 18.72, 10.55 |
| 265 | — | — | ESIMS m/z 614 ([M + Na]⁺) | ¹H NMR (CDCl₃) δ 7.54-7.47 (m, 2H), 7.07 (dd, J = 8.8, 0.9 Hz, 2H), 5.28 (dd, J = 9.1, 4.1 Hz, 1H), 5.04 (dq, J = 9.6, 6.2 Hz, 1H), 4.36-4.28 (m, 2H), 4.03-3.90 (m, 2H) 3.64 (dd, J = 11.0, 7.6 Hz, 1H), | ¹³C NMR (CDCl₃) δ 168.98, 161.92, 152.65, 126.68, 126.64, 115.98, 83.23, 83.18, 82.15, 75.40, 72.87, 72.81, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 3.52-3.40 (m, 2H), 3.29 (dt, J = 9.0, 6.6 Hz, 1H), 1.52 (s, 18H), 1.36 (d, J = 6.3 Hz, 3H), 1.28 (td, J = 7.6, 6.7 Hz, 2H), 0.64 (t, J = 7.4 Hz, 3H) | 71.95, 57.83, 27.95, 22.93, 18.75, 10.27 |
| 266 | — | — | ESIMS m/z 550 ([M − C$_4$H$_9$ + 2H]$^+$) | $^1$H NMR (CDCl$_3$) δ 7.58-7.45 (m, 2H), 7.06 (dd, J = 8.8, 0.9 Hz, 2H), 5.29 (dd, J = 9.0, 4.0 Hz, 1H), 5.05 (dq, J = 9.6, 6.3 Hz, 1H), 4.38-4.25 (m, 2H), 4.03-3.92 (m, 2H), 3.64 (dd, J = 11.0, 7.5 Hz, 1H), 3.43 (ddd, J = 8.8, 7.5, 1.5 Hz, 1H), 3.28 (dd, J = 8.9, 6.3 Hz, 1H), 3.11 (dd, J = 8.9, 6.4 Hz, 1H), 1.57-1.47 (m, 19H), 1.36 (d, J = 6.2 Hz, 3H), 0.66 (d, J = 6.7 Hz, 3H), 0.60 (d, J = 6.7 Hz, 3H) | $^{13}$C NMR (CDCl$_3$) δ 168.93, 161.87, 152.64, 142.04, 128.41, 128.39, 126.70, 126.66, 126.62, 126.59, 125.83, 115.92, 83.17, 83.02, 82.36, 77.89, 75.37, 72.90, 71.97, 57.88, 39.24, 32.05, 28.56, 27.95, 19.10, 18.97, 18.75 |
| 267 | — | — | ESIMS m/z 538 ([M + Na]$^+$) | $^1$H NMR (CDCl$_3$) δ 7.20 (t, J = 8.2 Hz, 1H), 7.03 (t, J = 2.2 Hz, 1H), 6.97 (ddd, J = 8.0, 1.9, 0.9 Hz, 1H), 6.90 (ddd, J = 8.4, 2.6, 0.9 Hz, 1H), 5.25 (dd, J = 8.5, 4.1 Hz, 1H), 5.04 (dq, J = 8.9, 6.4 Hz, 1H), 4.30 (dd, J = 12.2, 4.1 Hz, 1H), 4.22 (t, J = 8.7 Hz, 1H), 4.06 (dd, J = 11.1, 1.5 Hz, 1H), 3.98 (dd, J = 12.2, 8.6 Hz, 1H), 3.85 (ddd, J = 8.6, 7.4, 1.4 Hz, 1H), 3.68 (dd, J = 11.1, 7.4 Hz, 1H), 2.77 (bs, 1H), 1.51 (s, 18H), 1.34 (d, J = 6.5 Hz, 3H) | $^{13}$C NMR (CDCl$_3$) δ 168.72, 159.69, 152.58, 135.01, 130.46, 122.20, 116.82, 114.51, 84.76, 83.17, 73.73, 73.61, 71.89, 58.07, 27.98, 27.92, 18.88 |
| 268 | — | — | ESIMS m/z 538 ([M + Na]$^+$) | $^1$H NMR (CDCl$_3$) δ 7.19 (t, J = 8.1 Hz, 1H), 7.00-6.93 (m, 2H), 6.84 (ddd, J = 8.5, 2.5, 0.9 Hz, 1H), 5.33 (dd, J = 8.7, 2.4 Hz, 1H), 5.04 (dq, J = 9.0, 6.3 Hz, 1H), 4.27 (dd, J = 12.6, 2.4 Hz, 1H), 4.20-4.09 (m, 1H), 4.06 (dd, J = 11.0, 1.3 Hz, 1H), 3.93 (dd, J = 12.6, 8.7 Hz, 1H), 3.77 (t, J = 8.8 Hz, 1H), 3.60 (dd, J = 11.1, 7.6 Hz, 1H), 1.57-1.49 (m, 21H) | $^{13}$C NMR (CDCl$_3$) δ 168.34, 157.39, 152.55, 135.12, 130.50, 122.07, 116.31, 114.05, 83.25, 80.82, 76.14, 75.77, 74.27, 73.27, 58.33, 28.00, 27.95, 18.70 |
| 269 | — | — | ESIMS m/z 594 ([M + Na]$^+$) | $^1$H NMR (CDCl$_3$) δ 7.15 (t, J = 8.1 Hz, 1H), 7.03 (t, J = 2.2 Hz, 1H), 6.89 (dddd, J = 12.5, 8.4, 2.2, 0.9 Hz, 2H), 5.28 (dd, J = 9.0, 4.0 Hz, 1H), 5.02 (dq, J = 9.5, 6.3 Hz, 1H), 4.31 (dd, J = 12.1, 4.0 Hz, 1H), 4.23 (dd, J = 9.6, 8.7 Hz, 1H), 3.96 (dd, J = 11.9, 9.4 Hz, 2H), 3.63 (dd, J = 11.0, 7.5 Hz, 1H), 3.40 (ddd, J = 8.9, 7.5, 1.5 Hz, 1H), 3.29 (dd, J = 8.8, 6.4 Hz, 1H), 3.14 (dd, J = 8.8, 6.3 Hz, 1H), 1.61-1.55 (m, 1H), 1.52 (s, 18H), 1.36 (d, J = 6.3 Hz, 3H), 0.69 (d, J = 6.7 Hz, 3H), 0.65 (d, J = 6.7 Hz, 3H) | $^{13}$C NMR (CDCl$_3$) δ 168.93, 160.20, 152.61, 134.53, 129.92, 121.25, 116.63, 114.44, 83.39, 83.10, 82.39, 77.88, 75.38, 72.87, 72.05, 57.88, 28.61, 27.94, 19.15, 19.04, 18.76 |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 270 | — | — | ESIMS m/z 502 ([M + Na]$^+$) | $^1$H NMR (CDCl$_3$) δ 7.39-7.30 (m, 5H), 5.51 (d, J = 8.0 Hz, 1H), 5.10 (s, 2H), 4.89 (dd, J = 9.0, 6.0 Hz, 1H), 4.69 (q, J = 6.5 Hz, 1H), 3.99-3.90 (m, 1H), 3.86 (q, J = 7.9 Hz, 1H), 3.78 (d, J = 11.2 Hz, 1H), 3.74-3.66 (m, 1H), 3.66-3.45 (m, 4H), 3.18-3.10 (m, 2H), 1.77-1.59 (m, 2H), 1.45-1.39 (m, 7H), 0.89 (ddd, J = 6.4, 3.7, 2.4 Hz, 12H) | $^{13}$C NMR (CDCl$_3$) δ 170.96, 155.67, 136.08, 128.53, 128.47, 128.21, 128.07, 85.03, 83.64, 75.37, 74.53, 73.00, 72.44, 69.29, 67.09, 54.05, 39.22, 38.93, 24.94, 22.89, 22.65, 22.60, 22.49, 18.56 |
| 271 | — | (Thin Film) 3387, 2932, 1753, 1587, 1493, 1230 | ESIMS m/z 390.2 ([M + H]$^+$) | $^1$H NMR (CDCl$_3$) δ 7.69-6.69 (m, 5H), 5.39 (t, J = 8.0 Hz, 1H), 5.18-5.06 (m, 1H), 4.11 (d, J = 8.0 Hz, 2H), 3.94-3.48 (m, 7H), 2.26-1.94 (m, 4H), 1.80-1.37 (m, 9H) | — |
| 272 | — | (Thin Film) 2955, 2928, 2870, 2185, 1753, 1214, 1103 | HRMS-ESI (m/z) [M + H]$^+$ calcd for C$_{18}$H$_{36}$NO$_5$, 346.2588; found, 346.2604; | $^1$H NMR (CD$_3$OD) δ 5.06-4.93 (m, 1H), 4.45 (t, J = 4.1 Hz, 1H), 4.05 (d, J = 4.1 Hz, 2H), 3.99 (dd, J = 11.8, 1.1 Hz, 1H), 3.94-3.86 (m, 1H), 3.72-3.37 (m, 6H), 3.31 (p, J = 1.7 Hz, 1H), 3.22 (t, J = 9.1 Hz, 1H), 3.12 (ddd, J = 9.0, 6.6, 1.1 Hz 1H), 1.75-1.63 (m, 2H), 1.45 (dd, J = 6.6, 3.4 Hz, 6H), 0.91 (ddd, J = 6.7, 4.4, 2.2 Hz, 12H) | $^{13}$C NMR (CD$_3$OD) δ 167.82, 84.87, 83.77, 78.27, 73.16, 72.01, 71.93, 68.68, 53.80, 38.99, 38.75, 24.78, 24.68, 21.90, 21.68, 21.52, 17.47 |
| 273 | 181-185 | — | ESIMS m/z 314 ([M]$^+$) | $^1$H NMR (CDCl$_3$) δ 8.47 (s, 3H), 4.78-4.64 (m, 1H), 4.38 (s, 1H), 4.06 (d, J = 11.8 Hz, 1H), 3.87 (s, 1H), 3.66 (d, J = 12.0 Hz, 1H), 3.56 (dd, J = 9.9, 6.7 Hz, 1H), 3.37-3.26 (m, 1H), 3.19 (pd, J = 8.6, 7.0, 5.2 Hz, 3H), 3.10-2.94 (m, 2H), 1.26 (d, J = 6.1 Hz, 3H), 0.84 (dqd, J = 14.7, 7.9, 2.4 Hz, 2H), 0.42-0.24 (m, 4H), 0.09--0.06 (m, 4H) | $^{13}$C NMR (CDCl$_3$) δ 168.53, 84.43, 82.98, 78.67, 75.75, 73.74, 70.74, 67.05, 53.24, 18.49, 11.05, 10.92, 3.24, 3.13, 2.95, 2.80 |
| 274 | — | — | ESIMS m/z 394 ([M + H]$^+$) | $^1$H NMR (CD$_3$OD) δ 6.99 (s, 2H), 6.97 (d, J = 1.1 Hz, 2H), 6.96-6.89 (m, 2H), 6.73-6.65 (m, 2H), 5.41 (dq, J = 9.2, 6.3 Hz, 1H), 4.62 (t, J = 9.2 Hz, 1H), 4.53 (dd, J = 4.5, 2.9 Hz, 1H), 4.23 (dd, J = 9.2, 6.4 Hz, 1H), 4.19-4.08 (m, 3H), 3.90 (dd, J = 12.3, 6.6 Hz, 1H), 1.50 (d, J = 6.4 Hz, 3H) | — |
| 275 | 197-200 | — | ESIMS m/z 356 ([M + H]$^+$) | $^1$H NMR (CD$_3$OD) δ 7.04-6.96 (m, 2H), 6.93-6.87 (m, 2H), 5.17 (dq, J = 9.3, 6.3 Hz, 1H), 4.46 (t, J = 3.7 Hz, 1H), 4.12-4.02 (m, 4H), 3.78-3.67 (m, 2H), 3.52 (t, J = 9.3 Hz, 1H), 3.35 (dd, J = 8.5, 6.4 Hz, 1H), 1.70 (m, 1H), 1.52 (d, J = 6.3 Hz, 3H), 0.83 (dd, J = 13.8, 6.7 Hz, 6H) | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 276 | 213-216 | — | ESIMS m/z 386 ([M + H]$^+$) | $^1$H NMR (CD$_3$OD) δ 7.10-7.02 (m, 2H), 7.01-6.96 (m, 2H), 6.91-6.85 (m, 2H), 6.62-6.56 (m, 2H), 5.39 (dq, J = 9.2, 6.3 Hz, 1H), 4.58 (t, J = 9.2 Hz, 1H), 4.52 (dd, J = 4.9, 2.7 Hz, 1H), 4.26-4.18 (m, 1H), 4.18-4.08 (m, 3H), 3.87 (dd, J = 12.1, 6.6 Hz, 1H), 2.26 (s, 3H), 2.21 (s, 3H), 1.49 (d, J = 6.4 Hz, 3H) | — |
| 277 | 217-219 | — | ESIMS m/z 350 ([M + H]$^+$) | $^1$H NMR (CD$_3$OD) δ 7.35-7.17 (m, 2H), 7.03-6.84 (m, 3H), 5.09 (dq, J = 9.1, 6.3 Hz, 1H), 4.40 (dq, J = 5.4, 3.2, 2.5 Hz, 2H), 4.21-3.96 (m, 4H), 3.76 (dd, J = 12.1, 6.2 Hz, 1H), 3.67 (t, J = 9.1 Hz, 1H), 1.76-1.67 (m, 2H), 1.66-1.56 (m, 4H), 1.52 (m, 4H), 1.50-1.43 (m, 1H) | — |
| 278 | — | — | ESIMS m/z 350 ([M + H]$^+$) | $^1$H NMR (CD$_3$OD) δ 7.27-7.19 (m, 2H), 7.01-6.96 (m, 2H), 6.91 (tt, J = 7.3, 1.0 Hz, 1H), 5.23 (dq, J = 9.3, 6.3 Hz, 1H), 4.46 (dd, J = 5.9, 2.9 Hz, 1H), 4.36 (t, J = 9.1 Hz, 1H), 4.14-3.97 (m, 4H), 3.71 (dd, J = 11.7, 7.3 Hz, 1H), 3.40 (ddd, J = 8.7, 7.3, 1.3 Hz, 1H), 1.53 (tt, J = 9.0, 4.6 Hz, 2H), 1.45-1.27 (m, 9H) | — |
| 279 | 217-219 | — | ESIMS m/z 324 ([M + H]$^+$) | $^1$H NMR (CD$_3$OD) δ 7.30-7.22 (m, 2H), 6.98-6.88 (m, 3H), 5.14 (dq, J = 9.3, 6.3 Hz, 1H), 4.43 (dd, J = 5.0, 2.8 Hz, 1H), 4.19-4.11 (m, 1H), 4.10-4.00 (m, 3H), 3.89 (dt, J = 8.8, 6.5 Hz, 1H), 3.74 (dd, J = 12.1, 6.6 Hz, 1H), 3.62-3.50 (m, 2H), 1.52 (d, J = 6.3 Hz, 3H), 1.50-1.42 (m, 2H), 0.84 (t, J = 7.4 Hz, 3H) | — |
| 280 | — | — | ESIMS m/z 324 ([M + H]$^+$) | $^1$H NMR (CD$_3$OD) δ 7.29-7.19 (m, 2H), 7.05-6.97 (m, 2H), 6.92 (tt, J = 7.5, 1.0 Hz, 1H), 5.25 (dq, J = 9.2, 6.4 Hz, 1H), 4.46 (dd, J = 5.7, 2.8 Hz, 1H), 4.40 (t, J = 9.1 Hz, 1H), 4.15-3.99 (m, 3H), 3.72 (dd, J = 11.8, 7.1 Hz, 1H), 3.52-3.42 (m, 1H), 3.40-3.32 (m, 2H), 1.41 (d, J = 6.4 Hz, 3H), 1.34-1.23 (m, 2H), 0.66 (t, J = 7.4 Hz, 3H) | — |
| 281 | — | — | ESIMS m/z 418 ([M + H]$^+$) | $^1$H NMR (CD$_3$OD) δ 7.01-6.88 (m, 2H), 6.86-6.71 (m, 4H), 6.71-6.61 (m, 2H), 5.43-5.31 (m, 1H), 4.57-4.43 (m, 2H), 4.22-4.06 (m, 4H), 3.85 (dd, J = 12.3, 6.8 Hz, 1H), 3.74 (d, J = 2.0 Hz, 3H), 3.70 (s, 3H), 1.50 (d, J = 6.3 Hz, 3H) | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 282 | 197-198 | — | ESIMS m/z 382 ([M + H]$^+$) | $^1$H NMR (CD$_3$OD) δ 6.85-6.75 (m, 4H), 5.36 (dq, J = 9.6, 6.3 Hz, 1H), 5.22 (t, J = 9.5 Hz, 1H), 4.53 (dd, J = 5.3, 2.5 Hz, 1H), 4.20-4.02 (m, 4H), 3.79 (dd, J = 12.2, 6.9 Hz, 1H), 3.73 (s, 3H), 2.47 (m, 1H), 1.40 (d, J = 6.3 Hz, 3H), 1.10 (d, J = 7.0 Hz, 3H), 1.05 (d, J = 7.0 Hz, 3H) | — |
| 283 | 207-208 | — | ESIMS m/z 383 ([M + H]$^+$) | $^1$H NMR (CD$_3$OD) δ 6.93-6.88 (m, 2H), 6.86-6.80 (m, 2H), 5.32 (dq, J = 9.2, 6.3 Hz, 1H), 4.97-4.89 (m, 1H), 4.60-4.47 (m, 2H), 4.13-4.09 (m, 2H), 3.99 (dd, J = 12.2, 1.3 Hz, 1H), 3.90 (dd, J = 12.2, 6.9 Hz, 1H), 3.73 (s, 3H), 2.16 (hept, J = 7.0 Hz, 1H), 1.43 (d, J = 6.3 Hz, 3H), 0.91 (d, J = 7.0 Hz, 3H), 0.82 (d, J = 6.9 Hz, 3H) | — |
| 284 | 212 | — | ESIMS m/z 414 ([M + H]$^+$) | $^1$H NMR (CD$_3$OD) δ 6.66-6.52 (m, 4H), 6.28-6.24 (m, 2H), 5.37 (dq, J = 9.1, 6.3 Hz, 1H), 4.61 (t, J = 9.2 Hz, 1H), 4.54 (dd, J = 4.7, 3.0 Hz, 1H), 4.22 (dd, J = 9.1, 6.7 Hz, 1H), 4.18-4.10 (m, 3H), 3.86 (dd, J = 12.1, 6.8 Hz, 1H), 2.25 (d, J = 0.8 Hz, 6H), 2.18 (d, J = 0.8 Hz, 6H), 1.49 (d, J = 6.3 Hz, 3H) | — |
| 285 | — | — | ESIMS m/z 392 ([M + H]$^+$) | $^1$H NMR (CD$_3$OD) δ 7.62-7.55 (m, 2H), 7.11-7.03 (m, 2H), 5.19 (dq, J = 9.3, 6.3 Hz, 1H), 4.52 (dd, J = 4.7, 2.5 Hz, 1H), 4.24 (dd, J = 9.2, 6.1 Hz, 1H), 4.18-4.04 (m, 2H), 3.82 (ddt, J = 12.3, 11.2, 6.4 Hz, 2H), 3.76-3.70 (m, 1H), 3.63-3.52 (m, 2H), 3.31 (p, J = 1.6 Hz, 2H), 1.53 (d, J = 6.3 Hz, 3H), 1.51-1.38 (m, 2H), 0.82 (t, J = 7.4 Hz, 3H) | $^{13}$C NMR (CD$_3$OD) δ 169.17, 161.65, 129.46, 129.44, 128.06, 128.02, 127.98, 116.66, 85.58, 82.73, 79.75, 76.72, 74.36, 73.98, 68.88, 68.15, 55.54, 54.83, 26.51, 24.43, 18.78, 10.96 |
| 286 | — | — | ESIMS m/z 392 ([M + H]$^+$) | $^1$H NMR (CD$_3$OD) δ 7.58-7.51 (m, 2H), 7.20-7.13 (m, 2H), 5.29 (dq, J = 9.2, 6.3 Hz, 1H), 4.61-4.49 (m, 2H), 4.14-4.05 (m, 3H), 3.79-3.71 (m, 1H), 3.47 (dt, J = 8.9, 6.3 Hz, 1H), 3.41-3.24 (m, 4H), 1.42 (d, J = 6.3 Hz, 3H), 1.31-1.18 (m, 2H), 0.61 (t, J = 7.4 Hz, 3H) | $^{13}$C NMR (CD$_3$OD) δ 169.26, 163.46, 127.70, 127.66, 127.63, 117.26, 83.95, 83.64, 78.96, 73.92, 73.81, 73.36, 68.15, 55.24, 54.83, 24.03, 18.79, 10.74 |
| 287 | — | — | ESIMS m/z 406 ([M + H]$^+$) | $^1$H NMR (CD$_3$OD) δ 7.57-7.51 (m, 2H), 7.15 (d, J = 8.6 Hz, 2H), 5.30 (dq, J = 9.2, 6.3 Hz, 1H), 4.58 (t, J = 9.2 Hz, 1H), 4.52 (t, J = 4.0 Hz, 1H), 4.16-4.05 (m, 2H), 3.81-3.70 (m, 1H), 3.38-3.24 (m, 3H), 3.11 (dd, J = 8.8, 6.2 Hz, 1H), 1.52-1.40 (m, 4H), | $^{13}$C NMR (CD$_3$OD) δ 169.24, 163.41, 129.46, 129.35, 127.66, 127.63, 127.59, 126.71, 117.20, 84.21, 83.40, 78.91, 78.84, 73.93, 73.44, 55.30, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
|  |  |  |  | 0.63 (d, J = 6.7 Hz, 3H), 0.59 (d, J = 6.7 Hz, 3H) | 54.84, 40.49, 29.82, 19.49, 19.37, 18.78 |
| 288 | 168-169 | — | ESIMS m/z 372 ([M + H]$^+$) | $^1$H NMR (CD$_3$OD) δ 7.21 (dd, J = 8.5, 7.9 Hz, 1H), 7.05 (t, J = 2.2 Hz, 1H), 6.97-6.89 (m, 2H), 5.26 (dq, J = 9.2, 6.3 Hz, 1H), 4.48 (dd, J = 5.2, 2.9 Hz, 1H), 4.43 (t, J = 9.2 Hz, 1H), 4.15-4.02 (m, 3H), 3.73 (dd, J = 12.0, 7.0 Hz, 1H), 3.34-3.27 (m, 2H), 3.14 (dd, J = 8.8, 6.1 Hz, 1H), 1.50 (hept, 6.6 Hz, 1H), 1.41 (d, J = 6.4 Hz, 3H), 0.67 (d, J = 6.7 Hz, 3H), 0.64 (d, J = 6.7 Hz, 3H) | — |

*$^1$H NMR were run at 400 MHz unless noted otherwise
*$^{13}$C NMR were run at 101 MHz unless noted otherwise

TABLE 3

Biological Testing Rating Scale
Rating Table for Fungal Pathogens

| % Control | Rating |
|---|---|
| 80-100 | A |
| More than 0-Less than 80 | B |
| Not Tested | C |
| No activity noticed in this bioassay | D |

TABLE 4

Biological Activity - Disease Control at 100 ppm

| Compound Number | PUCCRT* | | SEPTTR* | |
|---|---|---|---|---|
|  | 1DP* | 3DC* | 1DP | 3DC |
| 1 | A | A | A | A |
| 2 | A | A | A | A |
| 3 | A | A | A | A |
| 4 | A | C | A | A |
| 5 | B | B | B | B |
| 6 | A | C | B | B |
| 7 | A | C | A | A |
| 8 | B | A | B | B |
| 9 | B | B | B | B |
| 10 | B | B | B | B |
| 11 | A | A | A | B |
| 12 | A | A | A | A |
| 13 | A | A | A | C |
| 14 | A | B | B | C |
| 15 | D | B | B | C |
| 16 | B | B | B | C |
| 17 | B | B | B | C |
| 18 | B | B | B | C |
| 19 | D | D | B | B |
| 20 | D | D | B | B |
| 21 | A | A | A | B |
| 22 | D | D | B | B |
| 23 | A | A | A | A |
| 24 | B | B | B | B |
| 25 | A | B | A | B |
| 26 | A | A | A | B |
| 27 | B | B | B | B |
| 28 | A | A | A | A |
| 29 | B | B | B | B |
| 30 | B | B | B | B |
| 31 | B | B | B | B |
| 32 | A | A | A | B |
| 33 | A | A | A | B |
| 34 | A | A | A | A |
| 35 | A | A | A | A |
| 36 | A | A | B | B |
| 37 | A | A | B | B |
| 38 | A | B | B | B |
| 40 | A | B | B | B |
| 41 | B | D | B | B |
| 42 | A | A | B | B |
| 43 | A | A | A | B |
| 44 | A | A | A | A |
| 45 | A | A | A | A |
| 46 | A | A | A | A |
| 47 | A | A | A | A |
| 48 | A | A | A | A |
| 49 | B | B | B | B |
| 50 | A | A | A | A |
| 51 | B | B | B | B |
| 52 | D | A | B | B |
| 53 | A | A | B | B |
| 54 | A | A | B | B |
| 55 | A | A | A | A |
| 56 | A | A | B | A |
| 57 | A | A | A | A |
| 58 | A | A | B | B |
| 59 | A | A | A | B |
| 60 | A | A | A | B |
| 61 | A | A | A | A |
| 62 | C | A | C | A |
| 63 | C | D | C | B |
| 64 | A | A | A | A |
| 65 | C | B | C | B |
| 66 | A | A | A | B |
| 67 | A | B | B | B |
| 68 | A | A | A | A |
| 69 | A | A | A | A |

TABLE 4-continued

Biological Activity - Disease Control at 100 ppm

| Compound Number | PUCCRT* 1DP* | PUCCRT* 3DC* | SEPTTR* 1DP | SEPTTR* 3DC |
|---|---|---|---|---|
| 70 | B | B | B | B |
| 71 | A | B | A | B |
| 72 | B | B | B | B |
| 73 | A | A | A | A |
| 74 | B | B | B | B |
| 75 | A | A | A | B |
| 76 | A | A | A | A |
| 77 | A | A | A | A |
| 78 | A | A | A | A |
| 79 | A | A | A | A |
| 81 | A | A | A | A |
| 82 | A | A | A | B |
| 83 | A | A | A | A |
| 84 | A | A | A | A |
| 85 | A | A | A | A |
| 86 | A | A | A | A |
| 87 | C | C | C | C |
| 194 | A | A | C | C |
| 195 | A | D | C | C |
| 196 | C | C | C | C |
| 197 | A | D | C | C |
| 198 | B | D | A | D |
| 199 | A | D | B | D |
| 200 | D | D | B | D |
| 201 | A | D | A | B |
| 202 | A | A | A | A |
| 203 | A | A | A | A |
| 204 | A | A | A | A |
| 205 | A | A | A | A |
| 206 | A | A | A | A |
| 207 | A | A | A | A |
| 208 | A | D | A | B |
| 209 | B | B | D | B |
| 210 | C | C | C | C |
| 211 | B | C | D | B |
| 212 | A | B | A | B |
| 213 | C | C | C | C |
| 214 | C | C | C | C |
| 215 | C | C | C | C |
| 216 | C | C | C | C |
| 217 | C | C | C | C |
| 218 | C | C | C | C |
| 219 | A | A | A | B |
| 220 | A | A | A | A |
| 221 | A | A | A | A |
| 222 | A | A | A | A |
| 223 | A | A | A | A |
| 224 | A | A | A | A |
| 225 | A | A | A | A |
| 226 | A | A | A | A |
| 227 | A | A | A | A |
| 228 | A | A | A | A |
| 229 | C | C | C | C |
| 230 | A | A | A | A |
| 231 | C | C | C | C |
| 232 | A | A | A | B |
| 233 | A | A | A | B |
| 234 | A | A | A | A |
| 235 | A | A | A | A |
| 236 | A | A | A | A |
| 237 | A | A | A | A |
| 238 | A | A | A | A |

*PUCCRT—Wheat Brown Rust (*Puccinia triticina*)
*SEPTTR—Wheat Leaf Blotch (*Septoria tritici*)
*1DP—1 Day Protectant
*3DC—3 Day Curative

TABLE 5

Dropline Mobility Test at 1 ug/leaf

| Compound Number | PUCCRT* 1DPM* | PUCCRT* 3DCM* |
|---|---|---|
| 1 | A | A |
| 2 | A | A |
| 3 | A | A |
| 11 | B | B |
| 12 | B | B |
| 26 | B | D |
| 34 | B | A |
| 58 | A | B |
| 59 | D | D |
| 60 | B | D |
| 61 | A | B |
| 62 | B | D |
| 63 | B | D |
| 64 | B | B |
| 65 | B | B |
| 66 | B | B |
| 67 | B | B |
| 68 | B | B |
| 69 | B | B |
| 70 | B | B |
| 72 | B | B |
| 73 | B | B |
| 74 | B | B |
| 75 | B | B |
| 76 | A | B |
| 77 | A | B |
| 78 | B | B |
| 81 | A | B |
| 82 | A | B |
| 83 | A | B |
| 84 | A | D |
| 85 | A | A |
| 86 | A | B |
| 87 | B | A |
| 210 | C | C |
| 221 | C | C |
| 234 | A | D |
| 235 | B | D |
| 236 | B | D |
| 237 | A | A |
| 238 | A | A |

*PUCCRT—Wheat Brown Rust (*Puccinia triticina*)
*1DPM—1 Day Protectant Mobility
*3DCM—3 Day Curative Mobility

TABLE 6

Biological Activity - Disease Control at 100 ppm

| Compound Number | ALTESO* | CERCBE* | COLLLA* 1DP* | ERYSCI* | ERYSGH* |
|---|---|---|---|---|---|
| 2 | C | B | C | A | A |
| 3 | B | A | A | B | A |

TABLE 6-continued

Biological Activity - Disease Control at 100 ppm

| Compound. Number | ALTESO* | CERCBE* | COLLLA* 1DP* | ERYSCI* | ERYSGH* |
|---|---|---|---|---|---|
| 6 | C | C | C | C | C |
| 12 | B | A | A | D | B |
| 34 | C | C | C | C | C |
| 35 | C | C | C | C | C |
| 45 | C | C | C | C | C |
| 47 | C | C | C | C | C |
| 54 | D | B | A | D | B |
| 55 | D | A | A | D | D |
| 57 | B | A | A | B | B |
| 60 | B | A | A | D | D |
| 65 | D | B | B | D | D |
| 68 | B | A | A | B | B |
| 77 | B | A | A | B | B |
| 78 | B | B | A | A | B |
| 84 | B | A | A | B | B |
| 85 | B | A | A | B | B |
| 86 | A | A | A | B | B |
| 221 | D | A | A | D | C |
| 222 | B | A | A | D | C |
| 228 | C | B | C | C | B |
| 229 | B | A | A | B | B |
| 231 | B | B | A | B | B |

*ALTESO—Tomato Early Blight (*Alternaria solani*)
*CERCBE—Leaf Spot of Sugar Beets (*Cercospora beticola*)
*COLLLA—Cucumber Anthracnose (*Glomerella lagenarium*; Anamorph: *Colletotricum lagenarium*)
*ERYSCI—Powdery Mildew of Cucumber (*Erysiphe cichoracearum*)
*ERYSGH—Barley Powdery Mildew (*Blumeria graminis* f.sp. *hordei*; Synonym: *Erysiphe graminis* f.sp. *hordei*)
*1DP—1 Day Protectant

TABLE 7

Biological Activity - Disease Control at 100 ppm

| Compound. Number | ERYSGT* | LEPTNO* | PYRIOR* | RHYNSE* 1 DP* | UNCINE* | VENTIN* |
|---|---|---|---|---|---|---|
| 2 | C | C | C | C | C | C |
| 3 | A | A | A | C | A | B |
| 6 | C | C | C | C | B | B |
| 12 | B | A | A | C | B | B |
| 34 | C | C | C | C | A | A |
| 35 | C | C | C | C | B | B |
| 45 | C | C | C | C | A | B |
| 47 | C | C | A | C | B | A |
| 54 | B | A | B | C | B | D |
| 55 | B | A | A | C | B | C |
| 57 | B | B | A | C | B | C |
| 60 | B | A | A | C | D | B |
| 65 | D | B | D | C | B | D |
| 68 | B | A | A | C | B | B |
| 77 | B | A | A | C | A | B |
| 78 | A | A | A | C | A | A |
| 84 | B | A | A | A | B | B |
| 85 | B | A | A | C | A | B |
| 86 | A | A | A | C | A | B |
| 221 | C | C | A | A | C | C |
| 222 | C | C | A | A | C | C |
| 228 | C | A | C | C | C | C |
| 229 | C | A | A | A | A | D |
| 231 | C | A | A | A | A | B |

*ERYSGT—Wheat Powdery Mildew (*Blumeria graminis* f. sp. *tritici*; Synonym: *Erysiphe graminis* f. sp. *tritici*)
*LEPTNO—Wheat Glume Blotch (*Leptosphaeria nodorum*)
*PYRIOR—Rice Blast (*Magnaporthe grisea*; Anamorph: *Pyricularia oryzae*)
*RHYNSE—Barley Scald (*Rhyncosporium secalis*)
*UNCINE—Grape Powdery Mildew (*Uncinula necator*)
*VENTIN—Apple Scab (*Venturia inaequalis*)
*1 DP—1 Day Protectant

TABLE 8

Biological Activity - Disease Control at 25 ppm

| Compound Number | PHAKPA* 1DP* | 3DC* |
|---|---|---|
| 3 | A | C |
| 77 | B | C |
| 78 | A | C |
| 84 | A | A |
| 86 | A | A |
| 222 | A | A |
| 221 | A | A |

*PHAKPA—Asian Soybean Rust (*Phakopsora pachyrhizi*)
*1DP—1 Day Protectant
*3DC—3 Day Curative

What is claimed is:

1. A compound of Formula I:

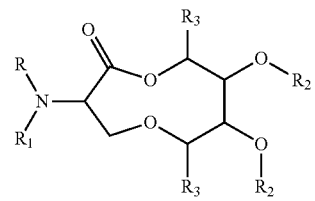

I wherein, R is H or C(O)R$_6$;
R$_1$ is C(O)R$_6$ or Q;
Q is

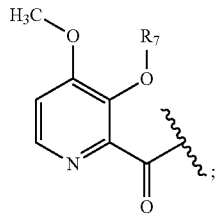

R$_2$ is independently H, alkyl, alkenyl, aryl, heterocyclyl, each substituted with 0, 1 or multiple R$_5$, or —C(O)R$_5$;

R$_3$ is independently H, alkyl, or alkenyl, each substituted with 0, 1 or multiple R$_5$;

R$_4$ is independently alkyl or alkoxy, substituted with 0, 1, or multiple R$_5$;

R$_5$ is alkyl, alkenyl, halo, haloalkyl, alkoxy, haloalkoxy, C(O)R$_8$, arylalkoxy, or aryl;

R$_6$ is alkoxy or benzyloxy;

R$_7$ is H, —C(O)R$_4$, or —CH$_2$OC(O)R$_4$; and

R$_8$ is H, alkenyl, halo, haloalkyl, alkoxy, haloalkoxy, arylalkoxy, or aryl.

2. A compound according to claim 1, wherein:
wherein, R is H or C(O)R$_6$;
R$_1$ is C(O)R$_6$;
R$_2$ is independently or separately H, alkyl, alkenyl, aryl, each substituted with 0, 1 or multiple R$_5$;
R$_3$ is independently or separately H, methyl;
R$_5$ is alkyl, alkoxy, halo, haloalkyl, or aryl; and
R$_6$ is alkoxy or benzyloxy.

3. The compound according to claim 1, wherein:
wherein, R is H;
R$_1$ is Q, wherein Q is,

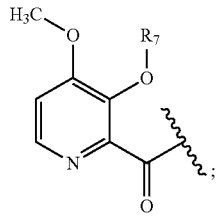

R$_2$ is independently or separately alkyl, aryl, each substituted with 0, 1 or multiple R$_5$;
R$_3$ is independently or separately H, methyl;
R$_4$ is alkyl, substituted with 0, 1, or multiple R$_5$;
R$_5$ is alkyl, alkoxy, halo, haloalkyl, or aryl; and
R$_7$ is H, —C(O)R$_4$, —CH$_2$OC(O)R$_4$.

4. The compound of claim 1, wherein R$_1$ is C(O)R$_6$.
5. The compound of claim 4, wherein R$_6$ is alkoxy.
6. The compound of claim 4, wherein R$_6$ is benzyloxy.
7. The compound of claim 4, wherein R is C(O)R$_6$.

8. The compound of claim 1, wherein the compound is:

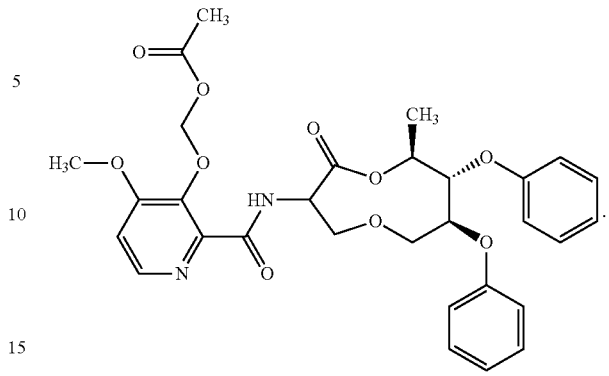

9. A compound of Formula I:

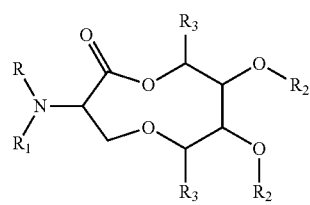

wherein, R is H;
R$_1$ is H;
R$_2$ is independently H, alkyl, alkenyl, aryl, heterocyclyl, each substituted with 0, 1 or multiple R$_5$, or —C(O)R$_5$; and
R$_3$ is independently H, alkyl, or alkenyl, each substituted with 0, 1 or multiple R$_5$.

10. The compound of claim 1, wherein R$_1$ is Q.
11. The compound of claim 10, where R$_7$ is H.
12. The compound of claim 10, where R$_7$ is —C(O)R$_4$.
13. The compound of claim 10, where R$_7$ is —CH$_2$OC(O)R$_4$.

14. A composition for treating plants, comprising a compound of Formula I:

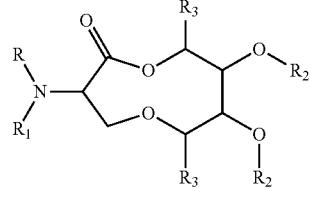

wherein, R is H or C(O)R$_6$;
R$_1$ is C(O)R$_6$ or Q;
Q is

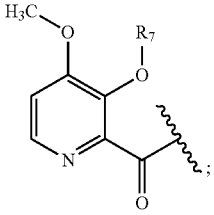

R$_2$ is independently H, alkyl, alkenyl, aryl, heterocyclyl, each substituted with 0, 1 or multiple R$_5$, or —C(O)R$_5$;

R_3 is independently H, alkyl, or alkenyl, each substituted with 0, 1 or multiple $R_5$;

$R_4$ is independently alkyl or alkoxy, substituted with 0, 1, or multiple $R_5$;

$R_5$ is alkyl, alkenyl, halo, haloalkyl, alkoxy, haloalkoxy, $C(O)R_8$, arylalkoxy, or aryl;

$R_6$ is alkoxy or benzyloxy;

$R_7$ is H, —$C(O)R_4$, or —$CH_2OC(O)R_4$; and $R_8$ is H, alkenyl, halo, haloalkyl, alkoxy, haloalkoxy, arylalkoxy, or aryl; and at least one of the following additional compounds selected from the group consisting of: phytologically acceptable carrier materials, pesticides, fungicides, insecticides, nematocides, miticides, arthropodicides, and bactericides.

15. The compositions according to claim 14, wherein the plant pathogen is least one pathogen selected from the group consisting of: *Mycosphaerella graminicola, Septoria tritici, Puccinia triticina, Puccinia striiformis, Venturia inaequalis, Ustilago maydis, Uncinula necator, Rhynchosporium secalis, Magnaporthe grisea, Pseudoperonospora cubensis, Phakopsora pachyrhizi, Leptosphaeria nodorum, Blumeria graminis, forma specialis tritici, Blumeria graminis, forma specialis hordei, Erysiphe cichoracearum, Glomerella lagenarium, Cercospora beticola, Alternaria solani*, and *Pyrenophora teres*.

16. The composition according to claim 15, wherein the fungal pathogen is at least one of *Septoria tritici, Puccinia triticina*, and *Phakopsora pachyrhizi*.

17. A method for treating a plant, comprising the steps of:
applying a agriculturally effective amount of at least one of the compounds of Formula I:

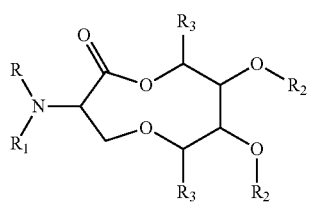

I wherein, R is H or $C(O)R_6$;

$R_1$ is H, $C(O)R_6$, or Q;

Q is

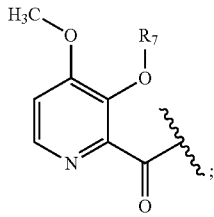

$R_2$ is independently H, alkyl, alkenyl, aryl, heterocyclyl, each substituted with 0, 1 or multiple $R_5$, or —$C(O)R_5$;

$R_3$ is independently H, alkyl, or alkenyl, each substituted with 0, 1 or multiple $R_5$;

$R_4$ is independently alkyl or alkoxy, substituted with 0, 1, or multiple $R_5$;

$R_5$ is alkyl, alkenyl, halo, haloalkyl, alkoxy, haloalkoxy, $C(O)R_8$, arylalkoxy, or aryl;

$R_6$ is alkoxy or benzyloxy;

$R_7$ is H, —$C(O)R_4$, or —$CH_2OC(O)R_4$; and $R_8$ is H, alkenyl, halo, haloalkyl, alkoxy, haloalkoxy, arylalkoxy, or aryl, to at least a protion of a plant, an area adjacent to a plant, and/or soil adapted to support growth of a plant.

18. The method according to claim 17, wherein the compound is applied in a mixture with at least one additional compound selected from the group consisting of: phytologically acceptable carrier materials, pesticides, fungicides, insecticides, nematocides, miticides, arthropodicides, and bactericides, wherein said compound is effective for the control of a plant pathogen.

19. The method according to claim 17, wherein the plant is infected with or at risk for becoming infected with a fungal pathogen.

20. The method according to claim 18, wherein the plant pathogen is least one pathogen selected from the group consisting of: *Mycosphaerella graminicola, Septoria tritici, Puccinia triticina, Puccinia striiformis, Venturia inaequalis, Ustilago maydis, Uncinula necator, Rhynchosporium secalis, Magnaporthe grisea, Pseudoperonospora cubensis, Phakopsora pachyrhizi, Leptosphaeria nodorum, Blumeria graminis, forma specialis tritici, Blumeria graminis, forma specialis hordei, Erysiphe cichoracearum, Glomerella lagenarium, Cercospora beticola, Alternaria solani*, and *Pyrenophora teres*.

* * * * *